(12) United States Patent
Maring et al.

(10) Patent No.: US 9,173,887 B2
(45) Date of Patent: Nov. 3, 2015

(54) HEPATITIS C INHIBITORS AND USES THEREOF

(75) Inventors: Clarence J. Maring, Palatine, IL (US); John K. Pratt, Kenosha, WI (US); William A. Carroll, Evanston, IL (US); Dachun Liu, Vernon Hills, IL (US); David A. Betebenner, Libertyville, IL (US); Douglas K. Hutchinson, Antioch, IL (US); Michael D. Tufano, Chicago, IL (US); Todd W. Rockway, Grayslake, IL (US); Uwe Schoen, Burgdorf (DE); Axel Pahl, Lindwedel (DE); Adreas Witte, Hannover (DE)

(73) Assignee: AbbVie Inc., North Chicago, IL (US)

( * ) Notice: Subject to any disclaimer, the term of this patent is extended or adjusted under 35 U.S.C. 154(b) by 47 days.

(21) Appl. No.: 13/995,701

(22) PCT Filed: Dec. 16, 2011

(86) PCT No.: PCT/US2011/065558
§ 371 (c)(1),
(2), (4) Date: Oct. 10, 2013

(87) PCT Pub. No.: WO2012/087833
PCT Pub. Date: Jun. 28, 2012

(65) Prior Publication Data
US 2014/0038919 A1     Feb. 6, 2014

Related U.S. Application Data

(60) Provisional application No. 61/426,312, filed on Dec. 22, 2010.

(51) Int. Cl.
| | | |
|---|---|---|
| *C07D 405/14* | (2006.01) | |
| *C07D 405/04* | (2006.01) | |
| *C07D 409/14* | (2006.01) | |
| *C07D 413/04* | (2006.01) | |
| *C07D 413/14* | (2006.01) | |
| *C07D 417/14* | (2006.01) | |
| *C07D 471/04* | (2006.01) | |
| *A61K 31/5395* | (2006.01) | |
| *A61K 31/4178* | (2006.01) | |
| *A61K 31/422* | (2006.01) | |
| *A61K 31/427* | (2006.01) | |
| *A61K 31/437* | (2006.01) | |
| *C07F 7/18* | (2006.01) | |
| *A61K 31/4245* | (2006.01) | |
| *A61K 31/513* | (2006.01) | |
| *A61K 31/5377* | (2006.01) | |
| *A61K 31/541* | (2006.01) | |
| *A61K 31/675* | (2006.01) | |
| *A61K 45/06* | (2006.01) | |
| *C07F 9/6558* | (2006.01) | |

(52) U.S. Cl.
CPC ......... *A61K 31/5395* (2013.01); *A61K 31/4178* (2013.01); *A61K 31/422* (2013.01); *A61K 31/427* (2013.01); *A61K 31/4245* (2013.01); *A61K 31/437* (2013.01); *A61K 31/513* (2013.01); *A61K 31/5377* (2013.01); *A61K 31/541* (2013.01); *A61K 31/675* (2013.01); *A61K 45/06* (2013.01); *C07D 405/04* (2013.01); *C07D 405/14* (2013.01); *C07D 409/14* (2013.01); *C07D 413/04* (2013.01); *C07D 413/14* (2013.01); *C07D 417/14* (2013.01); *C07D 471/04* (2013.01); *C07F 7/1856* (2013.01); *C07F 9/65586* (2013.01)

(58) Field of Classification Search
CPC .. C07D 405/04; C07D 405/14; C07D 409/14; C07D 413/04; C07D 413/14; C07D 417/14; C07D 471/04; A61K 31/5395; A61K 31/4378; A61K 31/422; A61K 31/4245; A61K 31/427; A61K 31/437; A61K 31/513; A61K 31/5377; A61K 31/541
USPC ............. 548/311.1, 311.4, 131; 514/364, 397
See application file for complete search history.

(56) References Cited

U.S. PATENT DOCUMENTS

| | | |
|---|---|---|
| 3,497,597 A | 2/1970 | Andrew et al. |
| 4,585,873 A | 4/1986 | Ingendoh et al. |
| 5,240,943 A | 8/1993 | Desai et al. |
| 5,314,895 A | 5/1994 | Desai et al. |
| 5,317,019 A | 5/1994 | Bender et al. |

(Continued)

FOREIGN PATENT DOCUMENTS

| | | |
|---|---|---|
| CN | 101195597 A | 6/2008 |
| DE | 19624289 A1 | 1/1998 |

(Continued)

OTHER PUBLICATIONS

Areschka et al. European Journal of Medicinal Chemistry (1977), 12(1), 87-91.*

(Continued)

*Primary Examiner* — Kahsay Habte
(74) *Attorney, Agent, or Firm* — Kevin A. O'Connor; Neal, Gerber & Eisenberg LLP

(57) ABSTRACT

This disclosure relates to: (a) compounds and salts thereof that, inter alia, inhibit HCV; (b) intermediates useful for the preparation of such compounds and salts; (c) compositions comprising such compounds and salts; (d) methods for preparing such intermediates, compounds, salts, and compositions; (e) methods of use of such compounds, salts, and compositions; and (f) kits comprising such compounds, salts, and compositions.

18 Claims, No Drawings

(56) References Cited

U.S. PATENT DOCUMENTS

| | | |
|---|---|---|
| 5,317,028 A | 5/1994 | McKnight et al. |
| 5,360,796 A | 11/1994 | Hansen, Jr. et al. |
| 5,369,105 A | 11/1994 | McKnight et al. |
| 5,616,537 A | 4/1997 | Yokota et al. |
| 5,633,237 A | 5/1997 | Hansen, Jr. et al. |
| 5,643,938 A | 7/1997 | Kohno et al. |
| 5,714,498 A | 2/1998 | Kulagowski et al. |
| 5,716,964 A | 2/1998 | Hansen, Jr. et al. |
| 5,747,508 A | 5/1998 | Richter et al. |
| 5,770,544 A | 6/1998 | Yokota et al. |
| 5,833,885 A | 11/1998 | Rickwood et al. |
| 5,858,995 A | 1/1999 | Kawai et al. |
| 5,919,955 A | 7/1999 | Fancelli et al. |
| 5,990,136 A | 11/1999 | Barbachyn et al. |
| 5,994,378 A | 11/1999 | Matsuo et al. |
| 6,008,229 A | 12/1999 | Oku et al. |
| 6,013,648 A | 1/2000 | Rinaldi et al. |
| 6,054,587 A | 4/2000 | Reddy et al. |
| 6,093,736 A | 7/2000 | Barbachyn et al. |
| 6,100,284 A | 8/2000 | Oku et al. |
| 6,110,959 A | 8/2000 | Tagami et al. |
| 6,121,309 A | 9/2000 | Tagami et al. |
| 6,214,801 B1 | 4/2001 | Townsend et al. |
| 6,214,843 B1 | 4/2001 | Kadowaki et al. |
| 6,218,413 B1 | 4/2001 | Hester, Jr. et al. |
| 6,232,324 B1 | 5/2001 | Mizuo et al. |
| 6,288,055 B1 | 9/2001 | Natarajan et al. |
| 6,294,672 B1 | 9/2001 | Reddy et al. |
| 6,303,624 B1 | 10/2001 | Nomura et al. |
| 6,313,139 B1 | 11/2001 | Dijcks et al. |
| 6,342,513 B1 | 1/2002 | Hester, Jr. et al. |
| 6,344,462 B1 | 2/2002 | Oku et al. |
| 6,358,995 B1 | 3/2002 | Tagami et al. |
| 6,362,189 B1 | 3/2002 | Hester, Jr. et al. |
| 6,410,562 B1 | 6/2002 | Jirousek et al. |
| 6,461,538 B2 | 10/2002 | Taguchi |
| 6,472,389 B1 | 10/2002 | Ohtani et al. |
| 6,521,656 B1 | 2/2003 | Kaneko et al. |
| 6,537,986 B2 | 3/2003 | Hester et al. |
| 6,586,638 B1 | 7/2003 | Zhang et al. |
| 6,602,895 B2 | 8/2003 | Galemmo et al. |
| 6,630,597 B1 | 10/2003 | Lin et al. |
| 6,653,320 B2 | 11/2003 | Hayakawa et al. |
| 6,828,044 B2 | 12/2004 | Conley |
| 6,897,223 B2 | 5/2005 | Wilson |
| 6,951,878 B2 | 10/2005 | Moller et al. |
| 7,008,950 B1 | 3/2006 | Ohkawa et al. |
| 7,144,907 B2 | 12/2006 | Wallace et al. |
| 7,208,495 B2 | 4/2007 | Ohkawa et al. |
| 7,229,480 B2 | 6/2007 | Glenn, Jr. et al. |
| 7,230,099 B2 | 6/2007 | Wallace et al. |
| 7,265,152 B2 | 9/2007 | Saha et al. |
| 7,271,178 B2 | 9/2007 | Wallace et al. |
| 7,271,190 B2 | 9/2007 | Miyoshi et al. |
| 7,351,726 B2 | 4/2008 | Elokdah et al. |
| 7,417,057 B2 | 8/2008 | Dixson et al. |
| 7,425,573 B2 | 9/2008 | Pelletier et al. |
| 7,511,058 B2 | 3/2009 | Wallace et al. |
| 7,538,120 B2 | 5/2009 | Koch et al. |
| 7,585,875 B2 | 9/2009 | Gaeta et al. |
| 7,666,863 B2 | 2/2010 | Saha et al. |
| 7,666,880 B2 | 2/2010 | Lee et al. |
| 7,696,365 B2 | 4/2010 | Cheng et al. |
| 7,759,373 B2 | 7/2010 | Hongu et al. |
| 7,759,389 B2 | 7/2010 | Krauss et al. |
| 7,767,667 B2 | 8/2010 | Dixson et al. |
| 7,790,741 B2 | 9/2010 | Calderwood et al. |
| 7,795,242 B2 | 9/2010 | Rhijn et al. |
| 2005/0054701 A1 | 3/2005 | Wallace et al. |
| 2005/0113283 A1 | 5/2005 | Solow-Cordero et al. |
| 2005/0137234 A1 | 6/2005 | Bressi et al. |
| 2005/0229333 A1 | 10/2005 | Glenn et al. |
| 2005/0256150 A1 | 11/2005 | Birman |
| 2006/0194777 A1 | 8/2006 | Gazit et al. |
| 2006/0287291 A1 | 12/2006 | Johansson et al. |
| 2007/0032515 A1 | 2/2007 | Anand et al. |
| 2007/0060565 A1 | 3/2007 | Meanwell et al. |
| 2007/0072002 A1 | 3/2007 | Kim et al. |
| 2007/0078122 A1 | 4/2007 | Bergstrom et al. |
| 2007/0093414 A1 | 4/2007 | Carini et al. |
| 2007/0099825 A1 | 5/2007 | D'andrea et al. |
| 2007/0112048 A1 | 5/2007 | Bavari et al. |
| 2007/0184024 A1 | 8/2007 | Meanwell et al. |
| 2007/0185083 A1 | 8/2007 | Bergstrom et al. |
| 2007/0270405 A1 | 11/2007 | Bender et al. |
| 2007/0270406 A1 | 11/2007 | Gentles et al. |
| 2007/0275930 A1 | 11/2007 | Gentles et al. |
| 2007/0275947 A1 | 11/2007 | Bergstrom |
| 2007/0275984 A1 | 11/2007 | Imogai et al. |
| 2007/0287694 A1 | 12/2007 | Yeung et al. |
| 2008/0014173 A1 | 1/2008 | Scola et al. |
| 2008/0044379 A1 | 2/2008 | Bachand et al. |
| 2008/0044380 A1 | 2/2008 | Bachand et al. |
| 2008/0050336 A1 | 2/2008 | Bachand et al. |
| 2008/0107623 A1 | 5/2008 | D'andrea et al. |
| 2008/0107624 A1 | 5/2008 | D'andrea et al. |
| 2008/0107625 A1 | 5/2008 | D'andrea et al. |
| 2008/0119461 A1 | 5/2008 | Sin et al. |
| 2008/0119490 A1 | 5/2008 | Poupart et al. |
| 2008/0145334 A1 | 6/2008 | Wang et al. |
| 2008/0146537 A1 | 6/2008 | Bender et al. |
| 2008/0159982 A1 | 7/2008 | Wang et al. |
| 2008/0171015 A1 | 7/2008 | Bender et al. |
| 2008/0188458 A1 | 8/2008 | Yeung et al. |
| 2008/0206191 A1 | 8/2008 | Nickel et al. |
| 2008/0221090 A1 | 9/2008 | Yeung et al. |
| 2008/0226591 A1 | 9/2008 | Gentles et al. |
| 2008/0226592 A1 | 9/2008 | Yeung et al. |
| 2008/0299075 A1 | 12/2008 | Bachand et al. |
| 2008/0311075 A1 | 12/2008 | Bachand et al. |
| 2009/0012107 A1 | 1/2009 | Aman et al. |
| 2009/0068140 A1 | 3/2009 | Bachand et al. |
| 2009/0068192 A1 | 3/2009 | Jure-Kunkel et al. |
| 2009/0074715 A1 | 3/2009 | Martin et al. |
| 2009/0130056 A1 | 5/2009 | Bender et al. |
| 2009/0130057 A1 | 5/2009 | Hewawasam et al. |
| 2009/0162318 A1 | 6/2009 | Bender et al. |
| 2009/0202478 A1 | 8/2009 | Bachand et al. |
| 2009/0202483 A1 | 8/2009 | Bachand et al. |
| 2009/0206448 A1 | 8/2009 | Cho et al. |
| 2009/0208449 A1 | 8/2009 | Labadie et al. |
| 2009/0209532 A1 | 8/2009 | Ahlmark et al. |
| 2009/0215816 A1 | 8/2009 | Thormann |
| 2009/0215818 A1 | 8/2009 | Adams et al. |
| 2009/0233925 A1 | 9/2009 | Bachand et al. |
| 2009/0253689 A1 | 10/2009 | Baeschlin et al. |
| 2009/0274648 A1 | 11/2009 | Wang et al. |
| 2009/0274652 A1 | 11/2009 | Sin et al. |
| 2009/0274656 A1 | 11/2009 | Wang et al. |
| 2009/0275561 A1 | 11/2009 | Martin et al. |
| 2009/0280083 A1 | 11/2009 | Martin et al. |
| 2009/0285773 A1 | 11/2009 | Sun et al. |
| 2009/0285774 A1 | 11/2009 | Sin et al. |
| 2009/0297472 A1 | 12/2009 | Wang et al. |
| 2009/0304626 A1 | 12/2009 | Wang et al. |
| 2009/0318437 A1 | 12/2009 | Gaeta et al. |
| 2009/0325953 A1 | 12/2009 | Sahoo et al. |
| 2010/0035920 A1 | 2/2010 | Gaeta et al. |
| 2010/0056491 A1 | 3/2010 | Schumacher et al. |
| 2010/0063068 A1 | 3/2010 | Pracitto et al. |
| 2010/0068176 A1 | 3/2010 | Belema et al. |
| 2010/0080770 A1 | 4/2010 | Hiebert et al. |
| 2010/0080771 A1 | 4/2010 | Hiebert et al. |
| 2010/0080772 A1 | 4/2010 | Belema et al. |
| 2010/0081700 A1 | 4/2010 | Wang et al. |
| 2010/0093694 A1 | 4/2010 | Yeung et al. |
| 2010/0105721 A1 | 4/2010 | Lee et al. |
| 2010/0130483 A1 | 5/2010 | Peters et al. |
| 2010/0150866 A1 | 6/2010 | Wang et al. |
| 2010/0158862 A1 | 6/2010 | Kim et al. |
| 2010/0183621 A1 | 7/2010 | Jure-Kunkel et al. |
| 2010/0184800 A1 | 7/2010 | Pracitto et al. |
| 2010/0190820 A1 | 7/2010 | Dhar et al. |
| 2010/0204265 A1 | 8/2010 | Baskaran et al. |

(56) References Cited

U.S. PATENT DOCUMENTS

| | | |
|---|---|---|
| 2010/0215616 A1 | 8/2010 | Romine et al. |
| 2010/0227880 A1 | 9/2010 | Gudmundsson et al. |
| 2010/0233120 A1 | 9/2010 | Bachand et al. |
| 2010/0249094 A1 | 9/2010 | Yeung et al. |
| 2010/0249190 A1 | 9/2010 | Lopez et al. |
| 2010/0260708 A1 | 10/2010 | Belema et al. |

FOREIGN PATENT DOCUMENTS

| | | |
|---|---|---|
| DE | 10117183 A1 | 10/2002 |
| EP | 1277754 B1 | 7/2005 |
| EP | 1972628 A1 | 9/2008 |
| EP | 2110374 A1 | 10/2009 |
| JP | 2778009 B2 | 7/1998 |
| JP | 2001057292 A | 2/2001 |
| JP | 2001139575 A | 5/2001 |
| JP | 2009203203 A | 9/2009 |
| WO | 8903833 A1 | 5/1989 |
| WO | 9119497 A1 | 12/1991 |
| WO | 9205177 A1 | 4/1992 |
| WO | 9210190 A1 | 6/1992 |
| WO | 9210498 A1 | 6/1992 |
| WO | 9210499 A1 | 6/1992 |
| WO | 9413665 A1 | 6/1994 |
| WO | 9619491 A1 | 6/1996 |
| WO | 9634866 A1 | 11/1996 |
| WO | 9748682 A1 | 12/1997 |
| WO | 9801428 A1 | 1/1998 |
| WO | 9906388 A2 | 2/1999 |
| WO | 2004041201 A2 | 5/2004 |
| WO | 2005014543 A1 | 2/2005 |
| WO | 2005112640 A2 | 12/2005 |
| WO | 2007059257 A2 | 5/2007 |
| WO | 2007081630 A2 | 7/2007 |
| WO | 2008014219 A2 | 1/2008 |
| WO | 2008057855 A2 | 5/2008 |
| WO | 2008125874 A1 | 10/2008 |
| WO | 2008134553 A1 | 11/2008 |
| WO | 2008153129 A1 | 12/2008 |
| WO | 2008154241 A1 | 12/2008 |
| WO | 2009040552 A2 | 4/2009 |
| WO | 2009101022 A1 | 8/2009 |
| WO | 2009124968 A1 | 10/2009 |
| WO | 2009126691 A1 | 10/2009 |
| WO | 2009128520 A1 | 10/2009 |
| WO | 2009137500 A1 | 11/2009 |
| WO | 2010019820 A1 | 2/2010 |
| WO | 2010030592 A1 | 3/2010 |
| WO | 2010033906 A2 | 3/2010 |
| WO | 2010047279 A1 | 4/2010 |

OTHER PUBLICATIONS

Ansel H.C., et al., Ansel's Pharmaceutical Dosage forms and Drug Delivery Systems, 8th Edition, Lippincott Williams & Wilkins, 2005, Table of Contents.

Hoover J.E., Remington's Pharmaceutical Sciences, 15th Edition, 1975, Mack Publishing Co., Table of Contents.

International Search Report and Written Opinion for Application No. PCT/US2011/065558, mailed on Mar. 21, 2012, 8 pages.

Palagiano F., et al., "Research on Heterocyclic Compounds. XXXIV. Synthesis and SAR Study of Some imidazo [2,1-b] thiazole Carboxylic and Acetic Acids with Antiinflammatory and Analgesic Activities," European Journal of Medicinal Chemistry, 1995, vol. 30 (11), pp. 901-909.

* cited by examiner

HEPATITIS C INHIBITORS AND USES THEREOF

PRIORITY CLAIM

This patent application claims priority to and the benefit of U.S. Provisional Patent Application No. 61/426,312, filed Dec. 22, 2010, which is incorporated herein in its entirety by reference.

TECHNICAL FIELD

This disclosure is directed to: (a) compounds and salts thereof that, inter alia, are useful for inhibiting hepatitis C virus (HCV); (b) intermediates useful for the preparation of such compounds and salts; (c) compositions comprising such compounds and salts; (d) methods for preparing such intermediates, compounds, salts, and compositions; (e) methods of use of such compounds, salts, and compositions; and (f) kits comprising such compounds, salts, and compositions.

BACKGROUND

Hepatitis C is a blood-borne, infectious, viral disease that is caused by a hepatotropic virus called HCV. At least six different HCV genotypes (with several subtypes within each genotype) are known to date. In North America, HCV genotype 1a predominates, followed by HCV genotypes 1b, 2a, 2b, and 3a. In the United States, HCV genotypes 1, 2, and 3 are the most common, with about 80% of the hepatitis C patients having HCV genotype 1. In Europe, HCV genotype 1b is predominant, followed by HCV genotypes 2a, 2b, 2c, and 3a. HCV genotypes 4 and 5 are found almost exclusively in Africa. As discussed below, the patient's HCV genotype is clinically important in determining the patient's potential response to therapy and the required duration of such therapy.

An HCV infection can cause liver inflammation (hepatitis) that is often asymptomatic, but ensuing chronic hepatitis can result in cirrhosis of the liver (fibrotic scarring of the liver), liver cancer, and/or liver failure. The World Health Organization estimates that about 170 million persons worldwide are chronically infected with HCV, and from about three to about four million persons are newly infected globally each year. According to the Centers for Disease Control and Prevention, about four million people in the United States are infected with HCV. Co-infection with the human immunodeficiency virus (HIV) is common, and rates of HCV infection among HIV positive populations are higher.

There is a small chance of clearing the virus spontaneously, but the majority of patients with chronic hepatitis C will not clear it without treatment. Indications for treatment typically include proven HCV infection and persistent abnormal liver function tests. There are two treatment regimens that are primarily used to treat hepatitis C: monotherapy (using an interferon agent—either a "conventional" or longer-acting pegylated interferon) and combination therapy (using an interferon agent and ribavirin). Interferon, which is injected into the bloodstream, works by bolstering the immune response to HCV; and ribavirin, which is taken orally, is believed to work by preventing HCV replication. Taken alone, ribavirin does not effectively suppress HCV levels, but an interferon/ribavirin combination is more effective than interferon alone. Typically, hepatitis C is treated with a combination of pegylated interferon alpha and ribavirin for a period of 24 or 48 weeks, depending on the HCV genotype.

The goal of treatment is sustained viral response—meaning that HCV is not measurable in the blood after therapy is completed. Current standard of care, including interferon and ribavirin, is known to require as many as 24-48 weeks of treatment to achieve any sustained viral response, and cure rates (sustained viral response) from treatment with standard of care in HCV genotypes 2 and 3 is often insufficient and even less sufficient in those with HCV genotypes 1 and 4.

Treatment may be physically demanding, particularly for those with prior history of drug or alcohol abuse, because both interferon and ribavirin have numerous side effects. Common interferon-associated side effects include flu-like symptoms, extreme fatigue, nausea, loss of appetite, thyroid problems, high blood sugar, hair loss, and skin reactions at the injection site. Possible serious interferon-associated side effects include psychoses (e.g., suicidal behavior), heart problems (e.g., heart attack, low blood pressure), other internal organ damage, blood problems (e.g., blood counts falling dangerously low), and new or worsening autoimmune disease (e.g., rheumatoid arthritis). Ribavirin-associated side effects include anemia, fatigue, irritability, skin rash, nasal stuffiness, sinusitis, and cough. Ribavirin can also cause birth defects, so pregnancy in female patients and female partners of male patients must be avoided during treatment and for six months afterward.

Some patients do not complete treatment because of the serious side effects discussed above; other patients (non-responders) continue to have measurable HCV levels despite treatment; and yet other patients (relapsers) "appear to clear" the virus during therapy, but the virus returns sometime after completion of the treatment regimen. Thus, there continues to be a need for alternative compounds, compositions, and methods of treatment (used either in combination with or in lieu of an interferon agent and/or ribavirin) to treat hepatitis C. This disclosure provides compounds (including salts thereof), compositions, and methods of treatment that address such a need.

SUMMARY

Disclosed herein are compounds of formula (I) and methods of making such compounds,

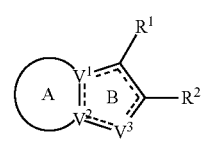

wherein:

$R^1$ is formula (i), (ii), (iii), (iv), or (v);

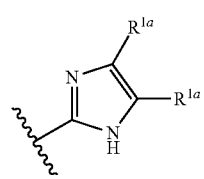

-continued

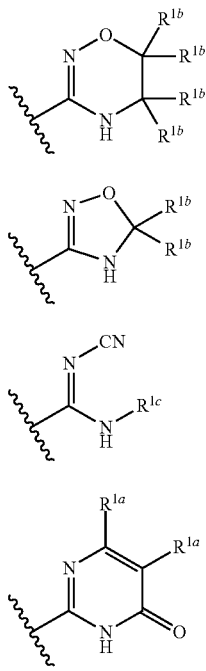

$R^{1a}$, at each occurrence, is each independently hydrogen, halogen, $C_1$-$C_3$alkyl, or $C_1$-$C_3$haloalkyl;
$R^{1b}$, at each occurrence, is each independently hydrogen, halogen, $C_1$-$C_3$alkyl, or $C_1$-$C_3$haloalkyl, wherein, optionally, two geminal $R^{1b}$ taken together are oxo;
$R^{1c}$ is $C_1$-$C_3$alkyl;
$R^2$ is $C_1$-$C_{10}$alkyl, $C_2$-$C_{10}$alkenyl, $C_2$-$C_{10}$alkynyl, $C_1$-$C_{10}$haloalkyl, $C_2$-$C_{10}$haloalkenyl, $C_2$-$C_{10}$haloalkynyl, or $L^{2A}$-$G^{2a}$;
$L^{2A}$ is a bond, $C_2$alkenylene, or $C_2$alkynylene;
$G^{2a}$ is $C_6$-$C_{10}$aryl or 5- to 10-membered heteroaryl, wherein the aryl or heteroaryl is optionally substituted with 1, 2, or 3 substituents selected from the group consisting of $R^{20}$, $L^{2B}$-$R^{21}$, $G^{2b}$ and $L^{2B}$-$G^{2b}$;
$L^{2B}$ and $L^{2C}$ are each independently $C_1$-$C_6$alkylene, $C_2$-$C_6$alkenylene, or $C_2$-$C_6$alkynylene;
$R^{20}$ is hydrogen, $C_1$-$C_{10}$alkyl, $C_2$-$C_{10}$alkenyl, $C_2$-$C_{10}$alkynyl, $C_1$-$C_{10}$haloalkyl, $C_2$-$C_{10}$haloalkenyl, $C_2$-$C_{10}$haloalkynyl, halogen, —N($R^{2a}$)C(O)$R^{2b}$, —C(O)N($R^{2a}$)($R^{2b}$), —O—$R^{2b}$, —C(O)$R^{2b}$, —OC(O)$R^{2b}$, —CO$_2$H, —CO$_2R^{2b}$, —N($R^{2a}$)C(O)N($R^{2a}$)($R^{2b}$), —S—$R^{2b}$, —S(O)$_2R^{2b}$, —S(O)$R^{2b}$, —SO$_2$N($R^{2a}$)($R^{2b}$), —N($R^{2a}$)($R^{2b}$), —N($R^{2a}$)S(O)$_2R^{2b}$, N($R^{2a}$)C(O)O($R^{2b}$), or —C(=CH$_2$)$R^{2b}$;
$R^{21}$ is —N($R^{2a}$)C(O)$R^{2b}$, —C(O)N($R^{2a}$)($R^{2b}$), —O—$R^{2b}$, —C(O)$R^{2b}$, —OC(O)$R^{2b}$, —CO$_2$H, —CO$_2R^{2b}$, —N($R^{2a}$)C(O)N($R^{2a}$)($R^{2b}$), —S—$R^{2b}$, —S(O)$_2R^{2b}$, —S(O)$R^{2b}$, —SO$_2$N($R^{2a}$)($R^{2b}$), —N($R^{2a}$)($R^{2b}$), —N($R^{2a}$)S(O)$_2R^{2b}$, N($R^{2a}$)C(O)O($R^{2b}$), or —C(=CH$_2$)$R^{2b}$;
$R^{2a}$, at each occurrence, is each independently hydrogen, $C_1$-$C_6$alkyl, $C_1$-$C_6$haloalkyl, or $C_3$-$C_8$cycloalkyl, wherein the $C_3$-$C_8$cycloalkyl is optionally substituted with 1, 2, 3, or 4 substituents selected from the group consisting of halogen, oxo, $C_1$-$C_3$alkyl, and $C_1$-$C_3$haloalkyl;
$R^{2b}$ is each independently hydrogen, $C_1$-$C_{10}$alkyl, $C_2$-$C_{10}$alkenyl, $C_2$-$C_{10}$alkynyl, $C_1$-$C_{10}$haloalkyl, $C_2$-$C_{10}$haloalkenyl, $C_2$-$C_{10}$haloalkynyl, -$L^{2C}$-$R^{2c}$, $G^{2b}$ or -$L^{2C}$-$G^{2b}$;

$R^{2c}$ is —N($R^{2d}$)C(O)$R^{2d}$, —C(O)N($R^{2d}$)($R^{2d}$), —O—$R^{2d}$, —C(O)$R^{2d}$, —OC(O)$R^{2d}$, —CO$_2$H, —CO$_2R^{2d}$, —N($R^{2d}$)C(O)N($R^{2d}$)($R^{2d}$), —S—$R^{2d}$, —S(O)$_2R^{2d}$, —S(O)$R^{2d}$, —SO$_2$N($R^2$)($R^{2d}$), —N($R^{2d}$)($R^{2d}$), —N($R^{2d}$)S(O)$_2R^{2d}$, or N($R^{2d}$)C(O)O($R^{2d}$);
$R^{2d}$, at each occurrence, is each independently hydrogen, $C_1$-$C_6$alkyl, $C_1$-$C_6$haloalkyl, $C_1$-$C_6$alkylene-OH, or $C_3$-$C_8$cycloalkyl, wherein the $C_3$-$C_8$cycloalkyl is optionally substituted with 1, 2, 3, or 4 substituents selected from the group consisting of halogen, oxo, $C_1$-$C_3$alkyl, and $C_1$-$C_3$haloalkyl;
$G^{2b}$ is $C_3$-$C_{10}$cycloalkyl, $C_5$-$C_{10}$cycloalkenyl, $C_6$-$C_{10}$aryl, 3- to 10-membered heterocyclyl, or 5- to 10-membered heteroaryl, wherein $G^{2b}$ is optionally substituted with 1, 2, 3, 4, or 5 substituents selected from the group consisting of $C_1$-$C_{10}$alkyl, $C_2$-$C_{10}$alkenyl, $C_2$-$C_{10}$alkynyl, $C_1$-$C_{10}$haloalkyl, $C_2$-$C_{10}$haloalkenyl, $C_2$-$C_{10}$haloalkynyl, halogen, oxo, cyano, hydroxy, —O—$C_1$-$C_6$alkyl, —O—$C_1$-$C_6$haloalkyl, —$C_1$-$C_3$alkylene-O—H, —$C_1$-$C_3$alkylene-O—$C_1$-$C_6$alkyl, C(O)H, —$C_1$-$C_3$alkylene-NH$_2$, —NH$_2$, —NO$_2$, —C(O)$C_1$-$C_6$alkyl, —C(O)O$C_1$-$C_6$alkyl, and $G^{2c}$;
$G^{2c}$ is $C_6$-$C_{10}$aryl or 5- to 10-membered heteroaryl, wherein $G^{2c}$ is optionally substituted with 1, 2, 3, 4, or 5 substituents selected from the group consisting of $C_1$-$C_{10}$alkyl, $C_2$-$C_{10}$alkenyl, $C_2$-$C_{10}$alkynyl, $C_1$-$C_{10}$haloalkyl, $C_2$-$C_{10}$haloalkenyl, $C_2$-$C_{10}$haloalkynyl, halogen, oxo, cyano, hydroxy, —O—$C_1$-$C_6$alkyl, —O—$C_1$-$C_6$haloalkyl, —$C_1$-$C_3$alkylene-O—H, —$C_1$-$C_3$alkylene-O—$C_1$-$C_6$alkyl, C(O)H, —$C_1$-$C_3$alkylene-NH$_2$, —NH$_2$, —NO$_2$, —C(O)$C_1$-$C_6$alkyl, and —C(O)O$C_1$-$C_6$alkyl;

A and B together are a bicyclic heteroaryl, wherein A is formula (vi) or formula (vii):

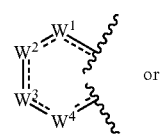

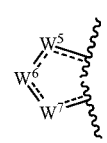

wherein,
$V^1$ and $V^2$ are each C, or one of $V^1$ and $V^2$ is N and the other is C, wherein, when $V^3$ is N, O or S or when A is (vii), $V^2$ is C; when A is (vi), $V^3$ is C$R^7$, N$R^7$, N, O, or S; or, when A is (vii), $V^3$ is N;
$R^7$ is hydrogen, $C_1$-$C_3$alkyl, $C_1$-$C_3$haloalkyl, or $C_3$-$C_6$cycloalkyl;
------ is a single or double bond;
$W^1$ is N or C$R^6$, $W^2$ is N or C$R^5$, $W^3$ is N or C$R^4$, and $W^4$ is N or C$R^3$, wherein none, one or two of $W^1$, $W^2$, $W^3$ and $W^4$ is N;
$W^5$ is N or C$R^6$, and $W^6$ is N or C$R^5$, wherein none or one of $W^5$ and $W^6$ is N;
$W^7$ is N, O, or S;
$R^3$ and $R^6$ are each independently hydrogen, $C_1$-$C_3$alkyl, $C_1$-$C_3$haloalkyl, halogen, —O$C_1$-$C_3$alkyl, or —O$C_1$-$C_3$haloalkyl;

R⁴ is hydrogen, halogen, $C_1$-$C_6$alkyl, $C_1$-$C_6$haloalkyl, —O—$C_1$-$C_6$alkyl, —O—$C_1$-$C_6$haloalkyl, cyano, —NH$_2$, $L^{4A}$-OH, 5-membered heteroaryl optionally substituted with 1 or 2 alkyl or halogen, 5-membered heterocycle or —N(R⁴⁰)(SO$_2$R⁴ᵃ);

R⁴⁰ is hydrogen, $C_1$-$C_{10}$alkyl, $C_2$-$C_{10}$alkenyl, $C_2$-$C_{10}$alkynyl, $C_1$-$C_{10}$haloalkyl, $C_2$-$C_{10}$haloalkenyl, $C_2$-$C_{10}$haloalkynyl, $C_3$-$C_8$cycloalkyl, 3- to 8-membered heterocyclyl, -$L^{4A}$-$G^{4a}$, -$L^{4A}$-C(O)-$L^{4B}$-$G^{4a}$, -$L^{4A}$-O-$L^{4B}$-$G^{4a}$, -$L^{4A}$-S(O)$_2$-$L^{4B}$-$G^{4a}$, -$L^{4A}$-N(R⁴ᵇ)($L^{4B}$-$G^{4a}$), -$L^{4A}$-N(R⁴ᵇ)C(O)-$L^{4B}$-$G^{4a}$, -$L^{4A}$-N(R⁴ᵇ)S(O)$_2$-$L^{4B}$-$G^{4a}$, -$L^{4A}$-R⁴ᶜ, wherein the $C_1$-$C_{10}$alkyl, $C_2$-$C_{10}$alkenyl, and $C_2$-$C_{10}$alkynyl are each optionally substituted with 2, 3, or 4 hydroxy substituents; and wherein the $C_3$-$C_8$cycloalkyl or 3- to 8-membered heterocyclyl is each optionally substituted with $L^{4B}$-$G^{4b}$ and optionally substituted with 1, 2, 3, or 4 substituents selected from the group consisting of halogen, oxo, $C_1$-$C_3$alkyl, $C_1$-$C_3$haloalkyl, —O—$C_1$-$C_3$alkyl, and —O—$C_1$-$C_3$haloalkyl;

$L^{4A}$ is $C_1$-$C_{10}$alkylene, $C_2$-$C_{10}$alkenylene, or $C_2$-$C_{10}$alkynylene, wherein $L^{4A}$ is optionally substituted with 1, 2, 3, 4, or 5 substituents selected from the group consisting of halogen, $C_1$-$C_6$alkyl, and $C_1$-$C_6$haloalkyl;

$G^{4a}$ is $C_3$-$C_{12}$cycloalkyl, $C_6$-$C_{12}$aryl, 3- to 12-membered heterocyclyl, or 5- to 12-membered heteroaryl, wherein $G^{4a}$ is optionally substituted with $L^{4C}$-$G^{4b}$ and optionally substituted with 1, 2, 3, 4, or 5 substituents selected from the group consisting of halogen, oxo, $C_1$-$C_3$alkyl, $C_1$-$C_3$haloalkyl, —OH, —O—$C_1$-$C_3$alkyl, —O—$C_1$-$C_3$haloalkyl, thioxo, —NH$_2$, —NH($C_1$-$C_3$alkyl), and —N($C_1$-$C_3$alkyl)$_2$;

$L^{4B}$ and $L^{4C}$, at each occurrence, are each independently a bond, $C_1$-$C_6$alkylene, $C_2$-$C_6$alkenylene, or $C_2$-$C_6$alkynylene, wherein $L^{4B}$ and $L^{4C}$ are each optionally substituted with 1, 2, 3, 4, or 5 substituents selected from the group consisting of halogen, $C_1$-$C_6$alkyl, and $C_1$-$C_6$haloalkyl;

$G^{4b}$ is $C_3$-$C_{12}$cycloalkyl, 3- to 12-membered heterocyclyl, $C_6$-$C_{12}$aryl, or 5- to 12-membered heteroaryl, wherein $G^{4b}$ is optionally substituted with 1, 2, 3, 4, or 5 substituents selected from the group consisting of halogen, oxo, $C_1$-$C_6$alkyl, $C_1$-$C_6$haloalkyl, hydroxy, —O—$C_1$-$C_6$haloalkyl, —S(O)—$C_1$-$C_6$alkyl, —S(O)$_2$-$C_1$-$C_6$alkyl, —C(O)—$C_1$-$C_6$alkyl, $C_1$-$C_3$alkylene-OH, $C_1$-$C_3$alkylene-O—$C_1$-$C_3$alkyl, $C_1$-$C_3$alkylene-N($C_1$-$C_3$alkyl)$_2$, and $C_1$-$C_3$alkylene-(N-heterocyclyl);

R⁴ᵃ and R⁴ᵇ, at each occurrence, are each independently hydrogen, $C_1$-$C_6$alkyl, $C_1$-$C_6$haloalkyl, or $C_3$-$C_8$cycloalkyl, wherein the $C_3$-$C_8$cycloalkyl is optionally substituted with 1, 2, 3, or 4 substituents selected from the group consisting of halogen, oxo, $C_1$-$C_3$alkyl, and $C_1$-$C_3$haloalkyl;

R⁴ᶜ is —O—R⁴ᵇ, —OC(O)R⁴ᵇ, —O—Si($C_1$-$C_6$alkyl)$_3$, —CN, —C(O)R⁴ᵇ, —CO$_2$R⁴ᵇ, —C(O)N(R⁴ᵇ)$_2$, —C(O)N(R⁴ᵇ)S(O)$_2$R⁴ᵇ, —S—R⁴ᵇ, —S(O)$_2$R⁴ᵇ, —S(O)R⁴ᵇ, —SO$_2$N(R⁴ᵇ)$_2$, —N(R⁴ᵇ)$_2$, —N(R⁴ᵇ)C(O)R⁴ᵇ, —N(R⁴ᵇ)S(O)$_2$R⁴ᵇ, —C(NOH)N(R⁴ᵇ)$_2$, —C(O)C(OH)(R⁴ᵇ)$_2$, or —P(O)(OR⁴ᵇ)$_2$;

R⁵ is hydrogen, $C_1$-$C_6$alkyl, $C_1$-$C_6$haloalkyl, $C_3$-$C_6$cycloalkyl, —O—$C_1$-$C_6$alkyl, —O—$C_1$-$C_6$haloalkyl, —O—$C_3$-$C_6$cycloalkyl, or $G^{5a}$, wherein the $C_3$-$C_6$cycloalkyl groups are optionally substituted with 1, 2, 3, or 4 substituents selected from the group consisting of halogen, $C_1$-$C_3$alkyl, $C_1$-$C_3$haloalkyl, and oxo;

$G^{5a}$ is phenyl, wherein $G^{5a}$ is substituted with —C(O)N(R⁵ᵃ)-$L^{5B}$-$G^{5b}$, —C(O)-$G^{5f}$, or —C(O)N(R⁵ᵃ)(R⁵ᵉ), and optionally substituted with 1, 2, or 3 substituents selected from the group consisting of $C_1$-$C_{10}$alkyl, $C_2$-$C_{10}$alkenyl, $C_2$-$C_{10}$alkynyl, $C_1$-$C_{10}$haloalkyl, halogen, —O—R⁵ᵇ, CN, —N(R⁵ᵇ)C(O)R⁵ᵇ, —C(O)N(R⁵ᵃ)(R⁵ᵇ), —C(O)R⁵ᵇ, —OC(O)R⁵ᵇ, —CO$_2$H, —CO$_2$R⁵ᵇ, —N(R⁵ᵇ)C(O)N(R⁵ᵃ)(R⁵ᵇ), —S—R⁵ᵇ, —S(O)$_2$R⁵ᵇ, —S(O)R⁵ᵇ, —SO$_2$N(R⁵ᵃ)(R⁵ᵇ), —N(R⁵ᵃ)(R⁵ᵇ), —N(R⁵ᵇ)S(O)$_2$R⁵ᵇ, N(R⁵ᵇ)C(O)O(R⁵ᵇ), $L^{5A}$-O-R⁵ᵇ, -$L^{5A}$-CN, -$L^{5A}$-N(R⁵ᵇ)C(O)R⁵ᵇ, -$L^{5A}$-C(O)N(R⁵ᵃ)(R⁵ᵇ), -$L^{5A}$-C(O)R⁵ᵇ, -$L^{5A}$-OC(O)R⁵ᵇ, -$L^{5A}$-CO$_2$H, -$L^{5A}$-CO$_2$R⁵ᵇ, -$L^{5A}$-N(R⁵ᵇ)C(O)N(R⁵ᵃ)(R⁵ᵇ), -$L^{5A}$-S—R⁵ᵇ, -$L^{5A}$-S(O)$_2$R⁵ᵇ, -$L^{5A}$-S(O)R⁵ᵇ, -$L^{5A}$-SO$_2$N(R⁵ᵃ)(R⁵ᵇ), -$L^{5A}$-N(R⁵ᵃ)(R⁵ᵇ), -$L^{5A}$-N(R⁵ᵇ)S(O)$_2$R⁵ᵇ, -$L^{5A}$-N(R⁵ᵇ)C(O)O(R⁵ᵇ), -$G^{5d}$, and -$L^{5A}$-$G^{5d}$;

$G^{5b}$ is $C_3$-$C_{12}$cycloalkyl, $C_6$-$C_{12}$aryl, 3- to 12-membered heterocyclyl, or 5- to 12-membered heteroaryl, wherein each $G^{5b}$ is optionally substituted with 1, 2, 3, 4, or 5 substituents selected from the group consisting of oxo, halogen, $C_1$-$C_6$alkyl, $C_1$-$C_6$haloalkyl, —O—R⁵ᵈ, —CN, —N(R⁵ᵈ)C(O)R⁵ᵈ, —CON(R⁵ᵃ)(R⁵ᵈ), —C(O)R⁵ᵈ, —OC(O)R⁵ᵈ, —CO$_2$H, —CO$_2$R⁵ᵈ, —N(R⁵ᵈ)C(O)N(R⁵ᵃ)$_2$, —S—R⁵ᵈ, —S(O)$_2$R⁵ᵈ, —S(O)R⁵ᵈ, —SO$_2$N(R⁵ᵃ)(R⁵ᵈ), —N(R⁵ᵃ)(R⁵ᵈ), —N(R⁵ᵈ)S(O)$_2$R⁵ᵈ, N(R⁵ᵈ)C(O)O(R⁵ᵈ), -$L^{5C}$-O—R⁵ᵈ, -$L^{5C}$-CN, -$L^{5C}$-N(R⁵ᵈ)C(O)R⁵ᵈ, -$L^{5C}$-CON(R⁵ᵃ)(R⁵ᵈ), -$L^{5C}$-C(O)R⁵ᵈ, -$L^{5C}$-OC(O)R⁵ᵈ, -$L^{5C}$-CO$_2$H, -$L^{5C}$-CO$_2$R⁵ᵈ, $L^{5C}$-N(R⁵ᵈ)C(O)N(R⁵ᵈ)$_2$, -$L^{5C}$-S—R⁵ᵈ, -$L^{5C}$-S(O)$_2$R⁵ᵈ, -$L^{5C}$-S(O)R⁵ᵈ, -$L^{5C}$-SO$_2$N(R⁵ᵃ)(R⁵ᵈ), -$L^{5C}$-N(R⁵ᵃ)(R⁵ᵈ), -$L^{5C}$-N(R⁵ᵈ)S(O)$_2$R⁵ᵈ, -$L^{5C}$-N(R⁵ᵈ)C(O)O(R⁵ᵈ), $G^{5C}$, and -$L^{5C}$-$G^{5C}$;

$G^{5c}$ is each independently $C_3$-$C_8$cycloalkyl, $C_6$-$C_{10}$aryl, 4- to 10-membered heterocyclyl, or 5- to 10-membered heteroaryl, wherein $G^{5c}$ is optionally substituted with 1, 2, 3, 4, or 5 substituents selected from the group consisting of halogen, oxo, $C_1$-$C_6$alkyl, $C_1$-$C_6$haloalkyl, —O—$C_1$-$C_6$alkyl, and —O—$C_1$-$C_6$haloalkyl;

$G^{5d}$ is each independently $C_3$-$C_8$cycloalkyl, $C_6$-$C_{10}$aryl, 4- to 10-membered heterocyclyl, or 5- to 10-membered heteroaryl, wherein $G^{5d}$ is optionally substituted with 1, 2, 3, 4, or 5 substituents selected from the group consisting of oxo, halogen, $C_1$-$C_6$alkyl, $C_1$-$C_6$haloalkyl, —O—R⁵ᵈ, —CN, —N(R⁵ᵈ)C(O)R⁵ᵈ, —CON(R⁵ᵃ)(R⁵ᵈ), —C(O)R⁵ᵈ, —OC(O)R⁵ᵈ, —CO$_2$H, —CO$_2$R⁵ᵈ, —N(R⁵ᵈ)C(O)N(R⁵ᵈ)$_2$, —S—R⁵ᵈ, —S(O)$_2$R⁵ᵈ, —S(O)R⁵ᵈ, —SO$_2$N(R⁵ᵃ)(R⁵ᵈ), —N(R⁵ᵃ)(R⁵ᵈ), —N(R⁵ᵈ)S(O)$_2$R⁵ᵈ, N(R⁵ᵈ)C(O)O(R⁵ᵈ), -$L^{5C}$-O—R⁵ᵈ, -$L^{5C}$-CN, -$L^{5C}$-N(R⁵ᵈ)C(O)R⁵ᵈ, -$L^{5C}$-CON(R⁵ᵃ)(R⁵ᵈ), -$L^{5C}$-C(O)R⁵ᵈ, -$L^{5C}$-OC(O)R⁵ᵈ, -$L^{5C}$-CO$_2$H, -$L^{5C}$-CO$_2$R⁵ᵈ, -$L^{5C}$-N(R⁵ᵈ)C(O)N(R⁵ᵈ)$_2$, -$L^{5C}$-S—R⁵ᵈ, -$L^{5C}$-S(O)$_2$R⁵ᵈ, -$L^{5C}$-S(O)R⁵ᵈ, -$L^{5C}$-SO$_2$N(R⁵ᵃ)(R⁵ᵈ), -$L^{5C}$-N(R⁵ᵃ)(R⁵ᵈ), -$L^{5C}$-N(R⁵ᵈ)S(O)$_2$R⁵ᵈ, -$L^{5C}$-N(R⁵ᵈ)C(O)O(R⁵ᵈ), $G^{5c}$, and -$L^{5C}$-$G^{5c}$;

R⁵ᵃ, at each occurrence, is each independently hydrogen, $C_1$-$C_6$alkyl, $C_1$-$C_6$haloalkyl, or $C_3$-$C_8$cycloalkyl, wherein the $C_3$-$C_8$cycloalkyl is optionally substituted with 1, 2, 3, or 4 substituents selected from the group consisting of halogen, oxo, $C_1$-$C_3$alkyl, and $C_1$-$C_3$haloalkyl;

R⁵ᵇ is each independently hydrogen, $C_1$-$C_{10}$alkyl, $C_2$-$C_{10}$alkenyl, $C_2$-$C_{10}$alkynyl, $C_1$-$C_{10}$haloalkyl, -$L^{5D}$-$G^{5e}$, or -$L^{5G}$-R⁵ᶜ;

R⁵ᶜ, at each occurrence, is each independently —CON(R⁵ᵃ)(R⁵ᵍ), —O—R⁵ᵍ, —OC(O)R⁵ᵍ, —CN, —C(O)R⁵ᵍ, —CO$_2$H, —CO$_2$R⁵ᵍ, —N(R⁵ᵍ)C(O)N(R⁵ᵍ)$_2$, —S—R⁵ᵍ, —S(O)$_2$R⁵ᵍ, —S(O)R⁵ᵍ, —SO$_2$N(R⁵ᵃ)(R⁵ᵍ), —N(R⁵ᵃ)(R⁵ᵍ), —N(R⁵ᵍ)C(O)R⁵ᵍ, or —N(R⁵ᵍ)S(O)$_2$R⁵ᵍ;

$R^{5d}$ is each independently hydrogen, $C_1$-$C_6$alkyl, $C_1$-$C_6$haloalkyl, or -$L^{5F}$-$G^{5c}$;

$R^{5e}$ is each independently hydrogen, $C_1$-$C_{10}$alkyl, $C_2$-$C_{10}$alkenyl, $C_2$-$C_{10}$alkynyl, $C_1$-$C_{10}$haloalkyl, or -$L^{5E}$-$R^{5f}$;

$R^{5f}$ is —CON($R^{5a}$)($R^{5d}$), —O—$R^{5d}$, —OC(O)$R^{5d}$, —CN, —C(O)$R^{5d}$, —CO$_2$H, —CO$_2R^{5d}$, —N($R^{5d}$)C(O)N($R^{5a}$)$_2$, —S—$R^{5d}$, —S(O)$_2R^{5d}$, —S(O)$R^{5d}$, —SO$_2$N($R^{5a}$)($R^{5d}$), —N($R^{5a}$)($R^{5d}$), —N($R^{5d}$)C(O)$R^{5d}$, or —N($R^{5d}$)S(O)$_2R^{5d}$;

$R^{5g}$ is hydrogen, $C_1$-$C_6$alkyl, $C_1$-$C_6$haloalkyl, or -$L^{5H}$-$G^{5e}$;

$G^{5e}$ is each independently $C_3$-$C_8$cycloalkyl, $C_6$-$C_{10}$aryl, 4- to 10-membered heterocyclyl, or 5- to 10-membered heteroaryl, wherein $G^{5e}$ is optionally substituted with 1, 2, 3, or 4 substituents selected from the group consisting of halogen, oxo, $C_1$-$C_6$alkyl, $C_1$-$C_6$haloalkyl, —OH, —O—$C_1$-$C_6$alkyl, and —O—$C_1$-$C_6$haloalkyl;

$G^{5f}$ is 4- to 10-membered heterocyclyl, wherein $G^{5f}$ is optionally substituted with 1, 2, 3, or 4 substituents selected from the group consisting of halogen, oxo, $C_1$-$C_6$alkyl, $C_1$-$C_6$haloalkyl, —O—$C_1$-$C_6$alkyl, and —O—$C_1$-$C_6$haloalkyl;

$L^{5A}$, at each occurrence, is each independently $C_1$-$C_6$alkylene or $C_3$-$C_8$cycloalkyl, wherein $L^{5A}$ is each optionally substituted with 1, 2, 3, or 4 halogen;

$L^{5B}$ is a bond, $C_1$-$C_6$alkylene, or $C_3$-$C_8$cycloalkyl, wherein $L^{5B}$ is optionally substituted with 1, 2, 3, or 4 halogen and 1 or 2 hydroxy;

$L^{5C}$, at each occurrence, is each independently $C_1$-$C_6$alkylene or $C_3$-$C_8$cycloalkyl, wherein $L^{5C}$ is each optionally substituted with 1, 2, 3, or 4 halogen and 1 or 2 hydroxy;

$L^{5D}$, at each occurrence, is each independently a bond, $C_1$-$C_6$alkylene, or $C_3$-$C_8$cycloalkyl, wherein $L^{5D}$ is each optionally substituted with 1, 2, 3, or 4 halogen and 1 or 2 hydroxy;

$L^{5E}$, at each occurrence, is each independently $C_1$-$C_6$alkylene, wherein $L^{5E}$ is optionally substituted with 1, 2, 3, or 4 halogen and 1 or 2 hydroxy;

$L^{5F}$, at each occurrence, is each independently bond or $C_1$-$C_6$alkylene, wherein $L^{5F}$ is optionally substituted with 1, 2, 3, or 4 halogen and 1 or 2 hydroxy; and $L^{5G}$, at each occurrence, is each independently $C_1$-$C_6$alkylene, wherein $L^{5G}$ is optionally substituted with 1, 2, 3, or 4 halogen and 1 or 2 hydroxy; and $L^{5H}$, at each occurrence, is each independently a bond, $C_1$-$C_6$alkylene, or $C_3$-$C_8$cycloalkyl, wherein $L^{5H}$ is each optionally substituted with 1, 2, 3, or 4 halogen and 1 or 2 hydroxy.

This disclosure also relates to pharmaceutical compositions comprising therapeutically effective amount of one or more compound(s) described herein or pharmaceutically acceptable salts, solvates, or salts of solvates thereof, in combination with one or more pharmaceutically acceptable carrier(s).

This disclosure also is directed to compositions (including pharmaceutical compositions) that comprise one or more of the disclosed compounds and/or salts, and, optionally, one or more additional therapeutic agents.

This disclosure also is directed to kits that comprise one or more compounds and/or salts of the disclosure, and, optionally, one or more additional therapeutic agents.

This disclosure also is directed to methods of use of the compounds, salts, compositions, and/or kits to, for example, inhibit replication of an RNA virus (including HCV), treat a disease treatable by inhibiting HCV ribonucleic acid (RNA) polymerase (including hepatitis C).

This disclosure also is directed to a use of one or more of the disclosed compounds and/or salts to prepare a medicament. The medicament optionally can comprise one or more additional therapeutic agents. In some embodiments, the medicament is useful for treating hepatitis C.

The compounds, compositions comprising the compounds, pharmaceutically acceptable salts, solvates, or salts of the solvates thereof, and methods for treating or preventing conditions and disorders by administering the compounds or compositions thereof, are further described herein. These and other objectives are described further in the following paragraphs. These objectives should not be deemed to narrow the scope of the disclosure.

This disclosure also is directed to kits that comprise one or more of the disclosed compounds and/or salts, and, optionally, one or more additional therapeutic agents.

DETAILED DESCRIPTION

This detailed description is intended only to acquaint others skilled in the art with the disclosed embodiments, their principles, and their practical application so that others skilled in the art may adapt and apply the embodiments in their numerous forms, as they may be best suited to the requirements of particular uses. This description and its specific examples are intended for purposes of illustration only. This disclosure, therefore, is not limited to the embodiments described in this patent application, and may be variously modified.

The present disclosure describes compounds of formula (I) and methods of preparing such compounds,

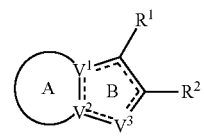

wherein A, B, $R^1$, $R^2$, $V^1$, $V^2$, and $V^3$ are as defined above in the Summary and below in the Detailed Description. Compositions comprising such compounds and methods for treating conditions and disorders using such compounds and compositions are also disclosed.

In various embodiments, compounds described herein may contain variables that occur more than one time in any substituent or in the compound described or any other formulae herein. Definition of a variable on each occurrence is independent of its definition at another occurrence. Further, combinations of variables are permissible only if such combinations result in stable compounds. Stable compounds are compounds that can be isolated from a reaction mixture.

DEFINITIONS

As used in the specification and the appended claims, unless specified to the contrary, the following terms have the meaning indicated:

As used herein, the number of carbon atoms present in certain substituents (e.g., alkyl, alkenyl, alkynyl, haloalkyl, alkylene, alkenylene, aryl, cycloalkyl, etc.) may be designated by a subscript. For example, "$C_3$alkyl" refers to an alkyl group of three carbons; "$C_1$-$C_3$alkyl" refers to an alkyl group that may have from one to three carbon atoms; "$C_1$-$C_6$alkylene" refers to an alkylene group of from one to six carbons; and so on.

The term "alkenyl" as used herein, means a straight or branched hydrocarbon chain containing at least one carbon-carbon double bond. The term "$C_2$-$C_{10}$ alkenyl" means an alkenyl group containing 2-10 carbon atoms. Non-limiting examples of alkenyl include buta-2,3-dienyl, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" means a divalent group derived from a straight or branched chain hydrocarbon and contains at least one carbon-carbon double. "$C_2$-$C_6$ alkenylene" means an alkenylene group containing 2-6 carbon atoms. Representative examples of alkenylene include, but are not limited to, —C(=$CH_2$)—, —CH=CH— and —$CH_2$CH=CH—.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, means a straight or branched, saturated hydrocarbon chain. For example "$C_1$-$C_{10}$ alkyl" means a straight or branched chain, saturated hydrocarbon containing 1 to 10 carbon atoms. For example "$C_1$-$C_3$ alkyl" means a straight or branched chain, saturated hydrocarbon containing 1 to 3 carbon atoms. Examples of alkyl include, but are not limited to, methyl, ethyl, n-propyl, iso-propyl, n-butyl, sec-butyl, iso-butyl, tert-butyl, n-pentyl, iso-pentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" means a divalent group derived from a straight or branched, saturated hydrocarbon chain. Examples of alkylene include, but are not limited to, —$CH_2$—, —$CH_2CH_2$—, —$CH_2CH_2CH_2$—, —$CH_2CH_2CH_2CH_2$—, —CH($CH_3$)—, and —$CH_2$CH($CH_3$)$CH_2$—.

The term "alkynyl" as used herein, means a straight or branched chain hydrocarbon group containing at least one carbon-carbon triple bond. The term "$C_2$-$C_{10}$ alkynyl" means an alkynyl group containing from 2 to 10 carbon atoms. Representative examples of alkynyl include, but are not limited, to acetylenyl, 1-propynyl, 2-propynyl, 3-butynyl, 2-pentynyl, and 1-butynyl.

The term "aryl" as used herein, means phenyl or a bicyclic aryl. For example, "$C_6$-$C_{10}$aryl" refers to an aryl group that may have from six to ten carbon atoms. The bicyclic aryl is naphthyl, or a phenyl fused to a monocyclic cycloalkyl, or a phenyl fused to a monocyclic cycloalkenyl. Non-limiting examples of the aryl groups include dihydroindenyl, indenyl, naphthyl, dihydronaphthalenyl, and tetrahydronaphthalenyl. The aryl groups can be unsubstituted or substituted, and the bicyclic aryl is attached to the parent molecular moiety through any substitutable carbon atom contained within the bicyclic ring system.

The term "cyano" as used herein, means a —CN group.

The term "cycloalkyl" or "cycloalkane" as used herein, means a monocyclic, a bicyclic, or a tricyclic cycloalkyl. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring. Tricyclic cycloalkyls are exemplified by a bicyclic cycloalkyl fused to a monocyclic cycloalkyl. The monocyclic or bicyclic cycloalkyl ring may contain one or two alkylene bridges, each consisting of one, two, or three carbon atoms, each linking two non-adjacent carbon atoms of the ring system. Non-limiting examples of such bridged cycloalkyl ring systems include bicyclo[3.1.1]heptane, bicyclo[2.2.1]heptane, bicyclo[2.2.2]octane, bicyclo[3.2.2]nonane, bicyclo[3.3.1]nonane, bicyclo[4.2.1]nonane, tricyclo[3.3.1.0$^{3,7}$]nonane (octahydro-2,5-methanopentalene or noradamantane), and tricyclo[3.3.1.1$^{3,7}$]decane (adamantane). The monocyclic, bicyclic, and tricyclic cycloalkyls can be unsubstituted or substituted, and are attached to the parent molecular moiety through any substitutable atom contained within the ring system.

The term "cycloalkenyl" or "cycloalkene" as used herein, means a monocyclic or a bicyclic hydrocarbon ring system. The monocyclic cycloalkenyl has four-, five-, six-, seven- or eight carbon atoms and zero heteroatoms. The four-membered ring systems have one double bond, the five- or six-membered ring systems have one or two double bonds, and the seven- or eight-membered ring systems have one, two, or three double bonds. Representative examples of monocyclic cycloalkenyl groups include, but are not limited to, cyclobutenyl, cyclopentenyl, cyclohexenyl, cycloheptenyl, and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group. The monocyclic or bicyclic cycloalkenyl ring may contain one or two alkylene bridges, each consisting of one, two, or three carbon atoms, each linking two non-adjacent carbon atoms of the ring system. Representative examples of the bicyclic cycloalkenyl groups include, but are not limited to, 4,5,6,7-tetrahydro-3aH-indene, octahydronaphthalenyl, and 1,6-dihydro-pentalene. The monocyclic and bicyclic cycloalkenyl can be attached to the parent molecular moiety through any substitutable atom contained within the ring systems, and can be unsubstituted or substituted.

The term "halo" or "halogen" as used herein, means Cl, Br, I, or F.

The term "haloalkyl" as used herein, means an alkyl group, as defined herein, in which one, two, three, four, five or six hydrogen atoms are replaced by halogen. The term "$C_1$-$C_{10}$haloalkyl" means a $C_1$-$C_{10}$ alkyl group, as defined herein, in which one, two, three, four, five or six hydrogen atoms are replaced by halogen. Representative examples of haloalkyl include, but are not limited to, chloromethyl, 2-fluoroethyl, 2,2,2-trifluoroethyl, trifluoromethyl, difluoromethyl, pentafluoroethyl, 2-chloro-3-fluoropentyl, trifluorobutyl (such as, but not limited to, 4,4,4-trifluorobutyl), and trifluoropropyl (such as, but not limited thereto, 3,3,3-trifluoropropyl).

The term "haloalkenyl", as used herein, refers to an alkenyl group, as defined herein, substituted by one, two, three, or four halogen atoms.

The term "haloalkynyl", as used herein, refers to an alkynyl group, as defined herein, substituted by one, two, three, or four halogen atoms.

The term "heterocycle", "heterocyclyl", or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond and one heteroatom selected from the group consisting of O, N, and S. The five-membered ring contains zero or one double bond and one, two, or three heteroatoms selected from the group consisting of O, N, and S. The six-membered ring contains zero, one, or two double bonds and one, two, or three heteroatoms selected from the group consisting of O, N, and S. The seven- and eight-membered rings contain zero, one, two, or three double bonds and one, two, or three heteroatoms selected from the group consisting of O, N, and S. Non-limiting examples of monocyclic heterocycles include azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl (including, but not limited thereto, pyrrolidin-1-yl, pyrrolidin-2-yl, pyrrolidin-3-yl), tetrahydrofuranyl (including, but not limited thereto, tetrahydrofuran-3-yl), tetrahydropyranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle. Non-limiting examples of bicyclic heterocycles include benzopyranyl, benzothiopyranyl, 2,3-dihydrobenzofuranyl, 2,3-dihydrobenzothienyl, benzo[d][1,3]dioxolyl and 2,3-dihydro-1H-indolyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle. The monocyclic and the bicyclic heterocycles may contain an alkenylene bridge of two, three, or four carbon atoms, or one or two alkylene bridges of 1, 2, 3, or 4 carbon atoms, or combinations thereof, wherein each bridge links two non-adjacent atoms of the ring system. Non-limiting examples of such bridged heterocycles include octahydro-2,5-epoxypentalene, azabicyclo[2.2.1]heptyl (including 2-azabicyclo[2.2.1]hept-2-yl), hexahydro-2H-2,5-methanocyclopenta[b]furan, hexahydro-1H-1,4-methanocyclopenta[c]furan, aza-admantane (1-azatricyclo[3.3.1.1$^{3,7}$]decane), and oxa-adamantane (2-oxatricyclo[3.3.1.1$^{3,7}$]decane). The monocyclic, bicyclic, and tricyclic heterocycles can be unsubstituted or substituted, and are connected to the parent molecular moiety through any substitutable carbon atom or any substitutable nitrogen atom contained within the rings. The nitrogen and sulfur heteroatoms in the heterocycle rings may optionally be oxidized and the nitrogen atoms may optionally be quaternized. The term "N-heterocyclyl" refers to a nitrogen-containing heterocyclic group attached to the parent molecular moiety through a nitrogen atom.

The term "heteroaryl" as used herein, means a monocyclic heteroaryl or a bicyclic heteroaryl. The monocyclic heteroaryl is a five- or six-membered ring. The five-membered ring contains two double bonds. The five membered ring may contain one heteroatom selected from O or S; or one, two, three, or four nitrogen atoms and optionally one oxygen or one sulfur atom. The six-membered ring contains three double bonds and one, two, three or four nitrogen atoms. Representative examples of monocyclic heteroaryl include, but are not limited to, furanyl (including, but not limited thereto, furan-2-yl), imidazolyl (including, but not limited thereto, 1H-imidazol-1-yl), isoxazolyl, isothiazolyl, oxadiazolyl, 1,3-oxazolyl, pyridinyl (e.g. pyridin-4-yl, pyridin-2-yl, pyridin-3-yl), pyridazinyl, pyrimidinyl, pyrazinyl, pyrazolyl, pyrrolyl, tetrazolyl, thiadiazolyl, 1,3-thiazolyl, thienyl (including, but not limited thereto, thien-2-yl, thien-3-yl), triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Non-limiting examples of bicyclic heteroaryl groups include benzofuranyl, benzothienyl, benzoxazolyl, benzimidazolyl, benzoxadiazolyl, 6,7-dihydro-1,3-benzothiazolyl, furo[3,2-c]pyridazinyl, furo[3,2-d]pyrimidinyl, furo[2,3-b]pyrazinyl, furo[2,3-c]pyridazinyl, furo[2,3-d]pyrimidinyl, furo[3,2-b]pyridinyl, furo[3,2-c]pyridinyl, furo[2,3-c]pyridinyl, furo[2,3-b]pyridine, imidazo[2,1-b]oxazolyl, imidazo[1,2-c]pyridinyl, imidazo[2,1-b][1,3,4]thiadiazolyl, imidazo[2,1-b][1,3,4]thiadiazolyl, imidazo[1,2-d][1,2,4]thiadiazolyl, imidazo[2,1-b]thiazolyl, indazolyl, indolizinyl, indolyl, isoindolyl, isoquinolinyl, naphthyridinyl, pyrazolo[1,5-a]pyridinyl, pyrazolo[1,5-c]pyrimidinyl, pyrazolo[1,5-a]pyrimidinyl, pyrazolo[5,1-c][1,2,4]triazinyl, pyridoimidazolyl, quinolinyl, thiazolo[5,4-b]pyridin-2-yl, thiazolo[5,4-d]pyrimidin-2-yl, and 5,6,7,8-tetrahydroquinolin-5-yl. The monocyclic and bicyclic heteroaryl groups can be substituted or unsubstituted and are connected to the parent molecular moiety through any substitutable carbon atom or any substitutable nitrogen atom contained within the ring systems.

The term "heteroatom" as used herein, means a nitrogen, oxygen, or sulfur atom.

The term "hydroxyl" or "hydroxy" means a —OH group.

The term "oxo" as used herein, means a =O group.

The term "thioxo" as used herein, means a =S group.

A substituent is "substitutable" if it comprises at least one carbon or nitrogen atom that is bonded to one or more hydrogen atoms. Thus, for example, hydrogen, halogen, and cyano do not fall within this definition. In addition, a sulfur atom in a heterocyclyl containing such atom is substitutable with one or two oxo substituents.

If a substituent is described as being "substituted", a non-hydrogen radical is in the place of hydrogen radical on a carbon or nitrogen of the substituent. Thus, for example, a substituted alkyl substituent is an alkyl substituent in which at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there is more than one substitution on a substituent, each non-hydrogen radical may be identical or different (unless otherwise stated).

If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

This patent application uses the terms "substituent" and "radical" interchangeably.

The prefix "halo" indicates that the substituent to which the prefix is attached is substituted with one or more independently selected halogen radicals. For example, haloalkyl means an alkyl substituent in which at least one hydrogen radical is replaced with a halogen radical. Examples of haloalkyls include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals may be identical or different (unless otherwise stated).

The prefix "perhalo" indicates that every hydrogen radical on the substituent to which the prefix is attached is replaced with independently selected halogen radicals, i.e., each hydrogen radical on the substituent is replaced with a halogen radical. If all the halogen radicals are identical, the prefix typically will identify the halogen radical. Thus, for example, the term "perfluoro" means that every hydrogen radical on the substituent to which the prefix is attached is substituted with a fluorine radical. To illustrate, the term "perfluoroalkyl" means an alkyl substituent wherein a fluorine radical is in the place of each hydrogen radical.

A prefix attached to a multi-component substituent only applies to the first component. To illustrate, the term "alkylcycloalkyl" contains two components: alkyl and cycloalkyl. Thus, the $C_1$-$C_6$-prefix on $C_1$-$C_6$-alkylcycloalkyl means that the alkyl component of the alkylcycloalkyl contains from 1 to 6 carbon atoms; the $C_1$-$C_6$-prefix does not describe the cycloalkyl component. To illustrate further, the prefix "halo" on haloalkoxyalkyl indicates that only the alkoxy component of the alkoxyalkyl substituent is substituted with one or more halogen radicals. If halogen substitution may alternatively or additionally occur on the alkyl component, the substituent would instead be described as "halogen-substituted alkoxyalkyl" rather than "haloalkoxyalkyl." And finally, if the halogen substitution may only occur on the alkyl component, the substituent would instead be described as "alkoxyhaloalkyl."

If substituents are described as being "independently selected" from a group, each substituent is selected independent of the other. Each substituent, therefore, may be identical to or different from the other substituent(s).

When words are used to describe a substituent, the rightmost-described component of the substituent is the component that has the free valence.

When a chemical formula is used to describe a substituent, the dash on the left side of the formula indicates the portion of the substituent that has the free valence.

When a chemical formula is used to describe a linking element between two other elements of a depicted chemical structure, the leftmost dash of the substituent indicates the portion of the substituent that is bound to the left element in the depicted structure. The rightmost dash, on the other hand, indicates the portion of the substituent that is bound to the right element in the depicted structure. To illustrate, if the depicted chemical structure is X-L-Y and L is described as —C(O)—N(H)—, then the chemical would be X—C(O)—N(H)—Y.

Compounds

Compounds of formula (I) are as described herein.

Particular values of variable groups in compounds of formula (I) are as follows. Such values may be used where appropriate with any of the other values, definitions, claims or embodiments defined herein.

$R^1$ may be formula (i), (ii), (iii), (iv) or (v). In certain embodiments $R^1$ is (i), wherein $R^{1a}$ is as defined herein. For example, when $R^1$ is (i), $R^{1a}$ is hydrogen, $C_1$-$C_3$alkyl (e.g., methyl), $C_1$-$C_3$haloalkyl (e.g., trifluoromethyl), or halogen (e.g., fluoro, chloro, bromo). In certain embodiments, one $R^{1a}$ is methyl; for example, where one $R^{1a}$ is methyl and the other $R^{1a}$ is hydrogen. In other embodiments, both $R^{1a}$ are methyl. In certain embodiments, both $R^{1a}$ are hydrogen.

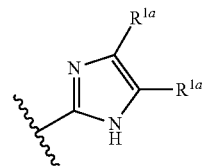

(i)

In certain embodiments, $R^1$ is (ii), wherein $R^{1b}$ is as defined herein. For example, when $R^1$ is (ii), $R^{1b}$ is hydrogen, $C_1$-$C_3$alkyl (e.g., methyl), $C_1$-$C_3$haloalkyl (e.g., trifluoromethyl), or halogen (e.g., fluoro), where two geminal $R^{1b}$ taken together optionally are oxo, as in formula (ii-1). In certain embodiments, $R^{1b}$ are each hydrogen.

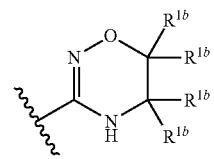

(ii)

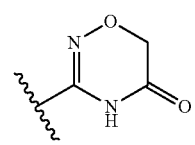

(ii-1)

In certain embodiments, $R^1$ is (iii), wherein $R^{1b}$ is as defined herein. For example, when $R^1$ is (iii), $R^{1b}$ is hydrogen, $C_1$-$C_3$alkyl (e.g., methyl, ethyl, propyl), $C_1$-$C_3$haloalkyl (e.g., trifluoromethyl), or halogen (e.g., fluoro), or two geminal $R^{1b}$ taken together are oxo, as in formula (iii-1). In certain embodiments, one $R^{1b}$ is methyl, ethyl, or propyl and the other $R^{1b}$ is hydrogen. In other embodiments, both $R^{1b}$ are methyl. In certain embodiments, both $R^{1b}$ are hydrogen.

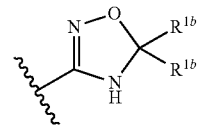

(iii)

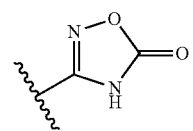

(iii-1)

In certain embodiments, $R^1$ is (iv), wherein $R^{1c}$ is as defined herein. For example, where $R^1$ is (iv), $R^{1c}$ is methyl.

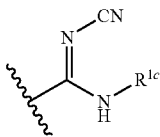

(iv)

In certain embodiments, $R^1$ is (v), wherein $R^{1a}$ is as defined herein. For example, when $R^1$ is (v), $R^{1a}$ is hydrogen.

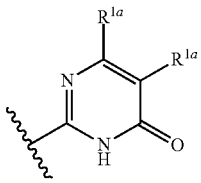

(v)

$R^2$ may be $C_1$-$C_{10}$alkyl, $C_2$-$C_{10}$alkenyl, $C_2$-$C_{10}$alkynyl, $C_1$-$C_{10}$haloalkyl, $C_2$-$C_{10}$haloalkenyl, $C_2$-$C_{10}$haloalkynyl, or $L^{2A}$-$G^{2a}$, wherein $L^{2A}$ and $G^{2a}$ are as described herein. In certain embodiments, $R^2$ is $L^{2A}$-$G^{2a}$ where $L^{2A}$ is a bond and $G^{2a}$ is optionally substituted $C_6$-$C_{10}$aryl or 5- to 10-membered heteroaryl. For example, in certain embodiments where $L^{2A}$ is a bond, $G^{2a}$ is phenyl substituted with $R^{20}$ where $R^{20}$ is halogen (e.g., fluoro, chloro); $C_1$-$C_{10}$alkyl; $C_2$-$C_{10}$alkenyl (e.g., hex-1-enyl); $C_2$-$C_{10}$alkynyl; $C_1$-$C_{10}$haloalkyl; $C_2$-$C_{10}$haloalkenyl; or $C_2$-$C_{10}$haloalkynyl. Particular embodiments include compounds where $G^{2a}$ is phenyl substituted in the 4-position with halogen (e.g., fluoro, chloro); $C_1$-$C_{10}$alkyl; $C_2$-$C_{10}$alkenyl (e.g., hex-1-enyl); $C_2$-$C_{10}$alkynyl; $C_1$-$C_{10}$haloalkyl; $C_2$-$C_{10}$haloalkenyl; or $C_2$-$C_{10}$haloalkynyl.

In certain embodiments where $L^{2A}$ is a bond, $G^{2a}$ is phenyl substituted with $G^{2b}$ (i.e., $R^2$ is

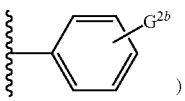

R²-I

)

and $G^{2b}$ is as defined herein. In certain embodiments, for example, $R^2$ is $R^2$-II,

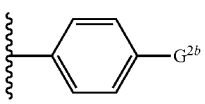

R²-II where $G^{2b}$ is phenyl, pyridyl, or thiophenyl where $G^{2b}$ is optionally substituted as described herein. For example, $G^{2b}$ can be substituted with halogen, hydroxy, cyano, nitro, $C_1$-$C_{10}$alkyl, —$C_1$-$C_3$alkylene-O—H, —O—$C_1$-$C_6$alkyl, $C_1$-$C_{10}$haloalkyl, —$C_1$-$C_3$alkylene-O—$C_1$-$C_6$alkyl, C(O)H, —$C_1$-$C_3$alkylene-NH$_2$, —NH$_2$, —NO$_2$, —C(O)$C_1$-$C_6$alkyl or —C(O)O$C_1$-$C_6$alkyl. In certain embodiments, $R^2$ is $R^2$-II, where $G^{2b}$ is phenyl optionally substituted with halogen (e.g., fluoro, chloro), hydroxy, cyano, nitro, $C_1$-$C_6$alkyl (e.g., methyl, ethyl, isopropyl), —$C_1$-$C_3$alkylene-O—H (e.g., CH$_2$OH), —O—$C_1$-$C_3$alkyl (e.g., methoxy), $C_1$-$C_6$haloalkyl (e.g., trifluoromethyl, trifluoroethyl, trifluorobutyl), —$C_1$-$C_3$alkylene-O—$C_1$-$C_3$alkyl (e.g., CH$_2$OCH$_3$), C(O)H, —$C_1$-$C_3$alkylene-NH$_2$ (e.g., CH$_2$NH$_2$), —NH$_2$, or —C(O)O$C_1$-$C_3$alkyl (e.g., C(O)OEt).

In embodiments, $R^2$ is $R^2$-II and $G^{2b}$ is pyridin-3-yl, optionally substituted with halogen (e.g., fluoro) or —O—$C_1$-$C_3$alkyl (e.g., methoxy). $G^{2b}$ includes, but is not limited to, 6-pyridin-3-yl, fluoropyridin-3-yl and 6-methoxy-pyridin-3-yl.

In embodiments, $R^2$ is $R^2$-II and $G^{2b}$ is pyridin-4-yl optionally substituted with halogen (e.g., fluoro). $G^{2b}$ includes, but is not limited to, pyridin-4-yl and 2-fluoropyridin-4-yl.

In embodiments, $R^2$ is $R^2$-II and $G^{2b}$ is thiophen-2-yl.

In embodiments, $R^2$ is $R^2$-II and $G^{2b}$ is thiophen-3-yl, optionally substituted with C(O)H. $G^{2b}$ includes, but is not limited to, thiophen-3-yl and 2-formylthiophen-3-yl.

In embodiments, $R^2$ is $R^2$-II and $G^{2b}$ is indol-5-yl,

In embodiments, $R^2$ is $R^2$-II and $G^{2b}$ is benzo[d][1,3]dioxol-5-yl).

In embodiments, $R^2$ is $R^2$-II and $G^{2b}$ is furan-2-yl.

In certain embodiments where $L^{2A}$ is a bond, $G^{2a}$ is phenyl substituted with $G^{2b}$ (i.e., $R^2$ is

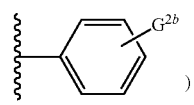

R²-I

)

and $G^{2b}$ is as defined herein. In certain embodiments, for example, $R^2$ is $R^2$-II,

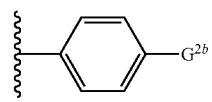

R²-II where $G^{2b}$ is $C_3$-$C_{10}$cycloalkyl and 3- to 10-membered heterocyclyl, where $G^{2b}$ is optionally substituted as described herein. For example, $G^{2b}$ can be substituted with halogen, hydroxy, cyano, nitro, $C_1$-$C_{10}$alkyl, —$C_1$-$C_3$alkylene-O—H, —O—$C_1$-$C_6$alkyl, $C_1$-$C_{10}$haloalkyl, —$C_1$-$C_3$alkylene-O—$C_1$-$C_6$alkyl, C(O)H, —$C_1$-$C_3$alkylene-NH$_2$, —NH$_2$, —C(O)$C_1$-$C_6$alkyl —C(O)O$C_1$-$C_6$alkyl, phenyl or pyridyl. In certain embodiments, $R^2$ is $R^2$-II, where $G^{2b}$ is cyclopropyl, pyrrolidinyl or morpholinyl optionally substituted with $C_1$-$C_6$alkyl (e.g., methyl, ethyl, isopropyl), phenyl or pyridyl.

In certain embodiments where $L^{2A}$ is a bond, $G^{2a}$ substituted with $R^{20}$ (i.e., $R^2$ is

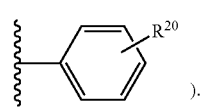

R²-III

).

In embodiments, $R^2$ is $R^2$-IV.

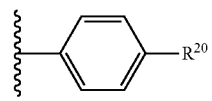

R²-IV

Embodiments according to $R^2$-IV include compounds where $R^{20}$ is hydrogen, halogen (e.g., fluoro, chloro); $C_1$-$C_{10}$alkyl (e.g., ethyl, butyl, n-hexyl, n-octyl); $C_2$-$C_{10}$alkenyl (e.g., but-1-enyl, hex-1-enyl, oct-1-enyl); $C_2$-$C_{10}$alkynyl (e.g., but-1-ynyl, hex-1-ynyl, oct-1-ynyl); $C_1$-$C_{10}$haloalkyl (e.g., trifluorobutyl, trifluorohexyl); $C_2$-$C_{10}$haloalkenyl; or $C_2$-$C_{10}$haloalkynyl.

Embodiments according to $R^2$-III and $R^2$-IV include compounds where $R^{20}$ is —N($R^{2a}$)($R^{2b}$); $R^{2a}$ is hydrogen or $C_1$-$C_3$alkyl (e.g., methyl); and $R^{2b}$ is $G^{2b}$; and $G^{2b}$ is as defined herein. Particular embodiments according to $R^2$-IV include compounds where $R^{20}$ is —N(H)($G^{2b}$), where $G^{2b}$ is phenyl optionally substituted with halogen (e.g., fluoro, chloro), —O—$C_1$-$C_3$haloalkyl (e.g., difluoromethoxy, trifluoromethoxy, trifluoroethoxy), cyano, or hydroxyl. For example $G^{2b}$ includes, but is not limited to, 3,4-difluorophenyl, 3-chlorophenyl, pentafluorophenyl, 3-difluoromethoxyphenyl, 3-cyanophenyl, and 2,4-dichlorophenyl.

Embodiments according to $R^2$-III and $R^2$-IV include compounds where $R^{20}$ is —N($R^{2a}$)($R^{2b}$); $R^{2a}$ is hydrogen or $C_1$-$C_3$alkyl (e.g., methyl); and $R^{2b}$ is $G^{2b}$; and $G^{2b}$ is as defined herein. Particular embodiments according to $R^2$-IV include compounds where $R^{20}$ is —N(H)($G^{2b}$), where $G^{2b}$ is $C_3$-$C_{10}$cycloalkyl optionally substituted with halogen (e.g., fluoro, chloro), —O—$C_1$-$C_3$haloalkyl (e.g., difluoromethoxy, trifluoromethoxy, trifluoroethoxy), cyano, or hydroxyl. For example $G^{2b}$ includes, but is not limited to, cyclopentyl and cyclohexyl.

Embodiments according to $R^2$-III and $R^2$-IV include compounds where $R^{20}$ is —N($R^{2a}$)($R^{2b}$); $R^{2a}$ is hydrogen or $C_1$-$C_3$alkyl (e.g., methyl); and $R^{2b}$ is alkyl, $C_1$-$C_{10}$haloalkyl or -$L^{2C}$-$R^{2c}$; and $L^{2C}$ and $R^{2c}$ are as defined herein. $L^{2C}$ is $C_1$-$C_3$alkylene (e.g., $CH_2$, —C($CH_3$)(H)—, $CH_2CH_2$) and $R^{2c}$ is —O—$R^{2d}$, wherein $R^{2d}$ is hydrogen, $C_1$-$C_6$alkyl, or $C_1$-$C_6$alkylene-OH.

Embodiments according to $R^2$-III and $R^2$-IV include compounds where $R^{20}$ is —N($R^{2a}$)($R^{2b}$); $R^{2a}$ is hydrogen or $C_1$-$C_3$alkyl (e.g., methyl); and $R^{2b}$ is -$L^{2C}$-$G^{2b}$; and $L^{2C}$ and $R^{2c}$ are as defined herein. $L^{2C}$ is $C_1$-$C_3$alkylene (e.g., $CH_2$, —C($CH_3$)(H)—, $CH_2CH_2$) and $G^{2b}$ is $C_3$-$C_{10}$cycloalkyl, $C_6$-$C_{10}$aryl, or 5- to 10-membered heteroaryl, wherein $G^{2b}$ is optionally substituted with $C_1$-$C_{10}$alkyl, halogen, cyano, hydroxy, —O—$C_1$-$C_6$alkyl, or —O—$C_1$-$C_6$haloalkyl.

Embodiments according to $R^2$-IV include compounds where $R^{20}$ is —N(H)($G^{2b}$), where $G^{2b}$ is $C_3$-$C_{10}$cycloalkyl optionally substituted with halogen (e.g., fluoro, chloro), —O—$C_1$-$C_3$haloalkyl (e.g., difluoromethoxy, trifluoromethoxy, trifluoroethoxy), cyano, or hydroxyl. For example $G^{2b}$ includes, but is not limited to, cyclopentyl and cyclohexyl.

Embodiments according to $R^2$-IV include compounds where $R^{20}$ is —N($CH_3$)($G^{2b}$), where $G^{2b}$ is phenyl optionally substituted.

Embodiments according to $R^2$-IV include compounds where $R^{20}$ is —N(H)($G^{2b}$), where $G^{2b}$ is a 5- to 10-membered heteroaryl (e.g., indolyl).

Embodiments according to $R^2$-IV include compounds where $R^{20}$ is —O—$R^{2b}$, where $R^{2b}$ is $G^{2b}$ or -$L^{2C}$-$G^{2b}$, where $L^{2C}$ is $C_1$-$C_3$alkylene (e.g., $CH_2$) and $G^{2b}$ is as defined herein. Particular embodiments according to $R^2$-IV include compounds where $R^{20}$ is —O-$L^{2C}$-$G^{2b}$ where $L^{2C}$ is $C_1$-$C_3$alkylene (e.g., $CH_2$, —C($CH_3$)(H)—, $CH_2CH_2$) and $G^{2b}$ is phenyl optionally substituted with halogen (e.g., fluoro, chloro), $C_1$-$C_{10}$alkyl (e.g., methyl, ethyl, t-butyl, hexyl), cyano, or —O—$C_1$-$C_3$haloalkyl (e.g., difluoromethoxy, trifluoromethoxy, trifluoroethoxy).

Embodiments according to $R^2$-IV include compounds where $R^{20}$ is —O-$G^{2b}$ or —O-$L^{2C}$-$G^{2b}$ where $L^{2C}$ is $C_1$-$C_3$alkylene (e.g., —$CH_2$—) and $G^{2b}$ is cycloalkyl (e.g., cyclopropyl, cyclobutyl) or cycloalkenyl (e.g., cyclohexenyl), wherein $G^{2b}$ may be optionally substituted as defined herein.

Embodiments according to $R^2$-IV include compounds where $R^{20}$ is —O—$R^{2b}$ where $R^{2b}$ is hydrogen or $C_1$-$C_{10}$alkyl (e.g., methyl, n-pentyl, isopentyl, isopropyl, n-hexyl) or $L^{2C}$-$R^{2c}$, where $L^{2C}$ is $C_1$-$C_6$alkylene (e.g., —C($CH_3$)(H)—, —($CH_2$)$_3$—) and $R^{2c}$ is $CO_2$($C_1$-$C_3$alkyl) or —OC(O)$C_1$-$C_3$alkyl.

Embodiments according to $R^2$-III and $R^2$-IV, include compounds where $R^{20}$ is —C(=$CH_2$)$R^{2b}$, where $R^{2b}$ is $G^{2b}$, and $G^{2b}$ is as defined herein. Particular embodiments according to $R^2$-IV include compounds where $R^{20}$ is —C(=$CH_2$)$G^{2b}$ where $G^{2b}$ is phenyl or indolyl optionally substituted with $C_1$-$C_{10}$alkyl (e.g., methyl, ethyl, t-butyl, hexyl) or —O—$C_1$-$C_3$haloalkyl (e.g., difluoromethoxy, trifluoromethoxy, trifluoroethoxy).

In certain embodiments where $L^{2A}$ is a bond, $G^{2a}$ is phenyl substituted with $L^{2B}$-$G^{2b}$ (i.e., $R^2$ is

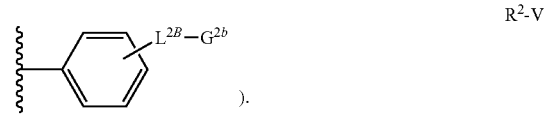

$R^2$-V

).

In embodiments, $R^2$ is $R^2$-VI.

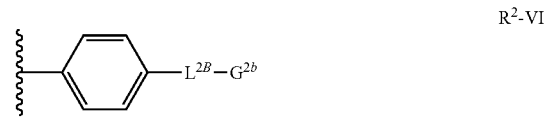

$R^2$-VI

Embodiments according to $R^2$-V and $R^2$-VI include compounds where $L^{2B}$ is $C_1$-$C_6$alkylene (e.g., —$CH_2$—, —CH($CH_3$)$_2$—, —$CH_2CH_2$—, —$CH_2CH_2CH_2$—) or $C_2$-$C_6$alkenylene (e.g., —CH=CH—, —CH=CH—CH2-) and $G^{2b}$ is $C_3$-$C_{10}$cycloalkyl, $C_5$-$C_{10}$cycloalkenyl, $C_6$-$C_{10}$aryl, 3- to 10-membered heterocyclyl, or 5- to 10-membered heteroaryl, wherein $G^{2b}$ is optionally substituted with 1, 2, 3, 4, or 5 substituents selected from the group consisting of $C_1$-$C_{10}$alkyl, $C_2$-$C_{10}$alkenyl, $C_2$-$C_{10}$alkynyl, $C_1$-$C_{10}$haloalkyl, $C_2$-$C_{10}$haloalkenyl, $C_2$-$C_{10}$haloalkynyl, halogen, oxo, cyano, hydroxy, —O—$C_1$-$C_6$alkyl, —O—$C_1$-$C_6$haloalkyl, —$C_1$-$C_3$alkylene-O—H, —$C_1$-$C_3$alkylene-O—$C_1$-$C_6$alkyl, C(O)H, —$C_1$-$C_3$alkylene-NH$_2$, —NH$_2$, —NO$_2$, —C(O)$C_1$-$C_6$alkyl, —C(O)O$C_1$-$C_6$alkyl, and $G^{2c}$.

In certain embodiments where $L^{2A}$ is a bond, $G^{2a}$ is phenyl substituted with $L^{2B}$-$R^{21}$ (i.e., $R^2$ is

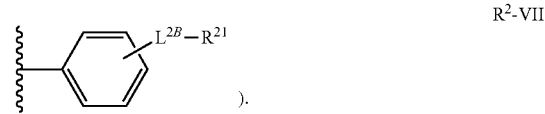

$R^2$-VII

).

In embodiments, $R^2$ is $R^2$-VII.

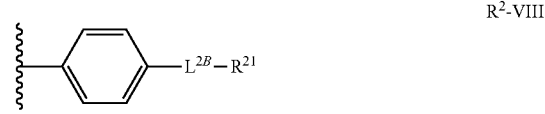

$R^2$-VIII

Embodiments according to R²-VII and R²-VIII include compounds where L²ᴮ is $C_1$-$C_6$alkylene (e.g., —$CH_2$—, —$CH(CH_3)_2$—, —$CH_2CH_2$—, —$CH_2CH_2CH_2$—) and R²¹ is —N(R²ᵃ)C(O)R²ᵇ, —C(O)N(R²ᵃ)(R²ᵇ), —O—R²ᵇ, —C(O)R²ᵇ, —OC(O)R²ᵇ, —$CO_2$H, —$CO_2$R²ᵇ, —N(R²ᵃ)C(O)N(R²ᵃ)(R²ᵇ), —S—R²ᵇ, —S(O)$_2$R²ᵇ, —S(O)R²ᵇ, —$SO_2$N(R²ᵃ)(R²ᵇ), —N(R²ᵃ)(R²ᵇ), —N(R²ᵃ)S(O)$_2$R²ᵇ, N(R²ᵃ)C(O)O(R²ᵇ), or —C(=$CH_2$)R²ᵇ; wherein R²ᵃ is hydrogen, $C_1$-$C_6$alkyl, $C_1$-$C_6$haloalkyl; and R²ᵇ is hydrogen, $C_1$-$C_{10}$alkyl, $C_2$-$C_{10}$alkenyl, $C_2$-$C_{10}$alkynyl, $C_1$-$C_{10}$haloalkyl, or -L²ᶜ-G²ᵇ; wherein -L²ᶜ-G²ᵇ is benzyl.

In certain embodiments, R² is L²ᴬ-G²ᵃ where L²ᴬ is $C_2$alkynyl and G²ᵃ is optionally substituted $C_6$-$C_{10}$aryl or 5- to 10-membered heteroaryl.

Exemplary R² moieties are shown in Table 1 below.

TABLE 1

| R2 | R2 |
|---|---|
| phenyl | 4-[(4-hydroxyphenyl)amino]phenyl |
| 4-fluorophenyl | 4-(1H-indol-4-ylamino)phenyl |
| 4-methoxyphenyl | 4-(morpholin-4-yl)phenyl |
| 4-anilinophenyl | 4-(1-phenylvinyl)phenyl |
| 3'-ethylbiphenyl-4-yl | 4-{methyl[(6-methylpyridin-2-yl)methyl]amino}phenyl |
| 3'-(hydroxymethyl)biphenyl-4-yl | 4-[(E)-2-(4-methylphenyl)vinyl]phenyl |
| 2'-methoxybiphenyl-4-yl | 4-[(1E)-hept-1-en-1-yl]phenyl |
| 3'-methylbiphenyl-4-yl | (4-methoxyphenyl)vinyl]phenyl |
| 4-(2-fluoropyridin-4-yl)phenyl | 4-[1-(1H-indol-3-yl)vinyl]phenyl |
| 4-(2-formyl-3-thienyl)phenyl | 4-[2-(pyridin-3-yl)pyrrolidin-1-yl]phenyl |
| 2'-(trifluoromethyl)biphenyl-4-yl | (4-fluorophenyl)vinyl]phenyl |
| 2'-fluoro-5'-methylbiphenyl-4-yl | 4-[(1Z)-prop-1-en-1-yl]phenyl |
| 3'-isopropylbiphenyl-4-yl | 4-(2,6-dimethylmorpholin-4-yl)phenyl |
| 2'-chlorobiphenyl-4-yl | 4-[1-(3,5-dimethylphenyl)vinyl]phenyl |
| 4'-methylbiphenyl-4-yl | 4-[(1E)-oct-1-en-1-yl]phenyl |
| 2'-(methoxymethyl)biphenyl-4-yl | 4-[(E)-2-(3-fluorophenyl)vinyl]phenyl |
| 3',5'-difluorobiphenyl-4-yl | 4-{1-[3,5-bis(trifluoromethyl)phenyl]vinyl}phenyl |
| 2'-fluorobiphenyl-4-yl | 4-[(E)-2-phenylvinyl]phenyl |
| 4'-chlorobiphenyl-4-yl | 4-[(1E)-3-phenylprop-1-en-1-yl]phenyl |
| 2'-isopropylbiphenyl-4-yl | 4-(2,5-dimethylpyrrolidin-1-yl)phenyl |
| 5'-chloro-2'-methoxybiphenyl-4-yl | 4-[(1E)-prop-1-en-1-yl]phenyl |
| 3',4'-difluorobiphenyl-4-yl | 4-(pyrrolidin-1-yl)phenyl |
| 4'-fluorobiphenyl-4-yl | 4-{(E)-2-[4-(trifluoromethyl)phenyl]vinyl}phenyl |
| 4-(6-fluoropyridin-3-yl)phenyl | 4-(isobutylamino)phenyl |
| 3'-cyanobiphenyl-4-yl | 4-[(cyclopropylmethyl)amino]phenyl |
| 4-(1,3-benzodioxol-5-yl)phenyl | 4-[(2,2,2-trifluoroethyl)amino]phenyl |
| 3'-chloro-4'-fluorobiphenyl-4-yl | 4-[(3-methylbutyl)amino]phenyl |
| 4-(2-thienyl)phenyl | 4-(cyclopentylamino)phenyl |
| 5'-fluoro-2'-methylbiphenyl-4-yl | 4-[(2-thienylmethyl)amino]phenyl |
| 4-(1H-indol-5-yl)phenyl | 4-{[2-(2-hydroxyethoxy)ethyl]amino}phenyl |
| 4-(pyridin-4-yl)phenyl | 4-(benzylamino)phenyl |
| 2'-methylbiphenyl-4-yl | 4-[(2-ethylbutyl)amino]phenyl |
| 4-(3-thienyl)phenyl | 4-[(cyclohexylmethyl)amino]phenyl |
| 2'-nitrobiphenyl-4-yl | 4-(butylamino)phenyl |
| 3'-chlorobiphenyl-4-yl | 4-[(2-methoxyethyl)amino]phenyl |
| 4'-formylbiphenyl-4-yl | 4-[(2-furylmethyl)amino]phenyl |
| 4-(1E)-hex-1-en-1-yl]phenyl | 4-[(3-fluorobenzyl)amino]phenyl |
| 4'-(aminomethyl)biphenyl-4-yl | 4-{[(1R)-1-phenylethyl]amino}phenyl |
| 4'-aminobiphenyl-4-yl | 4-(isopropylamino)phenyl |
| 3'-(trifluoromethyl)biphenyl-4-yl | 4-[(2-hydroxyethyl)amino]phenyl |
| 3',4'-dimethoxybiphenyl-4-yl | 4-(cyclohexylamino)phenyl |
| 5'-fluoro-2'-methoxybiphenyl-4-yl | 4-[2-(4-methylphenyl)ethyl]phenyl |
| ethyl 4'-biphenyl-2-carboxylate | 4-(1-phenylethyl)phenyl |
| 4-(6-methoxypyridin-3-yl)phenyl | 4-octylphenyl |
| 4'-hydroxybiphenyl-4-yl | 4-{2-[4-(trifluoromethyl)phenyl]ethyl}phenyl |
| 3'-fluorobiphenyl-4-yl | 4-[2-(4-fluorophenyl)ethyl]phenyl |
| 3'-methoxybiphenyl-4-yl | 4-[(4-methylpiperazin-1-yl)methyl]phenyl |
| 4-[(3,4-difluorophenyl)amino]phenyl | 4-[2-(3-fluorophenyl)ethyl]phenyl |
| 4-{[3-(difluoromethoxy)phenyl]amino}phenyl | 4-heptylphenyl |
| 4-[(3-cyanophenyl)amino]phenyl | 4-[3-(morpholin-4-yl)-3-oxopropyl]phenyl |
| 4-[(3-chlorophenyl)amino]phenyl | 4-(2-phenylethyl)phenyl |
| 4-[(pentafluorophenyl)amino]phenyl | 4-propylphenyl |
| 4-[(2,4-dichlorophenyl)amino]phenyl | 4-(3-phenylpropyl)phenyl |
| 4-(1-phenylethoxy)phenyl | 4-benzylphenyl |
| ethyl 2-(4-phenoxy)propanoate | 4-(3,3-dimethylbutyl)phenyl |
| 4-isopropoxyphenyl | 4-(pyrrolidin-1-ylmethyl)phenyl |
| 4-[(4-tert-butylbenzyl)oxy]phenyl | 4-cyclopropylphenyl |
| (4-phenoxy)ethyl acetate | 4-(cyclobutylmethyl)phenyl |
| 4-(2-phenylethoxy)phenyl | 4-(2,2-dimethylpropyl)phenyl |
| ethyl 4-(4-phenoxy)butanoate | 4-{[benzyl(methyl)amino]methyl}phenyl |
| ethyl 5-(4-phenoxy)pentanoate | 4-(cyclopentylmethyl)phenyl |
| 4-[(2-fluorobenzyl)oxy]phenyl | 4-(5-acetyl-2-thienyl)phenyl |
| 4-(cyclobutyloxy)phenyl | 4-butylphenyl |
| 4-[(3-cyanobenzyl)oxy]phenyl | tert-butyl [2-(4-phenyl)ethyl]carbamate |
| 4-(cyclohex-2-en-1-yloxy)phenyl | 4-(morpholin-4-ylmethyl)phenyl |
| 4-{[2-(difluoromethoxy)benzyl]oxy}phenyl | tert-butyl 3-(4-phenyl)propanoate |
| 4-[(2,4-dichlorophenyl)amino]phenyl | 4-(cyclohexylmethyl)phenyl |

TABLE 1-continued

| R2 | R2 |
|---|---|
| 4-[(3-cyanophenyl)amino]phenyl | 4-(2-furyl)phenyl |
| 4-[(3,4-difluorophenyl)amino]phenyl | 2'-aminobiphenyl-4-yl |
| 4-[(3-hydroxyphenyl)amino]phenyl | 4-(4-methyl-3-thienyl)phenyl |

In embodiments, A and B together are a bicyclic heteroaryl.
In embodiments, A is formula (vi) or formula (vii),

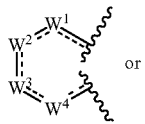

(vi)

or

(vii)

wherein $W^1$, $W^2$, $W^3$, $W^4$, $W^5$, $W^6$, and $W^7$ are as described herein, and B is

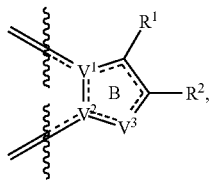

wherein, $V^1$, $V^2$, $V^3$, $R^1$, and $R^2$ are as described herein, and ----- is a single or double bond.

In embodiments, A and B together are a bicyclic heteroaryl of formula (viii) or formula (ix):

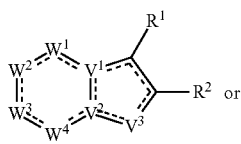

(viii) or

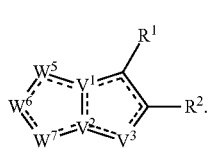

(ix)

In embodiments, A and B together are a bicyclic heteroaryl of formula (viii), wherein $W^1$, $W^2$, $W^3$, $W^4$, $V^1$, $V^2$, and $V^3$ are as described herein.

In embodiments including formula (viii), $W^1$, $W^2$, $W^3$, and $W^4$ are $CR^6$, $CR^5$, $CR^4$, $CR^3$, respectively; $V^1$ and $V^2$ are each C, and $V^3$ is $NR^7$, O, or S.

In embodiments of formula (viii), $W^1$, $W^2$, $W^3$, and $W^4$ are $CR^6$, $CR^5$, $CR^4$, $CR^3$, respectively; $V^1$ and $V^2$ are each C, and $V^3$ is $NR^7$ or O.

In embodiments including formula (viii), $W^1$, $W^2$, $W^3$, and $W^4$ are $CR^6$, $CR^5$, $CR^4$, $CR^3$, respectively; $V^1$ and $V^2$ are each C, and $V^3$ is O (i.e. benzofuranyl).

In embodiments including formula (viii), $W^1$, $W^2$, $W^3$, and $W^4$ are $CR^6$, $CR^5$, $CR^4$, $CR^3$, respectively; $V^1$ and $V^2$ are each C, and $V^3$ is $NR^7$ (i.e. indolyl).

In embodiments including formula (viii), $W^1$, $W^2$, $W^3$, and $W^4$ are $CR^6$, $CR^5$, $CR^4$, $CR^3$, respectively; $V^1$ is N, $V^2$ is C, and $V^3$ is $CR^7$, $NR^7$, N, O or S.

In embodiments including formula (viii), $W^1$, $W^2$, $W^3$, and $W^4$ are $CR^6$, $CR^5$, $CR^4$, $CR^3$, respectively; $V^1$ is N, $V^2$ is C, and $V^3$ is $CR^7$ (i.e. indolizinyl).

In embodiments including formula (viii), $W^1$, $W^2$, $W^3$, and $W^4$ are $CR^6$, $CR^5$, $CR^4$, $CR^3$, respectively; $V^1$ is C, $V^2$ is N, and $V^3$ is $CR^7$, or N.

In embodiments including formula (viii), $W^1$, $W^2$, $W^3$, and $W^4$ are $CR^6$, $CR^5$, $CR^4$, $CR^3$, respectively; $V^1$ is C, $V^2$ is N, and $V^3$ is $CR^7$ (i.e. indolizinyl).

In embodiments including formula (viii), $W^1$, $W^2$, $W^3$, and $W^4$ are $CR^6$, $CR^5$, $CR^4$, $CR^3$, respectively; $V^1$ is C, $V^2$ is N, and $V^3$ is N (i.e. pyrazolo[1,5-a]pyridinyl).

In embodiments, A and B together are bicyclic heteroaryl of formula (ix), wherein $W^5$, $W^6$, $W^7$, $V^1$, $V^2$, and $V^3$ are as described herein.

In embodiments including formula (ix), $W^5$ and $W^6$ are $CR^6$ and $CR^5$, respectively; $W^7$ is O or S; and $V^1$ is N, $V^2$ is C, and $V^3$ is N, O or S.

In embodiments including formula (ix), $W^5$ and $W^6$ are $CR^6$ and $CR^5$, respectively; $W^7$ is O; and $V^1$ is N, $V^2$ is C, and $V^3$ is N (i.e. imidazo[2,1-b]oxazolyl).

In embodiments including formula (ix), $W^5$ and $W^6$ are $CR^6$ and $CR^5$, respectively; $W^7$ is S; and $V^1$ is N, $V^2$ is C, and $V^3$ is N (i.e. imidazo[2,1-b]thiazolyl).

$R^3$ may be hydrogen, $C_1$-$C_3$alkyl, $C_1$-$C_3$haloalkyl, halogen, —$OC_1$-$C_3$alkyl, or —$OC_1$-$C_3$haloalkyl. In certain embodiments, $R^3$ is hydrogen.

$R^6$ may be hydrogen, $C_1$-$C_3$alkyl, $C_1$-$C_3$haloalkyl, halogen, —$OC_1$-$C_3$alkyl, or —$OC_1$-$C_3$haloalkyl. In certain embodiments, $R^6$ is halogen (e.g., fluoro, chloro). In embodiments, $R^6$ is hydrogen.

$R^7$ may be hydrogen, $C_1$-$C_3$alkyl, $C_1$-$C_3$haloalkyl, or $C_3$-$C_6$cycloalkyl. In certain embodiments, $R^7$ is hydrogen.

$R^4$ may be hydrogen, halogen, $C_1$-$C_6$alkyl, $C_1$-$C_6$haloalkyl, —O—$C_1$-$C_6$alkyl, —O—$C_1$-$C_6$haloalkyl, cyano, —$NH_2$, $L^{4A}$-OH, 5-membered heteroaryl optionally substituted with 1 or 2 alkyl or halogen, 5-membered heterocycle or —$N(R^{40})(SO_2R^{4a})$. In certain embodiments, $R^4$ is hydrogen. In certain embodiments, $R^4$ is —$N(R^{40})(SO_2R^{4a})$, where $R^{4a}$ is $C_1$-$C_3$alkyl (e.g., methyl, isopropyl). In certain embodiments, $R^4$ is $CH_3$. For example, in certain embodiments where $R^{4a}$ is $CH_3$, $R^{40}$ is hydrogen; $C_1$-$C_{10}$alkyl (e.g., ethyl, propyl, isobutyl, isopentyl, n-pentyl, n-hexyl, 4-methylpentyl); $C_1$-$C_{10}$alkyl substituted with 2 hydroxy substituents (e.g., 2,3-dihydroxypropyl, 3,4-dihydroxybutyl, 3,4-dihydroxy-4-methylpentyl); $C_2$-$C_{10}$alkenyl (e.g., allyl, 3-methylbut-2-enyl, 4-methylpent-3-enyl); $C_1$-$C_{10}$haloalkyl (e.g., 3-fluoropropyl, 3,3,3-trifluoropropyl, 4-fluorobutyl, 4,4,4-trifluorobutyl); or $C_2$-$C_{10}$haloalkenyl (e.g., 5,6,6-trifluorohex-5-enyl).

In certain embodiments, $R^{4a}$ is $CH_3$; $R^{40}$ is $-L^{4A}-R^{4c}$; $L^{4A}$ is $C_2$-$C_{10}$alkylene (e.g., $CH_2CH_2$, $(CH_2)_3$, $(CH_2)_4$, $CH_2C(H)(CH_3)$); and $R^{4c}$ is $—O—R^{4b}$, wherein $R^{4b}$ is hydrogen or $C_1$-$C_6$alkyl (e.g., methyl, propyl, pentyl); or $R^{4c}$ is $—O—Si(C_1$-$C_6$alkyl$)_3$ (e.g., $—O—SiMe_2t$-Bu); or $R^{4c}$ is $—S—R^{4b}$ where $R^{4b}$ is $C_1$-$C_6$alkyl (e.g., methyl, propyl, pentyl); or $R^{4c}$ is $—N(R^{4b})_2$ where $R^{4b}$ is each independently hydrogen or $C_1$-$C_6$alkyl (e.g., methyl, propyl, pentyl); or $R^{4c}$ is $—N(R^{4b})S(O)_2R^{4b}$, where each $R^{4b}$ is independently hydrogen or $C_1$-$C_6$alkyl (e.g., $CH_3$, $CH_2CH_3$); or $R^{4c}$ is $—OC(O)R^{4b}$, where $R^{4b}$ is $C_1$-$C_6$alkyl (e.g., $CH_3$, $CH_2CH_3$); or $R^{4c}$ is $—N(R^{4b})C(O)R^{4b}$, where each $R^{4b}$ is independently hydrogen or $C_1$-$C_6$alkyl (e.g., $CH_3$, $CH_2CH_3$).

In certain embodiments, $R^{4a}$ is $CH_3$; $R^{40}$ is $-L^{4A}-R^{4c}$; $L^{4A}$ is $C_1$-$C_{10}$alkylene (e.g., $CH_2$, $CH_2CH_2$, $(CH_2)_3$, $(CH_2)_4$, 5-methylhexyl); and $R^{4c}$ is cyano; or $R^{4c}$ is $—C(O)N(R^{4b})_2$, where $R^{4b}$ is each independently hydrogen or $C_1$-$C_6$alkyl (e.g., $CH_3$, $CH_2CH_3$); or $R^{4c}$ is $—C(O)N(R^{4b})S(O)_2R^{4b}$, where $R^{4b}$ is each independently hydrogen or $C_1$-$C_6$alkyl (e.g., $CH_3$, $CH_2CH_3$); or $R^{4c}$ is $—S(O)R^{4b}$, where $R^{4b}$ is $C_1$-$C_6$alkyl (e.g., $CH_3$, $CH_2CH_3$); or $R^{4c}$ is $—S(O)_2R^{4b}$, where $R^{4b}$ is $C_1$-$C_6$alkyl (e.g., $CH_3$, $CH_2CH_3$); or $R^{4c}$ is $—SO_2N(R^{4b})_2$, where $R^{4b}$ is each independently hydrogen or $C_1$-$C_6$alkyl (e.g., $CH_3$, $CH_2CH_3$); or $R^{4c}$ is $—CO_2R^{4b}$, where $R^{4b}$ is hydrogen or $C_1$-$C_6$alkyl (e.g., $CH_3$, $CH_2CH_3$); or $R^{4c}$ is $—C(NOH)N(R^{4b})_2$, where $R^{4b}$ is each independently hydrogen or $C_1$-$C_6$alkyl (e.g., $CH_3$, $CH_2CH_3$); or $R^{4c}$ is $—C(O)R^{4b}$, where $R^{4b}$ is $C_1$-$C_6$alkyl (e.g., $CH_3$, $CH_2CH_3$); or $R^{4c}$ is $—C(O)C(OH)(R^{4b})_2$, where $R^{4b}$ is each independently hydrogen or $C_1$-$C_6$alkyl (e.g., $CH_3$, $CH_2CH_3$); or $R^{4c}$ is $—P(O)(OR^{4b})_2$, where $R^{4b}$ is each independently $C_1$-$C_6$alkyl (e.g., $CH_3$, $CH_2CH_3$).

In certain embodiments, $R^4$ is $—N(R^{40})(SO_2R^{4a})$, where $R^{4a}$ is $C_1$-$C_3$alkyl (e.g., $CH_3$) and $R^{40}$ is $-L^{4A}-G^{4a}$, where $L^{4A}$ is $C_1$-$C_{10}$alkylene (e.g., $CH_2$, $CH_2CH_2$, $(CH_2)_3$, $(CH_2)_4$) and $G^{4a}$ is as defined herein. For example, in certain embodiments, $R^{4a}$ is $CH_3$, $L^{4A}$ is $C_1$-$C_{10}$alkylene (e.g., $CH_2$, $CH_2CH_2$, $(CH_2)_3$, $(CH_2)_4$), and $G^{4a}$ is optionally substituted $C_3$-$C_{12}$cycloalkyl; $C_6$-$C_{12}$aryl; 3- to 12-membered heterocyclyl; or 5- to 12-membered heteroaryl. In embodiments, $R^{4a}$ is $CH_3$, $L^{4A}$ is $C_1$-$C_3$alkylene (e.g., $CH_2$, $CH_2CH_2$, $(CH_2)_3$), and $G^{4a}$ is 5- to 6-membered heteroaryl substituted with $L^{4C}$-$G^{4b}$ where $L^{4C}$ is a bond and $G^{4b}$ is optionally substituted $C_6$-$C_{10}$aryl, 5- to 10-membered heterocyclyl, or 5- to 10-membered heteroaryl. For example, where $L^{4C}$ is a bond $G^{4a}-L^{4C}-G^{4b}$ is $G^{4a}-G^{4b}$. In embodiments, $G^{4a}$ is $C_3$-$C_8$cycloalkyl (e.g., cyclopropyl, 2,2-difluorocycloprop-1-yl, cyclopentyl, cyclohexyl); $C_6$-$C_{10}$aryl (e.g., phenyl, 4-methoxyphenyl, 3-trifluoromethylphenyl, naphthyl); 4- to 8-membered heterocyclyl (e.g., tetrahydrofuran-2-yl, pyrrolidin-1-yl, pyrrolidin-2-yl, 1,1-dioxotetrahydrothiephen-3-yl, tetrahydropyran-4-yl, morpholin-4-yl, 5-thioxo-4,5-dihydro-1,2,4-oxadiazol-3-yl, 5-oxo-4,5-dihydro-1,2,4-oxadiazol-3-yl, 5-oxo-4,5-dihydro-1,2,4-thiadiazol-3-yl, 5-oxo-4,5-dihydro-1,3,4-oxadiazol-2-yl, 1,1-dioxothiomorpholin-4-yl, piperidin-1-yl, 1,3-dioxoisoindolin-2-yl); or 5- to 10-membered heteroaryl (e.g., 1H-tetrazol-5-yl, 2-aminothiazol-4-yl, 2-bromothiazol-5-yl, 3-hydroxyisoxazol-5-yl, 4-methylthiazol-5-yl, pyrrol-1-yl, 2-bromo-4-(trifluoromethyl)thiazol-5-yl). In particular embodiments, $G^{4a}$ is 5- to 6-membered heteroaryl optionally substituted with $L^{4C}$-$G^{4b}$ where $L^{4C}$ is a bond and $G^{4b}$ is optionally substituted $C_6$-$C_{10}$aryl, 5- to 10-membered heterocyclyl, or 5- to 10-membered heteroaryl. In particular embodiments, $G^{4a}$ is thiazol-5-yl substituted in the 2-position with $G^{4b}$ (i.e., $G^{4b}$ 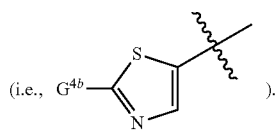 ).

For example, where $L^{4C}$ is a bond, $G^{4a}$-$G^{4b}$ includes, but is not limited to, 2-(1H-indol-5-yl)thiazol-5-yl; 2-(1-methyl-1H-indol-5-yl)thiazol-5-yl; 2-(1H-indol-6-yl)thiazol-5-yl; 2-(1H-pyrrolo[2,3-b]pyridin-5-yl)thiazol-5-yl; 2-(1H-indazol-5-yl)thiazol-5-yl; 2-(indolin-5-yl)thiazol-5-yl; 2-(2,3-dihydrobenzofuran-5-yl)thiazol-5-yl; 2-(2,5-dimethyl-1H-pyrrol-1-yl)thiazol-4-yl; (2-(1H-benzo[d]imidazol-6-yl)thiazol-5-yl); 2-(1-methyl-1H-benzo[d]imidazol-6-yl)thiazol-5-yl; 2-phenylthiazol-5-yl; 2-(4-(methylsulfinyl)phenyl)thiazol-5-yl; 2-(3-(hydroxymethyl)phenyl)thiazol-5-yl; 2-(3-(pyrrolidin-1-ylmethyl)phenyl)thiazol-5-yl; 2-(3-((dimethylamino)methyl)phenyl)thiazol-5-yl); 2-(6-oxo-1,6-dihydropyridin-3-yl)thiazol-5-yl; 2-(6-methoxypyridin-3-yl)thiazol-5-yl; 2-(2-methoxypyridin-3-yl)thiazol-5-yl; 2-(5-fluoropyridin-3-yl)thiazol-5-yl; 2-(pyridin-3-yl)thiazol-5-yl; 2-(2-methoxypyrimidin-5-yl)thiazol-5-yl; 2-(2,4-di-tert-butoxypyrimidin-5-yl)thiazol-5-yl; dioxo-1,2,3,4-tetrahydropyrimidin-5-yl)thiazol-5-yl; and 2-(1-methyl-1H-pyrazol-4-yl)thiazol-5-yl.

In certain embodiments, $R^4$ is $—N(R^{40})(SO_2R^{4a})$, where $R^{4a}$ is $C_1$-$C_3$alkyl (e.g., $CH_3$) and $R^{40}$ is $-L^{4A}-S(O)_2-L^{4B}-G^{4a}$, where $L^{4A}$ is $C_1$-$C_{10}$alkylene (e.g., $CH_2$, $CH_2CH_2$, $(CH_2)_3$, $(CH_2)_4$), $L^{4B}$ is a bond, and $G^{4a}$ is as defined here (i.e., $R^{40}$ is $-L^{4A}-S(O)_2-G^{4a}$). For example, in certain particular embodiments where $R^{40}$ is $-L^{4A}-S(O)_2-G^{4a}$ and $R^{4a}$ is $CH_3$, $L^{4A}$ is $C_1$-$C_{10}$alkylene (e.g., $CH_2$, $CH_2CH_2$, $(CH_2)_3$, $(CH_2)_4$), and $G^{4a}$ is 4- to 8-membered heterocyclyl (e.g., morpholin-4-yl), or $G^{4a}$ is $C_6$-$C_{10}$aryl (e.g., phenyl, naphthyl), either optionally substituted.

In certain embodiments, $R^4$ is $—N(R^{40})(SO_2R^{4a})$, where $R^{4a}$ is $C_1$-$C_3$alkyl (e.g., $CH_3$) and $R^{40}$ is $-L^{4A}-C(O)-L^{4B}-G^{4a}$, where $L^{4A}$ is $C_1$-$C_{10}$alkylene (e.g., $CH_2$, $CH_2CH_2$, $(CH_2)_3$, $(CH_2)_4$), $L^{4B}$ is a bond, and $G^{4a}$ is as defined herein (i.e., $R^{40}$ is $-L^{4A}-C(O)-G^{4a}$). For example, in certain particular embodiments where $R^{40}$ is $-L^{4A}-C(O)-G^{4a}$ and $R^{4a}$ is $CH_3$, $L^{4A}$ is $C_1$-$C_{10}$alkylene (e.g., $CH_2$, $CH_2CH_2$, $(CH_2)_3$, $(CH_2)_4$), and $G^{4a}$ is 4- to 8-membered heterocyclyl (e.g., morpholin-4-yl, piperidin-1-yl), optionally substituted.

In certain embodiments, $R^4$ is $—N(R^{40})(SO_2R^{4a})$, where $R^{4a}$ is $C_1$-$C_3$alkyl (e.g., $CH_3$) and $R^{40}$ is $-L^{4A}-O-L^{4B}-G^{4a}$, where $L^{4A}$ is $C_1$-$C_{10}$alkylene (e.g., $CH_2$, $CH_2CH_2$, $(CH_2)_3$, $(CH_2)_4$), $L^{4B}$ is a bond, and $G^{4a}$ is as defined herein (i.e., $R^{40}$ is $-L^{4A}-O-G^{4a}$). For example, in certain particular embodiments where $R^{40}$ is $-L^{4A}-O-G^{4a}$ and $R^{4a}$ is $CH_3$, $L^{4A}$ is $C_1$-$C_{10}$alkylene (e.g., $CH_2$, $CH_2CH_2$, $(CH_2)_3$, $(CH_2)_4$), and $G^{4a}$ is $C_6$-$C_{10}$aryl (e.g., phenyl, naphthyl), optionally substituted.

$R^5$ may be hydrogen, $C_1$-$C_6$alkyl (e.g., isopropyl, tert-butyl, ethyl), $C_1$-$C_6$haloalkyl (e.g., trifluoromethyl), $C_3$-$C_6$cycloalkyl (e.g., cyclopropyl), $—O—C_1$-$C_6$alkyl (e.g., methoxy, isopropoxy), $—O—C_1$-$C_6$haloalkyl (e.g., trifluoromethoxy), $—O—C_3$-$C_6$cycloalkyl (e.g., $—O$-cyclopropyl), or $G^{5a}$, wherein the $C_3$-$C_6$cycloalkyl groups are optionally substituted with 1, 2, 3, or 4 substituents selected from the group consisting of halogen, $C_1$-$C_3$alkyl, $C_1$-$C_3$haloalkyl, and oxo; and $G^{5a}$ is as defined herein. In certain embodiments, $R^5$ is hydrogen, $C_1$-$C_6$alkyl (e.g., isopropyl, tert-butyl, ethyl), $C_1$-$C_6$haloalkyl (e.g., trifluoromethyl), or $—O—C_1$-$C_6$alkyl (e.g., methoxy, isopropoxy). In certain embodiments $R^5$ is hydrogen, isopropyl, isopropoxy, or $C_3$-$C_6$cycloalkyl (e.g., cyclopropyl). In embodiments, $R^5$ is cyclopropyl.

In embodiments, $R^5$ is $G^{5a}$, where $G^{5a}$ is phenyl substituted with —C(O)N($R^{5a}$)-$L^{5B}$-$G^{5b}$, —C(O)-$G^{5f}$, or —C(O)N($R^{5a}$)($R^{5e}$) and optionally substituted with 1, 2, or 3 substituents selected from the group consisting of $C_1$-$C_{10}$alkyl, $C_2$-$C_{10}$alkenyl, $C_2$-$C_{10}$alkynyl, $C_1$-$C_{10}$haloalkyl. halogen, —O—$R^{5b}$, CN, and -$G^{5d}$; wherein:

$G^{5b}$ is $C_3$-$C_{12}$cycloalkyl, $C_6$-$C_{12}$aryl, 3- to 12-membered heterocyclyl, or 5- to 12-membered heteroaryl, wherein each $G^{5b}$ is optionally substituted with 1, 2, 3, 4, or 5 substituents selected from the group consisting of oxo, halogen, $C_1$-$C_6$alkyl, $C_1$-$C_6$haloalkyl, —O—$R^{5d}$, —CN, -$L^{5C}$-O—$R^{5d}$, -$L^{5C}$-CN, and $G^{5c}$;

$G^{5d}$ is each independently $C_3$-$C_8$cycloalkyl, $C_6$-$C_{10}$aryl, 4- to 10-membered heterocyclyl, or 5- to 10-membered heteroaryl, wherein $G^{5d}$ is optionally substituted with 1, 2, 3, 4, or 5 substituents selected from the group consisting of oxo, halogen, $C_1$-$C_6$alkyl, $C_1$-$C_6$haloalkyl, —O—$R^{5d}$, —CN, —N($R^{5d}$)C(O)$R^{5d}$, —CON($R^{5a}$)($R^{5d}$), —C(O)$R^{5d}$, —OC(O)$R^{5d}$, —CO$_2$H, —CO$_2$$R^{5d}$, —N($R^{5d}$)C(O)N($R^{5d}$)$_2$, —S—$R^{5d}$, —S(O)$_2$$R^{5d}$, —S(O)$R^{5d}$, —SO$_2$N($R^{5a}$)($R^{5d}$), —N($R^{5a}$)($R^{5d}$), —N($R^{5d}$)S(O)$_2$$R^{5d}$, N($R^{5d}$)C(O)O($R^{5d}$), -$L^{5C}$-O—$R^{5d}$, -$L^{5C}$-CN, $G^{5e}$, and -$L^{5C}$-$G^{5c}$;

wherein $G^{5e}$, $G^{5f}$, $R^{5a}$, $R^{5b}$, $R^{5d}$, $R^{5e}$, $L^{5B}$, and $L^{5C}$, are as defined herein.

In certain embodiments, the $G^{5a}$ of $R^5$ is phenyl substituted in the meta position by the group —C(O)N($R^{5a}$)-$L^{5B}$-$G^{5b}$ as depicted in formula $R^5$-I, and where $R^{5a}$, $L^{5B}$, and $G^{5b}$ are as described herein and $G^{5a}$ is further optionally substituted as described herein.

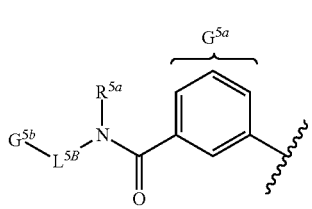

R⁵-I

In embodiments including formula $R^5$-I, wherein $G^{5a}$ may be further substituted by 1, 2, or 3 additional substituents including, for example, $C_1$-$C_6$alkyl (e.g., methyl, ethyl, isopropyl), $C_1$-$C_6$haloalkyl (e.g., trifluoromethyl), halogen (e.g., fluoro, chloro), $G^{5d}$, or —O—$R^{5b}$:

$R^{5a}$ is hydrogen or methyl;

$L^{5B}$ is $C_1$-$C_6$alkylene (e.g., —CH$_2$—, —C(CH$_3$)$_2$—, —C(CH$_3$)(H)CH$_2$—, —C(CH$_3$)$_2$CH$_2$—), or $C_3$-$C_6$cycloalkyl (e.g., cyclopropyl, cyclobutyl);

$G^{5b}$ is $C_3$-$C_8$cycloalkyl (e.g., cyclopropyl, cyclobutyl, cyclopentyl, cyclohexyl, cycloheptyl), $C_6$-$C_{10}$aryl (e.g., phenyl, naphthyl, indanyl), 3- to 8-membered heterocyclyl (e.g., tetrahydropyranyl, tetrahydropyranyl), or 5- to 10-membered heteroaryl (e.g., furanyl, imidazolyl, thiazolyl, thiadiazolyl, oxazolyl, isoxazolyl, triazolyl, oxadiazolyl, pyrazolyl, thienyl, thiazolyl, pyridinyl, pyrimidinyl, pyrazinyl), wherein each $G^{5b}$ is optionally substituted with 1, 2, 3, 4, or 5 substituents selected from the group consisting of oxo, halogen (e.g. fluoro), $C_1$-$C_6$alkyl (e.g., methyl, ethyl, isopropyl), $C_1$-$C_3$haloalkyl (e.g., trifluoromethyl), —O—$R^{5d}$ (e.g., hydroxy, methoxy), —CN, methoxymethyl, cyanomethyl, and $G^{5c}$;

$G^{5c}$, at each occurrence, is each independently cyclopropyl, phenyl, or 5- to 6-membered heteroaryl (e.g., pyridinyl, thiazolyl, isoxazolyl, pyrazolyl), wherein $G^{5c}$ is optionally substituted with 1, 2, 3, 4, or 5 substituents selected from the group consisting of halogen (e.g., fluoro, chloro), $C_1$-$C_6$alkyl (e.g., methyl, ethyl), $C_1$-$C_6$haloalkyl (e.g., trifluoromethyl), —O—$C_1$-$C_6$alkyl (e.g., methoxy), and —O—$C_1$-$C_6$haloalkyl (e.g., trifluoromethoxy);

$R^{5b}$, at each occurrence, is each independently hydrogen, $C_1$-$C_6$alkyl (e.g., methyl), $C_2$-$C_6$alkenyl (e.g., allyl), $C_2$-$C_6$alkynyl (e.g., propargyl), $C_1$-$C_6$haloalkyl (e.g., trifluoromethyl, 2,2-difluoroethyl), -$L^{5D}$-$G^{5c}$ (e.g., bond-$G^{5e}$, —CH$_2$CH$_2$-pyrrolidin-1-yl, —CH$_2$-pyrrolidin-2-yl, —CH$_2$-pyrrolidin-3-yl, —CH$_2$CH$_2$-morpholin-4-yl, —CH$_2$CH$_2$CH$_2$-morpholin-4-yl, —CH$_2$CH$_2$-morpholin-2-yl —CH$_2$CH$_2$-4-methylpiperazin-1-yl, —CH$_2$CH$_2$-piperidinyl, —CH$_2$CH$_2$-pyridin-2-yl, —CH$_2$-pyridin-4-yl, —CH$_2$-imidazol-4-yl), or -$L^{5G}$-$R^{5c}$ (e.g., —CH$_2$CH$_2$OH, —CH$_2$CH(CH$_3$)OH, —CH$_2$CH(CH$_2$CH$_3$)OH, —CH$_2$CH$_2$OMe, —CH$_2$CONH$_2$, —CH$_2$CH$_2$CONH$_2$, —CH$_2$CH$_2$NH$_2$, —CH$_2$CH$_2$N(CH$_3$)$_2$, —CH$_2$CH$_2$NHC(O)NH$_2$, —CH$_2$CN);

$L^{5D}$, at each occurrence, is each independently a bond, $C_1$-$C_6$alkylene (e.g., —CH$_2$—, —CH$_2$CH$_2$—, —CH$_2$CH$_2$CH$_2$—), or $C_3$-$C_6$cycloalkyl (e.g., cyclopropyl);

$L^{5G}$, at each occurrence, is each independently $C_1$-$C_6$alkylene (e.g. —(CH$_2$)$_2$—, —C(CH$_3$)$_2$—, —C(CH$_3$)$_2$CH$_2$—, —CH$_2$CH(CH$_3$)—);

$R^{5c}$, at each occurrence, is each independently —CON($R^{5a}$)($R^{5g}$) (e.g., CONH$_2$), —O—$R^{5g}$ (e.g., OH, OMe), —OC(O)$R^{5g}$, —CN, —C(O)$R^{5g}$, —CO$_2$H, —CO$_2$$R^{5g}$, —N($R^{5g}$)C(O)N($R^{5g}$)$_2$ (e.g., NHC(O)NH$_2$), —S—$R^{5g}$, —S(O)$_2$$R^{5g}$, —S(O)$R^{5g}$, —SO$_2$N($R^{5a}$)($R^{5g}$), —N($R^{5a}$)($R^{5g}$) (e.g., NH$_2$, N(CH$_3$)$_2$), —N($R^{5g}$)C(O)$R^{5g}$, or —N($R^{5g}$)S(O)$_2$$R^{5g}$;

$R^{5g}$ is independently, at each occurrence, hydrogen, $C_1$-$C_6$alkyl (e.g., methyl, ethyl), $C_1$-$C_6$haloalkyl (e.g., 2,2-difluoroethyl), or -$L^{5H}$-$G^{5e}$ (e.g., bond-$C_3$-$C_6$cycloalkyl, —CH$_2$—$C_3$-$C_6$cycloalkyl);

$L^{5H}$, at each occurrence, is each independently bond or $C_1$-$C_6$alkylene (e.g., —CH$_2$—);

$G^{5e}$, at each occurrence, is each independently $C_3$-$C_8$cycloalkyl (e.g., cyclobutyl, cyclopentyl), $C_6$-$C_{10}$aryl (e.g., phenyl), 4- to 10-membered heterocyclyl (e.g., morpholin-4-yl, pyrrolidin-1-yl, 4-methylpiperazin-1-yl, piperidinyl), or 5- to 10-membered heteroaryl (e.g., pyridin-2-yl, imidazol-4-yl), wherein $G^{5e}$ is optionally substituted with 1, 2, 3, or 4 substituents selected from the group consisting of halogen (e.g., fluoro), oxo, $C_1$-$C_6$alkyl (e.g., methyl, ethyl), $C_1$-$C_6$haloalkyl (e.g., trifluoromethyl), —OH, —O—$C_1$-$C_6$alkyl (e.g., OCH$_3$), and —O—$C_1$-$C_6$haloalkyl (e.g., OCF$_3$);

$G^{5d}$, at each occurrence, is each independently $C_3$-$C_8$cycloalkyl, $C_6$-$C_{10}$aryl (e.g., phenyl), 4- to 10-membered heterocyclyl (e.g., tetrahydropyrimidinyl), or 5- to 10-membered heteroaryl (e.g., furanyl, thienyl, pyrazolyl, pyridinyl, pyrimidinyl, oxadiazolyl, isoquinolinyl, indolyl), wherein $G^{5d}$ is optionally substituted with 1, 2, 3, 4 or 5 substituents selected from the group consisting of oxo, halogen (e.g. fluoro, chloro), $C_1$-$C_6$alkyl (e.g., methyl, ethyl, n-propyl, isopropyl), $C_1$-$C_6$haloalkyl (e.g., trifluoromethyl), —O—$R^{5d}$ (e.g., methoxy, ethoxy), —CN, —N($R^{5d}$)C(O)$R^{5d}$ (e.g., NHC(O)Me), —CON($R^{5a}$)($R^{5d}$) (e.g., CONH$_2$, CONHEt), —C(O)$R^{5d}$ (e.g., C(O)Me), —OC(O)$R^{5d}$, —CO$_2$H, —CO$_2$$R^{5d}$ (e.g., CO$_2$Me), —N($R^{5d}$)C(O)N($R^{5d}$)$_2$ (e.g., NHC(O)NHMe), —S—$R^{5d}$, —S(O)$_2$$R^{5d}$ (e.g., S(O)$_2$Me), —S(O)$R^{5d}$ (e.g., S(O)Me), —SO$_2$N($R^{5a}$)($R^{5d}$) (e.g., SO$_2$NH$_2$, SO$_2$NHEt), —N($R^{5a}$)($R^{5d}$) (e.g., NH$_2$), —N($R^{5d}$)S(O)$_2$$R^{5d}$ (e.g., —NHS(O)$_2$Me), N($R^{5d}$)C(O)O($R^{5d}$) (e.g., NHC(O)OMe), -$L^{5C}$-O—$R^{5d}$ (e.g., hydroxymethyl, methoxymethyl), and -$L^{5C}$-CN (e.g., cyanomethyl);

$R^{5d}$, at each occurrence, is each independently hydrogen, $C_1$-$C_6$alkyl, $C_1$-$C_6$haloalkyl, or -$L^{5F}$-$G^{5c}$;

$L^{5C}$, at each occurrence, is each independently $C_1$-$C_6$alkylene (e.g., —$CH_2$—) or $C_3$-$C_8$cycloalkyl (e.g., cyclopropyl); and $L^{5F}$, at each occurrence, is each independently bond or $C_1$-$C_6$alkylene (e.g., —$CH_2$—).

Such embodiments may further include compounds where $R^{5a}$ is hydrogen.

Particular embodiments may include compounds where $R^5$ is $R^5$-II, and

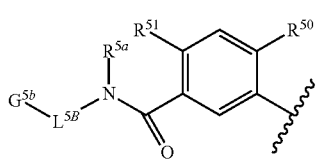

$R^5$-II $L^{5B}$ is $C_1$-$C_6$alkylene (e.g., —$CH_2$—, —$C(CH_3)_2$—, —$C(CH_3)(H)CH_2$—, —$C(CH_3)_2CH_2$—) or $C_3$-$C_8$cycloalkyl (e.g., cyclopropyl, cyclobutyl);

$G^{5b}$ is $C_3$-$C_8$cycloalkyl (e.g., cyclopropyl, cyclobutyl, cyclopentyl, cyclohexyl, cycloheptyl), $C_6$-$C_{10}$aryl (e.g., phenyl, naphthyl, indanyl), 3- to 8-membered heterocyclyl (e.g., tetrahydropyranyl, tetrahydropyranyl), or 5- to 10-membered heteroaryl (e.g., furanyl, imidazolyl, thiazolyl, thiadiazolyl, oxazolyl, isoxazolyl, triazolyl, oxadiazolyl, pyrazolyl, thienyl, thiazolyl, pyridinyl, pyrimidinyl, pyrazinyl), wherein each $G^{5b}$ is optionally substituted with 1, 2, 3, 4, or 5 substituents selected from the group consisting of oxo, halogen (e.g. fluoro), $C_1$-$C_6$alkyl (e.g., methyl, ethyl, isopropyl), $C_1$-$C_6$haloalkyl (e.g., trifluoromethyl), —O—$R^{5d}$ (e.g., hydroxy, methoxy), —CN, methoxymethyl, cyanomethyl, and $G^{5c}$; wherein $G^{5c}$ is each independently cyclopropyl, phenyl, 5- to 6-membered heteroaryl (e.g., pyridinyl, thiazolyl, isoxazolyl, pyrazolyl), wherein $G^{5c}$ is optionally substituted with 1, 2, 3, 4, or 5 substituents selected from the group consisting of halogen (e.g., fluoro, chloro), $C_1$-$C_6$alkyl (e.g., methyl, ethyl), $C_1$-$C_6$haloalkyl (e.g., trifluoromethyl), —O—$C_1$-$C_6$alkyl (e.g., methoxy), and —O—$C_1$-$C_6$haloalkyl (e.g., trifluoromethoxy);

$R^{50}$ is hydrogen, $C_1$-$C_3$alkyl (e.g., methyl, ethyl, isopropyl), $C_1$-$C_3$haloalkyl (e.g., trifluoromethyl), halogen (e.g., fluoro, chloro), or —O—$R^{5b}$;

$R^{51}$ is hydrogen, $C_1$-$C_3$alkyl (e.g., methyl, ethyl, isopropyl), $C_1$-$C_3$haloalkyl (e.g., trifluoromethyl), halogen (e.g., fluoro, chloro), —O—$C_1$-$C_6$alkyl (e.g., methoxy), —O—$C_1$-$C_6$haloalkyl (e.g., trifluoromethoxy), or $G^{5d}$;

$G^{5d}$ is phenyl, tetrahydropyrimidinyl, furanyl, thienyl, pyrazolyl, pyridinyl, oxadiazolyl, isoquinolinyl, or indolyl;

$R^{5b}$, at each occurrence, is each independently hydrogen, $C_1$-$C_6$alkyl (e.g., methyl), $C_2$-$C_6$alkenyl (e.g., allyl), $C_2$-$C_6$alkynyl (e.g., propargyl), $C_1$-$C_6$haloalkyl (e.g., trifluoromethyl, 2,2-difluoroethyl), -$L^{5D}$-$G^{5e}$ (e.g., bond-$G^{5e}$, —$CH_2CH_2$-pyrrolidin-1-yl, —$CH_2$-pyrrolidin-2-yl, —$CH_2$-pyrrolidin-3-yl, —$CH_2CH_2$-morpholin-4-yl, —$CH_2CH_2CH_2$-morpholin-4-yl, —$CH_2CH_2$-morpholin-2-yl —$CH_2CH_2$-4-methylpiperazin-1-yl, —$CH_2CH_2$-piperidinyl, $CH_2$-piperidin-3-yl, —$CH_2$-pyridin-2-yl, —$CH_2CH_2$-pyridin-2-yl, —$CH_2$-pyridin-4-yl, —$CH_2$-imidazol-4-yl), or -$L^{5G}$-$R^{5e}$ (e.g., —$CH_2CH_2$OH, —$CH_2CH(CH_3)$OH, —$CH_2CH(CH_2CH_3)$OH, —$CH_2CH_2$OMe, —$CH_2CH_2$CONH$_2$, —$CH_2CH_2$CONH$_2$, —$CH_2CH_2NH_2$, —$CH_2CH_2N(CH_3)_2$, —$CH_2CH_2$NHC(O)NH$_2$, —$CH_2$CN; $R^{5c}$ is —CON($R^{5a}$)

($R^{5g}$) (e.g., CONH$_2$), —O—$R^{5g}$ (e.g., OH, OMe), —OC(O)$R^{5g}$, —CN, —C(O)$R^{5g}$, —CO$_2$H, —CO$_2R^{5g}$, —N($R^{5g}$)C(O)N($R^{5g}$)$_2$ (e.g., NHC(O)NH$_2$), —S—$R^{5g}$, —S(O)$_2R^{5g}$, —S(O)$R^{5g}$, —SO$_2$N($R^{5a}$)($R^{5g}$), —N($R^{5a}$)($R^{5g}$) (e.g., NH$_2$, N(CH$_3$)$_2$), —N($R^{5g}$)C(O)$R^{5g}$, or —N($R^{5g}$)S(O)$_2R^{5g}$; $R^{5g}$ is, at each occurrence, independently hydrogen, $C_1$-$C_6$alkyl (e.g., methyl, ethyl), $C_1$-$C_6$haloalkyl (e.g., 2,2-difluoroethyl), or -$L^{5H}$-$G^{5e}$ (e.g., bond-$C_3$-$C_6$cycloalkyl, —$CH_2$—$C_3$-$C_6$cycloalkyl); $L^{5D}$, at each occurrence, is each independently a bond, $C_1$-$C_6$alkylene (e.g., —$CH_2$—, —$CH_2CH_2$—, —$CH_2CH_2CH_2$—), or $C_3$-$C_6$cycloalkyl (e.g., cyclopropyl); $G^{5e}$, at each occurrence, is each independently $C_3$-$C_6$cycloalkyl (e.g., cyclobutyl, cyclopentyl), $C_6$-$C_{10}$aryl (e.g., phenyl), 4- to 7-membered heterocyclyl (e.g., morpholin-4-yl, pyrrolidin-1-yl, 4-methylpiperazin-1-yl, piperidinyl), or 5- to 6-membered heteroaryl (e.g., pyridin-2-yl, imidazol-4-yl), wherein $G^{5e}$ is optionally substituted with 1, 2, 3, or 4 substituents selected from the group consisting of halogen (e.g., fluoro), oxo, $C_1$-$C_6$alkyl (e.g., methyl, ethyl), $C_1$-$C_6$haloalkyl (e.g., trifluoromethyl), —OH, —O—$C_1$-$C_6$alkyl (e.g., OCH$_3$), and —O—$C_1$-$C_6$haloalkyl (e.g., OCF$_3$); $L^{5G}$, at each occurrence, is each independently $C_1$-$C_6$alkylene (e.g. —(CH$_2$)$_2$—, —C(CH$_3$)$_2$—, —C(CH$_3$)$_2$CH$_2$—, —CH$_2$CH(CH$_3$)—);

$R^{5d}$, at each occurrence, is each independently hydrogen, $C_1$-$C_6$alkyl, or $C_1$-$C_6$haloalkyl; and $R^{5a}$ is hydrogen or methyl.

Such embodiments may further include compounds where:

$G^{5b}$ is phenyl or pyridinyl (e.g. pyridin-2-yl), wherein $G^{5b}$ is optionally substituted with 1, 2, 3, 4, or 5 substituents selected from the group consisting of halogen (e.g. fluoro), $C_1$-$C_6$alkyl (e.g., methyl, ethyl, isopropyl), $C_1$-$C_6$haloalkyl (e.g., trifluoromethyl), —O—$R^{5d}$ (e.g., hydroxy, methoxy), and —CN.

Such embodiments may further include compounds where $R^{5a}$ is hydrogen.

In certain embodiments, the $G^{5a}$ of $R^5$ is phenyl substituted in the meta position by the group —C(O)N($R^{5a}$)($R^{5e}$) as depicted in formula $R^5$-III, where $R^{5a}$ and $R^{5e}$ are as described herein and $G^{5a}$ is further optionally substituted as described herein.

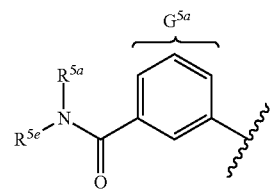

$R^5$-III

Particular embodiments may include compounds where $R^5$ is $R^5$-III wherein:

$G^{5a}$ is optionally substituted with additional substituents including, for example, $C_1$-$C_6$alkyl (e.g., methyl, ethyl, isopropyl), $C_1$-$C_6$haloalkyl (e.g., trifluoromethyl), halogen (e.g., fluoro, chloro), -$G^{5d}$, or —O—$R^{5b}$;

$R^{5a}$ is hydrogen or methyl;

$R^{5e}$ is hydrogen, $C_1$-$C_{10}$alkyl (e.g., methyl, ethyl, isopropyl, n-butyl, isobutyl, t-butyl), $C_2$-$C_{10}$alkenyl, $C_2$-$C_{10}$alkynyl (e.g., 2-methylbut-3-yn-2-yl), $C_1$-$C_{10}$haloalkyl (e.g., 1,1,1-trifluoro-2-methylpropan-2-yl), or -$L^{5E}$-$R^{5f}$ (e.g., —C(CH$_3$)$_2$—CONHMe, —C(CH$_3$)$_2$—CONHCH$_2$CHF$_2$, —C(CH$_3$)$_2$—CO$_2$CH$_3$, —C(CH$_3$)$_2$CH$_2$—C(O)CH$_3$, —C(CH$_3$)$_2$—CONH-thiazol-2-yl);

R$^{5f}$ is —CON(R$^{5a}$)(R$^{5d}$) (e.g., CONHMe, CONHCH$_2$CHF$_2$, CONH-thiazol-2-yl), —O—R$^{5d}$ (e.g., OMe), —CN, —C(O)R$^{5d}$ (e.g., C(O)CH$_3$), —CO$_2$H, —CO$_2$R$^{5d}$ (e.g., CO$_2$CH$_3$), —N(R$^{5d}$)C(O)N(R$^{5d}$)$_2$, —S(O)$_2$R$^{5d}$ (e.g., S(O)$_2$Me), —S(O)R$^{5d}$ (e.g., S(O)Me), —SO$_2$N(R$^{5a}$)(R$^{5d}$) (e.g., SO$_2$NH$_2$, SO$_2$NHEt), —N(R$^{5a}$)(R$^{5d}$), —N(R$^{5d}$)C(O)R$^{5d}$ (e.g., NHC(O)Me), or —N(R$^{5d}$)S(O)$_2$R$^{5d}$ (e.g., —NHS(O)$_2$Me);

G$^{5d}$, at each occurrence, is each independently C$_3$-C$_8$cycloalkyl, C$_6$-C$_{10}$aryl (e.g., phenyl), 4- to 10-membered heterocyclyl (e.g., tetrahydropyrimidinyl), or 5- to 10-membered heteroaryl (e.g., furanyl, thienyl, pyrazolyl, pyridinyl, pyrimidinyl, oxadiazolyl, isoquinolinyl, indolyl), wherein G$^{5d}$ is optionally substituted with 1, 2, 3, 4, or 5 substituents selected from the group consisting of oxo, halogen (e.g. fluoro, chloro), C$_1$-C$_6$alkyl (e.g., methyl, ethyl, n-propyl, isopropyl), C$_1$-C$_6$haloalkyl (e.g., trifluoromethyl), —O—R$^{5d}$ (e.g., methoxy, ethoxy), —CN, —N(R$^{5d}$)C(O)R$^{5d}$ (e.g., NHC(O)Me), —CON(R$^{5a}$)(R$^{5d}$) (e.g., CONH$_2$, CONHEt), —C(O)R$^{5d}$ (e.g., C(O)Me), —OC(O)R$^{5d}$, —CO$_2$H, —CO$_2$R$^{5d}$ (e.g., CO$_2$Me), —N(R$^{5d}$)C(O)N(R$^{5d}$)$_2$ (e.g., NHC(O)NHMe), —S—R$^{5d}$, —S(O)$_2$R$^{5d}$ (e.g., S(O)$_2$Me), —S(O)R$^{5d}$ (e.g., S(O)Me), —SO$_2$N(R$^{5a}$)(R$^{5d}$) (e.g., SO$_2$NH$_2$, SO$_2$NHEt), —N(R$^{5a}$)(R$^{5d}$) (e.g., NH$_2$), —N(R$^{5d}$)S(O)$_2$R$^{5d}$ (e.g., —NHS(O)$_2$Me), N(R$^{5d}$)C(O)O(R$^{5d}$) (e.g., NHC(O)OMe), -L$^{5C}$-O—R$^{5d}$ (e.g., hydroxymethyl, methoxymethyl), -L$^{5C}$-CN (e.g., cyanomethyl), G$^{5c}$ (e.g., phenyl), and -L$^{5C}$-G$^{5c}$ (e.g., benzyl);

R$^{5d}$, at each occurrence, is each independently hydrogen, C$_1$-C$_6$alkyl (e.g., methyl, ethyl), C$_1$-C$_6$haloalkyl (e.g., 2,2-difluoroethyl), or -L$^{5E}$-G$^{5e}$ (e.g., bond-thiazol-2-yl);

G$^{5c}$, at each occurrence, is each independently C$_3$-C$_8$cycloalkyl (e.g., cyclopropyl), C$_6$-C$_{10}$aryl (e.g., phenyl), 4- to 10-membered heterocyclyl, or 5- to 10-membered heteroaryl (e.g., pyridinyl, thiazolyl, isoxazolyl, pyrazolyl), wherein G$^{5c}$ is optionally substituted with 1, 2, 3, 4, or 5 substituents selected from the group consisting of halogen (e.g., fluoro, chloro), oxo, C$_1$-C$_6$alkyl, C$_1$-C$_6$haloalkyl, —O—C$_1$-C$_6$alkyl (e.g., methoxy), and —O—C$_1$-C$_6$haloalkyl;

R$^{5b}$, at each occurrence, is each independently hydrogen, C$_1$-C$_{10}$alkyl (e.g., methyl), C$_2$-C$_{10}$alkenyl (e.g., allyl), C$_2$-C$_{10}$alkynyl (e.g., propargyl), C$_1$-C$_{10}$haloalkyl (e.g., trifluoromethyl, 2,2-difluoroethyl), -L$^{5D}$-G$^{5e}$ (e.g., bond-G$^{5e}$, —CH$_2$CH$_2$-pyrrolidin-1-yl, —CH$_2$-pyrrolidin-2-yl, —CH$_2$-pyrrolidin-3-yl, —CH$_2$CH$_2$-morpholin-4-yl, —CH$_2$CH$_2$CH$_2$-morpholin-4-yl, —CH$_2$CH$_2$-morpholin-2-yl —CH$_2$CH$_2$-4-methylpiperazin-1-yl, —CH$_2$CH$_2$-piperidinyl, —CH$_2$-piperidin-3-yl, —CH$_2$-pyridin-2-yl, —CH$_2$CH$_2$-pyridin-2-yl, —CH$_2$-pyridin-4-yl, —CH$_2$-imidazol-4-yl), or -L$^{5G}$-R$^{5e}$ (e.g., —CH$_2$CH$_2$OH, —CH$_2$CH(CH$_3$)OH, —CH$_2$CH(CH$_2$CH$_3$)OH, —CH$_2$CH$_2$OMe, —CH$_2$CONH$_2$, —CH$_2$CH$_2$CONH$_2$, —CH$_2$CH$_2$NH$_2$, —CH$_2$CH$_2$N(CH$_3$)$_2$, —CH$_2$CH$_2$NHC(O)NH$_2$, —CH$_2$CN);

R$^{5c}$, at each occurrence, is each independently —CON(R$^{5a}$)(R$^{5g}$) (e.g., CONH$_2$), —O—R$^{5g}$ (e.g., OH, OMe), —OC(O)R$^{5g}$, —CN, —C(O)R$^{5g}$, —CO$_2$H, —CO$_2$R$^{5g}$, —N(R$^{5g}$)C(O)N(R$^{5g}$)$_2$ (e.g., NHC(O)NH$_2$), —S—R$^{5g}$, —S(O)$_2$R$^{5g}$, —S(O)R$^{5g}$, —SO$_2$N(R$^{5a}$)(R$^{5g}$), —N(R$^{5a}$)(R$^{5g}$) (e.g., NH$_2$, N(CH$_3$)$_2$), —N(R$^{5g}$)C(O)R$^{5g}$, or —N(R$^{5g}$)S(O)$_2$R$^{5g}$; R$^{5g}$ is hydrogen, C$_1$-C$_6$alkyl (e.g., methyl, ethyl), C$_1$-C$_6$haloalkyl (e.g., 2,2-difluoroethyl), or -L$^{5H}$-G$^{5e}$ (e.g., bond-C$_3$-C$_6$cycloalkyl, —CH$_2$—C$_3$-C$_6$cycloalkyl);

G$^{5e}$, at each occurrence, is each independently C$_3$-C$_8$cycloalkyl (e.g., cyclobutyl, cyclopentyl), C$_6$-C$_{10}$aryl (e.g., phenyl), 4- to 10-membered heterocyclyl (e.g., morpholin-4-yl, pyrrolidin-1-yl, 4-methylpiperazin-1-yl, piperidinyl), or 5- to 10-membered heteroaryl (e.g., pyridin-2-yl, imidazol-4-yl), wherein G$^{5e}$ is optionally substituted with 1, 2, 3, or 4 substituents selected from the group consisting of halogen (e.g., fluoro), oxo, C$_1$-C$_6$alkyl (e.g., methyl, ethyl), C$_1$-C$_6$haloalkyl (e.g., trifluoromethyl), —OH, —O—C$_1$-C$_6$alkyl (e.g., OCH$_3$), and —O—C$_1$-C$_6$haloalkyl (e.g., OCF$_3$); and L$^{5C}$, at each occurrence, is each independently C$_1$-C$_6$alkylene or C$_3$-C$_8$cycloalkyl, wherein L$^{5C}$ is each optionally substituted with 1, 2, 3, or 4 halogen and 1 or 2 hydroxy;

L$^{5D}$, at each occurrence, is each independently a bond, C$_1$-C$_6$alkylene (e.g., —CH$_2$—, —CH$_2$CH$_2$—, —CH$_2$CH$_2$CH$_2$—), or C$_3$-C$_8$cycloalkyl (e.g., cyclopropyl), and L$^{5D}$ is each optionally substituted with 1, 2, 3, or 4 halogen and 1 or 2 hydroxy;

L$^{5E}$, at each occurrence, is each independently C$_1$-C$_6$alkylene (e.g. —(CH$_2$)$_2$—, —C(CH$_3$)$_2$—, —C(CH$_3$)$_2$CH$_2$—), wherein L$^{5E}$ is optionally substituted with 1, 2, 3, or 4 halogen and 1 or 2 hydroxy;

L$^{5F}$, at each occurrence, is each independently a bond or C$_1$-C$_6$alkylene (e.g., —CH$_2$—), wherein L$^{5F}$ is optionally substituted with 1, 2, 3, or 4 halogen and 1 or 2 hydroxy;

L$^{5G}$ at each occurrence, is each independently C$_1$-C$_6$alkylene (e.g. —(CH$_2$)$_2$—, —C(CH$_3$)$_2$—, —C(CH$_3$)$_2$CH$_2$—, —CH$_2$CH(CH$_3$)—), wherein L$^{5G}$ is optionally substituted with 1, 2, 3, or 4 halogen and 1 or 2 hydroxy; and L$^{5H}$, at each occurrence, is each independently a bond, or C$_1$-C$_6$alkylene (e.g., —CH$_2$—), wherein L$^{5H}$ is each optionally substituted with 1, 2, 3, or 4 halogen and 1 or 2 hydroxy.

Such embodiments may further include compounds where R$^{5a}$ is hydrogen.

Particular embodiments may include compounds where R$^5$ is R$^5$-IV, and

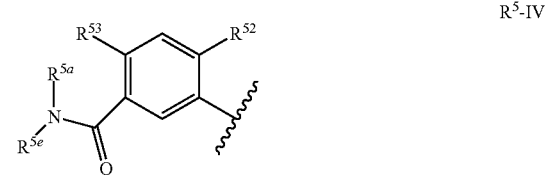

R$^5$-IV

R$^{5a}$ is hydrogen or methyl;

R$^{5e}$ is hydrogen, C$_1$-C$_{10}$alkyl (e.g., methyl, ethyl, isopropyl, n-butyl, isobutyl, t-butyl), C$_2$-C$_{10}$alkenyl, C$_2$-C$_{10}$alkynyl (e.g., 2-methylbut-3-yn-2-yl), C$_1$-C$_{10}$haloalkyl (e.g., 1,1,1-trifluoro-2-methylpropan-2-yl), or -L$^{5E}$-R$^{5f}$ (e.g., —C(CH$_3$)$_2$—CONHMe, —C(CH$_3$)$_2$—CONHCH$_2$CHF$_2$, —C(CH$_3$)$_2$—CO$_2$CH$_3$, —C(CH$_3$)$_2$CH$_2$—C(O)CH$_3$, —C(CH$_3$)$_2$—CONH-thiazol-2-yl);

R$^{5f}$ is —CON(R$^{5a}$)(R$^{5d}$) (e.g., CONHMe, CONHCH$_2$CHF$_2$, CONH-thiazol-2-yl), —O—R$^{5d}$ (e.g., OMe), —CN, —C(O)R$^{5d}$ (e.g., C(O)CH$_3$), —CO$_2$H, —CO$_2$R$^{5d}$ (e.g., CO$_2$CH$_3$), —N(R$^{5d}$)C(O)N(R$^{5d}$)$_2$, —S(O)$_2$R$^{5d}$ (e.g., S(O)$_2$Me), —S(O)R$^{5d}$ (e.g., S(O)Me), —SO$_2$N(R$^{5a}$)(R$^{5d}$) (e.g., SO$_2$NH$_2$, SO$_2$NHEt), —N(R$^{5a}$)(R$^{5d}$), —N(R$^{5d}$)C(O)R$^{5d}$ (e.g., NHC(O)Me), or —N(R$^{5d}$)S(O)$_2$R$^{5d}$ (e.g., —NHS(O)$_2$Me);

R$^{5d}$, at each occurrence, is each independently hydrogen, C$_1$-C$_6$alkyl (e.g., methyl, ethyl), C$_1$-C$_6$haloalkyl (e.g., 2,2-difluoroethyl), or -L$^{5E}$-G$^{5a}$ (e.g., bond-thiazol-2-yl);

$G^{5c}$, at each occurrence, is each independently $C_3$-$C_8$cycloalkyl (e.g., cyclopropyl), $C_6$-$C_{10}$aryl (e.g., phenyl), 4- to 10-membered heterocyclyl, or 5- to 10-membered heteroaryl (e.g., pyridinyl, thiazolyl, isoxazolyl, pyrazolyl), wherein $G^{5c}$ is optionally substituted with 1, 2, 3, 4, or 5 substituents selected from the group consisting of halogen (e.g., fluoro, chloro), oxo, $C_1$-$C_6$alkyl, $C_1$-$C_6$haloalkyl, —O—$C_1$-$C_6$alkyl (e.g., methoxy), and —O—$C_1$-$C_6$haloalkyl;

$R^{52}$ is hydrogen, $C_1$-$C_3$alkyl (e.g., methyl, ethyl, isopropyl), $C_1$-$C_{10}$haloalkyl (e.g., trifluoromethyl), halogen (e.g., fluoro, chloro), or —O—$R^{5b}$;

$R^{5b}$ is hydrogen, $C_1$-$C_3$alkyl (e.g., methyl, ethyl, isopropyl), $C_1$-$C_{10}$haloalkyl (e.g., trifluoromethyl), halogen (e.g., fluoro, chloro), —O—$C_1$-$C_6$alkyl (e.g., methoxy), or —O—$C_1$-$C_6$haloalkyl (e.g., trifluoromethoxy);

$R^{5b}$ is hydrogen, $C_1$-$C_6$alkyl (e.g., methyl), $C_2$-$C_6$alkenyl (e.g., allyl), $C_2$-$C_6$alkynyl (e.g., propargyl), $C_1$-$C_6$haloalkyl (e.g., trifluoromethyl, 2,2-difluoroethyl), -$L^{5D}$-$G^{5e}$ (e.g., bond-$G^{5e}$, —$CH_2CH_2$-pyrrolidin-1-yl, —$CH_2$-pyrrolidin-2-yl, —$CH_2$-pyrrolidin-3-yl, —$CH_2CH_2$-morpholin-4-yl, —$CH_2CH_2CH_2$-morpholin-4-yl, —$CH_2CH_2$-morpholin-2-yl —$CH_2CH_2$-4-methylpiperazin-1-yl, —$CH_2CH_2$-piperidinyl, —$CH_2$-piperidin-3-yl, —$CH_2$-pyridin-2-yl, —$CH_2CH_2$-pyridin-2-yl, —$CH_2$-pyridin-4-yl, —$CH_2$-imidazol-4-yl), or -$L^{5G}$-$R^{5c}$ (e.g., —$CH_2CH_2OH$, —$CH_2CH(CH_3)OH$, —$CH_2CH(CH_2CH_3)OH$, —$CH_2CH_2OMe$, —$CH_2CONH_2$, —$CH_2CH_2CONH_2$, —$CH_2CH_2NH_2$, —$CH_2CH_2N(CH_3)_2$, —$CH_2CH_2NHC(O)NH_2$, —$CH_2CN$);

$G^{5e}$ is $C_3$-$C_6$cycloalkyl (e.g., cyclobutyl, cyclopentyl), $C_6$-$C_{10}$aryl (e.g., phenyl), 4- to 7-membered heterocyclyl (e.g., morpholin-4-yl, pyrrolidin-1-yl, 4-methylpiperazin-1-yl, piperidinyl), or 5- to 6-membered heteroaryl (e.g., pyridin-2-yl, imidazol-4-yl), wherein $G^{5e}$ is optionally substituted with 1 or 2 substituents selected from the group consisting of halogen (e.g., fluoro), oxo, $C_1$-$C_6$alkyl (e.g., methyl, ethyl), $C_1$-$C_6$haloalkyl (e.g., trifluoromethyl), —OH, —O—$C_1$-$C_6$alkyl (e.g., $OCH_3$), and —O—$C_1$-$C_6$haloalkyl (e.g., $OCF_3$);

$R^{5c}$, at each occurrence, is each independently —CON($R^{5a}$)($R^{5g}$) (e.g., $CONH_2$), —O—$R^{5g}$ (e.g., OH, OMe), —OC(O)$R^{5g}$, —CN, —C(O)$R^{5g}$, —$CO_2H$, —$CO_2R^{5g}$, —N($R^{5g}$)C(O)N($R^{5g}$) (e.g., NHC(O)$NH_2$), —S—$R^{5g}$, —S(O)$_2R^{5g}$, —S(O)$R^{5g}$, —$SO_2N(R^{5a})(R^{5g})$, —N($R^{5a}$)($R^{5g}$) (e.g., $NH_2$, $N(CH_3)_2$), —N($R^{5g}$)C(O)$R^{5g}$, or —N($R^{5g}$)S(O)$_2R^{5g}$;

$R^{5g}$ is, at each occurrence, independently hydrogen, $C_1$-$C_6$alkyl (e.g., methyl, ethyl), $C_1$-$C_6$haloalkyl (e.g., 2,2-difluoroethyl), or -$L^{5H}$-$G^{5e}$ (e.g., bond-$C_3$-$C_6$cycloalkyl, —$CH_2$—$C_3$-$C_6$cycloalkyl);

$L^{5D}$, at each occurrence, is each independently a bond, $C_1$-$C_6$alkylene (e.g., —$CH_2$—, —$CH_2CH_2$—, —$CH_2CH_2CH_2$—), or $C_3$-$C_6$cycloalkyl (e.g., cyclopropyl);

$L^{5E}$, at each occurrence, is each independently $C_1$-$C_6$alkylene (e.g. —$(CH_2)_2$—, —$C(CH_3)_2$—, —$C(CH_3)_2CH_2$—), wherein $L^{5E}$ is optionally substituted with 1, 2, 3, or 4 halogen and 1 or 2 hydroxy;

$L^{5F}$, at each occurrence, is each independently a bond or $C_1$-$C_6$alkylene (e.g., —$CH_2$—), wherein $L^{5F}$ is optionally substituted with 1, 2, 3, or 4 halogen and 1 or 2 hydroxy;

$L^{5G}$ at each occurrence, is each independently $C_1$-$C_6$alkylene (e.g. —$(CH_2)_2$—, —$C(CH_3)_2$—, —$C(CH_3)_2CH_2$—, —$CH_2CH(CH_3)$—); and $L^{5H}$, at each occurrence, is each independently a bond or $C_1$-$C_6$alkylene (e.g., —$CH_2$—), wherein $L^{5H}$ is each optionally substituted with 1, 2, 3, or 4 halogen and 1 or 2 hydroxy.

Such embodiments may further include compounds where:

$R^{5e}$ is hydrogen, $C_1$-$C_{10}$alkyl (e.g., methyl, ethyl, isopropyl, n-butyl, isobutyl, t-butyl), $C_2$-$C_{10}$alkenyl, or $C_2$-$C_{10}$alkynyl (e.g., 2-methylbut-3-yn-2-yl), $C_1$-$C_{10}$haloalkyl (e.g., 1,1,1-trifluoro-2-methylpropan-2-yl);

$R^{52}$ is hydrogen, $C_1$-$C_3$alkyl (e.g., methyl, ethyl, isopropyl), $C_1$-$C_3$haloalkyl (e.g., trifluoromethyl), halogen (e.g., fluoro, chloro), —O—$C_1$-$C_6$alkyl (e.g., methoxy), or —O—$C_1$-$C_6$haloalkyl (e.g., trifluoromethoxy);

$R^{53}$ is hydrogen, $C_1$-$C_3$alkyl (e.g., methyl, ethyl, isopropyl), $C_1$-$C_3$haloalkyl (e.g., trifluoromethyl), halogen (e.g., fluoro, chloro), —O—$C_1$-$C_6$alkyl (e.g., methoxy), or —O—$C_1$-$C_6$haloalkyl (e.g., trifluoromethoxy), or $G^{5d}$;

$G^{5d}$ is $C_3$-$C_8$cycloalkyl, $C_6$-$C_{10}$aryl (e.g., phenyl), 4- to 10-membered heterocyclyl (e.g., tetrahydropyrimidinyl), or 5- to 10-membered heteroaryl (e.g., furanyl, thienyl, pyrazolyl, pyridinyl, pyrimidinyl, oxadiazolyl, isoquinolinyl, indolyl), wherein $G^{5d}$ is optionally substituted with 1, 2, 3, 4, or 5 substituents selected from the group consisting of oxo, halogen (e.g. fluoro, chloro), $C_1$-$C_6$alkyl (e.g., methyl, ethyl, n-propyl, isopropyl), $C_1$-$C_6$haloalkyl (e.g., trifluoromethyl), —O—$R^{5d}$ (e.g., methoxy, ethoxy), —CN, —N($R^{5a}$)C(O)$R^{5d}$ (e.g., NHC(O)Me), —CON($R^{5a}$)($R^{5d}$) (e.g., $CONH_2$, CON-HEt), —C(O)$R^{5d}$ (e.g., C(O)Me), —OC(O)$R^{5d}$, —$CO_2H$, —$CO_2R^{5d}$ (e.g., $CO_2Me$), —N($R^{5a}$)C(O)N($R^{5d}$)$_2$ (e.g., NHC(O)NHMe), —S—$R^{5d}$, —S(O)$_2R^{5d}$ (e.g., S(O)$_2$Me), —S(O)$R^{5d}$ (e.g., S(O)Me), —$SO_2N(R^{5a})(R^{5d})$ (e.g., $SO_2NH_2$, $SO_2NHEt$), —N($R^{5a}$)($R^{5d}$) (e.g., $NH_2$), —N($R^{5a}$)S(O)$_2R^{5d}$ (e.g., —NHS(O)$_2$Me), N($R^{5a}$)C(O)O($R^{5d}$) (e.g., NHC(O)OMe), -$L^{5C}$-O—$R^{5d}$ (e.g., hydroxymethyl, methoxymethyl), -$L^{5C}$-CN (e.g., cyanomethyl), $G^{5e}$ (e.g., phenyl), and -$L^{5C}$-$G^{5c}$ (e.g., benzyl);

Such embodiments may further include compounds where:

$R^{5e}$ is each independently hydrogen, $C_1$-$C_{10}$alkyl (e.g., methyl, ethyl, isopropyl, n-butyl, isobutyl, t-butyl), $C_2$-$C_{10}$alkenyl, or $C_2$-$C_{10}$alkynyl (e.g., 2-methylbut-3-yn-2-yl), $C_1$-$C_{10}$haloalkyl (e.g., 1,1,1-trifluoro-2-methylpropan-2-yl);

$R^{52}$ is hydrogen, $C_1$-$C_3$alkyl (e.g., methyl, ethyl, isopropyl), $C_1$-$C_3$haloalkyl (e.g., trifluoromethyl), halogen (e.g., fluoro, chloro), or —O—$R^{5b}$;

$R^{53}$ is hydrogen, $C_1$-$C_3$alkyl (e.g., methyl, ethyl, isopropyl), $C_1$-$C_3$haloalkyl (e.g., trifluoromethyl), halogen (e.g., fluoro, chloro), —O—$C_1$-$C_6$alkyl (e.g., methoxy), or —O—$C_1$-$C_6$haloalkyl (e.g., trifluoromethoxy); and $R^{5b}$ is hydrogen, $C_1$-$C_6$alkyl (e.g., methyl), $C_1$-$C_6$haloalkyl (e.g., trifluoromethyl, 2,2-difluoroethyl), -$L^{5D}$-$G^{5e}$ (e.g., bond-cyclopropyl, bond-cyclobutyl, —$CH_2CH_2$-pyrrolidin-1-yl, —$CH_2$-pyrrolidin-2-yl, —$CH_2$-pyrrolidin-3-yl, —$CH_2CH_2$-morpholin-4-yl, —$CH_2CH_2CH_2$-morpholin-4-yl, —$CH_2CH_2$-morpholin-2-yl —$CH_2CH_2$-4-methylpiperazin-1-yl, —$CH_2CH_2$-piperidinyl, —$CH_2$-piperidin-3-yl, —$CH_2$-pyridin-2-yl, —$CH_2CH_2$-pyridin-2-yl, —$CH_2$-pyridin-4-yl, —$CH_2$-imidazol-4-yl), or -$L^{5G}$-$R^{5c}$ (e.g., —$CH_2CH_2OH$, —$CH_2CH(CH_3)OH$, —$CH_2CH(CH_2CH_3)OH$, —$CH_2CH_2OMe$, —$CH_2CONH_2$, —$CH_2CH_2CONH_2$, —$CH_2CH_2NH_2$, —$CH_2CH_2N(CH_3)_2$, —$CH_2CH_2NHC(O)NH_2$, —$CH_2CN$);

$G^{5e}$ is $C_3$-$C_6$cycloalkyl (e.g., cyclobutyl, cyclopentyl), $C_6$-$C_{10}$aryl (e.g., phenyl), 4- to 7-membered heterocyclyl (e.g., morpholin-4-yl, pyrrolidin-1-yl, 4-methylpiperazin-1-yl, piperidinyl), or 5- to 6-membered heteroaryl (e.g., pyridin-2-yl, imidazol-4-yl), wherein $G^{5e}$ is optionally substituted with 1, 2, 3, or 4 substituents selected from the group consisting of halogen (e.g., fluoro), oxo, $C_1$-$C_6$alkyl (e.g., methyl, ethyl), $C_1$-$C_6$haloalkyl (e.g., trifluoromethyl), —OH, —O—$C_1$-$C_6$alkyl (e.g., $OCH_3$), and —O—$C_1$-$C_6$haloalkyl (e.g., $OCF_3$).

$R^{5c}$, at each occurrence, is each independently —CON$(R^{5a})(R^{5g})$ (e.g., $CONH_2$), —O—$R^{5g}$ (e.g., OH, OMe), —OC(O)$R^{5g}$, —CN, —C(O)$R^{5g}$, —$CO_2$H, —$CO_2R^{5g}$, —N($R^{5g}$)C(O)N($R^{5g}$)$_2$ (e.g., NHC(O)$NH_2$), —S—$R^{5g}$, —S(O)$_2R^{5g}$, —S(O)$R^{5g}$, —$SO_2$N($R^{5a}$)($R^{5g}$), —N($R^{5a}$)($R^{5g}$) (e.g., $NH_2$, N($CH_3$)$_2$), —N($R^{5g}$)C(O)$R^{5g}$, or —N($R^{5g}$)S(O)$_2R^{5g}$;

$R^{5g}$ is independently, at each occurrence, hydrogen, $C_1$-$C_6$alkyl (e.g., methyl, ethyl), $C_1$-$C_6$haloalkyl (e.g., 2,2-difluoroethyl), or -$L^{5H}$-$G^{5e}$ (e.g., bond-$C_3$-$C_6$cycloalkyl, —$CH_2$—$C_3$-$C_6$cycloalkyl);

$L^{5D}$ is a bond, $C_1$-$C_6$alkylene (e.g., —$CH_2$—, —$CH_2CH_2$—, —$CH_2CH_2CH_2$—), or $C_3$-$C_6$cycloalkyl (e.g., cyclopropyl);

$L^{5G}$ at each occurrence, is each independently $C_1$-$C_6$alkylene (e.g. —(CH$_2$)$_2$—, —C(CH$_3$)$_2$—, —C(CH$_3$)$_2$CH$_2$—, —CH$_2$CH(CH$_3$)—); and $L^{5H}$, at each occurrence, is each independently a bond, or $C_1$-$C_6$alkylene (e.g., —$CH_2$—), wherein $L^{5H}$ is each optionally substituted with 1, 2, 3, or 4 halogen and 1 or 2 hydroxy.

It will be appreciated that the present disclosure includes particular aspects, embodiments, and groups of compounds derived from combinations of the variables described hereinabove.

In embodiments are compounds of formula (I) wherein:
$W^1$ is $CR^6$, $W^2$ is $CR^5$, $W^3$ is $CR^4$, $W^4$ is $CR^3$, $V^1$ is C, $V^2$ is C and $V^3$ is O (i.e. benzofuranyl);

$R^1$ is (i), (ii), (iii), (iv), or (v);

$R^{1a}$, at each occurrence, is each independently hydrogen, halogen, $C_1$-$C_3$alkyl, or $C_1$-$C_3$haloalkyl;

$R^{1b}$, at each occurrence, is each independently hydrogen, halogen, $C_1$-$C_3$alkyl, or $C_1$-$C_3$haloalkyl, wherein two geminal $R^{1b}$ taken together optionally are oxo;

$R^{1c}$ is $C_1$-$C_3$alkyl;

$R^2$ is $L^{2A}$-$G^{2a}$;

$L^{2A}$ is a bond;

$G^{2a}$ is $C_6$-$C_{10}$aryl optionally substituted with a substituent selected from the group consisting of $R^{20}$ or $G^{2b}$;

$R^{20}$ is hydrogen, $C_1$-$C_{10}$alkyl, $C_2$-$C_{10}$alkenyl, $C_2$-$C_{10}$alkynyl, $C_1$-$C_{10}$haloalkyl, $C_2$-$C_{10}$haloalkenyl, $C_2$-$C_{10}$haloalkynyl, halogen, —N($R^{2a}$)($R^{2b}$), —O—$R^{2b}$, or —C(=$CH_2$)$R^{2b}$;

$R^{2a}$ is hydrogen or $C_1$-$C_3$alkyl;

$R^{2b}$ is $C_1$-$C_{10}$alkyl, $L^{2C}$-$R^{2c}$, $G^{2b}$, or -$L^{2C}$-$G^{2b}$;

$L^{2C}$ is $C_1$-$C_6$alkylene;

$R^{2c}$ is $CO_2$($C_1$-$C_3$alkyl) or —OC(O)$C_1$-$C_3$alkyl;

$G^{2b}$ is $C_3$-$C_{10}$cycloalkyl, $C_5$-$C_{10}$cycloalkenyl, $C_6$-$C_{10}$aryl, 3- to 10-membered heterocyclyl, or 5- to 10-membered heteroaryl, wherein $G^{2b}$ is optionally substituted with 1, 2, 3, 4, or 5 substituents selected from the group consisting of $C_1$-$C_{10}$alkyl, $C_2$-$C_{10}$alkenyl, $C_2$-$C_{10}$alkynyl, $C_1$-$C_{10}$haloalkyl, $C_2$-$C_{10}$haloalkenyl, $C_2$-$C_{10}$haloalkynyl, halogen, oxo, cyano, hydroxy, —O—$C_1$-$C_6$alkyl, —O—$C_1$-$C_6$haloalkyl, —$C_1$-$C_3$alkylene-O—H, —$C_1$-$C_3$alkylene-O—$C_1$-$C_6$alkyl, C(O)H, —$C_1$-$C_3$alkylene-$NH_2$, —$NH_2$, and —C(O)O$C_1$-$C_6$alkyl;

$R^3$ is hydrogen;

$R^4$ is —N($R^{40}$)(SO$_2R^{4a}$);

$R^{4a}$ is $C_1$-$C_6$alkyl;

$R^{40}$ is hydrogen, $C_1$-$C_{10}$alkyl, $C_1$-$C_{10}$alkyl substituted with 2 hydroxy substituents, $C_2$-$C_{10}$alkenyl, $C_1$-$C_{10}$haloalkyl, $C_2$-$C_{10}$haloalkenyl, -$L^{4A}$-$R^{4c}$, -$L^{4A}$-$G^{4a}$, -$L^{4A}$-S(O)$_2$-$G^{4a}$, -$L^{4A}$-C(O)-$G^{4a}$, or -$L^{4A}$-O-$G^{4a}$;

$L^{4A}$ is $C_1$-$C_{10}$alkylene;

$R^{4c}$ is —O—$R^{4b}$, —O—Si($C_1$-$C_6$alkyl)$_3$, —S—$R^{4b}$, —N($R^{4b}$)$_2$, —N($R^{4b}$)S(O)$_2R^{4b}$, —OC(O)$R^{4b}$, —N($R^{4b}$)C(O)$R^{4b}$, —C(O)N($R^{4b}$)S(O)$_2R^{4b}$, cyano, —C(O)N($R^{4b}$)$_2$, —S(O)$R^{4b}$, —S(O)$_2R^{4b}$, —SO$_2$N($R^{4b}$)$_2$, —$CO_2R^{4b}$, —C(NOH)N($R^{4b}$)$_2$, —C(O)$R^{4b}$, —C(O)C(OH)($R^{4b}$)$_2$, or —P(O)(O$R^{4b}$)$_2$;

$R^{4b}$, at each occurrence, is each independently hydrogen or $C_1$-$C_6$alkyl;

$G^{4a}$ is $C_3$-$C_{12}$cycloalkyl, $C_6$-$C_{12}$aryl, 3- to 12-membered heterocyclyl, or 5- to 12-membered heteroaryl wherein $G^{4a}$ is optionally substituted with $G^{4b}$ and optionally substituted with 1, 2, 3, 4, or 5 substituents selected from the group consisting of halogen, oxo, $C_1$-$C_3$alkyl, $C_1$-$C_3$haloalkyl, —OH, —O—$C_1$-$C_3$alkyl, —O—$C_1$-$C_3$haloalkyl, thioxo, —$NH_2$, —NH($C_1$-$C_3$alkyl), and —N($C_1$-$C_3$alkyl)$_2$;

$G^{4b}$ is $C_3$-$C_{12}$cycloalkyl, 3- to 12-membered heterocyclyl, $C_6$-$C_{12}$aryl, or 5- to 12-membered heteroaryl, wherein $G^{4b}$ is optionally substituted with 1, 2, 3, 4, or 5 substituents selected from the group consisting of halogen, oxo, $C_1$-$C_6$alkyl, $C_1$-$C_6$haloalkyl, hydroxy, —O—$C_1$-$C_6$alkyl, —O—$C_1$-$C_6$haloalkyl, —S(O)—$C_1$-$C_6$alkyl, —S(O)$_2$—$C_1$-$C_6$alkyl, —C(O)—$C_1$-$C_6$alkyl, $C_1$-$C_3$alkylene-OH, $C_1$-$C_3$alkylene-O—$C_1$-$C_3$alkyl, $C_1$-$C_3$alkylene-N($C_1$-$C_3$alkyl)$_2$, and $C_1$-$C_3$alkylene-(N-heterocyclyl);

$R^5$ is hydrogen, $C_3$-$C_6$cycloalkyl, or —O—$C_1$-$C_6$alkyl; and $R^6$ is hydrogen or fluorine.

Such embodiments may include compounds where $R^2$ is $R^2$-II or $R^2$-IV, and $G^{2b}$ and $R^{20}$ are as defined herein.

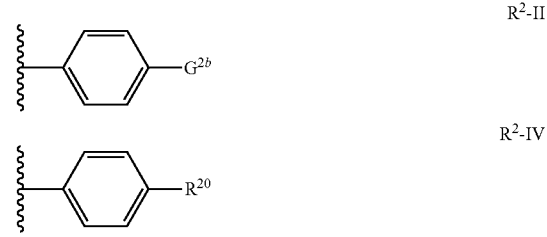

Embodiments also include compounds of formula (I), wherein $W^1$ is $CR^6$, $W^2$ is $CR^5$, $W^3$ is $CR^4$, $W^4$ is $CR^3$, $V^1$ is C, $V^2$ is C and $V^3$ is O (i.e. benzofuranyl); and wherein $R^1$ is (i), (ii), (iii), or (v). Embodiments include compounds of formula (I), wherein $W^1$ is $CR^6$, $W^2$ is $CR^5$, $W^3$ is $CR^4$, $W^4$ is $CR^3$, $V^1$ is C, $V^2$ is N, and $V^3$ is N (i.e. pyrazolo[1,5-c]pyridinyl), wherein $R^1$ is (i), (ii), (iii), or (v). Such embodiments may include groups of compounds wherein:

$R^{1a}$, at each occurrence, is each independently hydrogen, halogen (e.g., fluoro), $C_1$-$C_3$alkyl (e.g., methyl), or $C_1$-$C_3$haloalkyl (e.g., trifluoromethyl);

$R^{1b}$, at each occurrence, is each independently hydrogen, halogen, or $C_1$-$C_3$alkyl (e.g., methyl, ethyl, propyl), wherein two geminal $R^{1b}$ taken together optionally are oxo;

$R^2$ is $R^2$-II or $R^2$-IV;

$R^{20}$ is hydrogen, halogen (e.g., fluoro), $C_1$-$C_{10}$alkyl (e.g., ethyl, butyl, n-hexyl, n-octyl), $C_2$-$C_{10}$alkenyl (e.g., but-1-enyl, hex-1-enyl, oct-1-enyl), $C_2$-$C_{10}$alkynyl (e.g., but-1-ynyl, hex-1-ynyl, oct-1-ynyl), $C_1$-$C_{10}$haloalkyl (e.g., trifluorobutyl, trifluorohexyl), $C_2$-$C_{10}$haloalkenyl, $C_2$-$C_{10}$haloalkynyl, —N($R^{2a}$)($G^{2b}$), —O-$G^{2b}$, —O-$L^{2C}$-$G^{2b}$, —O—$C_1$-$C_{10}$alkyl (e.g., —O-methyl, —O-n-pentyl, —O-isopentyl, —O-isopropyl, —O-n-hexyl), —O-$L^{2C}$-$R^{2c}$, or —C(=$CH_2$)$G^{2b}$;

$R^{2a}$ is hydrogen or $C_1$-$C_3$alkyl (e.g., methyl);

$G^{2b}$ is $C_3$-$C_{10}$cycloalkyl (e.g., cyclopropyl, cyclobutyl), $C_5$-$C_{10}$cycloalkenyl (e.g., cyclohexenyl), $C_6$-$C_{10}$aryl (e.g., phenyl), 3- to 10-membered heterocyclyl, or 5- to 10-membered heteroaryl (e.g., pyridyl, thiophenyl, indolyl, benzo[d]oxadiazolyl), wherein $G^{2b}$ is optionally substituted with 1, 2, 3, 4, or 5 substituents selected from the group consisting of $C_1$-$C_6$alkyl (e.g., methyl, ethyl, t-butyl, hexyl), $C_2$-$C_6$alkenyl, $C_2$-$C_6$alkynyl, $C_1$-$C_6$haloalkyl (e.g., trifluoromethyl, trifluoroethyl, trifluorobutyl), $C_2$-$C_6$haloalkenyl, $C_2$-$C_6$haloalkynyl, halogen (e.g., fluoro, chloro), oxo, cyano, hydroxy, C(O)H, —O—$C_1$-$C_3$alkyl (e.g., methoxy), —$C_1$-$C_3$alkylene-O—H (e.g., CH$_2$OH), —$C_1$-$C_3$alkylene-O—$C_1$-$C_3$alkyl (e.g., CH$_2$OCH$_3$), C(O)H, —$C_1$-$C_3$alkylene-NH$_2$ (e.g., CH$_2$NH$_2$), —NH$_2$, and —C(O)OC$_1$-$C_3$alkyl (e.g., C(O)OEt);

$L^{2C}$ is $C_1$-$C_6$alkylene (e.g., CH$_2$, —C(CH$_3$)(H)—, CH$_2$CH$_2$, —(CH$_2$)$_3$—);

$R^{2c}$ is CO$_2$(C$_1$-$C_3$alkyl) or —OC(O)C$_1$-$C_3$alkyl;

$R^3$ is hydrogen;

$R^4$ is —N(R$^{40}$)(SO$_2$R$^{4a}$);

$R^{4a}$ is $C_1$-$C_3$alkyl (e.g., methyl);

$R^{40}$ is hydrogen, $C_1$-$C_{10}$alkyl (e.g., ethyl, propyl, isobutyl, isopentyl, n-pentyl, n-hexyl, 4-methylpentyl), $C_1$-$C_{10}$alkyl substituted with 2 hydroxy substituents (e.g., 2,3-dihydroxypropyl, 3,4-dihydroxybutyl, 3,4-dihydroxy-4-methylpentyl), $C_2$-$C_{10}$alkenyl (e.g., allyl, 3-methylbut-2-enyl, 4-methylpent-3-enyl), $C_1$-$C_{10}$haloalkyl (e.g., 3-fluoropropyl, 3,3,3-trifluoropropyl, 4-fluorobutyl, 4,4,4-trifluorobutyl), $C_2$-$C_{10}$haloalkenyl (e.g., 5,6,6-trifluorohex-5-enyl), -L$^{4A}$-R$^{4c}$, -L$^{4A}$-G$^{4a}$, -L$^{4A}$-S(O)$_2$-G$^{4a}$, -L$^{4A}$-C(O)-G$^{4a}$, or -L$^{4A}$-O-G$^{4a}$;

$L^{4A}$ is $C_1$-$C_{10}$alkylene (e.g., CH$_2$, CH$_2$CH$_2$, (CH$_2$)$_3$, (CH$_2$)$_4$, CH$_2$C(H)(CH$_3$), 5-methylhexyl);

$R^{4c}$ is —O—R$^{4b}$, —O—Si(C$_1$-$C_6$alkyl)$_3$ (e.g., —O—SiMe$_2$t-Bu), —S—R$^{4b}$, —N(R$^{4b}$)$_2$, —N(R$^{4b}$)S(O)$_2$R$^{4b}$, —OC(O)R$^{4b}$, —N(R$^{4b}$)C(O)R$^{4b}$, cyano, —C(O)N(R$^{4b}$)$_2$, —C(O)N(R$^{4b}$)S(O)$_2$R$^{4b}$, —S(O)R$^{4b}$, —S(O)$_2$R$^{4b}$, —SO$_2$N(R$^{4b}$)$_2$, —CO$_2$R$^{4b}$, —C(NOH)N(R$^{4b}$)$_2$, —C(O)R$^{4b}$, —C(O)C(OH)(R$^{4b}$)$_2$, or —P(O)(OR$^{4b}$)$_2$;

$R^{4b}$, at each occurrence, is each independently hydrogen or $C_1$-$C_6$alkyl (e.g., methyl, ethyl, propyl, pentyl);

$G^{4a}$ is $C_3$-$C_8$cycloalkyl (e.g., cyclopropyl, 2,2-difluorocycloprop-1-yl, cyclopentyl, cyclohexyl), $C_6$-$C_{10}$aryl (e.g., phenyl, 4-methoxyphenyl, 3-trifluoromethylphenyl, naphthyl), 4- to 8-membered heterocyclyl (e.g., tetrahydrofuran-2-yl, pyrrolidin-1-yl, pyrrolidin-2-yl, 1,1-dioxotetrahydrothiephen-3-yl, tetrahydropyran-4-yl, morpholin-4-yl, 5-thioxo-4,5-dihydro-1,2,4-oxadiazol-3-yl, 5-oxo-4,5-dihydro-1,2,4-oxadiazol-3-yl, 5-oxo-4,5-dihydro-1,2,4-thiadiazol-3-yl, 5-oxo-4,5-dihydro-1,3,4-oxadiazol-2-yl, 1,1-dioxothiomorpholin-4-yl, piperidin-1-yl, 1,3-dioxoisoindolin-2-yl), or 5- to 10-membered heteroaryl (e.g., 1H-tetrazol-5-yl, 2-aminothiazol-4-yl, 2-bromothiazol-5-yl, 3-hydroxyisoxazol-5-yl, 4-methylthiazol-5-yl, pyrrol-1-yl, 2-bromo-4-(trifluoromethyl)thiazol-5-yl), wherein $G^{4a}$ is optionally substituted with $G^{4b}$ and optionally substituted with 1, 2, 3, 4, or 5 substituents selected from the group consisting of halogen, oxo, $C_1$-$C_3$alkyl, $C_1$-$C_3$haloalkyl, —OH, —O—$C_1$-$C_3$alkyl, —O—$C_1$-$C_3$haloalkyl, thioxo, —NH$_2$, —NH(C$_1$-$C_3$alkyl), and —N(C$_1$-$C_3$alkyl)$_2$;

$G^{4b}$ is $C_6$-$C_{10}$aryl (e.g., phenyl), 5- to 10-membered heterocyclyl (e.g., dihydrobenzofuranyl), or 5- to 10-membered heteroaryl (e.g., indolyl, pyrrolyl, benzo[d]imidazolyl, pyridinyl), wherein $G^{4b}$ is optionally substituted with 1, 2, 3, 4, or 5 substituents selected from the group consisting of halogen, oxo, $C_1$-$C_6$alkyl, $C_1$-$C_6$haloalkyl, hydroxy, —O—$C_1$-$C_6$alkyl, —O—$C_1$-$C_6$haloalkyl, —S(O)—$C_1$-$C_6$alkyl, —S(O)$_2$—$C_1$-$C_6$alkyl, —C(O)—$C_1$-$C_6$alkyl, $C_1$-$C_3$alkylene-OH, $C_1$-$C_3$alkylene-O—$C_1$-$C_3$alkyl, $C_1$-$C_3$alkylene-N(C$_1$-$C_3$alkyl)$_2$, and $C_1$-$C_3$alkylene-(N-heterocyclyl);

$R^5$ is hydrogen, $C_3$-$C_6$cycloalkyl (e.g., cyclopropyl), —O—$C_1$-$C_3$alkyl (e.g., isopropoxy); and $R^6$ is hydrogen.

Such embodiments may further include compounds wherein:

$R^{40}$ is hydrogen, $C_1$-$C_{10}$alkyl, $C_1$-$C_{10}$alkyl substituted with 2 hydroxy substituents, $C_2$-$C_{10}$alkenyl, $C_1$-$C_{10}$haloalkyl, $C_2$-$C_{10}$haloalkenyl, -L$^{4A}$-R$^{4c}$, -L$^{4A}$-G$^{4a}$, -L$^{4A}$-S(O)$_2$-G$^{4a}$, -L$^{4A}$-C(O)-G$^{4a}$, -L$^{4A}$-O-G$^{4a}$, or

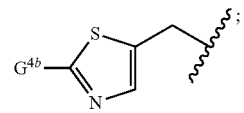

$G^{4a}$ is $C_3$-$C_6$cycloalkyl, phenyl, 4- to 8-membered heterocyclyl, or 5- to 6-membered heteroaryl, wherein $G^{4a}$ is optionally substituted with 1, 2, 3, 4, or 5 substituents selected from the group consisting of halogen, oxo, $C_1$-$C_3$alkyl, $C_1$-$C_3$haloalkyl, —OH, —O—$C_1$-$C_3$alkyl, —O—$C_1$-$C_3$haloalkyl, thioxo, —NH$_2$, —NH(C$_1$-$C_3$alkyl), and —N(C$_1$-$C_3$alkyl)$_2$; and $G^{4b}$ is phenyl, 5- to 10-membered heterocyclyl, or 5- to 10-membered heteroaryl wherein $G^{4b}$ is optionally substituted with 1, 2, 3, 4, or 5 substituents selected from the group consisting of halogen, oxo, $C_1$-$C_6$alkyl, $C_1$-$C_6$haloalkyl, —O—$C_1$-$C_6$alkyl, and —O—$C_1$-$C_6$haloalkyl.

Embodiments may include compounds of Formula (I), wherein $W^1$ is CR$^6$, $W^2$ is CR$^5$, $W^3$ is CR$^4$, $W^4$ is CR$^3$, $V^1$ is C, $V^2$ is C and $V^3$ is O (i.e. benzofuranyl), or wherein $W^1$ is CR$^6$, $W^2$ is CR$^5$, $W^3$ is CR$^4$, $W^4$ is CR$^3$, $V^1$ is C, $V^2$ is N, and $V^3$ is N (i.e. pyrazolo[1,5-a]pyridinyl), wherein:

$R^1$ is (i), (ii), or (iii);

$R^{1a}$, at each occurrence, is each independently hydrogen or methyl;

$R^{1b}$, at each occurrence, is each independently hydrogen or methyl;

$R^2$ is $R^2$-IV;

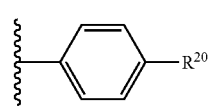

$R^{20}$ is hydrogen, halogen (e.g., fluoro), $C_2$-$C_{10}$alkenyl (e.g., hex-1-enyl), —N(R$^{2a}$)(G$^{2b}$), or —C(=CH$_2$)G$^{2b}$;

$R^{2a}$ is hydrogen;

$G^{2b}$ is $C_6$-$C_{10}$aryl (e.g., phenyl, naphthyl) or 5- to 10-membered heteroaryl (e.g., thienyl, pyridinyl), wherein $G^{2b}$ is optionally substituted with 1, 2, 3, 4, or 5 substituents selected from the group consisting of $C_1$-$C_6$alkyl, $C_2$-$C_6$alkenyl, $C_2$-$C_6$alkynyl, $C_1$-$C_6$haloalkyl, $C_2$-$C_{10}$haloalkenyl, $C_2$-$C_{10}$haloalkynyl, halogen, oxo, cyano, hydroxy, —O—$C_1$-$C_6$alkyl, and —O—$C_1$-$C_3$haloalkyl;

$R^3$ is hydrogen;

$R^4$ is —N(R$^{40}$)(SO$_2$R$^{4a}$);

$R^{4a}$ is methyl;

$R^{40}$ is hydrogen, $C_1$-$C_6$alkyl (e.g., ethyl, propyl, isobutyl, isopentyl, n-pentyl, n-hexyl, 4-methylpentyl), $C_1$-$C_6$haloalkyl (e.g., 3-fluoropropyl, 3,3,3-trifluoropropyl, 4-fluorobutyl, 4,4,4-trifluorobutyl), -$L^{4A}$-$R^{4c}$, -$L^{4A}$-$G^{4a}$, or

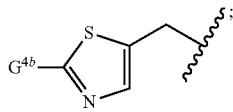

$L^{4A}$ is $C_1$-$C_{10}$alkylene (e.g., $CH_2$, $CH_2CH_2$, $(CH_2)_3$, $(CH_2)_4$, 5-methylhexyl, —$(CH_2)_3CH(CH_3)$—);

$R^{4c}$ is —O—$R^{4b}$, cyano, —C(O)N($R^{4b}$)$_2$, —S(O)$R^{4b}$, —S(O)$_2R^{4b}$, —SO$_2$N($R^{4b}$)$_2$, or —C(O)$R^{4b}$;

$R^{4b}$, at each occurrence, is each independently hydrogen or $C_1$-$C_3$alkyl (e.g., methyl, ethyl);

$G^{4a}$ is $C_3$-$C_6$cycloalkyl, phenyl, 4- to 8-membered heterocyclyl, or 5- to 6-membered heteroaryl, wherein $G^{4a}$ is optionally substituted with 1, 2, 3, 4, or 5 substituents selected from the group consisting of halogen, oxo, $C_1$-$C_3$alkyl, $C_1$-$C_3$haloalkyl, —OH, —O—$C_1$-$C_3$alkyl, —O—$C_1$-$C_3$haloalkyl, thioxo, —NH$_2$, —NH($C_1$-$C_3$alkyl), and —N($C_1$-$C_3$alkyl)$_2$;

$G^{4b}$ is phenyl, 5- to 10-membered heterocyclyl, or 5- to 10-membered heteroaryl wherein $G^{4b}$ is optionally substituted with 1, 2, 3, 4, or 5 substituents selected from the group consisting of halogen, oxo, $C_1$-$C_6$alkyl, $C_1$-$C_6$haloalkyl, —O—$C_1$-$C_6$alkyl, and —O—$C_1$-$C_6$haloalkyl;

$R^5$ is hydrogen, cyclopropyl, or isopropoxy; and $R^6$ is hydrogen.

Such embodiments may further include compounds wherein:

$R^5$ is cyclopropyl.

Embodiments may include compounds of Formula (I), wherein $W^1$ is $CR^6$, $W^2$ is $CR^5$, $W^3$ is $CR^4$, $W^4$ is $CR^3$, $V^1$ is C, $V^2$ is N, and $V^3$ is N (i.e. pyrazolo[1,5-a]pyridinyl), wherein:

$R^1$ is (i);

$R^{40}$ is $C_1$-$C_6$alkyl; and $R^{20}$ is hydrogen or halogen.

Embodiments may include compounds of Formula (I), wherein $W^1$ is $CR^6$, $W^2$ is $CR^5$, $W^3$ is $CR^4$, $W^4$ is $CR^3$, $V^1$ is C, $V^2$ is C and $V^3$ is O (i.e. benzofuranyl), or wherein $W^1$ is $CR^6$, $W^2$ is $CR^5$, $W^3$ is $CR^4$, $W^4$ is $CR^3$, $V^1$ is C, $V^2$ is N, and $V^3$ is N (i.e. pyrazolo[1,5-a]pyridinyl), are particular groups of compounds wherein:

$R^{40}$ is -$L^{4A}$-$G^{4a}$-$G^{4b}$;

$L^{4A}$- is $C_1$-$C_3$alkylene; and $G^{4a}$-$G^{4b}$ is

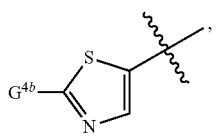

wherein $G^{4b}$ is $C_6$-$C_{10}$ aryl (e.g., phenyl, 4-(methylsulfinyl)phenyl, 3-(hydroxymethyl)phenyl, 3-(pyrrolidin-1-ylmethyl)phenyl, 3-((dimethylamino)methyl)phenyl), 5- to 10-membered heterocyclyl (e.g., 6-oxo-1,6-dihydropyridin-3-yl, 2,4-dioxo-1,2,3,4-tetrahydropyrimidin-5-yl, dihydrobenzofuranyl, indolin-5-yl), or 5- to 10-membered heteroaryl (e.g., 1H-indol-5-yl, 1-methyl-1H-indol-5-yl, 1H-indol-6-yl, 1H-pyrrolo[2,3-b]pyridin-5-yl, 1H-indazol-5-yl, 2,5-dimethyl-1H-pyrrol-1-yl, 1H-benzo[d]imidazol-6-yl, 1-methyl-1H-benzo[d]imidazol-6-yl, 6-methoxypyridin-3-yl, 2-methoxypyridin-3-yl, 5-fluoropyridin-3-yl, pyridin-3-yl, 2-methoxypyrimidin-5-yl, 2,4-di-tert-butoxypyrimidin-5-yl, 1-methyl-1H-pyrazol-4-yl), wherein $G^{4b}$ is optionally substituted with 1, 2, 3, 4, or 5 substituents selected from the group consisting of halogen, oxo, $C_1$-$C_6$alkyl, $C_1$-$C_6$haloalkyl, hydroxy, —O—$C_1$-$C_6$alkyl, —O—$C_1$-$C_6$haloalkyl, —S(O)—$C_1$-$C_6$alkyl, —S(O)$_2$—$C_1$-$C_6$alkyl, —C(O)—$C_1$-$C_6$alkyl, $C_1$-$C_3$alkylene-OH, $C_1$-$C_3$alkylene-O—$C_1$-$C_3$alkyl, $C_1$-$C_3$alkylene-N($C_1$-$C_3$alkyl)$_2$, and $C_1$-$C_3$alkylene-(N-heterocyclyl).

Embodiments may include compounds of Formula (I), wherein:

$R^1$ is (i), (ii), (iii), (iv), or (v);

$R^{1a}$ is hydrogen, halogen, $C_1$-$C_3$alkyl, or $C_1$-$C_3$haloalkyl;

$R^{1b}$, at each occurrence, is each independently hydrogen, halogen, $C_1$-$C_3$alkyl, or $C_1$-$C_3$haloalkyl, wherein two geminal $R^{1b}$ taken together optionally are oxo;

$R^{1c}$ is $C_1$-$C_3$alkyl;

$R^2$ is $G^{2a}$;

$G^{2a}$ is $C_6$-$C_{10}$aryl optionally substituted with a substituent selected from the group consisting of $R^{20}$ or $G^{2b}$;

$R^{20}$ is hydrogen, $C_1$-$C_{10}$alkyl, $C_2$-$C_{10}$alkenyl, $C_2$-$C_{10}$alkynyl, $C_1$-$C_{10}$haloalkyl, $C_2$-$C_{10}$haloalkenyl, $C_2$-$C_{10}$haloalkynyl, halogen, —N($R^{2a}$)($R^{2b}$), —O—$R^{2b}$, or —C(=$CH_2$)$R^{2b}$;

$R^{2a}$ is hydrogen or $C_1$-$C_3$alkyl;

$R^{2b}$ is $C_1$-$C_{10}$alkyl, $L^{2c}$-$R^{2c}$; $G^{2b}$, or -$L^{2c}$-$G^{2b}$;

$L^{2C}$ is $C_1$-$C_6$alkylene;

$R^{2c}$ is CO$_2$($C_1$-$C_3$alkyl) or —OC(O)$C_1$-$C_3$alkyl;

$G^{2b}$ is $C_3$-$C_{10}$cycloalkyl, $C_5$-$C_{10}$cycloalkenyl, $C_6$-$C_{10}$aryl, 3- to 10-membered heterocyclyl, or 5- to 10-membered heteroaryl, wherein $G^{2b}$ is optionally substituted with 1, 2, 3, 4, or 5 substituents selected from the group consisting of $C_1$-$C_{10}$alkyl, $C_2$-$C_{10}$alkenyl, $C_2$-$C_{10}$alkynyl, $C_1$-$C_{10}$haloalkyl, $C_2$-$C_{10}$haloalkenyl, $C_2$-$C_{10}$haloalkynyl, halogen, oxo, cyano, hydroxy, —O—$C_1$-$C_6$alkyl, —O—$C_1$-$C_6$haloalkyl, —$C_1$-$C_3$alkylene-O—H, —$C_1$-$C_3$alkylene-O—$C_1$-$C_6$alkyl, C(O)H, —$C_1$-$C_3$alkylene-NH$_2$, —NH$_2$, and —C(O)O$C_1$-$C_6$alkyl;

$R^3$ is hydrogen;

$R^4$ is hydrogen, halogen, $C_1$-$C_6$alkyl, $C_1$-$C_6$haloalkyl, —O—$C_1$-$C_6$alkyl, —O—$C_1$-$C_6$haloalkyl, cyano, —NH$_2$, or —N($R^{40}$)(SO$_2R^{4a}$);

$R^{4a}$ is $C_1$-$C_6$alkyl;

$R^{40}$ is hydrogen, $C_1$-$C_{10}$alkyl, $C_1$-$C_{10}$alkyl substituted with 2 hydroxy substituents, $C_2$-$C_{10}$alkenyl, $C_1$-$C_{10}$haloalkyl, $C_2$-$C_{10}$haloalkenyl, -$L^{4A}$-$R^{4c}$, -$L^{4A}$-$G^{4a}$, -$L^{4A}$-S(O)$_2$-$G^{4a}$, -$L^{4A}$-C(O)-$G^{4a}$, or -$L^{4A}$-O-$G^{4a}$;

$L^{4A}$ is $C_1$-$C_{10}$alkylene;

$R^{4c}$ is —O—$R^{4b}$, —S—$R^{4b}$, —N($R^{4b}$)$_2$, —N($R^{4b}$)S(O)$_2R^{4b}$, —OC(O)$R^{4b}$, —N($R^{4b}$)C(O)$R^{4b}$, cyano, —C(O)N($R^{4b}$)$_2$, —C(O)N($R^{4b}$)S(O)$_2R^{4b}$, —S(O)$R^{4b}$, —S(O)$_2R^{4b}$, —SO$_2$N($R^{4b}$)$_2$, —CO$_2R^{4b}$, —C(NOH)N($R^{4b}$)$_2$, —C(O)$R^{4b}$, —C(O)C(OH)($R^{4b}$)$_2$, or —P(O)(O$R^{4b}$)$_2$;

$R^{4b}$, at each occurrence, is each independently hydrogen or $C_1$-$C_6$alkyl;

$G^{4a}$ is $C_3$-$C_{12}$cycloalkyl, $C_6$-$C_{12}$aryl, 3- to 12-membered heterocyclyl, or 5- to 12-membered heteroaryl wherein $G^{4a}$ is optionally substituted with $G^{4b}$ and optionally substituted with 1, 2, 3, or 4 substituents selected from the group consisting of halogen, oxo, $C_1$-$C_3$alkyl, $C_1$-$C_3$haloalkyl, —OH, —O—$C_1$-$C_3$alkyl, —O—$C_1$-$C_3$haloalkyl, thioxo, —NH$_2$, —NH($C_1$-$C_3$alkyl), and —N($C_1$-$C_3$alkyl)$_2$;

$G^{4b}$ is $C_3$-$C_{12}$cycloalkyl, 3- to 12-membered heterocyclyl, $C_6$-$C_{12}$aryl, or 5- to 12-membered heteroaryl, wherein $G^{4b}$ is optionally substituted with 1, 2, 3, 4, or 5 substituents selected from the group consisting of halogen, oxo, $C_1$-$C_6$alkyl, $C_1$-$C_6$haloalkyl, hydroxy, —O—$C_1$-$C_6$alkyl, —O—$C_1$-

$C_6$haloalkyl, —S(O)—$C_1$-$C_6$alkyl, —S(O)$_2$—$C_1$-$C_6$alkyl, —C(O)—$C_1$-$C_6$alkyl, $C_1$-$C_3$alkylene-OH, $C_1$-$C_3$alkylene-O—$C_1$-$C_3$alkyl, $C_1$-$C_3$alkylene-N($C_1$-$C_3$alkyl)$_2$, and $C_1$-$C_3$alkylene-(N-heterocyclyl);

$R^5$ is $G^{5a}$;

$G^{5a}$ is phenyl, wherein $G^{5a}$ is substituted with —C(O)N($R^{5a}$)-$L^{5B}$-$G^{5b}$, —C(O)-$G^{5f}$, or —C(O)N($R^{5a}$)($R^{5e}$), and optionally substituted with 1, 2, or 3 substituents selected from the group consisting of $C_1$-$C_{10}$alkyl, $C_2$-$C_{10}$alkenyl, $C_2$-$C_{10}$alkynyl, $C_1$-$C_{10}$haloalkyl, halogen, —O—$R^{5b}$, CN, and -$G^{5d}$;

$G^{5b}$ is $C_3$-$C_{12}$cycloalkyl, $C_6$-$C_{12}$aryl, 3- to 12-membered heterocyclyl, or 5- to 12-membered heteroaryl, wherein each $G^{5b}$ is optionally substituted with 1, 2, 3, 4, or 5 substituents selected from the group consisting of oxo, halogen, $C_1$-$C_6$alkyl, $C_1$-$C_6$haloalkyl, —O—$R^{5d}$, —CN, -$L^{5C}$-O—$R^{5d}$, -$L^{5C}$-CN, and $G^{5c}$;

$G^{5c}$, at each occurrence, is each independently $C_3$-$C_8$cycloalkyl, $C_6$-$C_{10}$aryl, 4- to 10-membered heterocyclyl, or 5- to 10-membered heteroaryl, wherein $G^{5c}$ is optionally substituted with 1, 2, 3, 4, or 5 substituents selected from the group consisting of halogen, oxo, $C_1$-$C_6$alkyl, $C_1$-$C_6$haloalkyl, —O—$C_1$-$C_6$alkyl, and —O—$C_1$-$C_6$haloalkyl;

$G^{5d}$, at each occurrence, is each independently $C_3$-$C_8$cycloalkyl, $C_6$-$C_{10}$aryl, 4- to 10-membered heterocyclyl, or 5- to 10-membered heteroaryl, wherein $G^{5d}$ is optionally substituted with 1, 2, 3, 4, or 5 substituents selected from the group consisting of oxo, halogen, $C_1$-$C_6$alkyl, $C_1$-$C_6$haloalkyl, —O—$R^{5d}$, —CN, —N($R^{5d}$)C(O)$R^{5d}$, —CON($R^{5a}$)($R^{5d}$), —C(O)$R^{5d}$, —OC(O)$R^{5d}$, —CO$_2$H, —CO$_2R^{5d}$, —N($R^{5d}$)C(O)N($R^{5d}$)$_2$, —S—$R^{5d}$, —S(O)$_2R^{5d}$, —S(O)$R^{5d}$, —SO$_2$N($R^{5a}$)($R^{5d}$), —N($R^{5a}$)($R^{5d}$), —N($R^{5d}$)S(O)$_2R^{5d}$, N($R^{5d}$)C(O)O($R^{5d}$), -$L^{5C}$-O—$R^{5d}$, -$L^{5C}$-CN, $G^{5c}$, and -$L^{5C}$-$G^{5c}$;

$R^{5a}$, at each occurrence, is each independently hydrogen, $C_1$-$C_6$alkyl, $C_1$-$C_6$haloalkyl, or $C_3$-$C_8$cycloalkyl, wherein the $C_3$-$C_8$cycloalkyl is optionally substituted with 1, 2, 3, or 4 substituents selected from the group consisting of halogen, oxo, $C_1$-$C_3$alkyl, and $C_1$-$C_3$haloalkyl;

$R^{5b}$, at each occurrence, is each independently hydrogen, $C_1$-$C_{10}$alkyl, $C_2$-$C_{10}$alkenyl, $C_2$-$C_{10}$alkynyl, $C_1$-$C_{10}$haloalkyl, -$L^{5D}$-$G^{5c}$, or -$L^{5C}$-$R^{5c}$;

$R^{5c}$, at each occurrence, is each independently —CON($R^{5a}$)($R^{5g}$), —O—$R^{5g}$, —OC(O)$R^{5g}$, —CN, —C(O)$R^{5g}$, —CO$_2$H, —CO$_2R^{5g}$, —N($R^{5g}$)C(O)N($R^{5g}$)$_2$, —S—$R^{5g}$, —S(O)$_2R^{5g}$, —S(O)$R^{5g}$, —SO$_2$N($R^{5a}$)($R^{5g}$), —N($R^{5a}$)($R^{5g}$), —N($R^{5g}$)C(O)$R^{5g}$, or —N($R^{5g}$)S(O)$_2R^{5g}$;

$R^{5d}$, at each occurrence, is each independently hydrogen, $C_1$-$C_6$alkyl, $C_1$-$C_6$haloalkyl, or -$L^{5F}$-$G^{5e}$;

$R^{5e}$ is hydrogen, $C_1$-$C_{10}$alkyl, $C_2$-$C_{10}$alkenyl, $C_2$-$C_{10}$alkynyl, $C_1$-$C_{10}$haloalkyl, or -$L^{5E}$-$R^{5f}$;

$R^{5f}$ is —CON($R^{5a}$)($R^{5d}$), —O—$R^{5d}$, —CN, —C(O)$R^{5d}$, —CO$_2$H, —CO$_2R^{5d}$, —N($R^{5d}$)C(O)N($R^{5d}$)$_2$, —S(O)$_2R^{5d}$, —S(O)$R^{5d}$, —SO$_2$N($R^{5a}$)($R^{5d}$), —N($R^{5a}$)($R^{5d}$), —N($R^{5d}$)C(O)$R^{5d}$, or —N($R^{5d}$)S(O)$_2R^{5d}$;

$R^{5g}$, at each occurrence, is each independently hydrogen, $C_1$-$C_6$alkyl, $C_1$-$C_6$haloalkyl, or -$L^{5H}$-$G^{5e}$;

$G^{5e}$, at each occurrence, is each independently $C_3$-$C_8$cycloalkyl, $C_6$-$C_{10}$aryl, 4- to 10-membered heterocyclyl, or 5- to 10-membered heteroaryl, wherein $G^{5e}$ is optionally substituted with 1, 2, 3, or 4 substituents selected from the group consisting of halogen, oxo, $C_1$-$C_6$alkyl, $C_1$-$C_6$haloalkyl, —OH, —O—$C_1$-$C_6$alkyl, and —O—$C_1$-$C_6$haloalkyl;

$G^{5f}$ is 4- to 10-membered heterocyclyl, wherein $G^{5f}$ is optionally substituted with 1, 2, 3, or 4 substituents selected from the group consisting of halogen, oxo, $C_1$-$C_6$alkyl, $C_1$-$C_6$haloalkyl, —O—$C_1$-$C_6$alkyl, and —O—$C_1$-$C_6$haloalkyl;

$L^{5B}$ is a bond, $C_1$-$C_6$alkylene, or $C_3$-$C_8$cycloalkyl, wherein $L^{5B}$ is optionally substituted with 1, 2, 3, or 4 halogen and 1 or 2 hydroxy;

$L^{5C}$, at each occurrence, is each independently $C_1$-$C_6$alkylene or $C_3$-$C_8$cycloalkyl, wherein $L^{5C}$ is each optionally substituted with 1, 2, 3, or 4 halogen and 1 or 2 hydroxy;

$L^{5D}$, at each occurrence, is each independently bond, $C_1$-$C_6$alkylene, or $C_3$-$C_8$cycloalkyl, wherein $L^{5D}$ is each optionally substituted with 1, 2, 3, or 4 halogen and 1 or 2 hydroxy;

$L^{5E}$, at each occurrence, is each independently $C_1$-$C_6$alkylene, wherein $L^{5E}$ is optionally substituted with 1, 2, 3, or 4 halogen and 1 or 2 hydroxy;

$L^{5F}$, at each occurrence, is each independently bond or $C_1$-$C_6$alkylene, wherein $L^{5F}$ is optionally substituted with 1, 2, 3, or 4 halogen and 1 or 2 hydroxy;

$L^{5G}$, at each occurrence, is each independently $C_1$-$C_6$alkylene, wherein $L^{5G}$ is optionally substituted with 1, 2, 3, or 4 halogen and 1 or 2 hydroxy;

$L^{5H}$, at each occurrence, is each independently bond or $C_1$-$C_6$alkylene, wherein $L^{5H}$ is each optionally substituted with 1, 2, 3, or 4 halogen and 1 or 2 hydroxy;

$R^6$ is hydrogen or fluorine; and $R^7$ is hydrogen.

Such embodiments may include compounds where $R^2$ is $R^2$-II or $R^2$-IV, and $G^{2b}$ and $R^{20}$ are as defined herein.

R²-II

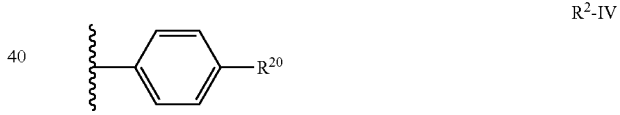

R²-IV

Such embodiments may include compounds where $R^5$ is $R^5$-I or $R^5$-III, and $G^{5b}$, $R^{5a}$, $R^{5e}$, and $L^{5B}$ are as defined hereinabove, and $G^{5a}$ is further optionally substituted as described herein.

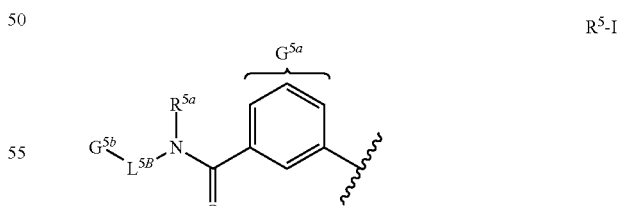

R⁵-I

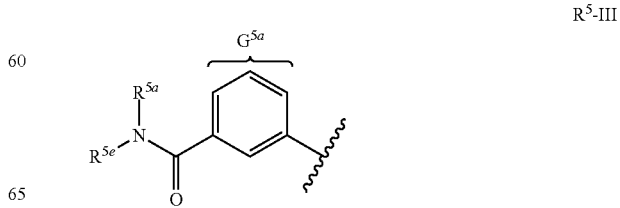

R⁵-III

Such embodiments may include compounds where $R^2$ is $R^2$-II or $R^2$-IV; $R^5$ is $R^5$-I or $R^5$-III; $G^{2b}$, $R^{20}$, $G^{5b}$, $R^{5a}$, $R^{5e}$, and $L^{5B}$ are as defined herein; and $G^{5a}$ is further optionally substituted as described herein.

Such embodiments may include compounds where:

$R^1$ is (i), (ii), (iii), (iv), or (v);

$R^{1a}$ is hydrogen, halogen, $C_1$-$C_3$alkyl, or $C_1$-$C_3$haloalkyl;

$R^{1b}$, at each occurrence, is each independently hydrogen, halogen, $C_1$-$C_3$alkyl, or $C_1$-$C_3$haloalkyl, wherein two geminal $R^{1b}$ taken together optionally are oxo;

$R^{1c}$ is $C_1$-$C_3$alkyl;

$R^2$ is $R^2$-II or $R^2$-IV;

$R^5$ is $R^5$-I or $R^5$-III;

$R^{20}$ is hydrogen, halogen (e.g., fluoro), $C_2$-$C_{10}$alkenyl (e.g., hex-1-enyl), —N($R^{2a}$)($G^{2b}$), —O-$G^{2b}$, —O-$L^{2C}$-$G^{2b}$, —O—$C_1$-$C_{10}$alkyl, —O-$L^{2C}$-$R^{2c}$, or —C(=$CH_2$)$G^{2b}$;

$R^{2a}$ is hydrogen or $C_1$-$C_3$alkyl (e.g. methyl);

$G^{2b}$ is $C_3$-$C_{10}$cycloalkyl (e.g., cyclopropyl, cyclobutyl), $C_5$-$C_{10}$cycloalkenyl (e.g., cyclohexenyl), $C_6$-$C_{10}$aryl (e.g., phenyl), 3- to 10-membered heterocyclyl, or 5- to 10-membered heteroaryl (e.g., pyridyl, thiophenyl, indolyl, benzo[d]oxadiazolyl), wherein $G^{2b}$ is optionally substituted with 1, 2, 3, 4, or 5 substituents selected from the group consisting of $C_1$-$C_6$alkyl (e.g., methyl, ethyl, t-butyl, hexyl), $C_2$-$C_6$alkenyl, $C_2$-$C_6$alkynyl, $C_1$-$C_6$haloalkyl (e.g., trifluoromethyl, trifluoroethyl, trifluorobutyl), $C_2$-$C_6$haloalkenyl, $C_2$-$C_6$haloalkynyl, halogen (e.g., fluoro, chloro), oxo, cyano, hydroxy, C(O)H, —O—$C_1$-$C_3$alkyl (e.g., methoxy), —$C_1$-$C_3$alkylene-O—H (e.g., $CH_2OH$), —$C_1$-$C_3$alkylene-O—$C_1$-$C_3$alkyl (e.g., $CH_2OCH_3$), C(O)H, —$C_1$-$C_3$alkylene-$NH_2$ (e.g., $CH_2NH_2$), —$NH_2$, and —C(O)O$C_1$-$C_3$alkyl (e.g., C(O)OEt);

$L^{2C}$ is $C_1$-$C_6$alkylene (e.g., $CH_2$, —C($CH_3$)(H)—, $CH_2CH_2$, —($CH_2$)$_3$—);

$R^{2c}$ is $CO_2$($C_1$-$C_3$alkyl) or —OC(O)$C_1$-$C_3$alkyl;

$R^3$ is hydrogen;

$R^4$ is hydrogen, halogen, $C_1$-$C_6$alkyl, $C_1$-$C_6$haloalkyl, —O—$C_1$-$C_6$alkyl, —O—$C_1$-$C_6$haloalkyl, cyano, —$NH_2$, or —N($R^{40}$)(SO$_2$$R^{4a}$);

$R^{4a}$ is $C_1$-$C_3$alkyl (e.g., methyl);

$R^{40}$ is hydrogen, $C_1$-$C_6$alkyl (e.g., ethyl, propyl, isobutyl, isopentyl, n-pentyl, n-hexyl, 4-methylpentyl), $C_1$-$C_6$haloalkyl (e.g., 3-fluoropropyl, 3,3,3-trifluoropropyl, 4-fluorobutyl, 4,4,4-trifluorobutyl), $C_2$-$C_6$haloalkenyl (e.g., 5,6,6-trifluorohex-5-enyl), or -$L^{4A}$-$R^{4c}$;

$L^{4A}$ is $C_1$-$C_{10}$alkylene (e.g., $CH_2$, $CH_2CH_2$, ($CH_2$)$_3$, ($CH_2$)$_4$, 5-methylhexyl);

$R^{4c}$ is —O—$R^{4b}$;

$R^{4b}$ is hydrogen or $C_1$-$C_6$alkyl (e.g., methyl, ethyl);

$R^6$ is hydrogen or fluorine;

$R^7$ is hydrogen; and wherein $G^{5b}$, $R^{5a}$, $R^{5e}$, and $L^{5B}$ are as defined herein; and $G^{5a}$ is further optionally substituted as described herein.

Embodiments may include compounds of formula (I), wherein $W^1$ is $CR^6$, $W^2$ is $CR^5$, $W^3$ is $CR^4$, $W^4$ is $CR^3$, $V^1$ is C, $V^2$ is C and $V^3$ is O (i.e. benzofuranyl), wherein $R^1$ is (i), (ii), (iii), or (v). Embodiments may include compounds of formula (I) wherein $R^1$ is (i), (ii), (iii), or (v). Such embodiments may include compounds wherein:

$R^{1a}$, at each occurrence, is each independently hydrogen, halogen (e.g., fluoro), $C_1$-$C_3$alkyl (e.g.), or $C_1$-$C_3$haloalkyl (e.g., trifluoromethyl);

$R^{1b}$, at each occurrence, is each independently hydrogen, $C_1$-$C_3$alkyl (e.g., methyl, ethyl, propyl), wherein two geminal $R^{1b}$ taken together optionally are oxo;

$R^2$ is $R^2$-II or $R^2$-IV;

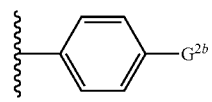

R²-II

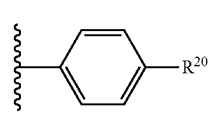

R²-IV $R^{20}$ is hydrogen, halogen (e.g., fluoro), $C_2$-$C_{10}$alkenyl (e.g., hex-1-enyl), —N($R^{2a}$)($G^{2b}$), —O-$G^{2b}$, —O-$L^{2C}$-$G^{2b}$, —O—$C_1$-$C_{10}$alkyl (e.g., —O-methyl), —O-$L^{2C}$-$R^{2c}$, or —C(=$CH_2$)$G^{2b}$;

$R^{2a}$ is hydrogen or $C_1$-$C_3$alkyl (e.g. methyl);

$R^{2b}$ is $C_1$-$C_{10}$alkyl (e.g., isopentyl, isopropyl) or $L^{2C}$-$R^{2c}$;

$G^{2b}$ is $C_3$-$C_{10}$cycloalkyl (e.g., cyclopropyl, cyclobutyl), $C_5$-$C_{10}$cycloalkenyl (e.g., cyclohexenyl), $C_6$-$C_{10}$aryl (e.g., phenyl), 3- to 10-membered heterocyclyl, or 5- to 10-membered heteroaryl (e.g., pyridyl, thiophenyl, indolyl, benzo[d]oxadiazolyl), wherein $G^{2b}$ is optionally substituted with 1, 2, 3, 4, or 5 substituents selected from the group consisting of $C_1$-$C_6$alkyl (e.g., methyl, ethyl, t-butyl, hexyl), $C_2$-$C_6$alkenyl, $C_2$-$C_6$alkynyl, $C_1$-$C_6$haloalkyl (e.g., trifluoromethyl, trifluoroethyl, trifluorobutyl), $C_2$-$C_6$haloalkenyl, $C_2$-$C_6$haloalkynyl, halogen (e.g., fluoro, chloro), oxo, cyano, hydroxy, C(O)H, —O—$C_1$-$C_3$alkyl (e.g., methoxy), —$C_1$-$C_3$alkylene-O—H (e.g., $CH_2OH$), —$C_1$-$C_3$alkylene-O—$C_1$-$C_3$alkyl (e.g., $CH_2OCH_3$), C(O)H, —$C_1$-$C_3$alkylene-$NH_2$ (e.g., $CH_2NH_2$), —$NH_2$, and —C(O)O$C_1$-$C_3$alkyl (e.g., C(O)OEt);

$L^{2C}$ is $C_1$-$C_6$alkylene (e.g., $CH_2$, —C($CH_3$)(H)—, $CH_2CH_2$, —($CH_2$)$_3$—);

$R^{2c}$ is $CO_2$($C_1$-$C_3$alkyl) or —OC(O)$C_1$-$C_3$alkyl;

$R^3$ is hydrogen;

$R^4$ is hydrogen, halogen, $C_1$-$C_6$alkyl, $C_1$-$C_6$haloalkyl, —O—$C_1$-$C_6$alkyl, —O—$C_1$-$C_6$haloalkyl, cyano, —$NH_2$, or —N($R^{40}$)(SO$_2$$R^{4a}$);

$R^{4a}$ is $C_1$-$C_3$alkyl (e.g., methyl);

$R^{40}$ is hydrogen, $C_1$-$C_6$alkyl (e.g., ethyl, propyl, isobutyl, isopentyl, n-pentyl, n-hexyl, 4-methylpentyl), $C_1$-$C_6$haloalkyl (e.g., 3-fluoropropyl, 3,3,3-trifluoropropyl, 4-fluorobutyl, 4,4,4-trifluorobutyl), $C_2$-$C_6$haloalkenyl (e.g., 5,6,6-trifluorohex-5-enyl), or -$L^{4A}$-$R^{4c}$;

$L^{4A}$ is $C_1$-$C_{10}$alkylene (e.g., $CH_2$, $CH_2CH_2$, ($CH_2$)$_3$, ($CH_2$)$_4$, 5-methylhexyl);

$R^{4c}$ is —O—$R^{4b}$;

$R^{4b}$ is hydrogen or $C_1$-$C_6$alkyl (e.g., methyl, ethyl);

$R^5$ is $R^5$-II;

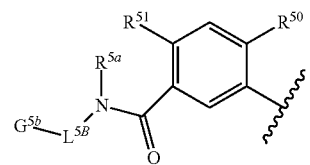

R⁵-II $L^{5B}$ is $C_1$-$C_6$alkylene (e.g., —$CH_2$—, —$C(CH_3)_2$—, —$C(CH_3)(H)CH_2$—, —$C(CH_3)_2CH_2$—) or $C_3$-$C_8$cycloalkyl (e.g., cyclopropyl, cyclobutyl);

$G^{5b}$ is $C_3$-$C_8$cycloalkyl (e.g., cyclopropyl, cyclobutyl, cyclopentyl, cyclohexyl, cycloheptyl), $C_6$-$C_{10}$aryl (e.g., phenyl, naphthyl, indanyl), 3- to 8-membered heterocyclyl (e.g., tetrahydropyranyl, tetrahydropyranyl), or 5- to 10-membered heteroaryl (e.g., furanyl, imidazolyl, thiazolyl, thiadiazolyl, oxazolyl, isoxazolyl, triazolyl, oxadiazolyl, pyrazolyl, thienyl, thiazolyl, pyridinyl, pyrimidinyl, pyrazinyl), wherein $G^{5b}$ is optionally substituted with 1, 2, 3, 4, or 5 substituents selected from the group consisting of oxo, halogen (e.g. fluoro), $C_1$-$C_6$alkyl (e.g., methyl, ethyl, isopropyl), $C_1$-$C_6$haloalkyl (e.g., trifluoromethyl), —O—$R^{5d}$ (e.g., hydroxy, methoxy), —CN, methoxymethyl, cyanomethyl, and $G^{5c}$;

$G^{5c}$, at each occurrence, is each independently cyclopropyl, phenyl, or 5- to 6-membered heteroaryl (e.g., pyridinyl, thiazolyl, isoxazolyl, pyrazolyl), wherein $G^{5c}$ is optionally substituted with 1, 2, 3, 4, or 5 substituents selected from the group consisting of halogen (e.g., fluoro, chloro), $C_1$-$C_6$alkyl (e.g., methyl, ethyl), $C_1$-$C_6$haloalkyl (e.g., trifluoromethyl), —O—$C_1$-$C_6$alkyl (e.g., methoxy), and —O—$C_1$-$C_6$haloalkyl (e.g., trifluoromethoxy);

$R^{50}$ is hydrogen, $C_1$-$C_3$alkyl (e.g., methyl, ethyl, isopropyl), $C_1$-$C_3$haloalkyl (e.g., trifluoromethyl), halogen (e.g., fluoro, chloro), or —O—$R^{5b}$;

$R^{51}$ is hydrogen, $C_1$-$C_3$alkyl (e.g., methyl, ethyl, isopropyl), $C_1$-$C_3$haloalkyl (e.g., trifluoromethyl), halogen (e.g., fluoro, chloro), —O—$C_1$-$C_6$alkyl (e.g., methoxy), —O—$C_1$-$C_6$haloalkyl (e.g., trifluoromethoxy), or $G^{5d}$;

$G^{5d}$ is phenyl, tetrahydropyrimidinyl, furanyl, thienyl, pyrazolyl, pyridinyl, pyrimidinyl, oxadiazolyl, isoquinolinyl, or indolyl;

$R^{5b}$ is hydrogen, $C_1$-$C_6$alkyl (e.g., methyl), $C_2$-$C_6$alkenyl (e.g., allyl), $C_2$-$C_6$alkynyl (e.g., propargyl), $C_1$-$C_6$haloalkyl (e.g., trifluoromethyl, 2,2-difluoroethyl), -$L^{5D}$-$G^{5e}$ (e.g., bond-$G^{5e}$, —$CH_2CH_2$-pyrrolidin-1-yl, —$CH_2$-pyrrolidin-2-yl, —$CH_2$-pyrrolidin-3-yl, —$CH_2CH_2$-morpholin-4-yl, —$CH_2CH_2CH_2$-morpholin-4-yl, —$CH_2CH_2$-morpholin-2-yl —$CH_2CH_2$-4-methylpiperazin-1-yl, —$CH_2CH_2$-piperidinyl, —$CH_2$-piperidin-3-yl, —$CH_2$-pyridin-2-yl, —$CH_2CH_2$-pyridin-2-yl, —$CH_2$-pyridin-4-yl, —$CH_2$-imidazol-4-yl), or -$L^{5G}$-$R^{5c}$ (e.g., —$CH_2CH_2OH$, —$CH_2CH(CH_3)OH$, —$CH_2CH(CH_2CH_3)OH$, —$CH_2CH_2OMe$, —$CH_2CONH_2$, —$CH_2CH_2CONH_2$, —$CH_2CH_2NH_2$, —$CH_2CH_2N(CH_3)_2$, —$CH_2CH_2NHC(O)NH_2$, —$CH_2CN$);

$R^{5c}$ is —$CON(R^{5a})(R^{5g})$ (e.g., $CONH_2$), —O—$R^{5g}$ (e.g., OH, OMe), —$OC(O)R^{5g}$, —CN, —$C(O)R^{5g}$, —$CO_2H$, —$CO_2R^{5g}$, —$N(R^{5g})C(O)N(R^{5g})_2$ (e.g., $NHC(O)NH_2$), —S—$R^{5g}$, —$S(O)_2R^{5g}$, —$S(O)R^{5g}$, —$SO_2N(R^{5a})(R^{5g})$, —$N(R^{5a})(R^{5g})$ (e.g., $NH_2$, $N(CH_3)_2$), —$N(R^{5g})C(O)R^{5g}$, or —$N(R^{5g})S(O)_2R^{5g}$;

$R^{5g}$, at each occurrence, is each independently hydrogen, $C_1$-$C_6$alkyl (e.g., methyl, ethyl), $C_1$-$C_6$haloalkyl (e.g., 2,2-difluoroethyl), or -$L^{5H}$-$G^{5e}$ (e.g., bond-$C_3$-$C_6$cycloalkyl, —$CH_2$—$C_3$-$C_6$cycloalkyl);

$L^{5D}$ is a bond, $C_1$-$C_6$alkylene (e.g., —$CH_2$—, —$CH_2CH_2$—, —$CH_2CH_2CH_2$—), or $C_3$-$C_6$cycloalkyl (e.g., cyclopropyl);

$G^{5e}$, at each occurrence, is each independently $C_3$-$C_6$cycloalkyl (e.g., cyclobutyl, cyclopentyl), $C_6$-$C_{10}$aryl (e.g., phenyl), 4- to 7-membered heterocyclyl (e.g., morpholin-4-yl, pyrrolidin-1-yl, 4-methylpiperazin-1-yl, piperidinyl), or 5- to 6-membered heteroaryl (e.g., pyridin-2-yl, imidazol-4-yl), wherein $G^{5e}$ is optionally substituted with 1, 2, 3, or 4 substituents selected from the group consisting of halogen (e.g., fluoro), oxo, $C_1$-$C_6$alkyl (e.g., methyl, ethyl), $C_1$-$C_6$haloalkyl (e.g., trifluoromethyl), —OH, —O—$C_1$-$C_6$alkyl (e.g., $OCH_3$), and —O—$C_1$-$C_6$haloalkyl (e.g., $OCF_3$);

$L^{5G}$ at each occurrence, is each independently $C_1$-$C_6$alkylene (e.g. —$(CH_2)_2$—, —$C(CH_3)_2$—, —$C(CH_3)_2CH_2$—, —$CH_2CH(CH_3)$—);

$R^{5d}$, at each occurrence, is each independently hydrogen, $C_1$-$C_6$alkyl, or $C_1$-$C_6$haloalkyl;

$R^{5a}$ is hydrogen or methyl; and $R^6$ is hydrogen.

Such embodiments may include compounds where:

$R^5$ is $R^5$-II; and $G^{5b}$ is phenyl or pyridinyl (e.g. pyridin-2-yl), wherein $G^{5b}$ is optionally substituted with 1, 2, 3, or 4 substituents selected from the group consisting of oxo, halogen (e.g. fluoro), $C_1$-$C_6$alkyl (e.g., methyl, ethyl, isopropyl), $C_1$-$C_6$haloalkyl (e.g., trifluoromethyl), —O—$R^{5d}$ (e.g., hydroxy, methoxy), and —CN.

Such embodiments may include compounds wherein:

$R^5$ is $R^5$-IV;

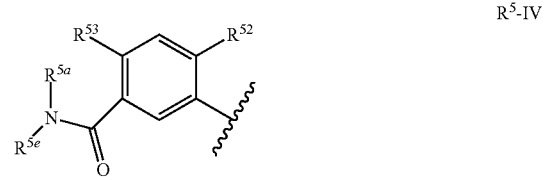

$R^5$-IV $R^{5a}$ is hydrogen or methyl;

$R^{5e}$ is hydrogen, $C_1$-$C_{10}$alkyl (e.g., methyl, ethyl, isopropyl, n-butyl, isobutyl, t-butyl), $C_2$-$C_{10}$alkenyl, $C_2$-$C_{10}$alkynyl (e.g., 2-methylbut-3-yn-2-yl), $C_1$-$C_{10}$haloalkyl (e.g., 1,1,1-trifluoro-2-methylpropan-2-yl), or -$L^{5E}$-$R^{5f}$ (e.g., —$C(CH_3)_2$—$CONHMe$, —$C(CH_3)_2$—$CONHCH_2CHF_2$, —$C(CH_3)_2$—$CO_2CH_3$, —$C(CH_3)_2CH_2$—$C(O)CH_3$, —$C(CH_3)_2$—$CONH$-thiazol-2-yl);

$R^{5f}$ is —$CON(R^{5a})(R^{5d})$ (e.g., $CONHMe$, $CONHCH_2CHF_2$, $CONH$-thiazol-2-yl), —O—$R^{5d}$ (e.g., OMe), —CN, —$C(O)R^{5d}$ (e.g., $C(O)CH_3$), —$CO_2H$, —$CO_2R^{5d}$ (e.g., $CO_2CH_3$), —$N(R^{5d})C(O)N(R^{5d})_2$, —$S(O)_2R^{5d}$ (e.g., $S(O)_2Me$), —$S(O)R^{5d}$ (e.g., $S(O)Me$), —$SO_2N(R^{5a})(R^{5d})$ (e.g., $SO_2NH_2$, $SO_2NHEt$), —$N(R^{5a})(R^{5d})$, —$N(R^{5d})C(O)R^{5d}$ (e.g., $NHC(O)Me$), or —$N(R^{5d})S(O)_2R^{5d}$ (e.g., —$NHS(O)_2Me$);

$R^{5d}$, at each occurrence, is each independently hydrogen, $C_1$-$C_6$alkyl (e.g., methyl, ethyl), $C_1$-$C_6$haloalkyl (e.g., 2,2-difluoroethyl), or -$L^{5F}$-$G^{5c}$ (e.g., bond-thiazol-2-yl);

$G^{5c}$, at each occurrence, is each independently $C_3$-$C_8$cycloalkyl (e.g., cyclopropyl), $C_6$-$C_{10}$aryl (e.g., phenyl), 4- to 10-membered heterocyclyl, or 5- to 10-membered heteroaryl (e.g., pyridinyl, thiazolyl, isoxazolyl, pyrazolyl), wherein $G^{5c}$ is optionally substituted with 1, 2, 3, 4, or 5 substituents selected from the group consisting of halogen (e.g., fluoro, chloro), oxo, $C_1$-$C_6$alkyl, $C_1$-$C_6$haloalkyl, —O—$C_1$-$C_6$alkyl (e.g., methoxy), and —O—$C_1$-$C_6$haloalkyl;

$R^{52}$ is hydrogen, $C_1$-$C_3$alkyl (e.g., methyl, ethyl, isopropyl), $C_1$-$C_{10}$haloalkyl (e.g., trifluoromethyl), halogen (e.g., fluoro, chloro), or —O—$R^{5b}$;

$R^{53}$ is hydrogen, $C_1$-$C_3$alkyl (e.g., methyl, ethyl, isopropyl), $C_1$-$C_{10}$haloalkyl (e.g., trifluoromethyl), halogen (e.g., fluoro, chloro), —O—$C_1$-$C_6$alkyl (e.g., methoxy), or —O—$C_1$-$C_6$haloalkyl (e.g., trifluoromethoxy);

$R^{5b}$ is hydrogen, $C_1$-$C_6$alkyl (e.g., methyl), $C_2$-$C_6$alkenyl (e.g., allyl), $C_2$-$C_6$alkynyl (e.g., propargyl), $C_1$-$C_6$haloalkyl (e.g., trifluoromethyl, 2,2-difluoroethyl), -$L^{5D}$-$G^{5e}$ (e.g., bond-$G^{5e}$, —CH$_2$CH$_2$-pyrrolidin-1-yl, —CH$_2$-pyrrolidin-2-yl, —CH$_2$-pyrrolidin-3-yl, —CH$_2$CH$_2$-morpholin-4-yl, —CH$_2$CH$_2$CH$_2$-morpholin-4-yl, —CH$_2$CH$_2$-morpholin-2-yl —CH$_2$CH$_2$-4-methylpiperazin-1-yl, —CH$_2$CH$_2$-piperidinyl, —CH$_2$-piperidin-3-yl, —CH$_2$-pyridin-2-yl, —CH$_2$CH$_2$-pyridin-2-yl, —CH$_2$-pyridin-4-yl, —CH$_2$-imidazol-4-yl), or -$L^{5G}$-$R^{5c}$ (e.g., —CH$_2$CH$_2$OH, —CH$_2$CH(CH$_3$)OH, —CH$_2$CH(CH$_2$CH$_3$)OH, —CH$_2$CH$_2$OMe, —CH$_2$CONH$_2$, —CH$_2$CH$_2$CONH$_2$, —CH$_2$CH$_2$NH$_2$, —CH$_2$CH$_2$N(CH$_3$)$_2$, —CH$_2$CH$_2$NHC(O)NH$_2$, —CH$_2$CN);

$G^{5e}$ is $C_3$-$C_6$cycloalkyl (e.g., cyclobutyl, cyclopentyl), $C_6$-$C_{10}$aryl (e.g., phenyl), 4- to 7-membered heterocyclyl (e.g., morpholin-4-yl, pyrrolidin-1-yl, 4-methylpiperazin-1-yl, piperidinyl), or 5- to 6-membered heteroaryl (e.g., pyridin-2-yl, imidazol-4-yl), wherein $G^{5e}$ is optionally substituted with 1 or 2 substituents selected from the group consisting of halogen (e.g., fluoro), oxo, $C_1$-$C_6$alkyl (e.g., methyl, ethyl), $C_1$-$C_6$haloalkyl (e.g., trifluoromethyl), —OH, —O—$C_1$-$C_6$alkyl (e.g., OCH$_3$), and —O—$C_1$-$C_6$haloalkyl (e.g., OCF$_3$);

$R^{5c}$, at each occurrence, is each independently —CON($R^{5a}$)($R^{5g}$) (e.g., CONH$_2$), —O—$R^{5g}$ (e.g., OH, OMe), —OC(O)$R^{5g}$, —CN, —C(O)$R^{5g}$, —CO$_2$H, —CO$_2$$R^{5g}$, —N($R^{5g}$)C(O)N($R^{5g}$)$_2$ (e.g., NHC(O)NH$_2$), —S—$R^{5g}$, —S(O)$_2$$R^{5g}$, —S(O)$R^{5g}$, —SO$_2$N($R^{5a}$)($R^{5g}$), —N($R^{5a}$)($R^{5g}$) (e.g., NH$_2$, N(CH$_3$)$_2$), —N($R^{5g}$)C(O)$R^{5g}$, or —N($R^{5g}$)S(O)$_2$$R^{5g}$;

$R^{5g}$ is hydrogen, $C_1$-$C_6$alkyl (e.g., methyl, ethyl), $C_1$-$C_6$haloalkyl (e.g., 2,2-difluoroethyl), or -$L^{5D}$-$G^{5e}$ (e.g., bond-$C_3$-$C_6$cycloalkyl, —CH$_2$—$C_3$-$C_6$cycloalkyl);

$L^{5D}$ is a bond, $C_1$-$C_6$alkylene (e.g., —CH$_2$—, —CH$_2$CH$_2$—, —CH$_2$CH$_2$CH$_2$—), or $C_3$-$C_6$cycloalkyl (e.g., cyclopropyl);

$L^{5E}$, at each occurrence, is each independently $C_1$-$C_6$alkylene (e.g. —(CH$_2$)$_2$—, —C(CH$_3$)$_2$—, —C(CH$_3$)$_2$CH$_2$—), wherein $L^{5E}$ is optionally substituted with 1, 2, 3, or 4 halogen and 1 or 2 hydroxy;

$L^{5F}$, at each occurrence, is each independently a bond or $C_1$-$C_6$alkylene (e.g., —CH$_2$—), wherein $L^{5F}$ is optionally substituted with 1, 2, 3, or 4 halogen and 1 or 2 hydroxy;

$L^{5G}$ at each occurrence, is each independently $C_1$-$C_6$alkylene (e.g. —(CH$_2$)$_2$—, —C(CH$_3$)$_2$—, —C(CH$_3$)$_2$CH$_2$—, —CH$_2$CH(CH$_3$)—); and $L^{5H}$, at each occurrence, is each independently a bond, or $C_1$-$C_6$alkylene (e.g., —CH$_2$—), wherein $L^{5H}$ is each optionally substituted with 1, 2, 3, or 4 halogen and 1 or 2 hydroxy.

Such embodiments may include compounds wherein:
$R^5$ is $R^5$-IV;
$R^{5a}$ is hydrogen or methyl;
$R^{5c}$ is hydrogen, $C_1$-$C_{10}$alkyl (e.g., methyl, ethyl, isopropyl, n-butyl, isobutyl, t-butyl), $C_2$-$C_{10}$alkenyl, or $C_2$-$C_{10}$alkynyl (e.g., 2-methylbut-3-yn-2-yl), $C_1$-$C_{10}$haloalkyl (e.g., 1,1,1-trifluoro-2-methylpropan-2-yl);

$R^{52}$ is hydrogen, $C_1$-$C_3$alkyl (e.g., methyl, ethyl, isopropyl), $C_1$-$C_3$haloalkyl (e.g., trifluoromethyl), halogen (e.g., fluoro, chloro), —O—$C_1$-$C_6$alkyl (e.g., methoxy), or —O—$C_1$-$C_6$haloalkyl (e.g., trifluoromethoxy);

$R^{53}$ is hydrogen, $C_1$-$C_3$alkyl (e.g., methyl, ethyl, isopropyl), $C_1$-$C_3$haloalkyl (e.g., trifluoromethyl), halogen (e.g., fluoro, chloro), —O—$C_1$-$C_6$alkyl (e.g., methoxy), —O—$C_1$-$C_6$haloalkyl (e.g., trifluoromethoxy), or $G^{5d}$;

$G^{5d}$ is $C_3$-$C_8$cycloalkyl, $C_6$-$C_{10}$aryl (e.g., phenyl), 4- to 10-membered heterocyclyl (e.g., tetrahydropyrimidinyl), or 5- to 10-membered heteroaryl (e.g., furanyl, thienyl, pyrazolyl, pyridinyl, pyrimidinyl, oxadiazolyl, isoquinolinyl, indolyl), wherein $G^{5d}$ is optionally substituted with 1, 2, 3, 4, or 5 substituents selected from the group consisting of oxo, halogen (e.g. fluoro, chloro), $C_1$-$C_6$alkyl (e.g., methyl, ethyl, n-propyl, isopropyl), $C_1$-$C_6$haloalkyl (e.g., trifluoromethyl), —O—$R^{5d}$ (e.g., methoxy, ethoxy), —CN, —N($R^{5a}$)C(O)$R^{5d}$ (e.g., NHC(O)Me), —CON($R^{5a}$)($R^{5d}$) (e.g., CONH$_2$, CONHEt), —C(O)$R^{5d}$ (e.g., C(O)Me), —OC(O)$R^{5d}$, —CO$_2$H, —CO$_2$$R^{5d}$ (e.g., CO$_2$Me), —N($R^{5a}$)C(O)N($R^{5d}$)$_2$ (e.g., NHC(O)NHMe), —S—$R^{5d}$, —S(O)$_2$$R^{5d}$ (e.g., S(O)$_2$Me), —S(O)$R^{5d}$ (e.g., S(O)Me), —SO$_2$N($R^{5a}$)($R^{5d}$) (e.g., SO$_2$NH$_2$, SO$_2$NHEt), —N($R^{5a}$)($R^{5d}$) (e.g., NH$_2$), —N($R^{5a}$)S(O)$_2$$R^{5d}$ (e.g., —NHS(O)$_2$Me), N($R^{5a}$)C(O)O($R^{5d}$) (e.g., NHC(O)OMe), -$L^{5C}$-O—$R^{5d}$ (e.g., hydroxymethyl, methoxymethyl), -$L^{5C}$-CN (e.g., cyanomethyl), $G^{5c}$ (e.g., phenyl), and -$L^{5C}$-$G^{5c}$ (e.g., benzyl);

$R^{5d}$, at each occurrence, is each independently hydrogen, $C_1$-$C_6$alkyl (e.g., methyl, ethyl), $C_1$-$C_6$haloalkyl (e.g., 2,2-difluoroethyl), or -$L^{5F}$-$G^{5c}$ (e.g., bond-thiazol-2-yl);

$L^{5C}$, at each occurrence, is each independently $C_1$-$C_6$alkylene or $C_3$-$C_8$cycloalkyl, wherein $L^{5C}$ is each optionally substituted with 1, 2, 3, or 4 halogen and 1 or 2 hydroxy;

$L^{5F}$, at each occurrence, is each independently a bond or $C_1$-$C_6$alkylene (e.g., —CH$_2$—), wherein $L^{5F}$ is optionally substituted with 1, 2, 3, or 4 halogen and 1 or 2 hydroxy; and $G^{5c}$, at each occurrence, is each independently $C_3$-$C_8$cycloalkyl (e.g., cyclopropyl), $C_6$-$C_{10}$aryl (e.g., phenyl), 4- to 10-membered heterocyclyl, or 5- to 10-membered heteroaryl (e.g., pyridinyl, thiazolyl, isoxazolyl, pyrazolyl), wherein $G^{5c}$ is optionally substituted with 1, 2, 3, 4, or 5 substituents selected from the group consisting of halogen (e.g., fluoro, chloro), oxo, $C_1$-$C_6$alkyl, $C_1$-$C_6$haloalkyl, —O—$C_1$-$C_6$alkyl (e.g., methoxy), and —O—$C_1$-$C_6$haloalkyl.

Such embodiments may include compounds wherein:
$R^{5a}$ is hydrogen or methyl;
$R^{5e}$ is hydrogen, $C_1$-$C_{10}$alkyl (e.g., methyl, ethyl, isopropyl, n-butyl, isobutyl, t-butyl), $C_2$-$C_{10}$alkenyl, or $C_2$-$C_{10}$alkynyl (e.g., 2-methylbut-3-yn-2-yl), $C_1$-$C_{10}$haloalkyl (e.g., 1,1,1-trifluoro-2-methylpropan-2-yl);

$R^{52}$ is hydrogen, $C_1$-$C_3$alkyl (e.g., methyl, ethyl, isopropyl), $C_1$-$C_3$haloalkyl (e.g., trifluoromethyl), halogen (e.g., fluoro, chloro), or —O—$R^{5b}$;

$R^{53}$ is hydrogen, $C_1$-$C_3$alkyl (e.g., methyl, ethyl, isopropyl), $C_1$-$C_3$haloalkyl (e.g., trifluoromethyl), halogen (e.g., fluoro, chloro), —O—$C_1$-$C_6$alkyl (e.g., methoxy), or —O—$C_1$-$C_6$haloalkyl (e.g., trifluoromethoxy);

$R^{5b}$ is hydrogen, $C_1$-$C_6$alkyl (e.g., methyl), $C_1$-$C_6$haloalkyl (e.g., trifluoromethyl, 2,2-difluoroethyl), -$L^{5D}$-$G^{5e}$ (e.g., bond-cyclopropyl, bond-cyclobutyl, —CH$_2$CH$_2$-pyrrolidin-1-yl, —CH$_2$-pyrrolidin-2-yl, —CH$_2$-pyrrolidin-3-yl, —CH$_2$CH$_2$-morpholin-4-yl, —CH$_2$CH$_2$CH$_2$-morpholin-4-yl, —CH$_2$CH$_2$-morpholin-2-yl —CH$_2$CH$_2$-4-methylpiperazin-1-yl, —CH$_2$CH$_2$-piperidinyl, —CH$_2$-piperidin-3-yl, —CH$_2$-pyridin-2-yl, —CH$_2$CH$_2$-pyridin-2-yl, —CH$_2$-pyridin-4-yl, —CH$_2$-imidazol-4-yl), or -$L^{5G}$-$R^{5c}$ (e.g., —CH$_2$CH$_2$OH, —CH$_2$CH(CH$_3$)OH, —CH$_2$CH(CH$_2$CH$_3$)OH, —CH$_2$CH$_2$OMe, —CH$_2$CONH$_2$, —CH$_2$CH$_2$CONH$_2$, —CH$_2$CH$_2$NH$_2$, —CH$_2$CH$_2$N(CH$_3$)$_2$, —CH$_2$CH$_2$NHC(O)NH$_2$, —CH$_2$CN);

$G^{5e}$ is $C_3$-$C_6$cycloalkyl (e.g., cyclobutyl, cyclopentyl), $C_6$-$C_{10}$aryl (e.g., phenyl), 4- to 7-membered heterocyclyl (e.g., morpholin-4-yl, pyrrolidin-1-yl, 4-methylpiperazin-1-yl, piperidinyl), or 5- to 6-membered heteroaryl (e.g., pyridin-2-yl, imidazol-4-yl), wherein $G^{5e}$ is optionally substituted with 1, 2, 3, or 4 substituents selected from the group consisting of halogen (e.g., fluoro), oxo, $C_1$-$C_6$alkyl (e.g., methyl, ethyl), $C_1$-$C_6$haloalkyl (e.g., trifluoromethyl), —OH, —O—$C_1$-$C_6$alkyl (e.g., $OCH_3$), and —O—$C_1$-$C_6$haloalkyl (e.g., $OCF_3$).

$R^{5c}$, at each occurrence, is each independently —CON($R^{5a}$)($R^{5g}$) (e.g., $CONH_2$), —O—$R^{5g}$ (e.g., OH, OMe), —OC(O)$R^{5g}$, —CN, —C(O)$R^{5g}$, —$CO_2H$, —$CO_2R^{5g}$, —N($R^{5g}$)C(O)N($R^{5g}$)$_2$ (e.g., $NHC(O)NH_2$), —S—$R^{5g}$, —S(O)$_2R^{5g}$, —S(O)$R^{5g}$, —$SO_2$N($R^{5a}$)($R^{5g}$), —N($R^{5a}$)($R^{5g}$) (e.g., $NH_2$, N($CH_3$)$_2$), —N($R^{5g}$)C(O)$R^{5g}$, or —N($R^{5g}$)S(O)$_2R^{5g}$;

$R^{5g}$ is hydrogen, $C_1$-$C_6$alkyl (e.g., methyl, ethyl), $C_1$-$C_6$haloalkyl (e.g., 2,2-difluoroethyl), or -$L^{5H}$-$G^{5e}$ (e.g., bond-$C_3$-$C_6$cycloalkyl, —$CH_2$—$C_3$-$C_6$cycloalkyl);

$L^{5D}$ is a bond, $C_1$-$C_6$alkylene (e.g., —$CH_2$—, —$CH_2CH_2$—, —$CH_2CH_2CH_2$—), or $C_3$-$C_6$cycloalkyl (e.g., cyclopropyl);

$L^{5G}$ at each occurrence, is each independently $C_1$-$C_6$alkylene (e.g. —($CH_2$)$_2$—, —C($CH_3$)$_2$—, —C($CH_3$)$_2CH_2$—, —$CH_2CH(CH_3$)—); and $L^{5H}$, at each occurrence, is each independently bond, or $C_1$-$C_6$alkylene (e.g., —$CH_2$—), wherein $L^{5H}$ is each optionally substituted with 1, 2, 3, or 4 halogen and 1 or 2 hydroxy.

According to each of the foregoing aspects, embodiments, and description of the disclosure of Formula (I), wherein $W^1$ is $CR^6$, $W^2$ is $CR^5$, $W^3$ is $CR^4$, $W^4$ is $CR^3$, $V^1$ is C, $V^2$ is C and $V^3$ is O (i.e. benzofuranyl), or wherein $W^1$ is $CR^6$, $W^2$ is $CR^5$, $W^3$ is $CR^4$, $W^4$ is $CR^3$, $V^1$ is C, $V^2$ is N, and $V^3$ is N (i.e. pyrazolo[1,5-a]pyridinyl), are embodiments which may include compounds where $R^1$ is (i), where each $R^{1a}$ is independently hydrogen or methyl.

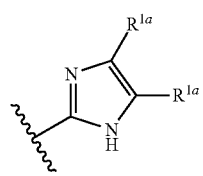

(i)

According to each of the foregoing aspects, embodiments, and description of the compounds of Formula (I), wherein $W^1$ is $CR^6$, $W^2$ is $CR^5$, $W^3$ is $CR^4$, $W^4$ is $CR^3$, $V^1$ is C, $V^2$ is C and $V^3$ is O (i.e. benzofuranyl), or wherein $W^1$ is $CR^6$, $W^2$ is $CR^5$, $W^3$ is $CR^4$, $W^4$ is $CR^3$, $V^1$ is C, $V^2$ is N, and $V^3$ is N (i.e. pyrazolo[1,5-a]pyridinyl), are embodiments which may include compounds where $R^1$ is (ii), where each $R^{1b}$ is independently hydrogen or methyl.

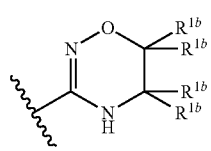

(ii)

According to each of the foregoing aspects, embodiments, and description of the compounds of Formula (I), wherein $W^1$ is $CR^6$, $W^2$ is $CR^5$, $W^3$ is $CR^4$, $W^4$ is $CR^3$, $V^1$ is C, $V^2$ is C and $V^3$ is O (i.e. benzofuranyl), or wherein $W^1$ is $CR^6$, $W^2$ is $CR^5$, $W^3$ is $CR^4$, $W^4$ is $CR^3$, $V^1$ is C, $V^2$ is N, and $V^3$ is N (i.e. pyrazolo[1,5-a]pyridinyl), are embodiments which may include compounds where $R^1$ is (ii-1).

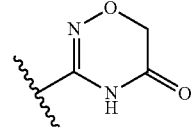

(ii-1)

According to each of the foregoing aspects, embodiments, and description of the compounds of Formula (I), wherein $W^1$ is $CR^6$, $W^2$ is $CR^5$, $W^3$ is $CR^4$, $W^4$ is $CR^3$, $V^1$ is C, $V^2$ is C and $V^3$ is O (i.e. benzofuranyl), or wherein $W^1$ is $CR^6$, $W^2$ is $CR^5$, $W^3$ is $CR^4$, $W^4$ is $CR^3$, $V^1$ is C, $V^2$ is N, and $V^3$ is N (i.e. pyrazolo[1,5-a]pyridinyl), are embodiments which may include compounds where $R^1$ is (iii), where each $R^{1b}$ is independently hydrogen or methyl.

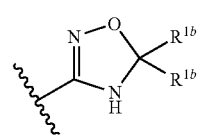

(ii)

According to each of the foregoing aspects, embodiments, and description of the compounds of Formula (I), wherein $W^1$ is $CR^6$, $W^2$ is $CR^5$, $W^3$ is $CR^4$, $W^4$ is $CR^3$, $V^1$ is C, $V^2$ is C and $V^3$ is O (i.e. benzofuranyl), or wherein $W^1$ is $CR^6$, $W^2$ is $CR^5$, $W^3$ is $CR^4$, $W^4$ is $CR^3$, $V^1$ is C, $V^2$ is N, and $V^3$ is N (i.e. pyrazolo[1,5-a]pyridinyl), are embodiments which may include compounds where $R^1$ is (iii-1).

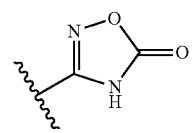

(iii-1)

According to each of the foregoing aspects, embodiments, and description of the compounds of Formula (I), wherein $W^1$ is $CR^6$, $W^2$ is $CR^5$, $W^3$ is $CR^4$, $W^4$ is $CR^3$, $V^1$ is C, $V^2$ is C and $V^3$ is O (i.e. benzofuranyl), or wherein $W^1$ is $CR^6$, $W^2$ is $CR^5$, $W^3$ is $CR^4$, $W^4$ is $CR^3$, $V^1$ is C, $V^2$ is N, and $V^3$ is N (i.e. pyrazolo[1,5-a]pyridinyl), are embodiments which may include compounds where $R^1$ is (v), where $R^{1a}$ is hydrogen.

Exemplary compounds include, but are not limited to:
N-[5-cyclopropyl-2-(4-fluorophenyl)-3-(1H-imidazol-2-yl)-1-benzofuran-6-yl]methanesulfonamide;
N-[5-cyclopropyl-2-(4-fluorophenyl)-3-(4-methyl-1H-imidazol-2-yl)-1-benzofuran-6-yl]methanesulfonamide;
N-{[2-(1H-benzimidazol-6-yl)-1,3-thiazol-5-yl]methyl}-N-[3-(1H-imidazol-2-yl)-2-phenyl-1-benzofuran-6-yl]methanesulfonamide;
N-[5-cyclopropyl-2-(4-fluorophenyl)-3-(1H-imidazol-2-yl)-1-benzofuran-6-yl]-N-(3-methylbutyl)methanesulfonamide;
N-[5-cyclopropyl-2-(4-fluorophenyl)-3-(1H-imidazol-2-yl)-1-benzofuran-6-yl]-N-(4-hydroxybutyl)methanesulfonamide;
N-[5-cyclopropyl-2-(4-fluorophenyl)-3-(1H-imidazol-2-yl)-1-benzofuran-6-yl]-N-[4-(methylsulfonyl)butyl]methanesulfonamide;

N-[5-cyclopropyl-2-(4-fluorophenyl)-3-(1H-imidazol-2-yl)-1-benzofuran-6-yl]-N-[3-(3-hydroxy-1,2-oxazol-5-yl)propyl]methanesulfonamide;
N-[5-cyclopropyl-3-(5,6-dihydro-4H-1,2,4-oxadiazin-3-yl)-2-(4-fluorophenyl)-1-benzofuran-6-yl]-N-(4-hydroxybutyl)methanesulfonamide;
N-[5-cyclopropyl-3-(5,6-dihydro-4H-1,2,4-oxadiazin-3-yl)-2-(4-fluorophenyl)-1-benzofuran-6-yl]-N-[2-(methylsulfonyl)ethyl]methanesulfonamide;
N-[5-cyclopropyl-3-(5,6-dihydro-4H-1,2,4-oxadiazin-3-yl)-2-(4-fluorophenyl)-1-benzofuran-6-yl]-N-(3-methylbutyl)methanesulfonamide;
N-[5-cyclopropyl-2-(4-fluorophenyl)-3-(5-methyl-4,5-dihydro-1,2,4-oxadiazol-3-yl)-1-benzofuran-6-yl]-N-(4-hydroxybutyl)methanesulfonamide;
N-[5-cyclopropyl-2-(4-fluorophenyl)-3-(5-methyl-4,5-dihydro-1,2,4-oxadiazol-3-yl)-1-benzofuran-6-yl]-N-[2-(methylsulfonyl)ethyl]methanesulfonamide;
N-[5-cyclopropyl-2-(4-fluorophenyl)-3-(5-methyl-4,5-dihydro-1,2,4-oxadiazol-3-yl)-1-benzofuran-6-yl]-N-[2-(methylsulfinyl)ethyl]methanesulfonamide;
N-[5-cyclopropyl-2-(4-fluorophenyl)-3-(5-methyl-4,5-dihydro-1,2,4-oxadiazol-3-yl)-1-benzofuran-6-yl]-N-(3-methylbutyl)methanesulfonamide;
3-{[5-cyclopropyl-3-(4,5-dihydro-1,2,4-oxadiazol-3-yl)-2-(4-fluorophenyl)-1-benzofuran-6-yl](methylsulfonyl)amino}propane-1-sulfonamide;
N-[5-cyclopropyl-3-(4,5-dihydro-1,2,4-oxadiazol-3-yl)-2-(4-fluorophenyl)-1-benzofuran-6-yl]-N-(4-hydroxybutyl)methanesulfonamide;
N-[5-cyclopropyl-2-(4-fluorophenyl)-3-(1H-imidazol-2-yl)pyrazolo[1,5-a]pyridin-6-yl]-N-(3-methylbutyl)methanesulfonamide;
N-[2-(4-anilinophenyl)-5-cyclopropyl-3-(1H-imidazol-2-yl)-1-benzofuran-6-yl]-N-(3-methylbutyl)methanesulfonamide;
3-[3-(5,6-dihydro-4H-1,2,4-oxadiazin-3-yl)-2-(4-methoxyphenyl)pyrazolo[1,5-a]pyridin-5-yl]-4-methyl-N-(1-phenylcyclopropyl)benzamide;
N-[3-(1H-imidazol-2-yl)-2-phenyl-1-benzofuran-6-yl]-N-(1-phenylethyl)methanesulfonamide;
N-benzyl-N-[3-(1H-imidazol-2-yl)-2-phenyl-1-benzofuran-6-yl]methanesulfonamide;
N-{[2-bromo-4-(trifluoromethyl)-1,3-thiazol-5-yl]methyl}-N-[3-(1H-imidazol-2-yl)-2-phenyl-1-benzofuran-6-yl]methanesulfonamide;
N-[3-(1H-imidazol-2-yl)-2-phenyl-1-benzofuran-6-yl]-N-{[2-(1H-indol-5-yl)-1,3-thiazol-5-yl]methyl}methanesulfonamide;
N-[3-(1H-imidazol-2-yl)-2-phenyl-1-benzofuran-6-yl]-N-({2-[4-(methylsulfinyl)phenyl]-1,3-thiazol-5-yl}methyl)methanesulfonamide;
N-[3-(1H-imidazol-2-yl)-2-phenyl-1-benzofuran-6-yl]-N-{[2-(1-methyl-1H-indol-5-yl)-1,3-thiazol-5-yl]methyl}methanesulfonamide;
N-[3-(1H-imidazol-2-yl)-2-phenyl-1-benzofuran-6-yl]-N-{[2-(1-methyl-1H-pyrazol-4-yl)-1,3-thiazol-5-yl]methyl}methanesulfonamide;
N-{[2-(2,4-di-tert-butoxypyrimidin-5-yl)-1,3-thiazol-5-yl]methyl}-N-[3-(1H-imidazol-2-yl)-2-phenyl-1-benzofuran-6-yl]methanesulfonamide;
N-({2-[3-(hydroxymethyl)phenyl]-1,3-thiazol-5-yl}methyl)-N-[3-(1H-imidazol-2-yl)-2-phenyl-1-benzofuran-6-yl]methanesulfonamide;
N-{[2-(2,4-dioxo-1,2,3,4-tetrahydropyrimidin-5-yl)-1,3-thiazol-5-yl]methyl}-N-[3-(1H-imidazol-2-yl)-2-phenyl-1-benzofuran-6-yl]methanesulfonamide;
N-[3-(1H-imidazol-2-yl)-2-phenyl-1-benzofuran-6-yl]-N-{[2-(1-methyl-1H-benzimidazol-6-yl)-1,3-thiazol-5-yl]methyl}methanesulfonamide;
N-[5-cyclopropyl-2-(4-fluorophenyl)-3-(1H-imidazol-2-yl)-1-benzofuran-6-yl]-N-{[2-(1H-indol-5-yl)-1,3-thiazol-5-yl]methyl}methanesulfonamide;
N-[3-(1H-imidazol-2-yl)-2-phenyl-1-benzofuran-6-yl]-N-[3-(trifluoromethyl)benzyl]methanesulfonamide;
ethyl N-[5-cyclopropyl-2-(4-fluorophenyl)-3-(1H-imidazol-2-yl)-1-benzofuran-6-yl]-N-ethylsulfonyl)glycinate;
N-(cyclopentylmethyl)-N-[5-cyclopropyl-2-(4-fluorophenyl)-3-(1H-imidazol-2-yl)-1-benzofuran-6-yl]methanesulfonamide;
N-[5-cyclopropyl-2-(4-fluorophenyl)-3-(1H-imidazol-2-yl)-1-benzofuran-6-yl]-N-(2-phenylethyl)methanesulfonamide;
$N^2$-[5-cyclopropyl-2-(4-fluorophenyl)-3-(1H-imidazol-2-yl)-1-benzofuran-6-yl]-$N^2$-(methylsulfonyl)glycinamide;
N-[5-cyclopropyl-2-(4-fluorophenyl)-3-(1H-imidazol-2-yl)-1-benzofuran-6-yl]-N-(3-phenoxypropyl)methanesulfonamide;
N-[5-cyclopropyl-2-(4-fluorophenyl)-3-(1H-imidazol-2-yl)-1-benzofuran-6-yl]-N-etrahydro-2H-pyran-4-ylmethyl)methanesulfonamide;
N-butyl-N-[5-cyclopropyl-2-(4-fluorophenyl)-3-(1H-imidazol-2-yl)-1-benzofuran-6-yl]methanesulfonamide;
N-[5-cyclopropyl-2-(4-fluorophenyl)-3-(1H-imidazol-2-yl)-1-benzofuran-6-yl]-N-(4-methylpentyl)methanesulfonamide;
N-[5-cyclopropyl-2-(4-fluorophenyl)-3-(1H-imidazol-2-yl)-1-benzofuran-6-yl]-N-(3-phenylpropyl)methanesulfonamide;
N-(4-{[tert-butyl(dimethyl)silyl]oxy}butyl)-N-[5-cyclopropyl-2-(4-fluorophenyl)-3-(1H-imidazol-2-yl)-1-benzofuran-6-yl]methanesulfonamide;
N-[5-cyclopropyl-2-(4-fluorophenyl)-3-(1H-imidazol-2-yl)-1-benzofuran-6-yl]-N-(2-phenoxyethyl)methanesulfonamide;
N-[5-cyclopropyl-2-(4-fluorophenyl)-3-(1H-imidazol-2-yl)-1-benzofuran-6-yl]-N-(4,4,4-trifluorobutyl)methanesulfonamide;
N-(cyclohexylmethyl)-N-[5-cyclopropyl-2-(4-fluorophenyl)-3-(1H-imidazol-2-yl)-1-benzofuran-6-yl]methanesulfonamide;
5-{[5-cyclopropyl-2-(4-fluorophenyl)-3-(1H-imidazol-2-yl)-1-benzofuran-6-yl](methylsulfonyl)amino}pentyl acetate;
N-[5-cyclopropyl-2-(4-fluorophenyl)-3-(1H-imidazol-2-yl)-1-benzofuran-6-yl]-N-(2-methoxyethyl)methanesulfonamide;
N-[5-cyclopropyl-2-(4-fluorophenyl)-3-(1H-imidazol-2-yl)-1-benzofuran-6-yl]-N-[2-(tetrahydro-2H-pyran-4-yl)ethyl]methanesulfonamide;
N-(3-cyanopropyl)-N-[5-cyclopropyl-2-(4-fluorophenyl)-3-(1H-imidazol-2-yl)-1-benzofuran-6-yl]methanesulfonamide;
ethyl 5-{[5-cyclopropyl-2-(4-fluorophenyl)-3-(1H-imidazol-2-yl)-1-benzofuran-6-yl](methylsulfonyl)amino}pentanoate;
N-[5-cyclopropyl-2-(4-fluorophenyl)-3-(1H-imidazol-2-yl)-1-benzofuran-6-yl]-N-yrrolidin-3-ylmethyl)methanesulfonamide;
N-[5-cyclopropyl-2-(4-fluorophenyl)-3-(1H-imidazol-2-yl)-1-benzofuran-6-yl]-N-isopropylmethanesulfonamide;
N-[5-cyclopropyl-2-(4-fluorophenyl)-3-(1H-imidazol-2-yl)-1-benzofuran-6-yl]-Nyclopropylmethyl)methanesulfonamide;

N-[5-cyclopropyl-2-(4-fluorophenyl)-3-(1H-imidazol-2-yl)-1-benzofuran-6-yl]-N-(3-methylbut-2-en-1-yl)methanesulfonamide;

N-[5-cyclopropyl-2-(4-fluorophenyl)-3-(1H-imidazol-2-yl)-1-benzofuran-6-yl]-N-[(2,2-difluorocyclopropyl)methyl]methanesulfonamide;

N-[5-cyclopropyl-2-(4-fluorophenyl)-3-(1H-imidazol-2-yl)-1-benzofuran-6-yl]-N-ethylmethanesulfonamide;

N-allyl-N-[5-cyclopropyl-2-(4-fluorophenyl)-3-(1H-imidazol-2-yl)-1-benzofuran-6-yl]methanesulfonamide;

N-[5-cyclopropyl-2-(4-fluorophenyl)-3-(1H-imidazol-2-yl)-1-benzofuran-6-yl]-N-[2-(morpholin-4-yl)ethyl]methanesulfonamide;

N-[5-cyclopropyl-2-(4-fluorophenyl)-3-(1H-imidazol-2-yl)-1-benzofuran-6-yl]-N-[3-(dimethylamino)propyl]methanesulfonamide;

N-[5-cyclopropyl-2-(4-fluorophenyl)-3-(1H-imidazol-2-yl)-1-benzofuran-6-yl]-N-[3-(morpholin-4-yl)propyl]methanesulfonamide;

N-[5-cyclopropyl-2-(4-fluorophenyl)-3-(1H-imidazol-2-yl)-1-benzofuran-6-yl]-N-[2-(1,1-dioxidotetrahydrothiophen-3-yl)ethyl]methanesulfonamide;

N-[5-cyclopropyl-2-(4-fluorophenyl)-3-(1H-imidazol-2-yl)-1-benzofuran-6-yl]-N-{3-[2-(2,5-dimethyl-1H-pyrrol-1-yl)-1,3-thiazol-4-yl]propyl}methanesulfonamide;

N-(cyanomethyl)-N-[5-cyclopropyl-2-(4-fluorophenyl)-3-(1H-imidazol-2-yl)-1-benzofuran-6-yl]methanesulfonamide;

N-[5-cyclopropyl-2-(4-fluorophenyl)-3-(1H-imidazol-2-yl)-1-benzofuran-6-yl]-N-propylmethanesulfonamide;

N-[5-cyclopropyl-2-(4-fluorophenyl)-3-(1H-imidazol-2-yl)-1-benzofuran-6-yl]-N-(3-hydroxypropyl)methanesulfonamide;

N-[5-cyclopropyl-2-(4-fluorophenyl)-3-(1H-imidazol-2-yl)-1-benzofuran-6-yl]-N-isobutylmethanesulfonamide;

N-[(2-bromo-1,3-thiazol-5-yl)methyl]-N-[5-cyclopropyl-2-(4-fluorophenyl)-3-(1H-imidazol-2-yl)-1-benzofuran-6-yl]methanesulfonamide;

methyl 4-{[5-cyclopropyl-2-(4-fluorophenyl)-3-(1H-imidazol-2-yl)-1-benzofuran-6-yl](methylsulfonyl)amino}butanoate;

N-[5-cyclopropyl-2-(4-fluorophenyl)-3-(1H-imidazol-2-yl)-1-benzofuran-6-yl]-N-(3-methoxypropyl)methanesulfonamide;

N-[5-cyclopropyl-2-(4-fluorophenyl)-3-(1H-imidazol-2-yl)-1-benzofuran-6-yl]-N-pentylmethanesulfonamide;

N-[5-cyclopropyl-2-(4-fluorophenyl)-3-(1H-imidazol-2-yl)-1-benzofuran-6-yl]-N-hexylmethanesulfonamide;

N-(2-cyclohexylethyl)-N-[5-cyclopropyl-2-(4-fluorophenyl)-3-(1H-imidazol-2-yl)-1-benzofuran-6-yl]methanesulfonamide;

N-[5-cyclopropyl-2-(4-fluorophenyl)-3-(1H-imidazol-2-yl)-1-benzofuran-6-yl]-N-(4-oxopentyl)methanesulfonamide;

N-[5-cyclopropyl-2-(4-fluorophenyl)-3-(1H-imidazol-2-yl)-1-benzofuran-6-yl]-N-[2-(methylthio)ethyl]methanesulfonamide;

N-[5-cyclopropyl-2-(4-fluorophenyl)-3-(1H-imidazol-2-yl)-1-benzofuran-6-yl]-Netrahydrofuran-2-ylmethyl)methanesulfonamide;

N-[5-cyclopropyl-2-(4-fluorophenyl)-3-(1H-imidazol-2-yl)-1-benzofuran-6-yl]-N-(4-methylpent-3-en-1-yl)methanesulfonamide;

N-[5-cyclopropyl-2-(4-fluorophenyl)-3-(1H-imidazol-2-yl)-1-benzofuran-6-yl]-N-(5-oxohexyl)methanesulfonamide;

N-[5-cyclopropyl-2-(4-fluorophenyl)-3-(1H-imidazol-2-yl)-1-benzofuran-6-yl]-N-[2-(4-methyl-1,3-thiazol-5-yl)ethyl]methanesulfonamide;

N-[5-cyclopropyl-2-(4-fluorophenyl)-3-(1H-imidazol-2-yl)-1-benzofuran-6-yl]-N-[3-(morpholin-4-ylsulfonyl)propyl]methanesulfonamide;

3-{[5-cyclopropyl-2-(4-fluorophenyl)-3-(1H-imidazol-2-yl)-1-benzofuran-6-yl](methylsulfonyl)amino}propane-1-sulfonamide;

N-[5-cyclopropyl-2-(4-fluorophenyl)-3-(1H-imidazol-2-yl)-1-benzofuran-6-yl]-N-[2-(pyrrolidin-1-yl)ethyl]methanesulfonamide;

N-[5-cyclopropyl-2-(4-fluorophenyl)-3-(1H-imidazol-2-yl)-1-benzofuran-6-yl]-N-[(1,3-dioxo-1,3-dihydro-2H-isoindol-2-yl)methyl]methanesulfonamide;

N-[5-cyclopropyl-2-(4-fluorophenyl)-3-(1H-imidazol-2-yl)-1-benzofuran-6-yl]-N-(4-fluorobutyl)methanesulfonamide;

N-[5-cyclopropyl-2-(4-fluorophenyl)-3-(1H-imidazol-2-yl)-1-benzofuran-6-yl]-N-(3,4-dihydroxy-4-methylpentyl)methanesulfonamide;

N-[5-cyclopropyl-2-(4-fluorophenyl)-3-(1H-imidazol-2-yl)-1-benzofuran-6-yl]-N-(3-fluoropropyl)methanesulfonamide;

3-{[5-cyclopropyl-2-(4-fluorophenyl)-3-(1H-imidazol-2-yl)-1-benzofuran-6-yl](methylsulfonyl)amino}-N-methylpropane-1-sulfonamide;

N-[5-cyclopropyl-2-(4-fluorophenyl)-3-(1H-imidazol-2-yl)-1-benzofuran-6-yl]-N-[2-(methylsulfonyl)ethyl]methanesulfonamide;

N-[5-cyclopropyl-2-(4-fluorophenyl)-3-(1H-imidazol-2-yl)-1-benzofuran-6-yl]-N-(5-hydroxypentyl)methanesulfonamide;

4-{[5-cyclopropyl-2-(4-fluorophenyl)-3-(1H-imidazol-2-yl)-1-benzofuran-6-yl](methylsulfonyl)amino}butanoic acid;

N-[5-cyclopropyl-2-(4-fluorophenyl)-3-(1H-imidazol-2-yl)-1-benzofuran-6-yl]-N-[3-(phenylsulfonyl)propyl]methanesulfonamide;

5-{[5-cyclopropyl-2-(4-fluorophenyl)-3-(1H-imidazol-2-yl)-1-benzofuran-6-yl](methylsulfonyl)amino}pentanamide;

5-{[5-cyclopropyl-2-(4-fluorophenyl)-3-(1H-imidazol-2-yl)-1-benzofuran-6-yl](methylsulfonyl)amino}pentanoic acid;

N-[5-cyclopropyl-2-(4-fluorophenyl)-3-(1H-imidazol-2-yl)-1-benzofuran-6-yl]-N-(2,3-dihydroxypropyl)methanesulfonamide;

N-[5-cyclopropyl-2-(4-fluorophenyl)-3-(1H-imidazol-2-yl)-1-benzofuran-6-yl]-N-(2,3-dihydroxy-3-methylbutyl)methanesulfonamide;

N-[5-cyclopropyl-2-(4-fluorophenyl)-3-(1H-imidazol-2-yl)-1-benzofuran-6-yl]-N-{3-[(methylsulfonyl)amino]propyl}methanesulfonamide;

N-[5-cyclopropyl-2-(4-fluorophenyl)-3-(1H-imidazol-2-yl)-1-benzofuran-6-yl]-N-[2-(ethylsulfonyl)ethyl]methanesulfonamide;

N-[2-(2-amino-1,3-thiazol-4-yl)ethyl]-N-[5-cyclopropyl-2-(4-fluorophenyl)-3-(1H-imidazol-2-yl)-1-benzofuran-6-yl]methanesulfonamide;

N-[5-cyclopropyl-2-(4-fluorophenyl)-3-(1H-imidazol-2-yl)-1-benzofuran-6-yl]-N-(2-hydroxypropyl)methanesulfonamide;

N-[5-cyclopropyl-2-(4-fluorophenyl)-3-(1H-imidazol-2-yl)-1-benzofuran-6-yl]-N-(4-hydroxy-4-methylpentyl)methanesulfonamide;

N-[5-cyclopropyl-2-(4-fluorophenyl)-3-(1H-imidazol-2-yl)-1-benzofuran-6-yl]-N-(4-hydroxypentyl)methanesulfonamide;

N-[5-cyclopropyl-2-(4-fluorophenyl)-3-(1H-imidazol-2-yl)-1-benzofuran-6-yl]-N-[3-(methylsulfonyl)propyl]methanesulfonamide;

4-{[5-cyclopropyl-2-(4-fluorophenyl)-3-(1H-imidazol-2-yl)-1-benzofuran-6-yl](methylsulfonyl)amino}-N,N-dimethylbutanamide;

N-[5-cyclopropyl-2-(4-fluorophenyl)-3-(1H-imidazol-2-yl)-1-benzofuran-6-yl]-N-[4-(morpholin-4-yl)-4-oxobutyl]methanesulfonamide;

N-[5-cyclopropyl-2-(4-fluorophenyl)-3-(1H-imidazol-2-yl)-1-benzofuran-6-yl]-N-[4-oxo-4-(piperidin-1-yl)butyl]methanesulfonamide;

4-{[5-cyclopropyl-2-(4-fluorophenyl)-3-(1H-imidazol-2-yl)-1-benzofuran-6-yl](methylsulfonyl)amino}-N-(methylsulfonyl)butanamide;

N-[5-cyclopropyl-2-(4-fluorophenyl)-3-(1H-imidazol-2-yl)-1-benzofuran-6-yl]-N-(4-hydroxy-4-methyl-3-oxopentyl)methanesulfonamide;

4-{[5-cyclopropyl-2-(4-fluorophenyl)-3-(1H-imidazol-2-yl)-1-benzofuran-6-yl](methylsulfonyl)amino}-N-methylbutanamide;

4-{[5-cyclopropyl-2-(4-fluorophenyl)-3-(1H-imidazol-2-yl)-1-benzofuran-6-yl](methylsulfonyl)amino}butanamide;

N-[5-cyclopropyl-2-(4-fluorophenyl)-3-(1H-imidazol-2-yl)-1-benzofuran-6-yl]-N-(2-hydroxyethyl)methanesulfonamide;

N-[5-cyclopropyl-2-(4-fluorophenyl)-3-(1H-imidazol-2-yl)-1-benzofuran-6-yl]-N-(3,4-dihydroxybutyl)methanesulfonamide;

N-(2-aminoethyl)-N-[5-cyclopropyl-2-(4-fluorophenyl)-3-(1H-imidazol-2-yl)-1-benzofuran-6-yl]methanesulfonamide;

N-(3-aminopropyl)-N-[5-cyclopropyl-2-(4-fluorophenyl)-3-(1H-imidazol-2-yl)-1-benzofuran-6-yl]methanesulfonamide;

N-[5-cyclopropyl-2-(4-fluorophenyl)-3-(1H-imidazol-2-yl)-1-benzofuran-6-yl]-N-[(1,1-$^2$H$_2$)hexyl]methanesulfonamide;

N-[5-cyclopropyl-3-(5,6-dihydro-4H-1,2,4-oxadiazin-3-yl)-2-(4-fluorophenyl)-1-benzofuran-6-yl]-N-[3-(1,1-dioxidothiomorpholin-4-yl)propyl]methanesulfonamide;

N-(5-cyano-5-methylhexyl)-N-[5-cyclopropyl-3-(5,6-dihydro-4H-1,2,4-oxadiazin-3-yl)-2-(4-fluorophenyl)-1-benzofuran-6-yl]methanesulfonamide;

diethyl(3-{[5-cyclopropyl-3-(5,6-dihydro-4H-1,2,4-oxadiazin-3-yl)-2-(4-fluorophenyl)-1-benzofuran-6-yl](methylsulfonyl)amino}propyl)phosphonate;

N-[5-cyclopropyl-3-(5,6-dihydro-4H-1,2,4-oxadiazin-3-yl)-2-(4-fluorophenyl)-1-benzofuran-6-yl]-N-(4,4,4-trifluorobutyl)methanesulfonamide;

N-[5-cyclopropyl-3-(5,6-dihydro-4H-1,2,4-oxadiazin-3-yl)-2-(4-fluorophenyl)-1-benzofuran-6-yl]-N-(3,3,3-trifluoropropyl)methanesulfonamide;

N-[5-cyclopropyl-3-(5,6-dihydro-4H-1,2,4-oxadiazin-3-yl)-2-(4-fluorophenyl)-1-benzofuran-6-yl]-N-[3-(1H-pyrrol-1-yl)propyl]methanesulfonamide;

N-[5-cyclopropyl-3-(5,6-dihydro-4H-1,2,4-oxadiazin-3-yl)-2-(4-fluorophenyl)-1-benzofuran-6-yl]-N-(5,6,6-trifluorohex-5-en-1-yl)methanesulfonamide;

ethyl 4-{[5-cyclopropyl-3-(5,6-dihydro-4H-1,2,4-oxadiazin-3-yl)-2-(4-fluorophenyl)-1-benzofuran-6-yl](methylsulfonyl)amino}butanoate;

N-[5-cyclopropyl-3-(5,6-dihydro-4H-1,2,4-oxadiazin-3-yl)-2-(4-fluorophenyl)-1-benzofuran-6-yl]-N-[4-(methylsulfonyl)butyl]methanesulfonamide;

N-[5-cyclopropyl-3-(5,6-dihydro-4H-1,2,4-oxadiazin-3-yl)-2-(4-fluorophenyl)-1-benzofuran-6-yl]-N-[2-(1,1-dioxidotetrahydrothiophen-3-yl)ethyl]methanesulfonamide;

3-{[5-cyclopropyl-3-(5,6-dihydro-4H-1,2,4-oxadiazin-3-yl)-2-(4-fluorophenyl)-1-benzofuran-6-yl](methylsulfonyl)amino}propane-1-sulfonamide;

N-[5-cyclopropyl-3-(5,6-dihydro-4H-1,2,4-oxadiazin-3-yl)-2-(4-fluorophenyl)-1-benzofuran-6-yl]-N-(3-hydroxy-3-methylbutyl)methanesulfonamide;

N-[5-cyclopropyl-3-(5,6-dihydro-4H-1,2,4-oxadiazin-3-yl)-2-(4-fluorophenyl)-1-benzofuran-6-yl]-N-[3-(morpholin-4-yl)propyl]methanesulfonamide;

N-[5-cyclopropyl-3-(5,6-dihydro-4H-1,2,4-oxadiazin-3-yl)-2-(4-fluorophenyl)-1-benzofuran-6-yl]-N-[3-(dimethylamino)propyl]methanesulfonamide;

N-[5-cyclopropyl-3-(5,6-dihydro-4H-1,2,4-oxadiazin-3-yl)-2-(4-fluorophenyl)-1-benzofuran-6-yl]-N-[2-(pyrrolidin-1-yl)ethyl]methanesulfonamide;

N-[5-cyclopropyl-3-(5,6-dihydro-4H-1,2,4-oxadiazin-3-yl)-2-(4-fluorophenyl)-1-benzofuran-6-yl]-N-[2-(diethylamino)ethyl]methanesulfonamide;

N-[5-cyclopropyl-3-(5,6-dihydro-4H-1,2,4-oxadiazin-3-yl)-2-(4-fluorophenyl)-1-benzofuran-6-yl]-N-[3-(piperidin-1-yl)propyl]methanesulfonamide;

N-[5-cyclopropyl-3-(5,6-dihydro-4H-1,2,4-oxadiazin-3-yl)-2-(4-fluorophenyl)-1-benzofuran-6-yl]-N-[3-(diethylamino)propyl]methanesulfonamide;

N-[5-cyclopropyl-3-(5,6-dihydro-4H-1,2,4-oxadiazin-3-yl)-2-(4-fluorophenyl)-1-benzofuran-6-yl]-N-[3-(pyrrolidin-1-yl)propyl]methanesulfonamide;

N-(3-cyanopropyl)-N-[5-cyclopropyl-3-(5,6-dihydro-4H-1,2,4-oxadiazin-3-yl)-2-(4-fluorophenyl)-1-benzofuran-6-yl]methanesulfonamide;

N-[5-cyclopropyl-3-(5,6-dihydro-4H-1,2,4-oxadiazin-3-yl)-2-(4-fluorophenyl)-1-benzofuran-6-yl]-N-(5-hydroxypentyl)methanesulfonamide;

4-{[5-cyclopropyl-3-(5,6-dihydro-4H-1,2,4-oxadiazin-3-yl)-2-(4-fluorophenyl)-1-benzofuran-6-yl](methylsulfonyl)amino}butanoic acid;

N-[5-cyclopropyl-3-(5,6-dihydro-4H-1,2,4-oxadiazin-3-yl)-2-(4-fluorophenyl)-1-benzofuran-6-yl]-N-(2-hydroxyethyl)methanesulfonamide;

N-[5-cyclopropyl-3-(5,6-dihydro-4H-1,2,4-oxadiazin-3-yl)-2-(4-fluorophenyl)-1-benzofuran-6-yl]-N-(3-hydroxypropyl)methanesulfonamide;

N-[5-cyclopropyl-3-(5,6-dihydro-4H-1,2,4-oxadiazin-3-yl)-2-(4-fluorophenyl)-1-benzofuran-6-yl]-N-[2-(methylsulfinyl)ethyl]methanesulfonamide;

N-[5-cyclopropyl-3-(5,6-dihydro-4H-1,2,4-oxadiazin-3-yl)-2-(4-fluorophenyl)-1-benzofuran-6-yl]-N-[3-(methylsulfinyl)propyl]methanesulfonamide;

N-[5-cyclopropyl-3-(5,6-dihydro-4H-1,2,4-oxadiazin-3-yl)-2-(4-fluorophenyl)-1-benzofuran-6-yl]-N-[3-(methylsulfonyl)propyl]methanesulfonamide;

N-[5-cyclopropyl-3-(5,6-dihydro-4H-1,2,4-oxadiazin-3-yl)-2-(4-fluorophenyl)-1-benzofuran-6-yl]-N-[2-(ethylsulfinyl)ethyl]methanesulfonamide;

N-[5-cyclopropyl-3-(5,6-dihydro-4H-1,2,4-oxadiazin-3-yl)-2-(4-fluorophenyl)-1-benzofuran-6-yl]-N-[2-(ethylsulfonyl)ethyl]methanesulfonamide;

N-[5-cyclopropyl-3-(5,6-dihydro-4H-1,2,4-oxadiazin-3-yl)-2-(4-fluorophenyl)-1-benzofuran-6-yl]-N-[3-(ethylsulfonyl)propyl]methanesulfonamide;

N-[5-cyclopropyl-3-(5,6-dihydro-4H-1,2,4-oxadiazin-3-yl)-2-(4-fluorophenyl)-1-benzofuran-6-yl]-N-[3-(ethylsulfinyl)propyl]methanesulfonamide;

N-[5-cyclopropyl-3-(4,5-dihydro-1,2,4-oxadiazol-3-yl)-2-(4-fluorophenyl)-1-benzofuran-6-yl]-N-(4-methoxybenzyl)methanesulfonamide;

N-[5-cyclopropyl-3-(4,5-dihydro-1,2,4-oxadiazol-3-yl)-2-(4-fluorophenyl)-1-benzofuran-6-yl]-N-(3,4-dihydroxy-4-methylpentyl)methanesulfonamide;

N-[5-cyclopropyl-3-(4,5-dihydro-1,2,4-oxadiazol-3-yl)-2-(4-fluorophenyl)-1-benzofuran-6-yl]-N-(5-hydroxypentyl)methanesulfonamide;

N-[5-cyclopropyl-3-(4,5-dihydro-1,2,4-oxadiazol-3-yl)-2-(4-fluorophenyl)-1-benzofuran-6-yl]-N-[4-(methylsulfonyl)butyl]methanesulfonamide;

N-[5-cyclopropyl-3-(4,5-dihydro-1,2,4-oxadiazol-3-yl)-2-(4-fluorophenyl)-1-benzofuran-6-yl]-N-[2-(1,1-dioxidotetrahydrothiophen-3-yl)ethyl]methanesulfonamide;

N-{5-cyclopropyl-3-[(5,5-$^2$H$_2$)-4,5-dihydro-1,2,4-oxadiazol-3-yl]-2-(4-fluorophenyl)-1-benzofuran-6-yl}-N-[4-(methylsulfonyl)butyl]methanesulfonamide;

N-[5-cyclopropyl-2-(4-fluorophenyl)-3-(5-methyl-4,5-dihydro-1,2,4-oxadiazol-3-yl)-1-benzofuran-6-yl]-N-(4-methoxybenzyl)methanesulfonamide;

N-[5-cyclopropyl-3-(5,5-dimethyl-4,5-dihydro-1,2,4-oxadiazol-3-yl)-2-(4-fluorophenyl)-1-benzofuran-6-yl]-N-(3-methylbutyl)methanesulfonamide;

N-[5-cyclopropyl-2-(4-fluorophenyl)-3-(5-propyl-1,2,4-oxadiazol-3-yl)-1-benzofuran-6-yl]-N-(3-methylbutyl)methanesulfonamide;

N-[5-cyclopropyl-2-(4-fluorophenyl)-3-(5-propyl-4,5-dihydro-1,2,4-oxadiazol-3-yl)-1-benzofuran-6-yl]-N-(3-methylbutyl)methanesulfonamide;

N-[5-cyclopropyl-3-(5-ethyl-4,5-dihydro-1,2,4-oxadiazol-3-yl)-2-(4-fluorophenyl)-1-benzofuran-6-yl]-N-(3-methylbutyl)methanesulfonamide;

N-[5-cyclopropyl-3-(4,5-dihydro-1,2,4-oxadiazol-3-yl)-2-(4-fluorophenyl)-1-benzofuran-6-yl]-N-(3-methylbutyl)methanesulfonamide;

4-{[5-cyclopropyl-3-(4,5-dihydro-1,2,4-oxadiazol-3-yl)-2-(4-fluorophenyl)-1-benzofuran-6-yl](methylsulfonyl)amino}butanoic acid;

N-[5-cyclopropyl-2-(4-fluorophenyl)-3-(5-methyl-4,5-dihydro-1,2,4-oxadiazol-3-yl)-1-benzofuran-6-yl]-N-(2-hydroxyethyl)methanesulfonamide;

N-[3-(4-chloro-1H-imidazol-2-yl)-5-cyclopropyl-2-(4-fluorophenyl)-1-benzofuran-6-yl]-N-(4-methoxybenzyl)methanesulfonamide;

N-[5-cyclopropyl-2-(4-fluorophenyl)-3-(5-oxo-5,6-dihydro-4H-1,2,4-oxadiazin-3-yl)-1-benzofuran-6-yl]-N-(4-methoxybenzyl)methanesulfonamide;

N-[5-cyclopropyl-2-(4-fluorophenyl)-3-(6-oxo-1,6-dihydropyrimidin-2-yl)-1-benzofuran-6-yl]-N-(3-methylbutyl)methanesulfonamide;

N-[5-cyclopropyl-2-(4-fluorophenyl)-3-(5-oxo-5,6-dihydro-4H-1,2,4-oxadiazin-3-yl)-1-benzofuran-6-yl]-N-(3-methylbutyl)methanesulfonamide;

N-[5-cyclopropyl-3-(4,5-dichloro-1H-imidazol-2-yl)-2-(4-fluorophenyl)-1-benzofuran-6-yl]methanesulfonamide;

N-[3-(4-chloro-1H-imidazol-2-yl)-5-cyclopropyl-2-(4-fluorophenyl)-1-benzofuran-6-yl]methanesulfonamide;

N-[5-cyclopropyl-3-(4,5-dibromo-1H-imidazol-2-yl)-2-(4-fluorophenyl)-1-benzofuran-6-yl]methanesulfonamide;

2-[6-(2,5-dimethyl-1H-pyrrol-1-yl)-2-phenyl-1-benzofuran-3-yl]-1H-imidazole;

N-{5-cyclopropyl-3-(1H-imidazol-2-yl)-2-[4-(1-phenylvinyl)phenyl]-1-benzofuran-6-yl}-N-(3-methylbutyl)methanesulfonamide;

N-[5-cyclopropyl-2-{4-[(1E)-hex-1-en-1-yl]phenyl}-3-(1H-imidazol-2-yl)-1-benzofuran-6-yl]-N-[4-(methylsulfonyl)butyl]methanesulfonamide;

N-[2-(4-anilinophenyl)-5-cyclopropyl-3-(1H-imidazol-2-yl)-1-benzofuran-6-yl]-N-[4-(methylsulfonyl)butyl]methanesulfonamide;

N-[2-(4-fluorophenyl)-3-(1H-imidazol-2-yl)-5-isopropoxy-1-benzofuran-6-yl]-N-(4-methoxybenzyl)methanesulfonamide;

N-{5-cyclopropyl-2-(4-fluorophenyl)-3-[4-(trifluoromethyl)-1H-imidazol-2-yl]-1-benzofuran-6-yl}-N-(3-methylbutyl)methanesulfonamide;

N-[5-cyclopropyl-2-(4-fluorophenyl)-3-(5-methyl-1H-imidazol-2-yl)-1-benzofuran-6-yl]-N-(3-methylbutyl)methanesulfonamide;

N-[5-cyclopropyl-3-(4,5-dihydro-1,2,4-oxadiazol-3-yl)-2-(4-fluorophenyl)-1-benzofuran-6-yl]methanesulfonamide;

N-[5-cyclopropyl-2-(4-fluorophenyl)-3-(1H-imidazol-2-yl)-1-benzofuran-6-yl]-N-[3-(1H-tetrazol-5-yl)propyl]methanesulfonamide;

N-[5-cyclopropyl-2-(4-fluorophenyl)-3-(1H-imidazol-2-yl)-1-benzofuran-6-yl]-N-[3-(5-oxo-4,5-dihydro-1,2,4-oxadiazol-3-yl)propyl]methanesulfonamide;

(1Z)-4-{[5-cyclopropyl-2-(4-fluorophenyl)-3-(1H-imidazol-2-yl)-1-benzofuran-6-yl](methylsulfonyl)amino}-N'-hydroxybutanimidamide;

N-[5-cyclopropyl-2-(4-fluorophenyl)-3-(1H-imidazol-2-yl)-1-benzofuran-6-yl]-N-[3-(5-thioxo-4,5-dihydro-1,2,4-oxadiazol-3-yl)propyl]methanesulfonamide;

N-[5-cyclopropyl-2-(4-fluorophenyl)-3-(1H-imidazol-2-yl)-1-benzofuran-6-yl]-N-[3-(5-oxo-4,5-dihydro-1,2,4-thiadiazol-3-yl)propyl]methanesulfonamide;

N-[5-cyclopropyl-2-(4-fluorophenyl)-3-(1H-imidazol-2-yl)-1-benzofuran-6-yl]-N-[3-(5-oxo-4,5-dihydro-1,3,4-oxadiazol-2-yl)propyl]methanesulfonamide;

N-[5-cyclopropyl-3-(5,6-dihydro-4H-1,2,4-oxadiazin-3-yl)-2-(4-fluorophenyl)-1-benzofuran-6-yl]-N-[3-(1H-tetrazol-5-yl)propyl]methanesulfonamide;

(1Z)-4-{[5-cyclopropyl-3-(5,6-dihydro-4H-1,2,4-oxadiazin-3-yl)-2-(4-fluorophenyl)-1-benzofuran-6-yl](methylsulfonyl)amino}-N-hydroxybutanimidamide;

N-[5-cyclopropyl-3-(5,6-dihydro-4H-1,2,4-oxadiazin-3-yl)-2-(4-fluorophenyl)-1-benzofuran-6-yl]-N-[3-(5-oxo-4,5-dihydro-1,2,4-oxadiazol-3-yl)propyl]methanesulfonamide;

N-[5-cyclopropyl-3-(5,6-dihydro-4H-1,2,4-oxadiazin-3-yl)-2-(4-fluorophenyl)-1-benzofuran-6-yl]-N-[3-(5-thioxo-4,5-dihydro-1,2,4-oxadiazol-3-yl)propyl]methanesulfonamide;

N-[5-cyclopropyl-3-(5,6-dihydro-4H-1,2,4-oxadiazin-3-yl)-2-(4-fluorophenyl)-1-benzofuran-6-yl]-N-[3-(5-oxo-4,5-dihydro-1,2,4-thiadiazol-3-yl)propyl]methanesulfonamide;

N-[5-cyclopropyl-2-(4-fluorophenyl)-3-(5-oxo-4,5-dihydro-1,2,4-oxadiazol-3-yl)-1-benzofuran-6-yl]-N-(4-hydroxybutyl)methanesulfonamide;

N-[5-cyclopropyl-3-(4,5-dimethyl-1H-imidazol-2-yl)-2-(4-fluorophenyl)-1-benzofuran-6-yl]-N-(4-methoxybenzyl)methanesulfonamide;

N-[5-cyclopropyl-2-(4-fluorophenyl)-3-(4-methyl-1H-imidazol-2-yl)-1-benzofuran-6-yl]-N-(4-hydroxybutyl)methanesulfonamide;

N-[5-cyclopropyl-2-(4-fluorophenyl)-3-(5-methyl-1H-imidazol-2-yl)-1-benzofuran-6-yl]-N-(4-methoxybenzyl)methanesulfonamide;

N-[5-cyclopropyl-2-(4-fluorophenyl)-3-(4-methyl-1H-imidazol-2-yl)-1-benzofuran-6-yl]-N-(2-hydroxyethyl)methanesulfonamide;

N-[5-cyclopropyl-2-(4-fluorophenyl)-3-(1H-imidazol-2-yl)-1-benzofuran-6-yl]-N-[(3-hydroxy-1,2-oxazol-5-yl)methyl]methanesulfonamide;

3-[3-(1H-imidazol-2-yl)-2-(4-methoxyphenyl)pyrazolo[1,5-a]pyridin-5-yl]-4-methyl-N-(1-phenylcyclopropyl)benzamide; and N-[5-cyclopropyl-3-(4,5-dimethyl-1H-imidazol-2-yl)-2-(4-fluorophenyl)-1-benzofuran-6-yl]methanesulfonamide.

Isomers

The present disclosure contemplates various stereoisomers and mixtures thereof, and these are specifically included within the scope of this disclosure. Stereoisomers include enantiomers and diastereomers, and mixtures of enantiomers or diastereomers. Individual stereoisomers of compounds of the present application may be prepared synthetically from commercially available starting materials which contain asymmetric or chiral centers or by preparation of racemic mixtures followed by resolution which is well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, or (2) direct separation of the mixture of optical enantiomers on chiral chromatographic columns.

Geometric isomers may exist in the disclosed compounds. The present disclosure contemplates the various geometric isomers and mixtures thereof resulting from the disposition of substituents around a carbon-carbon double bond, a carbon-nitrogen double bond, a cycloalkyl group, or a heterocycle group. Substituents around a carbon-carbon double bond or a carbon-nitrogen bond are designated as being of Z or E configuration and substituents around a cycloalkyl or a heterocycle are designated as being of cis or trans configuration.

It is to be understood that compounds disclosed herein may exhibit the phenomenon of tautomerism.

Thus, the formulae drawings within this specification can represent only one of the possible tautomeric or stereoisomeric forms. It is to be understood that the disclosed compounds encompass any tautomeric or stereoisomeric forms, and mixtures thereof, and are not to be limited merely to any one tautomeric or stereoisomeric form utilized within the naming of the compounds or formulae drawings.

Isotopes

The disclosure also include isotopically-labeled compounds, which are identical to disclosed compounds, but for the fact that one or more atoms are replaced by an atom having an atomic mass or mass number different from the atomic mass or mass number usually found in nature. Examples of isotopes suitable for inclusion in the disclosed compounds are hydrogen, carbon, nitrogen, oxygen, phosphorus, fluorine, and chlorine, such as but not limited to $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Substitution with heavier isotopes such as deuterium, i.e., $^2H$, can afford certain therapeutic advantages resulting from greater metabolic stability, for example increased in vivo half-life or reduced dosage requirements and, hence, may be employed in some circumstances. Compounds incorporating positron-emitting isotopes are useful in medical imaging and positron-emitting tomography (PET) studies for determining the distribution of receptors. Suitable positron-emitting isotopes that can be incorporated in compounds of formula (I) are $^{11}C$, $^{13}N$, $^{15}O$, and $^{18}F$. Isotopically-labeled compounds of the present disclosure can generally be prepared by conventional techniques known to those skilled in the art or by processes analogous to those described in the accompanying Examples using appropriate isotopically-labeled reagent in place of non-isotopically-labeled reagent.

Salts

This disclosure is also directed, in part, to all salts of the disclosed compounds. A salt of a compound may be advantageous due to one or more of the salt's properties, such as, for example, enhanced pharmaceutical stability in differing temperatures and humidities, or a desirable solubility in water or other solvents. Where a salt is intended to be administered to a patient (as opposed to, for example, being in use in an in vitro context), the salt may be pharmaceutically acceptable and/or physiologically compatible. The term "pharmaceutically acceptable" is used adjectivally in this disclosure to mean that the modified noun is appropriate for use as a pharmaceutical product or as a part of a pharmaceutical product. Pharmaceutically acceptable salts include, for example, salts commonly used to form alkali metal salts and to form addition salts of free acids or free bases. In general, these salts typically may be prepared by conventional means by reacting, for example, the appropriate acid or base with a disclosed compound.

Pharmaceutically acceptable acid addition salts of the disclosed compounds can be prepared from an inorganic or organic acid. Examples of suitable inorganic acids include hydrochloric, hydrobromic, hydroiodic, nitric, carbonic, sulfuric, and phosphoric acid. Suitable organic acids generally include, for example, aliphatic, cycloaliphatic, aromatic, araliphatic, heterocyclic, carboxylic, and sulfonic classes of organic acids. Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), ethanesulfonate, benzenesulfonate, pantothenate, 2-hydroxyethanesulfonate, sulfanilate, cyclohexylaminosulfonate, algenic acid, beta-hydroxybutyric acid, galactarate, galacturonate, adipate, alginate, bisulfate, butyrate, camphorate, camphorsulfonate, cyclopentanepropionate, dodecylsulfate, glycoheptanoate, glycerophosphate, heptanoate, hexanoate, nicotinate, oxalate, palmoate, pectinate, 2-naphthalesulfonate, 3-phenylpropionate, picrate, pivalate, thiocyanate, tosylate, and undecanoate.

Pharmaceutically acceptable base addition salts of the disclosed compounds include, for example, metallic salts and organic salts. Metallic salts may include alkali metal (group Ia) salts, alkaline earth metal (group IIa) salts, and other physiologically acceptable metal salts. Such salts may be made from aluminum, calcium, lithium, magnesium, potassium, sodium, and zinc. Organic salts can be made from amines, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups can be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

Purity

The disclosed compounds (and salts thereof) with any level of purity (including pure and substantially pure) are within the scope of the present disclosure. The term "substantially pure" in reference to a compound/salt/isomer, means that the preparation/composition containing the compound/salt/isomer contains more than about 85% by weight of the compound/salt/isomer, more than about 90% by weight of the compound/salt/isomer, more than about 95% by weight of the compound/salt/isomer, more than about 97% by weight of the compound/salt/isomer, and more than about 99% by weight of the compound/salt/isomer.

Compositions

This present disclosure is also directed, in part, to compositions comprising one or more of the disclosed compounds and/or salts thereof. In some embodiments, the compositions comprise one or more substantially phase pure crystalline forms. The compositions may be pharmaceutical compositions.

In some embodiments, the compositions further comprise one or more additional therapeutic agents. Such therapeutic agents may include one or more therapeutic agents used to treat hepatitis C (e.g., interferon or interferon/ribavirin combination, or an HCV inhibitor such as, for example, an HCV polymerase inhibitor or an HCV protease inhibitor). The disclosed compound(s) and/or salt(s) thereof can also be co-administered with therapeutic agents other than therapeutic agents used to treat hepatitis C (e.g., anti-HIV agents such as ritonavir).

The composition may depend on the method of administration, and may comprise one or more conventional pharmaceutically acceptable carriers, adjuvants, and/or vehicles (together referred to as "excipients"). Formulation of drugs is generally discussed in, for example, Hoover, J., *Remington's Pharmaceutical Sciences* (Mack Publishing Co., 1975) and Ansel's *Pharmaceutical Dosage Forms and Drug Delivery Systems* (Lippincott Williams & Wilkins, 2005).

Solid dosage forms for oral administration include, for example, capsules, tablets, pills, powders, and granules. In such solid dosage forms, the disclosed compounds or salts are ordinarily combined with one or more excipients. If administered per os, the compounds or salts can be mixed with, for example, lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation, as can be provided in, for example, a dispersion of the compound or salt in hydroxypropylmethyl cellulose. In the case of capsules, tablets, and pills, the dosage forms also can comprise buffering agents, such as sodium citrate, or magnesium or calcium carbonate or bicarbonate. Tablets and pills additionally can be prepared with enteric coatings.

Liquid dosage forms for oral administration include, for example, pharmaceutically acceptable emulsions (including both oil-in-water and water-in-oil emulsions), solutions (including both aqueous and non-aqueous solutions), suspensions (including both aqueous and non-aqueous suspensions), syrups, and elixirs containing inert diluents commonly used in the art (e.g., water). Such compositions may also comprise, for example, wetting, emulsifying, suspending, flavoring (e.g., sweetening), and/or perfuming agents.

Parenteral administration includes subcutaneous injections, intravenous injections, intramuscular injections, intrasternal injections, and infusion. Injectable preparations (e.g., sterile injectable aqueous or oleaginous suspensions) can be formulated according to the known art using suitable dispersing, wetting agents, and/or suspending agents. Acceptable vehicles and solvents include, for example, water, 1,3-butanediol, Ringer's solution, isotonic sodium chloride solution, bland fixed oils (e.g., synthetic mono- or diglycerides), fatty acids (e.g., oleic acid), dimethyl acetamide, surfactants (e.g., ionic and non-ionic detergents), and/or polyethylene glycols.

Formulations for parenteral administration may, for example, be prepared from sterile powders or granules having one or more of the excipients mentioned for use in the formulations for oral administration. A compound or salt of the invention can be dissolved in water, polyethylene glycol, propylene glycol, ethanol, corn oil, cottonseed oil, peanut oil, sesame oil, benzyl alcohol, sodium chloride, and/or various buffers. The pH may be adjusted, if necessary, with a suitable acid, base, or buffer.

Suppositories for rectal administration may be prepared by, for example, mixing a compound or salt of the invention with a suitable nonirritating excipient that is solid at ordinary temperatures, but liquid at the rectal temperature, and will, therefore, melt in the rectum to release the drug. Suitable excipients include, for example, cocoa butter; synthetic mono-, di-, or triglycerides, fatty acids, and/or polyethylene glycols.

Topical administration includes the use of transdermal administration, such as transdermal patches or iontophoresis devices.

Other excipients and modes of administration known in the pharmaceutical art also may be used.

The total daily dose of the compound or salt (administered in single or divided doses) may be from about 0.001 to about 100 mg/kg, from about 0.001 to about 30 mg/kg, or from about 0.01 to about 10 mg/kg (i.e., mg of the compound or salt per kg body weight). Dosage unit compositions may contain such amounts or submultiples thereof to make up the daily dose. In many instances, the administration of the compound or salt will be repeated a plurality of times. Multiple doses per day typically may be used to increase the total daily dose, if desired.

Factors affecting the dosage regimen include the type, age, weight, sex, diet, and condition of the patient; the severity of the pathological condition; the severity of the pathological condition; the route of administration; pharmacological considerations, such as the activity, efficacy, pharmacokinetic, and toxicology profiles of the particular compound or salt used; whether a drug delivery system is utilized; and whether the compound or salt is administered as part of a drug combination. Thus, the dosage regimen actually employed can vary widely, and therefore, can derive from the dosage regimen set forth above.

Kits

This disclosure is also directed, in part, to kits comprising one or more of the disclosed compounds and/or salts thereof. The kits may optionally contain one or more additional therapeutic agents and/or instructions for, for example, using the kit.

Methods of Use

This disclosure is also directed, in part, to methods for inhibiting replication of a ribonucleic acid (RNA) virus. The method comprises exposing the virus to one or more of the disclosed compounds and/or salts thereof. In some embodiments, replication of the RNA virus is inhibited in vitro. In other embodiments, replication of the RNA virus is inhibited in vivo. In some embodiments, the RNA virus whose replication is being inhibited is a single-stranded, positive sense RNA virus. In some such embodiments, the RNA virus whose replication is being inhibited is a virus from the Flaviviridae family. In some such embodiments, the RNA virus whose replication is being inhibited is HCV. In embodiments, the RNA virus whose replication is being inhibited is any one of HCV genotypes 1a, 1b, 2a, 3a and 4a. In embodiments, the RNA virus whose replication is being inhibited is a mutant form of HCV. In embodiments, the RNA virus whose replication is being inhibited is a mutant form of HCV genotype 1a or 1b. In embodiments, the mutation occurring in HCV genotype 1a or 1b is a C316Y mutation.

This disclosure is also directed, in part, to methods for inhibiting HCV RNA polymerase. The method comprises exposing the polymerase with one or more of the disclosed compounds and/or salts thereof. In some embodiments, HCV RNA polymerase activity is inhibited in vitro. In other embodiments, HCV RNA polymerase activity is inhibited in vivo. In embodiments, the HCV RNA polymerase whose replication is being inhibited is a mutant form of HCV RNA polymerase genotype 1a or 1b. In embodiments, the mutation occurring in HCV RNA polymerase genotype 1a or 1b is a C316Y mutation.

The term "inhibiting" means reducing the level of RNA virus replication/HCV polymerase activity either in vitro or in vivo. For example, if a disclosed compound/salt reduces the level of RNA virus replication by at least about 10% compared to the level of RNA virus replication before the virus was exposed to the compound/salt, then the compound/salt inhibits RNA virus replication. In some embodiments, the compound/salt can inhibit RNA virus replication by at least about 20%, at least about 30%, at least about 40%, at least about 50%, at least about 60%, at least about 70%, at least about 80%, at least about 90%, or at least about 95%.

This disclosure is also directed, in part, to methods for treating a disease that can be treated by inhibiting HCV RNA polymerase. Thus, this disclosure is also directed, in part, to methods for treating hepatitis C in an animal in need of such treatment. These methods comprise administering to the animal one or more of the disclosed compounds and/or salts thereof, and, optionally, one or more additional therapeutic agents. In some embodiments, a therapeutically effective amount of the compound(s) and/or salt(s) is administered to the animal "Treating" means ameliorating, suppressing, eradicating, preventing, reducing the risk of, and/or delaying the onset of the disease being treated. Applicants specifically intend that the term "treating" encompass administration of the disclosed compounds and/or salts thereof to an HCV-negative patient that is a candidate for an organ transplant. The methods of treatment are particularly suitable for use with humans, but may be used with other animals, particularly mammals. A "therapeutically-effective amount" or "effective amount" is an amount that will achieve the goal of treating the targeted condition.

In some embodiments, the methods comprise combination therapy, wherein the disclosed compound(s) and/or salt(s) is/are co-administered with a second (or even a third, fourth, etc.) compound, such as, for example, another antiviral therapeutic agent such as, for example, an antiviral therapeutic agent used to treat hepatitis C (e.g., interferon or interferon/ribavirin combination, or an HCV inhibitor such as, for example an HCV polymerase inhibitor or an HCV protease inhibitor). The disclosed compound(s) and/or salt(s) thereof can also be co-administered with therapeutic agents other than therapeutic agents used to treat hepatitis C (e.g., pharmacokinetic boosting agents such as ritonavir). In these co-administration embodiments, the disclosed compound(s) and/or salt(s) thereof and the second, etc. therapeutic agent(s) may be administered in a substantially simultaneous manner (e.g., or within about 5 minutes of each other), in a sequential manner, or both. It is contemplated that such combination therapies may include administering one therapeutic agent multiple times between the administrations of the other. The time period between the administration of each agent may range from a few seconds (or less) to several hours or days, and will depend on, for example, the properties of each composition and active ingredient (e.g., potency, solubility, bioavailability, half-life, and kinetic profile), as well as the condition of the patient. The disclosed compound(s) and/or salt(s) and the second, etc. therapeutic agent may also be administered in a single formulation.

This disclosure is also directed, in part, to uses of one or more of the disclosed compounds and/or salts thereof, and, optionally one or more additional therapeutic agents to prepare a medicament. In some embodiments, the medicament is for co-administration with one or more additional therapeutic agents.

In some embodiments, the medicament is for inhibiting replication of an RNA virus.

In some embodiments, the medicament is for treating hepatitis C.

This disclosure is also directed, in part, to one or more of the disclosed compounds and/or salts thereof, and, optionally one or more additional therapeutic agents, for use as a medicament. In some embodiments, the medicament is for inhibiting replication of an RNA virus. In other embodiments, the medicament is for treating hepatitis C.

Biological Data

Abbreviations:

ATP for adenosine triphosphate; cpms for counts per minute; CTP for cytidine triphosphate; DMEM for Dulbecco's modified Eagle's medium; DMSO for dimethyl sulfoxide; DNA for deoxyribonucleic acid; EDTA for ethylenediaminetetraacetic acid; FBS for fetal bovine serum; GTP for guanosine 5'-triphosphate; IRES for internal ribosome entry site; kb for kilobase; PCR for polymerase chain reaction; RNA for ribonucleic acid; RT for reverse transcriptase; RT-PCR for reverse transcriptase-polymerase chain reaction; Tris for tris(hydroxymethyl)aminomethane; Tris-HCl for tris (hydroxymethyl)aminomethane hydrochloride and v/v for volume/volume.

Biochemical Enzyme Inhibition Assays.

Purified HCV NS5B polymerase enzymes were used for polymerase inhibition assays. All recombinant HCV polymerases contained the first 570 amino acids of the 591 amino acid native protein sequence and a six-histidine tag at the N-terminus or C-terminus to facilitate purification by affinity chromatography. The DNA nucleotide sequence for the HCV polymerase 1b BK strain was codon optimized for expression in *E. coli*. A synthetic gene was prepared from a series of overlapping oligonucleotides that were filled in using a DNA polymerase and amplified by PCR. The patient isolate HCV polymerases were cloned by RT-PCR methods using HCV RNA extracted from the serum of infected subjects obtained from ProMedDx and BioCollections (genotypes 2a, 2b, 3a, and 4a). Laboratory strains were cloned from plasmid DNA (1a-H77 or 1a-H77-C316Y) or from existing replicon cells (1b Rice). In all cases the amplified DNA was cloned into a protein expression vector (typically a pET vector from Novagen) and then multiple clones were sequenced to identify one whose NS5B sequence agreed with the population sequence. This sequence-confirmed clone was then transfected into *E. coli* for protein expression and purification. *E. coli* cultures were grown to a maximum optical density (OD) of 2-3 and then induced with 0.4 mM isopropyl beta-D- thiogalactopyranoside (IPTG) and grown for 20 hours at 20° C. Proteins were purified using nickel affinity chromatography, and additional column steps were added including, ion exchange, size exclusion, hydrophobic ion, and poly-U affinity chromatography, as needed, depending on the sample being purified. The template RNA used in the polymerase enzymatic assay was a 2.1 kb construct that corresponds to the 3'-end of an HCV genotype 1b negative strand RNA.

For the polymerase enzymatic inhibition assay, dilutions of the inhibitors were incubated with 20 mM Tris-HCl, pH 7.4, 2 mM MnCl$_2$, 80 mM potassium glutamate, 1 mM dithiothreitol (DTT), 1 mM ethylenediaminetetraacetic acid (EDTA), 0.1 mg/mL bovine serum albumin (BSA), 60-125 µM of GTP and 10-50 nM of polymerase for approximately 15 minutes. The reaction was initiated by the addition of 20 µM CTP, 20 µM ATP, 0.284 µM (0.5 µCi) of 5,6-[$^3$H] UTP, 5 nM template RNA and 0.1 U/µL RNase inhibitor (RNasin, Promega), and allowed to proceed for three hours at 30° C. The final reaction volume was 50 µL. The reaction was terminated by the addition of 50 uL of 4 mM spermine in 10 mM Tris-HCl, pH 7.5, 1 mM EDTA. The quenched reaction was allowed to incubate for at least 15 minutes at room temperature, and then the precipitated RNA was captured by filtration through a glass fiber filter (GF/B, Millipore) in a 96 well format. The filter plate was washed five times with 200 µL of 2 mM spermine, 10 mM Tris-HCl, pH 8.0, 1 mM EDTA, and two times with ethanol. After drying thoroughly in air, 30 µL of Microscint-20 scintillation cocktail (Perkin Elmer) was added to each well, and the retained cpm were determined by scintillation counting. IC$_{50}$ values were determined by non-linear regression.

For weak inhibitors, the percent of inhibition was calculated at twelve inhibitor concentrations relative to the uninhibited control and then fit to equation 1.

% Inhibition=100*[[$I$]/([$I$]+[$IC_{50}$])]    equation 1

For potent inhibitors, the cpms at each inhibitor concentration were fit directly to equation 2, the tight-binding equation.

$V=k_{cat}[S]/2(K_m+[S])*(\mathrm{sqrt}((IC_{50}+I-E)^2+(4*IC_{50}*E))-(IC_{50}+I-E))$    equation 2

The IC$_{50}$ values from the inhibition assay for certain exemplified compounds are set forth in Table 2 below.

In the HCV polymerase assay with strain 1a H77, the disclosed compounds achieve IC$_{50}$s of less than about 200 µM, and, as illustrated in Table 2, certain disclosed compounds achieve IC$_{50}$s within a range of from about 0.001 to about 200 µM. Certain disclosed compounds have IC$_{50}$s less than 0.1 µM.

In the HCV polymerase assay with strain 1a H77-C316Y, the disclosed compounds achieve IC$_{50}$s of less than about 25 µM, and, as illustrated in Table 2, certain disclosed compounds achieve IC$_{50}$s within a range of from about 0.005 to about 25 µM. Certain disclosed compounds have IC$_{50}$s less than 0.1 µM.

In a comparison of IC$_{50}$s between the wild type 1a H77 and the mutant 1a H77-C316Y, the disclosed compounds achieve a fold resistance of less than about 600-fold, and, as illustrated in Table 2, certain compounds achieve a fold resistance within a range of about 1 to about 600. Certain disclosed compounds have a fold resistance of <20.

In the HCV polymerase assay with strain 1b BK, the disclosed compounds achieve IC$_{50}$s of less than 200 µM, and as illustrated in Table 2, certain disclosed compounds achieve IC$_{50}$s within a range of from about 0.005 to about 200 µM. Certain disclosed compounds have IC$_{50}$s less than 0.1 µM.

In the HCV polymerase assay with strain 1b Rice, the disclosed compounds achieve IC$_{50}$s of less than 0.1 µM, and as illustrated in Table 2, certain disclosed compounds achieve IC$_{50}$s within a range of from about 0.0025 to about 0.075 µM. Certain compounds have IC$_{50}$s less than about 0.070 µM.

TABLE 2

| Example # | HCV Polymerase Strain | | | | |
|---|---|---|---|---|---|
| | 1a H77 IC$_{50}$ (µM) | 1a H77-C316Y IC$_{50}$ (µM) | C316Y/1a Fold Resistance | 1b BK IC$_{50}$ (µM) | 1b Rice IC$_{50}$ (µM) |
| 1 | 0.0059 | 1.8 | 304 | 0.087 | |
| 2a | 0.015 | 0.224 | 15 | 0.055 | |
| 3 | 0.0030 | 0.011 | 4 | 0.010 | |
| 4 | 0.0053 | 0.057 | 11 | 0.011 | |
| 5 | 0.0039 | 0.053 | 14 | 0.017 | |
| 6 | 0.0052 | 0.069 | 13 | 0.016 | |
| 7 | 0.0030 | 0.012 | 4 | 0.011 | |
| 8 | 0.0049 | 0.031 | 6 | 0.027 | |
| 9 | 0.0039 | 0.030 | 8 | 0.034 | |
| 10 | 0.0070 | 0.064 | 9 | 0.105 | |
| 11 | 0.0059 | 0.030 | 5 | 0.020 | |
| 12 | 0.0055 | 0.043 | 8 | 0.017 | |
| 13 | 0.0074 | 0.115 | 16 | 0.026 | |
| 14 | 0.0085 | 0.070 | 8 | 0.035 | |
| 15 | 0.0030 | 0.031 | 10 | 0.011 | |
| 16 | 0.0030 | 0.035 | 12 | 0.018 | |
| 17 | 0.0349 | 1.8 | 52 | 0.438 | |
| 18 | 0.0258 | 0.101 | 4 | 0.0856 | 0.0304 |
| 19 | 0.0040 | 0.457 | 115 | 0.15 | 0.0072 |
| 20 | 0.0349 | 0.173 | 5 | 0.052 | |
| 21 | 0.0476 | 0.090 | 2 | 0.099 | |
| 22 | 0.159 | 0.179 | 1 | 0.055 | |
| 23 | 0.0039 | 0.027 | 7 | 0.010 | |
| 24 | 0.0069 | 0.036 | 5 | 0.018 | |
| 25 | 0.0063 | 0.043 | 7 | 0.015 | |
| 26 | 0.012 | 0.030 | 3 | 0.010 | |
| 27 | 0.214 | 3.8 | 18 | 0.099 | |
| 28 | 0.0059 | 0.028 | 5 | 0.012 | |
| 29 | 0.0030 | 0.0070 | 2 | 0.0090 | |
| 30 | 0.0050 | 0.019 | 4 | 0.012 | |
| 31 | 0.0035 | 0.172 | 50 | 0.0070 | |
| 32 | 0.132 | 0.147 | 1 | 0.0801 | |
| 33 | 0.0105 | 1.9 | 181 | 0.152 | |
| 34 | 0.0050 | 0.149 | 30 | 0.022 | |
| 35 | 0.0049 | 0.113 | 23 | 0.0070 | |
| 36 | 0.0079 | 3.4 | 428 | 0.188 | |
| 37 | 0.0055 | 0.144 | 26 | 0.024 | |
| 38 | 0.0050 | 0.148 | 30 | 0.033 | |
| 39 | 0.0050 | 0.078 | 16 | 0.017 | |
| 40 | 0.0065 | 0.070 | 11 | 0.019 | |
| 41 | 0.0050 | 0.058 | 12 | 0.016 | |
| 42 | 0.083 | | | 0.781 | |
| 43 | 0.0065 | 1.0 | 154 | 0.025 | |
| 44 | 0.0050 | 0.105 | 21 | 0.019 | |
| 45 | 0.0075 | 0.295 | 39 | 0.11 | |
| 46 | 0.0045 | 0.098 | 22 | 0.011 | |
| 47 | 0.0079 | 1.0 | 126 | 0.041 | |
| 48 | 0.0077 | 0.074 | 10 | 0.023 | |
| 49 | 0.0050 | 0.052 | 10 | 0.017 | |
| 50 | 0.0039 | 0.104 | 27 | 0.012 | |
| 51 | 0.0094 | 2.05 | 219 | 0.074 | |
| 52 | 0.0077 | 2.22 | 286 | 0.132 | |
| 53 | 0.0049 | 0.223 | 46 | 0.245 | |
| 54 | 0.0045 | 0.192 | 43 | 0.293 | |
| 55 | 0.0050 | 0.366 | 73 | 0.028 | |
| 56 | 0.0035 | 0.22 | 64 | 0.017 | |
| 57 | 0.0030 | 0.232 | 77 | 0.011 | |
| 58 | 0.0073 | 0.133 | 18 | 0.029 | |
| 59 | 0.0134 | 1.5 | 112 | 0.056 | |
| 60 | 0.0112 | 0.191 | 17 | 0.020 | |
| 61 | 0.0089 | 0.076 | 9 | 0.016 | |
| 62 | 0.0039 | 0.25 | 65 | 0.014 | |
| 63 | 0.0045 | 2.1 | 470 | 0.047 | |
| 64 | 0.0053 | 0.18 | 34 | 0.029 | |
| 65 | 0.0069 | 0.166 | 24 | 0.052 | |
| 66 | 0.0059 | 0.901 | 152 | 0.070 | |
| 67 | 0.0035 | 0.234 | 68 | 0.012 | |
| 68 | 0.0059 | 0.103 | 17 | 0.020 | |
| 69 | 0.0065 | 0.205 | 32 | 0.029 | |

TABLE 2-continued

| Example # | HCV Polymerase Strain | | | | |
|---|---|---|---|---|---|
| | 1a H77 $IC_{50}$ (μM) | 1a H77-C316Y $IC_{50}$ (μM) | C316Y/1a Fold Resistance | 1b BK $IC_{50}$ (μM) | 1b Rice $IC_{50}$ (μM) |
| 70 | 0.0085 | 0.069 | 8 | 0.024 | |
| 71 | 0.0089 | 0.136 | 15 | 0.028 | |
| 72 | 0.0143 | 0.164 | 11 | 0.046 | |
| 73 | 0.0035 | 0.053 | 15 | 0.015 | |
| 74 | 0.0030 | 0.107 | 36 | 0.013 | |
| 75 | 0.0065 | 1.6 | 247 | 0.060 | |
| 76 | 0.0059 | 0.131 | 22 | 0.023 | |
| 77 | 0.0050 | 0.049 | 10 | 0.010 | |
| 78 | 0.0040 | 0.107 | 27 | 0.013 | |
| 79 | 0.0055 | 0.141 | 26 | 0.020 | |
| 80 | 0.0050 | 0.055 | 11 | 0.016 | |
| 81 | 0.0318 | 4.8 | 151 | 0.137 | |
| 82 | 0.35 | | | 3.0 | |
| 83 | 0.0055 | 0.079 | 14 | 0.026 | |
| 84 | 0.0035 | 0.041 | 12 | 0.019 | |
| 85 | 0.0045 | 0.088 | 20 | 0.018 | |
| 86 | 0.0050 | 0.056 | 11 | 0.018 | |
| 87 | 0.0060 | 0.156 | 26 | 0.023 | |
| 88 | 0.0040 | 0.046 | 12 | 0.0090 | |
| 89 | 0.0050 | 0.077 | 15 | 0.065 | |
| 90 | 0.0035 | 0.042 | 12 | 0.010 | |
| 91 | 0.0053 | 0.080 | 15 | 0.026 | |
| 92 | 0.0049 | 0.043 | 9 | 0.0060 | |
| 93 | 0.0050 | 1.6 | 320 | 0.117 | |
| 94 | 0.0094 | 1.0 | 107 | 0.028 | |
| 95 | 0.0045 | 0.085 | 19 | 0.013 | |
| 96 | 0.0089 | 0.058 | 6 | 0.034 | |
| 97 | 0.0060 | 0.549 | 92 | 0.039 | |
| 98 | 0.0245 | 3.2 | 131 | 0.24 | |
| 99 | 0.0045 | 0.058 | 13 | 0.011 | |
| 100 | 0.0035 | 0.053 | 15 | 0.0080 | |
| 101 | 0.0050 | 0.046 | 9 | 0.011 | |
| 102 | 0.0077 | 0.168 | 22 | 0.047 | |
| 103 | 0.0079 | 0.40 | 50 | 0.055 | |
| 104 | 0.0069 | 0.18 | 26 | 0.052 | |
| 105 | 0.0080 | 0.111 | 14 | 0.016 | |
| 106 | 0.0073 | 0.101 | 14 | 0.019 | |
| 107 | 0.0055 | 0.122 | 22 | 0.028 | |
| 108 | 0.0035 | 0.060 | 17 | 0.028 | |
| 109 | 0.0059 | 0.536 | 90 | 0.0617 | 0.0169 |
| 110 | 0.0065 | 0.125 | 19 | 0.012 | |
| 111 | 0.0099 | 2.0 | 201 | 0.111 | |
| 112 | 0.0106 | 0.868 | 82 | 0.051 | |
| 113 | 0.0065 | 0.14 | 22 | 0.016 | |
| 114 | 0.0070 | 0.070 | 10 | 0.043 | |
| 115 | 0.0039 | 0.037 | 10 | 0.033 | |
| 116 | 0.0075 | 0.063 | 8 | 0.035 | |
| 117 | 0.0045 | 0.036 | 8 | 0.031 | |
| 118 | 0.0059 | 0.114 | 19 | 0.049 | |
| 119 | 0.0070 | 0.041 | 6 | 0.038 | |
| 120 | 0.0050 | 0.028 | 6 | 0.047 | |
| 121 | 0.0035 | 0.040 | 12 | 0.055 | |
| 122 | 0.0069 | 0.046 | 7 | 0.025 | |
| 123 | 0.0095 | 0.076 | 8 | 0.014 | |
| 124 | 0.0045 | 0.037 | 8 | 0.029 | |
| 125 | 0.011 | 0.112 | 10 | 0.060 | |
| 126 | 0.0215 | 0.091 | 4 | 0.111 | |
| 127 | 0.0254 | 0.663 | 26 | 0.302 | |
| 128 | 0.0456 | 0.995 | 22 | 0.667 | |
| 129 | 0.024 | 0.632 | 26 | 0.466 | |
| 130 | 0.0205 | 0.412 | 20 | 0.229 | |
| 131 | 0.0302 | 0.876 | 29 | 0.171 | |
| 132 | 0.022 | 0.934 | 42 | 0.246 | |
| 133 | 0.0080 | 0.050 | 6 | 0.046 | |
| 134 | 0.0080 | 0.042 | 5 | 0.082 | |
| 135 | 0.0039 | 0.041 | 11 | 0.028 | |
| 136 | 0.0064 | 0.256 | 40 | 0.20 | 0.057 |
| 137 | 0.0042 | 0.039 | 9 | 0.079 | |
| 138 | 0.0098 | 0.232 | 24 | 0.049 | |
| 139 | 0.0077 | 0.089 | 11 | 0.0090 | |
| 140 | 0.0050 | 0.038 | 8 | 0.042 | |
| 141 | 0.015 | 0.209 | 14 | 0.167 | |
| 142 | 0.0070 | 0.059 | 8 | 0.042 | |
| 143 | 0.0090 | 0.075 | 8 | 0.042 | |
| 144 | 0.0070 | 0.089 | 13 | 0.092 | |
| 145 | 0.0060 | 2.0 | 333 | 0.035 | |
| 146 | 0.0049 | 0.045 | 9 | 0.025 | |
| 147 | 0.0035 | 0.049 | 14 | 0.0090 | |
| 148 | 0.0039 | 0.030 | 8 | 0.0060 | |
| 149 | 0.0035 | 0.041 | 12 | 0.0090 | |
| 150 | 0.0040 | 0.042 | 11 | 0.0050 | |
| 151 | 0.0090 | 0.102 | 11 | 0.048 | |
| 152 | 0.118 | | | 3.6 | |
| 153 | 179 | | | 200 | |
| 154 | 21.31 | | | 63.25 | |
| 155 | 0.053 | 0.554 | 10 | 0.0 | |
| 156 | 0.0063 | 0.034 | 5 | 0.027 | |
| 157 | 0.0050 | 0.054 | 11 | 0.016 | |
| 158 | 0.0083 | 0.16 | 19 | 0.0363 | |
| 159 | 0.045 | 8.0 | 178 | 0.438 | |
| 160 | 0.11 | | | 0.93 | |
| 161 | 0.0475 | 0.219 | 5 | 0.791 | |
| 162 | 0.0357 | 1.2 | 34 | 0.711 | |
| 163 | 0.212 | | | 0.555 | |
| 164 | 0.136 | | | 0.906 | |
| 165 | 1.5 | | | 2.7 | |
| 166 | 1.6 | | | 7.0 | |
| 167 | 0.0492 | 7.9 | 161 | 0.16 | 0.0616 |
| 168 | 0.0049 | 0.0085 | 2 | 0.0392 | 0.0049 |
| 169 | 0.0060 | 0.0198 | 3 | 0.0391 | 0.0094 |
| 170 | 0.036 | 20.0 | 556 | 0.338 | |
| 171 | 2.86 | | | 88.7 | |
| 172 | 0.0133 | 0.087 | 7 | 0.179 | |
| 173 | 0.0071 | 1.4 | 198 | 0.086 | |
| 174 | 0.0035 | 0.040 | 12 | 0.0186 | |
| 175 | 0.0060 | 0.043 | 7 | 0.025 | |
| 176 | 0.0050 | 0.134 | 27 | 0.033 | |
| 177 | 0.0040 | 0.038 | 10 | 0.036 | |
| 178 | 0.013 | 0.828 | 64 | 0.065 | |
| 179 | 0.0040 | 0.045 | 11 | 0.025 | |
| 180 | 0.0060 | 0.034 | 6 | 0.032 | |
| 181 | 0.010 | 0.103 | 10 | 0.056 | |
| 182 | 0.0070 | 0.026 | 4 | 0.044 | |
| 183 | 0.0060 | 0.022 | 4 | 0.039 | |
| 184 | 0.017 | 0.599 | 35 | 0.156 | |
| 185 | 2.3 | 20.0 | 9 | 9.0 | |
| 186 | 4.5 | | | 4.5 | |
| 187 | 0.0258 | 0.159 | 6 | 0.168 | |
| 188 | 0.0154 | 0.224 | 15 | 0.055 | |
| 189 | 0.0255 | 0.461 | 18 | 0.47 | |
| 190 | 0.0045 | 0.50 | 112 | 0.026 | |
| 191 | 0.012 | | | | 0.0084 |
| 192 | 10.3 | | | 18.0 | |

Stable Replicon Cell Culture Assays.

Several stable bicistronic subgenomic replicon cell lines were used for compound characterization in cell culture. The genotype 1 cell lines (1a-H77, 1b-BB7, and 1b-Con1) were derived from strains 1a-H77 (Genbank accession number AF011751) and 1b-Con1 (Genbank accession number AJ238799, both obtained from Apath, LLC, St. Louis, Mo.). The 1a-H77 replicon has a firefly luciferase reporter and a neomycin phosphotransferase (Neo) selectable marker. These two coding regions, separated by the FMDV 2a protease, comprise the first cistron of the bicistronic replicon construct, with the second cistron containing the NS3-NS5B coding region with addition of adaptive mutations E1202G, K1691R, K2040R and S2204I. The 1b-BB7 replicon construct is identical to the 1a-H77 replicon, except that the NS3-NS5B coding region was derived from the 1b-Con1 strain, and the adaptive mutations are E1202G, T12801 and S2204I. The 1b-Con1 replicon is also derived from the Con1 strain, but differs from the 1b-BB7 replicon in two respects:

1) it contains a poliovirus IRES between the HCV IRES and the luciferase gene, and 2) it has a different set of adaptive mutations (K1609E, K1846T, Y3005C). The cell line containing the C316Y substitution in the NS5B coding region was established based on the C316Y mutant replicon construct which was obtained by site-directed mutagenesis of the 1a-H77 construct. All replicon constructs are bicistronic subgenomic replicons similar to those described in Lohman V, et al. Science 1999; 285(5424): 110-113.

To characterize compound activity against polymerases of different HCV genotypes, novel chimeric replicons were established based on the two types of NS5B shuttle vectors developed by Middleton et al. (Middleton T, et al. J. Virological Methods 2007; 145(2): 137-145). The first shuttle vector, designated 1a, is based on a chimera of 1a-H77 and 1b-Con1 strains; the second shuttle vector, designated 1b, is based on the 1b-N strain (Genbank accession number AF139594). The original constructs for both shuttle vectors described in Middleton et al. were obtained from University of Texas Medical Branch (UTMB, Galveston, Tex.). To enable establishment of stable cell lines, a neomycin phosphotransferase (Neo) selectable marker coding region was introduced into the 1a and 1b shuttle vectors by molecular cloning. HCV NS5B coding regions were amplified from the plasma of patients infected with HCV genotypes 2b, 3a and 4a. The plasma samples were obtained from ProMedDx and BioCollections. The NS5B coding regions from genotypes 2b and 3a were digested with PacI and AscI restriction enzymes and cloned into the 1a cassette (H77-Con1 chimera), and the genotype 4a NS5B was cloned into the 1b cassette (N-strain). The replicon construct containing NS5B derived from genotype 2a (J6CF strain) was obtained by introducing a neomycin phosphotransferase (Neo) selectable marker into the transient chimeric replicon construct obtained from UTMB (Galveston, Tex.). This construct is a chimera with 2a-J6CF-derived NS5B coding region (aa 15-591) cloned into the 1b-N strain background. Replicon cell lines were maintained in Dulbecco's modified Eagles medium (DMEM) containing 10% (v/v) fetal bovine serum (FBS), 100 IU/mL penicillin, 100 mg/mL streptomycin (Invitrogen), and 200 mg/mL G418 (Invitrogen).

The inhibitory effects of compounds on HCV replication were determined by measuring activity of the luciferase reporter gene. Briefly, replicon-containing cells were seeded into 96 well plates at a density of 5000 cells per well in 100 µL DMEM containing 5% FBS. The following day compounds were diluted in dimethyl sulfoxide (DMSO) to generate a 200× stock in a series of eight half-log dilutions. The dilution series was then further diluted 100-fold in the medium containing 5% FBS. Medium with the inhibitor was added to the overnight cell culture plates already containing 100 µl of DMEM with 5% FBS. In assays measuring inhibitory activity in the presence of human plasma, the medium from the overnight cell culture plates was replaced with DMEM containing 40% human plasma and 5% FBS. The cells were incubated for three days in the tissue culture incubators and were then lysed for RNA extraction. For the luciferase assay, 30 µL of Passive Lysis buffer (Promega) was added to each well, and then the plates were incubated for 15 minutes with rocking to lyse the cells. Luciferin solution (100 µL, Promega) was added to each well, and luciferase activity was measured with a Victor II luminometer (Perkin-Elmer). The percent inhibition of HCV RNA replication was calculated for each compound concentration and the $EC_{50}$ value was calculated using nonlinear regression curve fitting to the 4-parameter logistic equation and GraphPad Prism 4 software.

The $EC_{50}$ values from the stable replicon assay for a genotype 1 cell line (1a-H77) and the corresponding C316Y mutant for certain exemplified compounds are set forth in Table 3 below. In the stable replicon HCV polymerase assay with strain 1a H77, the disclosed compounds achieved $EC_{50}$s of less than 15 µM, and, as illustrated in table 3, certain disclosed compounds achieved $EC_{50}$s within a range of from about 0.0010 to about 10 µM. Certain disclosed compounds have $EC_{50}$s of less than about 0.1 µM.

In the stable replicon HCV polymerase assay with mutant strain 1a H77-C316Y, the disclosed compounds achieved $EC_{50}$s of less than about 15 µM, and, as illustrated in table 3, certain disclosed compounds achieved $EC_{50}$s within a range of from about 0.0025 to about 10 µM. Certain disclosed compounds have $EC_{50}$s of less than about 0.1 µM.

In a comparison of $EC_{50}$s between the wild type 1a H77 and the mutant 1a H77-C316Y the disclosed compounds achieved a fold resistance of less than about 100-fold, and, as illustrated in table 3, certain disclosed compounds achieved a fold resistance within a range of about 0.70 to about 75. Certain disclosed compounds have a fold resistance of <20.

The $EC_{50}$ values from the stable replicon assay for genotype 1 cell lines (1a-H77, 1b-BB7, and 1b-Con1) and the chimeras for genotypes 2a, 2b, 3a and 3b for certain exemplified compounds are set forth in Table 4 below. In the stable replicon HCV polymerase assay with strain 1a H77, the disclosed compounds achieved $EC_{50}$s of less than about 15 µM, and, as illustrated in Table 4, certain disclosed compounds achieved $EC_{50}$s within a range of from about 0.0010 to about 10 µM. Certain disclosed compounds have $EC_{50}$s of less than about 0.1 µM.

In the stable replicon HCV polymerase assay with strain 1b BB7, the disclosed compounds achieved $EC_{50}$s of less than about 15 µM, and, as illustrated in Table 4, certain disclosed compounds achieved $EC_{50}$s within a range of from about 0.0025 to about 10 µM. Certain disclosed compounds have $EC_{50}$s of less than about 0.1 µM.

In the stable replicon HCV polymerase assay with strain 1b Con1, the disclosed compounds achieved $EC_{50}$s of less than about 0.01 µM, and, as illustrated in Table 4, certain disclosed compounds achieved $EC_{50}$s within a range of from about 0.0025 to about 0.0100 µM. Certain disclosed compounds have $EC_{50}$s of less than about 0.010 µM.

In the stable replicon HCV polymerase assay with chimeric 2a strain, the disclosed compounds achieved $EC_{50}$s of less than about 2 µM, and, as illustrated in Table 4, certain disclosed compounds achieved $EC_{50}$s within a range of from about 0.0050 to about 1.50 µM. Certain disclosed compounds have $EC_{50}$s of less than about 0.1 µM.

In the stable replicon HCV polymerase assay with chimeric 2b strain, the disclosed compounds achieved $EC_{50}$s of less than about 2 µM, and, as illustrated in Table 4, certain disclosed compounds achieved $EC_{50}$s within a range of from about 0.0100 to about 2.00 µM. Certain disclosed compounds have $EC_{50}$s of less than about 0.1 µM.

In the stable replicon HCV polymerase assay with chimeric 3a strain, the disclosed compounds achieved $EC_{50}$s of less than about 2 µM, and, as illustrated in Table 4, certain disclosed compounds achieved $EC_{50}$s within a range of from about 0.0010 to about 1 µM. Certain disclosed compounds have $EC_{50}$s of less than about 0.1 µM.

In the stable replicon HCV polymerase assay with chimeric 4a strain, the disclosed compounds achieved $EC_{50}$s of less than about 15 µM, and, as illustrated in Table 4, certain disclosed compounds achieved $EC_{50}$s within a range of from about 0.0025 to >1 µM. Certain disclosed compounds have $EC_{50}$s of less than about 0.1 µM.

The $EC_{50}$ values from the stable replicon assay for genotype 1 cell lines (1a-H77, 1b-BB7, and 1b-Con1) in the absence and presence of 40% human plasma for certain exemplified compounds are set forth in Table 5 below. In the stable replicon HCV polymerase assay with strain 1a H77, the disclosed compounds achieved $EC_{50}$s of less than about 15 µM, and, as illustrated in Table 5, certain compounds achieved $EC_{50}$s within a range of from about 0.0010 to about 10 µM in the absence of human plasma and from about 0.0150 to about 10 µM in the presence of 40% human plasma. Certain disclosed compounds have an increase in $EC_{50}$s of less than about 20 fold in the presence of 40% human plasma.

In the stable replicon HCV polymerase assay with strain 1b BB7, the disclosed compounds achieved $EC_{50}$s of less than about 15 µM, and, as illustrated in Table 5, certain disclosed compounds achieved $EC_{50}$s within a range of from about 0.0025 to about 10 µM in the absence of human plasma and from about 0.0150 to about 100 µM in the presence of 40% human plasma. Certain disclosed compounds have an increase in $EC_{50}$s of less than about 20 fold in the presence of 40% human plasma.

In the stable replicon HCV polymerase assay with strain 1b Con1, the disclosed compounds achieved $EC_{50}$s of less than about 15 µM, and, as illustrated in Table 5, certain disclosed compounds achieved $EC_{50}$s within a range of from about 0.0025 to about 0.0100 µM in the absence of human plasma and from about 0.0010 to about 1.00 µM in the presence of 40% human plasma. Certain disclosed compounds have an increase in $EC_{50}$s of less than 20 fold in the presence of 40% human plasma.

TABLE 3

| | Stable Replicon HCV Polymerase Strain | | |
|---|---|---|---|
| Example # | 1a H77 5% FBS EC50 (µM) | 1a H77-C316Y 5% FBS EC50 (µM) | Fold Resistance C316Y/1a |
| 1 | 0.207 | | |
| 3 | 0.048 | | |
| 4 | 0.029 | | |
| 5 | 0.0032 | | |
| 6 | 0.0083 | | |
| 7 | 0.015 | | |
| 8 | 0.0063 | | |
| 9 | 0.0084 | | |
| 10 | 0.0105 | | |
| 11 | 0.0080 | | |
| 12 | 0.0426 | | |
| 13 | 0.0148 | | |
| 14 | 0.0243 | | |
| 15 | 0.0065 | | |
| 16 | 0.0038 | | |
| 17 | 0.0989 | | |
| 18 | 0.0054 | 0.0038 | 0.711 |
| 19 | 0.0332 | 1.32 | 41.0 |
| 20 | 1.0 | | |
| 21 | 3.44 | | |
| 22 | 2.38 | | |
| 23 | 0.23 | | |
| 24 | 0.157 | | |
| 25 | 0.266 | | |
| 26 | 0.343 | | |
| 27 | 0.866 | | |
| 28 | 0.405 | | |
| 29 | 1.0 | | |
| 30 | 0.108 | | |
| 31 | 0.0416 | | |
| 32 | 2.37 | | |
| 33 | 0.163 | | |
| 34 | 0.070 | | |
| 35 | 0.102 | | |
| 36 | 0.301 | | |
| 37 | 0.348 | | |
| 38 | 0.0102 | | |
| 39 | 0.0331 | | |
| 40 | 0.023 | | |
| 41 | 0.073 | | |
| 42 | 0.214 | | |
| 43 | 0.269 | | |
| 44 | 0.0237 | | |
| 45 | 0.0874 | | |
| 46 | 0.0045 | | |
| 47 | 0.0817 | | |
| 48 | 0.0114 | | |
| 49 | 0.0037 | | |
| 50 | 0.0122 | | |
| 51 | 1.0 | | |
| 52 | 0.13 | | |
| 53 | 0.111 | | |
| 54 | 0.089 | | |
| 55 | 0.068 | | |
| 56 | 0.0278 | | |
| 57 | 0.0352 | | |
| 58 | 0.0218 | | |
| 59 | 0.0851 | | |
| 60 | 0.020 | | |
| 61 | 0.0054 | | |
| 62 | 0.0887 | | |
| 63 | 0.067 | | |
| 64 | 0.0243 | | |
| 65 | 0.0103 | | |
| 66 | 0.0598 | | |
| 67 | 0.0543 | | |
| 68 | 0.057 | | |
| 69 | 0.0139 | | |
| 70 | 0.0418 | | |
| 71 | 0.0654 | | |
| 72 | 0.0737 | | |
| 73 | 0.0079 | | |
| 74 | 0.0136 | | |
| 75 | 0.0696 | | |
| 76 | 0.0485 | | |
| 77 | 0.0060 | | |
| 78 | 0.0385 | | |
| 79 | 0.0147 | | |
| 80 | 0.0121 | | |
| 81 | 0.205 | | |
| 82 | 2.63 | | |
| 83 | 0.0069 | | |
| 84 | 0.0149 | | |
| 85 | 0.0218 | | |
| 86 | 0.0123 | | |
| 87 | 0.0076 | | |
| 88 | 0.0041 | | |
| 89 | 0.269 | | |
| 90 | 0.0102 | | |
| 91 | 0.0063 | | |
| 92 | 0.0214 | | |
| 93 | 0.0832 | | |
| 94 | 0.0602 | | |
| 95 | 0.0112 | | |
| 96 | 0.0063 | | |
| 97 | 0.108 | 3.77 | 34.9 |
| 98 | 0.158 | | |
| 99 | 0.0077 | | |
| 100 | 0.0060 | | |
| 101 | 0.0041 | | |
| 102 | 0.0241 | | |
| 103 | 0.0446 | | |
| 104 | 0.0319 | | |
| 105 | 0.108 | | |
| 106 | 0.0544 | | |
| 107 | 0.0175 | | |
| 108 | 0.0153 | | |
| 109 | 0.0198 | 0.467 | 23.6 |
| 110 | 0.0143 | | |

TABLE 3-continued

Stable Replicon HCV Polymerase Strain

| Example # | 1a H77 5% FBS EC50 (µM) | 1a H77-C316Y 5% FBS EC50 (µM) | Fold Resistance C316Y/1a |
|---|---|---|---|
| 111 | 0.152 | | |
| 112 | 0.262 | | |
| 113 | 0.0599 | | |
| 114 | 0.0271 | | |
| 115 | 0.0095 | | |
| 116 | 0.0359 | | |
| 117 | 0.022 | | |
| 118 | 0.0198 | | |
| 119 | 0.0194 | | |
| 120 | 0.0175 | | |
| 121 | 0.0387 | | |
| 122 | 0.0084 | | |
| 123 | 0.0109 | | |
| 124 | 0.0443 | | |
| 125 | 0.0126 | | |
| 126 | 0.0253 | | |
| 127 | 0.0648 | | |
| 128 | 0.161 | | |
| 129 | 0.0809 | | |
| 130 | 0.0442 | | |
| 131 | 0.122 | | |
| 132 | 0.142 | | |
| 133 | 0.0063 | | |
| 134 | 0.0065 | | |
| 135 | 0.969 | | |
| 136 | 0.0266 | 0.561 | 42.0 |
| 137 | 0.015 | | |
| 138 | 0.0465 | | |
| 139 | 0.0592 | | |
| 140 | 0.0145 | | |
| 141 | 0.0385 | | |
| 142 | 0.0115 | | |
| 143 | 0.0218 | | |
| 144 | 0.039 | | |
| 145 | 0.134 | | |
| 146 | 0.0126 | | |
| 147 | 0.0089 | | |
| 148 | 0.0041 | | |
| 149 | 0.0088 | | |
| 150 | 0.0050 | | |
| 151 | 0.119 | | |
| 152 | 10.0 | | |
| 155 | 3.06 | | |
| 156 | 0.0418 | | |
| 157 | 0.109 | | |
| 158 | 0.0233 | 1.15 | 49.4 |
| 159 | 0.99 | | |
| 160 | 2.16 | | |
| 161 | 0.124 | | |
| 162 | 0.248 | | |
| 163 | 7.83 | | |
| 164 | 1.0 | | |
| 168 | 0.0018 | 0.0176 | 9.72 |
| 169 | 0.0021 | 0.0114 | 5.33 |
| 170 | 0.54 | | |
| 171 | 7.62 | | |
| 172 | 0.0674 | | |
| 173 | 0.809 | | |
| 174 | 0.32 | | |
| 175 | 0.079 | | |
| 176 | 0.0365 | | |
| 177 | 0.032 | | |
| 178 | 0.0544 | 0.544 | 10.0 |
| 179 | 0.0098 | 0.686 | 70.0 |
| 180 | 1.0 | | |
| 181 | 0.0557 | | |
| 182 | 0.356 | | |
| 183 | 0.104 | | |
| 184 | 0.0697 | | |
| 185 | 1.0 | 10.0 | 10.0 |
| 187 | 0.0419 | | |
| 188 | 0.399 | | |
| 189 | 0.163 | | |
| 190 | 0.263 | | |

TABLE 4

Stable Replicon HCV Polymerase Strain

| Example # | 1a H77 5% FBS EC50 (µM) | 1b BB7 5% FBS EC50 (µM) | 1b Con1 5% FBS EC50 (µM) | 2a chimera 5% FBS EC50 (µM) | 2b chimera 5% FBS EC50 (µM) | 3a chimera 5% FBS EC50 (µM) | 4a chimera 5% FBS EC50 (µM TABLE 4-continued Stable Replicon HCV Polymerase Strain

| Example # | 1a H77 5% FBS EC50 (μM) | 1b BB7 5% FBS EC50 (μM) | 1b Con1 5% FBS EC50 (μM) | 2a chimera 5% FBS EC50 (μM) | 2b chimera 5% FBS EC50 (μM) | 3a chimera 5% FBS EC50 (μM) | 4a chimera 5% FBS EC50 (μM) |
|---|---|---|---|---|---|---|---|
| 27 | 0.866 | 0.075 | | | | | |
| 28 | 0.405 | 0.0241 | | 0.234 | 0.561 | 0.0143 | 0.378 |
| 29 | 1.0 | 0.207 | | | | | |
| 30 | 0.108 | 0.0040 | | 0.0407 | 0.109 | 0.0028 | 0.15 |
| 31 | 0.0416 | 0.0284 | | 0.185 | 0.151 | 0.0 | 0.084 |
| 32 | 2.37 | 0.599 | | | | | |
| 33 | 0.163 | 0.20 | | | | | |
| 34 | 0.070 | 0.065 | | | | | |
| 35 | 0.102 | 0.051 | | | | | |
| 36 | 0.301 | 0.18 | | | | | |
| 37 | 0.348 | 0.145 | | 0.522 | 0.751 | 0.166 | 0.598 |
| 38 | 0.0102 | 0.0127 | | 0.0882 | 0.0814 | 0.0252 | 0.161 |
| 39 | 0.0331 | 0.0297 | | 0.105 | 0.133 | 0.0284 | 0.187 |
| 40 | 0.023 | 0.023 | | | | | |
| 41 | 0.073 | 0.040 | | | | | |
| 42 | 0.214 | 0.119 | | | | | |
| 43 | 0.269 | 0.080 | | | | | |
| 44 | 0.0237 | 0.0161 | | 0.0937 | 0.0977 | 0.0151 | 0.176 |
| 45 | 0.0874 | 0.18 | | | | | |
| 46 | 0.0045 | 0.0046 | | 0.0275 | 0.0237 | 0.0027 | 0.0311 |
| 47 | 0.0817 | 0.0256 | | | | | |
| 48 | 0.0114 | 0.0085 | | 0.0837 | 0.0692 | 0.010 | 0.0464 |
| 49 | 0.0037 | 0.0030 | | 0.0224 | 0.0415 | 0.0037 | 0.0339 |
| 50 | 0.0122 | 0.0087 | | 0.0907 | 0.147 | 0.0153 | 0.149 |
| 51 | 1.0 | 0.194 | | | | | |
| 52 | 0.13 | 0.114 | | | | | |
| 53 | 0.111 | 0.052 | | 0.154 | 0.267 | 0.023 | 0.379 |
| 54 | 0.089 | 0.064 | | 0.267 | 0.601 | 0.051 | 0.635 |
| 55 | 0.068 | 0.037 | | 0.184 | 0.348 | 0.018 | 0.557 |
| 56 | 0.0278 | 0.0121 | | 0.0493 | 0.0426 | 0.0096 | 0.0819 |
| 57 | 0.0352 | 0.0177 | | 0.0515 | 0.0724 | 0.0091 | 0.138 |
| 58 | 0.0218 | 0.0119 | | 0.0789 | 0.13 | 0.0098 | 0.13 |
| 59 | 0.0851 | 0.0112 | | 0.065 | 0.127 | 0.0103 | 0.424 |
| 60 | 0.020 | 0.0086 | | 0.0447 | 0.0796 | 0.0081 | 0.0648 |
| 61 | 0.0054 | 0.0030 | | 0.041 | 0.0299 | 0.0062 | 0.0184 |
| 62 | 0.0887 | 0.071 | | 0.309 | 0.471 | 0.0499 | 0.364 |
| 63 | 0.067 | 0.0144 | | 0.131 | 0.108 | 0.0068 | 0.702 |
| 64 | 0.0243 | 0.012 | | 0.0579 | 0.0674 | 0.0016 | 0.125 |
| 65 | 0.0103 | 0.0068 | | 0.0424 | 0.0685 | 0.0040 | 0.0875 |
| 66 | 0.0598 | 0.0564 | | 0.215 | 0.293 | 0.0839 | 0.318 |
| 67 | 0.0543 | 0.0139 | | 0.0873 | 0.0772 | 0.0079 | 0.232 |
| 68 | 0.057 | 0.062 | | | | | |
| 69 | 0.0139 | 0.0066 | | 0.0611 | 0.0672 | 0.0094 | 0.0828 |
| 70 | 0.0418 | 0.0356 | | 0.173 | 0.234 | 0.0268 | 0.285 |
| 71 | 0.0654 | 0.039 | | 0.409 | 0.377 | 0.0725 | 0.596 |
| 72 | 0.0737 | 0.061 | | | | | |
| 73 | 0.0079 | 0.0049 | | 0.027 | 0.0219 | 0.0029 | 0.0425 |
| 74 | 0.0136 | 0.0064 | | 0.064 | 0.0578 | 0.0045 | 0.0865 |
| 75 | 0.0696 | 0.045 | | | | | |
| 76 | 0.0485 | 0.0269 | | | | | |
| 77 | 0.0060 | 0.0057 | | 0.0325 | 0.0268 | 0.0049 | 0.0427 |
| 78 | 0.0385 | 0.0157 | | | | | |
| 79 | 0.0147 | 0.0069 | | 0.0906 | 0.0993 | 0.0116 | 0.0728 |
| 80 | 0.0121 | 0.0107 | | 0.211 | 0.283 | 0.0122 | 0.373 |
| 81 | 0.205 | 0.0369 | | | | | |
| 82 | 2.63 | 1.58 | | | | | |
| 83 | 0.0069 | 0.0082 | | 0.0467 | 0.0473 | 0.0061 | 0.0673 |
| 84 | 0.0149 | 0.0141 | | 0.103 | 0.0309 | 0.0151 | 0.142 |
| 85 | 0.0218 | 0.0098 | | 0.0662 | 0.131 | 0.0064 | 0.0738 |
| 86 | 0.0123 | 0.0067 | | 0.0642 | 0.137 | 0.0115 | 0.1082 |
| 87 | 0.0076 | 0.0049 | | 0.0645 | 0.0849 | 0.0032 | 0.0484 |
| 88 | 0.0041 | 0.0049 | | 0.0253 | 0.0245 | 0.0032 | 0.0339 |
| 89 | 0.269 | 0.0915 | | | | | |
| 90 | 0.0102 | 0.0060 | | 0.0475 | 0.068 | 0.0128 | 0.02749 |
| 91 | 0.00634 | 0.0049 | | 0.0858 | 0.0994 | 0.0080 | 0.0888 |
| 92 | 0.0214 | 0.0259 | | 0.409 | 0.352 | 0.043 | 0.283 |
| 93 | 0.0832 | 0.0634 | | | | | |
| 94 | 0.0602 | 0.0763 | | | | | |
| 95 | 0.0112 | 0.0048 | | 0.0331 | 0.0808 | 0.0057 | 0.0461 |
| 96 | 0.0063 | 0.0040 | | 0.0437 | 0.126 | 0.0059 | 0.0419 |
| 97 | 0.108 | 0.062 | | 0.595 | 0.895 | 0.036 | 0.528 |
| 98 | 0.158 | 0.136 | | | | | |
| 99 | 0.0077 | 0.0054 | | 0.0296 | 0.0173 | 0.0038 | 0.0314 |
| 100 | 0.0060 | 0.0034 | | 0.0198 | 0.0163 | 0.0031 | 0.0216 |

TABLE 4-continued

Stable Replicon HCV Polymerase Strain

| Example # | 1a H77 5% FBS EC50 (μM) | 1b BB7 5% FBS EC50 (μM) | 1b Con1 5% FBS EC50 (μM) | 2a chimera 5% FBS EC50 (μM) | 2b chimera 5% FBS EC50 (μM) | 3a chimera 5% FBS EC50 (μM) | 4a chimera 5% FBS EC50 (μM) |
|---|---|---|---|---|---|---|---|
| 101 | 0.00412 | 0.0059 | | 0.033 | 0.0334 | 0.0043 | 0.0564 |
| 102 | 0.0241 | 0.010 | | 0.108 | 0.134 | 0.0097 | 0.145 |
| 103 | 0.0446 | 0.0139 | | | | | |
| 104 | 0.0319 | 0.0133 | | | | | |
| 105 | 0.108 | 0.0686 | | | | | |
| 106 | 0.0544 | 0.0273 | | | | | |
| 107 | 0.0175 | 0.011 | | 0.135 | 0.141 | 0.0093 | 0.1294 |
| 108 | 0.0153 | 0.0101 | | 0.156 | 0.187 | 0.011 | 0.1044 |
| 109 | 0.0198 | 0.0127 | | 0.115 | 0.12 | 0.0068 | 0.1665 |
| 110 | 0.0143 | 0.0167 | | | | | |
| 111 | 0.152 | 0.0404 | | | | | |
| 112 | 0.262 | 0.034 | | | | | |
| 113 | 0.0599 | 0.028 | | 0.209 | 0.279 | 0.041 | 0.144 |
| 114 | 0.0271 | 0.033 | | 0.299 | 0.331 | 0.0562 | 0.307 |
| 115 | 0.0095 | 0.014 | | 0.167 | 0.146 | 0.030 | 0.124 |
| 116 | 0.0359 | 0.032 | | 0.535 | 0.396 | 0.084 | 0.247 |
| 117 | 0.022 | 0.030 | | 0.214 | 0.24 | 0.031 | 0.233 |
| 118 | 0.0198 | 0.026 | | 0.23 | 0.477 | 0.047 | 0.449 |
| 119 | 0.0194 | 0.017 | | 0.079 | 0.189 | 0.030 | 0.142 |
| 120 | 0.0175 | 0.018 | | 0.125 | 0.157 | 0.036 | 0.082 |
| 121 | 0.0387 | 0.068 | | 1.0 | 1.0 | 0.121 | 0.988 |
| 122 | 0.0084 | 0.011 | | 0.13 | 0.127 | 0.032 | 0.0839 |
| 123 | 0.0109 | 0.018 | | 0.162 | 0.105 | 0.0364 | 0.0581 |
| 124 | 0.0443 | 0.044 | | 1.0 | 1.0 | 0.139 | 0.962 |
| 125 | 0.0126 | 0.020 | | 0.222 | 0.182 | 0.050 | 0.085 |
| 126 | 0.0253 | 0.030 | | 0.35 | 0.453 | 0.070 | 0.36 |
| 127 | 0.0648 | 0.021 | | 0.344 | 0.309 | 0.057 | 0.814 |
| 128 | 0.161 | 0.044 | | 0.699 | 0.839 | 0.216 | >1.0 |
| 129 | 0.0809 | 0.038 | | 0.625 | 0.625 | 0.149 | >1.0 |
| 130 | 0.0442 | 0.026 | | 0.074 | | 0.0426 | 0.416 |
| 131 | 0.122 | 0.026 | | 0.38 | 0.446 | 0.131 | 0.782 |
| 132 | 0.142 | 0.040 | | 0.244 | 0.428 | 0.093 | >1.0 |
| 133 | 0.00632 | 0.0060 | | 0.092 | 0.082 | 0.011 | 0.075 |
| 134 | 0.00648 | 0.0090 | | 0.084 | 0.069 | 0.020 | 0.053 |
| 135 | 0.969 | 0.783 | | | | | |
| 136 | 0.0266 | 0.035 | | 0.204 | 0.426 | 0.042 | 0.2912 |
| 137 | 0.015 | 0.017 | | 0.182 | 0.214 | 0.033 | 0.172 |
| 138 | 0.0465 | 0.036 | | 1.0 | 1.0 | 0.102 | 0.524 |
| 139 | 0.0592 | 0.068 | | 1.0 | 0.787 | 0.102 | 0.572 |
| 140 | 0.0145 | 0.011 | | 0.274 | 0.211 | 0.044 | 0.189 |
| 141 | 0.0385 | 0.031 | | 0.623 | 1.0 | 0.053 | 0.621 |
| 142 | 0.0115 | 0.011 | | 0.193 | 0.368 | 0.021 | 0.161 |
| 143 | 0.0218 | 0.012 | | 0.131 | 0.137 | 0.035 | 0.15 |
| 144 | 0.039 | 0.037 | | 0.38 | 0.419 | 0.062 | 0.38 |
| 145 | 0.134 | 0.080 | | 0.372 | 0.836 | 0.163 | >1.0 |
| 146 | 0.0126 | 0.0179 | | 0.179 | 0.169 | 0.017 | 0.277 |
| 147 | 0.0089 | 0.0098 | | 0.0848 | 0.062 | 0.0103 | 0.0659 |
| 148 | 0.0041 | 0.0040 | | 0.0458 | 0.032 | 0.0082 | 0.0397 |
| 149 | 0.0088 | 0.0040 | | 0.054 | 0.034 | 0.0070 | 0.021 |
| 150 | 0.0050 | 0.0040 | | 0.043 | 0.0309 | 0.0070 | 0.025 |
| 151 | 0.119 | 0.030 | | | | | |
| 152 | 10.0 | 10.0 | | | | | |
| 155 | 3.06 | 6.25 | | | | | |
| 156 | 0.0418 | 0.0709 | | 0.718 | 0.893 | 0.0651 | 0.6228 |
| 157 | 0.109 | 0.0942 | | 1.0 | 1.0 | 0.108 | >1.0 |
| 158 | 0.0233 | 0.0235 | | 0.302 | 0.205 | 0.043 | 0.1762 |
| 159 | 0.99 | 0.544 | | | | | |
| 160 | 2.16 | 0.604 | | | | | |
| 161 | 0.124 | 0.188 | | | | | |
| 162 | 0.248 | 0.327 | | 1.0 | 1.0 | 1.0 | >1.0 |
| 163 | 7.83 | 5.4 | | | | | |
| 164 | 1.0 | 1.0 | | | | | |
| 168 | 0.0018 | | 0.0034 | 0.0060 | 0.0133 | 0.0127 | 0.0144 |
| 169 | 0.00214 | | 0.00450 | 0.0169 | 0.0123 | 0.015 | 0.0043 |
| 170 | 0.54 | 0.121 | | | | | |
| 171 | 7.62 | 9.27 | | | | | |
| 172 | 0.0674 | 0.111 | | 1.0 | 1.0 | 0.233 | >1.0 |
| 173 | 0.809 | 0.301 | | 1.0 | 1.0 | 0.146 | >1.0 |
| 174 | 0.32 | 0.192 | | 1.0 | 1.0 | 0.29 | >1.0 |
| 175 | 0.079 | 0.062 | | 0.66 | 0.723 | 0.062 | 0.407 |
| 176 | 0.0365 | 0.020 | | 0.146 | 0.155 | 0.012 | 0.159 |
| 177 | 0.032 | 0.023 | | 0.427 | 0.606 | 0.030 | 0.401 |
| 178 | 0.0544 | 0.018 | | 0.116 | 0.0913 | 0.0244 | 0.239 |
| 179 | 0.0098 | 0.0090 | | 0.066 | 0.0849 | 0.0105 | 0.0778 |

TABLE 4-continued

Stable Replicon HCV Polymerase Strain

| Example # | 1a H77 5% FBS EC50 (μM) | 1b BB7 5% FBS EC50 (μM) | 1b Con1 5% FBS EC50 (μM) | 2a chimera 5% FBS EC50 (μM) | 2b chimera 5% FBS EC50 (μM) | 3a chimera 5% FBS EC50 (μM) | 4a chimera 5% FBS EC50 (μM) |
|---|---|---|---|---|---|---|---|
| 180 | 1.0 | 1.0 | | 1.0 | 1.0 | 1.0 | >1.0 |
| 181 | 0.0557 | 0.046 | | 0.785 | 0.548 | 0.108 | 0.594 |
| 182 | 0.356 | 0.31 | | 1.0 | 1.0 | 0.661 | >1.0 |
| 183 | 0.104 | 0.088 | | 1.0 | 1.0 | 0.306 | >1.0 |
| 184 | 0.0697 | 0.028 | | 0.539 | 0.353 | 0.084 | 0.507 |
| 185 | 1.0 | 1.0 | | 1.0 | 1.0 | 0.77 | >1.0 |
| 186 | | | | | | | |
| 187 | 0.0419 | 0.0632 | | 0.703 | 1.0 | 0.0917 | >1.0 |
| 188 | 0.399 | 0.208 | | | | | |
| 189 | 0.163 | 0.114 | | 1.05 | 1.86 | 0.231 | 2.94 |
| 190 | 0.263 | 0.116 | | | | | |
| 191 | | | | | | | 0.0176 |

TABLE 5

Stable Replicon HCV Polymerase Strain

| Example # | 1a H77 5% FBS EC50 (μM) | 1a H77 5% FBS + 40% Human Plasma EC50 (μM) | 1b BB7 5% FBS EC50 (μM) | 1b BB7 5% FBS + 40% Human Plasma EC50 (μM) | 1b Con1 5% FBS EC50 (μM) | 1b Con1 5% FBS + 40% Human Plasma EC50 (μM) |
|---|---|---|---|---|---|---|
| 1 | 0.207 | 4.71 | 0.0182 | 0.281 | | |
| 3 | 0.048 | 7.93 | 0.0050 | 0.76 | | |
| 4 | 0.029 | 0.512 | 0.025 | 0.297 | | |
| 5 | 0.00319 | 0.050 | 0.00369 | 0.022 | | |
| 6 | 0.0083 | 0.0613 | 0.0039 | 0.0362 | | |
| 7 | 0.015 | 0.111 | 0.0057 | 0.106 | | |
| 8 | 0.0063 | 0.036 | 0.010 | 0.064 | | |
| 9 | 0.0084 | 0.067 | 0.015 | 0.138 | | |
| 10 | 0.0105 | 0.134 | 0.0162 | 0.171 | | |
| 11 | 0.0080 | 0.10 | 0.0103 | 0.199 | | |
| 12 | 0.0426 | 0.050 | 0.011 | 0.082 | | |
| 13 | 0.0148 | 0.163 | 0.0159 | 0.146 | | |
| 14 | 0.0243 | 0.805 | 0.0935 | 1.06 | | |
| 15 | 0.0065 | 1.77 | 0.010 | 0.818 | | |
| 16 | 0.0038 | 0.411 | 0.0025 | 2.19 | | |
| 17 | 0.0989 | 1.2 | 0.0572 | 0.395 | | |
| 18 | 0.0054 | 0.234 | | | 0.0095 | 0.602 |
| 19 | 0.0332 | 0.444 | | | 0.0067 | 0.0868 |
| 20 | 1.0 | 10.0 | 0.133 | 7.3 | | |
| 21 | 3.44 | | 0.593 | 10.0 | | |
| 22 | 2.38 | | 0.866 | | | |
| 23 | 0.23 | 10.0 | 0.0264 | 9.24 | | |
| 24 | 0.157 | 10.0 | 0.0124 | 3.85 | | |
| 25 | 0.266 | 10.0 | 0.0082 | 10.0 | | |
| 26 | 0.343 | 10.0 | 0.015 | 5.45 | | |
| 27 | 0.866 | 10.0 | 0.075 | 5.46 | | |
| 28 | 0.405 | 10.0 | 0.0241 | 10.0 | | |
| 29 | 1.0 | 10.0 | 0.207 | 9.83 | | |
| 30 | 0.108 | 10.0 | 0.0040 | 1.32 | | |
| 31 | 0.0416 | 0.382 | 0.0284 | 0.201 | | |
| 32 | 2.37 | | 0.599 | 79.6 | | |
| 33 | 0.163 | 8.84 | 0.20 | 4.81 | | |
| 34 | 0.070 | 1.29 | 0.065 | 0.854 | | |
| 35 | 0.102 | 1.58 | 0.051 | 1.13 | | |
| 36 | 0.301 | 2.14 | 0.18 | 1.12 | | |
| 37 | 0.348 | 1.39 | 0.145 | 0.529 | | |
| 38 | 0.0102 | 0.117 | 0.0127 | 0.245 | | |
| 39 | 0.0331 | 0.132 | 0.0297 | 0.059 | | |
| 40 | 0.023 | 0.525 | 0.023 | 0.445 | | |
| 41 | 0.073 | 0.911 | 0.040 | 0.364 | | |
| 42 | 0.214 | 7.41 | 0.119 | 3.39 | | |
| 43 | 0.269 | 5.21 | 0.080 | 0.616 | | |
| 44 | 0.0237 | 0.42 | 0.0161 | 0.081 | | |
| 45 | 0.0874 | 3.01 | 0.18 | 4.41 | | |
| 46 | 0.0045 | 0.112 | 0.0047 | 0.036 | | |
| 47 | 0.0817 | 0.771 | 0.0256 | 0.148 | | |
| 48 | 0.0114 | 0.147 | 0.0084 | 0.075 | | |
| 49 | 0.0037 | 0.0539 | 0.0030 | 0.0281 | | |

TABLE 5-continued

Stable Replicon HCV Polymerase Strain

| Example # | 1a H77 5% FBS EC50 (μM) | 1a H77 5% FBS + 40% Human Plasma EC50 (μM) | 1b BB7 5% FBS EC50 (μM) | 1b BB7 5% FBS + 40% Human Plasma EC50 (μM) | 1b Con1 5% FBS EC50 (μM) | 1b Con1 5% FBS + 40% Human Plasma EC50 (μM) |
|---|---|---|---|---|---|---|
| 50 | 0.0122 | 0.097 | 0.0087 | 0.067 | | |
| 51 | 1.0 | 4.59 | 0.194 | 0.835 | | |
| 52 | 0.13 | 1.41 | 0.114 | 0.661 | | |
| 53 | 0.111 | 1.01 | 0.052 | 0.224 | | |
| 54 | 0.089 | 0.935 | 0.064 | 0.734 | | |
| 55 | 0.068 | 1.02 | 0.037 | 0.363 | | |
| 56 | 0.0278 | 0.192 | 0.0121 | 0.062 | | |
| 57 | 0.0352 | 0.306 | 0.0177 | 0.069 | | |
| 58 | 0.0218 | 0.333 | 0.0119 | 0.193 | | |
| 59 | 0.0851 | 0.159 | 0.0112 | 0.020 | | |
| 60 | 0.020 | 0.152 | 0.0086 | 0.0995 | | |
| 61 | 0.0054 | 0.0722 | 0.0030 | 0.0184 | | |
| 62 | 0.0887 | 0.342 | 0.071 | 0.328 | | |
| 63 | 0.067 | 1.16 | 0.0144 | 0.195 | | |
| 64 | 0.0243 | 0.267 | 0.012 | 0.11 | | |
| 65 | 0.0103 | 0.121 | 0.0068 | 0.0595 | | |
| 66 | 0.0598 | 0.683 | 0.0564 | 0.569 | | |
| 67 | 0.0543 | 1.01 | 0.0139 | 0.256 | | |
| 68 | 0.057 | 1.21 | 0.062 | 0.496 | | |
| 69 | 0.0139 | 0.259 | 0.0066 | 0.059 | | |
| 70 | 0.0418 | 0.641 | 0.0356 | 0.298 | | |
| 71 | 0.0654 | 2.29 | 0.039 | 1.07 | | |
| 72 | 0.0737 | 3.39 | 0.061 | 2.21 | | |
| 73 | 0.0079 | 0.072 | 0.0049 | 0.055 | | |
| 74 | 0.0136 | 0.254 | 0.0065 | 0.127 | | |
| 75 | 0.0696 | 1.08 | 0.045 | 1.16 | | |
| 76 | 0.0485 | 3.96 | 0.0269 | 0.661 | | |
| 77 | 0.0060 | 0.066 | 0.0057 | 0.047 | | |
| 78 | 0.0385 | 1.06 | 0.0157 | 0.514 | | |
| 79 | 0.0147 | 0.117 | 0.0069 | 0.062 | | |
| 80 | 0.0121 | 0.052 | 0.0107 | 0.072 | | |
| 81 | 0.205 | 0.732 | 0.0369 | 0.129 | | |
| 82 | 2.63 | | 1.58 | | | |
| 83 | 0.0069 | 0.089 | 0.00819 | 0.096 | | |
| 84 | 0.0149 | 0.218 | 0.0141 | 0.146 | | |
| 85 | 0.0218 | 0.162 | 0.0098 | 0.095 | | |
| 86 | 0.0123 | 0.086 | 0.0067 | 0.041 | | |
| 87 | 0.0076 | 0.065 | 0.0049 | 0.057 | | |
| 88 | 0.0041 | 0.119 | 0.0049 | 0.108 | | |
| 89 | 0.269 | 2.44 | 0.0915 | 0.376 | | |
| 90 | 0.0102 | 0.093 | 0.0060 | 0.048 | | |
| 91 | 0.0063 | 0.032 | 0.0049 | 0.034 | | |
| 92 | 0.0214 | 0.175 | 0.0259 | 0.142 | | |
| 93 | 0.0832 | 0.915 | 0.0634 | 0.88 | | |
| 94 | 0.0602 | 0.599 | 0.0763 | 0.36 | | |
| 95 | 0.0112 | 0.121 | 0.0048 | 0.0761 | | |
| 96 | 0.0062 | 0.058 | 0.0040 | 0.037 | | |
| 97 | 0.108 | 0.721 | 0.062 | 0.644 | | |
| 98 | 0.158 | 1.63 | 0.136 | 2.06 | | |
| 99 | 0.0077 | 0.126 | 0.0054 | 0.105 | | |
| 100 | 0.0060 | 0.088 | 0.0034 | 0.057 | | |
| 101 | 0.0041 | 0.11 | 0.0059 | 0.075 | | |
| 102 | 0.0241 | 0.242 | 0.010 | 0.066 | | |
| 103 | 0.0446 | 0.563 | 0.0139 | 0.114 | | |
| 104 | 0.0319 | 0.502 | 0.0133 | 0.268 | | |
| 105 | 0.108 | 1.06 | 0.0686 | 0.519 | | |
| 106 | 0.0544 | 0.915 | 0.0273 | 0.221 | | |
| 107 | 0.0175 | 0.082 | 0.011 | 0.066 | | |
| 108 | 0.0153 | 0.049 | 0.0101 | 0.057 | | |
| 109 | 0.0198 | 0.42 | 0.0127 | 0.184 | | |
| 110 | 0.0143 | 0.206 | 0.0167 | 0.315 | | |
| 111 | 0.152 | 1.0 | 0.0404 | 0.092 | | |
| 112 | 0.262 | 1.03 | 0.034 | 0.101 | | |
| 113 | 0.0599 | 0.646 | 0.028 | 0.549 | | |
| 114 | 0.0271 | 0.406 | 0.033 | 0.377 | | |
| 115 | 0.0095 | 0.038 | 0.014 | 0.127 | | |
| 116 | 0.0359 | 0.157 | 0.032 | 0.213 | | |
| 117 | 0.022 | 0.159 | 0.030 | 0.245 | | |
| 118 | 0.0198 | 0.165 | 0.026 | 0.253 | | |
| 119 | 0.0194 | 0.247 | 0.017 | 0.129 | | |
| 120 | 0.0175 | 0.19 | 0.018 | 0.189 | | |
| 121 | 0.0387 | 0.311 | 0.068 | 0.388 | | |

TABLE 5-continued

| | Stable Replicon HCV Polymerase Strain | | | | | |
|---|---|---|---|---|---|---|
| Example # | 1a H77 5% FBS EC50 (µM) | 1a H77 5% FBS + 40% Human Plasma EC50 (µM) | 1b BB7 5% FBS EC50 (µM) | 1b BB7 5% FBS + 40% Human Plasma EC50 (µM) | 1b Con1 5% FBS EC50 (µM) | 1b Con1 5% FBS + 40% Human Plasma EC50 (µM) |
| 122 | 0.0084 | 0.050 | 0.011 | 0.081 | | |
| 123 | 0.0109 | 0.108 | 0.018 | 0.211 | | |
| 124 | 0.0443 | 0.501 | 0.044 | 0.984 | | |
| 125 | 0.0126 | 0.156 | 0.020 | 0.347 | | |
| 126 | 0.0253 | 0.258 | 0.030 | 0.379 | | |
| 127 | 0.0648 | 0.123 | 0.021 | 0.090 | | |
| 128 | 0.161 | 0.383 | 0.044 | 0.268 | | |
| 129 | 0.0809 | 0.30 | 0.038 | 0.163 | | |
| 130 | 0.0442 | 0.296 | 0.026 | 0.11 | | |
| 131 | 0.122 | 0.35 | 0.026 | 0.102 | | |
| 132 | 0.142 | 0.313 | 0.040 | 0.122 | | |
| 133 | 0.0063 | 0.037 | 0.0060 | 0.055 | | |
| 134 | 0.0065 | 0.069 | 0.0090 | 0.093 | | |
| 135 | 0.969 | 7.91 | 0.783 | 5.52 | | |
| 136 | 0.0266 | 0.347 | 0.035 | 0.281 | | |
| 137 | 0.015 | 0.059 | 0.017 | 0.113 | | |
| 138 | 0.0465 | 0.183 | 0.036 | 0.27 | | |
| 139 | 0.0592 | 0.648 | 0.068 | 0.948 | | |
| 140 | 0.0145 | 0.122 | 0.011 | 0.15 | | |
| 141 | 0.0385 | 0.275 | 0.031 | 0.296 | | |
| 142 | 0.0115 | 0.041 | 0.011 | 0.11 | | |
| 143 | 0.0218 | 0.125 | 0.012 | 0.108 | | |
| 144 | 0.039 | 0.254 | 0.037 | 0.333 | | |
| 145 | 0.134 | 1.0 | 0.080 | 1.0 | | |
| 146 | 0.0126 | 1.66 | 0.0179 | 2.71 | | |
| 147 | 0.0089 | 1.71 | 0.0098 | 1.83 | | |
| 148 | 0.0041 | 1.29 | 0.0040 | 0.688 | | |
| 149 | 0.0088 | 1.02 | 0.0040 | 0.643 | | |
| 150 | 0.0050 | 0.32 | 0.0040 | 0.231 | | |
| 151 | 0.119 | 2.28 | 0.030 | 1.5 | | |
| 152 | 10.0 | | 10.0 | | | |
| 155 | 3.06 | 10.0 | 6.25 | 10.0 | | |
| 156 | 0.0418 | 2.3 | 0.0709 | 2.98 | | |
| 157 | 0.109 | 2.79 | 0.0942 | 2.46 | | |
| 158 | 0.0233 | 0.26 | 0.0235 | 0.335 | | |
| 159 | 0.99 | 10.0 | 0.544 | 10.0 | | |
| 160 | 2.16 | 10.0 | 0.604 | 9.28 | | |
| 161 | 0.124 | 7.91 | 0.188 | 10.0 | | |
| 162 | 0.248 | 10.0 | 0.327 | 9.71 | | |
| 163 | 7.83 | 10.0 | 5.4 | 10.0 | | |
| 164 | 1.0 | 10.0 | 1.0 | 10.0 | | |
| 168 | 0.0018 | 0.0184 | | | 0.0034 | 0.0243 |
| 169 | 0.0021 | 0.0148 | | | 0.0050 | 0.0344 |
| 170 | 0.54 | | 0.121 | | | |
| 171 | 7.62 | | 9.27 | | | |
| 172 | 0.0674 | 1.22 | 0.111 | 1.13 | | |
| 173 | 0.809 | 9.72 | 0.301 | 5.06 | | |
| 174 | 0.32 | 4.78 | 0.192 | 3.69 | | |
| 175 | 0.079 | 1.18 | 0.062 | 0.57 | | |
| 176 | 0.0365 | 0.133 | 0.020 | 0.080 | | |
| 177 | 0.032 | 0.52 | 0.023 | 0.461 | | |
| 178 | 0.0544 | 0.431 | 0.018 | 0.274 | | |
| 179 | 0.0098 | 0.052 | 0.0090 | 0.078 | | |
| 180 | 1.0 | 10.0 | 1.0 | 10.0 | | |
| 181 | 0.0557 | 0.611 | 0.046 | 0.702 | | |
| 182 | 0.356 | 4.23 | 0.31 | 5.25 | | |
| 183 | 0.104 | 2.06 | 0.088 | 2.2 | | |
| 184 | 0.0697 | 1.87 | 0.028 | 1.09 | | |
| 185 | 1.0 | 10.0 | 1.0 | 10.0 | | |
| 187 | 0.0419 | 0.409 | 0.0632 | 0.244 | | |
| 188 | 0.399 | 8.46 | 0.208 | 2.03 | | |
| 189 | 0.163 | 0.774 | 0.114 | 0.445 | | |
| 190 | 0.263 | 3.46 | 0.116 | 1.37 | | |

Transient Replicon Inhibition Assays.

In addition to the stable replicon inhibition assays, transient replicon assays were performed. Transient replicons are identical to the 1a-H77 and 1a-H77-C316Y constructs, except they lack the Neo gene, making it impossible to establish stable cell lines. A T7 Megascript RNA synthesis kit (Ambion) was used to transcribe the HCV subgenomic RNA. The HCV RNA was then precipitated with lithium chloride according to manufacturer's instructions. The HCV subgenomic replicon RNA was transfected via electroporation into a Huh-7 derived cell line as described (Middleton T, et al. J. Virological Methods 2007; 145(2): 137-145). Transfected cells were diluted and plated in 96 well plates at 5×10³ cells per well in DMEM. Four hours post-transfection, the wells from one plate were harvested for luciferase measurement. This plate provides a measure of the amount of translatable input RNA, and therefore transfection efficiency. To the wells of the remaining plates, a 3-fold dilution series of test compounds was added in DMSO (0.5% DMSO final concentration), and plates were incubated at 37° C., 5% $CO_2$ in a humidified incubator for 4 days. After this period, the media was removed and the plates were washed with 100 µL phosphate-buffered saline per well. For the luciferase assay, 30 µL of Passive Lysis buffer (Promega) was added to each well, and then the plates were incubated for 15 minutes with rocking to lyse the cells. Luciferin solution (100 µL, Promega) was added to each well, and luciferase activity was measured with a Victor II luminometer (Perkin-Elmer). The $EC_{50}$ values were calculated using GraphPad Prism 4 software. The signal to noise window was determined as the ratio of luciferase activity from mock-treated cells (addition of 0.5% DMSO only) versus activity from cells where replication was essentially fully inhibited.

The $EC_{50}$ values from the inhibition assay for certain exemplified compounds are set forth in Table 6 below. In the transient replicon HCV polymerase assay with strain 1a H77, the disclosed compounds achieved $EC_{50}$s of less than 2 µM, and, as illustrated in Table 6, certain disclosed compounds achieved $EC_{50}$s within a range of from about 0.0005 to about 1 µM. Certain compounds have $EC_{50}$s of less than about 0.1 µM.

In the transient replicon HCV polymerase assay with mutant strain 1a H77-C316Y, the disclosed compounds achieved $EC_{50}$s of less than 15 µM, and, as illustrated in Table 6, certain disclosed compounds achieved $EC_{50}$s within a range of from about 0.0001 to about 10 µM. Certain compounds have $EC_{50}$s of less than about 0.1 µM.

In a comparison of $EC_{50}$s between the wild type 1a H77 and the mutant 1a H77-C316Y, disclosed compounds achieved a fold resistance of less than a 100-fold, and, as illustrated in Table 6, certain disclosed compounds achieved a fold resistance within a range of about 0.25 to about 100. Certain compounds have a fold resistance of <20.

TABLE 6

Transient Replicon HCV Polymerase Strain

| Example # | 1a H77 5% FBS $EC_{50}$ (µM) | 1a H77-C316Y 5% FBS $EC_{50}$ (µM) | Fold Resistance C316Y/1a |
|---|---|---|---|
| 1 | 0.192 | | |
| 3 | 0.0213 | 0.109 | 5 |
| 4 | 0.0079 | 0.0694 | 9 |
| 5 | 0.0030 | 0.0881 | 29 |
| 6 | 0.0032 | 0.105 | 33 |
| 7 | 0.0099 | 0.327 | 33 |
| 8 | 0.0031 | 0.0314 | 10 |
| 9 | 0.0077 | 0.0575 | 7 |
| 10 | 0.0060 | 0.0335 | 6 |
| 11 | 0.0030 | 0.0344 | 11 |
| 12 | 0.078 | 1.22 | 16 |
| 13 | 0.0111 | 0.134 | 12 |
| 14 | 0.0281 | 0.152 | 5 |
| 15 | 0.0082 | 0.166 | 20 |
| 16 | 0.0026 | 0.0437 | 17 |
| 17 | 0.055 | 0.838 | 15 |
| 18 | 0.0007 | 0.0003 | 0.4 |
| 31 | 0.0309 | 0.828 | 27 |
| 49 | 0.0022 | 0.0768 | 35 |
| 50 | 0.0095 | 0.169 | 18 |
| 61 | 0.0036 | 0.0458 | 13 |
| 62 | 0.0606 | 0.899 | 15 |
| 63 | 0.0756 | 1.9 | 25 |
| 64 | 0.0202 | | |
| 65 | 0.0054 | 0.228 | 42 |
| 66 | 0.0689 | | |
| 80 | 0.0083 | 0.162 | 20 |
| 83 | 0.0060 | 0.128 | 21 |
| 84 | 0.0254 | 0.184 | 7 |
| 86 | 0.0028 | 0.0921 | 33 |
| 87 | 0.0061 | 0.155 | 25 |
| 88 | 0.0012 | 0.0382 | 32 |
| 90 | 0.0027 | 0.0658 | 24 |
| 91 | 0.0056 | 0.121 | 22 |
| 92 | 0.0194 | 0.48 | 25 |
| 96 | 0.0011 | 0.0806 | 73 |
| 99 | 0.0076 | 0.0854 | 11 |
| 100 | 0.0042 | 0.0891 | 21 |
| 101 | 0.0037 | 0.102 | 28 |
| 108 | 0.0079 | 0.203 | 26 |
| 109 | 0.038 | 1.3 | 34 |
| 114 | 0.0218 | 0.238 | 11 |
| 115 | 0.0073 | 0.0907 | 12 |
| 121 | 0.028 | 0.287 | 10 |
| 122 | 0.0067 | 0.0623 | 9 |
| 123 | 0.0107 | 0.0789 | 7 |
| 124 | 0.0334 | 0.276 | 8 |
| 126 | 0.0336 | 0.26 | 8 |
| 135 | 0.372 | 3.04 | 8 |
| 136 | 0.0324 | 0.679 | 21 |
| 137 | 0.0101 | 0.107 | 11 |
| 145 | 0.10 | 1.0 | 10 |
| 146 | 0.0112 | 0.237 | 21 |
| 147 | 0.0097 | 0.0778 | 8 |
| 148 | 0.0052 | 0.109 | 21 |
| 149 | 0.0073 | 0.124 | 17 |
| 151 | 0.0332 | 2.93 | 88 |
| 156 | 0.0291 | 0.37 | 13 |
| 157 | 0.111 | 6.89 | 62 |
| 158 | 0.0195 | 0.304 | 16 |
| 167 | 0.0081 | 0.00611 | 1 |
| 168 | 0.0006 | 0.0144 | 24 |
| 169 | 0.0006 | 0.0041 | 6 |
| 172 | 0.0404 | 0.103 | 3 |
| 173 | 1.0 | 10.0 | 10 |
| 187 | 0.0289 | 0.128 | 4 |
| 189 | 0.139 | 0.326 | 2 |

General Synthesis

Additional information about the preparation of compounds of formulas I and II (and their salts) is provided in the general discussion and/or specific synthesis examples below. In the discussion below, $R^1$, $R^2$, $R^3$, $R^4$, $R^5$, $R^6$, $R^{20}$, $R^{21}$, $R^{40}$, $R^{1a}$, $R^{1b}$, $R^{2a}$, $R^{2b}$, $R^{4a}$, $R^{5a}$, $R^{5e}$, $G^{2b}$, $G^{5b}$, and $L^{5B}$ have the meaning discussed above unless otherwise stated.

Abbreviations which have been used in the descriptions of the Schemes that follow are: Bn for benzyl; DBU for 1,8-diazabicyclo[5.4.0]undec-7-ene; DMA for N,N-dimethylacetamide; DME for 1,2-dimethoxyethane; DMF for N,N-dimethylformamide; DMSO for dimethyl sulfoxide; HATU for O-(7-azabenzotriazol-1-yl)-N,N,N',N'-tetramethyluronium hexafluorophosphate; MS for methanesulfonyl; NBS for N-bromosuccinimide; and NMP for N-methylpyrrolidinone.

The disclosed compounds may be made by methods known in the art including the methods described below and variations thereof.

Scheme 1

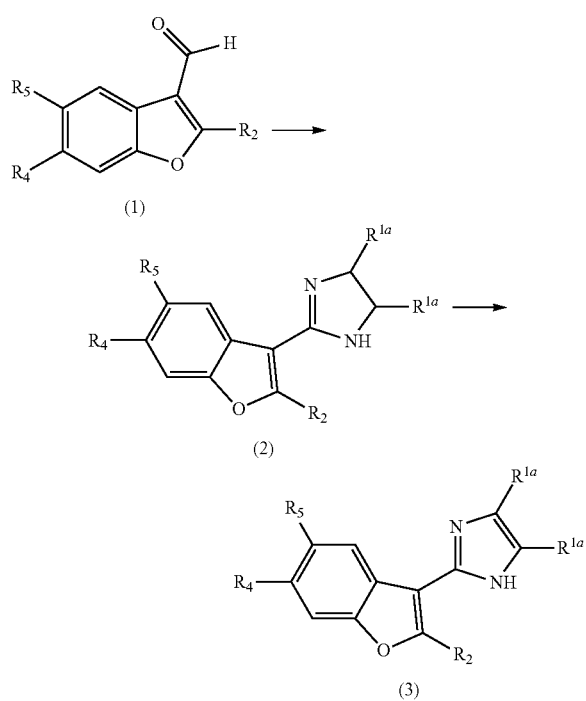

Certain compounds where $R^1$ is (i) can be prepared using the general method outlined in Scheme 1. See Fujioka H, et al. *Tetrahedron Letters* 2005; 46: 2197-2200 and Ishihara M, et al. *Synlett* 2006; 227-230. 3-Formyl benzofurans (1) can be converted to imidazoline (2) by reaction with a diamine (e.g., ethylene diamine) followed by N-bromosuccinimide (NBS) and molecular sieves in dichloromethane at ambient temperature over a period of 3-5 days. Imidazolines (2) can be converted to imidazoles (3), wherein $R^{1a}$, $R^2$, $R^4$ and $R^5$ are as described herein, by treatment with iodobenzene diacetate and excess potassium carbonate in DMSO at ambient temperature for 24-48 hours.

Scheme 2

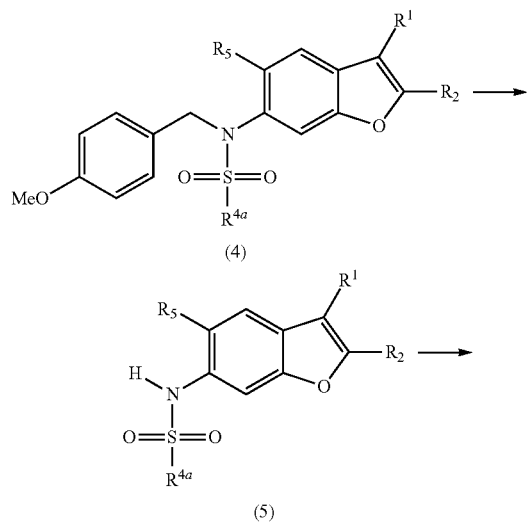

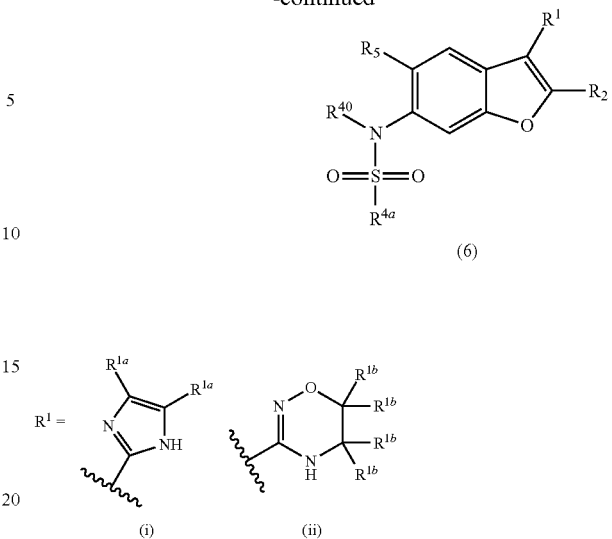

Certain disclosed compounds can be prepared where $R^1$ is (i) or (ii) and $R^{40}$ is a para-methoxybenzyl group. The para-methoxylbenzyl (PMB) group can be removed from compounds (4) under acidic conditions such as accomplished by treatment with trifluoroacetic acid (TFA) in dichloromethane or 4 M HCl to give compounds (5). Compounds (5) can be converted to compounds (6) using a standard alkylation reaction. Conditions to effect this transformation include reacting (5) with an alkylating agent (e.g., halide, mesylate, tosylate) and a base (e.g., potassium carbonate) in a solvent such as N,N-dimethylformamide (DMF) at temperatures from about room temperature to around 80° C. Certain functional groups in $R^{40}$ may be transformed to other functional groups after alkylation, for example, using standard transformations such as oxidation, reduction, deprotection, Suzuki, dihydroxylation, hydrolysis, amide formation, etc. to produce additional compounds of the present disclosure. For example, an ester may be hydrolyzed to an acid (i.e., saponification) or reduced to an alcohol (e.g., with lithium aluminum hydride). Alternatively, an arylbromide in $R^{40}$ may be reacted with a suitable boronic acid or derivative using a Suzuki reaction to produce additional disclosed compounds. It is understood that the foregoing example transformations are merely for illustration purposes and do not constitute a limitation on the variety of transformations that may be accomplished through functional group manipulation in $R^{40}$. Additional representative types of transformation are shown below in the various Examples. Other functional group manipulations not shown herein will be readily apparent to one of ordinary skill.

Scheme 3

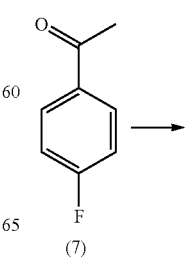

87
-continued
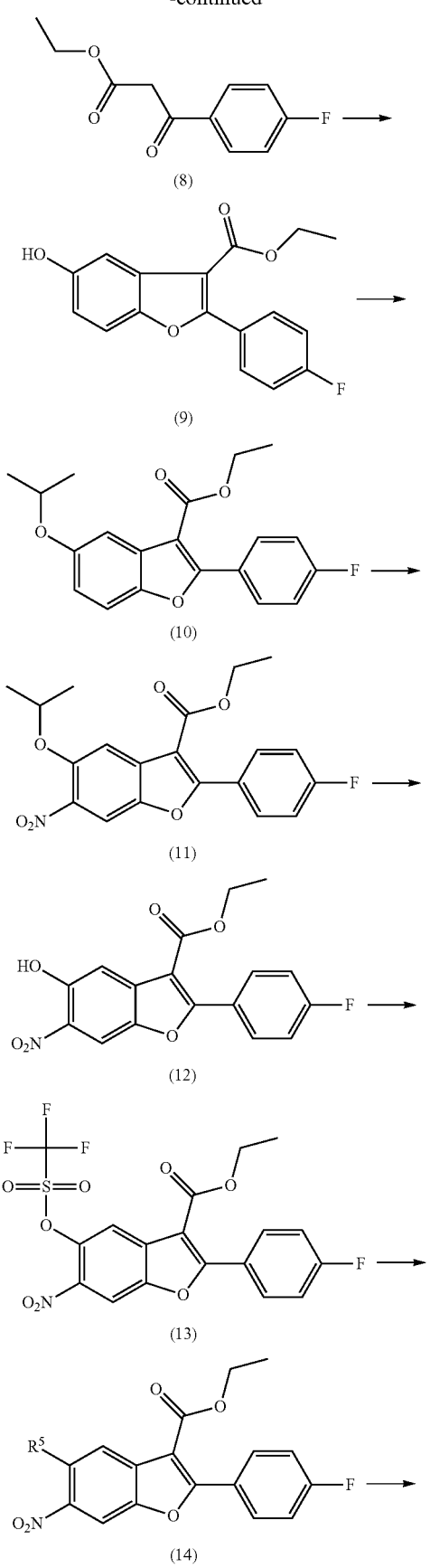
88
-continued
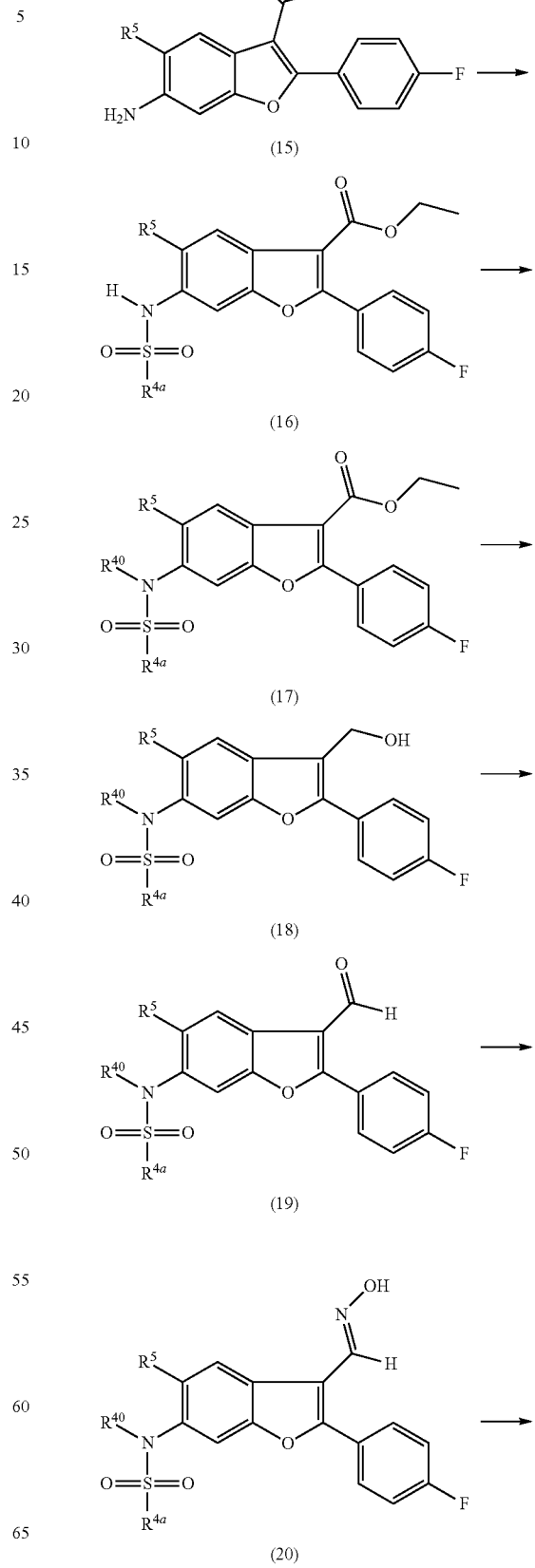

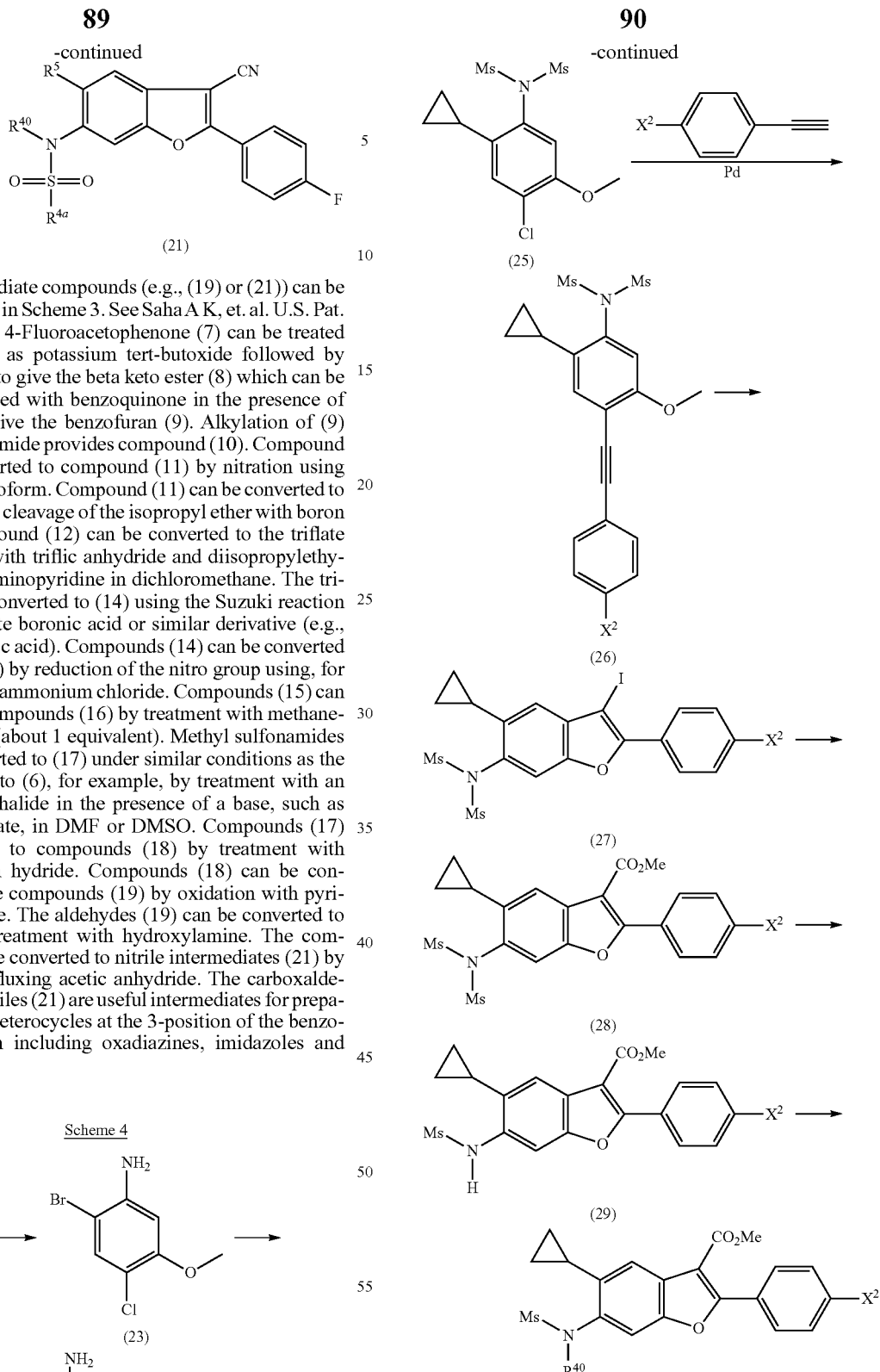

Certain intermediate compounds (e.g., (19) or (21)) can be prepared as shown in Scheme 3. See Saha A K, et. al. U.S. Pat. No. 7,265,152B2. 4-Fluoroacetophenone (7) can be treated with a base such as potassium tert-butoxide followed by diethyl carbonate to give the beta keto ester (8) which can be subsequently treated with benzoquinone in the presence of zinc chloride to give the benzofuran (9). Alkylation of (9) with isopropyl bromide provides compound (10). Compound (10) can be converted to compound (11) by nitration using nitric acid in chloroform. Compound (11) can be converted to compound (12) by cleavage of the isopropyl ether with boron trichloride. Compound (12) can be converted to the triflate (13) by reaction with triflic anhydride and diisopropylethylamine/dimethylaminopyridine in dichloromethane. The triflate (13) can be converted to (14) using the Suzuki reaction with an appropriate boronic acid or similar derivative (e.g., cyclopropylboronic acid). Compounds (14) can be converted to compounds (15) by reduction of the nitro group using, for example, iron and ammonium chloride. Compounds (15) can be converted to compounds (16) by treatment with methanesulfonyl chloride (about 1 equivalent). Methyl sulfonamides (16) can be converted to (17) under similar conditions as the conversion of (5) to (6), for example, by treatment with an appropriate alkyl halide in the presence of a base, such as potassium carbonate, in DMF or DMSO. Compounds (17) can be converted to compounds (18) by treatment with lithium aluminum hydride. Compounds (18) can be converted to aldehyde compounds (19) by oxidation with pyridinium dichromate. The aldehydes (19) can be converted to oximes (20) by treatment with hydroxylamine. The compounds (20) can be converted to nitrile intermediates (21) by dehydration in refluxing acetic anhydride. The carboxaldehydes (19) and nitriles (21) are useful intermediates for preparation of various heterocycles at the 3-position of the benzofuran ring system including oxadiazines, imidazoles and oxadiazoles.

Scheme 4

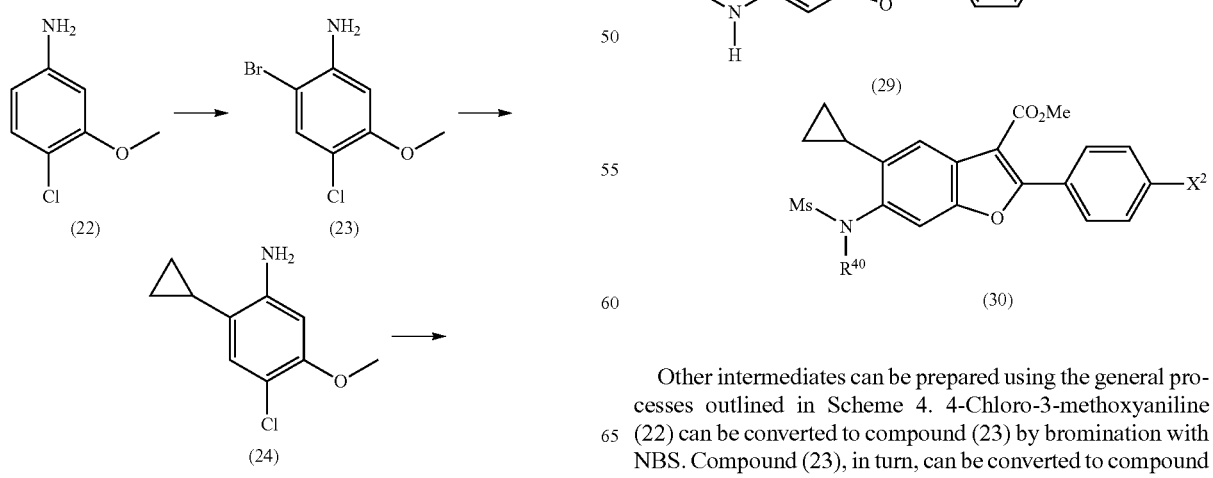

Other intermediates can be prepared using the general processes outlined in Scheme 4. 4-Chloro-3-methoxyaniline (22) can be converted to compound (23) by bromination with NBS. Compound (23), in turn, can be converted to compound (24) by a Suzuki coupling with an appropriate boronic acid or similar derivative (e.g., cyclopropylboronic acid). Compound (24) can be converted to compound (25) by reaction with excess methanesulfonyl chloride. Compound (25) can be converted to compounds (26) by a Sonogashira coupling with an appropriately substituted aryl alkyne (e.g., 1-(benzyloxy)-4-ethynylbenzene). $X^2$ of the substituted aryl alkyne can be, for example, fluoro, methoxy or benzyloxy. Compounds (26) can be converted to compounds (27) by intramolecular cyclization with iodine (Yue, D, et. al. *J. Org. Chem.,* 2005; 70: pp 10292-10296). Iodides (27) can be converted to the methyl esters (28) by carbonylation in methanol at elevated pressure and temperature. Compounds (28) can be converted to compounds (29) by selective removal of one methanesulfonyl group by heating with tetrabutylammonium fluoride (TBAF) for a period of several hours. Compounds (29) can be converted to compounds (30) by alkylation employing conditions similar to those outlined in Schemes 2 and 3.

Scheme 5

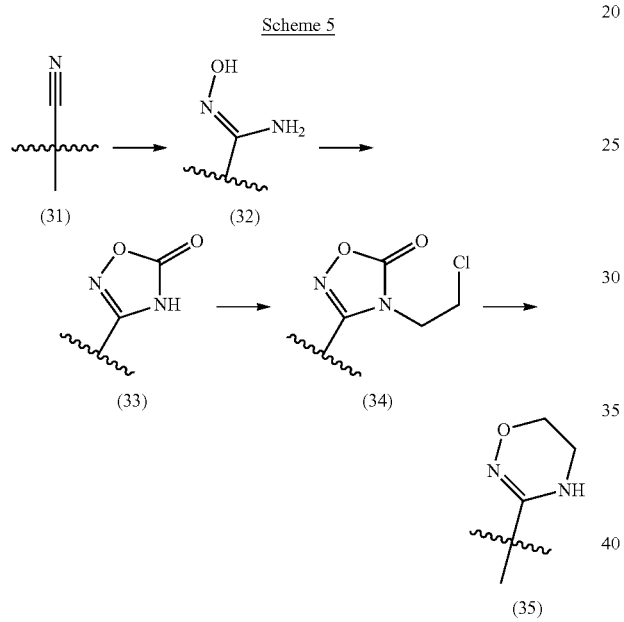

For disclosed compounds where $R^1$ is (ii), a general procedure for the formation of the 5,6-dihydro-4H-1,2,4-oxadiazine heterocycle is shown in Scheme 5. See Takacs, K. et al. *Chemische Berichte* 1975; 108: 1911-1923. A nitrile (31) may be treated with an excess of 50% hydroxylamine at elevated temperatures in a sealed system to afford the hydroxylated amidine (32). The reaction may be conducted with 10-200 mole equivalents amount of hydroxylamine at temperatures from about 130-160° C. in solvents such as ethanol or DMSO. Reaction times may range from 30 minutes to 3 hours. Sealed tube systems may include crimp seal microwave pressure vials or threaded glass cap pressure tubes. Heat sources may include microwave reactors, oil baths or heating mantles. Cyclization of the hydroxyamidine (32) to the oxadiazolone (33) may be accomplished by treatment with equimolar amounts of carbonyldiimidazole and DBU in refluxing dioxane for 1-2 hours. Compounds (33) may be converted to (34) by alkylation of the oxadiazolone with 1-bromo-2-chloroethane (2 to 5 mole equivalents) and DBU (1.5-3 mole equivalents) in DMF or DMA at 100° C. for a period of 2 to 24 hours. Other solvents that may be used are NMP and DMSO. Treatment of (34) with 1 M aqueous sodium hydroxide in refluxing ethanol affords the oxadiazine heterocycle (35). Typical amounts of 1 M sodium hydroxide are 2-4 mole equivalents with reaction durations of 1-2 hours.

Scheme 6

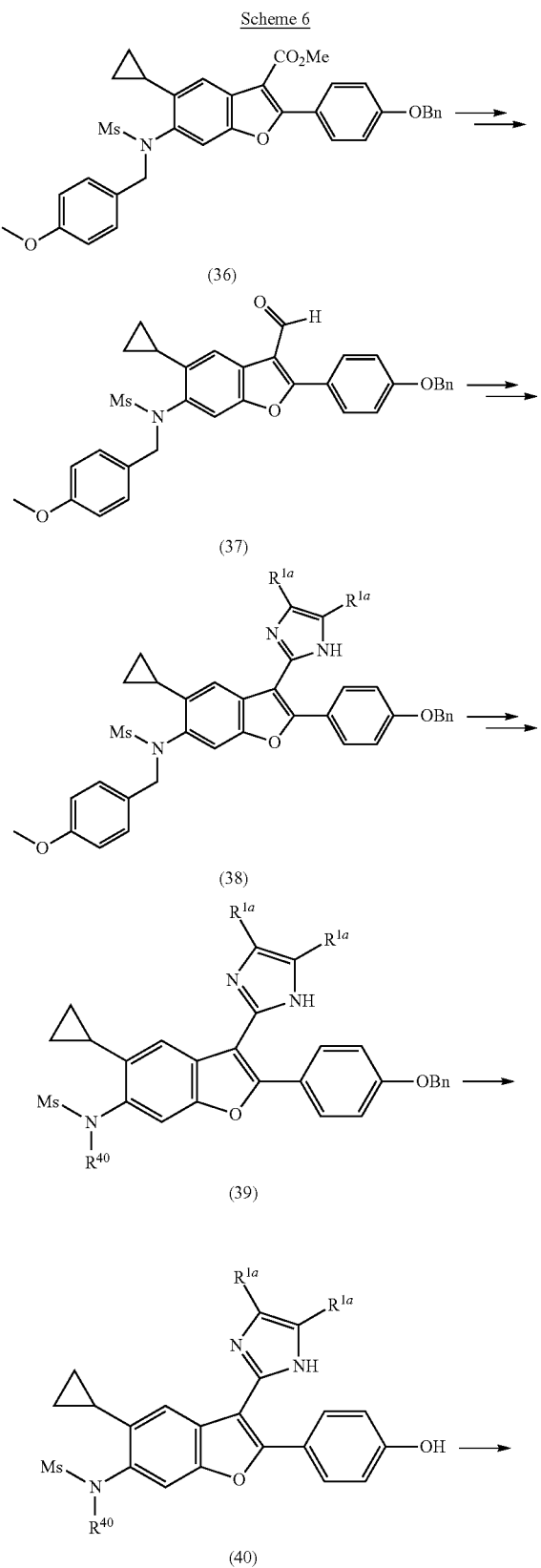

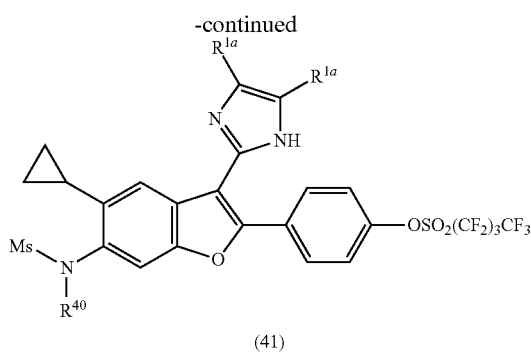

(41)

Certain disclosed compounds can be prepared as shown generally in Scheme 6. Compounds (30) where $X^2$ is O-benzyl and $R^{40}$ is para-methoxybenzyl can be represented by formula (36). Compound (36) can be converted to compounds (37) and (38) using the general methodology outlined in Schemes 1 and 3. Compounds (38) can be converted to compounds (39) by removal of the para-methoxybenzyl group and alkylation using the general methodology shown in Scheme 2. Compounds (39) can be converted to compounds (40) by removal of the benzyl group by hydrogenolysis using, for example, hydrogen gas and palladium hydroxide. Compounds (40) can be converted to nonaflate compounds (41) by reaction with 1,1,2,2,3,3,4,4-nonafluorobutane-1-sulfonyl fluoride and base (e.g., potassium carbonate) in DMF.

Analogs of compounds (40) and (41) wherein $R^1$ is (ii), (iii), (iv), or (v) can be prepared using the methodologies similar to that described in Schemes 6, 5, and 17 and the Examples.

As generally illustrated in Scheme 7, nonaflates (41) can be converted to a variety of other disclosed compounds bearing diverse substitutions. For example, (41) may be converted to alkene-substituted compounds (42) or (43) using Suzuki or Heck reactions. Alternatively, (41) may be converted to amino-substituted compounds (44) or ether compounds (45) using Buchwald-Hartwig type reaction conditions. Still other types of transformations of (41) include the Sonogashira reaction to install an alkyne substitution as in (46). It is understood that the foregoing example transformations are merely for illustration purposes and do not constitute a limitation on the variety of transformations that may be accomplished through functional group manipulation of the nonaflate (or triflate). Other functional group manipulations not shown herein will be readily apparent to one of ordinary skill.

Analogs of compounds (42), (43) and (44) wherein $R^1$ is (ii), (iii), (iv), or (v) can be prepared using the methodologies similar to that described in Schemes 7, 5, and 17 and the Examples.

Scheme 8

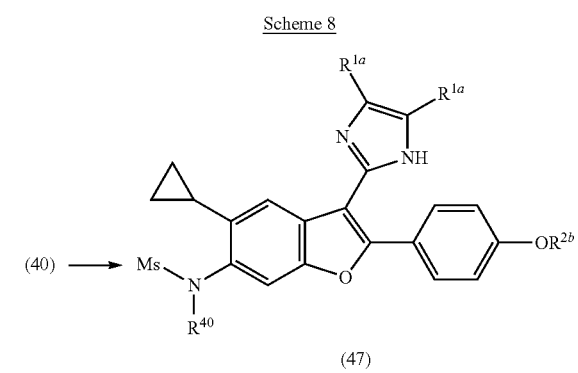

Scheme 7

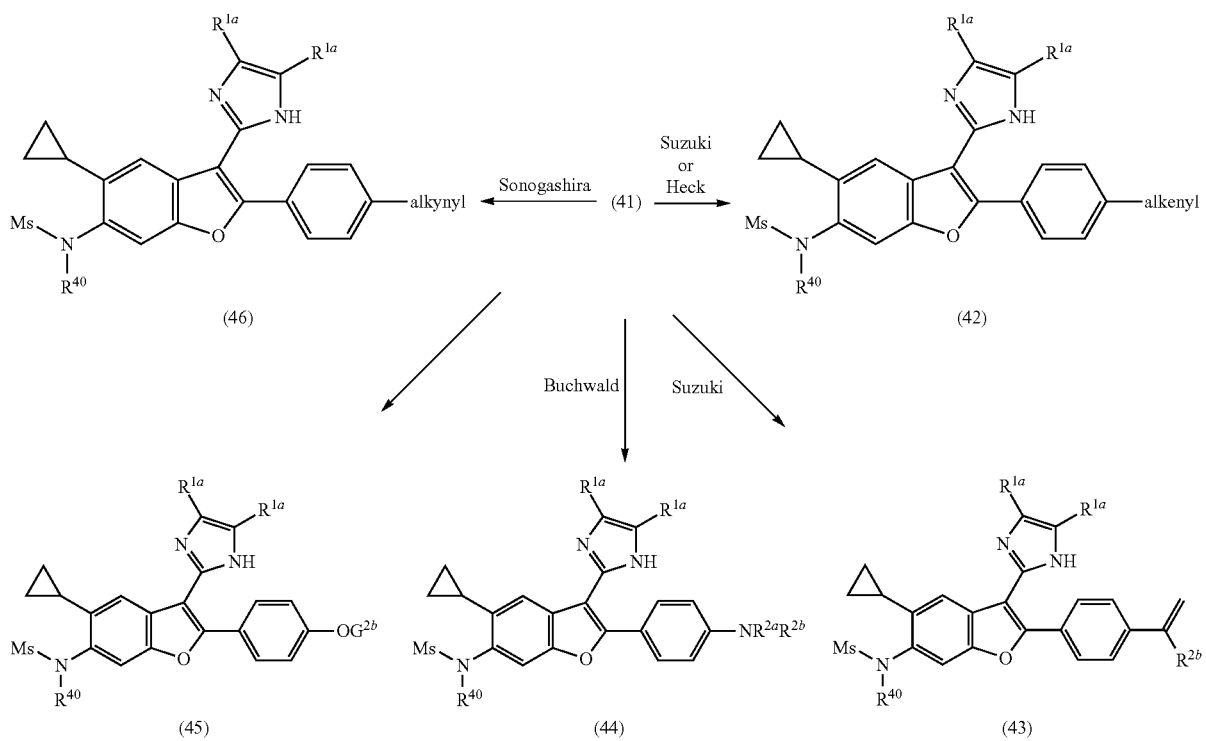

As shown in Scheme 8, phenol compounds (40) may be transformed to ether compounds (47) by alkylation with a suitable alkylating agent in the presence of a base, wherein $R^{2b}$ is as described herein.

Analogs of compounds (40) wherein $R^1$ is (ii), (iii), (iv), or (v) can be prepared using methodologies similar to that described in Schemes 8, 5, and 17 and the Examples.

Shown in Scheme 9 are general methods of preparing disclosed compounds having a pyrazolo[1,5-a]pyridine core. See generally Gudmundsson K S, et al. *Bioorg. Med. Chem. Lett.* 2008; 18: 1157-1161 and Chamberlin S D, et al., US20040072853A1. 4-Bromo-2-methylpyridine (48) can be converted to compound (49) by deprotonation with lithium bistrimethylsilylamide and reaction with a substituted alkyl-

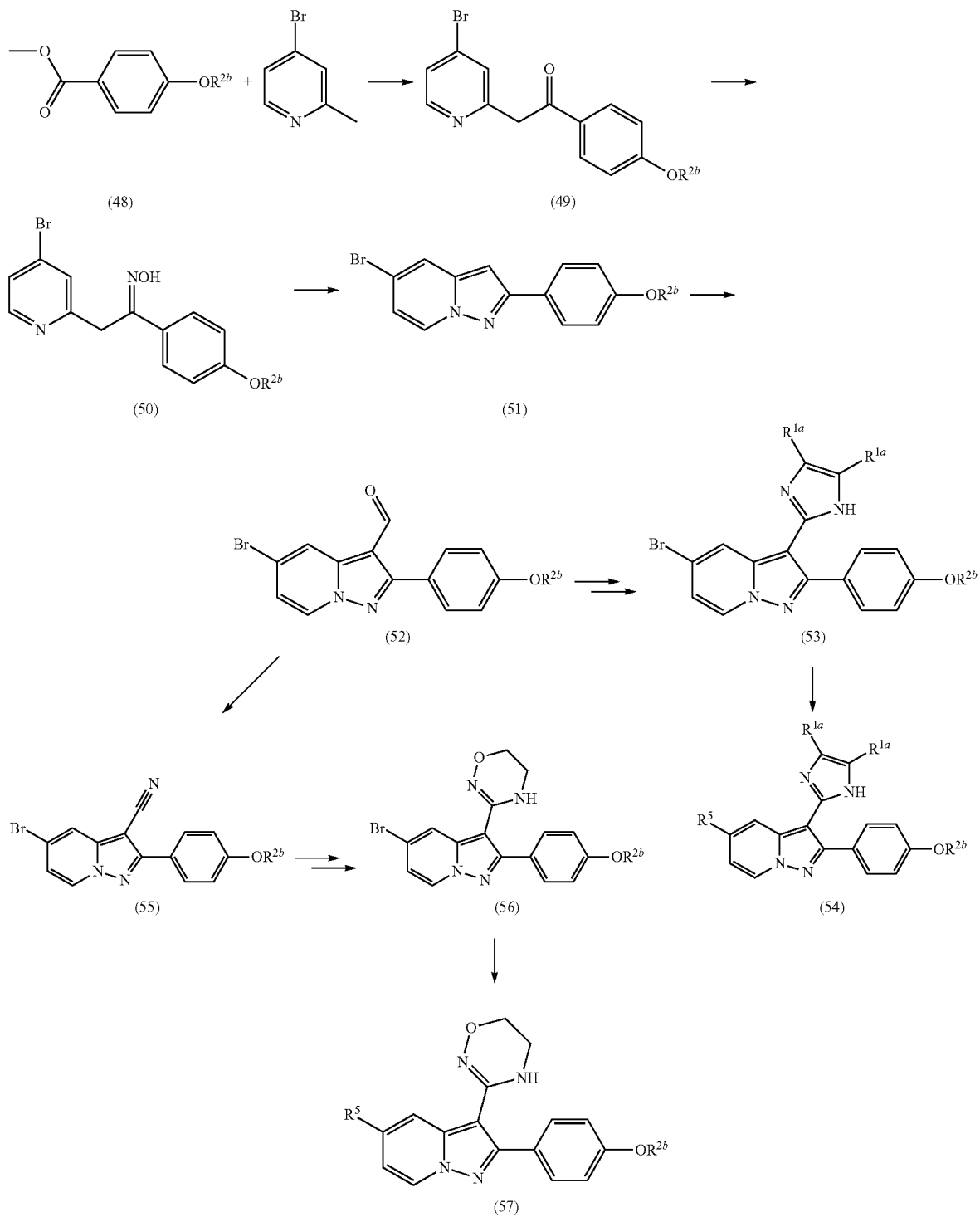

benzoate (e.g. methyl 4-methoxybenzoate). The ketone (49) can be converted to oxime (50) by treatment with hydroxylamine hydrochloride and sodium hydroxide. The oxime (50) can be converted to pyrazolopyridine (51) by treatment with trifluoroacetic anhydride and triethylamine in DME, to form an intermediate azirine, followed treatment of the azirine in situ with catalytic ferrous chloride and heating at 70-80° C. for a period of 6-24 hours. The desired pyrazolo[1,5-a]pyridine can then be isolated by filtration of the crude reaction mixture or by chromatography on silica gel. Compounds (51) can be converted to compounds (52) using standard Vilsmeier conditions. Compounds (52) can be converted to the imidazoles (53) using condition analogous to those described in Scheme 1. Alternatively, compounds (52) can be converted to compounds nitriles (55) via dehydration of the oxime in a manner similar to that depicted in Scheme 3. The nitriles (55) may be used to prepare the 5,6-dihydro-4H-1,2,4-oxadiazine (56) using the methodology shown generally in Scheme 5. Compounds (53) and (56) may be converted to compounds (54) and (57) having a variety of groups at $R^5$, either directly through carbon-carbon bond forming reactions (e.g., Suzuki) known to those skilled in the art, or such reactions in combination with a subsequent transformation (e.g., hydrogenation of a cycloalkene, amide formation from a carboxylic acid). For example, one may prepare compounds where $R^5$ is cycloalkyl or aryl by reaction with an appropriate boronic acid or derivative, followed by optional further manipulation in the case of cycloalkyl (i.e., cycloalkenyl to cycloalkyl). Where the $R^{2b}$ of (54) and (57) can be treated as a protecting group and removed (e.g., $R^{2b}$ is benzyl or methyl), the corresponding phenol can be formed. The phenol of (54) and (57) may be further converted to a reactive compound, such as a mesylate or nonaflate, and further transformed using the methodology illustrated in Scheme 7. Alternatively, the phenol of (54) and (57) may be further reacted using the methodology shown in Scheme 8 to produce disclosed compounds.

Scheme 10

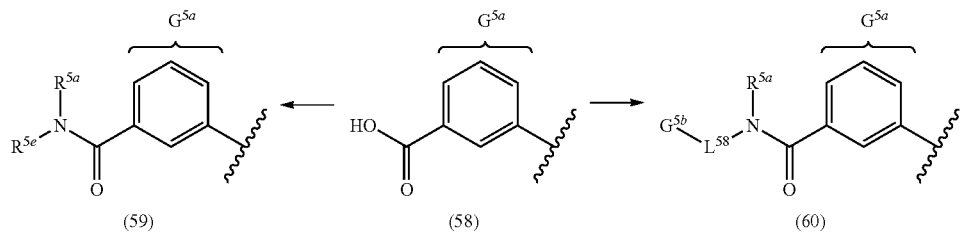

Certain disclosed compounds where $R^5$ is $G^{5a}$ can be prepared as shown generally in Scheme 10. Carboxylic acids (58), can be converted to amides (59) or (60) using standard amide bond forming reactions such as, but not limited to, reaction with an amine, HATU and triethylamine in solvents such as DMF.

Scheme 11

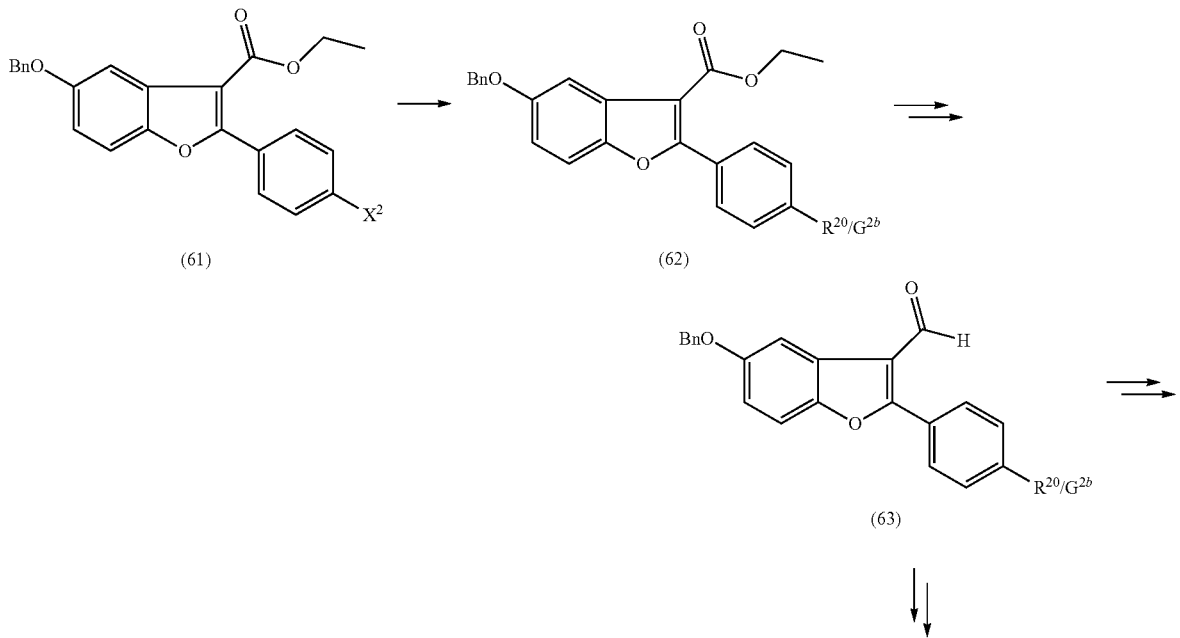

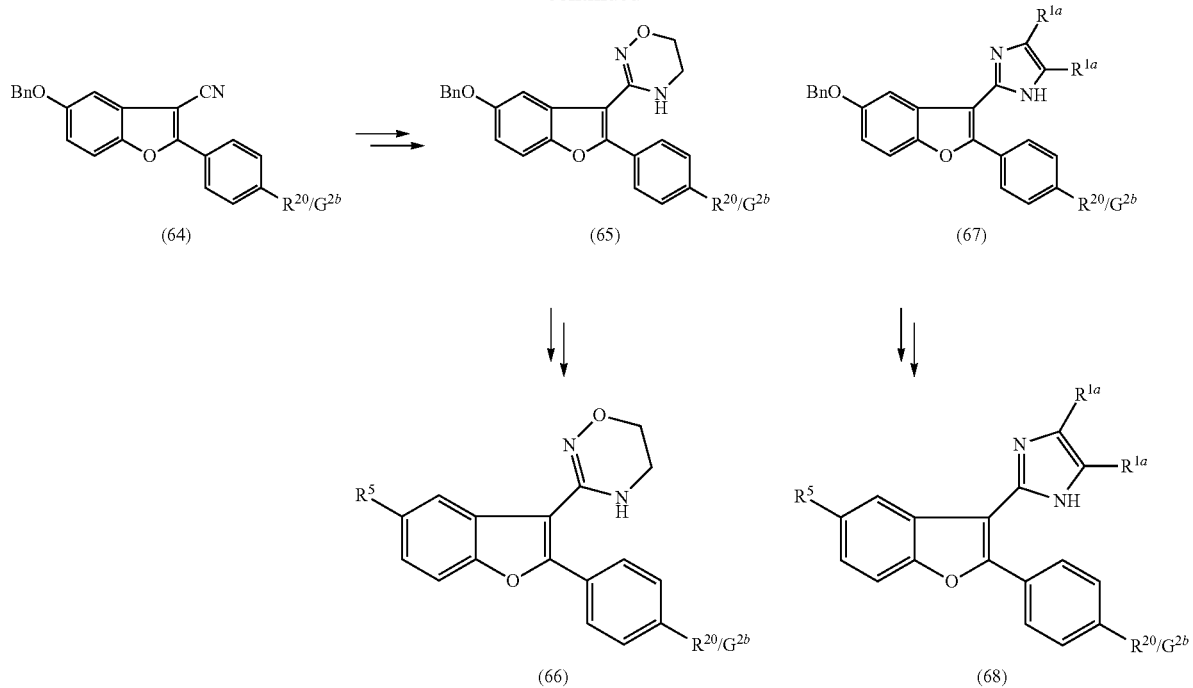

Other disclosed compounds may be made using the general methodology of Scheme 11. Ester compounds (61), where $X^2$ is chloro, bromo, or iodo, may be converted to compounds (62) using the types of chemistries shown in Scheme 7. In Scheme 11, $R^{20}$ and $G^{2b}$ are groups as defined herein and that are compatible with the methodology of Scheme 11. Compounds (62) may be converted to the intermediate compounds (63) and (64) using the general approach outlined in Scheme 3. Compounds (63) and (64) may, in turn, be converted to compounds (68) and (66) using, respectively, the approaches shown in Schemes 1 and 5.

An alternative synthesis to the 3-imidazole pyrazolo[1,5-a]pyridine may be used as shown in Scheme 12. The C-5 bromine on the pyrazolopyridine core may be converted to groups $R^5$ as in the conversion of (53) to (54). The compounds (69) may be converted to compounds (70) by treatment with an electrophilic halogen reagent such as N-bromosuccinimide or N-iodosuccinimide, wherein $X^1$ is bromine or iodine. The compounds (70) may be converted to compounds (72) by reaction directly with a metal imidazole species (73) (PG=protecting group) in a manner similar to that described for a zinc mediated Negishi coupling (Romine J L, et al., *J.*

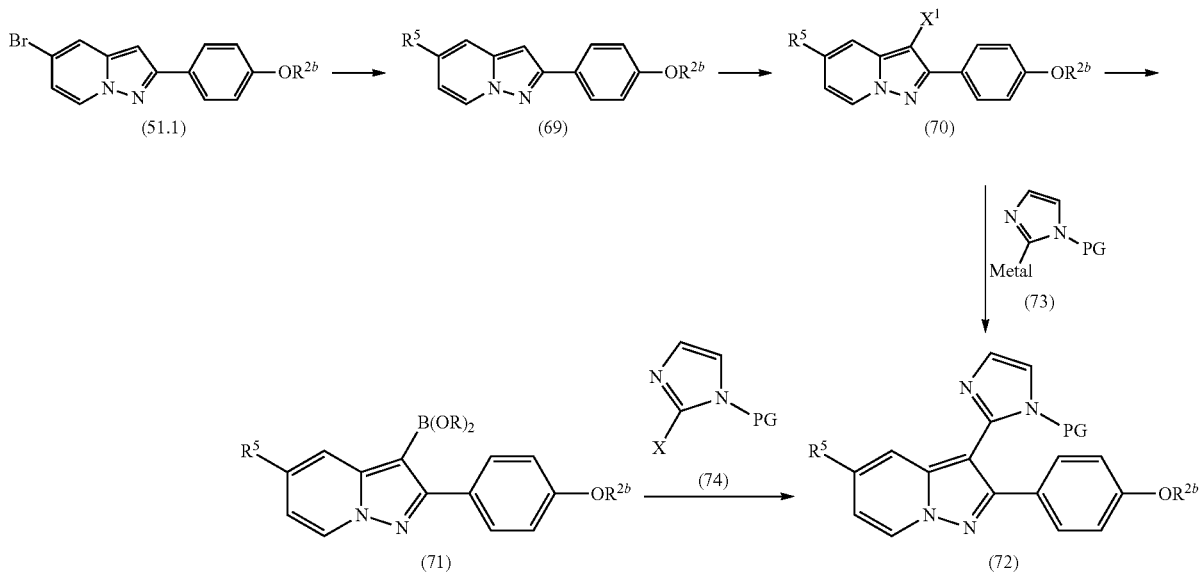

Med. Chem. 2007; 50: 528-542) or a tin mediated Stille coupling (Quan M L, et al., *J. Med. Chem.* 2005; 48; 1729-1744). Compound (70) may alternatively be converted to (71) that may then be reacted with an N-protected 2-haloimidazole species (74), wherein X is, for example, iodo, (see Knapp S, et al., *J. Org. Chem.* 1993; 58: 997-998) in a Suzuki coupling. Where the $R^{2b}$ of (72) may be treated as a protecting group and removed (e.g., $R^{2b}$ is benzyl or methyl), the corresponding phenol can be formed. The phenol may be converted to a reactive intermediate, such as a mesylate or nonaflate, and once again reacted to introduce other groups as shown generally in Schemes 7 and 11.

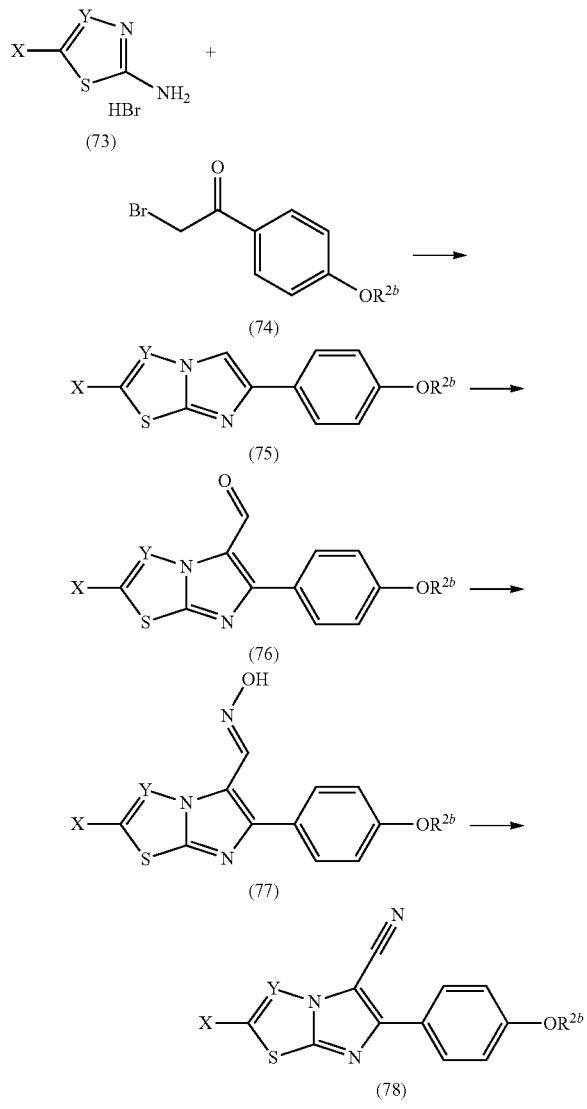

Y = CH, N

Schemes 13 and 14 illustrate syntheses of 5-heterocyclic imidazo[2,1-b]thiazoles and imidazo[2,1-b][1,3,4]thiadiazoles. In Scheme 13, an appropriately substituted thiazole or thiadiazole (73), wherein Y is CH or N and X is, for example hydrogen, halogen, $C_1$-$C_6$alkyl, $C_1$-$C_6$haloalkyl, $C_3$-$C_6$cycloalkyl, —O—$C_1$-$C_6$alkyl, —O—$C_1$-$C_6$haloalkyl, —O—$C_3$-$C_6$cycloalkyl, or optionally substituted phenyl, may be reacted with a substituted 2-bromoacetophenone (74) (e.g. 2-bromo-1-(4-methoxyphenyl)ethanone) to give (75). Compounds (75) may be converted to compounds (76) by Vilsmeyer formylation, which may be converted to the nitrile (78) as shown above. Compounds (76) and (78) may further be elaborated to give compounds where $R^1$ is (i) or (ii) using methods described generally herein. In Scheme 14, (73) may be reacted with an α-bromo ketoester (79) (e.g. ethyl 2-bromo-3-(4-methoxyphenyl)-3-oxopropanoate) to provide the core ring system (80). Compounds (80) may be converted to compounds (82) by methods known to those skilled in the art. Compounds (82) may be converted to the nitrile as described generally herein. The aldehyde of (82) and nitrile of (83) may be transformed to heterocycles as described in other schemes; and where $R^{2b}$ is a protecting group, it may be removed and the phenol converted to other groups as shown in Schemes 7 and 11.

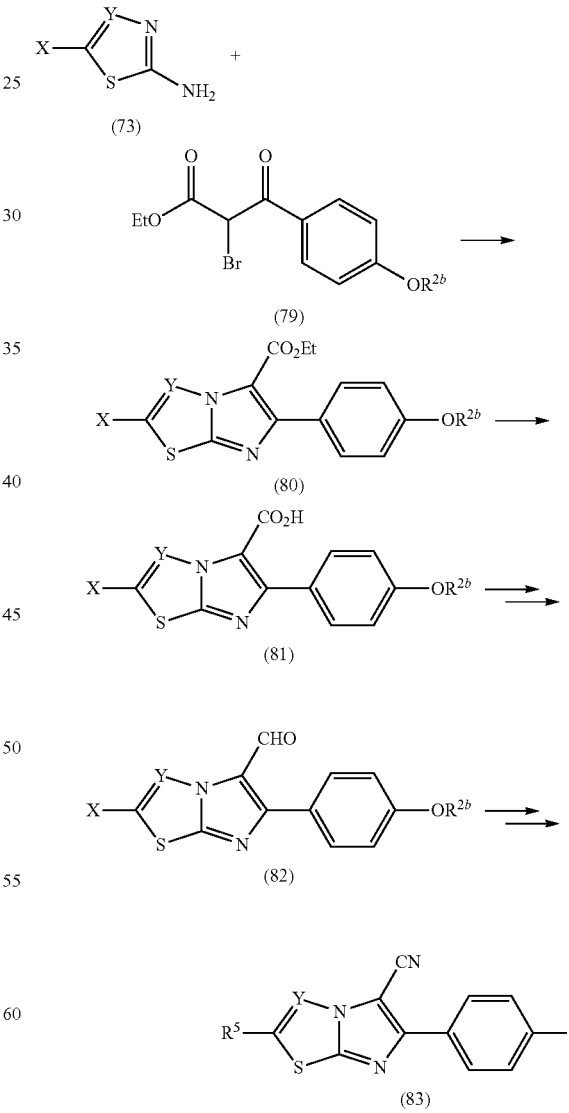

Y = CH, N

Scheme 15

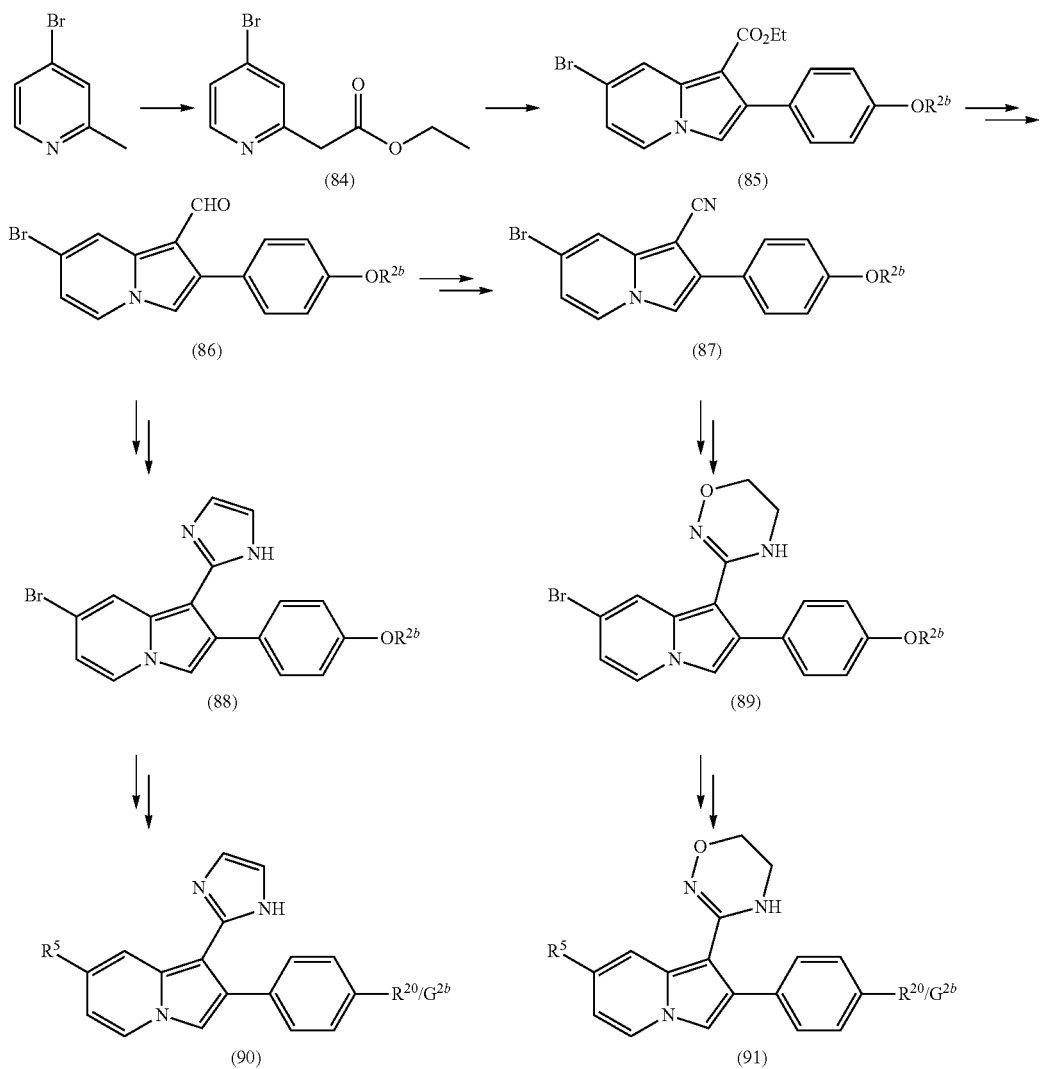

Scheme 15 illustrates a synthesis of the indolizine-1-carboxylate ring system. In a similar manner to that in the literature (Parrick J, et al. *J. Chem. Research* (Synopses) 1990; 64-65), 2-methyl-4-bromopyridine may be deprotonated and treated with diethyl carbonate to give ethyl 2-(4-bromopyridin-2-yl)acetate (84). The ester (84) may then be treated with a bromoacetophenone (e.g. 2-bromo-1-(4-methoxyphenyl) ethanone) to give the indolizine ring system (85). The ester may be converted to the carboxaldehyde (86) by methods known to those skilled in the art. The aldehyde may be manipulated to the nitrile (87); and (86) and (87) both further transformed as described hereinabove.

Scheme 16

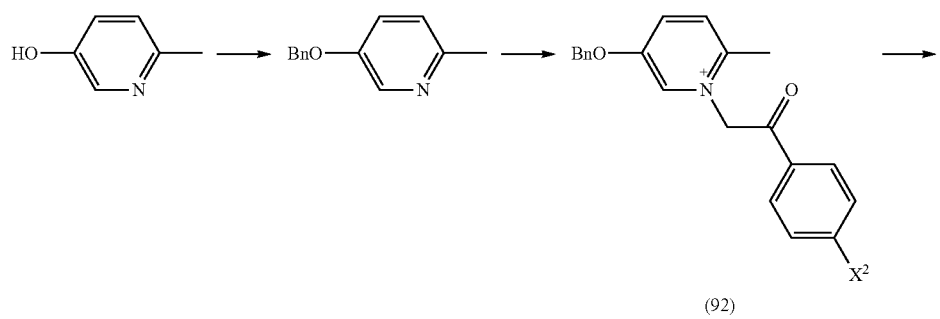

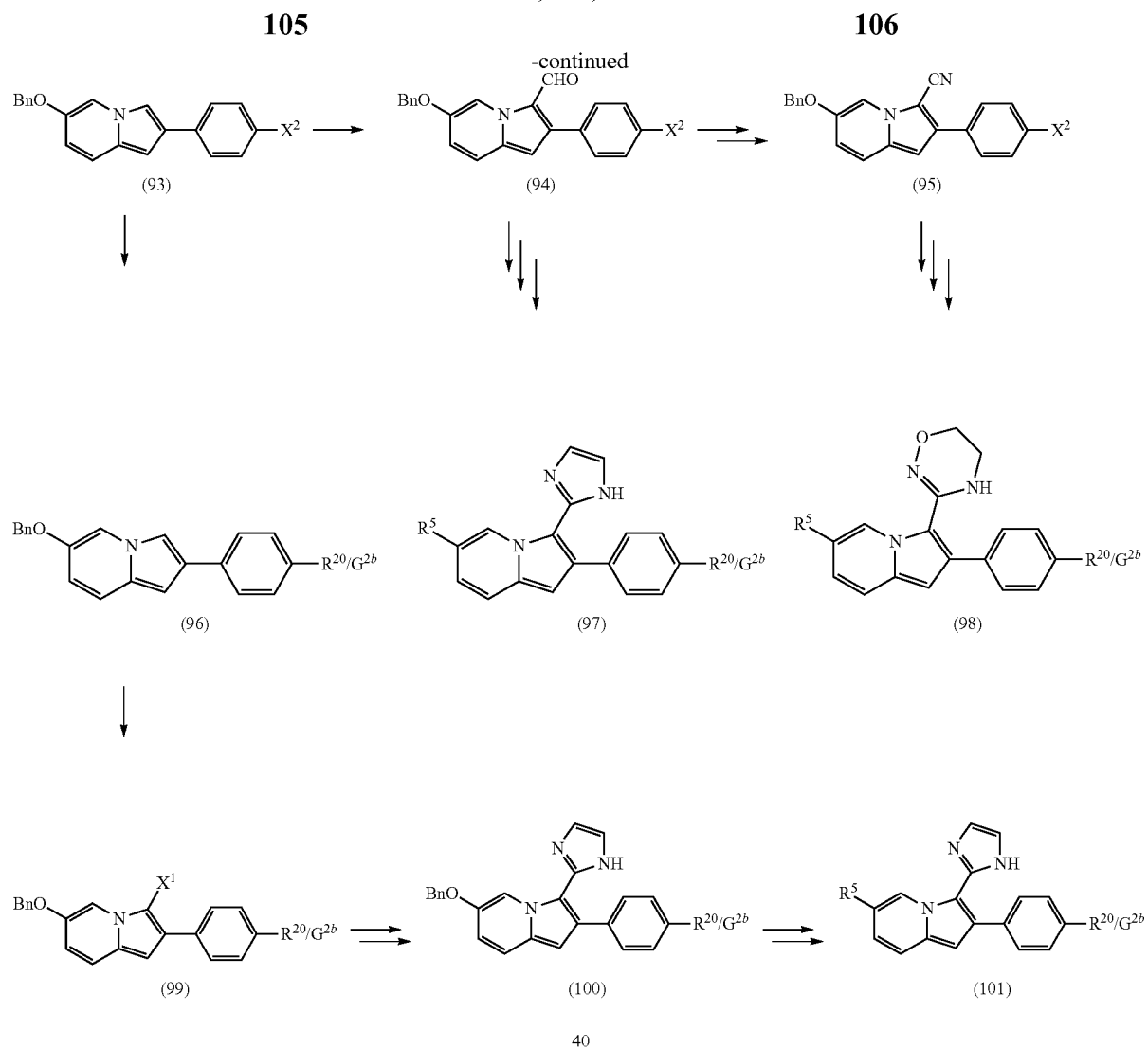

Further disclosed compounds may be prepared as shown in Scheme 16. The 3-indolizine ring system is constructed according to the procedures of Sliwa, et al., *Journal of Chemical Research*, miniprint, 1982; 2515-2527. 2-Methyl-5-hydroxypryidine is protected as the benzyl ester and treated with an α-bromo ketone to give the pyridinium salt (92). Heating with an excess of aqueous sodium bicarbonate may afford the indolizine core (93). Vilsmeyer formylation may provide the 3-formyl indolizine (94) that may be manipulated to the nitrile (95) and desired heterocycles as shown in earlier schemes. The benzyl ether and aryl halide $X^2$ may then be manipulated as described earlier to provide elaborated indolizines.

Scheme 17

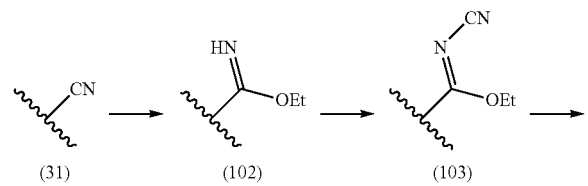

-continued

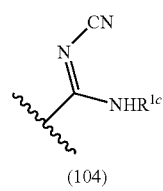

(104)

Disclosed compounds where $R^1$ is (iv) may be prepared using a method of converting a nitrile to a cyanoamidine (Scheme 17). A nitrile may be converted to the corresponding imidate by reaction with an alcohol, such as ethanol, in dichloromethane by bubbling HCl gas through the solution at 0° C. and allowing the reaction to proceed at 0° C. for several days. The free base of an imidate may be converted to a cyanoimidate by reaction with cyanamide, sodium phosphate monobasic monohydrate, and sodium phosphate dibasic heptahydrate in acetonitrile at about room temperature. A cyanoimidate may be converted to a cyanoamidine by reaction with an appropriate primary amine (e.g., $R^{1c}NH_2$). See also Fiorino, F, et al., *Bioorganic & Medicinal Chemistry Letters* 2010; 2978-2982; WO2006010756 (Examples 14-16).

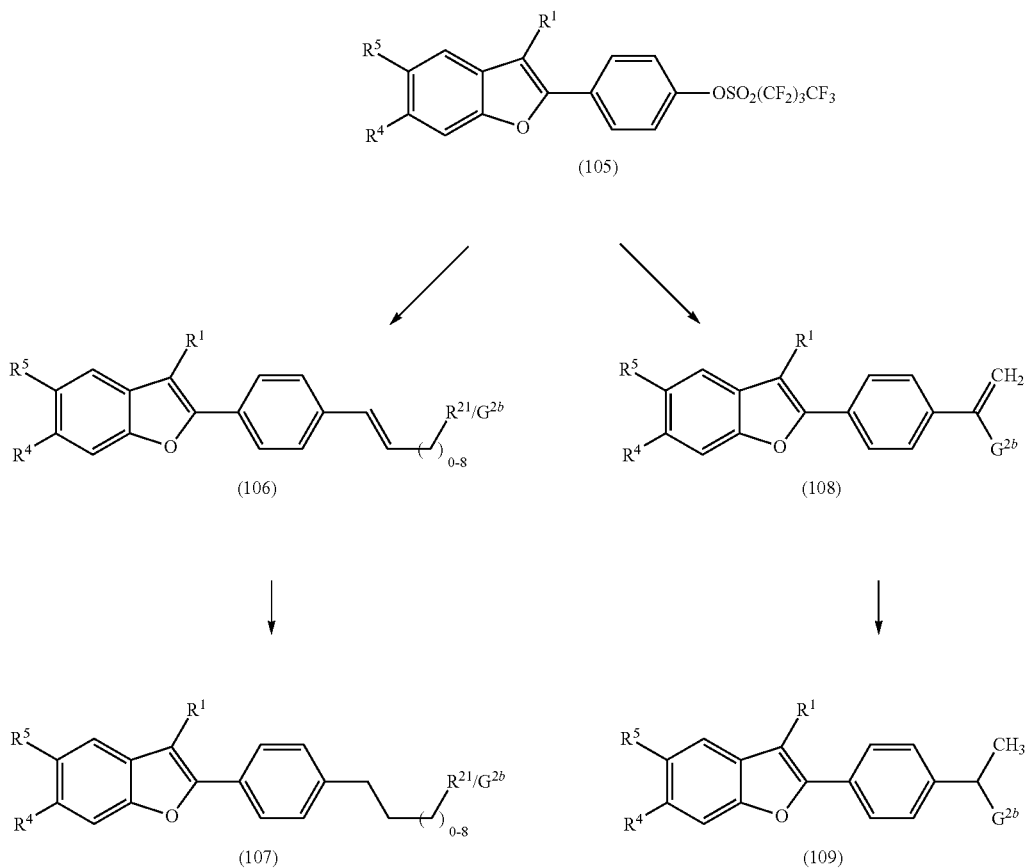

Scheme 18

As generally illustrated in Scheme 18, nonaflates (105), wherein $R^1$, $R^4$ and $R^5$ are as described in the Summary can be converted to alkene-substituted compounds (106) or (108) using Suzuki or Heck reactions. Compounds of formula (105) can be prepared similarly to the methods described for the preparation of compounds of formula (41) in Schemes 7, 5, and 17 and the Examples. Compounds of formula (105) can be reacted under Suzuki reaction conditions with boronic acids $R^{21}/G^{2b}$-$(CH_2)_{0-8}$—CH=CH—B(OH)$_2$ or $G^{2b}$-C(=CH$_2$)—B(OH)$_2$ to give compounds of formulas (106) and (108), respectively. $R^{21}$ and $G^{2b}$ are as defined in the Summary. An exemplary set of reaction conditions include combining compounds of formula (105), a boronic acid or functional equivalent, a catalyst such as palladium(II) acetate, a ligand such as 2-dicyclohexylphosphino-2',4',6'-triisopropylbiphenyl (X-Phos), a base such as sodium carbonate, and solvents such as a mixture of dimethoxyethane, water, and ethanol heated either conventionally or with microwave irradiation to give compounds of formulas (105) or (108). Compounds of formula (106) can be hydrogenated in the presence of a catalyst such as palladium hydroxide in a solvent such as but not limited to ethanol to give compounds of formula (107). Similarly, compounds of formula (108) can be hydrogenated to give compounds of formula (109). Compounds of formula (106), (107), (108), and (109) are representative of compounds of formula (I).

Scheme 19

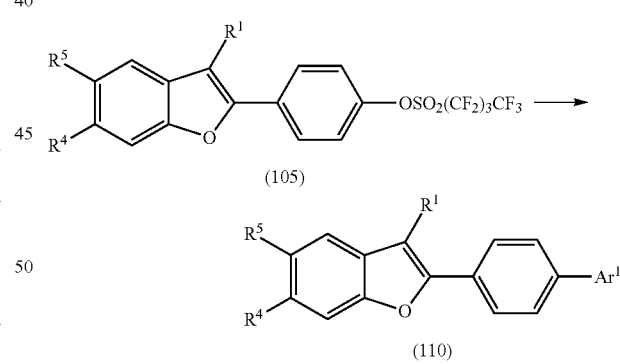

As generally illustrated in Scheme 19, nonaflates (105), wherein $R^1$, $R^4$ and $R^5$ are as described in the Summary can be converted to aryl/heteroaryl-substituted compounds (110) using Suzuki reactions. Compounds of formula (105) can be prepared as described in Scheme 18. Compounds of formula (105) can be reacted under Suzuki reaction conditions with boronic acids $Ar^1$—B(OH)$_2$ to give compounds of formula (110). $Ar^1$ is aryl or heteroaryl optionally substituted as described herein for $G^{2b}$. An exemplary set of reaction conditions include combining compounds of formula (105), a boronic acid or functional equivalent, a catalyst such as palladium(II) acetate, a ligand such as 2-dicyclohexylphosphino-2',4',6'-triisopropylbiphenyl (X-Phos), a base such as sodium carbonate, and solvents such as a mixture of dimethoxyethane, water, and ethanol heated either conventionally or with microwave irradiation to give compounds of formulas (110). Compounds of formula (110) are representative of compounds of formula (I).

Scheme 20

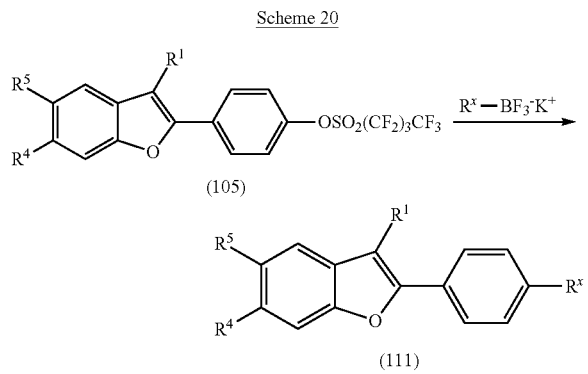

As generally illustrated in Scheme 20, nonaflates (105), wherein $R^1$, $R^4$ and $R^5$ are as described in the Summary can be converted to alkyl or cycloalkyl substituted compounds (111). Compounds of formula (105) can be prepared as described in Scheme 18. Compounds of formula (105) can be reacted with potassium trifluoroborates of formula $R^x$—$BF_3^-$ $K^+$ to give compounds of formula (111). $R^x$ is —$C_1$-$C_6$alkylene$R^{21}$ or $C_3$-$C_{10}$cycloalkyl optionally substituted as described herein for $G^{2b}$. $R^{21}$ is as described herein. An exemplary set of reaction conditions include combining compounds of formula (105), a potassium trifluoroborate, a catalyst such as palladium(II) acetate, a ligand such as 2-dicyclohexylphosphino-2',6'-dimethoxybiphenyl (S-Phos), a base such as tribasic potassium phosphate, and solvents such as a mixture of water and toluene heated either conventionally or with microwave irradiation to give compounds of formulas (111). Compounds of formula (111) are representative of compounds of formula (I).

In the foregoing Schemes, compounds are shown wherein an aromatic ring (e.g., phenyl) is substituted with groups in a particular regiochemistry (e.g., para). A starting material or intermediate with para-substitution provides a final product with para-substitution in the foregoing Schemes. It is understood by one of skill in the art that substitution in the foregoing Schemes of a starting material or intermediate with a different regiochemistry (e.g., meta) would provide a final product with a different regiochemistry. For example, replacement of a para-substituted starting material or intermediate in the foregoing Schemes with a meta substituted starting material or intermediate would lead to a meta-substituted product.

If a moiety described herein (e.g., —$NH_2$ or —OH) is not compatible with the synthetic methods, the moiety may be protected with a suitable protecting group that is stable to the reaction conditions used in the methods. The protecting group may be removed at any suitable point in the reaction sequence to provide a desired intermediate or target compound. Suitable protecting groups and methods for protecting or deprotecting moieties are well known in the art, examples of which can be found in Greene T W and Wuts P G M, *Protective Groups in Organic Synthesis*, (3$^{rd}$ ed., John Wiley & Sons, NY (1999)). Optimum reaction conditions and reaction times for each individual step may vary depending on the particular reactants employed and substituents present in the reactants used. Solvents, temperatures and other reaction conditions may be readily selected by one of ordinary skill in the art based on the present disclosure.

Other disclosed compounds can be similarly prepared according to the above-described schemes as well as the procedures described in the following intermediates, general procedures, and examples disclosure, as appreciated by those skilled in the art. It should be understood that the above-described embodiments and schemes and the following intermediates, general procedures, and examples disclosure are given by way of illustration, not limitation. Various changes and modifications within the scope of the present disclosure will become apparent to those skilled in the art from the present description.

EXAMPLES

Abbreviations: aq for aqueous; DCI for desorption chemical ionization; DMSO for dimethyl sulfoxide; ESI for electrospray ionization; HPLC for high performance liquid chromatography; LCMS for liquid chromatography-mass spectrometry; psi for pounds per square inch; TLC for thin layer chromatography; and v/v for volume/volume.

Analytical LCMS was performed on a Finnigan Navigator mass spectrometer and Agilent 1100 HPLC system running Xcalibur 1.2, Open-Access 1.3, and custom login software. The mass spectrometer was operated under positive APCI ionization conditions. The HPLC system comprised an Agilent Quaternary pump, degasser, column compartment, autosampler and diode-array detector, with a Sedere Sedex 75 evaporative light-scattering detector. The column used was a Phenomenex® Luna® Combi-HTS C8(2) 5 µm 100 Å (2.1 mm×30 mm). A gradient of 10-100% acetonitrile (A) and 0.1% trifluoroacetic acid in water (B) was used, at a flow rate of 2.0 mL/minute (0-0.1 minutes 10% A, 0.1-2.6 minutes 10-100% A, 2.6-2.9 minutes 100% A, 2.9-3.0 minutes 100-10% A 0.5 minutes post-run delay).

Certain compounds in the Examples below may have been purified using reverse-phase HPLC. Purification may have been conducted using either a C18 or C8 reverse-phase column. Compounds may have been eluted using a gradient of about 10-100% acetonitrile in 0.1% aqueous trifluoroacetic acid; about 60-100% methanol in 10 mM aqueous ammonium acetate; or about 10-95% methanol in 10 mM aqueous ammonium acetate. For purifications conducted with trifluoroacetic acid, the product thus obtained may have been in the form of a trifluoroacetic acid salt. Compounds may have been characterized as the trifluoroacetic acid salt or as the free base following neutralization, extraction and isolation.

Certain compounds in the Examples below may have been purified using normal phase silica gel chromatography including traditional flash chromatography or an automated purification system (e.g., Isco CombiFlash®, Analogix Intelliflash) using pre-packed silica gel columns (55 or 35 µm silica gel, Isco Gold columns). Compounds may have been also be purified by prep-TLC.

Typical solvents for silica gel chromatography included: ethyl acetate in hexanes, diethyl ether in hexanes, tetrahydrofuran in hexanes, ethyl acetate in methylene chloride, methanol in methylene chloride, methanol in methylene chloride with $NH_4OH$, acetone in hexanes, and methylene chloride in hexanes.

Example 1

N-[5-cyclopropyl-2-(4-fluorophenyl)-3-(1H-imidazol-2-yl)-1-benzofuran-6-yl]methanesulfonamide

Example 1A ethyl 3-(4-fluorophenyl)-3-oxopropanoate

Diethyl carbonate (801 mL, 6.79 mole) was added dropwise over a 30 minute period to a stirring slurry of potassium t-butoxide (609.2 g, 5.43 mole) in toluene (9.5 L) under a nitrogen atmosphere. The reaction mixture was heated to 78° C. and 4-fluoroacetophenone (250 g, 1.81 mole) in toluene (250 mL) was added over a one hour time period. Heating of the reaction mixture was continued overnight. Then the reaction mixture was quenched with 1.5 N HCl(aq) and extracted with ethyl acetate (3×1 L). The combined organic extracts were washed with saturated sodium bicarbonate, dried over anhydrous sodium sulfate, filtered and concentrated in vacuo leaving a brown liquid. The liquid was distilled to give the title compound as a colorless liquid (250 g, 79%). MS m/z 209 (M−H)⁻.

Example 1B ethyl 2-(4-fluorophenyl)-5-hydroxybenzofuran-3-carboxylate

The material prepared in Example 1A (250 g, 1.19 mole) was combined with zinc chloride (243.5 g, 1.784 mole) and toluene (3.75 L). The reaction mixture was heated to reflux under a nitrogen atmosphere. Benzoquinone (167 g, 1.546 mole) in tetrahydrofuran (500 mL) was added dropwise to the reaction, and upon completion of the addition, the reaction mixture was heated at reflux for 6 hours. The reaction mixture was quenched with water and extracted with ethyl acetate. The organic layer was concentrated in vacuo to a brown solid. The solid was recrystallized from acetonitrile yielding the title compound as a brown solid (125 g, 35%). MS m/z 301 (M+H)⁺.

Example 1C ethyl 2-(4-fluorophenyl)-5-isopropoxy-1-benzofuran-3-carboxylate

Example 1B (210 g, 0.6993 mole), cesium carbonate (455.7 g, 1.3986 mole) and N-methylpyrrolidone (1 L) were combined. The reaction mixture was treated under a nitrogen atmosphere with 2-bromopropane (196 mL, 2.098 mole), and the reaction mixture was heated for 4 hours at 50° C. Upon completion of the reaction as determined by TLC (petroleum ether/ethyl acetate, 8/2), the reaction mixture was treated with aqueous ammonium hydroxide solution (200 mL), and the solution was extracted with heptane. The organic extracts were washed with water and brine, dried over anhydrous sodium sulfate, filtered and concentrated in vacuo leaving a brown oil as the title compound (220 g, 92%). MS (LCMS) m/z 342 (M+).

Example 1D ethyl 2-(4-fluorophenyl)-5-isopropoxy-6-nitro-1-benzofuran-3-carboxylate Example 1C (220 g, 0.6432 mole) was dissolved in chloroform (4.4 L). The mixture was cooled in an ice bath to 0° C., and the reaction mixture was treated dropwise with 70% nitric acid (29 mL, 0.65 mole) maintaining the internal temperature less than 10° C. Upon completion of the nitric acid addition, the ice bath was removed, and the reaction mixture was stirred for one hour at room temperature. The reaction mixture was quenched with water and extracted with chloroform (2×2 L). The combined organic extracts were washed with water and brine, dried over anhydrous sodium sulfate, filtered and concentrated in vacuo leaving a yellow solid. The solid was triturated with hexanes and filtered to give the title compound as a light yellow solid (220 g, 88%). MS m/z 388 (M+H)⁺.

Example 1E ethyl 2-(4-fluorophenyl)-5-hydroxy-6-nitro-1-benzofuran-3-carboxylate Example 1D (220 g, 0.643 mole) was combined with dichloromethane (4.4 L). The mixture was cooled in an ice bath to 0° C. and was then treated dropwise with 1 M boron trichloride solution in dichloromethane (625 mL, 0.625 mole) maintaining the internal temperature less than 10° C. Upon completion of the boron trichloride addition, the ice bath was removed and the reaction mixture was stirred for one hour at room temperature. The reaction mixture was quenched with water and extracted with dichloromethane (3×2 L). The combined organic extracts were washed with water and brine, dried over anhydrous sodium sulfate, filtered and concentrated in vacuo leaving a yellow solid. The solid was triturated with hexanes and filtered to give the title compound as a white solid (180 g, 81%). MS (LC-MSD-trap-XCT) m/z 344 (M−H)⁻.

Example 1F ethyl 2-(4-fluorophenyl)-6-nitro-5-{[(trifluoromethyl)sulfonyl]oxy}-1-benzofuran-3-carboxylate Example 1E (10 g, 29.0 mmol), 4-(dimethylamino)pyridine (0.354 g, 2.90 mmol), N,N-diisopropylethylamine (7.52 mL, 43.4 mmol) and phenyl triflimide (13.97 g, 39.1 mmol) were combined in dichloromethane (150 mL) to give a light brown slurry that slowly dissolved. The solution was stirred for 18 hours. The reaction mixture was then washed sequentially with 1 M NaOH, 1 M HCl, and brine, dried (Na₂SO₄), filtered through a plug of silica, and concentrated to a yellow solid. The crude product was triturated in 100 mL of hexane, sonicated for five minutes, and the solid was collected by filtration and dried to constant mass to give the title compound as a fine, yellow powder (13.1 g, 95%).

Example 1G ethyl 5-cyclopropyl-2-(4-fluorophenyl)-6-nitro-1-benzofuran-3-carboxylate Example 1F (13.12 g, 27.5 mmol), cyclopropylboronic acid (3.54 g, 41.2 mmol), sodium bromide (2.91 g, 28.3 mmol), potassium fluoride dihydrate (3.42 mL, 91 mmol) and tetrakis(triphenylphosphine)palladium(0) (0.953 g, 0.825 mmol) were combined in toluene (140 mL). The mixture was sparged with nitrogen for fifteen minutes. The vessel was sealed and heated at 125° C. for 18 hours. The resulting black reaction mixture was partitioned between ethyl acetate (200 mL) and water (100 mL) and filtered through a 1 inch plug of diatomaceous earth to remove the solid catalyst. The filtrate layers were separated. The ethyl acetate layer was washed with saturated aqueous NaHCO$_3$, H$_2$O, and brine. The organic layer was dried (Na$_2$SO$_4$), treated simultaneously with Darco G-60 carbon black (5 g) and 3-mercaptopropyl functionalized silica (5 g, Aldrich 538086), stirred for 30 minutes, and filtered through a 1 inch pad of diatomaceous earth. The light red filtrate was concentrated to near dryness and diluted with hexane (200 mL) producing a tan solid that was collected by filtration and dried to give the title compound (7.95 g, 78%).

Example 1H ethyl 6-amino-5-cyclopropyl-2-(4-fluorophenyl)-1-benzofuran-3-carboxylate Ethanol (188 mL), tetrahydrofuran (188 mL) and deionized water (63 mL) were combined under a nitrogen atmosphere. Example 1G (18.62 g, 50.4 mmol) was added to the solvent mixture, and the resultant slurry was stirred while iron powder (14.08 g, 252 mmol) and ammonium chloride (4.05 g, 76 mmol) were added. The reaction mixture was then refluxed for 1.5 hours. The hot reaction mixture was filtered through a bed of diatomaceous earth, with tetrahydrofuran/ethanol washing. The filtrate was concentrated in vacuo to dryness, and the residue was partitioned between ethyl acetate (~700 mL) and deionized water. The organic layer was washed with brine, dried over anhydrous sodium sulfate and concentrated in vacuo to give the title compound (17.1 g) as a of a tan solid.

Example 1I ethyl 5-cyclopropyl-2-(4-fluorophenyl)-6-[(methylsulfonyl)amino]-1-benzofuran-3-carboxylate Example 1H (17.1 g, 50.4 mmol) was dissolved in dichloromethane (300 mL) under nitrogen. The mixture was stirred while pyridine (39.9 g/40.8 mL, 504 mmol) was added. Methanesulfonyl chloride (6.93 g/4.7 mL, 60.5 mmol) in dichloromethane (36 mL) was added dropwise over 20 minutes to the reaction mixture followed by continued stirring at room temperature for 3 hours. The reaction mixture was concentrated in vacuo to dryness. The resulting solid was taken up in ethyl acetate (750 mL) and washed with water, 1 N aqueous HCl and brine. The organic layer was dried over anhydrous sodium sulfate, filtered and concentrated in vacuo giving the title compound (19.98 g, 95%) as a white solid.

Example 1J ethyl 5-cyclopropyl-2-(4-fluorophenyl)-6-[(4-methoxybenzyl)(methylsulfonyl)amino]-1-benzofuran-3-carboxylate Example 1I (19.96 g, 47.8 mmol) was dissolved in N,N-dimethylformamide (120 mL). To the reaction mixture was added potassium carbonate (7.93 g, 57.4 mmol) followed by the dropwise addition over 15 minutes of benzyl bromide (12.98 g, 64.5 mmol). The reaction mixture was placed in an oil bath at 50° C. and stirred 3 hours. The reaction mixture was cooled to room temperature and the N,N-dimethylformamide was removed in vacuo to dryness at ~35° C. bath temperature. The dark oil was dissolved in ethyl acetate (500 mL) and washed with water (150 mL) and brine (2×150 mL) and dried over anhydrous magnesium sulfate. A 150 mL sinter funnel was set up with silica and the dried organic solution was filtered through the silica gel rinsing with an equal volume of ethyl acetate. The collected filtrate was concentrated in vacuo to dryness and the resulting solid was treated with hexane (300 mL). The slurry was stirred for 15 minutes, filtered and washed with hexane. The solid was dried overnight in a vacuum oven. The title compound was isolated as a tan solid (23.45, 91%).

Example 1K

N-[5-cyclopropyl-2-(4-fluorophenyl)-3-(hydroxymethyl)-1-benzofuran-6-yl]-N-(4-methoxybenzyl)methanesulfonamide Example 1J (18.4 g, 34.2 mmol) was dissolved in dry tetrahydrofuran (98 mL), and the reaction mixture was immersed in an ice water bath at 5° C. under a nitrogen atmosphere. When the internal temperature of the ester solution reached 10° C., a 1 M lithium aluminum hydride solution in tetrahydrofuran (34.2 mL, 34.2 mmol) was added dropwise over 20 minutes. After the addition was complete, the reaction mixture was stirred ten additional minutes, the ice bath was removed and the mixture was stirred for 1.5 hours at room temperature. The reaction mixture was quenched by cautious dropwise addition of 1.4 mL of water to minimize vigorous foaming. When the foaming subsided, aqueous 15% sodium hydroxide solution (1.4 mL) was added and a thick slurry formed. Finally, 4.2 mL of water was added dropwise and the resulting slurry was stirred for 20 minutes. The slurry was diluted with ethyl acetate and filtered through a pre-wetted bed of diatomaceous earth. The diatomaceous earth pad was washed with additional ethyl acetate. The filtrate was concentrated in vacuo, and the resulting foamy solid was dried in vacuo overnight at room temperature. The title compound was collected as a white foamy material (16.78 g, 99%).

Example 1L

N-[5-cyclopropyl-2-(4-fluorophenyl)-3-formyl-1-benzofuran-6-yl]-N-(4-methoxybenzyl)methanesulfonamide Example 1K (12.0 g, 24.21 mmol) was dissolved in dichloromethane (240 mL), and the resulting solution was treated with pyridinium dichromate (13.66 g, 36.3 mmol). The resulting dark solution was stirred at room temperature for 18 hours. The very dark reaction mixture slurry was filtered through a bed of diatomaceous earth that had been pre-wetted with dichloromethane. The diatomaceous earth bed was washed with additional dichloromethane (400 mL). The organic filtrate was washed with 1.2 N aqueous HCl (2×100 mL) and brine (200 mL) and dried over anhydrous magnesium sulfate. The drying agent was removed by filtration, and the solvent was removed in vacuo leaving an oily residue. The residue was dissolved in dichloromethane (10 mL) and applied to silica gel (40 g). The sample was eluted with ethyl acetate/hexane (1:1, 700 mL). The solvent was removed in vacuo, and the residue was treated with diethyl ether (75 mL). The resulting slurry was stirred for ten minutes and then filtered. The collected solid was washed with additional ether (40 mL) and dried in vacuo overnight. The title compound was collected as a tan solid (10.13 g, 85%).

Example 1M

N-[5-cyclopropyl-3-(4,5-dihydro-1H-imidazol-2-yl)-2-(4-fluorophenyl)-1-benzofuran-6-yl]-N-(4-methoxybenzyl)methanesulfonamide To a mixture of Example 1L (7.0 g, 14.18 mmol) in dichloromethane (117 mL) under nitrogen was added ethylenediamine (0.938 g/1.043 mL, 15.60 mmol) dissolved in 2 mL of dichloromethane (2 mL) in 200 µL portions over 7 minutes. The mixture was stirred at room temperature for 4.5 hours. The reaction mixture was immersed in an ice bath and N-bromosuccinimide (2.65 g, 14.89 mmol) and powdered 4 Å molecular sieves (3.63 g) were added over ~1 minute. The reaction mixture was stirred in the ice bath for 10 minutes, then the ice bath was removed and the reaction mixture was stirred at room temperature for a total of 72 hours. Reaction progress was monitored by LCMS. After each 24 hour period, additional ethylenediamine and N-bromosuccinimide were added followed by continued stirring at room temperature for 64 hours. The resulting slurry was filtered through a pad of diatomaceous earth with dichloromethane (2×100 mL) washes. The combined dichloromethane layers were washed with 10% sodium bicarbonate and 10% sodium chloride and dried over anhydrous sodium sulfate. The drying agent was removed by filtration, and the organic layer was concentrated in vacuo to an oily residue. The residue is treated with dichloromethane/acetonitrile (4:1, 100 mL), and the solvent was removed in vacuo leaving a tan foamy solid. The foamy solid was stirred for 20 minutes with hexane/ethyl acetate (4:1, 35 mL), filtered and dried in vacuo giving the title compound as a tan solid (6.86 g, 91%).

Example 1N

N-[5-cyclopropyl-2-(4-fluorophenyl)-3-(1H-imidazol-2-yl)-1-benzofuran-6-yl]-N-(4-methoxybenzyl) methanesulfonamide (ACD v12)

Example 1M (6.83 g, 12.8 mmol) and anhydrous dimethyl sulfoxide (64 mL) were combined and stirred under nitrogen. Powdered potassium carbonate (3.54 g, 25.6 mmol) and iodobenzene diacetate (4.53 g, 14.08 mmol) were added, and the resulting reaction mixture was stirred at room temperature for 2.5 hours. The reaction mixture was partitioned between water and ethyl acetate. The organic layer was washed with brine and dried over anhydrous sodium sulfate. The drying agent was removed by filtration, and the solvent was removed in vacuo leaving a reddish solid. The solid was combined with hexane:ethyl acetate (1:1), and the resulting slurry was stirred for twenty minutes at room temperature. The slurry was filtered and the resulting white solid was dried in vacuo for 15 hours to give the title compound (4.86 g, 71.4%): $^1$H NMR (300 MHz, DMSO-$d_6$) δ ppm 0.20 (m, 1H) 0.69 (m, 2H) 0.89 (m, 1H) 2.19 (m, 1H) 3.21 (s, 3H) 3.67 (s, 3H) 4.76 (m, 2H) 6.80 (d, J=8.46 Hz, 2H) 6.93 (s, 1H) 7.14 (m, 3H) 7.34 (m, 3H) 7.78 (s, 1H) 7.99 (m, 2H) 12.39 (s, 1H); MS (DCI+) m/z 532.1 (M+H)$^+$.

Example 1O

N-[5-cyclopropyl-2-(4-fluorophenyl)-3-(1H-imidazol-2-yl)-1-benzofuran-6-yl]methanesulfonamide Example 1N (4.83 g, 9.09 mmol) was dissolved in anhydrous dichloromethane (35 mL), and the resulting solution was placed in an ice bath while stirring under nitrogen. When the internal temperature of the reaction mixture reached 10° C., trifluoroacetic acid (35 mL) was added dropwise over ~35 minutes from an addition funnel. The reaction mixture turned dark cherry red. The ice bath was removed, and the reaction mixture was stirred for three hours at room temperature. The reaction mixture was concentrated in vacuo to a dark red oil. The oil was treated three times with dichloromethane and concentrated to dryness in vacuo leaving a foamy solid. The foamy solid was treated with 5% sodium bicarbonate solution (100 mL) followed by stirring for 20 minutes at room temperature. The resulting solid was collected by filtration, washed twice thoroughly with water, and dried in a vacuum oven at 70° C. for 15 hours. The recovered solid was treated with ethyl acetate, filtered and dried in vacuo giving the title compound as a light pink solid (3.13 g, 84%). $^1$H NMR (500 MHz, DMSO-$d_6$) δ ppm 0.59-0.73 (m, 2H) 0.93-1.03 (m, 2H) 2.27-2.34 (m, 1H) 3.03-3.10 (m, 3H) 7.13-7.22 (m, 2H) 7.25-7.41 (m, 3H) 7.62 (s, 1H) 7.96-8.05 (m, 2H) 9.25-9.36 (m, 1H) 12.38 (s, 1H); MS (DCI+) m/z 412.2 (M+H)$^+$.

Example 2

N-[5-cyclopropyl-2-(4-fluorophenyl)-3-(4-methyl-1H-imidazol-2-yl)-1-benzofuran-6-yl]methanesulfonamide Example 2A N-[5-cyclopropyl-2-(4-fluorophenyl)-3-(4-methyl-4,5-dihydro-1H-imidazol-2-yl)-1-benzofuran-6-yl]-N-(4-methoxybenzyl)methanesulfonamide The title compound was prepared by the method described in Example 1M using the product aldehyde from Example 1L, (2.0 g, 4.05 mmol) and substituting 1,2 diaminopropane (330 mg, 4.46 mmol) for ethylenediamine giving the title compound as a brown foamy solid (0.93 g, 42%).

Example 2B

N-[5-cyclopropyl-2-(4-fluorophenyl)-3-(4-methyl-1H-imidazol-2-yl)-1-benzofuran-6-yl]-N-(4-methoxybenzyl)methanesulfonamide The title compound was prepared according to the procedure described in Example 1N using the imidazoline prepared in Example 2A (0.816 g, 1.49 mmol), anhydrous dimethyl sulfoxide (7.5 mL), powdered potassium carbonate (0.412 g, 2.98 mmol) and iodobenzene diacetate (0.528 g, 1.639 mmol) giving the title compound as a tan solid (0.65 g, 71%). $^1$H NMR (300 MHz, DMSO-$d_6$) δ ppm 0.19-0.41 (m, 1H) 0.64-1.02 (m, 2H) 2.18-2.32 (m, 2H) 2.37 (s, 3H) 3.23 (s, 3H) 3.68 (s, 3H) 4.67-4.79 (m, 1H) 4.81-4.97 (m, 1H) 6.80 (d, J=8.82 Hz, 2H) 6.98 (s, 1H) 7.07-7.25 (m, 2H) 7.33-7.49 (m, 2H) 7.54-7.74 (m, 3H) 7.92 (s, 1H) 14.47 (s, 1H); MS (ESI+) m/z 546.1 (M+H)$^+$, (ESI−) 544.1 (M−H)$^-$.

Example 2C

N-[5-cyclopropyl-2-(4-fluorophenyl)-3-(4-methyl-1H-imidazol-2-yl)-1-benzofuran-6-yl]methanesulfonamide The title compound was prepared according to the procedure described in Example 1O using the compound prepared in Example 2B, (0.64 g, 1.17 mmol) and 20% trifluoroacetic acid in $CH_2Cl_2$. The title compound was isolated as a yellow solid (0.18 g, 35%). MS (ESI+) m/z 426 (M+H)$^+$.

Example 3

N-{[2-(1H-benzimidazol-6-yl)-1,3-thiazol-5-yl]methyl}-N-[3-(1H-imidazol-2-yl)-2-phenyl-1-benzofuran-6-yl]methanesulfonamide

Example 3A (2-bromo-1,3-thiazol-5-yl)methanol

2-Bromothiazole-5-carbaldehyde (3.00 g, 15.62 mmol) and methanol (50 mL) were combined. The mixture was cooled to 0° C. under nitrogen and sodium borohydride (0.591 g, 15.62 mmol) was added portion wise. Stirring was continued at this temperature for 2 hours. The reaction was then warmed to room temperature and stirred for two additional hours. The solvent was concentrated and saturated aqueous $NH_4Cl$ was added to the residue. The acidity was first adjusted to pH~6 using 1 M aqueous HCl followed by adjusting the pH~10 by the addition of 1 M aqueous NaOH. The mixture was extracted with ethyl acetate. The organic layer was then washed with brine, dried with sodium sulfate, filtered and concentrated. The residue was purified by chromatography on silica gel eluting with ethyl acetate/hexane (10% to 25%) to give the title compound as a light yellow oil. MS (DCI+) m/z 194, 196 (M+H)$^+$.

Example 3B 2-bromo-5-(bromomethyl)-1,3-thiazole

Example 3A (1.90 g, 9.79 mmol), carbon tetrabromide (3.57 g, 10.77 mmol), and triphenylphosphine (2.82 g, 10.77 mmol) were combined in tetrahydrofuran (30 mL). The mixture was stirred at room temperature for 2 hours. The solvent was concentrated and the residue was partitioned between water and ethyl acetate. The organic layer was washed with brine, dried with sodium sulfate, filtered and concentrated. The residue was purified with silica gel eluting with ethyl acetate/hexane (0% to 5%) to give the title compound as a solid (0.70 g, 28%). MS (DCI+) m/z 256, 258, 260, (M+H)$^+$.

Example 3C 2-methoxy-4-nitro-1-(phenylethynyl)benzene

To a mixture of triethylamine (60 mL) and tetrahydrofuran (20 mL) were added 1-iodo-2-methoxy-4-nitrobenzene (10 g, 35.8 mmol) and bis(triphenylphosphine)palladium (II) chloride (0.503 g, 0.717 mmol). Phenylacetylene (4.48 g, 43.0 mmol) in tetrahydrofuran (10 mL) was added dropwise to the reaction mixture and the mixture was stirred for 5 minutes. Copper iodide (0.068 g, 0.358 mmol) was added, and the reaction mixture was stirred and purged with nitrogen for 10 minutes. The reaction flask was sealed and stirred for 2 hours at room temperature. The reaction mixture was treated with 200 mL of dichloromethane, washed with water, dried over anhydrous magnesium sulfate, filtered and concentrated in vacuo leaving a solid. The crude solid was recrystallized from absolute ethanol. The solid was collected by filtration and washed with cold ethanol and dried in vacuo to give the title compound as a tan solid (8.87 g, 98%).

Example 3D 3-iodo-6-nitro-2-phenyl-1-benzofuran

Example 3C (31.11 g, 123 mmol) was dissolved in dichloromethane (300 mL). To this solution was added iodine (62.4 g, 246 mmol), and the mixture was refluxed for five hours. The mixture was cooled to room temperature and treated with 20% aqueous sodium thiosulfate (180 mL). The mixture was stirred vigorously for 15 minutes. The product was extracted with dichloromethane (4×300 mL), and the combined organic extracts were washed with water and brine and dried over anhydrous magnesium sulfate. The drying agent was removed by filtration, and the solvent was removed in vacuo leaving a crude solid. The solid was purified on silica gel eluting with dichloromethane to give the title compound as a white solid (34.44 g, 77%).

Example 3E methyl 6-nitro-2-phenyl-1-benzofuran-3-carboxylate

A pressure vessel was charged with Example 3D (20 g, 54.8 mmol), methanol:acetonitrile (1:1, 220 mL), dichloro[1,1'-bis(diphenylphosphino)ferrocene]palladium(II) dichloromethane adduct (0.802 g, 1.1 mmol) and triethylamine (15.3 mL, 110 mmol). The mixture was pressurized with carbon monoxide (60 psi), and stirred for 16 hours at 80° C. The reaction mixture was filtered, and the filtrate was concentrated in vacuo to a black solid. This solid was dissolved in 600 mL of 1:1 ethyl acetate/acetonitrile at reflux and treated with 10 g of mercaptopropyl silica and 10 g of decolorizing carbon. The mixture was stirred with heating for 30 minutes and filtered through diatomaceous earth. The filtrate was concentrated and the residue was stirred vigorously in 300 mL of water for 30 minutes. The title compound was collected as an orange powder that was dried to constant mass (15.78 g, 97%).

Example 3F methyl 6-amino-2-phenyl-1-benzofuran-3-carboxylate

Example 3E (15.8 g, 53.2 mmol), iron powder (14.84 g, 266 mmol), and ammonium chloride (4.26 g, 80 mmol) were combined in tetrahydrofuran, ethanol, and water (3:3:2, 500 mL) to give an orange suspension. The suspension was heated with vigorous stirring at 95° C. for 3 hours, cooled, filtered through diatomaceous earth, followed by rinsing the diatomaceous earth pad with hot tetrahydrofuran. The filtrate was concentrated and the residue was partitioned between ethyl acetate and water. The ethyl acetate layer was washed with brine, dried ($Na_2SO_4$), filtered and concentrated to give a yellow oil as the title compound (14.21 g, 100%).

Example 3G methyl 6-[(methylsulfonyl)amino]-2-phenyl-1-benzofuran-3-carboxylate Example 3F (14.22 g, 53.2 mmol) and pyridine (21.51 mL, 266 mmol) were combined in dichloromethane (200 mL) at 10-15° C. to give a yellow solution. Methanesulfonyl chloride (4.56 mL, 58.5 mmol) was added dropwise to give a deep red/purple solution. The reaction mixture was stirred for 16 hours, concentrated, and the residue was partitioned between ethyl acetate and 1 M aqueous HCl. The ethyl acetate layer was washed with water and brine, dried over anhydrous $Na_2SO_4$, filtered and concentrated. The residue was triturated in 9:1 hexane/ethyl acetate, and the solid was collected by filtration and dried to give the title compound (16.4 g, 89%).

Example 3H methyl 6-[(4-methoxybenzyl)(methylsulfonyl) amino]-2-phenyl-1-benzofuran-3-carboxylate Example 3G (16.4 g, 47.5 mmol), 1-(bromomethyl)-4-methoxybenzene (12 g, 59.7 mmol), and potassium carbonate (8.53 g, 61.7 mmol) were combined in N,N-dimethylformamide (120 mL) to give an orange suspension. The reaction mixture was heated under nitrogen for 16 hours at 50° C. The reaction mixture was cooled and partitioned between 700 mL of ethyl acetate and 100 mL of water. The organic layer was washed with $H_2O$ (2×100 mL) and brine (2×100 mL). The organic layer was dried over anhydrous sodium sulfate, treated with decolorizing charcoal, filtered through a silica plug and concentrated to an orange-red oil. The oil was dissolved in a minimal amount of dichloromethane (50 mL) and heated while adding hexane. A small amount of solid began to form upon cooling and standing. More hexane was added to give a volume of about 500 mL. The mixture was stirred for 30 minutes and the granular solid was collected by filtration and dried to give the title compound (19 g 86%).

Example 3I

N-[3-(hydroxymethyl)-2-phenyl-1-benzofuran-6-yl]-N-(4-methoxybenzyl)methanesulfonamide Example 3H (6.8 g, 14.61 mmol) and tetrahydrofuran (40 mL) were combined at 0° C. under nitrogen to give a yellow solution. 1 M $LiAlH_4$ (14.61 mL, 14.61 mmol, tetrahydrofuran) was added dropwise resulting in immediate bubbling. The solution was then stirred at ambient temperature for one hour and quenched by adding 0.6 mL of water dropwise followed by 0.6 mL of 15% aqueous NaOH added dropwise followed by 1.8 mL of water added dropwise. The mixture was stirred for 20 minutes, filtered through diatomaceous earth and concentrated to give the title compound as a yellow oil (6.3 g, 99%).

Example 3J

N-(3-formyl-2-phenyl-1-benzofuran-6-yl)-N-(4-methoxybenzyl)methanesulfonamide

Example 3I (6.39 g, 14.6 mmol), molecular sieves (6.4 g, 14.60 mmol), and N-methylmorpholine N-oxide (2.57 g, 21.90 mmol) were combined in dichloromethane (100 mL) to give a yellow suspension that was cooled in an ice bath. Tetrapropylammonium perruthenate (0.257 g, 0.730 mmol) was added portionwise producing an exotherm. The mixture was stirred at ambient temperature for 1 hour, filtered through diatomaceous earth, and the diatomaceous earth plug was rinsed well with dichloromethane. The filtrate was diluted with ethyl acetate to give a final ratio of 9:1 dichloromethane/ethyl acetate. This solution was first filtered through a 1 inch deep silica plug and then through a 20 g pre-packed silica cartridge to remove dark solids and baseline material. The filtrate was concentrated and the residue was triturated in dichloromethane/ethyl acetate/hexane 1:1:18 (100 mL). The light grey solid was collected by filtration and dried to give the title compound (3.78, 59.5%).

Example 3K

N-[3-(4,5-dihydro-1H-imidazol-2-yl)-2-phenyl-1-benzofuran-6-yl]-N-(4-methoxybenzyl)methanesulfonamide Example 3J (3.78 g, 8.68 mmol) and molecular sieves (4.0 g, 8.68 mmol) were combined in dichloromethane (40 mL) under nitrogen to give a yellow suspension. The mixture was cooled to 0° C. and ethylenediamine (0.638 mL, 9.55 mmol) was added dropwise. The solution was stirred at 0° C. for 30 minutes, N-bromosuccinimide (1.622 g, 9.11 mmol) was added in one portion, and the reaction mixture was stirred for 16 hours with gradual warming to ambient temperature. The suspension was again cooled to 0° C. and additional molecular sieves (4.0 g, 8.68 mmol) and ethylenediamine (0.638 mL, 9.55 mmol) were added. The solution was stirred at 0° C. for 30 minutes, whereupon N-bromosuccinimide (NHS, 1.622 g, 9.11 mmol) was added in one portion and the resultant mixture was stirred for 8 hours with gradual warming to room temperature. The reaction mixture was cooled to 0° C. and an additional 0.25 mole equivalents of ethylenediamine was added followed by stirring for 30 minutes and then the subsequent addition of 0.25 mole equivalents of N-bromosuccinimide. This mixture was stirred for 16 hours at ambient temperature. The reaction mixture was diluted with dichloromethane and filtered through diatomaceous earth. The filtrate was washed with saturated sodium bicarbonate and brine, dried with sodium sulfate, filtered and concentrated in vacuo leaving a foamy brown residue. The residue was purified with silica gel eluting with methanol/dichloromethane gradient (2% to 10%) to give a brown solid as the title compound (4.3 g, 99%).

Example 3L

N-[3-(1H-imidazol-2-yl)-2-phenyl-1-benzofuran-6-yl]-N-(4-methoxybenzyl)methanesulfonamide Example 3K (0.80 g, 1.682 mmol), iodobenzene diacetate (0.596 g, 1.850 mmol), potassium carbonate (0.465 g, 3.36 mmol) and dimethyl sulfoxide (10 mL) were combined. The mixture was purged with nitrogen for 5 minutes and stirred at room temperature for 3 hours. The mixture was partitioned between water and ethyl acetate. The organic layer was washed with brine twice, dried over anhydrous sodium sulfate, filtered and concentrated in vacuo leaving a crude solid. The residue was triturated with ethyl acetate/hexane to give a tan solid as the title compound (0.72 g, 91%). $^1$H NMR (300 MHz, DMSO-$d_6$) δ ppm 3.13 (s, 3H) 3.66 (s, 3H) 4.87 (s, 2H) 6.81 (d, J=8.82 Hz, 2H) 7.19 (m, 3H) 7.30 (m, 2H) 7.46 (m, 3H) 7.52 (d, J=8.46 Hz, 1H) 7.76 (d, J=1.84 Hz, 1H) 7.84 (dd, J=7.72, 1.84 Hz, 2H) 12.38 (s, 1H); MS (DCI+) m/z 474 $(M+H)^+$.

Example 3M

N-[3-(1H-imidazol-2-yl)-2-phenyl-1-benzofuran-6-yl]methanesulfonamide

Example 3L (720 mg, 1.520 mmol) was combined with 4 M hydrogen chloride in dioxane (10 mL, 40.0 mmol). The mixture was stirred at room temperature overnight. The volatiles were removed in vacuo, and the residue was mixed with methanol and concentrated twice. The residue was triturated with dichloromethane to give the hydrochloric acid salt of the title compound as a tan solid (0.565 g, 95%). MS (DCI+) m/z 354 $(M+H)^+$.

Example 3N

N-[(2-bromo-1,3-thiazol-5-yl)methyl]-N-[3-(1H-imidazol-2-yl)-2-phenyl-1-benzofuran-6-yl]methanesulfonamide Example 3M (1.03 g, 2.64 mmol) and potassium carbonate (0.767 g, 5.55 mmol) were combined in N,N-dimethylformamide (20 mL). The mixture was stirred at room temperature for 30 minutes. Then Example 3B (0.679 g, 2.64 mmol) was added and stirring was continued at room temperature overnight. The mixture was partitioned between water and ethyl acetate. The organic layer was washed with brine, dried with sodium sulfate, filtered and concentrated. The residue was purified with silica gel chromatography eluting with methanol/dichloromethane (2% methanol) to give the title compound as a solid (1.15 g, 81%). $^1$H NMR (300 MHz, DMSO-d$_6$) δ ppm 3.17 (s, 3H) 5.17 (s, 2H) 7.27 (m, 3H) 7.48 (m, 4H) 7.61 (d, J=8.46 Hz, 1H) 7.85 (m, 3H) 12.41 (s, 1H); MS (DCI+) m/z 529, 531 (M+H)$^+$.

Example 3O

N-{[2-(1H-benzimidazol-6-yl)-1,3-thiazol-5-yl]methyl}-N-[3-(1H-imidazol-2-yl)-2-phenyl-1-benzofuran-6-yl]methanesulfonamide In a 5 mL microwave tube were combined Example 3N (106 mg, 0.2 mmol), tert-butyl 6-(4,4,5,5-tetramethyl-1,3,2-dioxaborolan-2-yl)-1H-benzo[d]imidazole-1-carboxylate (138 mg, 0.400 mmol), 1,1'-bis(di-tert-butylphosphino)ferrocene palladium dichloride (13.03 mg, 0.020 mmol) and potassium phosphate (170 mg, 0.800 mmol) in tetrahydrofuran (3.0 mL) and water (1.0 mL). The mixture was purged with nitrogen for 5 minutes and microwaved (Personal Chemistry (Biotage), Emrys Creator, 300 W maximum) at 100° C. for 3 hours. The mixture was partitioned between water and ethyl acetate. The organic layer was washed with brine, dried with sodium sulfate, and filtered. The filtrate was treated with 3-mercaptopropyl functionalized silica gel, filtered and concentrated. The residue was purified with silica gel eluting with methanol/dichloromethane (2% to 6% methanol) to give a solid. The solid was triturated with ethyl acetate to give the title compound as a yellow solid (10 mg, 8%). $^1$H NMR (300 MHz, DMSO-d$_6$) δ ppm 3.19 (s, 3H) 5.23 (s, 2H) 7.25 (s, br, 2H) 7.38 (dd, J=8.46, 1.84 Hz, 1H) 7.46 (m, 3H) 7.66 (m, 4H) 7.87 (m, 3H) 8.06 (s, 1H) 8.30 (s, 1H) 12.39 (s, 1H) 12.64 (s, 1H); MS (DCI+) m/z 567 (M+H)$^+$.

Example 4

N-[5-cyclopropyl-2-(4-fluorophenyl)-3-(1H-imidazol-2-yl)-1-benzofuran-6-yl]-N-(3-methylbutyl)methanesulfonamide In a 2 mL microwave tube was added Example 1O (61.7 mg, 0.15 mmol), 1-iodo-3-methylbutane (0.022 mL, 0.165 mmol), and potassium carbonate (22.80 mg, 0.165 mmol) in N,N-dimethylacetamide (0.4 mL) to give a brown solution. The reaction mixture was stirred at ambient temperature for 24 hours. The reaction mixture was diluted with ethyl acetate and washed with brine (3×20 mL), dried (Na$_2$SO$_4$), filtered and concentrated. The crude material was flash chromatographed on an Isco 12 g silica cartridge eluting with 2% methanol in dichloromethane to give the title compound as a pinkish powder (42 mg, 56%). $^1$H NMR (300 MHz, DMSO-d$_6$) δ ppm 0.44-0.61 (m, 1H) 0.83 (dd, J=6.62, 3.31 Hz, 7H) 0.95-1.03 (m, 2H) 1.20-1.48 (m, 2H) 1.55-1.70 (m, 1H) 2.32-2.46 (m, 1H) 3.14 (s, 3H) 3.57-3.83 (m, 2H) 7.06 (s, 1H) 7.29-7.39 (m, 3H) 7.87 (s, 1H) 8.01 (dd, J=9.19, 5.52 Hz, 2H) 12.43 (s, 1H); MS (ESI+) m/z 482 (M+H)$^+$, (ESI−) m/z 480 (M−H)$^−$.

Example 5

N-[5-cyclopropyl-2-(4-fluorophenyl)-3-(1H-imidazol-2-yl)-1-benzofuran-6-yl]-N-(4-hydroxybutyl)methanesulfonamide Example 5A methyl 4-{[5-cyclopropyl-2-(4-fluorophenyl)-3-(1H-imidazol-2-yl)-1-benzofuran-6-yl](methylsulfonyl)amino}butanoate (ACD v12)

In a 20 mL microwave tube under nitrogen were combined Example 1O (3 g, 7.29 mmol), sodium iodide (1.203 g, 8.01 mmol), and potassium carbonate (1.11 g, 8.01 mmol) in dimethyl sulfoxide (30 mL) to give a yellow solution. The reaction mixture was stirred for ten minutes and ethyl 4-bromobutyrate (1.1 mL, 7.65 mmol) was added dropwise. The reaction mixture in the sealed tube was stirred at ambient temperature for 72 hours. LCMS indicated the reaction was complete. The reaction mixture was partitioned between ethyl acetate and water. The aqueous layer was extracted with ethyl acetate (3×). The combined organic washes were washed with water and brine, dried (Na$_2$SO$_4$), filtered and concentrated. The crude material was absorbed onto silica and flash chromatographed on an Isco 80 g silica cartridge eluting with dichloromethane to 4.5% methanol in dichloromethane to give the desired material as a light tan foam. The material was triturated in 14:1 hexane/ethyl acetate to give the title compound as a tan powder (3.6 g, 94%). $^1$H NMR (300 MHz, DMSO-d$_6$) δ ppm 0.52 (m, 1H) 0.87 (m, 1H) 0.99 (m, 2H) 1.69 (m, 2H) 2.40 (m, 3H) 3.15 (s, 3H) 3.56 (s, 3H) 3.71 (m, 2H) 7.08 (s, 1H) 7.19 (s, 1H) 7.34 (m, 3H) 7.87 (s, 1H) 8.03 (m, 2H) 12.42 (s, 1H).

Example 5B

N-[5-cyclopropyl-2-(4-fluorophenyl)-3-(1H-imidazol-2-yl)-1-benzofuran-6-yl]-N-(4-hydroxybutyl)methanesulfonamide Example 5A (1.50 g, 2.85 mmol) was dissolved in tetrahydrofuran (40 mL) to give a yellow solution which was cooled to 10° C. under nitrogen. LiAlH$_4$ (4.00 mL, 4.00 mmol, tetrahydrofuran) was added at a fast drip producing bubbling and the slow formation of a thick precipitate. The mixture was stirred for two hours at 25° C. LCMS indicated the reaction was 50% complete. The reaction mixture was carefully heated at 35° C. for two hours. LCMS indicated complete reaction. The mixture was cooled and quenched by adding dropwise 152 μL of water, 152 μL of 15% NaOH and 460 μL of water. The mixture was stirred for 15 minutes, and then the mixture was filtered through a plug of diatomaceous earth. The diatomaceous earth pad was rinsed repeatedly with tetrahydrofuran. The tetrahydrofuran filtrate was concentrated to a cream colored foam that was triturated in 10:1 hexane/ethyl acetate to give the title compound as a light pink powder that was collected and dried (1.33 g, 94%). $^1$H NMR (300 MHz, DMSO-d$_6$) δ ppm 0.50-0.62 (m, 1H) 0.78-0.90 (m, 1H) 0.94-1.05 (m, 2H) 1.38-1.54 (m, 4H) 2.33-2.43 (m, 1H) 3.14 (s, 3H) 3.34-3.40 (m, 2H) 3.60-3.75 (m, 2H) 4.37 (t, J=4.96 Hz, 1H) 7.07 (s, 1H) 7.18 (s, 1H) 7.29-7.38 (m, 3H) 7.85 (s, 1H) 7.98-8.06 (m, 2H) 12.42 (s, 1H); MS (ESI+) m/z 484 (M+H)$^+$, (ESI−) m/z 482 (M−H)$^−$.

Example 6

N-[5-cyclopropyl-2-(4-fluorophenyl)-3-(1H-imidazol-2-yl)-1-benzofuran-6-yl]-N-[4-(methylsulfonyl)butyl]methanesulfonamide

Example 6A 4-(methylsulfonyl)butan-1-ol 4-(Methylthio)butan-1-ol (721 mg, 6.0 mmol) was dissolved in methanol (15 mL) and cooled to 0° C. in an ice bath. $2KHSO_5 \cdot KHSO_4 \cdot K_2SO_4$ (4057 mg, 6.60 mmol), dissolved in water (15 mL), was added dropwise over a 10 minute period. Upon completion of addition, the reaction mixture was removed from the ice bath and warmed to room temperature and stirred for one hour. The reaction mixture was diluted with water (15 mL) and extracted with ethyl acetate (50 mL). The aqueous layer was concentrated to dryness, and the residue was diluted with dichloromethane, stirred 30 minutes and filtered. The filtrate was concentrated to give the title compound as a clear oil (825 mg, 90%).

Example 6B 4-(methylsulfonyl)butyl 4-methylbenzenesulfonate

Example 6A (820 mg, 5.39 mmol) and triethylamine (2.253 mL, 16.16 mmol) were combined in dichloromethane (50 mL). The reaction mixture was cooled to 0° C. in an ice bath and p-toluenesulfonylchloride (1232 mg, 6.46 mmol) was added. The ice bath was removed, and the reaction mixture was warmed to room temperature and stirred for 64 hours. The mixture was partitioned between dichloromethane and 1 M aqueous HCl. The organic layer was washed with brine, dried with sodium sulfate, filtered and concentrated. The residue was purified with silica gel chromatography eluting with ethyl acetate/hexane (20% to 50%) to give the title compound as a clear oil (845 mg, 51%). MS (ESI+) m/z 323.9 $(M+NH_4)^+$.

Example 6C

N-[5-cyclopropyl-2-(4-fluorophenyl)-3-(1H-imidazol-2-yl)-1-benzofuran-6-yl]-N-[4-(methylsulfonyl)butyl]methanesulfonamide In a 20 mL microwave tube were combined Example 1O (411 mg, 1.0 mmol), Example 6B (337 mg, 1.100 mmol), potassium carbonate (166 mg, 1.200 mmol) and dimethyl sulfoxide (6.0 mL). The mixture was heated in an oil bath at 50° C. for 24 hours. Additional Example 6B (0.122 g, 0.4 mmol) and additional potassium carbonate (55 mg, 0.4 mmol) were added and the resultant mixture was heated at 50° C. for another 16 hours. The reaction mixture was partitioned between ethyl acetate and water. The organic layer was washed with brine twice, dried with sodium sulfate, filtered and concentrated. The residue was purified with silica gel eluting with 20% to 50% ethyl acetate/dichloromethane to give the title compound as a white solid (237 mg, 42%). $^1$H NMR (500 MHz, DMSO-$d_6$) δ ppm 0.55 (m, 1H) 0.86 (m, 1H) 1.01 (m, 1H) 1.57 (m, 2H) 1.75 (m, 2H) 2.39 (m, 1H) 2.91 (s, 3H) 3.09 (m, 2H) 3.16 (s, 3H) 3.71 (m, 2H) 7.08 (s, 1H) 7.19 (s, 1H) 7.35 (m, 3H) 7.87 (s, 1H) 8.00 (m, 2H) 12.42 (s, 1H); MS (ESI+) m/z 546 $(M+H)^+$.

Example 7

N-[5-cyclopropyl-2-(4-fluorophenyl)-3-(1H-imidazol-2-yl)-1-benzofuran-6-yl]-N-[3-(3-hydroxy-1,2-oxazol-5-yl)propyl]methanesulfonamide

Example 7A methyl 3-(benzyloxy)isoxazole-5-carboxylate

Methyl 3-hydroxyisoxazole-5-carboxylate (5.18 g, 36.2 mmol) was dissolved in acetone (90 mL) and treated with potassium carbonate (10.21 g, 73.8 mmol) at reflux for 1 hour. At that time, benzyl bromide (6.5 mL, 54.3 mmol) was added, and the mixture was heated at reflux for an additional 3 hours. The reaction mixture was removed from the oil bath and stirred at room temperature for 18 hours. The mixture was filtered and concentrated in vacuo leaving a yellow oil. The oil was purified by silica gel chromatography eluting with hexane/ethyl acetate (3:1) which gave the title compound as a light yellow solid (5.0 g, 59%).

Example 7B

[3-(benzyloxy)-1,2-oxazol-5-yl]methanol

Example 7A (0.52 g, 2.23 mmol) was dissolved in methanol (25 mL) and treated with solid sodium borohydride (0.110 g, 2.90 mmol). The solution began foaming which subsided approximately 10 minutes later. The reaction mixture was stirred at room temperature for 20 hours. Methanol (50 mL) and 1 N aqueous HCl (100 mL) were then added to the mixture which was subsequently stirred for 2 hours at room temperature. The reaction mixture was concentrated in vacuo. The aqueous layer was extracted with dichloromethane (3×100 mL). The combined organic washes were dried over anhydrous $Na_2SO_4$(s), filtered and concentrated in vacuo leaving the title compound as a clear oil (0.4 g, 87%).

Example 7C 3-(benzyloxy)-1,2-oxazole-5-carbaldehyde

Example 7B (0.45 g, 2.19 mmol) was dissolved in dichloromethane and treated with solid pyridinium dichromate (PDC, 1.24 g, 3.3 mmol). The resulting slurry was stirred at room temperature for 16 hours and then filtered through diatomaceous earth eluting with dichloromethane (3×75 mL). The organic layer was washed with 1 N aqueous HCl (2×50 mL) and 10% aqueous NaCl (100 mL), dried over anhydrous $Na_2SO_4$(s), filtered, and concentrated in vacuo leaving a brown oil. The oil was purified by silica gel chromatography eluting with a gradient of hexane/ethyl acetate (95/5 to 70/30) to give the title compound as a tan solid (0.3 g, 67%).

Example 7D ethyl (2E)-3-[3-(benzyloxy)-1,2-oxazol-5-yl]acrylate

Sodium hydride (46 mg, 1.83 mmol, 95%) was added to tetrahydrofuran (5 mL) and the resulting slurry was treated dropwise to minimize foaming with triethyl phosphonoacetate (0.321 mL, 1.602 mmol) dissolved in tetrahydrofuran (5 mL). The resulting mixture was stirred for one hour at room temperature. At that time, Example 7C (0.31 g, 1.526 mmol) dissolved in tetrahydrofuran (5 mL) was added dropwise, and the resulting solution was stirred at room temperature for 18 hours. The reaction mixture was treated with aqueous saturated NH$_4$Cl (15 mL), the layers were separated, and the organic portion was concentrated in vacuo to an oily residue. The residue was taken up in dichloromethane (50 mL), washed with water and 10% aqueous NaCl, and dried over anhydrous Na$_2$SO$_4$(s). The solution was filtered and the filtrate was concentrated in vacuo leaving a clear oil that solidified upon standing to give the title compound as a white waxy solid (0.38 g, 91%).

Example 7E

3-[3-(benzyloxy)-1,2-oxazol-5-yl]propan-1-ol and (2E)-3-[3-(benzyloxy)-1,2-oxazol-5-yl]prop-2-en-1-ol Lithium borohydride (15 mg, 0.626 mmol) was added in portions under an atmosphere of nitrogen to a solution of Example 7D (114 mg, 0.42 mmol) in tetrahydrofuran (3 mL). The reaction mixture was stirred for 4 hours at room temperature. Another portion of lithium borohydride (9.5 mg, 0.396 mmol) was added, and the reaction mixture was stirred at room temperature for an additional 18 hours. The reaction mixture was quenched by the addition of 10% aqueous HCl and was extracted with ethyl acetate (2×50 mL). The combined organic extracts were washed with water and brine, dried over anhydrous magnesium sulfate and filtered. The filtrate was concentrated in vacuo leaving the title compounds as a 70:30 mixture as a clear oil (0.1032 g).

Example 7F

3-[3-(benzyloxy)-1,2-oxazol-5-yl]propyl 4-methylbenzenesulfonate

The alcohol(s) (~70:30 mixture, 0.10 g, 0.446 mmol) prepared in Example 7E were dissolved in pyridine (2 mL) and placed in an ice bath. p-Toluenesulfonyl chloride (88 mg, 0.464) was added in portions over 3.5 minutes. The resulting light yellow solution was stirred in the ice bath for 24 hours. The reaction mixture was then partitioned between water (20 mL) and dichloromethane (30 mL). The aqueous layer was extracted twice more with dichloromethane. The combined organic extracts were washed with 10% aqueous HCl, water, and brine and dried over anhydrous magnesium sulfate. The drying agent was removed by filtration, and the filtrate was concentrated in vacuo leaving a clear oil. The oil was purified on silica gel with a gradient of hexane:ethyl acetate (98:2 to 90:10) giving the title compound as a clear oil (24 mg, 23%).

Example 7G

N-{3-[3-(benzyloxy)-1,2-oxazol-5-yl]propyl}-N-[5-cyclopropyl-2-(4-fluorophenyl)-3-(1H-imidazol-2-yl)-1-benzofuran-6-yl]methanesulfonamide Example 1O (21 mg, 0.050 mmol), Example 7F (21.5 mg, 0.055 mmol), and potassium carbonate (16.8 mg, 0.122 mmol) were combined in dimethyl sulfoxide (1 mL) and heated at 50° C. for 20 hours. Then the reaction mixture was partitioned between ethyl acetate and water. The aqueous layer was extracted twice more with ethyl acetate. The combined organic extracts were washed with water and dried over anhydrous magnesium sulfate. The drying agent was removed by filtration, and the filtrate was concentrated in vacuo leaving a yellow oil. The oil was purified on silica gel with a gradient of hexane:ethyl acetate (10:1 to 1:1) producing the title compound as a white solid (17.3 mg, 52%).

Example 7H

N-[5-cyclopropyl-2-(4-fluorophenyl)-3-(1H-imidazol-2-yl)-1-benzofuran-6-yl]-N-[3-(3-hydroxy-1,2-oxazol-5-yl)propyl]methanesulfonamide Example 7G (173 mg, 0.028 mmol) was dissolved in a 2:1 mixture of methanol:tetrahydrofuran (3 mL) and was treated with 5% Pd on barium sulfate (1105 mg, 0.00519 mmol). The resulting slurry was hydrogenated for 24 hours at atmospheric pressure and room temperature. The reaction mixture was filtered to remove catalyst, and the filtrate was concentrated in vacuo leaving a yellow oil. The oil was purified by reverse phase HPLC [Samples were purified by preparative HPLC on a Phenomenex® Luna® C8(2) 5 um 100 Å AXIA™ column (30 mm×75 mm). A gradient of acetonitrile (A) and 0.1% trifluoroacetic acid in water (B) was used, at a flow rate of 50 mL/minute (0-0.5 minutes 10% A, 0.5-7.0 minute linear gradient 10-95% A, 7.0-10.0 minutes 95% A, 10.0-12.0 minutes linear gradient 95-10% A). Samples were injected in 1.5 mL DMSO:CH$_3$OH (1:1). A custom purification system was used, consisting of the following modules: Waters LC4000 preparative pump; Waters 996 diode-array detector; Waters 717+ autosampler; Waters SAT/IN module, Alltech Varex III evaporative light-scattering detector; Gilson 506C interface box; and two Gilson FC204 fraction collectors. The system was controlled using Waters Millennium32 software, automated using an Abbott developed Visual Basic application for fraction collector control and fraction tracking. Fractions were collected based upon UV signal threshold and selected fractions subsequently analyzed by flow injection analysis mass spectrometry using positive APCI ionization on a Finnigan LCQ using 70:30 CH$_3$OH:10 mM NH$_4$OH(aq) at a flow rate of 0.8 mL/minute. Loop-injection mass spectra were acquired using a Finnigan LCQ running LCQ Navigator 1.2 software and a Gilson 215 liquid handler for fraction injection controlled by an Abbott developed Visual Basic application) producing the title compound as a white solid (4.9 mg, 33%). $^1$H NMR (500 MHz, DMSO-d$_6$) δ ppm 0.46-0.60 (m, 1H) 0.83-0.92 (m, 1H) 0.96-1.04 (m, 2H) 1.72-1.80 (m, 2H) 2.34-2.43 (m, 1H) 2.69 (q, J=7.27 Hz, 2H) 3.16 (s, 3H) 3.63-3.82 (m, 2H) 5.73 (s, 1H) 7.08 (s, 1H) 7.17-7.20 (m, 1H) 7.29-7.39 (m, 3H) 7.89 (s, 1H) 7.99-8.06 (m, 2H) 11.02 (s, 1H) 12.41 (s, 1H); MS (ESI+) m/z 537.1 (M+H)$^+$, 1073.2 (2M+H)$^+$, (ESI−) m/z 535.2 (M−H)$^−$, 1071.3 (2M−H)$^−$.

Example 8

N-[5-cyclopropyl-3-(5,6-dihydro-4H-1,2,4-oxadiazin-3-yl)-2-(4-fluorophenyl)-1-benzofuran-6-yl]-N-(4-hydroxybutyl)methanesulfonamide

Example 8A

N-{5-cyclopropyl-2-(4-fluorophenyl)-3-[(hydroxyimino)methyl]-1-benzofuran-6-yl}-N-(4-methoxybenzyl)methanesulfonamide Example 1L (1.234 g, 2.5 mmol), hydroxylamine hydrochloride (0.608 g, 8.75 mmol), and sodium carbonate (0.477 g, 4.50 mmol) were combined in ethanol (30 mL) and water (10 mL) to give a white suspension. The mixture was heated at reflux for two hours, cooled, concentrated, diluted with water and extracted with ethyl acetate (3×50 mL). The extracts were combined, washed with brine, dried (Na$_2$SO$_4$), filtered and concentrated to give the title compound as a light yellow foam (1.3 g, quantitative yield).

Example 8B

N-[3-cyano-5-cyclopropyl-2-(4-fluorophenyl)-1-benzofuran-6-yl]-N-(4-methoxybenzyl)methanesulfonamide A mixture of Example 8A (1.3 g, 2.56 mmol) in acetic anhydride (40 mL) was heated at 140° C. for 16 hours, cooled and concentrated. The residue was dissolved in ethyl acetate, washed with water and brine, dried (Na$_2$SO$_4$), filtered and concentrated. The residue was flash chromatographed on an Isco 12 g silica cartridge eluting with hexane followed by 3:2 hexane/ethyl acetate to give the title compound as a white foam (1.23 g, 98%).

Example 8C 5-cyclopropyl-2-(4-fluorophenyl)-N'-hydroxy-6-[(4-methoxybenzyl)(methylsulfonyl)amino]-1-benzofuran-3-carboximidamide To a 20 mL microwave tube was added the product from Example 8B (340 mg, 0.693 mmol) and hydroxylamine (50 weight % in water, 6.0 mL, 102 mmol) in ethanol (6 mL). The vial was sealed and heated in a microwave reactor (Personal Chemistry (Biotage), Emrys Creator, 300 W maximum) at 140° C. for 30 minutes. The mixture was partitioned between ethyl acetate and water. The organic layer was washed with brine, dried over sodium sulfate, filtered and concentrated to give the title compound which was used without purification (363 mg, quantitative yield). MS (ESI+) m/z 524 (M+H)$^+$.

Example 8D

N-[5-cyclopropyl-2-(4-fluorophenyl)-3-(5-oxo-4,5-dihydro-1,2,4-oxadiazol-3-yl)-1-benzofuran-6-yl]-N-(4-methoxybenzyl)methanesulfonamide A mixture of Example 8C (2.62 g, 5.0 mmol), carbonyl diimidazole (0.973 g, 6.00 mmol), and 1,8-diazabicyclo[5.4.0]undec-7-ene (0.829 mL, 5.50 mmol) in dioxane (20 mL) was refluxed for one hour, cooled and partitioned between ethyl acetate and 1 M aqueous HCl. The organic layer was washed with brine, dried with sodium sulfate, filtered and concentrated. The residue was triturated with ethyl acetate/hexane (1:3) to give the title compound as a solid (2.19 g, 80%).

Example 8E

N-{3-[4-(2-chloroethyl)-5-oxo-4,5-dihydro-1,2,4-oxadiazol-3-yl]-5-cyclopropyl-2-(4-fluorophenyl)-1-benzofuran-6-yl}-N-(4-methoxybenzyl)methanesulfonamide A mixture of Example 8D (3.20 g, 5.82 mmol), 1-bromo-2-chloroethane (2.413 mL, 29.1 mmol) and 1,8-diazabicyclo[5.4.0]undec-7-ene (1.843 mL, 12.23 mmol) in N,N-dimethylformamide (30 mL) was heated at 100° C. for 2 hours. Additional 1-bromo-2-chloroethane (2.413 mL, 29.1 mmol) and 1,8-diazabicyclo[5.4.0]undec-7-ene (1.843 mL, 12.23 mmol) were added and the mixture was heated at 100° C. for another 1 hour. The mixture was cooled and partitioned between ethyl acetate and water. The organic layer was washed repeatedly with brine, dried with sodium sulfate, filtered and concentrated to give the title compound as a solid which was used without purification (3.55 g, quantitative yield).

Example 8F

N-[5-cyclopropyl-3-(5,6-dihydro-4H-1,2,4-oxadiazin-3-yl)-2-(4-fluorophenyl)-1-benzofuran-6-yl]-N-(4-methoxybenzyl)methanesulfonamide A mixture of Example 8E (3.54 g, 5.78 mmol) and 1.0 M aqueous sodium hydroxide (14.46 mL, 14.46 mmol) in ethanol (50 mL) was refluxed for 2 hours, cooled, and partitioned between water and ethyl acetate. The organic layer was washed with brine, dried with sodium sulfate, filtered and concentrated. The residue was purified on silica gel eluting with methanol (2% to 4%) in dichloromethane to give the title compound as a solid (2.13 g, 67%). $^1$H NMR (500 MHz, DMSO-d$_6$) δ ppm 0.16-0.27 (m, 1H) 0.65-0.82 (m, 2H) 0.85-1.00 (m, 1H) 2.15-2.25 (m, 1H) 3.20 (s, 3H) 3.66-3.69 (m, 3H) 4.54 (s, 2H) 4.69-4.91 (m, 2H) 6.77-6.82 (m, 2H) 7.03 (s, 1H) 7.10-7.16 (m, 2H) 7.37-7.45 (m, 2H) 7.80 (s, 1H) 7.83-7.91 (m, 2H) 11.32 (s, 1H); MS (ESI+) m/z 550.1 (M+H)$^+$.

Example 8G

N-[5-cyclopropyl-3-(5,6-dihydro-4H-1,2,4-oxadiazin-3-yl)-2-(4-fluorophenyl)-1-benzofuran-6-yl]methanesulfonamide Example 8F (2.12 g, 3.86 mmol) was treated with trifluoroacetic acid (8 mL) in dichloromethane (12 mL), stirred for 2 hours, and concentrated. The residue was partitioned between saturated sodium bicarbonate and ethyl acetate. The organic layer was washed with brine producing a solid at the organic/aqueous interface that was collected and dried to give the title compound. The filtrate layers were separated. The organic layer was dried with sodium sulfate, filtered and concentrated. The residue was triturated with a minimal volume of 1:1 ethyl acetate/hexane to give additional title compound that was collected by filtration, dried and combined with the previously isolated solid (1.04 g, 62.8% yield). $^1$H NMR (500 MHz, DMSO-d$_6$) δ ppm 0.68 (m, 2H) 0.99 (m, 2H) 2.30 (m, 1H) 3.05 (s, 3H) 3.44 (m, 2H) 3.99 (t, J=4.58 Hz, 2H) 7.15 (s, 1H) 7.20 (t, J=3.13 Hz, 1H) 7.38 (m, 2H) 7.59 (s, 1H) 7.95 (m, 2H) 9.29 (s, 1H); MS (ESI+) m/z 430 (M+H)$^+$.

Example 8H

N-(4-{[tert-butyl(dimethyl)silyl]oxy}butyl)-N-[5-cyclopropyl-3-(5,6-dihydro-4H-1,2,4-oxadiazin-3-yl)-2-(4-fluorophenyl)-1-benzofuran-6-yl]methanesulfonamide A mixture of Example 8G (51.5 mg, 0.12 mmol), tert-butyl (4-iodobutoxy)dimethylsilane (0.034 mL, 0.132 mmol) and potassium carbonate (19.90 mg, 0.144 mmol) in dimethyl sulfoxide (1 mL) was stirred for 24 hours and then partitioned between water and ethyl acetate. The organic layer was washed with brine, dried with sodium sulfate, filtered and concentrated. The residue was purified by chromatography on silica gel eluting with 0.5% to 4% methanol in dichlo-

Example 8I

N-[5-cyclopropyl-3-(5,6-dihydro-4H-1,2,4-oxadiazin-3-yl)-2-(4-fluorophenyl)-1-benzofuran-6-yl]-N-(4-hydroxybutyl)methanesulfonamide Example 8H (67 mg, 0.109 mmol) in tetrahydrofuran (2 mL) was treated with 1.0 M tetrabutylammonium fluoride in tetrahydrofuran (0.326 mL, 0.326 mmol), stirred for 2 hours and partitioned between water and ethyl acetate. The organic layer was washed with brine, dried with sodium sulfate, filtered and concentrated. The residue was purified by chromatography on silica eluting with 1% to 4% methanol in dichloromethane to give the title compound (38 mg, 68.9%). $^1$H NMR (500 MHz, DMSO-$d_6$) δ ppm 0.56 (m, 1H) 0.87 (m, 1H) 1.00 (m, 2H) 1.44 (m, 4H) 2.39 (m, 1H) 3.12 (s, 3H) 3.32 (m, 2H) 3.45 (m, 2H) 3.67 (m, 2H) 3.99 (t, J=4.50 Hz, 2H) 4.37 (t, J=4.96 Hz, 1H) 7.06 (s, 1H) 7.24 (t, J=3.13 Hz, 1H) 7.42 (m, 2H) 7.82 (s, 1H) 8.00 (m, 2H); MS (ESI+) m/z 502 (M+H)$^+$.

Example 9

N-[5-cyclopropyl-3-(5,6-dihydro-4H-1,2,4-oxadiazin-3-yl)-2-(4-fluorophenyl)-1-benzofuran-6-yl]-N-[2-(methylsulfonyl)ethyl]methanesulfonamide

Example 9A

N-[5-cyclopropyl-3-(5,6-dihydro-4H-1,2,4-oxadiazin-3-yl)-2-(4-fluorophenyl)-1-benzofuran-6-yl]-N-[2-(methylthio)ethyl]methanesulfonamide A mixture of Example 8G (129 mg, 0.30 mmol), (2-bromoethyl)(methyl)sulfane (0.035 mL, 0.360 mmol), potassium carbonate (53.9 mg, 0.390 mmol) and sodium iodide (58.5 mg, 0.390 mmol) in dimethyl sulfoxide (2 mL) was heated at 50° C. for 16 hours and then partitioned between water and ethyl acetate. The organic layer was washed with brine, dried with sodium sulfate, filtered and concentrated. The residue was purified by chromatography on silica gel eluting with 1% to 4% methanol in dichloromethane to give the title compound as a light colored solid (120 mg, 77%). MS (ESI+) m/z 504 (M+H)$^+$.

Example 9B

N-[5-cyclopropyl-3-(5,6-dihydro-4H-1,2,4-oxadiazin-3-yl)-2-(4-fluorophenyl)-1-benzofuran-6-yl]-N-[2-(methylsulfonyl)ethyl]methanesulfonamide A solution of the product from Example 9A (88 mg, 0.175 mmol) in methanol (4 mL) was cooled to 0° C. and treated with 2 KHSO$_5$.KHSO$_4$.K$_2$SO$_4$ (226 mg, 0.367 mmol) dropwise in water (4 mL). The reaction mixture was warmed to ambient temperature followed by stirring for 2 hours. The mixture was partitioned between water and ethyl acetate. The organic layer was washed with brine, dried with sodium sulfate, filtered and concentrated. The residue was purified by chromatography on silica gel eluting with 1% to 4% methanol in dichloromethane to give a solid. The solid was triturated with a minimal volume of 9:1 hexane/ethyl acetate to give the title compound as a light yellow solid. $^1$H NMR (500 MHz, DMSO-$d_6$) δ ppm 0.54-0.62 (m, 1H) 0.91-0.96 (m, 1H) 0.97-1.02 (m, 1H) 1.03-1.10 (m, 1H) 2.27-2.33 (m, 1H) 3.03 (s, 3H) 3.23 (s, 3H) 3.31-3.37 (m, 1H) 3.42-3.49 (m, 3H) 3.99 (t, J=4.58 Hz, 2H) 4.03-4.18 (m, 2H) 7.12 (s, 1H) 7.23 (t, J=3.20 Hz, 1H) 7.36-7.45 (m, 2H) 7.88 (s, 1H) 7.97-8.04 (m, 2H); MS (ESI+) m/z 536 (M+H)$^+$.

Example 10

N-[5-cyclopropyl-3-(5,6-dihydro-4H-1,2,4-oxadiazin-3-yl)-2-(4-fluorophenyl)-1-benzofuran-6-yl]-N-(3-methylbutyl)methanesulfonamide

Example 10A ethyl 5-cyclopropyl-2-(4-fluorophenyl)-6-(N-isopentylmethylsulfonamido)benzofuran-3-carboxylate To Example 1I (3.0 g, 7.19 mmol) was added potassium carbonate (1.490 g, 10.78 mmol), and 1-iodo-3-methylbutane (1.409 mL, 10.78 mmol) in dimethyl sulfoxide (20.53 mL) to give a yellow suspension. The mixture was stirred under nitrogen for 3 hours and then partitioned between ethyl acetate and water. The organic layer was washed with water and brine, dried (MgSO$_4$), filtered and concentrated. The crude product was flash chromatographed on an Isco 80 g silica cartridge eluting with 3:1 hexane/ethyl acetate to give the title compound (3.38 g, 92%).

Example 10B

N-[5-cyclopropyl-2-(4-fluorophenyl)-3-(hydroxymethyl)-1-benzofuran-6-yl]-N-(3-methylbutyl)methanesulfonamide Example 10A (3.38 g, 6.93 mmol) in tetrahydrofuran (40.8 mL) was treated dropwise with 1.0 M lithium aluminum hydride in tetrahydrofuran (6.93 mL, 6.93 mmol). After stirring for 2 hours, the reaction mixture was carefully quenched by the dropwise addition of water (300 μL), 15% aqueous NaOH (300 μL) and water (900 μL). The mixture was stirred for twenty minutes and filtered through a plug of diatomaceous earth to remove the solids. The diatomaceous earth plug was rinsed repeatedly with ethyl acetate. The filtrate was dried with sodium sulfate, filtered and concentrated to give the title compound as a yellow foam (3.08 g, quantitative yield).

Example 10C

N-[5-cyclopropyl-2-(4-fluorophenyl)-3-formyl-1-benzofuran-6-yl]-N-(3-methylbutyl)methanesulfonamide Example 10B (3.08 g, 6.91 mmol) in dichloromethane (57.6 mL) was treated portion wise with pyridinium dichromate (3.90 g, 10.37 mmol) to give a dark red suspension. The mixture was stirred for 3 hours, filtered through diatomaceous earth to remove the solids, and the diatomaceous earth pad was washed repeatedly with dichloromethane. The dichloromethane filtrate was washed with 1 M aqueous HCl, water, and brine. The organic layer was dried (MgSO$_4$), filtered and concentrated to a brown foam. The crude material was purified by flash chromatography on an Isco 40 g silica cartridge eluting with 5% to 60% ethyl acetate in hexane to give the title compound as a sticky, yellow foam (2.84 g, 93%).

Example 10D

N-{5-cyclopropyl-2-(4-fluorophenyl)-3-[(hydroxyimino)methyl]-1-benzofuran-6-yl}-N-(3-methylbutyl)methanesulfonamide A mixture of Example 10C (2.84 g, 6.40 mmol), hydroxylamine hydrochloride (1.33 g, 19.21 mmol), and sodium carbonate (1.22 g, 11.53 mmol) in ethanol (60 mL) and water (20 mL) was heated at reflux for 2.5 hours, cooled and concentrated. The residue was dissolved in ethyl acetate, and the ethyl acetate layer was washed with water and brine, dried ($Na_2SO_4$), filtered and concentrated to give the title compound as a yellow foam (2.9 g, 99%).

Example 10E

N-[3-cyano-5-cyclopropyl-2-(4-fluorophenyl)-1-benzofuran-6-yl]-N-(3-methylbutyl)methanesulfonamide Example 10D (1.3 g, 2.56 mmol) in acetic anhydride (40 mL) was heated at 135° C. for 16 hours, cooled and concentrated. The residue was dissolved in ethyl acetate, washed with water and brine, dried ($Na_2SO_4$), filtered and concentrated. The residue was flash chromatographed on an Isco 12 g silica cartridge eluting with hexane to 3:2 hexane/ethyl acetate to give the title product as a white foam (2.26 g, 80%).

Example 10F 5-cyclopropyl-2-(4-fluorophenyl)-N-hydroxy-6-[(3-methylbutyl)(methylsulfonyl)amino]-1-benzofuran-3-carboximidamide Example 10E (600 mg, 1.362 mmol) and hydroxylamine (50 weight % in water, 6 mL, 102 mmol) in ethanol (6 mL) were combined in a 20 mL microwave tube, sealed and heated by a microwave reactor (Personal Chemistry (Biotage), Emrys Creator, 300 W maximum) at 140° C. for 30 minutes. The mixture was partitioned between ethyl acetate and water. The organic layer was washed twice with brine, dried ($Na_2SO_4$), filtered and concentrated to give the title compound (610 mg, 95%).

Example 10G

N-[5-cyclopropyl-2-(4-fluorophenyl)-3-(5-oxo-4,5-dihydro-1,2,4-oxadiazol-3-yl)-1-benzofuran-6-yl]-N-(3-methylbutyl)methanesulfonamide A mixture of Example 10F (355 mg, 0.75 mmol), carbonyldiimidazole (146 mg, 0.900 mmol), and 1,8-diazabicyclo[5.4.0]undec-7-ene (0.124 mL, 0.825 mmol) in dioxane (6 mL) was refluxed for 1 hour, cooled and partitioned between ethyl acetate and 1 M aqueous HCl. The organic layer was washed with brine, dried with sodium sulfate, filtered and concentrated. The residue was chromatographed on silica gel eluting with 10-40% ethyl acetate in hexane to give the title compound as a solid (225 mg, 60%). MS (ESI−) m/z 498 (M−H)⁻.

Example 10H

N-{3-[4-(2-chloroethyl)-5-oxo-4,5-dihydro-1,2,4-oxadiazol-3-yl]-5-cyclopropyl-2-(4-fluorophenyl)-1-benzofuran-6-yl}-N-(3-methylbutyl)methanesulfonamide A mixture of Example 10G (188 mg, 0.376 mmol), 1-bromo-2-chloroethane (0.033 mL, 0.395 mmol) and 1,8-diazabicyclo[5.4.0]undec-7-ene (0.062 mL, 0.414 mmol) in N,N-dimethylacetamide (6 mL) was heated in a sealed tube at 100° C. for 16 hours, cooled and concentrated. The residue was chromatographed on silica gel eluting with hexane to 3:1 hexane/ethyl acetate to give the title compound as a solid (64 mg, 30%). MS (ESI+) m/z 579 (M+$NH_4$)⁺.

Example 10I

N-[5-cyclopropyl-3-(5,6-dihydro-4H-1,2,4-oxadiazin-3-yl)-2-(4-fluorophenyl)-1-benzofuran-6-yl]-N-(3-methylbutyl)methanesulfonamide A mixture of Example 10H (61 mg, 0.109 mmol) and 1.0 M sodium hydroxide (0.271 mL, 0.271 mmol) in ethanol (2 mL) was refluxed for 1 hour, cooled and partitioned between water and ethyl acetate. The organic layer was washed with brine, dried with sodium sulfate, filtered and concentrated. The residue was purified by chromatography on silica gel eluting with 1% to 4% methanol in dichloromethane to give the title compound as a solid (26 mg, 47%). $^1$H NMR (500 MHz, DMSO-$d_6$) δ ppm 0.55 (m, 1H) 0.83 (m, 6H) 0.88 (m, 1H) 0.99 (m, 2H) 1.26 (m, 1H) 1.38 (m, 1H) 1.61 (m, 1H) 2.38 (m, 1H) 3.12 (s, 3H) 3.45 (m, 2H) 3.63 (m, 1H) 3.73 (m, 1H) 3.99 (t, J=4.65 Hz, 2H) 7.05 (s, 1H) 7.24 (t, J=3.20 Hz, 1H) 7.40 (m, 2H) 7.83 (s, 1H) 8.00 (m, 2H); MS (ESI+) m/z 500 (M+H)⁺.

Example 11

N-[5-cyclopropyl-2-(4-fluorophenyl)-3-(5-methyl-4,5-dihydro-1,2,4-oxadiazol-3-yl)-1-benzofuran-6-yl]-N-(4-hydroxybutyl)methanesulfonamide

Example 11A

N-[3-cyano-5-cyclopropyl-2-(4-fluorophenyl)-1-benzofuran-6-yl]methanesulfonamide Example 8B (0.92 g, 1.88 mmol) was dissolved in dichloromethane (10 mL), cooled in an ice bath, and treated with trifluoroacetic acid (10 mL). The resulting yellow solution was stirred in the ice bath for 3 hours during which time the reaction turned red. The reaction mixture was concentrated in vacuo to a red oil which was taken up in ethyl acetate (100 mL), washed with 10% aqueous $NaHCO_3$ and 10% aqueous NaCl, dried over anhydrous $Na_2SO_4$, filtered, and concentrated in vacuo to afford the title compound as a light yellow solid (0.65 g, 94%). MS (ESI−) m/z 369 (M−H)⁻.

Example 11B

N-(4-{[tert-butyl(dimethyl)silyl]oxy}butyl)-N-[3-cyano-5-cyclopropyl-2-(4-fluorophenyl)-1-benzofuran-6-yl]methanesulfonamide A mixture of Example 11A (0.1302 g, 0.352 mmol) and potassium carbonate (0.058 g, 0.422 mmol) in acetonitrile (2 mL) was heated at reflux for 30 minutes, then (4-iodobutoxy)-tert-butyldimethylsilane (0.122 g, 0.387 mmol) was added and the resultant mixture was stirred at reflux for 0.5 hour. The reaction mixture became thick so additional acetonitrile (2 mL) and dimethyl sulfoxide (2 mL) were added, and the resultant mixture was stirred at room temperature for 16 hours. The reaction mixture was concentrated in vacuo to a yellow oil that was taken up in ethyl acetate (100 mL) and washed with 1 N aqueous $H_3PO_4$, 10% aqueous $NaHCO_3$, and 10% aqueous NaCl. The organic phase was dried over anhydrous Na$_2$SO$_4$, filtered, and concentrated in vacuo leaving a yellow oil. Purification on a silica gel column (12 g) eluting with a gradient of 10/90 ethyl acetate/hexane to 50/50 ethyl acetate/hexane over 20 minutes afforded the title compound (0.135 g, 69%).

Example 11C

6-[(4-{[tert-butyl(dimethyl)silyl]oxy}butyl)(methylsulfonyl)amino]-5-cyclopropyl-2-(4-fluorophenyl)-N-hydroxy-1-benzofuran-3-carboximidamide To a 20-mL microwave tube was added a solution of Example 11B (0.1346 g, 0.242 mmol) in ethanol (3 mL) followed by hydroxylamine (50 weight % in water, 3 mL, 50.9 mmol). The tube was sealed and the thick slurry was heated in a microwave reactor (Personal Chemistry (Biotage), Emrys Creator, 300 W maximum) for 30 minutes at 140° C. The reaction mixture was concentrated in vacuo to a cloudy solution that was taken up in ethyl acetate (60 mL), washed with 10% aqueous NaCl, dried over anhydrous Na$_2$SO$_4$, filtered, and concentrated in vacuo to afford the title compound as a foamy white solid (0.119 g, 84%).

Example 11D 5-cyclopropyl-2-(4-fluorophenyl)-N-hydroxy-6-[(4-hydroxybutyl)(methylsulfonyl)amino]-1-benzofuran-3-carboximidamide A solution of Example 11C (0.1193 g, 0.202 mmol) in tetrahydrofuran (5 mL) was treated with 1 M tetrabutylammonium fluoride in tetrahydrofuran (0.607 mL, 0.607 mmol), and the resulting yellow solution was stirred at room temperature for 1.5 hours. The reaction mixture was concentrated in vacuo, the yellow oily residue was taken up in dichloromethane (10 mL), filtered, and purified on a silica gel column (12 g) eluting with a gradient of 99.5/0.5 dichloromethane/methanol to 95/5 dichloromethane/methanol over 30 minutes to afford the title compound (0.095 g, 99%).

Example 11E

N-[5-cyclopropyl-2-(4-fluorophenyl)-3-(5-methyl-4,5-dihydro-1,2,4-oxadiazol-3-yl)-1-benzofuran-6-yl]-N-(4-hydroxybutyl)methanesulfonamide A solution of Example 11D (0.10 g, 0.210 mmol) in ethanol (3 mL) and H$_2$O (3 mL) was treated with acetaldehyde (3 mL, 53.1 mmol) and stirred in a sealed microwave tube at room temperature for 73 hours. The solvent was removed in vacuo leaving a cloudy slurry which was dissolved in ethyl acetate (50 mL) and treated with 5% aqueous HCl (5 mL). The mixture was stirred for 30 minutes at room temperature. The aqueous layer was removed and the ethyl acetate layer was washed with 10 mL 10% aqueous NaCl, dried over anhydrous sodium sulfate (solid), filtered. The solvent was removed in vacuo leaving a clear yellow oil. Purification on a silica gel column (4 g) eluting with a gradient of 99.5/0.5 dichloromethane/methanol to 94/6 dichloromethane/methanol over 25 minutes afforded the title compound (0.021 g, 20%). $^1$H NMR (500 MHz, DMSO-d$_6$) δ ppm 0.56 (s, 1H), 0.84 (m, 2H), 1.07 (dd, J=6.3, 4.5 Hz, 2H), 1.37 (dd, J=5.1, 2.1 Hz, 3H), 1.32-1.48 (m, 2H), 2.37 (ddd, J=12.7, 6.9, 5.5 Hz, 4H), 3.13 (s, 3H), 3.66 (m, 2H), 4.36 (t, J=5.1 Hz, 1H), 5.74-5.80 (m, 1H), 7.22 (s, 1H), 7.30 (s, 1H), 7.42 (t, J=8.9 Hz, 2H), 7.86 (s, 1H), 8.02 (dd, J=9.0, 5.4 Hz, 2H); MS (ESI+) m/z 502 (M+H)$^+$, (ESI−) m/z 500 (M−H)$^−$.

Example 12

N-[5-cyclopropyl-2-(4-fluorophenyl)-3-(5-methyl-4,5-dihydro-1,2,4-oxadiazol-3-yl)-1-benzofuran-6-yl]-N-[2-(methylsulfonyl)ethyl]methanesulfonamide Example 12A N-[3-cyano-5-cyclopropyl-2-(4-fluorophenyl)-1-benzofuran-6-yl]-N-[2-(methylthio)ethyl]methanesulfonamide A microwave tube was charged with Example 11A (0.150 g, 0.405 mmol), potassium carbonate (0.112 g, 0.810 mmol), sodium iodide (0.121 g, 0.810 mmol), and N,N-dimethylacetamide (4 mL), and then (2-chloroethyl)(methyl)sulfane (0.062 mL, 0.607 mmol) was added. The tube was sealed and heated in an oil bath at 53° C. for 20 hours. The reaction mixture was partitioned between ethyl acetate (35 mL) and water (20 mL). The aqueous phase was further extracted with ethyl acetate (3×10 mL). The combined organic washes were dried over anhydrous MgSO$_4$, filtered, and concentrated in vacuo. The resulting yellow solid was triturated with diethyl ether (5 mL), and the solid was collected by vacuum filtration. The solid was washed with additional diethyl ether and then dried in vacuo to afford the title compound as a white solid (0.142 g, 79%). MS (ESI−) m/z 443 (M−H)$^−$.

Example 12B

N-[3-cyano-5-cyclopropyl-2-(4-fluorophenyl)-1-benzofuran-6-yl]-N-[2-(methylsulfonyl)ethyl]methanesulfonamide and N-[3-cyano-5-cyclopropyl-2-(4-fluorophenyl)-1-benzofuran-6-yl]-N-[2-(methylsulfinyl)ethyl]methanesulfonamide To a mixture of Example 12A (0.142 g, 0.320 mmol) in methanol (3 mL) cooled to 0-5° C. was slowly added dropwise a solution of 2 KHSO$_5$.KHSO$_4$.K$_2$SO$_4$ (0.216 g, 0.352 mmol) in water (1 mL). The reaction mixture was stirred for 10 minutes in the ice bath, then at room temperature for 22 hours. The reaction was incomplete by analytical LCMS so additional 2 KHSO$_5$.KHSO$_4$.K$_2$SO$_4$ (111 mg) was added in portions, followed by stirring at room temperature for 2.5 hours. Then more 2KHSO$_5$.KHSO$_4$.K$_2$SO$_4$ (245 mg) was added in portions followed by water (1 mL). The reaction mixture was heated at 50° C. for 4 hours. The reaction mixture was cooled to room temperature and partitioned between ethyl acetate and brine. The aqueous phase was further extracted with ethyl acetate (1×). The combined organic extracts were washed with water (2×), dried over anhydrous MgSO$_4$, filtered, and concentrated in vacuo to give a mixture of the title compounds (0.1436 g). MS (ESI+) m/z 494 (M+NH$_4$)$^+$ for sulfone; MS (ESI+) m/z 461 (M+H)$^+$ for sulfoxide.

Example 12C 5-cyclopropyl-2-(4-fluorophenyl)-N'-hydroxy-6-{(methylsulfonyl)[2-(methylsulfonyl)ethyl]amino}-1-benzofuran-3-carboximidamide and 5-cyclopropyl-2-(4-fluorophenyl)-N'-hydroxy-6-{[2-(methylsulfinyl)ethyl](methylsulfonyl)amino}-1-benzofuran-3-carboximidamide A 20-mL microwave tube was charged with Example 12B (sulfone/sulfoxide mixture, 0.0981 g), hydroxylamine (50 weight % in water, 2.04 mL, 24.09 mmol), and absolute ethanol (2 mL). The tube was sealed and heated in a microwave reactor (Personal Chemistry (Biotage), Emrys Creator, 300 W maximum) at 140° C. for 30 minutes. The solution was partitioned between ethyl acetate (35 mL) and brine (15 mL). The organic layer was washed with brine (2×15 mL), dried over anhydrous MgSO$_4$, filtered, and concentrated in vacuo to afford the title compounds (sulfone/sulfoxide mixture) as a waxy white solid (0.1086 g).

Example 12D

N-[5-cyclopropyl-2-(4-fluorophenyl)-3-(5-methyl-4,5-dihydro-1,2,4-oxadiazol-3-yl)-1-benzofuran-6-yl]-N-[2-(methylsulfonyl)ethyl]methanesulfonamide A suspension of Example 12C (sulfone/sulfoxide mixture, 0.105 g) in ethanol (2 mL) and water (2 mL) was treated with acetaldehyde (1.92 mL, 34 mmol), and the reaction mixture was stirred at room temperature for 3 days. Additional acetaldehyde (1 mL) was added and stirring was continued at room temperature for 3 more days. The reaction mixture was partitioned between ethyl acetate (50 mL) and water (50 mL). The organic layer was washed with water (3×25 mL), dried over anhydrous MgSO$_4$, filtered, and concentrated in vacuo. Purification by silica gel flash chromatography eluting with a gradient of 1:10 ethyl acetate/hexane to 1:2 ethyl acetate/hexane, then 2:1 ethyl acetate/hexane containing 2% methanol, followed by 2% methanol/dichloromethane, afforded the title compound (0.0115 g). $^1$H NMR (500 MHz, DMSO-d$_6$) δ ppm 0.58 (dd, J=5.80, 2.90 Hz, 1H), 0.89 (dd, J=9.61, 4.27 Hz, 1H), 0.98-1.14 (m, 2H), 1.38 (t, J=5.42 Hz, 3H), 2.28-2.35 (m, 1H), 3.03 (s, 3H), 3.23 (s, 3H), 3.99-4.20 (m, 2H), 5.73-5.81 (m, 1H), 7.27-7.33 (m, 2H), 7.38-7.47 (m, 2H), 7.92 (s, 1H), 8.02 (dd, J=8.24, 5.49 Hz, 2H); MS (ESI+) m/z 536 (M+H)$^+$; (ESI−) m/z 534 (M−H)$^−$.

Example 13

N-[5-cyclopropyl-2-(4-fluorophenyl)-3-(5-methyl-4,5-dihydro-1,2,4-oxadiazol-3-yl)-1-benzofuran-6-yl]-N-[2-(methylsulfinyl)ethyl]methanesulfonamide Purification of the crude material in Example 12D also afforded the title compound (0.0385 g). $^1$H NMR (DMSO-d$_6$, 500 MHz) δ ppm 0.52-0.58 (m, 1H), 0.84-0.92 (m, 1H), 0.99-1.09 (m, 2H), 1.37 (t, J=5.04 Hz, 3H), 2.35 (d, J=5.34 Hz, 1H), 2.52-2.57 (m, 3H), 2.75-2.99 (m, 2H), 3.20 (d, J=4.12 Hz, 3H), 4.04-4.11 (m, 2H), 5.74-5.79 (m, 1H), 7.23-7.25 (m, 1H), 7.26-7.32 (m, 1H), 7.90 (d, J=1.07 Hz, 1H), 7.98-8.04 (m, 2H); MS (ESI+) m/z 520 (M+H)$^+$; (ESI−) m/z 518 (M−H)$^−$.

Example 14

N-[5-cyclopropyl-2-(4-fluorophenyl)-3-(5-methyl-4,5-dihydro-1,2,4-oxadiazol-3-yl)-1-benzofuran-6-yl]-N-(3-methylbutyl)methanesulfonamide A mixture of Example 10F (0.040 g, 0.084 mmol) and Amberlite® IRP-64 H-form (0.010 g) in ethanol (1 mL) and H$_2$O (0.5 mL) was treated with acetaldehyde (1 mL, 17.7 mmol) and stirred in a sealed microwave tube at room temperature for 6 days. The mixture was filtered through a bed of diatomaceous earth that was washed thoroughly with ethyl acetate. The filtrate was washed with brine, dried over anhydrous Na$_2$SO$_4$, filtered, and concentrated in vacuo. The residue was purified by flash chromatography on an Isco silica gel cartridge (12 g) eluting with a gradient of hexane to 3:1 hexane/ethyl acetate to afford the title compound as a white foam (0.020 g, 47%). $^1$H NMR (DMSO-d$_6$) δ ppm 0.48-0.61 (m, 1H), 0.78-0.88 (7H), 1.00-1.05 (m, 2H), 1.22-1.31 (m, 1H), 1.38 (dd, J=5.04, 2.90 Hz, 4H), 1.55-1.66 (m, 1H), 2.34-2.44 (m, 1H), 3.13 (s, 3H), 3.59-3.79 (m, 2H), 5.74-5.80 (m, 1H), 7.22 (s, 1H), 7.30 (dd, J=4.20, 2.37 Hz, 1H), 7.42 (t, J=8.85 Hz, 2H), 7.88 (s, 1H), 8.00-8.04 (m, 2H); MS (ESI+) m/z 500 (M+H)$^+$.

Example 15

3-{[5-cyclopropyl-3-(4,5-dihydro-1,2,4-oxadiazol-3-yl)-2-(4-fluorophenyl)-1-benzofuran-6-yl](methylsulfonyl)amino}propane-1-sulfonamide

Example 15A

3-{[3-cyano-5-cyclopropyl-2-(4-fluorophenyl)-1-benzofuran-6-yl](methylsulfonyl)amino}propane-1-sulfonamide A solution of Example 11A (0.150 g, 0.405 mmol) in dry dimethyl sulfoxide (1.3 mL) under a nitrogen atmosphere was treated with potassium carbonate (0.090 g, 0.648 mmol), and the bright yellow mixture was stirred at room temperature for 30 minutes. Then 3-chloropropane-1-sulfonamide (0.096 g, 0.607 mmol) and sodium iodide (0.091 g, 0.607 mmol) were added, and the resultant mixture was heated at 50° C. for 22 hours. Additional potassium carbonate (0.090 g, 0.648 mmol), 3-chloropropane-1-sulfonamide (0.096 g, 0.607 mmol) and sodium iodide (0.091 g, 0.607 mmol) were added and stirring was continued at 50° C. for 23 hours. The reaction was incomplete by LCMS, so additional potassium carbonate (0.090 g, 0.648 mmol), 3-chloropropane-1-sulfonamide (0.096 g, 0.607 mmol) and sodium iodide (0.091 g, 0.607 mmol) were added followed by continued stirring at 50° C. for 22 hours. The reaction mixture was cooled to room temperature, diluted with ethyl acetate (50 mL), and washed with water (3×25 mL) and brine (10 mL). The organic phase was dried over anhydrous MgSO$_4$, filtered, and concentrated in vacuo. Purification by silica gel flash chromatography (10 g) eluting with 3% methanol/dichloromethane followed by trituration with diethyl ether (3×5 mL) afforded the title compound as white solid (0.128 g, 64%). MS (ESI+) m/z 509 (M+NH$_4$)$^+$, (ESI−) m/z 490 (M−H)$^−$.

Example 15B 5-cyclopropyl-2-(4-fluorophenyl)-N-hydroxy-6-[(methylsulfonyl)(3-sulfamoylpropyl)amino]-1-benzofuran-3-carboximidamide A 5-mL microwave tube was charged with Example 15A (0.125 g, 0.254 mmol), hydroxylamine (50 weight % in water, 2 mL, 33.9 mmol), and absolute ethanol (2 mL). The tube was sealed and heated in a microwave reactor (Personal Chemistry (Biotage), Emrys Creator, 300 W maximum) at 140° C. for 30 minutes. The reaction mixture was taken up in ethyl acetate (50 mL), and washed with water (3×25 mL) and brine (25 mL). The organic phase was dried over anhydrous $MgSO_4$, filtered, and concentrated in vacuo to afford the title compound as a white solid (0.133 g, quantitative). MS (ESI+) m/z 525 $(M+H)^+$, (ESI−) m/z 523 $(M-H)^-$.

Example 15C

3-{[5-cyclopropyl-3-(4,5-dihydro-1,2,4-oxadiazol-3-yl)-2-(4-fluorophenyl)-1-benzofuran-6-yl](methylsulfonyl)amino}propane-1-sulfonamide A 5-mL microwave tube was charged with Example 15B (0.133 g, 0.254 mmol), paraformaldehyde (0.024 g, 0.761 mmol), absolute ethanol (2.4 mL), and water (0.60 mL). The tube was sealed and heated in a microwave reactor at 130° C. for 30 minutes. The reaction was incomplete by LCMS, so additional paraformaldehyde (0.024 g, 0.761 mmol) was added followed by heating at 130° C. for 30 minutes in a microwave reactor (Personal Chemistry (Biotage), Emrys Creator, 300 W maximum). The reaction mixture was diluted with ethyl acetate (50 mL), washed with water (2×25 mL) and brine (25 mL), dried over anhydrous $MgSO_4$, filtered, and concentrated in vacuo. The residue was dissolved in 1:1 v/v methanol/dimethyl sulfoxide (2 mL) and purified by RP-$C_{18}$ HPLC (Waters Prep LC, 40 mm Module with Nova-Pak HR $C_{18}$ 6 µm 40×100 mm Prep-Pak cartridge) eluting with a 30 minute gradient of 95:5 0.1% trifluoroacetic acid in water/acetonitrile to 25:75 0.1% trifluoroacetic acid in water/acetonitrile, then 10 minutes to 100% acetonitrile at 20 mL/minute. Pure fractions were diluted in ethyl acetate (100 mL) and the aqueous phase was adjusted to pH~7 with saturated aqueous $NaHCO_3$. The layers were separated, and the organic phase was washed with water (25 mL) and brine (10 mL), The organic phase was dried over anhydrous $MgSO_4$, filtered, and concentrated in vacuo to afford the title compound as a white solid (0.010 g, 7%). $^1$H NMR (500 MHz, DMSO-$d_6$) δ ppm 0.55-0.69 (m, 1H), 0.81-0.92 (m, 2H), 0.99-1.08 (m, 1H), 1.81-1.94 (m, 2H), 2.32-2.37 (m, 1H), 2.97-3.11 (m, 2H), 3.16 (s, 3H), 3.72-3.88 (m, 2H), 5.34 (t, J=2.82 Hz, 2H), 6.80 (s, 2H), 7.17 (t, J=3.05 Hz, 1H), 7.29 (s, 1H), 7.42 (t, J=8.85 Hz, 2H), 7.87 (s, 1H), 8.02 (dd, J=8.93, 5.42 Hz, 2H); MS (ESI+) m/z 537 $(M+H)^+$, (ESI−) m/z 535 $(M-H)^-$.

Example 16

N-[5-cyclopropyl-3-(4,5-dihydro-1,2,4-oxadiazol-3-yl)-2-(4-fluorophenyl)-1-benzofuran-6-yl]-N-(4-hydroxybutyl)methanesulfonamide Example 16A N-(4-{[tert-butyl(dimethyl)silyl]oxy}butyl)-N-[3-cyano-5-cyclopropyl-2-(4-fluorophenyl)-1-benzofuran-6-yl]methanesulfonamide A 5-mL microwave tube was charged with Example 11A (0.200 g, 0.540 mmol), dry dimethyl sulfoxide (1.8 mL), potassium carbonate (0.112 g, 0.810 mmol), and tert-butyl(4-iodobutoxy)dimethylsilane (0.214 g, 0.648 mmol). The tube was sealed and heated in an oil bath at 50° C. for 16.5 hours. The reaction mixture was cooled to room temperature, diluted with ethyl acetate (50 mL), and washed with water (3×25 mL) and brine (10 mL). The organic phase was dried over anhydrous $MgSO_4$, filtered, and concentrated in vacuo. Purification by silica gel flash chromatography (10 g column) eluting with 100% dichloromethane to 5% ethyl acetate/dichloromethane afforded the title compound as a light yellow foam (0.257 g, 85%). MS (ESI+) m/z 557 $(M+H)^+$.

Example 16B

6-[(4-{[tert-butyl(dimethyl)silyl]oxy}butyl)(methylsulfonyl)amino]-5-cyclopropyl-2-(4-fluorophenyl)-N'-hydroxy-1-benzofuran-3-carboximidamide A 20-mL microwave tube was charged with Example 16A (1.2 g, 2.155 mmol), hydroxylamine (50 weight % in water, 6.6 mL, 108 mmol), and absolute ethanol (8 mL). The tube was sealed and heated in a microwave reactor (Personal Chemistry (Biotage), Emrys Creator, 300 W maximum) at 140° C. for 30 minutes. The reaction mixture was taken up in ethyl acetate, washed with water and brine, dried over anhydrous $MgSO_4$, filtered, and concentrated in vacuo. Purification of the residue by flash chromatography on an Isco silica gel cartridge (40 g) eluting with a gradient of dichloromethane to 3% methanol/dichloromethane afforded the title compound as an off-white foam (1.06 g, 83%). MS (ESI+) m/z 590 $(M+H)^+$, (ESI−) m/z 588 $(M-H)^-$.

Example 16C 5-cyclopropyl-2-(4-fluorophenyl)-N-hydroxy-6-[(4-hydroxybutyl)(methylsulfonyl)amino]-1-benzofuran-3-carboximidamide To a solution of Example 16B (0.760 g, 1.289 mmol) in tetrahydrofuran (12 mL) was added 1 M tetrabutylammonium fluoride in tetrahydrofuran (3.22 mL, 3.22 mmol) in a fast drip, and the resulting yellow solution was stirred at room temperature for 1 hour. The reaction mixture was partitioned between ethyl acetate and water. The aqueous layer was further washed with ethyl acetate (2×). The combined organic extracts were washed with brine, dried over anhydrous $MgSO_4$, filtered, and concentrated in vacuo to a clear oil that crystallized upon standing. Trituration with 1:2 v/v dichloromethane/hexane afforded the title compound as a white powder (0.588 g, 92%). MS (ESI+) m/z 476 $(M+H)^+$, (ESI−) m/z 474 $(M-H)^-$.

Example 16D

N-[5-cyclopropyl-3-(4,5-dihydro-1,2,4-oxadiazol-3-yl)-2-(4-fluorophenyl)-1-benzofuran-6-yl]-N-(4-hydroxybutyl)methanesulfonamide A 5-mL microwave tube was charged with Example 16C (0.20 g, 0.421 mmol), paraformaldehyde (0.051 g, 1.682 mmol), absolute ethanol (6.7 mL), and water (1.7 mL). The tube was sealed and heated in a microwave reactor (Personal Chemistry (Biotage), Emrys Creator, 300 W maximum) at 130° C. for 30 minutes. The reaction was incomplete by LCMS, so additional paraformaldehyde (0.051 g, 1.682 mmol) was added and the mixture was heated at 130° C. in the microwave reactor for 30 minutes. The reaction was still incomplete by LCMS, so additional paraformaldehyde (0.051 g, 1.682 mmol) was added and the mixture was heated at 130° C. in the microwave reactor for 30 minutes. The reaction mixture was diluted with ethyl acetate, washed with water and brine, dried over anhydrous $Na_2SO_4$, filtered, and concentrated in vacuo. Purification by flash chromatography on a silica gel cartridge (24 g) eluting with a gradient of dichloromethane to 2.5% methanol/dichloromethane afforded the title compound (0.70 g, 34%). $^1$H NMR (DMSO-$d_6$) δ ppm 0.53-0.63 (m, 1H), 0.80-0.91 (m, 1H), 0.97-1.08 (m, 2H), 1.37-1.53 (m, 4H), 2.35-2.44 (m, 1H), 3.13 (s, 3H), 3.24-3.47 (m, 2H), 3.59-3.77 (m, 2H), 4.37 (t, J=5.04 Hz, 1H), 5.34 (dd, J=3.05, 1.98 Hz, 2H), 7.17 (t, J=3.13 Hz, 1H), 7.27 (s, 1H), 7.37-7.49 (m, 2H), 7.86 (s, 1H), 7.96-8.10 (m, 2H); MS (ESI+) m/z 488 (M+H)$^+$, (ESI−) m/z 486 (M−H)$^−$.

Example 17

N-[5-cyclopropyl-2-(4-fluorophenyl)-3-(1H-imidazol-2-yl)pyrazolo[1,5-a]pyridin-6-yl]-N-(3-methylbutyl)methanesulfonamide

Example 17A tert-butyl pyridin-3-ylcarbamate

To a solution of pyridin-3-amine (2.5 g, 26.3 mmol) in anhydrous tetrahydrofuran (80 mL) was added 1 M sodium bis(trimethylsilyl)amide in tetrahydrofuran (52.6 mL, 52.6 mmol) in a steady stream. The mixture was stirred for 30 minutes, treated dropwise with a solution of di-tert-butyl dicarbonate (5.92 g, 26.3 mmol) in anhydrous tetrahydrofuran (20 mL), stirred for 3 hours and concentrated. The residue was dissolved in ethyl acetate, washed with saturated aqueous sodium chloride, dried over anhydrous MgSO$_4$, filtered, and concentrated by rotary evaporation. Purification by chromatography on silica eluting with 3% methanol in dichloromethane afforded an amber semi-solid. The material was dissolved in ethyl acetate, treated with decolorizing charcoal and vacuum filtered through diatomaceous earth. Concentration of the filtrate by rotary evaporation afforded the title compound as a light gold solid (4.35 g, 85%). MS (DCI+) m/z 195 (M+H)$^+$.

Example 17B tert-butyl 4-iodopyridin-3-ylcarbamate

A solution of Example 17A (2.16 g, 11.12 mmol) in anhydrous tetrahydrofuran (50 mL) under N$_2$ was cooled to −78° C. and treated dropwise with 1.7 M tert-butyl lithium in pentane (16.35 mL, 27.8 mmol). The mixture was stirred at −78° C. for 15 minutes, warmed to −30° C. and stirred for 2.5 hours. The dark brick-red solution was re-cooled to −78° C. and a solution of iodine (7.06 g, 27.8 mmol) in anhydrous tetrahydrofuran (18.5 mL) was added dropwise over 20 minutes to give a thick reaction mixture that was difficult to stir. The mixture was swirled at −78° C. for 15 minutes, warmed to −30° C., stirred for 40 minutes and warmed to 0° C. The mixture was quenched by addition of H$_2$O (100 mL) and treated with solid Na$_2$SO$_3$ until a constant yellow color was achieved. The mixture was diluted with ethyl acetate and the layers were separated. The organic layer was washed with saturated sodium chloride solution, dried over anhydrous Na$_2$SO$_4$, filtered, and the filtrate was concentrated by rotary evaporation. Purification by chromatography on silica eluting with 10%-20% ethyl acetate in dichloromethane afforded the title compound as an amber oil which crystallized upon standing (2.32 g, 65%). MS (DCI+) m/z 321 (M+H)$^+$.

Example 17C tert-butyl 4-cyclopropylpyridin-3-ylcarbamate

A pressure tube purged with nitrogen was charged with tert-butyl 4-iodopyridin-3-ylcarbamate (1.0 g, 3.12 mmol), potassium phosphate (2.393 g, 10.93 mmol), toluene (16 mL) and H$_2$O (0.800 mL). The mixture was sparged with nitrogen for 20 minutes. Then cyclopropylboronic acid (0.349 g, 4.06 mmol), tricyclohexylphosphonium tetrafluoroborate (0.116 g, 0.312 mmol), and palladium(II) acetate (0.035 g, 0.156 mmol) were added, and the mixture was sparged with nitrogen for 15 minutes. The tube was closed with a pressure release valve top, and the mixture was heated at 100° C. for 20 hours. TLC (SiO$_2$, 50% ethyl acetate/CH$_2$Cl$_2$) showed no starting material and a lower. Rf product. LCMS showed no starting material, and a large product peak, m/z 235. The reaction was cooled to room temperature, and the residue was taken up in ethyl acetate (100 mL), and washed with H$_2$O (50 mL). The aqueous phase was re-extracted with ethyl acetate (50 mL), and the combined organic extracts were washed with brine (25 mL), dried over anhydrous MgSO$_4$, filtered, and concentrated by rotary evaporation. The crude material was purified by SiO$_2$ flash chromatography (2.5 cm×15 cm) eluting with CH$_2$Cl$_2$ to 6:4 ethyl acetate/CH$_2$Cl$_2$ to afford the product as a colorless viscous oil (634 mg).

Example 17D 4-cyclopropylpyridin-3-amine

Tert-butyl 4-cyclopropylpyridin-3-ylcarbamate (393 mg, 1.677 mmol) was dissolved in 4 M HCl in dioxane (30 mL), and stirred at room temperature for 1 hour, the reaction rapidly becoming a white heterogeneous mixture. TLC (SiO$_2$, 5% methanol/CH$_2$Cl$_2$) showed reaction complete after 1 hour. The solvent was removed by rotary evaporation, the residue was triturated with diethyl ether and vacuum filtered to collect the solid, and the solid was dried in a vacuum oven at 50° C. for 1 hour to afford the product as a beige solid (325 mg).

Example 17E

N-(4-cyclopropylpyridin-3-yl)-N-(methylsulfonyl)methanesulfonamide

A suspension of 4-cyclopropylpyridin-3-amine hydrochloride (297 mg, 1.741 mmol) in anhydrous CH$_2$Cl$_2$ (8.5 mL) was cooled to 0° C. and treated with triethylamine (0.849 mL, 6.09 mmol) and methanesulfonyl chloride (0.298 mL, 3.83 mmol). The mixture was stirred at 0° C. for 1 hour, then at room temperature for 1 hour. TLC (SiO$_2$, 5% methanol/CH$_2$Cl$_2$; used sample of free base 10036010-0967 as starting material reference) showed the reaction was complete. The mixture was diluted with CH$_2$Cl$_2$ (50 mL), washed with saturated aqueous NaHCO$_3$ (25 mL), dried over anhydrous Na$_2$SO$_4$, filtered, and concentrated by rotary evaporation to give a tan solid. The solid was purified by SiO$_2$ flash chromatography (3.8 cm×10 cm) eluting with 3% methanol/CH$_2$Cl$_2$ to afford the product as a white solid (403 mg).

Example 17F

N-(4-cyclopropylpyridin-3-yl)methanesulfonamide

A suspension of Example 17E (1.85 g, 6.37 mmol) in tetrahydrofuran (32 mL) was treated with sodium hydroxide solution (1.0 N, 16 mL, 16 mmol) and then stirred at room temperature for 1 hour. The mixture was concentrated in vacuo to remove the tetrahydrofuran and the mixture was diluted with water and cooled to 0° C. The solution was acidified to pH 7 by addition of 1 N aqueous hydrochloric acid solution. The mixture was extracted with dichloromethane (2×) and the combined extracts were dried ($Na_2SO_4$), filtered and the filtrate was concentrated in vacuo. These procedures afforded the product (1.14 g, 84%) as a light beige solid.

Example 17G

N-(4-cyclopropylpyridin-3-yl)-N-isopentylmethane-sulfonamide

A suspension of Example 17F (814 mg, 3.83 mmol) and cesium carbonate (1.87 g, 5.75 mmol) in N,N-dimethylformamide was treated with isoamyl iodide (555 µL, 835 mg, 4.22 mmol) followed by stirring at room temperature for 48 hours. The mixture was diluted with ethyl acetate and extracted with water (3×) and saturated sodium chloride solution. Drying ($Na_2SO_4$) and concentration in vacuo afforded an amber oil, which was chromatographed over a 50 g silica gel cartridge, eluting with 15-70% ethyl acetate in dichloromethane. These procedures afforded the product (474 mg, 44%) as an off-white solid.

Example 17H

O-(mesitylsulfonyl)hydroxylamine tert-Butyl mesitylsulfonyloxycarbamate (1.51 g, 5.42 mmol) was added to cold (0° C.) trifluoroacetic acid (10.8 mL) and the mixture was stirred at 0° C. for 45 minutes. The mixture was diluted with cold (0° C.) water and the white precipitate was collected by filtration and washed with 1000 mL of cold (0° C.) water. The solid was dried by suction for about 5 minutes and then dissolved in cold (0° C.) dichloromethane and dried ($Na_2SO_4$). The solution was filtered and the filtrate was concentrated to a volume of about 12 mL on the rotary evaporator without heating. The solution was then directly used in the next step.

Example 17I 1-amino-4-cyclopropyl-3-(N-isopentylmethylsul-fonamido)pyridinium 2,4,6-trimethylbenzene-sulfonate A solution of N-(4-cyclopropylpyridin-3-yl)-N-isopentyl-methanesulfonamide (Example 17G, 474 mg, 1.68 mmol) in dichloromethane (3 mL) at 0° C. was treated with the solution of O-(mesitylsulfonyl)hydroxylamine (solution used directly from Example 17H). The solution was immediately warmed to room temperature and stirred for 1 hour. The solution was then used directly in Example 17K.

Example 17J methyl 3-(4-fluorophenyl)propiolate

A solution of 4-fluorophenylacetylene (2.86 mL, 3.00 g, 24.97 mmol) in tetrahydrofuran at −78° C. was treated with a solution of n-butyllithium in hexanes (2.29 M, 12.0 mL, 27.5 mmol) followed by stirring at −78° C. for 45 minutes. The solution was then treated rapidly with methyl chloroformate (2.12 mL, 2.60 g, 27.5 mmol) followed by stirring at −78° C. for 30 minutes and warming to room temperature for 18 hours. The mixture was treated with water and concentrated in vacuo to remove tetrahydrofuran. The residue was dissolved in ethyl acetate and washed with water and saturated sodium chloride solution. Drying ($Na_2SO_4$) and concentration in vacuo afforded a yellow solid, which was chromatographed over a 340 g silica gel cartridge, eluting with 15-50% dichloromethane in hexanes. These procedures afforded the product (2.95 g, 66%) as an off-white fluffy solid.

Example 17K methyl 5-cyclopropyl-2-(4-fluorophenyl)-6-(N-iso-pentylmethylsulfonamido)-1,3a-dihydropyrazolo[1,5-a]pyridine-3-carboxylate A solution of the Example 17I (775 mg, 1.56 mmol) in dichloromethane (13 mL) was treated with methyl 3-(4-fluorophenyl)propiolate (277 mg, 1.56 mmol) and then dropwise with 1,8-diazabicyclo[5.4.0]undec-7-ene (469 µL, 474 mg, 3.11 mmol), and the mixture was stirred for 18 hours. The solution was diluted with dichloromethane, washed with water, dried ($Na_2SO_4$), filtered and concentrated to give a yellow oil that was used without purification.

Example 17L methyl 5-cyclopropyl-2-(4-fluorophenyl)-6-(N-iso-pentylmethylsulfonamido)pyrazolo[1,5-a]pyridine-3-carboxylate A solution of Example 17K in dimethyl sulfoxide (8 mL) was treated with potassium carbonate (237 mg, 1.71 mmol) and iodobenzene diacetate (552 mg, 1.71 mmol) followed by stirring for 1 hour. The mixture was diluted with ethyl acetate and the organic layer was washed with water and saturated sodium chloride solution, dried ($Na_2SO_4$), filtered and concentrated in vacuo to afford a brown oil. Purification by chromatography on a 100 g silica gel cartridge, eluting with 15-80% ethyl acetate in hexanes, afforded the title compound as a rigid foam (166 mg, 23% over two steps). $^1$H NMR (500 MHz, $CDCl_3$) δ ppm 8.48 (s, 1H), 7.75 (m, 2H), 7.67 (s, 1H), 7.15 (m, 2H), 3.82 (s, 3H), 3.68 (m, 1H), 3.64 (m, 1H), 3.07 (s, 3H), 2.29 (m, 1H), 1.62 (m, 1H), 1.51 (m, 1H), 1.23 (m, 2H), 1.07 (m, 1H), 0.94 (m, 6H), 0.82 (m, 1H); MS (ESI+) m/z 474 (M+H)$^+$.

Example 17M 5-cyclopropyl-2-(4-fluorophenyl)-6-(N-isopentylm-ethylsulfonamido)pyrazolo[1,5-a]pyridine-3-car-boxylic acid A suspension of the Example 17L (162 mg, 0.34 mmol) and potassium trimethylsilanoate (244 mg of 90%, 219 mg, 1.71 mmol) in tetrahydrofuran (4 mL) was warmed at reflux for 3 hours. The mixture was concentrated in vacuo to remove tetrahydrofuran and then diluted with water and cooled to 0° C. The mixture was adjusted to pH 3 by addition of 1 N aqueous hydrochloric acid solution producing an off-white precipitate that was collected by filtration and dried to constant mass (152 mg, 97%). $^1$H NMR (500 MHz, $CDCl_3$) δ ppm 8.56 (d, J=0.5 Hz, 1H), 7.81 (m, 2H), 7.69 (s, 1H), 7.17 (m, 2H), 3.82 (m, 1H), 3.64 (ddd, J=6.1, 10.0, 13.7 Hz, 1H), 3.09 (m, 3H), 2.30 (dq, J=5.2, 8.4 Hz, 1H), 1.63 (m, 1H), 1.52

(m, 2H), 1.24 (m, 3H), 1.11 (dd, J=5.2, 9.4 Hz, 1H), 0.91 (m, 6H), 0.84 (m, 1H); MS (ESI+) m/z 460 (M+H)+.

Example 17N

N-(3-bromo-5-cyclopropyl-2-(4-fluorophenyl)pyrazolo[1,5-a]pyridin-6-yl)-N-isopentylmethanesulfonamide A solution of Example 17M (19 mg, 0.041 mmol) in dry N,N-dimethylformamide (300 µL) was treated with sodium bicarbonate (10.4 mg, 0.124 mmol) and N-bromosuccinimide (7.4 mg, 0.041 mmol) and stirred for 1 hour. The mixture was diluted with ethyl acetate and the organic layer was washed with water and saturated sodium chloride solution, dried (Na$_2$SO$_4$), filtered and concentrated in vacuo to afford the title compound as an oil (19 mg, 93%). MS (ESI+) m/z 494,496 (M+H)+.

Example 17O 1-((2-(trimethylsilyl)ethoxy)methyl)-1H-imidazole

A suspension of sodium hydride (3.08 g of 60% in oil, 1.85 g, 77 mmol) in dry tetrahydrofuran (80 mL) at 0° C. was treated dropwise with a solution of imidazole (5.00 g, 73.4 mmol) in dry tetrahydrofuran (20 mL) over 15 minutes. The mixture was stirred at ambient temperature for 30 minutes, cooled to 0° C. and treated dropwise with 2-trimethylsilylethyoxymethyl chloride (13.7 mL, 12.86 g, 77 mmol). The mixture was stirred at ambient temperature for 18 hours and quenched by the addition of saturated ammonium chloride solution. The mixture was diluted with water and concentrated in vacuo to remove tetrahydrofuran. The residue was diluted with ethyl acetate and the organic layer was washed with saturated sodium chloride solution, dried (Na$_2$SO$_4$), filtered and concentrated in vacuo to afford an orange oil. Distillation (93-94° C./0.2 mm Hg) afforded the title compound as a colorless liquid (12.97 g, 89%). MS (ESI+) m/z 199 (M+H)+.

Example 17P (1-((2-(trimethylsilyl)ethoxy)methyl)-1H-imidazol-2-yl)zinc(II) chloride A solution of Example 17O (73 mg, 0.37 mmol) in dry tetrahydrofuran (1.5 mL) at −78° C. under N$_2$ was treated with a solution of n-butyllithium in hexanes (2.29 M, 169 µL, 0.39 mmol) followed by stirring at −78° C. for 30 minutes. The solution was treated dropwise with a solution of zinc chloride in tetrahydrofuran (0.5 M, 2.20 mL, 1.10 mmol) followed by warming to 0° C. for 1 hour.

Example 17Q

N-(5-cyclopropyl-2-(4-fluorophenyl)-3-(1-((2-(trimethylsilyl)ethoxy)methyl)-1H-imidazol-2-yl)pyrazolo[1,5-a]pyridin-6-yl)-N-isopentylmethanesulfonamide A solution of Example 17P (110 mg, 0.37 mmol) was treated with a solution of Example 17N (52 mg, 0.11 mmol) in dry tetrahydrofuran (2×0.5 mL) followed by the addition of a solution of 1,1'-bis(diphenylphosphino)ferrocene palladium (II) chloride dichloromethane complex (13 mg, 0.016 mmol) which had been treated with a solution of diisobutylaluminum hydride in tetrahydrofuran (1.0 M, 32 µL, 0.032 mmol). The reaction mixture was sealed, warmed at 120° C. for 42 hours, cooled and partitioned with ethyl acetate and water. The organic layer was extracted with a solution of ethylene diamine tetraacetic acid disodium salt, water, and saturated sodium chloride solution. The organic layer was dried over anhydrous Na$_2$SO$_4$, stirred for 1 hour with 3-(mercaptopropyl) silica gel, filtered and concentrated in vacuo. The residue was chromatographed over a 10 g silica gel cartridge, eluting with 10-70% ethyl acetate in dichloromethane to afford the title compound as an amber oil (8.5 mg, 13%). $^1$H NMR (500 MHz, CDCl$_3$) δ ppm 8.47 (d, J=0.6 Hz, 1H), 7.49 (m, 2H), 7.28 (d, J=1.3 Hz, 1H), 7.16 (d, J=1.4 Hz, 1H), 7.02 (m, 2H), 6.93 (s, 1H), 4.77 (m, 2H), 3.78 (m, 2H), 3.59 (m, 1H), 3.08 (m, 5H), 2.18 (m, 1H), 1.60 (m, 5H), 1.49 (m, 3H), 1.35 (t, J=6.8 Hz, 1H), 1.22 (m, 2H), 1.07 (q, J=4.9 Hz, 2H), 0.89 (m, 6H), 0.67 (d, J=4.3 Hz, 1H), 0.61 (m, 2H), −0.18 (m, 9H); MS (ESI+) m/z 612 (M+H)+.

Example 17R

N-[5-cyclopropyl-2-(4-fluorophenyl)-3-(1H-imidazol-2-yl)pyrazolo[1,5-a]pyridin-6-yl]-N-(3-methylbutyl)methanesulfonamide Example 17Q (8.5 mg, 0.014 mmol) was dissolved in ethanol (1.5 mL), treated with 4 N hydrochloric acid solution (1.5 mL) and warmed at 75° C. for 48 hours and then at 90° C. for 4 hours. The mixture was cooled and concentrated in vacuo, azeotroping with benzene-ethanol (3×) to remove last traces of water. The resulting oil was concentrated in vacuo from diethyl ether (2×) to give the title compound as a light brown solid (7.3 mg). $^1$H NMR (500 MHz, methanol-d$_4$) δ ppm 8.99 (s, 1H), 7.65 (s, 2H), 7.55 (om, 2H), 7.20 (m, 4H), 3.79 (dd, J=4.6, 11.2 Hz, 2H), 3.18 (s, 3H), 2.38 (m, 1H), 1.69 (dt, J=6.7, 13.3 Hz, 1H), 1.52 (td, J=6.9, 15.6 Hz, 2H), 1.26 (m, 7H), 1.08 (dd, J=4.4, 9.5 Hz, 1H), 0.90 (m, 7H), 0.85 (m, 1H); MS (ESI+) m/z 483 (M+H)+.

Example 18

N-[2-(4-anilinophenyl)-5-cyclopropyl-3-(1H-imidazol-2-yl)-1-benzofuran-6-yl]-N-(3-methylbutyl)methanesulfonamide Example 18A 2-bromo-4-chloro-5-methoxyaniline A solution of 4-chloro-3-methoxyaniline (1.0 equivalent) dissolved in CH$_2$Cl$_2$ (15 volumes) at 5° C. was treated portion wise with N-bromosuccinimide (1.03 equivalents), warmed to 20° C. and mixed for 5 minutes. A 5% aqueous Na$_2$SO$_3$ solution (10 volumes) was added and the mixture was stirred for 10 minutes. The layers were separated and the organic layer was washed with water and saturated brine, dried (Na$_2$SO$_4$), filtered and concentrated. The resulting solid was triturated with a minimal volume of heptane and the solid was collected by filtration and dried to constant mass (80% yield).

Example 18B 4-chloro-2-cyclopropyl-5-methoxyaniline

A mixture of Example 18A (1.0 equivalents), cyclopropyl boronic acid (1.1 equivalents), tricyclohexylphosphine (0.05 equivalents), palladium acetate (0.025 equivalents) and $K_3PO_4$ (2 equivalents) in a 20:1 volume ratio of toluene and water was sparged with nitrogen for 15 minutes. The reaction mixture was then heated to 100° C. for 12 hours, cooled, diluted with water, stirred for 1 hour and filtered through a diatomaceous earth pad, and the pad was rinsed with toluene. The filtrate was mixed and the layers were separated. The organic layer was washed with water and saturated brine, dried ($Na_2SO_4$), filtered and concentrated to an oil that was used without further purification.

Example 18C

N-(4-chloro-2-cyclopropyl-5-methoxyphenyl)-N-(methylsulfonyl)methanesulfonamide

A mixture of Example 18B (1.0 equivalent) and triethylamine (2.3 equivalents) in tetrahydrofuran (0.5 M final concentration based on product from Example 18B) was cooled to 5° C. and treated dropwise with methane sulfonyl chloride (2.3 equivalents) maintaining the temperature below 20° C. After the addition was completed, the reaction mixture was warmed up to ambient temperature for 20 minutes and partitioned with water and methylene chloride. The organic layer was washed with 5% aqueous NaCl solution, dried ($Na_2SO_4$), filtered and concentrated. The resulting solid was triturated with isopropyl acetate/heptane (2:1), and the solid was collected by filtration and dried to constant mass (80% yield).

Example 18D

N-(4-((4-(benzyloxy)phenyl)ethynyl)-2-cyclopropyl-5-methoxyphenyl)-N-(methylsulfonyl)methanesulfonamide To a degassed solution of dry propionitrile (2.5 L) in a three-necked round bottom flask at room temperature was added Example 18C (250 g, 0.71 mol, 1 equivalent), anhydrous potassium carbonate (194 g, 1.4 mol, 2 equivalents), 2-dicyclohexylphosphino-2',4',6'-triisopropylbiphenyl (47 g, 0.098 mol, 0.14 equivalents) and bis(acetonitrile)palladium dichloride (9.2 g, 0.035 mol, 0.05 equivalents) one after another, and the reaction mixture was heated at 93° C. for 10 minutes. To the above mixture was added a degassed solution of 1-(benzyloxy)-4-ethynylbenzene (Khabnadideh S, et al. Bioorg. Med. Chem. 2005; 13: 2637-2649; 175 g, 0.84 mol, 1.19 equivalents) in dry propionitrile (2 L) drop by drop over a period of 1 hour (degassing was done for 30 minutes in a separate reaction flask). The reaction mixture was allowed to stir at this temperature (93° C.) for 1 hour. The reaction was monitored by TLC which indicated two spots (mono-mesyl and di-mesyl compounds). The reaction mixture was quenched with water (2.5 L), and extracted with ethyl acetate (5 L). The organic layer was separated, and the aqueous layer was further extracted with ethyl acetate (2×1.5 L). The combined organic layer was washed with water (2 L) and brine (1×1.5 L) and dried over anhydrous sodium sulfate. The organic layer was filtered and concentrated under reduced pressure to give a crude mixture of mono-mesyl and di-mesyl compounds.

To a cooled (0° C.) solution of the above crude mixture in dimethoxyethane (2.5 L) was added triethylamine (85 g, 0.84 mol, 1.19 equivalents) followed by dropwise addition of methanesulfonyl chloride (125 mL) over a period of 10 minutes and the reaction mixture was stirred at room temperature for 1 hour, quenched with water (2 L) and extracted with ethyl acetate (5 L). The organic layer was separated and the aqueous layer was further extracted with ethyl acetate (2×1.5 L). The combined organic layers were washed with water (2 L) and brine (1×1.5 L) and dried over anhydrous sodium sulfate. The organic layer was filtered and concentrated under vacuo. The crude mixture was stirred in isopropyl alcohol (2.5 L) and heated at 85° C. for 1 hour, then cooled, and the resulting solid was collected by filtration, washed with acetonitrile (2 L) and dried to give the title compound (230 g, 40% yield) as yellow solid. $^1$H NMR (300 MHz, $CDCl_3$) δ ppm 7.44-7.30 (m, 7H), 7.07-7.02 (m, 4H), 5.13 (s, 2H), 3.87 (s, 3H), 3.59 (s, 6H), 2.03-2.01 (m, 1H), 1.01-0.97 (m, 2H), 0.75-0.74 (m, 2H); LCMS (APCI+) m/z 446.60 $(M+H)^+$ (for mono-mesyl cleaved).

Example 18E

N-(2-(4-(benzyloxy)phenyl)-5-cyclopropyl-3-iodo-benzofuran-6-yl)-N-(methylsulfonyl)methanesulfonamide To a solution Example 18D (230 g, 0.44 mol, 1 equivalent) in dry dichloromethane (2.5 L) was added iodine (221 g, 0.87 mol, 2 equivalents) in one portion. The resulting mixture was stirred at room temperature for 4 hours, further diluted with dichloromethane (2 L) and washed with saturated sodium bisulfate (2 L). The organic layer was separated and the aqueous layer was further extracted with dichloromethane (2×500 mL). The combined organic layers were washed with saturated sodium thiosulfate (2 L), brine (1×500 mL) and dried over anhydrous sodium sulfate. The organic layer was filtered and concentrated. The crude mixture thus obtained was dissolved in acetonitrile (500 mL) and stirred for 2 hours. The resulting solid was collected by filtration, washed with 5% water in acetonitrile (2 L) and dried under vacuum to give a light brown solid. The solid was further purified by column chromatography (silica gel, 60-120 mesh) to remove the color impurities using dichloromethane as eluent to give the title compound (193 g, 69% yield) as colorless solid. $^1$H NMR (400 MHz, $CDCl_3$) δ ppm 8.11 (dd, J=6.92, 1.96 Hz, 2H), 7.49-7.39 (m, 6H), 7.12 (dd, J=7.0, 1.96 Hz, 2H), 7.02 (s, 1H), 5.16 (s, 2H), 3.55 (s, 6H), 2.35-2.31 (m, 1H), 1.14-1.10 (m, 2H), 0.96-0.94 (m, 2H); LCMS (APCI+) m/z 558.30 $(M+H)^+$ (for mono-mesyl cleaved).

Example 18F methyl 2-(4-(benzyloxy)phenyl)-5-cyclopropyl-6-(N-(methylsulfonyl)methylsulfonamido)benzofuran-3-carboxylate In a 50 mL Parr Stirrer reactor were combined Example 18E (3.5 g, 5.5 mmol), 1,4-bis(diphenylphosphino)butane (0.094 g, 0.22 mmol, 4 mol %), palladium acetate (0.025 g, 0.11 mmol, 2 mole %) and triethylamine (1.53 mL, 11 mmol) in methanol (17.5 mL) and acetonitrile (17.5 mL). The mixture was degassed with nitrogen, sealed, purged again with nitrogen followed by purging with carbon monoxide, and pressurized to 60 psig with carbon monoxide. The mixture was heated to 80° C. for 16 hours, cooled and diluted with dichloromethane to afford dissolution. The mixture was filtered through diatomaceous earth to remove solids. The filtrate was washed with water and saturated brine, dried ($Na_2SO_4$), filtered and concentrated to give the title compound (94% yield).

Example 18G methyl 2-(4-(benzyloxy)phenyl)-5-cyclopropyl-6-(methylsulfonamido)benzofuran-3-carboxylate To Example 18F (1 equivalent) in 3 volumes of tetrahydrofuran was added 2 mole equivalents of tetrabutyl ammonium fluoride (1 M in tetrahydrofuran). The mixture was heated at 60° C. for 7 hours, cooled and diluted with ethyl acetate. The organic layer was washed with water and brine, dried (Na$_2$SO$_4$), filtered and concentrated. The residue was triturated in a minimal amount of methanol and the resulting solid was collected by filtration, rinsed with cold methanol and dried to give the title compound as a light yellow solid (93%). $^1$H NMR (400 MHz, DMSO-d$_6$) δ ppm 0.64-0.71 (m, 2H) 0.98-1.06 (m, 2H) 2.30-2.36 (m, 1H) 3.06 (s, 3H) 3.86 (s, 3H) 5.22 (s, 2H) 7.18 (d, J=9.00 Hz, 2H) 7.31-7.38 (m, 1H) 7.42 (t, J=7.32 Hz, 2H) 7.49 (d, J=9.54 Hz, 3H) 7.61 (s, 1H) 7.97 (d, J=8.89 Hz, 2H) 9.30 (s, 1H); MS (ESI–) m/z 490 (M–H)$^-$.

Example 18H methyl 2-(4-(benzyloxy)phenyl)-5-cyclopropyl-6-(N-(4-methoxybenzyl)methylsulfonamido)benzofuran-3-carboxylate A mixture of Example 18G (4.0 g, 8.14 mmol), 4-methoxybenzyl bromide 2.21 g, 11 mmol) and potassium carbonate (1.35 g, 9.76 mmol) in N,N-dimethylformamide (25 mL) under N$_2$ was heated at 50° C. for 2 hours, cooled and concentrated. The residue was partitioned between ethyl acetate and water. The organic layer was washed with water, saturated brine, dried (MgSO$_4$), filtered and concentrated. The solid was triturated in hexanes and the solid was collected by filtration and dried to give the title compound as a white solid (4.49 g, 90% yield). MS (ESI+) m/z 612 (M+H)$^+$.

Example 18I

N-(2-(4-(benzyloxy)phenyl)-5-cyclopropyl-3-(hydroxymethyl)benzofuran-6-yl)-N-(4-methoxybenzyl) methanesulfonamide A solution of Example 18H (4.34 g, 7.09 mmol) in tetrahydrofuran (20 mL) at 5° C. under nitrogen was treated dropwise with a solution of 1 M lithium aluminum hydride (7.1 mL, 7.1 mmol). The reaction mixture was stirred for two hours at ambient temperature, and treated sequentially and dropwise with water (0.29 mL), 15% aqueous sodium hydroxide (0.29 mL) and water (0.875 mL). The resulting slurry was stirred for 20 minutes, diluted with ethyl acetate and filtered through diatomaceous earth. The diatomaceous earth was rinsed with ethyl acetate, and the combined filtrate was concentrated to an oil. The oil was diluted with dichloromethane and hexane and concentrated once again to give the title compound as a yellow foam (4.08 g, 99%). MS (ESI+) m/z 601 (M+NH$_4$)$^+$.

Example 18J

N-(2-(4-(benzyloxy)phenyl)-5-cyclopropyl-3-formylbenzofuran-6-yl)-N-(4-methoxybenzyl)methanesulfonamide Example 18I (4.04 g, 6.92 mmol) in anhydrous dichloromethane (70 mL) was treated with pyridinium dichromate (3.91 g, 10.38 mmol) according to the procedure described in Example 1L. Purification by flash chromatography on a 120 g silica cartridge eluting with 0 to 30% ethyl acetate in hexane afforded the title compound as a solid (2.6 g, 65%). MS (ESI+) m/z 582 (M+H)$^+$.

Example 18K

N-(2-(4-(benzyloxy)phenyl)-5-cyclopropyl-3-(4,5-dihydro-1H-imidazol-2-yl)benzofuran-6-yl)-N-(4-methoxybenzyl)methanesulfonamide Example 18J (2.27 g, 3.90 mmol) was treated with ethylene diamine and N-bromo succinimide as described in Example 1M to give the title compound that was used without purification (2.35 g, 97%). MS (APCI+) m/z 622 (M+H)$^+$.

Example 18L

N-(2-(4-(benzyloxy)phenyl)-5-cyclopropyl-3-(1H-imidazol-2-yl)benzofuran-6-yl)-N-(4-methoxybenzyl)methanesulfonamide Example 18K (2.35 g, 3.70 mmol) was treated with potassium carbonate (1.0 g, 7.4 mmol) and iodobenzene diacetate (1.3 g, 4.07 mmol) in dimethylsulfoxide (18 mL) as described in Example 1N. Purification by flash chromatography on silica eluting with 0 to 60% ethyl acetate in hexane afforded the title compound as an off-white solid (0.91 g, 40%). MS (ESI+) m/z 620 (M+H)$^+$.

Example 18M

N-(2-(4-(benzyloxy)phenyl)-5-cyclopropyl-3-(1H-imidazol-2-yl)benzofuran-6-yl)methanesulfonamide Example 18L ((0.56 g, 0.904 mmol)) was treated with trifluoroacetic acid in dichloromethane as described in Example 1O to afford the title compound as a solid (0.445 g, 99%). MS (ESI+) m/z 500 (M+H)$^+$.

Example 18N

N-(2-(4-(benzyloxy)phenyl)-5-cyclopropyl-3-(1H-imidazol-2-yl)benzofuran-6-yl)-N-isopentylmethanesulfonamide To a mixture of Example 18M (0.25 g, 0.50 mmol) and potassium carbonate (0.097 g, 0.70 mmol) in dimethylsulfoxide (5.00 mL) was added dropwise 1-iodo-3-methylbutane (0.082 mL, 0.626 mmol). The mixture was stirred for 24 hours and partitioned between ethyl acetate and water. The aqueous layer was back extracted twice with ethyl acetate. The organics were combined, washed three times with 20 mL brine, dried (Na$_2$SO$_4$), filtered and concentrated to give the title compound which was used without purification. MS (APCI+) m/z 570 (M+H)$^+$.

Example 18O

N-(5-cyclopropyl-2-(4-hydroxyphenyl)-3-(1H-imidazol-2-yl)benzofuran-6-yl)-N-isopentylmethanesulfonamide Example 18N (285 mg, 0.5 mmol) and palladium hydroxide on carbon (54.0 mg, 0.385 mmol) were combined in N,N-dimethylformamide (10 mL) in a pressure bottle and stirred for 6 hours under 30 psi hydrogen. The mixture was filtered through a nylon membrane, concentrated, and the residue was partitioned between ethyl acetate and water. The ethyl acetate layer was washed repeatedly with brine, dried (Na$_2$SO$_4$), filtered and concentrated to a tan solid. Purification by flash chromatography on silica eluting with 1-5% methanol in dichloromethane afforded the title compound (0.16 g, 67%). MS (ESI+) m/z 480 (M+H)+.

Example 18P 4-(5-cyclopropyl-3-(1H-imidazol-2-yl)-6-(N-isopentylmethylsulfonamido)benzofuran-2-yl)phenyl 1,1,2,2,3,3,4,4,4-nonafluorobutane-1-sulfonate A mixture of Example 18O (0.146 g, 0.304 mmol), 1,1,2,2,3,3,4,4,4-nonafluorobutane-1-sulfonyl fluoride (101 mg, 0.335 mmol), and potassium carbonate (54.7 mg, 0.396 mmol) in N,N-dimethylformamide (3 mL) was stirred for 1 hour. The mixture was partitioned with ethyl acetate and water. The organic layer was washed with brine twice, dried with sodium sulfate, filtered and concentrated. The resulting solid was triturated with hexane and the solid was collected by filtration (0.229 g, 99%). MS (ESI+) m/z 762 (M+H)+.

Example 18Q

N-[2-(4-anilinophenyl)-5-cyclopropyl-3-(1H-imidazol-2-yl)-1-benzofuran-6-yl]-N-(3-methylbutyl)methanesulfonamide In a 2 mL microwave tube were combined Example 18P (100 mg, 0.131 mmol), aniline (0.014 mL, 0.158 mmol), 2-dicyclohexylphosphino-2',4',6'-triisopropylbiphenyl (3.80 mg, 6.56 µmol), palladium(II) acetate (1.474 mg, 6.56 µmol) and cesium carbonate (64.2 mg, 0.197 mmol) in toluene (1 mL). The tube was sealed and the mixture was sparged with nitrogen for 5 minutes, heated by microwave (Personal Chemistry, Emrys Creator, 300 W) at 120° C. for 1 hour, cooled and partitioned into ethyl acetate and water. The organic layer was washed with brine, dried with sodium sulfate, filtered and concentrated. Purification on silica eluting with 1-3% methanol in dichloromethane afforded the title compound as an off-white solid (0.038 g, 52%). $^1$H NMR (400 MHz, DMSO-$d_6$) δ ppm 0.48-0.56 (m, 1H) 0.77-0.88 (m, 7H) 0.94-1.00 (m, 2H) 1.22-1.32 (m, 1H) 1.34-1.42 (m, 1H) 1.57-1.67 (m, 1H) 2.35-2.41 (m, 1H) 3.13 (s, 3H) 3.59-3.69 (m, 1H) 3.69-3.78 (m, 1H) 6.92 (t, J=7.32 Hz, 1H) 6.98 (s, 1H) 7.09 (d, J=8.89 Hz, 2H) 7.13-7.19 (m, 3H) 7.26-7.34 (m, 3H) 7.74-7.81 (m, 3H) 8.56 (s, 1H) 12.33 (s, 1H); MS (ESI+) m/z 555 (M+H)+.

Example 19

3-[3-(5,6-dihydro-4H-1,2,4-oxadiazin-3-yl)-2-(4-methoxyphenyl)pyrazolo[1,5-a]pyridin-5-yl]-4-methyl-N-(1-phenylcyclopropyl)benzamide

Example 19A 2-(4-bromopyridin-2-yl)-1-(4-methoxyphenyl)ethanone

In a 250 mL round-bottomed flask at 0° C. under nitrogen was added methyl 4-methoxybenzoate (Aldrich, 3.32 g, 20.00 mmol) and 4-bromo-2-methylpyridine (Frontier, 1.72 g, 10.00 mmol) in anhydrous tetrahydrofuran (40.0 mL) to give a yellow solution. Lithium hexamethyldisilazide (1 M in tetrahydrofuran, 20 mL, 20 mmol) was added dropwise over 15 minutes via a dropping addition funnel to produce an orange transparent solution that was stirred for 18 hours at ambient temperature. The mixture was partitioned between ethyl acetate and water. The organic layer was washed with brine, dried (Na$_2$SO$_4$), filtered and concentrated to a reddish oil. Purification by flash chromatography on a silica 80 g cartridge eluting with 10-60% ethyl acetate in hexane gave the title compound (2.68 g, 88%). MS (APCI+) m/z 306/308 (M+H)+.

Example 19B 2-(4-bromopyridin-2-yl)-1-(4-methoxyphenyl)ethanone oxime

To a solution of Example 19A (13.41 g, 43.8 mmol) in methanol (231 mL) was added hydroxylamine hydrochloride (15.22 g, 219 mmol) to give a thick slurry. The mixture was treated with a solution of sodium hydroxide (8.76 g, 219 mmol) in water (58 mL), heated at reflux for two hours, cooled and concentrated to a paste. The paste was treated with 100-150 mL of water and stirred for 15 minutes to give a solid that was collected by filtration, washed with water and dried to constant mass to give the title compound as a powder (11.86 g, 84%). MS (ESI+) m/z 321/323 (M+H)+.

Example 19C 5-bromo-2-(4-methoxyphenyl)pyrazolo[1,5-a]pyridine

A slurry of Example 19B (11.86 g, 36.9 mmol) in dimethoxyethane (50 mL) 0° C. under nitrogen was treated dropwise with trifluoroacetic anhydride (5.16 mL, 36.9 mmol) over ten minutes to give a solution that was stirred at ambient temperature for 30 minutes, cooled to 0° C. and treated dropwise over 30 minutes with a solution of triethylamine (10.3 mL, 73.9 mmol) in dimethoxyethane (10 mL). The reaction mixture was stirred for 6 hours at ambient temperature, treated with ferrous chloride (0.049 g, 0.384 mmol), heated at 70° C. for 16 hours and cooled to give a dark colored slurry. The solid was collected by filtration and rinsed with a minimal amount of cold dimethoxyethane to remove the color. The solid was suspended in water (100 mL), stirred for twenty minutes and the solid was collected by filtration and dried to a constant mass to give the title compound (5.76 g, 51.5%). MS (ESI+) m/z 303/305 (M+H)+.

Example 19D 5-bromo-2-(4-methoxyphenyl)pyrazolo[1,5-a]pyridine-3-carbaldehyde To a 500 mL round bottom, 3-neck flask equipped with an overhead mechanical stirrer was added N,N-dimethylformamide (13.0 mL, 168 mmol) in dimethoxyethane (120 mL) at 0° C. under nitrogen. The solution was treated with POCl$_3$ (2.64 mL, 28.4 mmol) at a fast drip, stirred for 20 minutes and treated portion wise with Example 19C (3.91 g, 12.9 mmol). The resulting mixture was stirred at ambient temperature for three hours and concentrated to remove most of the solvent leaving a paste that was slurried in water and carefully neutralized to pH 7 with 1 M aqueous NaOH. The neutralized mixture was stirred for 30 minutes and the solid was collected by filtration, washed with additional portions of water and dried to constant mass to give the title compound (4.08 g, 96%). MS (ESI+) m/z 331/333 (M+H)+.

Example 19E 5-bromo-2-(4-methoxyphenyl)pyrazolo[1,5-a]pyridine-3-carbaldehyde oxime Example 19D (3.00 g, 9.06 mmol) and hydroxylamine hydrochloride (0.944 g, 13.59 mmol) in ethanol (120 mL)/ water (60 mL) was refluxed for 2 hours, cooled and concentrated. The residue was suspended in water and neutralized with sodium bicarbonate. The solid was collected by filtration, washed with water and dried to give the title compound (3.1 g, 99%). MS (ESI+) m/z 346/348 (M+H)$^+$.

Example 19F 5-bromo-2-(4-methoxyphenyl)pyrazolo[1,5-a]pyridine-3-carbonitrile

A mixture of Example 19E (3.09 g, 8.93 mmol) in acetic anhydride (100 mL, 1060 mmol) was heated at 140° C. for 24 hours, cooled and concentrated. The residue was triturated with diethyl ether to give a brown solid that was collected by filtration and dried (2.33 g, 80%). MS (ESI+) m/z 328/330 (M+H)$^+$.

Example 19G (Z)-5-bromo-N'-hydroxy-2-(4-methoxyphenyl)pyrazolo[1,5-a]pyridine-3-carboximidamide In a 20 mL microwave tube were combined Example 19F (492 mg, 1.5 mmol) and hydroxylamine (0.919 mL, 15.00 mmol) in dimethylsulfoxide (10 mL). The vessel was sealed and heated by microwave (Personal Chemistry, Emrys Creator, 300 W) at 130° C. for 3 hours. The mixture was diluted into a 1:1 mixture of ethyl acetate and water and stirred for 5 minutes. The solid at the interface of the layers was collected by filtration and dried to provide the title compound (0.186 g, 34%). The filtrate was placed in a separatory funnel and the layers were separated. The organic layer was washed twice with brine, dried with sodium sulfate, filtered and concentrated to give additional solid (350 mg) that was contaminated with approximately 10% of the primary amide. The total recovery of title compound was 0.536 g (98%). MS (ESI+) m/z 361/363 (M+H)$^+$.

Example 19H 3-(5-bromo-2-(4-methoxyphenyl)pyrazolo[1,5-a]pyridin-3-yl)-1,2,4-oxadiazol-5(4H)-one A mixture of Example 19G (0.74 g, 2.049 mmol), 1,1'-carbonyldiimidazole (0.365 g, 2.254 mmol), and 1,8-diazabicyclo[5.4.0]undec-7-ene (0.340 mL, 2.254 mmol) in dioxane (10 mL) was refluxed for 1 hour, cooled and diluted with 1 M aqueous HCl. The resulting solid was collected by filtration, washed with water and dried. The solid was triturated twice with 1% methanol in dichloromethane to give the title compound (0.62 g, 78%). MS (ESI+) m/z 387/389 (M+H)$^+$.

Example 19I 3-(5-bromo-2-(4-methoxyphenyl)pyrazolo[1,5-a]pyridin-3-yl)-4-(2-chloroethyl)-1,2,4-oxadiazol-5(4H)-one A mixture of Example 19H (0.64 g, 1.653 mmol), 1-bromo-2-chloroethane (0.206 mL, 2.479 mmol), and 1,8-diazabicyclo[5.4.0]undec-7-ene (0.374 mL, 2.479 mmol) in N,N-dimethylacetamide (8 mL) was heated at 100° C. for 20 hours, cooled and partitioned with ethyl acetate and 1 M aqueous HCl. The organic layer was washed with brine twice, dried with sodium sulfate, filtered and concentrated. Purification on a 40 g silica cartridge eluting with 1-2% methanol in dichloromethane provided the title compound as a solid (0.139 g, 19%). MS (ESI+) m/z 449/451 (M+H)$^+$.

Example 19J 3-(5-bromo-2-(4-methoxyphenyl)pyrazolo[1,5-a]pyridin-3-yl)-5,6-dihydro-4H-1,2,4-oxadiazine Example 19I (0.125 g, 0.278 mmol) and 1 M sodium hydroxide (0.695 mL, 0.695 mmol) in ethanol (10 mL) was refluxed for 1 hour, cooled, diluted with water and the resulting solid was collected by filtration. Purification on a 24 g silica cartridge eluting with 2-5% methanol in dichloromethane provided the title compound as a white solid (0.04 g, 37%). MS (ESI+) m/z 387/389 (M+H)$^+$.

Example 19K 3-(3-(5,6-dihydro-4H-1,2,4-oxadiazin-3-yl)-2-(4-methoxyphenyl)pyrazolo[1,5-a]pyridin-5-yl)-4-methylbenzoic acid In a 5 mL microwave tube were combined 4-methyl-3-(4,4,5,5-tetramethyl-1,3,2-dioxaborolan-2-yl)benzoic acid (35.5 mg, 0.136 mmol), Example 19J (35 mg, 0.090 mmol), tetrakis(triphenylphosphine)palladium(0) (10.44 mg, 9.04 µmol) and cesium carbonate (58.9 mg, 0.181 mmol) in dioxane (2.5 mL)/water (0.5 mL). The mixture was sparged with nitrogen for 5 minutes, and the vessel was sealed and heated at 100° C. for 2 hours. The mixture was cooled, filtered, and the filter paper was rinsed with additional dioxane. The filtrate was concentrated to give a solid that was triturated with dichloromethane, collected by filtration, washed with 2 mL of water and dried to a constant mass (0.04 g, 100%). MS (APCI+) m/z 443 (M+H)$^+$.

Example 19L

3-[3-(5,6-dihydro-4H-1,2,4-oxadiazin-3-yl)-2-(4-methoxyphenyl)pyrazolo[1,5-a]pyridin-5-yl]-4-methyl-N-(1-phenylcyclopropyl)benzamide In a 10 mL round-bottomed flask were combined 1-phenylcyclopropanamine, hydrochloric acid (36.8 mg, 0.216 mmol), Example 19K (40 mg, 0.090 mmol), O-(7-azabenzotriazol-1-yl)-N,N,N',N'-tetramethyluronium hexafluorophosphate (82.4 mg, 0.216 mmol) and triethylamine (0.1 mL, 0.724 mmol) in N,N-dimethylformamide (2 mL). The mixture was stirred for 4 hours, diluted with water, stirred for 5 minutes and the solid was collected by filtration. The solid was then purified by chromatography on a 12 g silica cartridge eluting with 1-2% methanol in dichloromethane to give the title compound (31 mg, 65%). $^1$H NMR (400 MHz, DMSO-d$_6$) δ ppm 1.22-1.31 (m, 4H) 2.34 (s, 3H) 3.35-3.39 (m, 2H) 3.82 (s, 3H) 3.92 (t, J=4.50 Hz, 2H) 6.94 (t, J=3.25 Hz, 1H) 7.02 (dd, J=7.10, 1.90 Hz, 1H) 7.04-7.09 (m, 2H) 7.15 (t, J=7.16 Hz, 1H) 7.17-7.31 (m, 4H) 7.46 (d, J=7.81 Hz, 1H) 7.57 (d, J=0.87 Hz, 1H) 7.84-7.91 (m, 4H) 8.79 (d, J=7.26 Hz, 1H) 9.25 (s, 1H); MS (ESI+) m/z 558 (M+H)$^+$.

The compounds of Examples 20-22 can be made from Example 3M in accordance with procedures analogous to those described in Example 3N with the appropriate choice of electrophile.

Example 20

N-[3-(1H-imidazol-2-yl)-2-phenyl-1-benzofuran-6-yl]-N-(1-phenylethyl)methanesulfonamide $^1$H NMR (300 MHz, DMSO-d$_6$) δ ppm 1.57 (d, J=7.35 Hz, 3H) 3.19 (s, 3H) 5.44-5.63 (m, J=6.99 Hz, 1H) 6.85 (dd, J=8.46, 1.84 Hz, 1H) 7.17 (s, 1H) 7.24-7.35 (m, 7H) 7.41-7.53 (m, 4H) 7.82 (dd, J=7.54, 2.02 Hz, 2H) 12.39 (s, 1H); MS (DCI+) m/z 458.1 (M+H)$^+$.

Example 21

N-benzyl-N-[3-(1H-imidazol-2-yl)-2-phenyl-1-benzofuran-6-yl]methanesulfonamide $^1$H NMR (300 MHz, DMSO-d$_6$) δ ppm 3.15 (s, 3H) 4.96 (s, 2H) 7.26 (m, 8H) 7.46 (m, 3H) 7.53 (d, J=8.09 Hz, 1H) 7.80 (d, J=1.84 Hz, 1H) 7.85 (m, 2H) 12.37 (s, 1H); MS (DCI+) m/z 444 (M+H)$^+$.

Example 22

N-{[2-bromo-4-(trifluoromethyl)-1,3-thiazol-5-yl]methyl}-N-[3-(1H-imidazol-2-yl)-2-phenyl-1-benzofuran-6-yl]methanesulfonamide $^1$H NMR (300 MHz, DMSO-d$_6$) δ ppm 3.19 (s, 3H) 5.34 (s, 2H) 7.19 (s, 1H) 7.34 (s, 1H) 7.47 (m, 4H) 7.65 (d, J=8.46 Hz, 1H) 7.87 (m, 2H) 7.93 (d, J=1.84 Hz, 1H) 12.41 (s, 1H); MS (DCI+) m/z 596.9 598.9 (M+H)$^+$.

The compounds of Examples 23-31 can be made via a Suzuki reaction in accordance with procedures analogous to those described in Example 3O.

Example 23

N-[3-(1H-imidazol-2-yl)-2-phenyl-1-benzofuran-6-yl]-N-{[2-(1H-indol-5-yl)methyl}methanesulfonamide $^1$H NMR (300 MHz, DMSO-d$_6$) δ ppm 3.18 (s, 3H) 5.21 (s, 2H) 6.51 (s, 1H) 7.17 (s, br, 1H) 7.31 (s, br, 1H) 7.43 (m, 6H) 7.60 (m, 3H) 7.87 (m, 3H) 8.07 (s, 1H) 11.33 (s, 1H) 12.39 (s, 1H); MS (DCI+) m/z 566 (M+H)$^+$.

Example 24

N-[3-(1H-imidazol-2-yl)-2-phenyl-1-benzofuran-6-yl]-N-({2-[4-(methylsulfinyl)phenyl]-1,3-thiazol-5-yl}methyl)methanesulfonamide $^1$H NMR (300 MHz, DMSO-d$_6$) δ ppm 2.76 (s, 3H) 3.19 (s, 3H) 5.25 (s, 2H) 7.17 (s, 1H) 7.32 (s, 1H) 7.37 (dd, J=8.46, 1.84 Hz, 1H) 7.46 (m, 3H) 7.60 (d, J=8.46 Hz, 1H) 7.73 (s, 1H) 7.76 (d, J=8.46 Hz, 2H) 7.86 (m, 3H) 8.06 (d, J=8.46 Hz, 2H) 12.39 (s, 1H); MS (ESI+) m/z 589 (M+H)$^+$.

Example 25

N-[3-(1H-imidazol-2-yl)-2-phenyl-1-benzofuran-6-yl]-N-{[2-(1-methyl-1H-indol-5-yl)-1,3-thiazol-5-yl]methyl}methanesulfonamide $^1$H NMR (300 MHz, DMSO-d$_6$) δ ppm 3.18 (s, 3H) 3.80 (s, 3H) 5.21 (s, 2H) 6.52 (d, J=3.31 Hz, 1H) 7.17 (s, 1H) 7.32 (s, 1H) 7.44 (m, 6H) 7.60 (m, 2H) 7.68 (dd, J=8.64, 1.65 Hz, 1H) 7.87 (m, 3H) 8.07 (d, J=1.05 Hz, 1H) 12.39 (s, 1H); MS (ESI+) m/z 580 (M+H)$^+$.

Example 26

N-[3-(1H-imidazol-2-yl)-2-phenyl-1-benzofuran-6-yl]-N-{[2-(1-methyl-1H-pyrazol-4-yl)-1,3-thiazol-5-yl]methyl}methanesulfonamide $^1$H NMR (500 MHz, DMSO-d$_6$) δ ppm 3.16 (s, 3H) 3.84 (s, 3H) 5.17 (s, 2H) 7.17 (s, 1H) 7.33 (dd, J=8.47, 1.75 Hz, 2H) 7.47 (m, 4H) 7.59 (d, J=8.39 Hz, 1H) 7.84 (m, 4H) 8.24 (s, 1H) 12.40 (s, 1H); MS (ESI+) m/z 531 (M+H)$^+$.

Example 27

N-{[2-(2,4-di-tert-butoxypyrimidin-5-yl)-1,3-thiazol-5-yl]methyl}-N-[3-(1H-imidazol-2-yl)-2-phenyl-1-benzofuran-6-yl]methanesulfonamide $^1$H NMR (500 MHz, DMSO-d$_6$) δ ppm 1.56 (s, 9H) 1.60 (s, 9H) 3.17 (s, 3H) 5.23 (s, 2H) 7.18 (s, 1H) 7.33 (s, 1H) 7.35 (dd, J=8.39, 1.83 Hz, 1H) 7.46 (m, 3H) 7.61 (d, J=8.39 Hz, 1H) 7.72 (s, 1H) 7.86 (m, 3H) 8.96 (s, 1H) 12.38 (s, 1H); MS (ESI+) m/z 673 (M+H)$^+$.

Example 28

N-({2-[3-(hydroxymethyl)phenyl]-1,3-thiazol-5-yl}methyl)-N-[3-(1H-imidazol-2-yl)-2-phenyl-1-benzofuran-6-yl]methanesulfonamide $^1$H NMR (300 MHz, DMSO-d$_6$) δ ppm 3.19 (s, 3H) 4.54 (d, J=5.88 Hz, 2H) 5.23 (s, 2H) 5.30 (t, J=5.88 Hz, 1H) 7.17 (t, J=1.26 Hz, 1H) 7.41 (m, 7H) 7.59 (d, J=8.09 Hz, 1H) 7.66 (s, 1H) 7.73 (m, 1H) 7.85 (m, 4H) 12.39 (s, 1H); MS (ESI+) m/z 557 (M+H)$^+$.

Example 29

N-{[2-(2,4-dioxo-1,2,3,4-tetrahydropyrimidin-5-yl)-1,3-thiazol-5-yl]methyl}-N-[3-(1H-imidazol-2-yl)-2-phenyl-1-benzofuran-6-yl]methanesulfonamide $^1$H NMR (300 MHz, DMSO-d$_6$) δ ppm 3.16 (s, 3H) 5.17 (s, 2H) 7.17 (s, 1H) 7.32 (m, 2H) 7.46 (m, 3H) 7.52 (s, 1H) 7.57 (d, J=8.46 Hz, 1H) 7.79 (d, J=1.47 Hz, 1H) 7.86 (m, 2H) 8.19 (s, 1H) 11.53 (s, br, 2H) 12.41 (s, 1H); MS (DCI+) m/z 561 (M+H)$^+$.

Example 30

N-[3-(1H-imidazol-2-yl)-2-phenyl-1-benzofuran-6-yl]-N-[2-(1-methyl-1H-benzimidazol-6-yl)-1,3-thiazol-5-yl]methyl methanesulfonamide $^1$H NMR (300 MHz, DMSO-d$_6$) δ ppm 3.19 (s, 3H) 3.88 (s, 3H) 5.24 (s, 2H) 7.16 (t, J=1.38 Hz, 1H) 7.31 (m, 1H) 7.37 (dd, J=8.46, 1.84 Hz, 1H) 7.46 (m, 3H) 7.60 (d, J=8.46 Hz, 1H) 7.71 (m, 3H) 7.85 (m, 3H) 8.09 (d, J=1.23 Hz, 1H) 8.27 (s, 1H) 12.39 (s, 1H); MS (ESI+) m/z 581 (M+H)⁺.

Example 31

N-[5-cyclopropyl-2-(4-fluorophenyl)-3-(1H-imidazol-2-yl)-1-benzofuran-6-yl]-N-{[2-(1H-indol-5-yl)-1,3-thiazol-5-yl]methyl}methanesulfonamide ¹H NMR (300 MHz, DMSO-$d_6$) δ ppm 0.35 (m, 1H) 0.75 (m, 2H) 0.92 (m, 1H) 2.27 (m, 1H) 3.28 (s, 3H) 5.15 (s, 2H) 6.52 (m, 1H) 7.01 (s, 1H) 7.16 (s, 1H) 7.32 (m, 3H) 7.43 (m, 2H) 7.50 (s, 1H) 7.63 (dd, J=8.46, 1.84 Hz, 1H) 7.85 (s, 1H) 8.01 (m, 2H) 8.08 (s, 1H) 11.34 (s, 1H) 12.41 (s, 1H); MS (DCI+) m/z 624.2 (M+H)⁺.

Example 32

N-[3-(1H-imidazol-2-yl)-2-phenyl-1-benzofuran-6-yl]-N-[3-(trifluoromethyl)benzyl]methanesulfonamide Example 32 can be prepared from Example 3G by analogy with the general methods of the sequence 3H through 3L. ¹H NMR (300 MHz, DMSO-$d_6$) δ ppm 3.20 (s, 3H), 5.10 (s, 2H), 7.42 (dd, J=8.46, 1.84 Hz, 1H), 7.49-7.69 (m, 10H), 7.74-7.85 (m, 2H), 7.98 (d, J=1.84 Hz, 1H); MS (ESI+) m/z 512 (M+H)⁺; MS (ESI−) m/z 510 (M−H)⁻.

The compounds of Examples 33-83, 85, and 86 can be made from Example 1O using procedures analogous to those described in the above alkylation reaction of Example 5A with the appropriate choice of electrophile.

Example 33 ethyl N-[5-cyclopropyl-2-(4-fluorophenyl)-3-(1H-imidazol-2-yl)-1-benzofuran-6-yl]-N-ethylsulfonyl)glycinate ¹H NMR (300 MHz, DMSO-$d_6$) δ ppm 0.63 (s, 1H) 0.84 (s, 1H) 0.94-1.08 (m, 2H) 1.20 (t, J=6.99 Hz, 3H) 2.28-2.40 (m, 1H) 3.27 (s, 3H) 4.09-4.18 (m, 2H) 4.23-4.35 (m, 1H) 4.70-4.81 (m, 1H) 7.13 (s, 1H) 7.18 (s, 1H) 7.29-7.39 (m, 3H) 7.88 (s, 1H) 7.98-8.06 (m, 2H) 12.42 (s, 1H); MS (ESI+) m/z 498 (M+H)⁺.

Example 34

N-(cyclopentylmethyl)-N-[5-cyclopropyl-2-(4-fluorophenyl)-3-(1H-imidazol-2-yl)-1-benzofuran-6-yl]methanesulfonamide ¹H NMR (300 MHz, DMSO-$d_6$) δ ppm 0.53-2.07 (m, 13H) 2.40-2.48 (m, 1H) 3.12 (s, 3H) 3.61 (d, J=6.99 Hz, 2H) 7.02 (s, 1H) 7.21-7.39 (m, 4H) 7.89 (s, 1H) 8.01 (dd, J=8.82, 5.52 Hz, 2H) 12.44 (s, 1H); MS (ESI+) m/z 494 (M+H)⁺.

Example 35

N-[5-cyclopropyl-2-(4-fluorophenyl)-3-(1H-imidazol-2-yl)-1-benzofuran-6-yl]-N-(2-phenylethyl)methanesulfonamide ¹H NMR (300 MHz, DMSO-$d_6$) δ ppm 0.48-0.64 (m, 1H) 0.79-1.03 (m, 3H) 2.27-2.40 (m, 1H) 2.67-2.94 (m, 2H) 3.13 (s, 3H) 3.85-3.99 (m, 2H) 7.10 (s, 1H) 7.17-7.40 (m, 9H) 7.87 (s, 1H) 7.98-8.08 (m, 2H) 12.44 (s, 1H); MS (ESI+) m/z 516 (M+H)⁺.

Example 36

N²-[5-cyclopropyl-2-(4-fluorophenyl)-3-(1H-imidazol-2-yl)-1-benzofuran-6-yl]-N²-(methylsulfonyl)glycinamide ¹H NMR (300 MHz, DMSO-$d_6$) δ ppm 0.57 (s, 1H) 0.83-1.07 (m, 3H) 2.25-2.38 (m, 1H) 3.39 (s, 3H) 3.94-4.03 (m, 1H) 4.59 (d, J=16.18 Hz, 1H) 7.15-7.21 (m, 3H) 7.29-7.38 (m, 3H) 7.47 (s, 1H) 7.91 (s, 1H) 7.96-8.16 (m, 2H) 12.42 (s, 1H); MS (ESI+) m/z 469 (M+H)⁺.

Example 37

N-[5-cyclopropyl-2-(4-fluorophenyl)-3-(1H-imidazol-2-yl)-1-benzofuran-6-yl]-N-(3-phenoxypropyl)methanesulfonamide ¹H NMR (300 MHz, DMSO-$d_6$) δ ppm 0.41-0.62 (m, 1H) 0.84-1.07 (m, 3H) 1.85-1.96 (m, 2H) 2.31-2.46 (m, 1H) 3.17 (s, 3H) 3.72-4.12 (m, 4H) 6.77-6.96 (m, 3H) 7.09 (s, 1H) 7.17-7.43 (m, 6H) 7.91 (s, 1H) 8.02 (dd, J=8.64, 5.70 Hz, 2H) 12.42 (s, 1H).). MS (ESI+) m/z 546 (M+H)⁺.

Example 38

N-[5-cyclopropyl-2-(4-fluorophenyl)-3-(1H-imidazol-2-yl)-1-benzofuran-6-yl]-N-tetrahydro-2H-pyran-4-ylmethyl)methanesulfonamide ¹H NMR (300 MHz, DMSO-$d_6$) δ ppm 0.39-0.61 (m, 1H) 0.75-1.08 (m, 3H) 1.11-1.35 (m, 2H) 1.45-1.64 (m, 2H) 1.86 (d, J=12.87 Hz, 1H) 2.31-2.48 (m, 1H) 3.13 (s, 3H) 3.12-3.23 (m, 2H) 3.48-3.71 (m, 2H) 3.72-3.95 (m, 2H) 7.04 (s, 1H) 7.18 (s, 1H) 7.28-7.41 (m, 3H) 7.91 (s, 1H) 7.97-8.04 (m, 2H) 12.42 (s, 1H); MS (ESI+) m/z 510 (M+H)⁺.

Example 39

N-butyl-N-[5-cyclopropyl-2-(4-fluorophenyl)-3-(1H-imidazol-2-yl)-1-benzofuran-6-yl]methanesulfonamide ¹H NMR (300 MHz, DMSO-$d_6$) δ ppm 0.47-0.61 (m, 1H) 0.84 (t, J=7.17 Hz, 4H) 0.99 (dd, J=8.46, 2.21 Hz, 2H) 1.20-1.63 (m, 4H) 2.34-2.46 (m, 1H) 3.14 (s, 3H) 3.58-3.80 (m, 2H) 7.07 (s, 1H) 7.18 (s, 1H) 7.30-7.40 (m, 3H) 7.86 (s, 1H) 7.97-8.13 (m, 2H) 12.42 (s, 1H); MS (ESI+) m/z 468 (M+H)⁺.

Example 40

N-[5-cyclopropyl-2-(4-fluorophenyl)-3-(1H-imidazol-2-yl)-1-benzofuran-6-yl]-N-(4-methylpentyl)methanesulfonamide ¹H NMR (300 MHz, DMSO-$d_6$) δ ppm 0.48-0.62 (m, 1H) 0.80 (dd, J=6.62, 3.31 Hz, 6H) 0.84-0.90 (m, 1H) 0.99 (dd, J=8.27, 2.39 Hz, 2H) 1.09-1.30 (m, 2H) 1.38-1.60 (m, 3H) 2.33-2.46 (m, 1H) 3.13 (s, 3H) 3.55-3.74 (m, 2H) 7.06 (s, 1H) 7.18 (s, 1H) 7.29-7.38 (m, 3H) 7.86 (s, 1H) 7.98-8.04 (m, 2H) 12.42 (s, 1H); MS (ESI+) m/z 496 (M+H)⁺.

Example 41

N-[5-cyclopropyl-2-(4-fluorophenyl)-3-(1H-imidazol-2-yl)-1-benzofuran-6-yl]-N-(3-phenylpropyl)methanesulfonamide $^1$H NMR (300 MHz, DMSO-d$_6$) δ ppm 0.45-0.59 (m, 1H) 0.78-0.89 (m, 1H) 0.92-1.05 (m, 2H) 1.69-1.82 (m, 2H) 2.35-2.46 (m, 1H) 2.59-2.67 (m, 2H) 3.15 (s, 3H) 3.68-3.76 (m, 2H) 7.07 (s, 1H) 7.11-7.28 (m, 6H) 7.29-7.38 (m, 3H) 7.87 (s, 1H) 7.98-8.05 (m, 2H) 12.41 (s, 1H); MS (ESI+) m/z 530 (M+H)$^+$.

Example 42

N-(4-{[tert-butyl(dimethyl)silyl]oxy}butyl)-N-[5-cyclopropyl-2-(4-fluorophenyl)-3-(1H-imidazol-2-yl)-1-benzofuran-6-yl]methanesulfonamide $^1$H NMR (300 MHz, DMSO-d$_6$) δ ppm −0.06 (s, 3H) −0.05 (s, 3H) 0.44-0.59 (m, 1H) 0.76 (s, 9H) 0.80-1.04 (m, 3H) 1.47 (s, 4H) 2.31-2.43 (m, 1H) 3.12 (s, 3H) 3.48-3.78 (m, 4H) 7.06 (s, 1H) 7.17 (s, 1H) 7.28-7.37 (m, 3H) 7.83 (s, 1H) 7.96-8.02 (m, 2H) 12.39 (s, 1H); MS (ESI+) m/z 598 (M+H)$^+$.

Example 43

N-[5-cyclopropyl-2-(4-fluorophenyl)-3-(1H-imidazol-2-yl)-1-benzofuran-6-yl]-N-(2-phenoxyethyl)methanesulfonamide $^1$H NMR (300 MHz, DMSO-d$_6$) δ ppm 0.42-0.56 (m, 1H) 0.77-1.06 (m, 3H) 2.32-2.42 (m, 1H) 3.25 (s, 3H) 3.97-4.24 (m, 4H) 6.84-6.98 (m, 3H) 7.08 (s, 1H) 7.18 (s, 1H) 7.23-7.38 (m, 5H) 7.81 (s, 1H) 7.92-8.08 (m, 2H) 12.41 (s, 1H); MS (ESI+) m/z 532 (M+H)$^+$.

Example 44

N-[5-cyclopropyl-2-(4-fluorophenyl)-3-(1H-imidazol-2-yl)-1-benzofuran-6-yl]-N-(4,4,4-trifluorobutyl)methanesulfonamide $^1$H NMR (300 MHz, DMSO-d$_6$) δ ppm 0.40-0.68 (m, 1H) 0.83-1.09 (m, 3H) 1.55-1.78 (m, 2H) 2.18-2.46 (m, 3H) 3.18 (s, 3H) 3.66-3.89 (m, 2H) 7.08 (s, 1H) 7.18 (s, 1H) 7.29-7.42 (m, 3H) 7.90 (s, 1H) 8.01 (dd, J=9.19, 5.52 Hz, 2H) 12.42 (s, 1H); MS (APCI+) m/z 522 (M+H)$^+$.

Example 45

N-(cyclohexylmethyl)-N-[5-cyclopropyl-2-(4-fluorophenyl)-3-(1H-imidazol-2-yl)-1-benzofuran-6-yl]methanesulfonamide $^1$H NMR (300 MHz, DMSO-d$_6$) δ ppm 0.46-0.61 (m, 1H) 0.81-2.20 (m, 15H) 3.11 (s, 3H) 3.45-3.70 (m, 2H) 7.04 (s, 1H) 7.18 (s, 1H) 7.29-7.39 (m, 3H) 7.90 (s, 1H) 7.98-8.08 (m, 2H) 12.42 (s, 1H); MS (ESI+) m/z 508 (M+H)$^+$.

Example 46

5-{[5-cyclopropyl-2-(4-fluorophenyl)-3-(1H-imidazol-2-yl)-1-benzofuran-6-yl](methylsulfonyl)amino}pentyl acetate $^1$H NMR (300 MHz, DMSO-d$_6$) δ ppm 0.44-0.61 (m, J=5.52 Hz, 1H) 0.72-0.90 (m, 1H) 0.99 (d, J=8.46 Hz, 2H) 1.28-1.60 (m, 6H) 1.95 (s, 3H) 2.34-2.44 (m, 1H) 3.14 (s, 3H) 3.59-3.79 (m, 2H) 3.94 (t, J=6.43 Hz, 2H) 7.07 (s, 1H) 7.18 (s, 1H) 7.30-7.38 (m, 3H) 7.86 (s, 1H) 8.01 (dd, J=8.82, 5.52 Hz, 2H) 12.41 (s, 1H); MS (ESI+) m/z 540 (M+H)$^+$.

Example 47

N-[5-cyclopropyl-2-(4-fluorophenyl)-3-(1H-imidazol-2-yl)-1-benzofuran-6-yl]-N-(2-methoxyethyl)methanesulfonamide $^1$H NMR (300 MHz, DMSO-d$_6$) δ ppm 0.58-0.72 (m, 1H) 0.77-0.94 (m, 1H) 0.96-1.04 (m, 2H) 2.32-2.43 (m, 1H) 3.19 (s, 3H) 3.23 (s, 3H) 3.39 (t, J=5.52 Hz, 2H) 3.73-3.96 (m, 2H) 7.14 (s, 1H) 7.36-7.45 (m, 2H) 7.62-7.69 (m, 2H) 7.90 (d, J=6.62 Hz, 3H); MS (ESI+) m/z 470 (M+H)$^+$.

Example 48

N-[5-cyclopropyl-2-(4-fluorophenyl)-3-(1H-imidazol-2-yl)-1-benzofuran-6-yl]-N-[2-(tetrahydro-2H-pyran-4-yl)ethyl]methanesulfonamide $^1$H NMR (300 MHz, DMSO-d$_6$) δ ppm 0.38-1.76 (m, 11H) 2.34-2.46 (m, 1H) 3.14 (s, 3H) 3.18-3.28 (m, 2H) 3.59-3.87 (m, 4H) 7.06 (s, 1H) 7.18 (s, 1H) 7.27-7.39 (m, 3H) 7.88 (s, 1H) 8.01 (dd, J=8.82, 5.52 Hz, 2H) 12.42 (s, 1H); MS (ESI+) m/z 524 (M+H)$^+$.

Example 49

N-(3-cyanopropyl)-N-[5-cyclopropyl-2-(4-fluorophenyl)-3-(1H-imidazol-2-yl)-1-benzofuran-6-yl]methanesulfonamide $^1$H NMR (300 MHz, DMSO-d$_6$) δ ppm 0.43-0.61 (m, 1H) 0.85-1.11 (m, 3H) 1.70-1.85 (m, 2H) 2.27-2.44 (m, 1H) 2.60 (t, J=7.17 Hz, 2H) 3.18 (s, 3H) 3.65-3.87 (m, 2H) 7.10 (s, 1H) 7.19 (s, 1H) 7.30-7.38 (m, 3H) 7.91 (s, 1H) 7.99-8.05 (m, 2H) 12.42 (s, 1H); MS (ESI+) m/z 479 (M+H)$^+$.

Example 50 ethyl 5-{[5-cyclopropyl-2-(4-fluorophenyl)-3-(1H-imidazol-2-yl)-1-benzofuran-6-yl](methylsulfonyl)amino}pentanoate $^1$H NMR (500 MHz, DMSO-d$_6$) δ ppm 0.49-0.58 (m, 1H) 0.85 (dd, J=8.09, 4.12 Hz, 1H) 0.98 (dd, J=8.32, 2.06 Hz, 2H) 1.09-1.13 (m, 3H) 1.38-1.64 (m, 4H) 2.24-2.28 (m, 2H) 2.34-2.43 (m, 2H) 3.14 (s, 3H) 3.59-3.77 (m, 2H) 3.97-4.02 (m, 2H) 7.07 (s, 1H) 7.18 (s, 1H) 7.30-7.37 (m, 3H) 7.85 (s, 1H) 7.97-8.07 (m, 2H) 12.42 (s, 1H); MS (ESI+) m/z 540 (M+H)$^+$.

Example 51

N-[5-cyclopropyl-2-(4-fluorophenyl)-3-(1H-imidazol-2-yl)-1-benzofuran-6-yl]-Nyrrolidin-3-ylmethyl)methanesulfonamide $^1$H NMR (trifluoroacetic acid salt)(300 MHz, DMSO-d$_6$) δ ppm 0.50-0.71 (m, 1H) 0.92-1.12 (m, 3H) 7.11 (s, 1H) 7.32-7.49 (m, 2H) 7.68 (dd, J=8.46, 5.52 Hz, 2H) 7.81 (s, 2H) 8.02 (d, J=4.41 Hz, 1H) 8.72 (s, 2H); MS (ESI+) m/z 495.1 (M+H)$^+$ (ESI−) m/z 493.2 (M−H)$^-$.

Example 52

N-[5-cyclopropyl-2-(4-fluorophenyl)-3-(1H-imidazol-2-yl)-1-benzofuran-6-yl]-N-isopropylmethanesulfonamide $^1$H NMR (trifluoroacetic acid salt)(300 MHz, DMSO-d$_6$) δ ppm 0.66 (d, J=4.78 Hz, 1H) 0.86-1.07 (m, 3H) 1.11 (d, J=6.62 Hz, 3H) 1.29 (d, J=6.62 Hz, 3H) 2.32-2.44 (m, 1H) 3.18 (s, 3H) 4.37-4.54 (m, 1H) 7.06 (s, 1H) 7.35-7.46 (m, 2H) 7.67 (dd, J=8.82, 5.15 Hz, 2H) 7.82 (s, 1H) 7.87 (s, 2H); MS (ESI+) m/z 454.1 (M+H)$^+$ (ESI−) m/z 452.1 (M−H)$^−$.

Example 53

N-[5-cyclopropyl-2-(4-fluorophenyl)-3-(1H-imidazol-2-yl)-1-benzofuran-6-yl]-N-yclopropylmethyl)methanesulfonamide $^1$H NMR (trifluoroacetic acid salt) (300 MHz, DMSO-d$_6$) δ ppm 0.02-0.21 (m, 2H) 0.35-0.45 (m, 2H) 0.57-0.70 (m, 1H) 0.85-1.09 (m, 4H) 3.17 (s, 3H) 7.13 (s, 1H) 7.42 (q, J=8.58 Hz, 2H) 7.67 (dd, J=8.82, 5.52 Hz, 2H) 7.85 (s, 2H) 7.96 (s, 1H); MS (ESI+) m/z 466.1 (M+H)$^+$, m/z 931.3 (2M+H)$^+$, (ESI−) m/z 464.1 (M−H)$^−$, m/z 929.1 (2M−H)$^−$.

Example 54

N-[5-cyclopropyl-2-(4-fluorophenyl)-3-(1H-imidazol-2-yl)-1-benzofuran-6-yl]-N-(3-methylbut-2-en-1-yl)methanesulfonamide $^1$H NMR (trifluoroacetic acid salt) (300 MHz, DMSO-d$_6$) δ ppm 0.54 (d, J=5.52 Hz, 1H) 0.83-1.06 (m, 3H) 1.45 (s, 3H) 1.60 (s, 3H) 2.37 (t, J=5.33 Hz, 1H) 3.18 (s, 3H) 4.29 (t, J=7.91 Hz, 2H) 5.24 (s, 1H) 7.11 (s, 1H) 7.35-7.46 (m, 2H) 7.58-7.68 (m, 2H) 7.90 (s, 2H) 7.97 (s, 1H); MS (ESI+) m/z 480.1, 959.3 (M+H)$^+$, (2M+H)$^+$ (ESI−) m/z 478.1 (M−H)$^−$.

Example 55

N-[5-cyclopropyl-2-(4-fluorophenyl)-3-(1H-imidazol-2-yl)-1-benzofuran-6-yl]-N-[(2,2-difluorocyclopropyl)methyl]methanesulfonamide $^1$H NMR (trifluoroacetic acid salt) (300 MHz, DMSO-d$_6$) δ ppm 0.53-0.70 (m, 1H) 0.83-1.11 (m, 3H) 1.14-1.33 (m, 1H) 1.51-1.70 (m, 1H) 1.79-2.03 (m, 1H) 2.26-2.47 (m, 1H) 3.22 (d, J=6.62 Hz, 3H) 3.90-4.13 (m, 2H) 7.14 (d, J=8.09 Hz, 1H) 7.33-7.49 (m, 2H) 7.68 (dd, J=8.09, 5.52 Hz, 2H) 7.84 (s, 2H) 7.98 (d, J=6.25 Hz, 1H); MS (ESI+) m/z 502.1, 1003.2 (M+H)$^+$, (2M+H)$^+$ (ESI−) m/z 500.1 (m−H)$^−$.

Example 56

N-[5-cyclopropyl-2-(4-fluorophenyl)-3-(1H-imidazol-2-yl)-1-benzofuran-6-yl]-N-ethylmethanesulfonamide $^1$H NMR (trifluoroacetic acid salt) (300 MHz, DMSO-d$_6$) δ ppm 0.60 (s, 1H) 0.90-1.12 (m, 6H) 2.32-2.41 (m, 1H) 3.17 (s, 3H) 7.15 (s, 1H) 7.35-7.47 (m, 2H) 7.60-7.71 (m, 2H) 7.89 (s, 2H) 7.96 (s, 1H); MS (ESI+) m/z 440.2 (M+H)$^+$, m/z 879.0 (2M+H)$^+$ (ESI−) m/z 438.0 (M−H)$^−$.

Example 57

N-allyl-N-[5-cyclopropyl-2-(4-fluorophenyl)-3-(1H-imidazol-2-yl)-1-benzofuran-6-yl]methanesulfonamide $^1$H NMR (trifluoroacetic acid salt) (300 MHz, DMSO-d$_6$) δ ppm 0.60 (d, J=6.25 Hz, 1H) 0.81-1.07 (m, 3H) 2.28-2.39 (m, 1H) 3.21 (s, 3H) 4.31 (d, J=6.62 Hz, 2H) 5.00-5.16 (m, 2H) 5.81-5.97 (m, 1H) 7.13 (s, 1H) 7.35-7.45 (m, 2H) 7.66 (dd, J=8.82, 5.52 Hz, 2H) 7.85 (s, 2H) 7.93 (s, 1H); MS (ESI+) m/z 452.1, 903.0 (M+H)$^+$, (2M+H)$^+$, (ESI−) m/z 450.0 (M−H)$^−$.

Example 58

N-[5-cyclopropyl-2-(4-fluorophenyl)-3-(1H-imidazol-2-yl)-1-benzofuran-6-yl]-N-[2-(morpholin-4-yl)ethyl]methanesulfonamide $^1$H NMR (300 MHz, DMSO-d$_6$) δ ppm 0.53-0.64 (m, 1H) 0.82 (s, 1H) 0.97-1.02 (m, 2H) 2.26-2.46 (m, 7H) 3.22 (s, 3H) 3.53 (s, 4H) 3.79 (d, J=28.31 Hz, 2H) 7.08 (s, 1H) 7.18 (s, 1H) 7.24-7.47 (m, 3H) 7.84 (s, 1H) 7.92-8.09 (m, 2H) 12.42 (s, 1H); MS (ESI+) m/z 525.1 (M+H)$^+$, (ESI−) m/z 523.1 (M−H)$^−$.

Example 59

N-[5-cyclopropyl-2-(4-fluorophenyl)-3-(1H-imidazol-2-yl)-1-benzofuran-6-yl]-N-[3-(dimethylamino)propyl]methanesulfonamide $^1$H NMR (300 MHz, DMSO-d$_6$) δ ppm 0.48-0.62 (m, 1H) 0.78-0.91 (m, 1H) 0.96-1.03 (m, 2H) 1.46-1.67 (m, 2H) 2.05 (s, 6H) 2.16-2.29 (m, 2H) 2.33-2.44 (m, 1H) 3.15 (s, 3H) 3.57-3.84 (m, 2H) 7.07 (s, 1H) 7.16-7.22 (m, 1H) 7.26-7.43 (m, 3H) 7.87 (s, 1H) 7.97-8.06 (m, 2H) 12.42 (s, 1H); MS (ESI+) m/z 497.1 (M+H)$^+$, (ESI−) m/z 495.1, 991.7 (M−H)$^−$, (2M−H)$^−$.

Example 60

N-[5-cyclopropyl-2-(4-fluorophenyl)-3-(1H-imidazol-2-yl)-1-benzofuran-6-yl]-N-[3-(morpholin-4-yl)propyl]methanesulfonamide $^1$H NMR (300 MHz, DMSO-d$_6$) δ ppm 0.52-0.61 (m, 1H) 0.78-1.05 (m, 3H) 1.60 (d, J=6.99 Hz, 2H) 2.20-2.44 (m, 7H) 3.15 (s, 3H) 3.51 (t, J=4.41 Hz, 4H) 3.59-3.84 (m, 2H) 7.07 (s, 1H) 7.18 (s, 1H) 7.27-7.46 (m, 3H) 7.87 (s, 1H) 7.94-8.11 (m, 2H) 12.42 (s, 1H); MS (ESI+) m/z 539.2 (M+H)$^−$ (ESI−) m/z 537.2 (M−H) m/z 1075.5 (2M−H)$^−$.

Example 61

N-[5-cyclopropyl-2-(4-fluorophenyl)-3-(1H-imidazol-2-yl)-1-benzofuran-6-yl]-N-[2-(1,1-dioxidotetrahydrothiophen-3-yl)ethyl]methanesulfonamide $^1$H NMR (300 MHz, DMSO-d$_6$) δ ppm 0.48-0.61 (m, 1H) 0.88 (d, J=5.52 Hz, 1H) 1.00 (d, J=8.09 Hz, 2H) 1.47-1.80 (m, 3H) 2.09-2.46 (m, J=6.62 Hz, 3H) 2.63-2.78 (m, 1H) 2.91-3.28 (m, 6H) 3.60-3.81 (m, 2H) 7.08 (d, J=1.47 Hz, 1H) 7.19

(s, 1H) 7.26-7.45 (m, 3H) 7.88 (d, J=2.57 Hz, 1H) 7.96-8.06 (m, 2H) 12.42 (s, 1H); MS (ESI+) m/z 558.1 (M+H)$^+$ m/z 1114.8 (2M+H)$^+$ (ESI−) m/z 556.1 (M−H)$^−$ m/z 1113.3 (2M−H)$^−$.

Example 62

N-[5-cyclopropyl-2-(4-fluorophenyl)-3-(1H-imidazol-2-yl)-1-benzofuran-6-yl]-N-{3-[2-(2,5-dimethyl-1H-pyrrol-1-yl)-1,3-thiazol-4-yl]propyl}methanesulfonamide $^1$H NMR (500 MHz, DMSO-d$_6$) δ ppm 0.42-0.60 (m, 1H) 0.83-0.90 (m, 1H) 0.91-1.02 (m, 2H) 1.82-1.90 (m, 2H) 2.04 (s, 6H) 2.37-2.44 (m, 1H) 2.73-2.83 (m, 2H) 3.15 (s, 3H) 3.65-3.82 (m, 2H) 5.78-5.83 (m, 2H) 7.07 (s, 1H) 7.18 (s, 1H) 7.29-7.37 (m, 4H) 7.87 (s, 1H) 7.97-8.06 (m, 2H) 12.41 (s, 1H); MS (ESI+) m/z 630.2, 1259.7 (M+H)$^+$, (2M+H)$^+$ (ESI−) m/z 628.2 (M−H)$^−$.

Example 63

N-(cyanomethyl)-N-[5-cyclopropyl-2-(4-fluorophenyl)-3-(1H-imidazol-2-yl)-1-benzofuran-6-yl]methanesulfonamide $^1$H NMR (300 MHz, DMSO-d$_6$) δ ppm 0.65 (m, 1H) 0.83 (m, 1H) 0.98 (m, 2H) 2.27 (m, 1H) 3.33 (m, 3H) 4.89 (m, 2H) 7.19 (s, 1H) 7.22 (s, 1H) 7.35 (m, 3H) 7.89 (s, 1H) 8.04 (m, 2H) 12.45 (s, 1H); MS (DCI+) m/z 451 (M+H)$^+$.

Example 64

N-[5-cyclopropyl-2-(4-fluorophenyl)-3-(1H-imidazol-2-yl)-1-benzofuran-6-yl]-N-propylmethanesulfonamide $^1$H NMR (300 MHz, DMSO-d$_6$) δ ppm 0.55 (m, 1H) 0.87 (m, 4H) 1.00 (m, 2H) 1.44 (m, 2H) 2.40 (m, 1H) 3.14 (s, 3H) 3.61 (m, 2H) 7.07 (s, 1H) 7.18 (s, 1H) 7.34 (m, 3H) 7.86 (s, 1H) 8.02 (m, 2H) 12.42 (s, 1H); MS (DCI+) m/z 454.2 (M+H)$^+$.

Example 65

N-[5-cyclopropyl-2-(4-fluorophenyl)-3-(1H-imidazol-2-yl)-1-benzofuran-6-yl]-N-(3-hydroxypropyl)methanesulfonamide $^1$H NMR (300 MHz, DMSO-d$_6$) δ ppm 0.54 (m, 1H) 0.86 (m, 1H) 1.00 (m, 2H) 1.61 (m, 2H) 2.37 (m, 1H) 3.15 (s, 3H) 3.43 (m, 2H) 3.74 (m, 2H) 4.48 (t, J=4.96 Hz, 1H) 7.08 (s, 1H) 7.18 (s, 1H) 7.34 (m, 3H) 7.86 (s, 1H) 8.01 (m, 2H) 12.42 (s, 1H); MS (DCI+) m/z 470.2 (M+H)$^+$.

Example 66

N-[5-cyclopropyl-2-(4-fluorophenyl)-3-(1H-imidazol-2-yl)-1-benzofuran-6-yl]-N-isobutylmethanesulfonamide $^1$H NMR (300 MHz, DMSO-d$_6$) δ ppm 0.56 (m, 1H) 0.86 (m, 4H) 0.99 (m, 5H) 1.57 (m, 1H) 2.46 (m, 1H) 3.12 (s, 3H) 3.51 (m, 2H) 7.03 (s, 1H) 7.18 (s, 1H) 7.32 (m, 3H) 7.90 (s, 1H) 8.02 (m, 2H) 12.41 (s, 1H); MS (DCI+) m/z 468.3 (M+H)$^+$.

Example 67

N-[(2-bromo-1,3-thiazol-5-yl)methyl]-N-[5-cyclopropyl-2-(4-fluorophenyl)-3-(1H-imidazol-2-yl)-1-benzofuran-6-yl]methanesulfonamide $^1$H NMR (300 MHz, DMSO-d$_6$) δ ppm 0.32 (m, 1H) 0.75 (m, 2H) 0.95 (m, 1H) 2.18 (m, 1H) 3.27 (s, 3H) 5.10 (m, 2H) 7.02 (s, 1H) 7.18 (s, 1H) 7.34 (m, 3H) 7.43 (s, 1H) 7.81 (s, 1H) 8.02 (m, 2H) 12.41 (s, 1H); MS (DCI+) m/z 587, 589 (M+H)$^+$.

Example 68 methyl 4-{[5-cyclopropyl-2-(4-fluorophenyl)-3-(1H-imidazol-2-yl)-1-benzofuran-6-yl](methylsulfonyl)amino}butanoate $^1$H NMR (300 MHz, DMSO-d$_6$) δ ppm 0.52 (m, 1H) 0.87 (m, 1H) 0.99 (m, 2H) 1.69 (m, 2H) 2.40 (m, 3H) 3.15 (s, 3H) 3.56 (s, 3H) 3.71 (m, 2H) 7.08 (s, 1H) 7.19 (s, 1H) 7.34 (m, 3H) 7.87 (s, 1H) 8.03 (m, 2H) 12.42 (s, 1H); MS (ESI+) m/z 512 (M+H)$^+$.

Example 69

N-[5-cyclopropyl-2-(4-fluorophenyl)-3-(1H-imidazol-2-yl)-1-benzofuran-6-yl]-N-(3-methoxypropyl)methanesulfonamide $^1$H NMR (300 MHz, DMSO-d$_6$) δ ppm 0.54 (m, 1H) 0.86 (m, 1H) 1.00 (m, 2H) 1.66 (m, 2H) 2.38 (m, 1H) 3.15 (s, 3H) 3.18 (s, 3H) 3.38 (m, 2H) 3.74 (m, 2H) 7.08 (s, 1H) 7.18 (s, 1H) 7.35 (m, 3H) 7.88 (s, 1H) 8.03 (m, 2H) 12.42 (s, 1H); MS (ESI+) m/z 484 (M+H)$^+$.

Example 70

N-[5-cyclopropyl-2-(4-fluorophenyl)-3-(1H-imidazol-2-yl)-1-benzofuran-6-yl]-N-pentylmethanesulfonamide $^1$H NMR (300 MHz, DMSO-d$_6$) δ ppm 0.55 (m, 1H) 0.82 (m, 4H) 0.99 (m, 2H) 1.25 (m, 4H) 1.45 (m, 2H) 2.40 (m, 1H) 3.14 (s, 3H) 3.66 (m, 2H) 7.06 (s, 1H) 7.18 (s, 1H) 7.35 (m, 3H) 7.86 (s, 1H) 8.01 (m, 2H) 12.42 (s, 1H); MS (ESI+) m/z 482.1 (M+H)$^+$.

Example 71

N-[5-cyclopropyl-2-(4-fluorophenyl)-3-(1H-imidazol-2-yl)-1-benzofuran-6-yl]-N-hexylmethanesulfonamide $^1$H NMR (300 MHz, DMSO-d$_6$) δ ppm 0.53 (m, 1H) 0.82 (m, 4H) 0.98 (m, 2H) 1.21 (m, 4H) 1.29 (m, 2H) 1.43 (m, 2H) 2.40 (m, 1H) 3.13 (s, 3H) 3.67 (m, 2H) 7.06 (s, 1H) 7.18 (s, 1H) 7.34 (m, 3H) 7.86 (s, 1H) 8.03 (m, 2H) 12.42 (s, 1H); MS (ESI+) m/z 496.1 (M+H)$^+$.

Example 72

N-(2-cyclohexylethyl)-N-[5-cyclopropyl-2-(4-fluorophenyl)-3-(1H-imidazol-2-yl)-1-benzofuran-6-yl]methanesulfonamide $^1$H NMR (300 MHz, DMSO-d$_6$) δ ppm 0.56 (m, 1H) 0.83 (m, 3H) 0.99 (m, 2H) 1.11 (m, 2H) 1.32 (m, 4H) 1.62 (m, 5H)

2.40 (m, 1H) 3.13 (s, 3H) 3.62 (m, 1H) 3.76 (m, 1H) 7.06 (s, 1H) 7.19 (s, 1H) 7.35 (m, 3H) 7.86 (s, 1H) 8.00 (m, 2H) 12.42 (s, 1H); MS (ESI+) m/z 522.2 (M+H)$^+$.

Example 73

N-[5-cyclopropyl-2-(4-fluorophenyl)-3-(1H-imidazol-2-yl)-1-benzofuran-6-yl]-N-(4-oxopentyl)methanesulfonamide $^1$H NMR (300 MHz, DMSO-d$_6$) δ ppm 0.54 (m, 1H) 0.86 (m, 1H) 0.99 (m, 2H) 1.61 (m, 2H) 2.05 (s, 3H) 2.38 (m, 1H) 2.54 (t, J=6.99 Hz, 2H) 3.14 (s, 3H) 3.64 (m, 2H) 7.08 (s, 1H) 7.18 (s, 1H) 7.35 (m, 3H) 7.86 (s, 1H) 8.03 (m, 2H) 12.42 (s, 1H); MS (ESI+) m/z 496.1 (M+H)$^+$.

Example 74

N-[5-cyclopropyl-2-(4-fluorophenyl)-3-(1H-imidazol-2-yl)-1-benzofuran-6-yl]-N-[2-(methylthio)ethyl]methanesulfonamide $^1$H NMR (300 MHz, DMSO-d$_6$) δ ppm 0.53 (m, 1H) 0.84 (m, 1H) 1.01 (m, 2H) 2.05 (s, 3H) 2.40 (m, 1H) 2.62 (m, 2H) 3.20 (s, 3H) 3.86 (t, J=7.72 Hz, 2H) 7.09 (s, 1H) 7.19 (s, 1H) 7.34 (m, 3H) 7.88 (s, 1H) 8.02 (m, 2H) 12.42 (s, 1H); MS (ESI+) m/z 486 (M+H)$^+$.

Example 75

N-[5-cyclopropyl-2-(4-fluorophenyl)-3-(1H-imidazol-2-yl)-1-benzofuran-6-yl]-N-etrahydrofuran-2-ylmethyl)methanesulfonamide $^1$H NMR (300 MHz, DMSO-d$_6$) δ ppm 0.59 (m, 1H) 0.82 (m, 1H) 0.99 (m, 2H) 1.65 (m, 4H) 2.34 (m, 1H) 3.19 (m, 3H) 3.71 (m, 5H) 7.09 (m, 1H) 7.23 (m, 1H) 7.34 (m, 3H) 7.83 (m, 1H) 8.01 (m, 2H) 12.44 (s, 1H); MS (ESI+) m/z 496.1 (M+H)$^+$.

Example 76

N-[5-cyclopropyl-2-(4-fluorophenyl)-3-(1H-imidazol-2-yl)-1-benzofuran-6-yl]-N-(4-methylpent-3-en-1-yl)methanesulfonamide $^1$H NMR (300 MHz, DMSO-d$_6$) δ ppm 0.55 (m, 1H) 0.85 (m, 1H) 0.98 (m, 2H) 1.48 (s, 3H) 1.63 (s, 3H) 2.15 (m, 2H) 2.39 (m, 1H) 3.14 (s, 3H) 3.63 (m, 2H) 5.10 (t, J=6.99 Hz, 1H) 7.07 (s, 1H) 7.19 (s, 1H) 7.34 (m, 3H) 7.85 (s, 1H) 8.02 (m, 2H) 12.42 (s, 1H); MS (ESI+) m/z 494.1 (M+H)$^+$.

Example 77

N-[5-cyclopropyl-2-(4-fluorophenyl)-3-(1H-imidazol-2-yl)-1-benzofuran-6-yl]-N-(5-oxohexyl)methanesulfonamide $^1$H NMR (300 MHz, DMSO-d$_6$) δ ppm 0.53 (m, 1H) 0.86 (m, 1H) 0.99 (m, 2H) 1.45 (m, 4H) 2.03 (s, 3H) 2.38 (m, 3H) 3.14 (s, 3H) 3.67 (m, 2H) 7.07 (s, 1H) 7.18 (s, 1H) 7.35 (m, 3H) 7.85 (s, 1H) 8.02 (m, 2H) 12.42 (s, 1H); MS (DCI+) m/z 510 (M+H)$^+$.

Example 78

N-[5-cyclopropyl-2-(4-fluorophenyl)-3-(1H-imidazol-2-yl)-1-benzofuran-6-yl]-N-[2-(4-methyl-1,3-thiazol-5-yl)ethyl]methanesulfonamide $^1$H NMR (300 MHz, DMSO-d$_6$) δ ppm 0.55 (m, 1H) 0.86 (m, 1H) 0.96 (m, 2H) 2.18 (s, 3H) 2.30 (m, 1H) 3.01 (m, 2H) 3.17 (s, 3H) 3.88 (t, J=7.91 Hz, 2H) 7.09 (s, 1H) 7.20 (s, 1H) 7.33 (m, 3H) 7.87 (s, 1H) 8.03 (m, 2H) 8.82 (s, 1H) 12.43 (s, 1H); MS (ESI+) m/z 537.1 (M+H)$^+$.

Example 79

N-[5-cyclopropyl-2-(4-fluorophenyl)-3-(1H-imidazol-2-yl)-1-benzofuran-6-yl]-N-[3-(morpholin-4-ylsulfonyl)propyl]methanesulfonamide $^1$H NMR (300 MHz, DMSO-d$_6$) δ ppm 0.57 (m, 1H) 0.88 (m, 1H) 1.01 (m, 2H) 1.87 (m, 2H) 2.36 (m, 1H) 3.08 (m, 4H) 3.17 (m, 5H) 3.59 (m, 4H) 3.82 (m, 2H) 7.10 (s, 1H) 7.19 (s, 1H) 7.36 (m, 3H) 7.90 (s, 1H) 8.03 (m, 2H) 12.42 (s, 1H); MS (ESI+) m/z 603 (M+H)$^+$.

Example 80

3-{[5-cyclopropyl-2-(4-fluorophenyl)-3-(1H-imidazol-2-yl)-1-benzofuran-6-yl](methylsulfonyl)amino}propane-1-sulfonamide $^1$H NMR (500 MHz, DMSO-d$_6$) δ ppm 0.60 (m, 1H) 0.87 (m, 1H) 1.03 (m, 2H) 1.89 (m, 2H) 2.37 (m, 1H) 3.05 (m, 2H) 3.17 (s, 3H) 3.78 (m, 2H) 6.80 (s, 2H) 7.10 (s, 1H) 7.18 (s, 1H) 7.38 (m, 3H) 7.86 (s, 1H) 8.03 (m, 2H) 12.42 (s, 1H); MS (ESI+) m/z 533.1 (M+H)$^+$.

Example 81

N-[5-cyclopropyl-2-(4-fluorophenyl)-3-(1H-imidazol-2-yl)-1-benzofuran-6-yl]-N-[2-(pyrrolidin-1-yl)ethyl]methanesulfonamide $^1$H NMR (trifluoroacetic acid salt) (300 MHz, DMSO-d$_6$) δ ppm 0.62 (m, 1H) 1.02 (m, 4H) 1.93 (m, 5H) 2.31 (m, 3H) 2.95-3.08 (m, 2H) 3.10-3.20 (m, 2H) 3.26 (s, 3H) 3.91-4.10 (m, 2H) 7.13-7.23 (m, 1H) 7.41 (t, J=8.82 Hz, 2H) 7.69 (s, 1H) 7.82 (s, 1H) 8.01 (s, 1H) 13.28 (s, 1H); MS (ESI+) m/z 509.1 (M+H)$^+$ (ESI−) m/z 507.1 (M−H)$^−$.

Example 82

N-[5-cyclopropyl-2-(4-fluorophenyl)-3-(1H-imidazol-2-yl)-1-benzofuran-6-yl]-N-[(1,3-dioxo-1,3-dihydro-2H-isoindol-2-yl)methyl]methanesulfonamide $^1$H NMR (trifluoroacetic acid salt)(300 MHz, DMSO-d$_6$) δ ppm 0.54 (d, J=3.68 Hz, 1H) 0.81-0.98 (m, 2H) 2.20 (d, J=5.15 Hz, 2H) 3.09 (s, 3H) 5.64 (d, J=5.88 Hz, 2H) 6.98 (s, 1H) 7.13 (t, J=8.82 Hz, 2H) 7.27-7.45 (m, 2H) 7.61-8.10 (m, 7H) 9.35 (s, 1H); MS (ESI+) m/z 571.1 (M+H)$^+$, (ESI−) m/z 569.1.

Example 83

N-[5-cyclopropyl-2-(4-fluorophenyl)-3-(1H-imidazol-2-yl)-1-benzofuran-6-yl]-N-(4-fluorobutyl)methanesulfonamide $^1$H NMR (300 MHz, DMSO-d$_6$) δ ppm 1.00 (d, J=8.46 Hz, 1H) 1.52 (s, 2H) 1.61-1.81 (m, 2H) 2.32-2.45 (m, 2H) 3.17 (s, 3H) 3.65-3.85 (m, 2H) 4.26-4.40 (m, 2H) 4.49 (t, J=5.88 Hz, 2H) 7.03-7.18 (m, 2H) 7.34-7.48 (m, 2H) 7.67 (dd, J=8.64, 5.70 Hz, 2H) 7.85 (s, 1H) 7.98 (s, 1H) 13.29 (s, 1H); MS (ESI+) m/z 486.0.1 (M+H)$^+$ (ESI–) m/z 484.1 (M–H)$^-$.

Example 84

N-[5-cyclopropyl-2-(4-fluorophenyl)-3-(1H-imidazol-2-yl)-1-benzofuran-6-yl]-N-(3,4-dihydroxy-4-methylpentyl)methanesulfonamide The title compound was prepared by dihydroxylation (OsO$_4$) of Example 76. $^1$H NMR (300 MHz, DMSO-d$_6$) δ ppm 0.53 (m, 1H) 0.85 (m, 1H) 0.98 (m, 8H) 1.44 (m, 1H) 1.75 (m, 1H) 2.37 (m, 1H) 3.12 (m, 4H) 3.77 (m, 2H) 4.10 (s, 1H) 4.48 (m, 1H) 7.06 (m, 1H) 7.21 (s, 1H) 7.34 (m, 3H) 7.86 (s, 1H) 8.05 (m, 2H) 12.42 (s, 1H); MS (ESI+) m/z 528.1 (M+H)$^+$.

Example 85

N-[5-cyclopropyl-2-(4-fluorophenyl)-3-(1H-imidazol-2-yl)-1-benzofuran-6-yl]-N-(3-fluoropropyl)methanesulfonamide $^1$H NMR (trifluoroacetic acid salt)(300 MHz, DMSO-d$_6$) δ ppm 0.49-0.61 (m, 1H) 0.87-1.09 (m, 2H) 1.70-1.95 (m, 2H) 2.30-2.42 (m, 2H) 3.18 (s, 3H) 3.64-4.00 (m, 2H) 4.36-4.49 (m, 1H) 4.50-4.71 (m, 1H) 7.13 (s, 1H) 7.30-7.49 (m, 2H) 7.70 (dd, J=8.64, 5.33 Hz, 3H) 7.80 (s, 1H) 8.01 (s, 1H) 14.21-14.84 (bs, 1H); MS (ESI+) m/z 472 (M+H)$^+$ (ESI–) m/z 470.1 (M–H)$^-$.

Example 86

3-{[5-cyclopropyl-2-(4-fluorophenyl)-3-(1H-imidazol-2-yl)-1-benzofuran-6-yl](methylsulfonyl)amino}-N-methylpropane-1-sulfonamide $^1$H NMR (trifluoroacetic acid salt) (300 MHz, DMSO-d$_6$) δ ppm 0.55-0.80 (m, 1H) 0.88-1.15 (m, 1H) 1.72-1.95 (m, 1H) 2.31-2.43 (m, 2H) 3.03-3.13 (m, 5H) 3.19 (s, 3H) 3.72-3.99 (m, 4H) 6.91 (q, J=4.90 Hz, 1H) 7.15 (s, 1H) 7.33-7.48 (m, 2H) 7.57-7.74 (m, 2H) 7.88 (s, 2H) 8.00 (s, 1H) 14.50 (s, 1H); MS (ESI+) m/z 547.1 (M+H)$^+$ (ESI–) m/z 545.2 (M–H)$^-$.

Example 87

N-[5-cyclopropyl-2-(4-fluorophenyl)-3-(1H-imidazol-2-yl)-1-benzofuran-6-yl]-N-[2-(methylsulfonyl)ethyl]methanesulfonamide The title compound can be prepared by oxidation of Example 74. $^1$H NMR (300 MHz, DMSO-d$_6$) δ ppm 0.57 (m, 1H) 0.89 (m, 1H) 1.02 (m, 2H) 2.31 (m, 1H) 3.03 (s, 3H) 3.24 (s, 3H) 3.45 (m, 2H) 4.12 (m, 2H) 7.14 (s, 1H) 7.20 (s, 1H) 7.36 (m, 3H) 7.91 (s, 2H) 8.03 (s, 1H) 12.42 (s, 1H); MS (ESI+) m/z 18 (M+H)$^+$.

Example 88

N-[5-cyclopropyl-2-(4-fluorophenyl)-3-(1H-imidazol-2-yl)-1-benzofuran-6-yl]-N-(5-hydroxypentyl)methanesulfonamide The title compound can be prepared by saponification of Example 46. $^1$H NMR (300 MHz, DMSO-d$_6$) δ ppm 0.55 (d, J=4.41 Hz, 1H) 0.78-0.91 (m, 1H) 0.99 (d, J=8.46 Hz, 2H) 1.25-1.52 (m, 7H) 2.33-2.45 (m, 1H) 3.14 (s, 4H) 3.59-3.71 (m, 2H) 4.35 (t, J=4.23 Hz, 1H) 7.06 (s, 1H) 7.19 (s, 1H) 7.28-7.40 (m, 3H) 7.86 (s, 1H) 7.97-8.05 (m, 2H) 12.42 (s, 1H); MS (ESI+) m/z 498 (M+H)$^+$.

Example 89

4-{[5-cyclopropyl-2-(4-fluorophenyl)-3-(1H-imidazol-2-yl)-1-benzofuran-6-yl](methylsulfonyl)amino}butanoic acid The title compound can be prepared by saponification of Example 68. $^1$H NMR (300 MHz, DMSO-d$_6$) δ ppm 0.45-0.63 (m, J=4.04 Hz, 1H) 0.79-0.91 (m, 1H) 0.99 (d, J=8.46 Hz, 2H) 1.55-1.75 (m, 2H) 2.24-2.44 (m, 3H) 3.15 (s, 3H) 3.59-3.81 (m, 2H) 7.08 (s, 1H) 7.18 (s, 1H) 7.29-7.38 (m, 3H) 7.87 (s, 1H) 8.02 (dd, J=8.46, 5.52 Hz, 2H) 12.09 (s, 1H) 12.42 (s, 1H); MS (ESI+) m/z 498 (M+H)$^+$.

Example 90

N-[5-cyclopropyl-2-(4-fluorophenyl)-3-(1H-imidazol-2-yl)-1-benzofuran-6-yl]-N-[3-(phenylsulfonyl)propyl]methanesulfonamide The title compound can be prepared by alkylation of Example 1O followed by oxidation of the resultant product. $^1$H NMR (300 MHz, DMSO-d$_6$) δ ppm 0.32-0.52 (m, 1H) 0.77-1.02 (m, 3H) 1.62-1.85 (m, 2H) 2.20-2.34 (m, 1H) 3.14 (s, 3H) 3.34-3.48 (m, 2H) 3.60-3.93 (m, 2H) 7.05 (s, 1H) 7.19 (s, 1H) 7.34 (t, J=8.72 Hz, 2H) 7.37 (s, 1H) 7.55-7.73 (m, 3H) 7.77-7.83 (m, 3H) 8.02 (dd, J=8.92, 5.35 Hz, 2H) 12.41 (s, 1H); MS (ESI+) m/z 594 (M+H)$^+$.

Example 91

5-{[5-cyclopropyl-2-(4-fluorophenyl)-3-(1H-imidazol-2-yl)-1-benzofuran-6-yl](methylsulfonyl)amino}pentanamide The title compound can be prepared from Example 89 by coupling with ammonia. $^1$H NMR (500 MHz, DMSO-d$_6$) δ ppm 0.53-0.66 (m, 1H) 0.87-0.96 (m, 1H) 0.97-1.06 (m, 2H) 1.33-1.66 (m, 4H) 2.01 (t, J=7.10 Hz, 2H) 2.36-2.41 (m, 1H) 3.15 (s, 3H) 3.56-3.77 (m, 2H) 6.68 (s, 1H) 7.12 (s, 1H) 7.20 (s, 1H) 7.35-7.44 (m, 2H) 7.66 (dd, J=8.85, 5.34 Hz, 2H) 7.87 (s, 2H) 7.97 (s, 1H) 11.94-12.07 (m, 1H); MS (ESI+) m/z 511 (M+H)$^+$.

Example 92

5-{[5-cyclopropyl-2-(4-fluorophenyl)-3-(1H-imidazol-2-yl)-1-benzofuran-6-yl](methylsulfonyl)amino}pentanoic acid The title compound can be prepared by saponification of Example 50. $^1$H NMR (500 MHz, DMSO-d$_6$) δ ppm 0.51-0.58 (m, 1H) 0.82-0.90 (m, 1H) 0.95-1.02 (m, 2H) 1.38-1.62

(m, 4H) 2.16-2.22 (m, 2H) 2.34-2.42 (m, 1H) 3.14 (s, 3H) 3.60-3.78 (m, 2H) 7.07 (s, 1H) 7.28-7.38 (m, 4H) 7.86 (s, 1H) 7.96-8.03 (m, 2H) 11.98 (s, 1H) 12.66 (s, 1H); MS (ESI+) m/z 512 (M+H)$^+$.

Example 93

N-[5-cyclopropyl-2-(4-fluorophenyl)-3-(1H-imidazol-2-yl)-1-benzofuran-6-yl]-N-(2,3-dihydroxypropyl)methanesulfonamide The title compound can be prepared by dihydroxylation of Example 57. $^1$H NMR (300 MHz, DMSO-d$_6$) δ ppm 0.43-1.10 (m, 4H) 2.20-2.38 (m, 1H) 3.70-3.86 (m, 1H) 4.52-4.65 (m, 1H) 5.09 (d, J=5.15 Hz, 1H) 7.01-7.13 (m, 1H) 7.18 (s, 1H) 7.26-7.39 (m, 3H) 7.82 (s, 1H) 8.03 (dd, J=8.82, 5.15 Hz, 2H) 12.42 (s, 1H); MS (ESI+) m/z 486.1, 971.2 (M+H)$^+$, (2M+H)$^+$, (ESI−) m/z 484.1, 969.4 (M−H)$^-$, (2M−H)$^-$.

Example 94

N-[5-cyclopropyl-2-(4-fluorophenyl)-3-(1H-imidazol-2-yl)-1-benzofuran-6-yl]-N-(2,3-dihydroxy-3-methylbutyl)methanesulfonamide The title compound can be prepared by dihydroxylation of Example 54. $^1$H NMR (300 MHz, DMSO-d$_6$) δ ppm 0.95-1.09 (m, 8H) 2.25 (s, 1H) 3.13-3.28 (m, 3H) 3.42-4.07 (m, 3H) 4.24-4.33 (m, 1H) 5.17 (d, J=6.25 Hz, 1H) 7.00-7.23 (m, 2H) 7.27-7.43 (m, 3H) 7.79-7.85 (m, 1H) 7.96-8.08 (m, 2H) 12.43 (s, 1H); MS (ESI+) m/z 514.1, 1027.0 (M+H)$^+$, (2M+H)$^+$, (ESI−) m/z 512.1, 1025.4 (M−H)$^-$, (2M−H)$^-$.

Example 95

N-[5-cyclopropyl-2-(4-fluorophenyl)-3-(1H-imidazol-2-yl)-1-benzofuran-6-yl]-N-{3-[(methylsulfonyl)amino]propyl}methanesulfonamide The title compound can be prepared in three steps from Example 1O by alkylation with 3-bromopropylphthalimide; cleavage of the phthalimide with hydrazine; and reaction of the resultant primary amine with methanesulfonyl chloride. $^1$H NMR (trifluoroacetic acid salt) (300 MHz, DMSO-d$_6$) δ ppm 0.60 (d, J=6.62 Hz, 1H) 0.88-1.09 (m, 3H) 1.52-1.75 (m, 2H) 2.32-2.41 (m, 1H) 2.85 (s, 3H) 2.99 (q, J=6.62 Hz, 2H) 3.18-3.20 (m, 3H) 6.99 (t, J=5.88 Hz, 1H) 7.14 (s, 1H) 7.36-7.45 (m, 2H) 7.66 (dd, J=8.82, 5.52 Hz, 2H) 7.87 (s, 2H) 7.98 (s, 1H); MS (ESI+) m/z 547.1, 1093.3 (M+H)$^+$, (2M+H)$^+$, (ESI−) m/z 545.1, 1091.5 (M−H)$^-$, (2M−H)$^-$.

Example 96

N-[5-cyclopropyl-2-(4-fluorophenyl)-3-(1H-imidazol-2-yl)-1-benzofuran-6-yl]-N-[2-(ethylsulfonyl)ethyl]methanesulfonamide The title compound can be prepared from Example 1O by alkylation with 2-(ethylthio)ethyl 4-methylbenzenesulfonate and oxidation of the resultant product with 2KHSO$_5$.KHSO$_4$.K$_2$SO$_4$. $^1$H NMR (300 MHz, DMSO-d$_6$) δ ppm 0.56 (d, J=5.42 Hz, 1H) 0.80-1.09 (m, 3H) 1.18 (t, J=7.29 Hz, 3H) 2.22-2.39 (m, 1H) 3.15 (q, J=7.46 Hz, 2H) 3.24 (s, 3H) 3.42 (dd, J=10.00, 5.59 Hz, 1H) 3.87-4.24 (m, 2H) 7.14 (s, 1H) 7.19 (s, 1H) 7.27-7.41 (m, 3H) 7.92 (s, 1H) 7.96-8.08 (m, 2H) 12.41 (s, 1H); MS (ESI+) m/z 532.1, 1063.2 (M+H)$^{-1}$, (2M+H)$^+$, (ESI−) m/z 530.1, 1061.6 (M−H)$^-$, (2M−H)$^-$.

Example 97

N-[2-(2-amino-1,3-thiazol-4-yl)ethyl]-N-[5-cyclopropyl-2-(4-fluorophenyl)-3-(1H-imidazol-2-yl)-1-benzofuran-6-yl]methanesulfonamide The title compound can be prepared from Example 1O by alkylation with 2-(2-(2,5-dimethyl-1H-pyrrol-1-yl)thiazol-4-yl)ethyl 4-methylbenzenesulfonate and reaction of the resultant product with hydroxylamine hydrochloride. $^1$H NMR (trifluoroacetic acid salt)(400 MHz, DMSO-d$_6$) δ ppm 0.59-0.66 (m, 1H) 0.86-1.05 (m, 2H) 2.18-2.37 (m, 1H) 2.64-2.80 (m, 1H) 3.01-3.30 (m, 3H) 3.96 (t, J=7.70 Hz, 2H) 6.55 (s, 1H) 7.13 (s, 1H) 7.34-7.46 (m, 2H) 7.58-7.70 (m, 2H) 7.86-7.91 (m, 2H) 7.96 (s, 1H); MS (ESI+) m/z 538.1, 1074.8 (M+H)$^+$, (2M+H)$^+$.

Example 98

N-[5-cyclopropyl-2-(4-fluorophenyl)-3-(1H-imidazol-2-yl)-1-benzofuran-6-yl]-N-(2-hydroxypropyl)methanesulfonamide The title compound can be prepared by alkylation of Example 1O and deprotection of a tert-butyldimethylsilylether in accordance with procedures analogous to those described in Example 8. $^1$H NMR (300 MHz, DMSO-d$_6$) δ ppm 0.59 (m, 1H) 0.83 (m, 1H) 0.98 (m, 2H) 1.06 (m, 3H) 2.36 (m, 1H) 3.18 (m, 3H) 3.51 (m, 2H) 3.75 (m, 1H) 4.84 (m, 1H) 7.08 (m, 1H) 7.18 (s, 1H) 7.32 (m, 3H) 7.84 (m, 1H) 8.03 (m, 2H) 12.42 (s, 1H); MS (ESI+) m/z 470 (M+H)$^+$.

Example 99

N-[5-cyclopropyl-2-(4-fluorophenyl)-3-(1H-imidazol-2-yl)-1-benzofuran-6-yl]-N-(4-hydroxy-4-methylpentyl)methanesulfonamide The title compound can be prepared from Example 73 by reaction with methylmagnesium bromide. $^1$H NMR (300 MHz, DMSO-d$_6$) δ ppm 0.56 (m, 1H) 0.84 (m, 1H) 0.99 (m, 8H) 1.32 (m, 2H) 1.49 (m, 2H) 2.39 (m, 1H) 3.14 (s, 3H) 3.64 (m, 2H) 4.09 (s, 1H) 7.07 (s, 1H) 7.19 (s, 1H) 7.35 (m, 3H) 7.86 (s, 1H) 8.02 (m, 2H) 12.42 (s, 1H); MS (ESI+) m/z 512.1 (M+H)$^+$.

Example 100

N-[5-cyclopropyl-2-(4-fluorophenyl)-3-(1H-imidazol-2-yl)-1-benzofuran-6-yl]-N-(4-hydroxypentyl)methanesulfonamide The title compound can be prepared by reduction of Example 73. $^1$H NMR (300 MHz, DMSO-d$_6$) δ ppm 0.56 (m, 1H) 0.83 (m, 1H) 1.00 (m, 5H) 1.34 (m, 2H) 1.50 (m, 2H) 2.38 (m, 1H) 3.14 (s, 3H) 3.53 (m, 1H) 3.65 (m, 2H) 4.34 (d, J=4.78 Hz, 1H) 7.07 (s, 1H) 7.19 (s, 1H) 7.34 (m, 3H) 7.85 (s, 1H) 8.01 (m, 2H) 12.42 (s, 1H); MS (ESI+) m/z 498.1 (M+H)$^+$.

Example 101

N-[5-cyclopropyl-2-(4-fluorophenyl)-3-(1H-imidazol-2-yl)-1-benzofuran-6-yl]-N-[3-(methylsulfonyl)propyl]methanesulfonamide The title compound can be prepared from Example 1O in accordance with procedures analogous to those described in Examples 9A and 9B. $^1$H NMR (300 MHz, DMSO-$d_6$) δ ppm 0.56 (m, 1H) 0.88 (m, 1H) 1.03 (m, 2H) 1.90 (m, 2H) 2.37 (m, 1H) 2.95 (s, 3H) 3.20 (m, 5H) 3.81 (m, 2H) 7.10 (s, 1H) 7.25 (s, 1H) 7.35 (m, 3H) 7.90 (s, 1H) 8.05 (m, 2H) 12.43 (s, 1H); MS (ESI+) m/z 532.1 (M+H)$^1$.

Example 102

4-{[5-cyclopropyl-2-(4-fluorophenyl)-3-(1H-imidazol-2-yl)-1-benzofuran-6-yl](methylsulfonyl)amino}-N,N-dimethylbutanamide The title compound can be prepared by coupling Example 89 with dimethylamine. $^1$H NMR (300 MHz, DMSO-$d_6$) δ ppm 0.55 (m, 1H) 0.84 (m, 1H) 0.99 (m, 2H) 1.65 (m, 2H) 2.36 (m, 3H) 2.77 (s, 3H) 2.91 (s, 3H) 3.15 (s, 3H) 3.69 (m, 2H) 7.08 (s, 1H) 7.18 (s, 1H) 7.34 (m, 3H) 7.86 (s, 1H) 8.03 (m, 2H) 12.42 (s, 1H); MS (ESI+) m/z 525.1 (M+H)$^+$.

Example 103

N-[5-cyclopropyl-2-(4-fluorophenyl)-3-(1H-imidazol-2-yl)-1-benzofuran-6-yl]-N-[4-(morpholin-4-yl)-4-oxobutyl]methanesulfonamide The title compound can be prepared by coupling Example 89 with morpholine. $^1$H NMR (300 MHz, DMSO-$d_6$) δ ppm 0.56 (m, 1H) 0.85 (m, 1H) 1.00 (m, 2H) 1.68 (m, 2H) 2.38 (m, 3H) 3.15 (s, 3H) 3.39 (m, 4H) 3.51 (m, 4H) 3.70 (m, 2H) 7.08 (s, 1H) 7.18 (s, 1H) 7.35 (m, 3H) 7.87 (s, 1H) 8.02 (m, 2H) 12.42 (s, 1H); MS (ESI+) m/z 567.2 (M+H)$^+$.

Example 104

N-[5-cyclopropyl-2-(4-fluorophenyl)-3-(1H-imidazol-2-yl)-1-benzofuran-6-yl]-N-[4-oxo-4-(piperidin-1-yl)butyl]methanesulfonamide The title compound can be prepared by coupling Example 89 with piperidine. $^1$H NMR (300 MHz, DMSO-$d_6$) δ ppm 0.55 (m, 1H) 0.84 (m, 1H) 0.99 (m, 2H) 1.37 (m, 4H) 1.52 (m, 2H) 1.67 (m, 2H) 2.37 (m, 3H) 3.15 (s, 3H) 3.35 (m, 4H) 3.70 (m, 2H) 7.08 (s, 1H) 7.18 (s, 1H) 7.35 (m, 3H) 7.86 (s, 1H) 8.05 (m, 2H) 12.42 (s, 1H); MS (ESI+) m/z 565.2 (M+H)$^+$.

Example 105

4-{[5-cyclopropyl-2-(4-fluorophenyl)-3-(1H-imidazol-2-yl)-1-benzofuran-6-yl](methylsulfonyl)amino}-N-(methylsulfonyl)butanamide The title compound can be prepared by coupling Example 89 with methanesulfonamide. $^1$H NMR (300 MHz, DMSO-$d_6$) δ ppm 0.53 (m, 1H) 0.87 (m, 1H) 1.00 (m, 2H) 1.67 (m, 2H) 2.39 (m, 3H) 3.15 (s, 3H) 3.17 (s, 3H) 3.70 (m, 2H) 7.09 (s, 1H) 7.29 (m, 4H) 7.88 (s, 1H) 8.04 (m, 2H) 11.69 (s, 1H) 12.43 (s, 1H); MS (ESI+) m/z 575.1 (M+H)$^+$.

Example 106

N-[5-cyclopropyl-2-(4-fluorophenyl)-3-(1H-imidazol-2-yl)-1-benzofuran-6-yl]-N-(4-hydroxy-4-methyl-3-oxopentyl)methanesulfonamide The title compound can be prepared from Example 84 by oxidation with Dess-Martin periodinane. $^1$H NMR (300 MHz, DMSO-$d_6$) δ ppm 0.58 (m, 1H) 0.84 (m, 1H) 1.00 (m, 2H) 1.10 (s, 3H) 1.12 (s, 3H) 2.32 (m, 1H) 2.93 (m, 2H) 3.18 (s, 3H) 3.88 (m, 2H) 5.25 (s, 1H) 7.10 (s, 1H) 7.18 (s, 1H) 7.33 (m, 3H) 7.82 (s, 1H) 8.00 (m, 2H) 12.41 (s, 1H); MS (ESI+) m/z 526.1 (M+H)$^+$.

Example 107

4-{[5-cyclopropyl-2-(4-fluorophenyl)-3-(1H-imidazol-2-yl)-1-benzofuran-6-yl](methylsulfonyl)amino}-N-methylbutanamide The title compound can be prepared by coupling Example 89 with methylamine. $^1$H NMR (500 MHz, DMSO-$d_6$) δ ppm 0.55 (m, 1H) 0.84 (m, 1H) 0.99 (m, 2H) 1.64 (m, 2H) 2.11 (m, 2H) 2.37 (m, 1H) 2.52 (d, J=4.58 Hz, 3H) 3.15 (s, 3H) 3.65 (m, 2H) 7.08 (s, 1H) 7.19 (s, 1H) 7.34 (m, 3H) 7.71 (q, J=4.43 Hz, 1H) 7.86 (s, 1H) 8.03 (m, 2H) 12.42 (s, 1H); MS (ESI+) m/z 511 (M+H)$^+$.

Example 108

4-{[5-cyclopropyl-2-(4-fluorophenyl)-3-(1H-imidazol-2-yl)-1-benzofuran-6-yl](methylsulfonyl)amino}butanamide The title compound can be prepared by coupling Example 89 with ammonia. $^1$H NMR (500 MHz, DMSO-$d_6$) δ ppm 0.56 (m, 1H) 0.85 (m, 1H) 1.00 (m, 2H) 1.66 (m, 2H) 2.12 (m, 2H) 2.38 (m, 1H) 3.15 (s, 3H) 3.66 (m, 2H) 6.72 (s, 1H) 7.08 (s, 1H) 7.18 (s, 1H) 7.25 (s, 1H) 7.34 (m, 3H) 7.86 (s, 1H) 8.02 (m, 2H) 12.42 (s, 1H); MS (ESI+) m/z 497 (M+H)$^+$.

Example 109

N-[5-cyclopropyl-2-(4-fluorophenyl)-3-(1H-imidazol-2-yl)-1-benzofuran-6-yl]-N-(2-hydroxyethyl)methanesulfonamide The title compound can be made by alkylation of Example 1O with 2-iodoethyl benzoate and saponification of the resultant ester. $^1$H NMR (400 MHz, DMSO-$d_6$) δ ppm 0.52-0.59 (m, 1H) 0.81-0.87 (m, 1H) 0.93-1.02 (m, 2H) 2.28-2.38 (m, 1H) 3.21 (s, 3H) 3.40-3.47 (m, 1H) 3.48-3.56 (m, 1H) 3.57-3.66 (m, 1H) 3.79-3.86 (m, 1H) 4.91 (t, J=5.20 Hz, 1H) 7.10 (s, 1H) 7.19 (s, 1H) 7.28-7.41 (m, 3H) 7.82 (s, 1H) 7.92-8.09 (m, 2H) 12.42 (s, 1H); MS (ESI+) m/z 456.0 (M+H)$^+$, (ESI−) m/z 454.1 (M−H)$^−$.

Example 110

N-[5-cyclopropyl-2-(4-fluorophenyl)-3-(1H-imidazol-2-yl)-1-benzofuran-6-yl]-N-(3,4-dihydroxybutyl)methanesulfonamide The title compound can be prepared by dihydroxylation ($OsO_4$) of a N-(but-3-enyl) derivative. $^1$H NMR (trifluoroacetic acid salt) (300 MHz, DMSO-$d_6$) δ ppm 0.61 (d, 2H) 0.85-1.14 (m, 2H) 1.70 (d, J=31.99 Hz, 2H) 2.32 (d, 2H)

3.05-3.14 (m, 2H) 3.19 (s, 3H) 3.19-3.30 (m, 1H) 3.47 (d, 1H) 4.25 (s, 2H) 7.03-7.19 (m, 1H) 7.41 (t, J=8.82 Hz, 2H) 7.54-7.73 (m, 2H) 7.82-8.09 (m, 3H) 14.24 (s, 1H); MS (ESI+) m/z 500.0 (M+H)$^+$, (ESI−) m/z 498.1 (M−H)$^−$.

Example 111

N-(2-aminoethyl)-N-[5-cyclopropyl-2-(4-fluorophenyl)-3-(1H-imidazol-2-yl)-1-benzofuran-6-yl]methanesulfonamide The title compound can be made in accordance with procedures analogous to those described in Example 112. $^1$H NMR (trifluoroacetic acid salt) (300 MHz, DMSO-d$_6$) δ ppm 0.55 (s, 2H) 0.89-1.12 (m, 3H) 2.36 (s, 2H) 2.96 (s, 2H) 3.24 (s, 3H) 3.82-4.01 (m, 2H) 7.16 (s, 1H) 7.40 (t, J=8.82 Hz, 2H) 7.89 (dd, J=5.88, 3.31 Hz, 4H) 8.04 (s, 1H), 11.63 (bs, 1H); MS (ESI+) m/z 455.0 (M+H)$^+$ (ESI−) m/z 453.1 (M−H)$^−$.

Example 112

N-(3-aminopropyl)-N-[5-cyclopropyl-2-(4-fluorophenyl)-3-(1H-imidazol-2-yl)-1-benzofuran-6-yl]methanesulfonamide The title compound can be prepared from Example 1O by alkylation with 3-bromopropylphthalimide and cleavage of the phthalimide with hydrazine. $^1$H NMR (trifluoroacetic acid salt) (300 MHz, DMSO-d$_6$) δ ppm 0.55-0.68 (m, 1H) 0.93-0.97 (m, 1H) 0.97-1.07 (m, 1H) 1.59-1.90 (m, 2H) 2.35 (s, 2H) 2.87 (d, J=6.25 Hz, 2H) 3.18 (s, 3H) 3.70-3.86 (m, 2H) 7.15 (s, 1H) 7.40 (t, J=8.82 Hz, 2H) 7.72 (d, J=8.46 Hz, 7H) 7.95 (s, 1H); MS (ESI+) m/z 469.1 (M+H)$^+$ (ESI−) m/z 467.1 (M−H)$^−$.

Example 113

N-[5-cyclopropyl-2-(4-fluorophenyl)-3-(1H-imidazol-2-yl)-1-benzofuran-6-yl]-N-[(1,1-$^2$H$_2$)hexyl]methanesulfonamide $^1$H NMR (500 MHz, DMSO-d$_6$) δ ppm 0.54-0.65 (m, 1H), 0.81-0.84 (m, 3H), 0.90-0.94 (m, 1H), 1.00 (dd, J=8.24, 2.44 Hz, 2H), 1.17-1.47 (m, 8H), 2.37-2.45 (m, 1H), 3.14 (s, 3H), 7.11 (s, 1H), 7.40 (t, J=8.85 Hz, 2H), 7.68 (dd, J=8.24, 5.34 Hz, 2H), 7.84 (s, 2H), 7.97 (s, 1H); MS (ESI+) m/z 498 (M+H)$^+$, 995 (2M+H)$^+$; MS (ESI−) m/z 496 (M−H)$^−$, 532/534 (M+Cl)$^−$, 610 (M+trifluoroacetic acid-H)$^−$.

The compounds of Example 114-133 can be made from Example 8G using procedures analogous to those described in the above alkylation reaction of Example 8H with the appropriate choice of electrophile.

Example 114

N-[5-cyclopropyl-3-(5,6-dihydro-4H-1,2,4-oxadiazin-3-yl)-2-(4-fluorophenyl)-1-benzofuran-6-yl]-N-[3-(1,1-dioxidothiomorpholin-4-yl)propyl]methanesulfonamide $^1$H NMR (500 MHz, DMSO-d$_6$) δ ppm 0.49-0.65 (m, 1H) 0.82-0.95 (m, 1H) 0.96-1.08 (m, 2H) 1.46-1.70 (m, 4H) 2.32-2.39 (m, 1H) 2.75-2.87 (m, 4H) 2.98-3.08 (m, 4H) 3.14 (s, 3H) 3.41-3.49 (m, 2H) 3.60-3.86 (m, 2H) 3.99 (q, J=4.78 Hz, 2H) 7.06 (s, 1H) 7.23 (t, J=3.20 Hz, 1H) 7.34-7.46 (m, 2H) 7.86 (s, 1H) 7.94-8.05 (m, 2H); MS (ESI+) m/z 605 (M+H)$^+$.

Example 115

N-(5-cyano-5-methylhexyl)-N-[5-cyclopropyl-3-(5,6-dihydro-4H-1,2,4-oxadiazin-3-yl)-2-(4-fluorophenyl)-1-benzofuran-6-yl]methanesulfonamide $^1$H NMR (500 MHz, DMSO-d$_6$) δ ppm 0.52-0.62 (m, 1H) 0.82-0.91 (m, 1H) 0.96-1.08 (m, 2H) 1.25 (s, 6H) 1.35-1.56 (m, 6H) 2.34-2.40 (m, 1H) 3.13 (s, 3H) 3.41-3.48 (m, 2H) 3.60-3.80 (m, 2H) 3.99 (t, J=4.58 Hz, 2H) 7.06 (s, 1H) 7.23 (t, J=3.20 Hz, 1H) 7.37-7.44 (m, 2H) 7.84 (s, 1H) 7.96-8.02 (m, 2H); MS (ESI+) m/z 553 (M+H)$^+$.

Example 116 diethyl (3-{[5-cyclopropyl-3-(5,6-dihydro-4H-1,2,4-oxadiazin-3-yl)-2-(4-fluorophenyl)-1-benzofuran-6-yl](methylsulfonyl)amino}propyl)phosphonate $^1$H NMR (400 MHz, DMSO-d$_6$) δ ppm 0.48-0.62 (m, 1H) 0.85-0.96 (m, 1H) 1.01 (d, J=8.57 Hz, 2H) 1.12-1.21 (m, 6H) 1.56-1.87 (m, J=51.40 Hz, 4H) 2.32-2.41 (m, 1H) 3.15 (s, 3H) 3.41-3.48 (m, 2H) 3.61-3.84 (m, J=31.23 Hz, 2H) 3.86-4.06 (m, 6H) 7.08 (s, 1H) 7.23 (t, J=3.14 Hz, 1H) 7.36-7.51 (m, 2H) 7.83 (s, 1H) 7.95-8.05 (m, 2H); MS (ESI+) m/z 608 (M+H)$^+$.

Example 117

N-[5-cyclopropyl-3-(5,6-dihydro-4H-1,2,4-oxadiazin-3-yl)-2-(4-fluorophenyl)-1-benzofuran-6-yl]-N-(4,4,4-trifluorobutyl)methanesulfonamide $^1$H NMR (500 MHz, DMSO-d$_6$) δ ppm 0.40-0.67 (m, 1H) 0.88-0.97 (m, 1H) 0.95-1.05 (m, 2H) 1.57-1.77 (m, 2H) 2.27-2.45 (m, 3H) 3.16 (s, 3H) 3.45 (q, J=4.12 Hz, 2H) 3.68-3.91 (m, 2H) 3.99 (t, J=4.58 Hz, 2H) 7.07 (s, 1H) 7.23 (t, J=3.20 Hz, 1H) 7.33-7.51 (m, 2H) 7.87 (s, 1H) 7.93-8.18 (m, 2H); MS (ESI+) m/z 540 (M+H)$^+$.

Example 118

N-[5-cyclopropyl-3-(5,6-dihydro-4H-1,2,4-oxadiazin-3-yl)-2-(4-fluorophenyl)-1-benzofuran-6-yl]-N-(3,3,3-trifluoropropyl)methanesulfonamide $^1$H NMR (400 MHz, DMSO-d$_6$) δ ppm 0.49-0.61 (m, 1H) 0.88-0.97 (m, 1H) 0.98-1.12 (m, 2H) 2.33-2.38 (m, 1H) 2.54-2.65 (m, 2H) 3.20 (s, 3H) 3.42-3.48 (m, 2H) 3.93 (t, J=7.64 Hz, 2H) 3.99 (t, J=4.55 Hz, 2H) 7.10 (s, 1H) 7.23 (t, J=3.20 Hz, 1H) 7.37-7.44 (m, 2H) 7.89 (s, 1H) 7.97-8.03 (m, 2H); MS (ESI+) m/z 526 (M+H)$^+$.

Example 119

N-[5-cyclopropyl-3-(5,6-dihydro-4H-1,2,4-oxadiazin-3-yl)-2-(4-fluorophenyl)-1-benzofuran-6-yl]-N-[3-(1H-pyrrol-1-yl)propyl]methanesulfonamide $^1$H NMR (400 MHz, DMSO-d$_6$) δ ppm 0.49-0.60 (m, 1H) 0.79-0.95 (m, 1H) 0.96-1.07 (m, 2H) 1.76-1.90 (m, 2H) 2.35-2.43 (m, 1H) 3.13 (s, 3H) 3.44 (q, J=4.12 Hz, 2H) 3.57-3.72 (m, 2H) 3.93 (t, J=6.83 Hz, 2H) 3.99 (t, J=4.50 Hz, 2H) 5.94 (t, J=2.01 Hz, 2H) 6.68 (t, J=2.06 Hz, 2H) 7.07 (s, 1H) 7.22 (t, J=3.14 Hz, 1H) 7.37-7.44 (m, 2H) 7.84 (s, 1H) 7.96-8.02 (m, 2H); MS (ESI+) m/z 537 (M+H)$^+$.

Example 120

N-[5-cyclopropyl-3-(5,6-dihydro-4H-1,2,4-oxadiazin-3-yl)-2-(4-fluorophenyl)-1-benzofuran-6-yl]-N-(5,6,6-trifluorohex-5-en-1-yl)methanesulfonamide $^1$H NMR (400 MHz, DMSO-d$_6$) δ ppm 0.45-0.61 (m, 1H) 0.82-0.95 (m, 1H) 0.96-1.06 (m, 2H) 1.38-1.68 (m, 4H) 2.25-2.45 (m, 3H) 3.13 (s, 3H) 3.44 (q, J=4.08 Hz, 2H) 3.57-3.83 (m, 2H) 3.99 (t, J=4.55 Hz, 2H) 7.06 (s, 1H) 7.22 (t, J=3.20 Hz, 1H) 7.34-7.46 (m, 2H) 7.83 (s, 1H) 7.94-8.07 (m, 2H); MS (ESI+) m/z 566 (M+H)$^+$.

Example 121 ethyl 4-{[5-cyclopropyl-3-(5,6-dihydro-4H-1,2,4-oxadiazin-3-yl)-2-(4-fluorophenyl)-1-benzofuran-6-yl](methylsulfonyl)amino}butanoate $^1$H NMR (500 MHz, DMSO-d$_6$) δ ppm 0.54 (m, 1H) 0.91 (m, 1H) 1.00 (m, 2H) 1.14 (t, J=7.10 Hz, 3H) 1.67 (m, 2H) 2.37 (m, 3H) 3.13 (s, 3H) 3.44 (m, 2H) 3.68 (m, 2H) 4.02 (m, 4H) 7.07 (s, 1H) 7.24 (s, br, 1H) 7.40 (m, 2H) 7.84 (s, 1H) 8.00 (m, 2H); MS (ESI+) m/z 544.1 (M+H)$^+$.

Example 122

N-[5-cyclopropyl-3-(5,6-dihydro-4H-1,2,4-oxadiazin-3-yl)-2-(4-fluorophenyl)-1-benzofuran-6-yl]-N-[4-(methylsulfonyl)butyl]methanesulfonamide $^1$H NMR (500 MHz, DMSO-d$_6$) δ ppm 0.55 (m, 1H) 0.86 (m, 1H) 1.00 (m, 2H) 1.53 (m, 2H) 1.72 (m, 2H) 2.35 (m, 1H) 2.90 (s, 3H) 3.07 (m, 2H) 3.13 (s, 3H) 3.43 (m, 2H) 3.68 (m, 2H) 3.98 (t, J=4.35 Hz, 2H) 7.06 (s, 1H) 7.22 (s, 1H) 7.39 (m, 2H) 7.82 (s, 1H) 7.98 (m, 2H); MS (ESI+) m/z 564.1 (M+H)$^+$.

Example 123

N-[5-cyclopropyl-3-(5,6-dihydro-4H-1,2,4-oxadiazin-3-yl)-2-(4-fluorophenyl)-1-benzofuran-6-yl]-N-[2-(1,1-dioxidotetrahydrothiophen-3-yl)ethyl]methanesulfonamide $^1$H NMR (500 MHz, DMSO-d$_6$) δ ppm 0.57 (m, 1H) 0.91 (m, 1H) 1.03 (m, 2H) 1.62 (m, 3H) 2.22 (m, 1H) 2.38 (m, 2H) 2.71 (m, 1H) 3.02 (m, 1H) 3.20 (m, 5H) 3.45 (m, 2H) 3.70 (m, 2H) 3.99 (t, J=4.58 Hz, 2H) 7.07 (d, J=2.44 Hz, 1H) 7.23 (t, J=3.13 Hz, 1H) 7.41 (m, 2H) 7.85 (d, J=3.81 Hz, 1H) 8.00 (m, 2H); MS (ESI+) m/z 576 (M+H)$^+$.

Example 124

3-{[5-cyclopropyl-3-(5,6-dihydro-4H-1,2,4-oxadiazin-3-yl)-2-(4-fluorophenyl)-1-benzofuran-6-yl](methylsulfonyl)amino}propane-1-sulfonamide $^1$H NMR (500 MHz, DMSO-d$_6$) δ ppm 0.54-0.63 (m, 1H) 0.86-0.92 (m, 1H) 0.98-1.08 (m, 2H) 1.82-1.92 (m, 2H) 2.31-2.35 (m, 1H) 2.97-3.11 (m, 2H) 3.16 (s, 3H) 3.44 (q, J=4.12 Hz, 2H) 3.73-3.84 (m, 2H) 3.99 (t, J=4.58 Hz, 2H) 6.80 (s, 2H) 7.09 (s, 1H) 7.24 (t, J=3.20 Hz, 1H) 7.36-7.45 (m, 2H) 7.83 (s, 1H) 7.92-8.04 (m, 2H); MS (ESI+) m/z 551 (M+H)$^+$.

Example 125

N-[5-cyclopropyl-3-(5,6-dihydro-4H-1,2,4-oxadiazin-3-yl)-2-(4-fluorophenyl)-1-benzofuran-6-yl]-N-(3-hydroxy-3-methylbutyl)methanesulfonamide $^1$H NMR (400 MHz, DMSO-d$_6$) δ ppm 0.53-0.58 (m, 1H) 0.86-0.91 (m, 1H) 0.97-1.02 (m, 2H) 1.04 (d, J=3.25 Hz, 6H) 1.43-1.53 (m, 1H) 1.58-1.68 (m, 1H) 2.33-2.40 (m, 1H) 3.13 (s, 3H) 3.45 (q, J=4.01 Hz, 2H) 3.65-3.75 (m, 1H) 3.76-3.85 (m, 1H) 3.99 (t, J=4.55 Hz, 2H) 4.29 (s, 1H) 7.08 (s, 1H) 7.24 (t, J=3.14 Hz, 1H) 7.34-7.45 (m, 2H) 7.82 (s, 1H) 7.94-8.05 (m, 2H); MS (ESI+) m/z 516 (M+H)$^+$.

Example 126

N-[5-cyclopropyl-3-(5,6-dihydro-4H-1,2,4-oxadiazin-3-yl)-2-(4-fluorophenyl)-1-benzofuran-6-yl]-N-[3-(morpholin-4-yl)propyl]methanesulfonamide $^1$H NMR (trifluoroacetic acid salt) (500 MHz, DMSO-d$_6$) δ ppm 0.69-0.54 (m, 1H), 0.84-1.00 (m, 1H), 1.78-1.97 (m, 2H), 2.36 (m, 2H), 2.96-3.12 (m, 2H), 3.17 (s, 3H), 3.36 (m, 2H), 3.48 (m, 2H), 3.59 (m, 2H), 3.73 (m, 2H), 3.95 (m, 2H), 4.05 (m, 2H), 7.11 (s, 1H), 7.42 (t, J=8.9, 2H), 7.63-7.50 (m, 1H), 7.88 (s, 1H), 7.97 (dd, J=5.4, 9.0, 2H), 9.65-9.48 (m, 1H); MS (ESI+) 557.2 (M+H)$^+$, (ESI−) 555.2 (M−H)$^-$.

Example 127

N-[5-cyclopropyl-3-(5,6-dihydro-4H-1,2,4-oxadiazin-3-yl)-2-(4-fluorophenyl)-1-benzofuran-6-yl]-N-[3-(dimethylamino)propyl]methanesulfonamide $^1$H NMR (500 MHz, DMSO-d$_6$) δ ppm 0.56 (s, 1H), 0.83-1.63 (m, 5H), 2.03-2.06 (m, 4H), 2.15-2.28 (m, 2H), 2.29 (s, 1H), 2.34-2.39 (m, 1H), 2.98 (s, 1H), 3.13 (s, 3H), 3.44 (d, J=4.5, 2H), 3.57-3.69 (m, 1H), 3.70-3.76 (m, 1H), 3.99 (t, J=4.6, 2H), 7.06 (s, 1H), 7.23 (s, 1H), 7.40 (t, J=8.9, 2H), 7.84 (s, 1H), 8.03-7.95 (m, 2H); MS (ESI+) 515.1 (M+H)$^+$, (ESI−) 513.2 (M−H)$^-$.

Example 128

N-[5-cyclopropyl-3-(5,6-dihydro-4H-1,2,4-oxadiazin-3-yl)-2-(4-fluorophenyl)-1-benzofuran-6-yl]-N-[2-(pyrrolidin-1-yl)ethyl]methanesulfonamide $^1$H NMR (400 MHz, DMSO-d$_6$) δ ppm 0.47-0.66 (m, 2H), 0.73-0.93 (m, 2H), 0.93-1.07 (m, 2H), 1.65 (s, 2H), 1.95-2.14 (m, 2H), 2.39-2.48 (m, 2H), 3.18 (s, 3H), 3.26-3.28 (m, 1H), 3.64-3.71 (m, 2H), 3.76-3.93 (m, 2H), 3.94-4.07 (m, 2H), 4.07-4.26 (m, 1H), 7.08 (s, 1H), 7.18-7.36 (t, 1H), 7.40 (m, 2H), 7.79 (s, 1H), 7.89-7.91 (m, 1H), 7.95-8.15 (m, 2H); MS (ESI+) 527.1 (M+H)$^+$, (ESI−) 525.2 (M−H)$^-$.

Example 129

N-[5-cyclopropyl-3-(5,6-dihydro-4H-1,2,4-oxadiazin-3-yl)-2-(4-fluorophenyl)-1-benzofuran-6-yl]-N-[2-(diethylamino)ethyl]methanesulfonamide $^1$H NMR (500 MHz, DMSO-d$_6$) δ ppm 0.57 (m, 2H), 0.88 (t, J=7.1, 6H), 1.02 (m, 3H), 2.43 (dd, J=6.7, 13.6, 2H), 2.45

(d, J=6.6, 2H), 3.17 (s, 3H), 3.23 (d, J=9.5, 2H), 3.73 (m, 4H), 3.99 (t, 2H), 7.07 (s, 1H), 7.24 (t, 1H), 7.40 (t, J=8.9, 2H), 7.81 (s, 1H), 7.99 (dd, J=5.4, 8.9, 2H); MS (ESI+) 529.2 (M+H)+.

Example 130

N-[5-cyclopropyl-3-(5,6-dihydro-4H-1,2,4-oxadiazin-3-yl)-2-(4-fluorophenyl)-1-benzofuran-6-yl]-N-[3-(piperidin-1-yl)propyl]methanesulfonamide $^1$H NMR (400 MHz, DMSO-d$_6$) δ ppm 0.52-0.62 (m, 2H), 0.84-0.93 (m, 2H), 1.03 (s, 2H), 1.44 (s, 7H), 2.33 (s, 6H), 3.14 (s, 3H), 3.45 (s, 2H), 3.62-3.79 (m, 2H), 3.99 (s, 2H), 7.07 (s, 1H), 7.22 (s, 1H), 7.40 (t, J=8.9, 2H), 7.83 (s, 1H), 7.99 (dd, J=5.4, 8.9, 2H); MS (ESI+) 555.2 (M+H)+, (ESI−) 553.2 (M−H)−.

Example 131

N-[5-cyclopropyl-3-(5,6-dihydro-4H-1,2,4-oxadiazin-3-yl)-2-(4-fluorophenyl)-1-benzofuran-6-yl]-N-[3-(diethylamino)propyl]methanesulfonamide $^1$H NMR (400 MHz, DMSO-d$_6$) δ ppm 0.59 (m, 2H), 0.88 (t, J=7.0, 6H), 1.01 (d, J=8.6, 2H), 1.55 (s, 2H), 2.34 (dd, J=10.5, 12.3, 5H), 3.12 (s, 3H), 3.45 (s, 2H), 3.63 (s, 2H), 3.69-3.77 (m, 2H), 3.99 (s, 2H), 7.06 (s, 1H), 7.40 (t, J=8.9, 2H), 7.23 (s, 1H), 7.83 (s, 1H), 7.99 (dd, J=5.4, 8.9, 2H); MS (ESI+) 543.2 (M+H)+, (ESI−) 541.1 (M−H)−.

Example 132

N-[5-cyclopropyl-3-(5,6-dihydro-4H-1,2,4-oxadiazin-3-yl)-2-(4-fluorophenyl)-1-benzofuran-6-yl]-N-[3-(pyrrolidin-1-yl)propyl]methanesulfonamide $^1$H NMR (400 MHz, DMSO-d$_6$) δ ppm 0.55 (m, 2H), 0.89 (m, 2H), 1.01 (d, J=8.5, 2H), 1.63 (m, 4H), 2.31-2.34 (m, 4H), 3.13 (s, 3H), 3.45 (t, 2H), 3.65 (m, 2H), 3.74 (m, 2H), 3.99 (t, 2H), 5.76 (s, 1H), 7.06 (s, 1H), 7.23 (s, 1H), 7.40 (t, J=8.9, 2H), 7.83 (s, 1H), 7.99 (dd, J=5.4, 8.9, 2H); MS (ESI+) 541.2 (M+H)+.

Example 133

N-(3-cyanopropyl)-N-[5-cyclopropyl-3-(5,6-dihydro-4H-1,2,4-oxadiazin-3-yl)-2-(4-fluorophenyl)-1-benzofuran-6-yl]methanesulfonamide $^1$H NMR (400 MHz, DMSO-d$_6$) δ ppm 0.49-0.61 (m, 1H), 0.90-1.09 (m, 3H), 1.68-1.81 (m, 2H), 2.35-2.42 (m, 1H), 2.59 (t, J=7.21 Hz, 2H), 3.16 (s, 3H), 3.45 (q, J=4.08 Hz, 2H), 3.66-3.84 (m, 2H), 3.99 (t, J=4.55 Hz, 2H), 7.09 (s, 1H), 7.22 (t, J=3.20 Hz, 1H), 7.40 (t, J=8.95 Hz, 2H), 7.88 (s, 1H), 7.99 (dd, J=8.89, 5.42 Hz, 2H); MS (ESI+) m/z 497 (M+H)+, 993 (2M+H)+; MS (ESI−) m/z 495 (M−H)−, 991 (2M−H)−.

Example 134

N-[5-cyclopropyl-3-(5,6-dihydro-4H-1,2,4-oxadiazin-3-yl)-2-(4-fluorophenyl)-1-benzofuran-6-yl]-N-(5-hydroxypentyl)methanesulfonamide The title compound can be prepared from Example 8G by alkylation and saponification. $^1$H NMR (400 MHz, DMSO-d$_6$) δ ppm 0.50-0.61 (m, J=4.88 Hz, 1H) 0.82-0.93 (m, 1H) 0.97-1.04 (m, J=8.46 Hz, 2H) 1.21-1.48 (m, 6H) 2.36-2.43 (m, 1H) 3.12 (s, 3H) 3.32-3.35 (m, 2H) 3.44 (q, J=4.08 Hz, 2H) 3.55-3.75 (m, 2H) 3.99 (t, J=4.45 Hz, 2H) 4.32 (t, J=5.10 Hz, 1H) 7.06 (s, 1H) 7.23 (t, J=3.09 Hz, 1H) 7.36-7.44 (m, 2H) 7.83 (s, 1H) 7.95-8.03 (m, 2H); MS (ESI+) m/z 516 (M+H)+.

Example 135

4-{[5-cyclopropyl-3-(5,6-dihydro-4H-1,2,4-oxadiazin-3-yl)-2-(4-fluorophenyl)-1-benzofuran-6-yl](methylsulfonyl)amino}butanoic acid The title compound can be prepared by saponification of Example 121. $^1$H NMR (500 MHz, DMSO-d$_6$) δ ppm 0.54 (m, 1H) 0.89 (m, 1H) 1.00 (m, 2H) 1.65 (m, 2H) 2.29 (m, 2H) 2.38 (m, 1H) 3.13 (s, 3H) 3.45 (m, 2H) 3.68 (m, 2H) 3.99 (t, J=4.58 Hz, 2H) 7.07 (s, 1H) 7.24 (t, J=3.05 Hz, 1H) 7.41 (m, 2H) 7.84 (s, 1H) 8.00 (m, 2H) 12.10 (s, br, 1H); MS (ESI+) m/z 516 (M+H)+.

Example 136

N-[5-cyclopropyl-3-(5,6-dihydro-4H-1,2,4-oxadiazin-3-yl)-2-(4-fluorophenyl)-1-benzofuran-6-yl]-N-(2-hydroxyethyl)methanesulfonamide The title compound can be prepared from Example 8G by alkylation with 2-iodoethyl benzoate and saponification of the resultant ester. $^1$H NMR (500 MHz, DMSO-d$_6$) δ ppm 0.50-0.59 (m, 1H) 0.85-0.91 (m, 1H) 0.96-1.04 (m, 2H) 2.30-2.34 (m, 1H) 3.19 (s, 3H) 3.37-3.42 (m, 1H) 3.43-3.47 (m, 2H) 3.47-3.54 (m, 1H) 3.56-3.65 (m, 1H) 3.77-3.84 (m, 1H) 3.99 (t, J=4.58 Hz, 2H) 4.90 (t, J=5.26 Hz, 1H) 7.09 (s, 1H) 7.23 (t, J=3.20 Hz, 1H) 7.35-7.47 (m, 2H) 7.79 (s, 1H) 7.96-8.03 (m, 2H); MS (ESI+) m/z 474 (M+H)+.

Example 137

N-[5-cyclopropyl-3-(5,6-dihydro-4H-1,2,4-oxadiazin-3-yl)-2-(4-fluorophenyl)-1-benzofuran-6-yl]-N-(3-hydroxypropyl)methanesulfonamide The title compound can be prepared in accordance with procedures analogous to those described in Example 8. $^1$H NMR (500 MHz, DMSO-d$_6$) δ ppm 0.52-0.58 (m, 1H) 0.85-0.91 (m, 1H) 0.96-1.04 (m, 2H) 1.50-1.57 (m, 1H) 1.59-1.65 (m, 1H) 2.33-2.37 (m, 1H) 3.14 (s, 3H) 3.39-3.43 (m, 2H) 3.43-3.46 (m, 2H) 3.64-3.71 (m, 1H) 3.74-3.82 (m, 1H) 3.99 (t, J=4.58 Hz, 2H) 4.47 (t, J=5.04 Hz, 1H) 7.07 (s, 1H) 7.23 (t, J=3.28 Hz, 1H) 7.35-7.45 (m, 2H) 7.83 (s, 1H) 7.97-8.03 (m, 2H); MS (ESI+) m/z 488 (M+H)+.

Example 138

N-[5-cyclopropyl-3-(5,6-dihydro-4H-1,2,4-oxadiazin-3-yl)-2-(4-fluorophenyl)-1-benzofuran-6-yl]-N-[2-(methylsulfinyl)ethyl]methanesulfonamide The title compound can be prepared from Example 9A by oxidation with m-chloroperoxybenzoic acid. $^1$H NMR (400 MHz, DMSO-d$_6$) δ ppm 0.51-0.60 (m, 1H) 0.87-0.95 (m, 1H) 0.97-1.07 (m, 2H) 2.32-2.38 (m, 1H) 2.54 (d, J=6.51 Hz, 3H) 2.76-3.00 (m, 2H) 3.20 (d, J=3.25 Hz, 3H) 3.41-3.46 (m, 2H) 3.98 (t, J=4.55 Hz, 2H) 4.03-4.10 (m, 2H) 7.08 (d, J=3.04 Hz, 1H) 7.22 (s, 1H) 7.35-7.43 (m, 2H) 7.87 (d, J=8.57 Hz, 1H) 7.95-8.03 (m, 2H); MS (ESI+) m/z 520 (M+H)+.

Example 139

N-[5-cyclopropyl-3-(5,6-dihydro-4H-1,2,4-oxadiazin-3-yl)-2-(4-fluorophenyl)-1-benzofuran-6-yl]-N-[3-(methylsulfinyl)propyl]methanesulfonamide The title compound can be prepared from Example 8G in accordance with procedures analogous the alkylation used to prepare Example 9A followed by the oxidation used to prepare Example 138. $^1$H NMR (400 MHz, DMSO-$d_6$) δ ppm 0.53-0.60 (m, 1H) 0.86-0.94 (m, 1H) 0.99-1.06 (m, 2H) 1.77-1.84 (m, 2H) 1.85 (s, 3H) 2.34-2.41 (m, 1H) 2.67-2.74 (m, 1H) 2.78-2.87 (m, 1H) 3.16 (s, 3H) 3.42-3.46 (m, 2H) 3.74-3.84 (m, 2H) 3.97-4.01 (m, 2H) 7.08 (s, 1H) 7.24 (t, J=3.64 Hz, 1H) 7.36-7.43 (m, 2H) 7.87 (d, J=4.99 Hz, 1H) 7.95-8.03 (m, 2H); MS (ESI+) m/z 534.1 (M+H)$^+$.

Example 140

N-[5-cyclopropyl-3-(5,6-dihydro-4H-1,2,4-oxadiazin-3-yl)-2-(4-fluorophenyl)-1-benzofuran-6-yl]-N-[3-(methylsulfonyl)propyl]methanesulfonamide The title compound can be prepared from Example 8G by analogy with the methods to prepare Example 9. $^1$H NMR (400 MHz, DMSO-$d_6$) δ ppm 0.53-0.59 (m, 1H) 0.88-0.94 (m, 1H) 0.99-1.10 (m, 2H) 1.83-1.93 (m, 2H) 2.33-2.39 (m, 1H) 2.94 (s, 3H) 3.15-3.22 (m, 5H) 3.42-3.48 (m, 2H) 3.72-3.87 (m, 2H) 3.99 (t, J=4.55 Hz, 2H) 7.09 (s, 1H) 7.23 (t, J=3.25 Hz, 1H) 7.34-7.45 (m, 2H) 7.87 (s, 1H) 7.95-8.04 (m, 2H); MS (ESI+) m/z 550.1 (M+H)$^+$.

Example 141

N-[5-cyclopropyl-3-(5,6-dihydro-4H-1,2,4-oxadiazin-3-yl)-2-(4-fluorophenyl)-1-benzofuran-6-yl]-N-[2-(ethylsulfinyl)ethyl]methanesulfonamide The title compound can be prepared from Example 8G by analogy with the methods to prepare Example 138. $^1$H NMR (400 MHz, DMSO-$d_6$) δ ppm 0.53-0.61 (m, 1H) 0.89-0.95 (m, 1H) 0.98-1.06 (m, 2H) 1.11-1.17 (m, 3H) 2.33-2.40 (m, 1H) 2.61-2.66 (m, 1H) 2.74-2.82 (m, 1H) 2.84-2.95 (m, 2H) 3.21 (d, J=4.12 Hz, 3H) 3.40-3.46 (m, 2H) 3.99 (t, J=4.50 Hz, 2H) 4.03-4.09 (m, 2H) 7.09 (d, J=5.10 Hz, 1H) 7.21-7.25 (s, 1H) 7.35-7.44 (m, 2H) 7.89 (d, J=10.52 Hz, 1H) 7.96-8.05 (m, 2H); MS (ESI+) m/z 534 (M+H)$^+$.

Example 142

N-[5-cyclopropyl-3-(5,6-dihydro-4H-1,2,4-oxadiazin-3-yl)-2-(4-fluorophenyl)-1-benzofuran-6-yl]-N-[2-(ethylsulfonyl)ethyl]methanesulfonamide The title compound can be prepared from Example 8G by analogy with the methods to prepare Example 9. $^1$H NMR (400 MHz, DMSO-$d_6$) δ ppm 0.55-0.60 (m, 1H) 0.90-0.96 (m, 1H) 0.98-1.10 (m, 2H) 1.18 (t, J=7.43 Hz, 3H) 2.28-2.34 (m, 1H) 3.15 (q, J=7.45 Hz, 2H) 3.23 (s, 3H) 3.25-3.31 (m, 1H) 3.39-3.50 (m, 3H) 3.99 (t, J=4.50 Hz, 2H) 4.04-4.19 (m, 2H) 7.12 (s, 1H) 7.22 (t, J=3.14 Hz, 1H) 7.36-7.44 (m, 2H) 7.89 (s, 1H) 7.97-8.05 (m, 2H); MS (ESI+) m/z 550.1 (M+H)$^+$.

Example 143

N-[5-cyclopropyl-3-(5,6-dihydro-4H-1,2,4-oxadiazin-3-yl)-2-(4-fluorophenyl)-1-benzofuran-6-yl]-N-[3-(ethylsulfonyl)propyl]methanesulfonamide The title compound can be prepared from Example 8G by analogy with the methods to prepare Example 9. $^1$H NMR (400 MHz, DMSO-$d_6$) δ ppm 0.53-0.61 (m, 1H) 0.89-0.94 (m, 1H) 1.00-1.06 (m, 2H) 1.18 (t, J=7.43 Hz, 3H) 1.82-1.91 (m, 2H) 2.33-2.39 (m, 1H) 3.05 (q, J=7.41 Hz, 2H) 3.12-3.20 (m, 5H) 3.44 (q, J=4.05 Hz, 2H) 3.72-3.87 (m, 2H) 3.99 (t, J=4.50 Hz, 2H) 7.09 (s, 1H) 7.23 (t, J=3.14 Hz, 1H) 7.35-7.47 (m, 2H) 7.86 (s, 1H) 7.95-8.05 (m, 2H); MS (ESI+) m/z 564 (M+H)$^+$.

Example 144

N-[5-cyclopropyl-3-(5,6-dihydro-4H-1,2,4-oxadiazin-3-yl)-2-(4-fluorophenyl)-1-benzofuran-6-yl]-N-[3-(ethylsulfinyl)propyl]methanesulfonamide The title compound can be prepared from Example 8G by analogy with the methods to prepare Example 138. $^1$H NMR (400 MHz, DMSO-$d_6$) δ ppm 0.53-0.60 (m, 1H) 0.87-0.94 (m, 1H) 0.97-1.06 (m, 2H) 1.09-1.18 (m, 3H) 1.75-1.87 (m, 2H) 2.34-2.40 (m, 1H) 2.53-2.66 (m, 2H) 2.69-2.82 (m, 2H) 3.16 (s, 3H) 3.44 (q, J=4.19 Hz, 2H) 3.74-3.87 (m, 2H) 3.99 (t, J=4.55 Hz, 2H) 7.08 (s, 1H) 7.24 (t, J=3.14 Hz, 1H) 7.34-7.46 (m, 2H) 7.87 (d, J=6.18 Hz, 1H) 7.97-8.03 (m, 2H); MS (ESI+) m/z 548 (M+H)$^+$.

The compounds of Examples 145-158 can be made using the methods shown generally in Examples 11-16 with appropriate choice of reagents.

Example 145

N-[5-cyclopropyl-3-(4,5-dihydro-1,2,4-oxadiazol-3-yl)-2-(4-fluorophenyl)-1-benzofuran-6-yl]-N-(4-methoxybenzyl)methanesulfonamide $^1$H NMR (500 MHz, DMSO-$d_6$) δ ppm 0.11-0.29 (m, 1H), 0.67-0.79 (m, 2H), 0.89-0.99 (m, 1H), 2.16-2.26 (m, 1H), 3.20 (s, 3H), 3.68 (s, 3H), 4.68-4.89 (m, 2H), 5.31 (dd, J=3.05, 1.98 Hz, 2H), 6.80 (d, J=8.85 Hz, 2H), 7.08-7.19 (m, 3H), 7.13 (s, 1H), 7.41 (t, J=8.93 Hz, 2H), 7.79 (s, 1H), 7.97-8.05 (m, 2H); MS (ESI+) m/z 536 (M+H)$^+$, 1071 (2M+H)$^+$, 1093 (2M+Na)$^+$, MS (ESI−) m/z 534 (M−H)$^−$, 1069 (2M−H)$^−$.

Example 146

N-[5-cyclopropyl-3-(4,5-dihydro-1,2,4-oxadiazol-3-yl)-2-(4-fluorophenyl)-1-benzofuran-6-yl]-N-(3,4-dihydroxy-4-methylpentyl)methanesulfonamide $^1$H NMR (500 MHz, DMSO-$d_6$) δ ppm 0.50-0.58 (m, 1H), 0.82-0.89 (m, 1H), 0.92 (d, J=9.92 Hz, 3H), 0.97-1.06 (m, 2H), 1.00 (d, J=12.66 Hz, 3H), 1.29-1.52 (m, 1H), 1.63-1.84 (m, 1H), 2.35-2.43 (m, 1H), 3.04-3.18 (m, 1H), 3.14 (s, 3H), 3.57-3.97 (m, 2H), 4.09 (s, 1H), 4.48 (dd, J=40.28, 6.10 Hz, 1H), 5.34 (dd, J=3.13, 1.45 Hz, 2H), 7.18 (q, J=3.05 Hz, 1H), 7.28 (d, J=9.61 Hz, 1H), 7.41 (t, J=8.93 Hz, 2H), 7.87 (s, 1H), 7.99-8.06 (m, 2H); MS (ESI+) m/z 532 (M+H)$^+$, 549 (M+NH$_4$)$^+$, 554 (M+Na)$^+$, 590 (M+CH$_3$CN+NH$_4$)$^+$, 1066 (2M+H)$^+$, MS (ESI−) m/z 530 (M−H)$^−$.

Example 147

N-[5-cyclopropyl-3-(4,5-dihydro-1,2,4-oxadiazol-3-yl)-2-(4-fluorophenyl)-1-benzofuran-6-yl]-N-(5-hydroxypentyl)methanesulfonamide $^1$H NMR (500 MHz, DMSO-d$_6$) δ ppm 0.50-0.61 (m, 1H), 0.80-0.93 (m, 1H), 0.98-1.07 (m, 2H), 1.21-1.53 (m, 8H), 2.38-2.45 (m, 1H), 3.13 (s, 3H), 3.56-3.82 (m, 2H), 4.33 (t, J=5.11 Hz, 1H), 5.34 (t, J=2.90 Hz, 2H), 7.17 (t, J=3.13 Hz, 1H), 7.26 (s, 1H), 7.41 (t, J=8.93 Hz, 2H), 7.87 (s, 1H), 8.02 (dd, J=9.08, 5.42 Hz, 2H); MS (ESI+) m/z 502 (M+H)$^+$.

Example 148

N-[5-cyclopropyl-3-(4,5-dihydro-1,2,4-oxadiazol-3-yl)-2-(4-fluorophenyl)-1-benzofuran-6-yl]-N-[4-(methylsulfonyl)butyl]methanesulfonamide $^1$H NMR (500 MHz, DMSO-d$_6$) δ ppm 0.49-0.66 (m, 1H), 0.84-0.91 (m, 1H), 0.98-1.13 (m, 2H), 1.46-1.61 (m, 2H), 1.64-1.86 (m, 2H), 2.36-2.43 (m, 1H), 2.91 (s, 3H), 3.09 (dd, J=14.65, 5.95 Hz, 2H), 3.15 (s, 3H), 3.60-3.79 (m, 2H), 5.32-5.37 (m, 2H), 7.17 (t, J=3.13 Hz, 1H), 7.27 (s, 1H), 7.42 (t, J=8.93 Hz, 2H), 7.88 (s, 1H), 8.02 (dd, J=8.93, 5.42 Hz, 2H); MS (ESI+) m/z 550 (M+H)$^+$, 567 (MH-NH$_4$)$^+$, 608 (M+CH$_3$CN+NH$_4$)$^+$, 1121 (2M+Na)$^+$, MS (ESI−) m/z 548 (M−H)$^−$, 1097 (2M−H)$^−$.

Example 149

N-[5-cyclopropyl-3-(4,5-dihydro-1,2,4-oxadiazol-3-yl)-2-(4-fluorophenyl)-1-benzofuran-6-yl]-N-[2-(1,1-dioxidotetrahydrothiophen-3-yl)ethyl]methanesulfonamide $^1$H NMR (500 MHz, DMSO-d$_6$) δ ppm 0.51-0.62 (m, 1H), 0.84-0.93 (m, 1H), 0.98-1.10 (m, 2H), 1.51-1.82 (m, 3H), 2.13-2.32 (m, 1H), 2.36-2.43 (m, 1H), 2.64-2.77 (m, 1H), 2.95-3.10 (m, 1H), 3.10-3.31 (m, 3H), 3.15 (s, 3H), 3.61-3.81 (m, 2H), 5.28-5.44 (m, 2H), 7.17 (t, J=2.90 Hz, 1H), 7.27 (d, J=2.14 Hz, 1H), 7.42 (t, J=8.93 Hz, 2H), 7.90 (d, J=4.12 Hz, 1H), 8.02 (dd, J=9.00, 5.49 Hz, 2H); MS (ESI+) m/z 562 (M+H)$^+$, 579 (M+NH$_4$)$^+$, 584 (M+Na)$^+$, MS (ESI−) m/z 560 (M−H)$^−$, 596/598 (M+Cl)$^−$, 1121 (2M−H)$^−$.

Example 150

N-{5-cyclopropyl-3-[(5,5-$^2$H$_2$)-4,5-dihydro-1,2,4-oxadiazol-3-yl]-2-(4-fluorophenyl)-1-benzofuran-6-yl}-N-[4-(methylsulfonyl)butyl]methanesulfonamide $^1$H NMR (400 MHz, DMSO-d$_6$) δ ppm 0.51-0.64 (m, 1H), 0.82-0.92 (m, 1H), 0.99-1.10 (m, 2H), 1.48-1.63 (m, 2H), 1.64-1.85 (m, 2H), 2.34-2.44 (m, 1H), 2.91 (s, 3H), 3.05-3.12 (m, 2H), 3.15 (s, 3H), 3.60-3.80 (m, 2H), 7.13 (s, 1H), 7.28 (s, 1H), 7.41 (t, J=8.89 Hz, 2H), 7.88 (s, 1H), 8.02 (dd, J=8.89, 5.42 Hz, 2H); MS (ESI+) m/z 552 (M+H)$^+$, 569 (M+NH$_4$)$^+$, 610 (M+CH$_3$CN+NH$_4$)$^+$, MS (ESI−) m/z 550 (M−H)$^−$, 1101 (2M−H)$^−$.

Example 151

N-[5-cyclopropyl-2-(4-fluorophenyl)-3-(5-methyl-4,5-dihydro-1,2,4-oxadiazol-3-yl)-1-benzofuran-6-yl]-N-(4-methoxybenzyl)methanesulfonamide $^1$H NMR (300 MHz, DMSO-d$_6$) δ ppm 0.14-0.26 (m, 1H) 0.64-0.81 (m, 2H) 0.83-1.00 (m, 1H) 1.35 (d, J=4.75 Hz, 3H) 2.14-2.24 (m, 1H) 3.20 (s, 3H) 3.68 (s, 3H) 4.69-4.88 (m, 2H) 5.70-5.78 (m, 1H) 6.76-6.84 (m, 2H) 7.07-7.15 (m, 3H) 7.26 (dd, J=4.75, 2.37 Hz, 1H) 7.36-7.47 (m, 2H) 7.77 (s, 1H) 7.95-8.07 (m, 2H); MS (ESI+) m/z 550 (M+H)$^+$.

Example 152

N-[5-cyclopropyl-3-(5,5-dimethyl-4,5-dihydro-1,2,4-oxadiazol-3-yl)-2-(4-fluorophenyl)-1-benzofuran-6-yl]-N-(3-methylbutyl)methanesulfonamide $^1$H NMR (500 MHz, DMSO-d$_6$) δ ppm 0.50-0.58 (m, 1H) 0.78-0.88 (m, 1H) 0.83 (dd, J=6.56, 4.88 Hz, 6H) 1.03 (dd, J=8.24, 1.98 Hz, 2H) 1.21-1.29 (m, 1H) 1.34-1.42 (m, 1H) 1.49 (d, J=1.53 Hz, 6H) 1.57-1.67 (m, 1H) 2.38-2.43 (m, 1H) 3.13 (s, 3H) 3.59-3.67 (m, 1H) 3.71-3.77 (m, 1H) 7.19 (s, 1H) 7.33 (s, 1H) 7.40-7.44 (m, 2H) 7.88 (s, 1H) 8.00-8.05 (m, 2H); MS (ESI+) m/z 514 (M+H)$^+$.

Example 153

N-[5-cyclopropyl-2-(4-fluorophenyl)-3-(5-propyl-1,2,4-oxadiazol-3-yl)-1-benzofuran-6-yl]-N-(3-methylbutyl)methanesulfonamide $^1$H NMR (500 MHz, DMSO-d$_6$) δ ppm 0.48-0.58 (m, 1H) 0.79-0.90 (m, 1H) 0.83 (dd, J=6.56, 5.49 Hz, 6H) 1.01 (t, J=7.40 Hz, 3H) 1.03-1.06 (m, 2H) 1.23-1.31 (m, 1H) 1.35-1.43 (m, 1H) 1.58-1.66 (m, 1H) 1.77-1.85 (m, 2H) 2.39-2.46 (m, 1H) 2.99 (t, J=7.32 Hz, 2H) 3.14 (s, 3H) 3.60-3.67 (m, 1H) 3.72-3.79 (m, 1H) 7.37-7.42 (m, 2H) 7.51 (s, 1H) 7.94 (s, 1H) 8.02-8.08 (m, 2H); MS (ESI+) m/z 526 (M+H)$^+$.

Example 154

N-[5-cyclopropyl-2-(4-fluorophenyl)-3-(5-propyl-4,5-dihydro-1,2,4-oxadiazol-3-yl)-1-benzofuran-6-yl]-N-(3-methylbutyl)methanesulfonamide $^1$H NMR (500 MHz, DMSO-d$_6$) δ ppm 0.48-0.57 (m, 1H) 0.74-0.86 (m, 1H) 0.83 (dd, J=6.49, 5.26 Hz, 6H) 0.94-0.98 (m, 3H) 1.03 (dd, J=8.39, 1.98 Hz, 2H) 1.21-1.29 (m, 1H) 1.33-1.48 (m, 3H) 1.56-1.75 (m, 3H) 2.34-2.44 (m, 1H) 3.13 (s, 3H) 3.59-3.66 (m, 1H) 3.70-3.78 (m, 1H) 5.63-5.67 (m, 1H) 7.21 (s, 1H) 7.38 (dd, J=4.96, 2.67 Hz, 1H) 7.40-7.46 (m, 2H) 7.89 (s, 1H) 7.98-8.10 (m, 2H); MS (ESI+) m/z 528 (M+H)$^+$.

Example 155

N-[5-cyclopropyl-3-(5-ethyl-4,5-dihydro-1,2,4-oxadiazol-3-yl)-2-(4-fluorophenyl)-1-benzofuran-6-yl]-N-(3-methylbutyl)methanesulfonamide $^1$H NMR (500 MHz, DMSO-d$_6$) δ ppm 0.51-0.57 (m, 1H) 0.79-0.86 (m, 1H) 0.83 (dd, J=6.56, 5.04 Hz, 6H) 0.92-0.96 (m, 3H) 1.03 (dd, J=8.39, 1.98 Hz, 2H) 1.21-1.43 (m, 2H) 1.58-1.75 (m, 3H) 2.38-2.43 (m, 1H) 3.13 (s, 3H) 3.59-3.79 (m, 2H) 5.61-5.64 (m, 1H) 7.22 (s, 1H) 7.35-7.37 (m, 1H) 7.39-7.44 (m, 2H) 7.88 (s, 1H) 8.01-8.06 (m, 2H); MS (ESI+) m/z 514 (M+H)$^+$.

Example 156

N-[5-cyclopropyl-3-(4,5-dihydro-1,2,4-oxadiazol-3-yl)-2-(4-fluorophenyl)-1-benzofuran-6-yl]-N-(3-methylbutyl)methanesulfonamide $^1$H NMR (500 MHz, DMSO-d$_6$) δ ppm 0.56 (m, 1H) 0.83 (m, 7H) 1.02 (m, 2H) 1.27 (m, 1H) 1.37 (m, 1H) 1.62 (m, 1H)

2.40 (m, 1H) 3.13 (s, 3H) 3.62 (m, 1H) 3.74 (m, 1H) 5.34 (m, 2H) 7.18 (t, J=3.13 Hz, 1H) 7.26 (s, 1H) 7.41 (m, 2H) 7.88 (s, 1H) 8.02 (m, 2H); MS (ESI+) m/z 486.1 (M+H)$^+$.

Example 157

4-{[5-cyclopropyl-3-(4,5-dihydro-1,2,4-oxadiazol-3-yl)-2-(4-fluorophenyl)-1-benzofuran-6-yl](methylsulfonyl)amino}butanoic acid $^1$H NMR (500 MHz, DMSO-d$_6$) δ ppm 0.55 (m, 1H) 0.85 (m, 1H) 1.03 (m, 2H) 1.61 (m, 2H) 2.22 (m, 2H) 2.37 (m, 1H) 3.14 (s, 3H) 3.67 (m, 2H) 5.34 (d, J=2.44 Hz, 2H) 7.19 (t, J=2.44 Hz, 1H) 7.27 (s, 1H) 7.41 (m, 2H) 7.87 (s, 1H) 8.03 (m, 2H); MS (ESI+) m/z 502 (M+H)$^+$.

Example 158

N-[5-cyclopropyl-2-(4-fluorophenyl)-3-(5-methyl-4,5-dihydro-1,2,4-oxadiazol-3-yl)-1-benzofuran-6-yl]-N-(2-hydroxyethyl)methanesulfonamide $^1$H NMR (500 MHz, DMSO-d$_6$) δ ppm 0.55 (s, 1H), 0.85 (dd, J=12.8, 18.0, 1H), 0.94-1.12 (m, 2H), 1.23-1.54 (m, 3H), 2.34 (td, J=4.3, 8.5, 1H), 3.20 (s, 3H), 3.40 (d, J=11.0, 1H), 3.51 (d, J=5.6, 1H), 3.52-3.67 (m, 1H), 3.81 (dt, J=6.8, 13.7, 1H), 5.67-5.86 (m, 1H), 7.25 (s, 1H), 7.28 (d, J=24.6, 1H), 7.42 (t, J=8.9, 2H), 7.83 (s, 1H), 8.03 (dd, J=5.5, 8.8, 2H); MS (ESI+) m/z 474.0 (M+H)$^+$, MS (ESI−) m/z 472.1 (M−H)$^−$.

Example 159

N-[3-(4-chloro-1H-imidazol-2-yl)-5-cyclopropyl-2-(4-fluorophenyl)-1-benzofuran-6-yl]-N-(4-methoxybenzyl)methanesulfonamide A mixture of Example 164 (0.040 g, 0.071 mmol), 4-methoxybenzyl bromide (0.012 mL, 0.086 mmol), sodium iodide (0.012 g, 0.079 mmol) and potassium carbonate (0.022 g, 0.157 mmol) in dimethylsulfoxide (1.0 mL) was stirred for 16 hours and diluted into ethyl acetate. The organic layer was washed with brine, dried (Na$_2$SO$_4$), filtered and concentrated. The crude material was purified by reverse phase chromatography (C8 support, 10-100% acetonitrile in 0.1% trifluoroacetic acid/water) to give the title compound as an off-white powder, trifluoroacetic acid salt (10 mg, 20%). $^1$H NMR (300 MHz, DMSO-d$_6$) δ ppm 0.12-0.27 (m, 1H) 0.62-0.98 (m, 3H) 2.09-2.24 (m, 1H) 3.21 (s, 3H) 3.68 (s, 3H) 4.68-4.89 (m, 2H) 6.80 (d, J=8.46 Hz, 2H) 6.92 (s, 1H) 7.13 (d, J=8.46 Hz, 2H) 7.32-7.39 (m, 2H) 7.43 (s, 1H) 7.79 (s, 1H) 7.84-7.90 (m, 2H) 12.74 (s, 1H); MS (ESI+) m/z 566 (M+H)$^+$.

Example 160

N-[5-cyclopropyl-2-(4-fluorophenyl)-3-(5-oxo-5,6-dihydro-4H-1,2,4-oxadiazin-3-yl)-1-benzofuran-6-yl]-N-(4-methoxybenzyl)methanesulfonamide In a 5 mL round-bottomed flask under nitrogen at 10° C. was added Example 8C (52.4 mg, 0.1 mmol) in dry tetrahydrofuran (1 mL) to give a colorless solution. The solution was treated dropwise via syringe with chloroacetyl chloride (8.01 μl, 0.100 mmol). The reaction mixture was stirred for 1 hour at ambient temperature, then cooled to 5° C. and treated portion wise with 95% sodium hydride (7.58 mg, 0.300 mmol). The mixture was stirred at ambient temperature for 16 hours, treated with dilute aqueous HCl to pH 7 and extracted into ethyl acetate. The ethyl acetate layer was washed with brine, dried (Na$_2$SO$_4$) filtered and concentrated. Purification by chromatography on a 12 g silica cartridge eluting with 0-40% ethyl acetate in hexane gave the title compound as a white powder (20 mg, 35%). $^1$H NMR (500 MHz, DMSO-d$_6$) δ ppm 0.16-0.27 (m, 1H) 0.65-0.82 (m, 2H) 0.85-1.00 (m, 1H) 2.15-2.25 (m, 1H) 3.20 (s, 3H) 3.66-3.69 (m, 3H) 4.54 (s, 2H) 4.69-4.91 (m, 2H) 6.77-6.82 (m, 2H) 7.03 (s, 1H) 7.10-7.16 (m, 2H) 7.37-7.45 (m, 2H) 7.80 (s, 1H) 7.83-7.91 (m, 2H) 11.32 (s, 1H); MS (APCI+) m/z 564 (M+H)$^+$.

Example 161

N-[5-cyclopropyl-2-(4-fluorophenyl)-3-(6-oxo-1,6-dihydropyrimidin-2-yl)-1-benzofuran-6-yl]-N-(3-methylbutyl)methanesulfonamide Example 161A 5-cyclopropyl-2-(4-fluorophenyl)-6-(N-isopentylmethylsulfonamido)benzofuran-3-carboximidamide In a 25-mL round bottom flask purged with nitrogen was added Example 10F (200 mg, 0.422 mmol), glacial acetic acid (4 mL), ammonium formate (133 mg, 2.112 mmol) and 10% Pd—C (100 mg, 0.094 mmol). The mixture was heated in an oil bath at 120° C. for 2.5 hours, cooled, filtered through diatomaceous earth, and the filtrate was concentrated. The residue was partitioned into ethyl acetate and water and the pH was adjusted to 12 with 1 N aqueous NaOH. The organic layer was washed with brine (25 mL), dried over anhydrous MgSO$_4$, filtered, and concentrated by rotary evaporation to give the title compound as a yellow solid (175 mg, 91%). MS (ESI+) m/z 458 (M+H)$^+$.

Example 161B

N-[5-cyclopropyl-2-(4-fluorophenyl)-3-(6-oxo-1,6-dihydropyrimidin-2-yl)-1-benzofuran-6-yl]-N-(3-methylbutyl)methanesulfonamide To a 2 mL microwave tube was added Example 161A (22.88 mg, 0.05 mmol) and ethyl propiolate (5.60 μl, 0.055 mmol) in ethanol (0.5 mL) to give a yellow solution. The tube was sealed and heated under nitrogen at 60° C. for 15 minutes. The mixture was cooled and a solution of KOH (3.3 mg) in ethanol (0.5 mL) was added via syringe. The mixture was heated at 80° C. for 16 hours, cooled and concentrated. The crude material was purified by reverse phase chromatography (C8 support, 10-100% acetonitrile in 0.1% trifluoroacetic acid/water) to give the title compound (7 mg 26%). $^1$H NMR (500 MHz, DMSO-d$_6$) δ ppm 0.52-0.58 (m, 1H) 0.83 (dd, J=6.56, 5.80 Hz, 6H) 0.84-0.91 (m, 1H) 0.95-1.02 (m, 2H) 1.22-1.32 (m, 1H) 1.34-1.43 (m, 1H) 1.57-1.66 (m, 1H) 2.35-2.42 (m, 1H) 3.14 (s, 3H) 3.60-3.67 (m, 1H) 3.70-3.78 (m, 1H) 6.41 (s, 1H) 7.13-7.17 (m, 1H) 7.38 (t, J=8.77 Hz, 2H) 7.73 (s, 2H) 7.89 (s, 1H) 8.11 (s, 1H) 12.86 (s, 1H); MS (APCI+) m/z 510 (M+H)$^+$.

Example 162

N-[5-cyclopropyl-2-(4-fluorophenyl)-3-(5-oxo-5,6-dihydro-4H-1,2,4-oxadiazin-3-yl)-1-benzofuran-6-yl]-N-(3-methylbutyl)methanesulfonamide Example 10F (95 mg, 0.2 mmol) was treated with chloroacetyl chloride (17.62 μA, 0.220 mmol), and 95% sodium hydride (15.16 mg, 0.600 mmol) according to procedures analogous to the procedure in Example 160. Purification by chromatography on a 12 g silica cartridge eluting with 0-40% ethyl acetate in hexane gave the title compound as a white powder (24 mg, 21%). $^1$H NMR (500 MHz, DMSO-$d_6$) δ ppm 0.52-0.63 (m, 1H) 0.83 (dd, J=6.56, 5.49 Hz, 6H) 0.87-0.95 (m, 1H) 0.98-1.04 (m, 2H) 1.21-1.30 (m, 1H) 1.34-1.43 (m, 1H) 1.56-1.68 (m, 1H) 2.38-2.43 (m, 1H) 3.13 (s, 3H) 3.56-3.79 (m, 2H) 4.57 (s, 2H) 7.17 (s, 1H) 7.39-7.45 (m, 2H) 7.86-7.90 (m, 2H) 7.89 (s, 1H) 11.34 (s, 1H); MS (APCI+) m/z 514 (M+H)$^+$.

Example 163

N-[5-cyclopropyl-3-(4,5-dichloro-1H-imidazol-2-yl)-2-(4-fluorophenyl)-1-benzofuran-6-yl]methanesulfonamide A mixture of Example 1O (20.57 mg, 0.05 mmol) and N-chlorosuccinimide (13.35 mg, 0.100 mmol) in tetrahydrofuran (1 mL) in a sealed tube was heated at 70° C. for 30 minutes and then stirred at ambient temperature for 16 hours. The reaction mixture was partitioned into ethyl acetate and water. The intensely pink organic layer was washed with brine, dried (Na$_2$SO$_4$), filtered and concentrated. The crude material was purified by reverse phase chromatography (C8 support, 10-100% acetonitrile in 0.1% trifluoroacetic acid/water) to give the title compound as a trifluoroacetic acid salt (5 mg, 16%). $^1$H NMR (300 MHz, DMSO-$d_6$) δ ppm 0.65-0.74 (m, 2H) 0.90-1.05 (m, 2H) 2.19-2.37 (m, 1H) 3.07 (s, 3H) 7.20 (s, 1H) 7.31-7.42 (m, 2H) 7.64 (s, 1H) 7.80-7.92 (m, 2H) 9.29 (s, 1H) 13.68 (s, 1H); MS (ESI+) m/z 480 (M+H)$^+$.

Example 164

N-[3-(4-chloro-1H-imidazol-2-yl)-5-cyclopropyl-2-(4-fluorophenyl)-1-benzofuran-6-yl]methanesulfonamide A mixture of Example 1O (123 mg, 0.3 mmol) and N-chlorosuccinimide (42.1 mg, 0.315 mmol) in a solvent mix of tetrahydrofuran (10 mL) and N,N-dimethylformamide (2 mL) was stirred for 72 hours. The reaction mixture was diluted with ethyl acetate, washed with water and saturated sodium chloride, dried (Na$_2$SO$_4$), filtered and concentrated. The residue was flash chromatographed on a 24 g silica cartridge eluting with 1-6% methanol in dichloromethane to give partial separation of the product mixture. The material was then purified by reverse phase chromatography (C8 support, 10-100% acetonitrile in 0.1% trifluoroacetic acid/water) to give the title compound as a trifluoroacetic acid salt (55 mg, 28%). $^1$H NMR (300 MHz, DMSO-$d_6$) δ ppm 0.62-0.78 (m, 2H) 0.92-1.08 (m, 2H) 2.24-2.36 (m, 1H) 3.07 (s, 3H) 7.17 (s, 1H) 7.35 (t, J=8.82 Hz, 2H) 7.45 (s, 1H) 7.64 (s, 1H) 7.86-7.91 (m, 2H) 9.32 (s, 1H) 12.77 (s, 1H); MS (ESI+) m/z 446 (M+H)$^+$.

Example 165

N-[5-cyclopropyl-3-(4,5-dibromo-1H-imidazol-2-yl)-2-(4-fluorophenyl)-1-benzofuran-6-yl]methanesulfonamide Example 1O (103 mg, 0.25 mmol) and N-bromosuccinimide (66 mg, 0.375 mmol) in tetrahydrofuran (10 mL) was stirred for 24 hours. The reaction mixture was diluted with ethyl acetate, washed with water and brine, dried (Na$_2$SO$_4$), filtered and concentrated to a dark purple solid. The crude material was purified by reverse phase chromatography (C8 support, 10-100% acetonitrile in 0.1% trifluoroacetic acid/water) to give the title compound as a trifluoroacetic acid salt (38 mg, 22%). $^1$H NMR (300 MHz, DMSO-$d_6$) δ ppm 0.66-0.74 (m, 2H) 0.94-1.03 (m, 2H) 2.23-2.36 (m, 1H) 3.07 (s, 3H) 7.18 (s, 1H) 7.33-7.40 (m, 2H) 7.64 (s, 1H) 7.80-7.87 (m, 2H) 9.32 (s, 1H) 13.63 (s, 1H); MS (ESI+) m/z 570 (M+H)$^+$.

Example 166

2-[6-(2,5-dimethyl-1H-pyrrol-1-yl)-2-phenyl-1-benzofuran-3-yl]-1H-imidazole

Example 166A 3-iodo-2-phenylbenzofuran-6-amine

In a round bottom flask were combined 3-iodo-6-nitro-2-phenylbenzofuran (3.65 g, 10.0 mmol), ammonium chloride (0.802 g, 15.00 mmol) and iron powder (2.79 g, 50.0 mmol). To this was added a mixture of tetrahydrofuran/methanol/water (1:1:2 v-v, 100 mL). The mixture was heated to reflux for a total of four hours. After cooling to room temperature, the reaction mixture was filtered through diatomaceous earth and the filtrate was concentrated in vacuo. The residue was partitioned between water and ethyl acetate. The organic layer was dried (Na$_2$SO$_4$) filtered and concentrated to give the title compound 3.35 gm (100%).

Example 166B 1-(3-iodo-2-phenylbenzofuran-6-yl)-2,5-dimethyl-1H-pyrrole

Example 166A (0.40 g, 1.194 mmol) was dissolved in benzene (10 mL). To this solution was added pyridinium p-toluenesulfonate (0.021 g, 0.064 mmol) and hexane-2,5-dione (0.140 mL, 1.194 mmol). A Dean-Stark trap and condenser was attached and the mixture was refluxed in an oil bath at 110° C. for one hour. The reaction mixture was partitioned between water (40 mL) and ethyl acetate (20 mL). The organic phase was washed with water then dried (MgSO$_4$) and concentrated in vacuo to provide the title compound (0.5116 g, quant.) as a sticky yellow foam.

Example 166C 6-(2,5-dimethyl-1H-pyrrol-1-yl)-2-phenylbenzofuran-3-carbonitrile

Example 166B (536 mg, 1.30 mmol) was combined in a round bottom flask with zinc dust (3.16 mg, 0.048 mmol), zinc cyanide (19.35 mg, 0.165 mmol), 1,1"-bis(diphenylphosphino)ferrocene (13.07 mg, 0.024 mmol), tris(dibenzylideneacetone)dipalladium(0) (11.97 mg, 0.013 mmol) and anhydrous N,N-dimethylformamide (5 mL). A septum was attached and nitrogen was bubbled through the reaction mixture for five minutes at which time all gas lines were removed and the sealed flask heated in an oil bath at 100° C. for ninety minutes. The flask was cooled to room temperature and the contents were vacuum filtered through a bed of sand and diatomaceous earth with an ethyl acetate rinse. The filtrate was partitioned between ethyl acetate (100 mL) and water (100 mL) plus enough solid sodium bicarbonate to bring the aqueous pH to 7 or 8. The organic phase was washed with water (100 mL), then dried (MgSO$_4$), filtered and concentrated in vacuo to provide the crude product. Purification by chromatography on silica gel (ethyl acetate and hexane) gave the title compound, 0.315 gm (78%) as a pale yellow solid.

Example 166D 2-(6-(2,5-dimethyl-1H-pyrrol-1-yl)-2-phenylbenzofuran-3-yl)-4,5-dihydro-1H-imidazole Example 166C, (2.37 g, 7.59 mmol) was combined under nitrogen at room temperature with phosphorous pentasulfide (0.209 g, 0.941 mol) as solids in a round bottom flask equipped with a Claisen head and a reflux condenser both capped with septa. Ethylenediamine (51 mL, 0.76 mole) was added via syringe and nitrogen was bubbled through the resulting green suspension for seven minutes. The gas lines were replaced by a nitrogen balloon and the flask was immersed in an oil bath at 120° C. for forty minutes. The reaction mixture was concentrated and the residue was slowly diluted with water (125 mL) with vigorous stirring. The resulting solid was collected by vacuum filtration, and the cake was water washed (75 mL) and then dried in vacuo to provide the title compound, (1.00 g, 37%), as a pale yellow solid sufficiently pure for use as isolated.

Example 166E

2-[6-(2,5-dimethyl-1H-pyrrol-1-yl)-2-phenyl-1-benzofuran-3-yl]-1H-imidazole

Example 166D (37.4 mg, 0.105 mmol) was combined with potassium carbonate (40.1 mg, 0.290 mmol), diacetoxy-iodobenzene (38.0 mg, 0.118 mmol) and dimethylsulfoxide (1.5 mL) in a microwave tube. The resulting suspension was allowed to stir overnight at room temperature under nitrogen. The reaction mixture was partitioned between water (40 mL) and ethyl acetate (15 mL). The organic phase was washed with water and concentrated in vacuo. The crude product was purified by chromatography on silica gel (ethyl acetate and hexane) to provide the title compound, (9.4 mg, 25%) as a pale yellow solid. $^1$H NMR (300 MHz, DMSO-d$_6$) δ ppm 2.02 (s, 6H) 5.83 (s, 2H) 7.15-7.24 (m, 2H) 7.36 (s, 1H) 7.41-7.54 (m, 3H) 7.69-7.75 (m, 2H) 7.85-7.93 (m, 2H) 12.46 (s, 1H); MS (DCI+) m/z 354.2 (M+H)$^+$.

Example 167

N-{5-cyclopropyl-3-(1H-imidazol-2-yl)-2-[4-(1-phenylvinyl)phenyl]-1-benzofuran-6-yl}-N-(3-methylbutyl)methanesulfonamide In a 5 mL microwave tube was added Example 18P (120 mg, 0.158 mmol), 1-phenylvinylboronic acid (40 mg, 0.237 mmol), 1,1'-bis(di-tert-butylphosphino)ferrocene palladium dichloride (5.13 mg, 7.88 µmol) and potassium phosphate (66.9 mg, 0.315 mmol) in tetrahydrofuran (1.5 mL) and water (0.5 mL). The mixture was sparged with nitrogen for 5 minutes; the vessel was sealed and heated at 50° C. for 4 hours. The mixture was cooled and partitioned with ethyl acetate and water. The organic layer was washed with brine, dried with sodium sulfate, filtered and concentrated. The residue was purified by chromatography on a 12 g silica cartridge eluting with 1-3% methanol in dichloromethane to give the title compound (49 mg, 55%). $^1$H NMR (400 MHz, DMSO-d$_6$) δ ppm 0.51-0.59 (m, 1H) 0.78-0.87 (m, 7H) 0.96-1.02 (m, 2H) 1.23-1.32 (m, 1H) 1.34-1.45 (m, 1H) 1.56-1.68 (m, 1H) 2.37-2.43 (m, 1H) 3.14 (s, 3H) 3.60-3.69 (m, 1H) 3.70-3.80 (m, 1H) 5.53 (s, 1H) 5.61 (s, 1H) 7.05 (s, 1H) 7.19 (s, 1H) 7.29-7.45 (m, 8H) 7.88 (s, 1H) 7.92 (d, J=8.46 Hz, 2H) 12.44 (s, 1H); MS (ESI+) m/z 566 (M+H)$^+$.

Example 168

N-[5-cyclopropyl-2-{4-[(1E)-hex-1-en-1-yl]phenyl}-3-(1H-imidazol-2-yl)-1-benzofuran-6-yl]-N-[4-(methylsulfonyl)butyl]methanesulfonamide Example 168A N-(2-(4-(benzyloxy)phenyl)-5-cyclopropyl-3-(1H-imidazol-2-yl)benzofuran-6-yl)-N-(4-(methylsulfonyl)butyl)methanesulfonamide A mixture of Example 18M (440 mg, 0.881 mmol), Example 6B (405 mg, 1.3332 mmol) and potassium carbonate (195 mg, 1.41 mmol) in dimethylsulfoxide (6 mL) was heated at 50° C. for 24 hours. The mixture was cooled and partitioned with ethyl acetate and water. The organic layer was washed with brine twice, dried with sodium sulfate, filtered and concentrated. The residue was purified on a 40 g silica cartridge eluting with 2-4% methanol in dichloromethane to give the title compound (335 mg, 60%). MS (ESI+) m/z 566 (M+H)$^+$.

Example 168B

N-(5-cyclopropyl-2-(4-hydroxyphenyl)-3-(1H-imidazol-2-yl)benzofuran-6-yl)-N-(4-(methylsulfonyl)butyl)methanesulfonamide Example 168A (300 mg, 0.473 mmol) and N,N-dimethylformamide (8.00 mL) were added to 20% palladium hydroxide on carbon, wet (60.0 mg, 0.427 mmol) in a 50 mL pressure bottle and the mixture was stirred for 32 hours under 30 psi hydrogen. The mixture was filtered through a nylon membrane and concentrated. The residue was partitioned between ethyl acetate and water. The ethyl acetate layer was washed repeatedly with brine, dried (Na$_2$SO$_4$), filtered and concentrated. Purification by flash chromatography on silica eluting with 2-5% methanol in dichloromethane afforded the title compound (0.193 g, 68%). MS (ESI+) m/z 544 (M+H)$^+$.

Example 168C 4-(5-cyclopropyl-3-(1H-imidazol-2-yl)-6-(N-(4-(methylsulfonyl)butyl)methylsulfonamido)benzofuran-2-yl)phenyl 1,1,2,2,3,3,4,4,4-nonafluorobutane-1-sulfonate A mixture of Example 168B (190 mg, 0.349 mmol) 1,1,2,2,3,3,4,4,4-nonafluorobutane-1-sulfonyl fluoride (116 mg, 0.384 mmol), and potassium carbonate (62.8 mg, 0.454 mmol) in N,N-dimethylformamide (3 mL) was stirred for 2 hours and partitioned with ethyl acetate and water. The organic layer was washed with brine twice, dried with sodium sulfate, filtered and concentrated. The resulting solid was triturated with hexane and filtered to give the title compound as a solid (275 mg, 95%). MS (ESI+) m/z 826 (M+H)$^+$.

Example 168D

N-[5-cyclopropyl-2-{4-[(1E)-hex-1-en-1-yl]phenyl}-3-(1H-imidazol-2-yl)-1-benzofuran-6-yl]-N-[4-(methylsulfonyl)butyl]methanesulfonamide In a 5 mL microwave tube was added Example 168C (83 mg, 0.10 mmol), (E)-2-(hex-1-enyl)-4,4,5,5-tetramethyl-1,3, 2-dioxaborolane (0.036 mL, 0.150 mmol), 1,1'-bis(di-tert-butylphosphino)ferrocene palladium dichloride (6.52 mg, 10.00 μmol) and potassium phosphate (42.5 mg, 0.200 mmol) in tetrahydrofuran (1.5 mL) and water (0.5 mL). The mixture was sparged with nitrogen for 5 minutes, sealed and heated at 50° C. for 2 hours. The mixture was partitioned with ethyl acetate and water. The organic layer was washed with brine, dried with sodium sulfate, filtered and concentrated. The residue was chromatographed on a 12 g silica cartridge eluting with 1-3% methanol in dichloromethane to give the title compound as an off-white solid (41 mg, 67%). $^1$H NMR (400 MHz, DMSO-$d_6$) δ ppm 0.48-0.57 (m, 1H) 0.79-0.85 (m, 1H) 0.89 (t, J=7.21 Hz, 3H) 0.95-1.02 (m, 2H) 1.28-1.36 (m, 2H) 1.38-1.47 (m, 2H) 1.51-1.60 (m, 2H) 1.66-1.79 (m, 2H) 2.16-2.24 (m, 2H) 2.34-2.39 (m, 1H) 2.90 (s, 3H) 3.04-3.12 (m, 2H) 3.14 (s, 3H) 3.63-3.76 (m, 2H) 6.39-6.43 (m, 2H) 7.04 (s, 1H) 7.17 (s, 1H) 7.33 (s, 1H) 7.47 (d, J=8.46 Hz, 2H) 7.80 (d, J=8.46 Hz, 2H) 7.84 (s, 1H) 12.37 (s, 1H); MS (ESI+) m/z 610 (M+H)$^+$.

Example 169

N-[2-(4-anilinophenyl)-5-cyclopropyl-3-(1H-imidazol-2-yl)-1-benzofuran-6-yl]-N-[4-(methylsulfonyl)butyl]methanesulfonamide In a 5 mL microwave tube was added Example 168C (57.8 mg, 0.070 mmol), aniline (7.66 μl, 0.084 mmol), dicyclohexyl(2',4',6'-triisopropylbiphenyl-2-yl)phosphine (3.34 mg, 7.00 μmol), palladium(II) acetate (1.572 mg, 7.00 μmol) and cesium carbonate (27.4 mg, 0.084 mmol) in benzotriflouride (2.5 mL) and tert-butanol (0.5 mL). The mixture was sparged with nitrogen for 5 minutes, sealed and heated by microwave (Personal Chemistry, Emrys Creator, 300 W) at 130° C. for 30 minutes. The reaction mixture was cooled and partitioned with ethyl acetate and water. The organic layer was washed with brine, dried with sodium sulfate, filtered and concentrated. The residue was chromatographed on a 12 g silica cartridge eluting with 1-3% methanol in dichloromethane to give the title compound (18 mg, 42%). $^1$H NMR (400 MHz, DMSO-$d_6$) δ ppm 0.47-0.58 (m, 1H) 0.78-0.86 (m, 1H) 0.91-1.03 (m, 2H) 1.51-1.62 (m, 2H) 1.67-1.80 (m, 2H) 2.35-2.41 (m, 1H) 2.91 (s, 3H) 3.06-3.12 (m, 2H) 3.15 (s, 3H) 3.63-3.79 (m, 2H) 6.92 (t, J=7.26 Hz, 1H) 7.00 (s, 1H) 7.09 (d, J=8.89 Hz, 2H) 7.13-7.18 (m, 3H) 7.26-7.34 (m, 3H) 7.76 (d, J=8.89 Hz, 2H) 7.79 (s, 1H) 8.56 (s, 1H) 12.32 (s, 1H); MS (ESI+) m/z 619 (M+H)$^+$.

Example 170

N-[2-(4-fluorophenyl)-3-(1H-imidazol-2-yl)-5-isopropoxy-1-benzofuran-6-yl]-N-(4-methoxybenzyl)methanesulfonamide Example 170A 2-(4-fluorophenyl)-3-(1H-imidazol-2-yl)-5-isopropoxybenzofuran-6-amine Methyl 2-(4-fluorophenyl)-5-isopropoxy-6-nitrobenzofuran-3-carboxylate (1.0 g, 2.68 mmol) was dissolved in tetrahydrofuran (12 mL) and methanol (12 mL). Ammonium chloride (0.21 g, 4.02 mmol) and iron powder (0.6 g, 10.71 mmol) were added followed by water (4 mL). The resulting mixture was heated at reflux for 1 hour, filtered, and washed with hot methanol. The solvent was removed in vacuo leaving a dark brown oil. The oil was redissolved in 100 mL ethyl acetate and washed with 100 mL water. The water layer was back extracted with 100 mL ethyl acetate and the combined organic extracts were washed with 10% sodium chloride, dried over anhydrous sodium sulfate(s), filtered and the solvent was removed in vacuo leaving a black oil. The oil was purified by a 50 g silica gel column eluted with 600 mL 5:1 hexane:ethyl acetate and 300 mL 3:1 hexane:ethyl acetate to give the title compound as a tan solid, 0.6 g, 65%.

Example 170B methyl 2-(4-fluorophenyl)-5-isopropoxy-6-(methylsulfonamido)benzofuran-3-carboxylate Methyl 6-amino-2-(4-fluorophenyl)-5-isopropoxybenzofuran-3-carboxylate (0.6 g, 1.75 mmol) was dissolved in dichloromethane. Pyridine (0.71 mL, 8.74 mmol) and methanesulfonyl chloride (0.27 mL, 3.5 mmol) were added and the resulting yellow orange solution was stirred at room temperature 15 hours. The solvent was removed in vacuo leaving an oily residue. The oil was redissolved in 100 mL ethyl acetate and 25 mL 10% aqueous HCl. The layers were separated and the organic layer was washed with 10% aqueous sodium bicarbonate and 10% aqueous sodium chloride, dried over anhydrous sodium sulfate(s), filtered and the solvent was removed in vacuo leaving an off-white solid, 0.65 g, 88%.

Example 170C methyl 2-(4-fluorophenyl)-5-isopropoxy-6-(N-(4-methoxybenzyl)methylsulfonamido)benzofuran-3-carboxylate Methyl 2-(4-fluorophenyl)-5-isopropoxy-6-(methylsulfonamido)benzofuran-3-carboxylate (0.65 g, 1.5 mmol) was dissolved in 10 mL N,N-dimethylformamide and treated sequentially with potassium carbonate (0.26 g, 1.85 mmol) and 4-methoxybenzyl bromide (0.27 mL, 1.85 mmol). The slurry was stirred and heated at 70° C. for 3 hours. The reaction mixture was concentrated in vacuo to a pasty solid. The residue was dissolved in 100 mL ethyl acetate, washed with 1 N aqueous $H_3PO_4$ and 10% aqueous sodium chloride, dried over anhydrous sodium sulfate(s), filtered and the solvent was removed in vacuo leaving a yellow oil, 0.8 g.

Example 170D

N-(2-(4-fluorophenyl)-3-(hydroxymethyl)-5-isopropoxybenzofuran-6-yl)-N-(4-methoxybenzyl)methanesulfonamide Methyl 2-(4-fluorophenyl)-5-isopropoxy-6-(N-(4-methoxybenzyl)methylsulfonamido)benzofuran-3-carboxylate (0.8 g, 1.48 mmol) was dissolved in tetrahydrofuran cooled in an ice bath and treated with lithium aluminum hydride in tetrahydrofuran (1.0 M, 1.48 mL). The resulting solution was stirred at room temperature for 45 minutes. The reaction was quenched with 0.3 mL water, 0.3 mL 15% aqueous NaOH and 0.6 mL water, stirred 15 minutes, and decanted. The solid was washed with ethyl acetate, diluted with 100 mL ethyl acetate, and washed with 1 N aqueous $H_3PO$, 10% aqueous sodium bicarbonate, and 10% aqueous sodium chloride. The mixture was dried over anhydrous sodium sulfate(s), filtered and the solvent was removed in vacuo leaving an oily residue, 0.68 g, 90%.

Example 170E

N-(2-(4-fluorophenyl)-3-formyl-5-isopropoxybenzofuran-6-yl)-N-(4-methoxybenzyl)methanesulfonamide N-(2-(4-fluorophenyl)-3-(hydroxymethyl)-5-isopropoxybenzofuran-6-yl)-N-(4-methoxybenzyl)methanesulfonamide (0.68 g, 1.32 mmol) was dissolved in dichloromethane. N-methyl morpholine oxide (0.23 g, 1.99 mmol), 4 Å molecular sieves (0.7 g) and finally tetrapropylammonium perruthenate (0.023 g, 0.066 mmol) were added. The resulting black slurry was stirred for 60 minutes at room temperature. The reaction mixture was filtered through a pad of diatomaceous earth, and the solid was washed with dichloromethane until the washes were clear. The combined dichloromethane washes were applied to a dry 10 g silica gel cartridge and the column was eluted with ethyl acetate until no more product was eluted. The solvent was removed in vacuo leaving a tan solid, 0.65 g, 96%.

Example 170F

N-(3-(4,5-dihydro-1H-imidazol-2-yl)-2-(4-fluorophenyl)-5-isopropoxybenzofuran-6-yl)-N-(4-methoxybenzyl)methanesulfonamide N-(2-(4-fluorophenyl)-3-formyl-5-isopropoxybenzofuran-6-yl)-N-(4-methoxybenzyl)methanesulfonamide (0.65 g, 1.27 mmol) was dissolved in dichloromethane, and powdered 4 Å molecular sieves (0.7 g) were added. The slurry was cooled to 0° C. in an ice bath and treated with dropwise addition of ethylenediamine (0.1 mL, 1.4 mmol). The resulting slurry was stirred under nitrogen for 30 minutes, then solid N-bromosuccinimide was added in one portion and the reaction was stirred at room temperature overnight. The reaction mixture was diluted with 100 mL dichloromethane and filtered through diatomaceous earth. The organic filtrate was washed with 10% aqueous sodium bicarbonate, 10% aqueous sodium chloride, dried over anhydrous sodium sulfate(s), filtered and the solvent was removed in vacuo leaving a foamy solid (0.54 g, 77%) which was placed under vacuum for 24 hours. The title compound was used without purification.

Example 170G

N-[2-(4-fluorophenyl)-3-(1H-imidazol-2-yl)-5-isopropoxy-1-benzofuran-6-yl]-N-(4-methoxybenzyl)methanesulfonamide N-(3-(4,5-dihydro-1H-imidazol-2-yl)-2-(4-fluorophenyl)-5-isopropoxybenzofuran-6-yl)-N-(4-methoxybenzyl)methanesulfonamide (0.54 g, 0.98 mmol) was dissolved in dimethylsulfoxide (5 mL) and was treated with potassium carbonate (0.15 g, 1.08 mmol) and iodobenzene diacetate (0.35 g, 1.08 mmol). The initially yellow solution changed to a reddish-brown solution within 15 minutes of iodobenzene diacetate addition. The reaction mixture was stirred for one hour at room temperature. The reaction mixture was stirred with 50 mL ethyl acetate and 50 mL 10% aqueous sodium bicarbonate for 20 minutes, the layers were separated and the aqueous layer was extracted with 50 mL additional ethyl acetate. The combined organic extracts were washed with 10% aqueous sodium chloride, dried over anhydrous sodium sulfate(s), and filtered. The solvent was removed in vacuo leaving an orange oily residue, which was purified by reverse phase HPLC yielding an off-white solid. 40 mg, 7.4%. $^1$H NMR (300 MHz, DMSO-$d_6$) δ ppm 1.39 (d, 6H) 3.13 (s, 3H) 3.67 (s, 3H) 4.37-5.02 (m, 3H) 6.73-6.92 (m, 2H) 7.06-7.22 (m, 4H) 7.22-7.41 (m, 4H) 7.79-7.98 (m, 2H) 12.37 (s, 1H); MS (ESI+) m/z 550.2 (M+H)$^+$, MS (ESI−) m/z 548.1.

Example 171

N-{5-cyclopropyl-2-(4-fluorophenyl)-3-[4-(trifluoromethyl)-1H-imidazol-2-yl]-1-benzofuran-6-yl}-N-(3-methylbutyl)methanesulfonamide To a mixture of (E)-3-(2,2-dimethylhydrazono)-1,1,1-trifluoropropan-2-one (9.48 mg, 0.056 mmol) and ammonium acetate (174 mg, 2.255 mmol) in acetic acid (450 μL) was added solid N-(5-cyclopropyl-2-(4-fluorophenyl)-3-formyl-benzofuran-6-yl)-N-isopentylmethanesulfonamide (50 mg, 0.113 mmol, prepared as described in Kamitori Y, et al. J Organic Chemistry 1988; 53: 129-135) under nitrogen, and the mixture was stirred at room temperature for one hour. The mixture was heated at 80° C. for 18 hours. TLC (SiO$_2$, 2% ethyl acetate/CH$_2$Cl$_2$) showed none of the trifluoroacylhydrazone reagent remaining, so additional (E)-3-(2,2-dimethylhydrazono)-1,1,1-trifluoropropan-2-one (9.48 mg, 0.056 mmol) was added and the mixture was continued to heat at 80° C. After 27 hours, additional (E)-3-(2,2-dimethylhydrazono)-1,1,1-trifluoropropan-2-one (9.48 mg, 0.056 mmol) was added and the mixture was heated overnight at 80° C. LCMS after a total of 42 hours showed ~1:1 starting material to product ratio. The amber-brown colored reaction was cooled to room temperature, and ethyl acetate (50 mL) was added. The mixture was washed with saturated aqueous NaHCO$_3$ (25 mL), the organic phase was dried over anhydrous Na$_2$SO$_4$, filtered, and concentrated by rotary evaporation. The residue was purified by SiO$_2$ flash chromatography (Alltech Extract-Clean™ column, 10 g bed) eluting with a step gradient of 2% to 3% ethyl acetate in CH$_2$Cl$_2$ to afford the title compound as a light yellow solid (7.2 mg, 0.013 mmol, 11%). $^1$H NMR (500 MHz, DMSO-$d_6$) δ ppm 0.53-0.61 (m, 1H), 0.80-0.90 (m, 1H), 0.83 (t, J=6.18 Hz, 6H), 0.97-1.02 (m, 2H), 1.22-1.31 (m, 1H), 1.34-1.44 (m, 1H), 1.54-1.69 (m, 1H), 2.35-2.44 (m, 1H), 3.14 (s, 3H), 3.61-3.79 (m, 2H), 7.09 (s, 1H), 7.35 (t, J=8.93 Hz, 2H), 7.90 (s, 1H), 7.92 (dd, J=8.47, 5.72 Hz, 2H), 8.01 (s, 1H), 13.13 (s, 1H); MS (ESI+) m/z 550 (M+H)$^+$, 1099 (2M+H)$^+$; MS (ESI−) m/z 548 (M−H)$^−$, 1097 (2M−H)$^−$.

Example 172

N-[5-cyclopropyl-2-(4-fluorophenyl)-3-(5-methyl-1H-imidazol-2-yl)-1-benzofuran-6-yl]-N-(3-methylbutyl)methanesulfonamide

Example 172A 5-cyclopropyl-2-(4-fluorophenyl)-6-(N-isopentylmethylsulfonamido)benzofuran-3-carboximidamide In a 25-mL round bottom flask purged with nitrogen, (Z)-5-cyclopropyl-2-(4-fluorophenyl)-N'-hydroxy-6-(N-isopentylmethylsulfonamido)benzofuran-3-carboximidamide (200 mg, 0.422 mmol) was dissolved in glacial acetic acid (4 mL), and ammonium formate (133 mg, 2.112 mmol) and 10% Pd—C (100 mg, 0.094 mmol) were added. The mixture was heated in an oil bath at 120° C. for 2.5 hours. TLC (SiO$_2$, 5% methanol/CH$_2$Cl$_2$) showed the reaction was complete. The reaction was cooled to room temperature, filtered through Celite® 545, washed with additional ethyl acetate, and concentrated the filtrate by rotary evaporation. The amidine acetic acid salt was dissolved in H$_2$O (25 mL) and ethyl acetate (50 mL), the pH was adjusted with 1 N aqueous NaOH, and the mixture was stirred for 10 minutes, re-adjusting the aqueous pH~12 as needed. The organic phase was washed with brine (25 mL), dried over anhydrous MgSO$_4$, filtered, and concentrated by rotary evaporation co-evaporating with CH$_2$Cl$_2$/hexanes to afford the title compound as a yellow solid (175 mg). The material was 84% pure by analytical HPLC. MS (ESI+) m/z 458 (M+H)$^+$, 915 (2M+H)$^+$; MS (ESI−) m/z 456 (M−H)$^-$.

Example 172B

N-[5-cyclopropyl-2-(4-fluorophenyl)-3-(5-methyl-1H-imidazol-2-yl)-1-benzofuran-6-yl]-N-(3-methyl-butyl)methanesulfonamide In a 5-mL round bottom flask, a mixture of 5-cyclopropyl-2-(4-fluorophenyl)-6-(N-isopentylmethylsulfonamido)benzofuran-3-carboximidamide (34 mg, 0.061 mmol) and potassium hydrogencarbonate (18.30 mg, 0.183 mmol) in tetrahydrofuran (500 μL) and H$_2$O (125 μL) was heated at reflux in an oil bath at 75° C. under a glass stoppered condenser with Teflon joint sleeve. A solution of chloroacetone (6.53 mg, 0.067 mmol) in tetrahydrofuran (125 μL) was added dropwise to the refluxing reaction mixture over 15 minutes. After 7 hours at reflux, the reaction was cooled to room temperature, diluted with ethyl acetate (25 mL), washed with H$_2$O (2×10 mL) and brine (10 mL), dried over anhydrous Na$_2$SO$_4$, filtered, and concentrated by rotary evaporation. The residue was dissolved in 1 mL acetonitrile and 1 mL 0.1% trifluoroacetic acid in H$_2$O, and purified by RP-C$_{18}$ HPLC (Waters Prep LC, 40 mm Module with Nova-Pak HR C$_{18}$ 6 μm 40×100 mm Prep Pak cartridge) eluting with a 30 minute gradient of 95:5 0.1% trifluoroacetic acid in H$_2$O/acetonitrile to 25:75 0.1% trifluoroacetic acid in H$_2$O/acetonitrile, then 10 minutes to 100% CH$_3$CN at 20 mL/minute. Pure fractions were concentrated by rotary evaporation and dried on a vacuum pump to afford the title compound as a white solid (20 mg, 0.033 mmol, 53%). $^1$H NMR (500 MHz, DMSO-d$_6$) δ ppm 0.58-0.65 (m, 1H), 0.83 (t, J=6.56 Hz, 6H), 0.91-0.96 (m, 1H), 0.98-1.05 (m, 2H), 1.21-1.31 (m, 2H), 1.34-1.43 (m, 1H), 1.57-1.68 (m, 1H), 2.37 (d, J=0.92 Hz, 3H), 2.38-2.43 (m, 1H), 3.15 (s, 3H), 3.60-3.68 (m, 1H), 3.72-3.80 (m, 1H), 7.12 (s, 1H), 7.41 (t, J=8.85 Hz, 2H), 7.61 (s, 1H), 7.66 (dd, J=8.70, 5.34 Hz, 2H), 7.99 (s, 1H); MS (ESI+) m/z 496 (M+H)$^+$, 991 (2M+H); MS (ESI−) m/z 494 (M−H)$^-$, 530/532 (M+Cl)$^-$, 608 (M+trifluoroacetic acid−H)$^-$.

Example 173

N-[5-cyclopropyl-3-(4,5-dihydro-1,2,4-oxadiazol-3-yl)-2-(4-fluorophenyl)-1-benzofuran-6-yl]methane-sulfonamide Example 145 (139 mg, 0.234 mmol) and pentamethylbenzene (350 mg, 2.336 mmol) were dissolved in anhydrous CH$_2$Cl$_2$ (2 mL) under nitrogen and cooled to 0° C. Trifluoroacetic acid (1 mL) was added dropwise, and the reaction was stirred at room temperature for 2 hours. The reaction was diluted with toluene (50 mL) and concentrated by rotary evaporation to azeotrope the trifluoroacetic acid. The residue was dried on high vacuum. The residue was purified by SiO$_2$ flash chromatography (Alltech Extract-Clean column, 10 g bed) eluting with CH$_2$Cl$_2$ (eluted pentamethylbenzene and p-methoxybenzylpentamethylbenzene), followed by a step gradient of 3% ethyl acetate/CH$_2$Cl$_2$ to 5% ethyl acetate/CH$_2$Cl$_2$ to afford the title compound as a white solid (95 mg, 0.225 mmol, 96%). $^1$H NMR (500 MHz, DMSO-d$_6$) δ ppm 0.63-0.72 (m, 2H), 0.98-1.05 (m, 2H), 2.27-2.35 (m, 1H), 3.06 (s, 3H), 5.33 (d, J=3.20 Hz, 2H), 7.14 (t, J=3.13 Hz, 1H), 7.36 (s, 1H), 7.40 (t, J=8.93 Hz, 2H), 7.63 (s, 1H), 8.02 (dd, J=9.00, 5.49 Hz, 2H), 9.33 (s, 1H); MS (ESI+) m/z 416 (M+H)$^+$, 438 (M+Na)$^+$; MS (ESI−) m/z 414 (M−H)$^-$.

Example 174

N-[5-cyclopropyl-2-(4-fluorophenyl)-3-(1H-imidazol-2-yl)-1-benzofuran-6-yl]-N-[3-(1H-tetrazol-5-yl)propyl]methanesulfonamide To a solution of Example 49 (50 mg, 0.104 mmol) and azidotrimethylsilane (29.2 μL, 0.209 mmol) in anhydrous toluene (500 μL) and anhydrous N,N-dimethylformamide (100 μL) under nitrogen was added di-n-butyltin oxide (2.65 mg, 10.45 μmol) and the light yellow solution was heated in an oil bath at 115° C. for 24 hours. The reaction was cooled to room temperature, concentrated by rotary evaporation, and dried in vacuo. The crude material was purified by SiO$_2$ flash chromatography (Alltech Extract-Clean™ column, 5 g bed) eluting with 10% methanol/CH$_2$Cl$_2$ to afford the title compound as a yellow solid (18 mg, 0.034 mmol, 33%). $^1$H NMR (400 MHz, DMSO-d$_6$) δ ppm 0.46-0.59 (m, 1H), 0.82-0.91 (m, 1H), 0.91-1.04 (m, 2H), 1.82-1.99 (m, 2H), 2.34-2.42 (m, 1H), 2.88-3.03 (m, 2H), 3.17 (s, 3H), 3.69-3.85 (m, 2H), 7.09 (s, 1H), 7.15-7.26 (m, 1H), 7.33 (t, J=8.89 Hz, 3H), 7.88 (s, 1H), 8.02 (dd, J=8.84, 5.48 Hz, 2H), 12.41 (s, 1H); MS (ESI+) m/z 522 (M+H)$^+$, 1043 (2M+H)$^+$; MS (ESI−) m/z 520 (M−H)$^-$, 1041 (2M−H)$^-$.

Example 175

N-[5-cyclopropyl-2-(4-fluorophenyl)-3-(1H-imidazol-2-yl)-1-benzofuran-6-yl]-N-[3-(5-oxo-4,5-dihydro-1,2,4-oxadiazol-3-yl)propyl]methanesulfona-mide A mixture of Example 176 (27.9 mg, 0.055 mmol), 1,1'-carbonyldiimidazole (11.64 mg, 0.068 mmol), and 1,8-diazabicyclo[5.4.0]undec-7-ene (9.23 μL, 0.060 mmol) was refluxed in anhydrous dioxane (700 μL) under nitrogen at 115° C. for 30 minutes. The reaction was cooled to room temperature, diluted with CH$_2$Cl$_2$ (50 mL) and H$_2$O (10 mL), and the pH was adjusted to pH~3 with 1 N aqueous HCl. The layers were separated, and the organic phase was washed with H$_2$O (25 mL) and brine (25 mL). The organic phase was dried over anhydrous Na$_2$SO$_4$, filtered, and concentrated by rotary evaporation to a solid (27 mg). The crude material was purified by SiO$_2$ flash chromatography (Alltech Extract-Clean™ column, 10 g bed) eluting with 3% methanol/CH$_2$Cl$_2$ to afford the title compound as a white solid (17 mg, 0.031 mmol, 57%). $^1$H NMR (400 MHz, DMSO-d$_6$) δ ppm 0.49-0.62 (m, 1H), 0.85-0.92 (m, 1H), 0.96-1.03 (m, 2H), 1.73-1.85 (m, 2H), 2.34-2.44 (m, 1H), 2.54-2.63 (m, 2H), 3.17 (s, 3H), 3.63-3.85 (m, 2H), 7.10 (s, 1H), 7.18 (s, 1H), 7.34 (t, J=8.95 Hz, 3H), 7.88 (s, 1H), 8.01 (dd, J=8.89, 5.42 Hz, 2H), 12.13 (s, 1H), 12.41 (s, 1H); MS (ESI+) m/z 538 (M+H)$^+$, 560 (M+Na)$^+$, 1075 (2M+H)$^+$; MS (ESI−) m/z 536 (M−H)$^-$, 1073 (2M−H)$^-$.

Example 176

(1Z)-4-{[5-cyclopropyl-2-(4-fluorophenyl)-3-(1H-imidazol-2-yl)-1-benzofuran-6-yl](methylsulfonyl)amino}-N'-hydroxybutanimidamide A mixture of Example 49 (50 mg, 0.104 mmol) and 50 wt % hydroxylamine in water (1 mL, 16.95 mmol) was added to a 5-mL microwave tube. The tube was sealed with an aluminum septum crimp cap, and heated in a microwave (Personal Chemistry, Emrys Creator, 300 W) for 25 minutes at 120° C. The reaction was cooled to room temperature, diluted with ethyl acetate (50 mL), and washed with $H_2O$ (2×10 mL). The aqueous layers were back-extracted with ethyl acetate (25 mL), and the combined organic extracts were washed with brine (10 mL). The organic phase was dried over anhydrous $MgSO_4$, filtered, and concentrated by rotary evaporation. The crude material was purified by $SiO_2$ flash chromatography (Alltech Extract-Clean™ column, 10 g bed) eluting with 7% methanol/$CH_2Cl_2$ to afford the title compound as a white solid (35 mg, 0.066 mmol, 63%). $^1$H NMR (400 MHz, DMSO-$d_6$) δ ppm 0.50-0.65 (m, 1H), 0.78-0.88 (m, 1H), 0.93-1.07 (m, 2H), 1.54-1.79 (m, 2H), 1.92-2.08 (m, 2H), 2.33-2.44 (m, 1H), 3.15 (s, 3H), 3.57-3.79 (m, 2H), 5.25-5.37 (m, 2H), 7.08 (s, 1H), 7.18 (s, 1H), 7.28-7.39 (m, 3H), 7.85 (s, 1H), 8.02 (dd, J=9.00, 5.53 Hz, 2H), 8.70 (s, 1H), 12.42 (s, 1H); MS (ESI+) m/z 512 (M+H)$^+$, 1023 (2M+H)$^+$; MS (ESI−) m/z 510 (M−H)$^−$, 1021 (2M−H)$^−$.

Example 177

N-[5-cyclopropyl-2-(4-fluorophenyl)-3-(1H-imidazol-2-yl)-1-benzofuran-6-yl]-N-[3-(5-thioxo-4,5-dihydro-1,2,4-oxadiazol-3-yl)propyl]methanesulfonamide In a 5-mL round bottom flask, a solution of Example 176 (25 mg, 0.049 mmol), 1,1'-thiocarbonyldiimidazole (13.75 mg, 0.073 mmol), and 1,8-diazabicyclo[5.4.0]undec-7-ene (30.1 µL, 0.195 mmol) in anhydrous acetonitrile (490 µL) was stirred under nitrogen at 25° C. for 2 hours. The reaction was diluted with ethyl acetate (50 mL) and $H_2O$ (10 mL), and the pH was adjusted to ~3 with 1 N aqueous HCl. The layers were separated, and the organic phase was washed with brine (10 mL), dried over anhydrous $MgSO_4$, filtered, and concentrated by rotary evaporation. The crude material was purified by $SiO_2$ flash chromatography (Alltech Extract-Clean™ column, 10 g bed) eluting with a step gradient of 5% to 7.5% methanol/$CH_2Cl_2$ to afford the title compound as a yellow solid (22 mg, 0.039 mmol, 80%). $^1$H NMR (400 MHz, DMSO-$d_6$) δ ppm 0.50-0.62 (m, 1H), 0.81-0.91 (m, 1H), 0.94-1.04 (m, 2H), 1.73-1.89 (m, 2H), 2.34-2.42 (m, 1H), 2.56-2.66 (m, 2H), 3.17 (s, 3H), 3.66-3.85 (m, 2H), 7.10 (s, 1H), 7.35 (t, J=8.89 Hz, 2H), 7.40 (s, 2H), 7.90 (s, 1H), 7.95 (dd, J=8.08, 5.80 Hz, 2H); MS (ESI+) m/z 554 (M+H)$^+$, 1107 (2M+H)$^+$; MS (ESI−) m/z 552 (M−H)$^−$, 1105 (2M−H)$^−$.

Example 178

N-[5-cyclopropyl-2-(4-fluorophenyl)-3-(1H-imidazol-2-yl)-1-benzofuran-6-yl]-N-[3-(5-oxo-4,5-dihydro-1,2,4-thiadiazol-3-yl)propyl]methanesulfonamide Example 178A (Z)—N'-(1H-imidazole-1-carbonothioyloxy)-4-(N-(5-cyclopropyl-2-(4-fluorophenyl)-3-(1H-imidazol-2-yl)benzofuran-6-yl)methylsulfonamido)butanimidamide A solution of Example 176 (69.3 mg, 0.135 mmol) and 1,1'-thiocarbonyldiimidazole (38.1 mg, 0.203 mmol) in anhydrous tetrahydrofuran (1.3 mL) was stirred under nitrogen at 25° C. for 1.5 hours. Ethyl acetate (25 mL) was added, the mixture was washed with $H_2O$ (2×10 mL) and brine (10 mL), dried over anhydrous $MgSO_4$, filtered, and concentrated by rotary evaporation to provide the title compound as a yellow foam (84 mg, 0.135 mmol, 100%).

Example 178B

N-[5-cyclopropyl-2-(4-fluorophenyl)-3-(1H-imidazol-2-yl)-1-benzofuran-6-yl]-N-[3-(5-oxo-4,5-dihydro-1,2,4-thiadiazol-3-yl)propyl]methanesulfonamide (Z)—N'-(1H-imidazole-1-carbonothioyloxy)-4-(N-(5-cyclopropyl-2-(4-fluorophenyl)-3-(1H-imidazol-2-yl)benzofuran-6-yl)methylsulfonamido)butanimidamide (84 mg, 0.135 mmol) was dissolved in anhydrous tetrahydrofuran (1.3 mL) under nitrogen, and boron trifluoride diethyl etherate (0.051 mL, 0.405 mmol) was added dropwise by gas-tight syringe to the yellow solution, and the mixture was stirred at 25° C. for 1 hour. Ethyl acetate (50 mL) and methanol (1 mL) were added, and the mixture was washed with $H_2O$ (2×25 mL) and brine (25 mL), dried over anhydrous $MgSO_4$, filtered, and concentrated by rotary evaporation. The residue was pre-purified by $SiO_2$ flash chromatography (Alltech Extract-Clean™ column, 10 g bed) eluting with 4% methanol/$CH_2Cl_2$ to afford a yellow solid (74 mg). The material was dissolved in 2 mL 1:1 (v/v) DMSO/methanol and purified by RP-$C_{18}$ HPLC (Waters Prep LC, 40 mm Module with Nova-Pak HR $C_{18}$ 6 µm 40×100 mm Prep Pak cartridge) eluting with a 20 minute gradient of 95:5 0.1% trifluoroacetic acid in $H_2O$/acetonitrile to 25:75 0.1% trifluoroacetic acid in $H_2O$/acetonitrile, then 10 minutes to 100% acetonitrile at 20 mL/minute. Pure fractions were concentrated by rotary evaporation and dried in vacuo to afford the title compound as a white solid (19 mg, 0.027 mmol, 20%). $^1$H NMR (400 MHz, DMSO-$d_6$) δ ppm 0.50-0.69 (m, 1H), 0.90-1.08 (m, 3H), 1.75-1.91 (m, 2H), 2.34-2.42 (m, 1H), 2.57-2.65 (m, 2H), 3.17 (s, 3H), 3.65-3.88 (m, 2H), 7.13 (s, 1H), 7.40 (t, J=8.78 Hz, 2H), 7.71 (dd, J=7.48, 5.96 Hz, 2H), 7.79 (br s, 2H), 7.97 (s, 1H), 12.67 (s, 1H), 14.47 (br s, 1H); MS (ESI+) m/z 554 (M+H)$^+$, 1107 (2M+H)$^+$.

Example 179

N-[5-cyclopropyl-2-(4-fluorophenyl)-3-(1H-imidazol-2-yl)-1-benzofuran-6-yl]-N-[3-(5-oxo-4,5-dihydro-1,3,4-oxadiazol-2-yl)propyl]methanesulfonamide Example 179A 4-(N-(5-cyclopropyl-2-(4-fluorophenyl)-3-(1H-imidazol-2-yl)benzofuran-6-yl)methylsulfonamido)butanoyl chloride Example 89 (50 mg, 0.100 mmol) was dissolved in anhydrous tetrahydrofuran (1 mL) under nitrogen, and neat oxalyl chloride (0.044 mL, 0.502 mmol) was added along with a drop of anhydrous N,N-dimethylformamide. The mixture was stirred at 25° C. for 1 hour. The mixture was concentrated by rotary evaporation, azeotroped with anhydrous toluene (2×5 mL), and dried on high vacuum to afford the title compound (51.9 mg, 0.100 mmol, 100%).

Example 179B tert-butyl 2-(4-(N-(5-cyclopropyl-2-(4-fluorophenyl)-3-(1H-imidazol-2-yl)benzofuran-6-yl)methylsulfonamido)butanoyl)hydrazinecarboxylate 4-(N-(5-cyclopropyl-2-(4-fluorophenyl)-3-(1H-imidazol-2-yl)benzofuran-6-yl)methylsulfonamido)butanoyl chloride (51.9 mg, 0.101 mmol) was dissolved in anhydrous tetrahydrofuran (1 mL) and anhydrous $CH_2Cl_2$ (1 mL) under nitrogen. Diisopropylethylamine (0.035 mL, 0.201 mmol) and tert-butyl carbazate (16.28 mg, 0.121 mmol) were added, and the mixture was stirred at 25° C. for 1 hour. Ethyl acetate (50 mL) was added, and the mixture was washed with $H_2O$ (3×10 mL) and brine (10 mL), dried over anhydrous $MgSO_4$, filtered, and concentrated by rotary evaporation. The crude material was purified by $SiO_2$ flash chromatography (Alltech Extract-Clean™ column, 10 g bed) eluting with 60:40 ethyl acetate/$CH_2Cl_2$, followed by 5% methanol/$CH_2Cl_2$ to afford the title compound as a white solid (41 mg, 0.067 mmol, 67%). MS (ESI+) m/z 612 (M+H)$^+$, 1223 (2M+H); MS (ESI-) m/z 610 (M-H)$^-$.

Example 179C

N-(5-cyclopropyl-2-(4-fluorophenyl)-3-(1H-imidazol-2-yl)benzofuran-6-yl)-N-(4-hydrazinyl-4-oxobutyl)methanesulfonamide A solution of tert-butyl 2-(4-(N-(5-cyclopropyl-2-(4-fluorophenyl)-3-(1H-imidazol-2-yl)benzofuran-6-yl)methylsulfonamido)butanoyl)hydrazinecarboxylate (40 mg, 0.065 mmol) in anhydrous $CH_2Cl_2$ (0.5 mL) under nitrogen was cooled to 0° C., and treated with trifluoroacetic acid (0.5 mL). The reaction was stirred at 25° C. for 1 hour. The mixture was concentrated by rotary evaporation, and the residue was diluted with ethyl acetate (50 mL), and washed with 5% aqueous $NaHCO_3$ (2×10 mL) and brine (10 mL). The organic phase was dried over anhydrous $MgSO_4$, filtered, and concentrated by rotary evaporation. The crude material was purified by $SiO_2$ flash chromatography (Alltech Extract-Clean™ column, 5 g bed) eluting with a step gradient of 5% methanol/$CH_2Cl_2$ to 10% methanol/$CH_2Cl_2$ to afford the title compound as a white solid (16 mg, 0.031 mmol, 48%). $^1$H NMR (400 MHz, DMSO-$d_6$) δ ppm 0.50-0.64 (m, 1H), 0.80-0.90 (m, 1H), 0.92-1.08 (m, 2H), 1.59-1.75 (m, 2H), 2.02-2.17 (m, 2H), 2.34-2.42 (m, 1H), 3.15 (s, 3H), 3.55-3.77 (m, 2H), 4.12 (d, J=4.12 Hz, 2H), 7.08 (s, 1H), 7.18 (s, 1H), 7.28-7.43 (m, 3H), 7.85 (s, 1H), 8.02 (dd, J=9.00, 5.53 Hz, 2H), 8.93 (t, J=3.36 Hz, 1H), 12.41 (s, 1H); MS (ESI+) m/z 512 (M+H)$^+$, 1023 (2M+H)$^+$.

Example 179D

N-[5-cyclopropyl-2-(4-fluorophenyl)-3-(1H-imidazol-2-yl)-1-benzofuran-6-yl]-N-[3-(5-oxo-4,5-dihydro-1,3,4-oxadiazol-2-yl)propyl]methanesulfonamide To a solution of N-(5-cyclopropyl-2-(4-fluorophenyl)-3-(1H-imidazol-2-yl)benzofuran-6-yl)-N-(4-hydrazinyl-4-oxobutyl)methanesulfonamide (13 mg, 0.025 mmol) in anhydrous $CHCl_3$ (400 μL) and anhydrous tetrahydrofuran (400 μL) was added 20 wt % phosgene in toluene (66.9 μL, 0.127 mmol) under nitrogen, and the mixture was heated at reflux in an oil bath at 85° C. for 30 minutes. The reaction was cooled to room temperature and concentrated by rotary evaporation to a white solid. The crude material was purified by $SiO_2$ flash chromatography (Alltech Extract-Clean™ column, 5 g bed) eluting with 5% methanol/$CH_2Cl_2$ to afford the title compound as a white solid (10 mg, 0.018 mmol, 71%). $^1$H NMR (400 MHz, DMSO-$d_6$) δ ppm 0.50-0.60 (m, 1H), 0.80-0.93 (m, 1H), 0.99 (d, J=8.57 Hz, 2H), 1.69-1.85 (m, 2H), 2.34-2.43 (m, 1H), 2.59-2.66 (m, 2H), 3.17 (s, 3H), 3.66-3.87 (m, 2H), 7.09 (s, 1H), 7.18 (s, 1H), 7.26-7.45 (m, 3H), 7.88 (s, 1H), 8.02 (dd, J=8.89, 5.53 Hz, 2H), 11.99 (br s, 1H), 12.41 (s, 1H); MS (ESI+) m/z 538 (M+H)$^+$, 1075 (2M+H)$^+$; MS (ESI-) m/z 536 (M-H)$^-$, 1073 (2M-H)$^-$.

Example 180

N-[5-cyclopropyl-3-(5,6-dihydro-4H-1,2,4-oxadiazin-3-yl)-2-(4-fluorophenyl)-1-benzofuran-6-yl]-N-[3-(1H-tetrazol-5-yl)propyl]methanesulfonamide The title compound can be prepared from Example 133 using procedures analogous to those described in Example 174. $^1$H NMR (400 MHz, DMSO-$d_6$) δ ppm 0.46-0.59 (m, 1H), 0.87-1.04 (m, 3H), 1.81-1.97 (m, 2H), 2.35-2.42 (m, 1H), 2.88-3.01 (m, 2H), 3.15 (s, 3H), 3.40-3.51 (m, 2H), 3.67-3.85 (m, 2H), 3.99 (t, J=4.39 Hz, 2H), 7.08 (s, 1H), 7.22 (t, J=2.87 Hz, 1H), 7.40 (t, J=8.89 Hz, 2H), 7.85 (s, 1H), 7.99 (dd, J=8.84, 5.48 Hz, 2H); MS (ESI+) m/z 540 (M+H)$^+$, 562 (M+Na)$^+$, 1079 (2M+H)$^+$; MS (ESI-) m/z 538 (M-H)$^-$, 1077 (2M-H)$^-$.

Example 181

(1Z)-4-{[5-cyclopropyl-3-(5,6-dihydro-4H-1,2,4-oxadiazin-3-yl)-2-(4-fluorophenyl)-1-benzofuran-6-yl](methylsulfonyl)amino}-N'-hydroxybutanimidamide The title compound can be prepared from Example 133 using procedures analogous to those described in Example 176. $^1$H NMR (400 MHz, DMSO-$d_6$) δ ppm 0.52-0.65 (m, 1H), 0.83-0.93 (m, 1H), 0.95-1.09 (m, 2H), 1.53-1.78 (m, 2H), 1.92-2.07 (m, 2H), 2.34-2.42 (m, 1H), 3.14 (s, 3H), 3.39-3.49 (m, 2H), 3.56-3.75 (m, 2H), 3.99 (t, J=4.50 Hz, 2H), 5.30 (s, 2H), 7.07 (s, 1H), 7.24 (t, J=3.20 Hz, 1H), 7.40 (t, J=8.89 Hz, 2H), 7.81 (s, 1H), 7.99 (dd, J=8.95, 5.48 Hz, 2H), 8.70 (s, 1H); MS (ESI+) m/z 530 (M+H)$^+$, 1059 (2M+H)$^+$; MS (ESI-) m/z 528 (M-H)$^-$, 564/566 (M+Cl)$^-$, 1057 (2M-H)$^-$.

Example 182

N-[5-cyclopropyl-3-(5,6-dihydro-4H-1,2,4-oxadiazin-3-yl)-2-(4-fluorophenyl)-1-benzofuran-6-yl]-N-[3-(5-oxo-4,5-dihydro-1,2,4-oxadiazol-3-yl)propyl]methanesulfonamide The title compound can be prepared from Example 181 using procedures analogous to those described in Example 175. $^1$H NMR (400 MHz, DMSO-$d_6$) δ ppm 0.48-0.61 (m, 1H), 0.89-0.96 (m, 1H), 0.96-1.06 (m, 2H), 1.71-1.83 (m, 2H), 2.35-2.42 (m, 1H), 2.55-2.64 (m, 2H), 3.15 (s, 3H), 3.41-3.49 (m, 2H), 3.64-3.82 (m, 2H), 3.99 (t, J=4.17 Hz, 2H), 7.08 (s, 1H), 7.22 (s, 1H), 7.40 (t, J=8.84 Hz, 2H), 7.85 (s, 1H), 7.99 (dd, J=8.51, 5.58 Hz, 2H), 12.13 (s, 1H); MS (ESI+) m/z 556 (M+H)$^+$, 1111 (2M+H)$^+$; MS (ESI-) m/z 554 (M-H)$^-$, 1109 (2M-H)$^-$.

Example 183

N-[5-cyclopropyl-3-(5,6-dihydro-4H-1,2,4-oxadiazin-3-yl)-2-(4-fluorophenyl)-1-benzofuran-6-yl]-N-[3-(5-thioxo-4,5-dihydro-1,2,4-oxadiazol-3-yl)propyl]methanesulfonamide The title compound can be prepared from Example 181 using procedures analogous to those described in Example 177. $^1$H NMR (400 MHz, DMSO-$d_6$) δ ppm 0.49-0.62 (m, 1H), 0.88-0.95 (m, 1H), 1.00 (d, J=8.57 Hz, 2H), 1.74-1.88 (m, 2H), 2.34-2.42 (m, 1H), 2.63-2.72 (m, 2H), 3.15 (s, 3H), 3.41-3.50 (m, 2H), 3.69-3.79 (m, 2H), 3.99 (t, J=4.45 Hz, 2H), 7.08 (s, 1H), 7.24 (s, 1H), 7.40 (t, J=8.89 Hz, 2H), 7.85 (s, 1H), 7.99 (dd, J=8.89, 5.42 Hz, 2H); MS (ESI+) m/z 572 (M+H)$^+$, 1143 (2M+H)$^+$; MS (ESI−) m/z 570 (M−H)$^−$, 1141 (2M−H)$^−$.

Example 184

N-[5-cyclopropyl-3-(5,6-dihydro-4H-1,2,4-oxadiazin-3-yl)-2-(4-fluorophenyl)-1-benzofuran-6-yl]-N-[3-(5-oxo-4,5-dihydro-1,2,4-thiadiazol-3-yl)propyl]methanesulfonamide The title compound can be prepared from Example 181 procedures analogous to those described in Example 178. $^1$H NMR (400 MHz, DMSO-$d_6$) δ ppm 0.48-0.62 (m, 1H), 0.87-0.94 (m, 1H), 1.00 (dd, J=7.92, 2.60 Hz, 2H), 1.74-1.89 (m, 2H), 2.34-2.43 (m, 1H), 2.56-2.65 (m, 2H), 3.14 (s, 3H), 3.44 (q, J=4.12 Hz, 2H), 3.66-3.78 (m, 2H), 3.99 (t, J=4.72 Hz, 2H), 7.10 (s, 1H), 7.41 (t, J=8.84 Hz, 2H), 7.62 (br s, 1H), 7.86 (s, 1H), 7.98 (dd, J=8.73, 5.48 Hz, 2H), 12.66 (s, 1H); MS (ESI+) m/z 572 (M+H)$^+$; MS (ESI−) m/z 570 (M−H)$^−$.

Example 185

N-[5-cyclopropyl-2-(4-fluorophenyl)-3-(5-oxo-4,5-dihydro-1,2,4-oxadiazol-3-yl)-1-benzofuran-6-yl]-N-(4-hydroxybutyl)methanesulfonamide The title compound can be made from Example 11C, using procedures analogous to those described in Examples 8D and 11D. $^1$H NMR (400 MHz, DMSO-$d_6$) δ ppm 0.57-0.71 (m, 1H), 0.87-0.97 (m, 1H), 0.97-1.05 (m, 2H), 1.34-1.59 (m, 4H), 2.34-2.43 (m, 1H), 3.14 (s, 3H), 3.58-3.76 (m, 2H), 4.37 (t, 1H), 7.25 (s, 1H), 7.42 (t, J=8.89 Hz, 2H), 7.92 (s, 1H), 7.96 (dd, J=8.84, 5.37 Hz, 2H), 12.78 (s, 1H); MS (ESI+) m/z 502 (M+H)$^+$, 519 (M+NH$_4$)$^+$, 1020 (2M+NH$_4$)$^+$.

The compounds of Examples 186-189 can be made using procedures analogous to those described in Examples 1-5.

Example 186

N-[5-cyclopropyl-3-(4,5-dimethyl-1H-imidazol-2-yl)-2-(4-fluorophenyl)-1-benzofuran-6-yl]-N-(4-methoxybenzyl)methanesulfonamide $^1$H NMR (300 MHz, DMSO-$d_6$) δ ppm 0.11-0.26 (m, 1H) 0.67-0.75 (m, 2H) 0.81-0.94 (m, 1H) 2.14 (s, 6H) 2.17-2.31 (m, 1H) 3.21 (s, 3H) 3.67 (s, 3H) 4.68-4.92 (m, 2H) 6.80 (d, J=8.82 Hz, 2H) 6.95 (s, 1H) 7.13 (d, J=8.46 Hz, 2H) 7.28-7.35 (m, 2H) 7.75 (s, 1H) 7.90-8.19 (m, 2H) 11.91 (s, 1H); MS (ESI+) m/z 560 (M+H)$^+$.

Example 187

N-[5-cyclopropyl-2-(4-fluorophenyl)-3-(4-methyl-1H-imidazol-2-yl)-1-benzofuran-6-yl]-N-(4-hydroxybutyl)methanesulfonamide $^1$H NMR (300 MHz, DMSO-$d_6$) δ ppm 0.56 (m, 1H) 0.86 (m, 1H) 0.99 (m, 2H) 1.45 (m, 4H) 2.22 (s, 1.5H) 2.26 (s, 1.5H) 2.39 (m, 1H) 3.14 (s, 3H) 3.37 (m, 2H) 3.67 (m, 2H) 4.37 (t, J=5.15 Hz, 1H) 6.85 (s, 0.5H) 7.03 (s, 0.5H) 7.06 (s, 0.5H) 7.09 (s, 0.5H) 7.32 (m, 2H) 7.84 (s, 1H) 8.05 (m, 2H) 12.09 (s, 0.5H) 12.19 (s, 0.5H); MS (ESI+) m/z 498.1 (M+H)$^+$.

Example 188

N-[5-cyclopropyl-2-(4-fluorophenyl)-3-(5-methyl-1H-imidazol-2-yl)-1-benzofuran-6-yl]-N-(4-methoxybenzyl)methanesulfonamide $^1$H NMR (trifluoroacetic acid salt)(300 MHz, DMSO-$d_6$) δ ppm 0.19-0.41 (m, 1H) 0.64-1.02 (m, 2H) 2.18-2.32 (m, 2H) 2.37 (s, 3H) 3.23 (s, 3H) 3.68 (s, 3H) 4.67-4.79 (m, 1H) 4.81-4.97 (m, 1H) 6.80 (d, J=8.82 Hz, 2H) 6.98 (s, 1H) 7.07-7.25 (m, 2H) 7.33-7.49 (m, 2H) 7.54-7.74 (m, 3H) 7.92 (s, 1H) 14.47 (s, 1H); MS (ESI+) m/z 546.1 (M+H)$^+$; MS (ESI−) m/z 544.1 (M−H)$^−$.

Example 189

N-[5-cyclopropyl-2-(4-fluorophenyl)-3-(4-methyl-1H-imidazol-2-yl)-1-benzofuran-6-yl]-N-(2-hydroxyethyl)methanesulfonamide $^1$H NMR (500 MHz, DMSO-$d_6$) δ ppm 0.86 (s, 2H), 0.98 (s, 2H), 2.22 (s, 3H), 3.20 (s, 3H), 3.42-3.55 (m, 2H), 3.61 (dd, J=5.7, 13.8, 1H), 3.88 (dq, J=6.9, 20.9, 1H), 4.91 (t, J=5.3, 1H), 6.85 (s, 1H), 7.04 (s, 1H), 7.11 (d, J=11.9, 1H), 7.33 (dd, J=5.5, 12.4, 2H), 7.81 (s, 1H), 7.91-8.26 (m, 2H), 12.13 (d, 1H); MS (ESI+) m/z 470.0 (M+H)$^+$; MS (ESI−) m/z 468.1 (M−H)$^−$.

Example 190

N-[5-cyclopropyl-2-(4-fluorophenyl)-3-(1H-imidazol-2-yl)-1-benzofuran-6-yl]-N-[(3-hydroxy-1,2-oxazol-5-yl)methyl]methanesulfonamide The title compound can be prepared from Example 7B and Example 10. Example 7B can be converted to the corresponding bromide with pyridine/triphenylphosphine/bromine, the bromide reacted with Example 1O under the alkylation conditions described above, and the alkylation product debenzylated in accordance with procedures analogous to those described in Example 7H to provide the title compound. $^1$H NMR (trifluoroacetic acid salt) (300 MHz, DMSO-$d_6$) δ ppm 0.40-0.63 (m, 1H) 0.76-1.08 (m, 2H) 2.18-2.37 (m, 2H) 3.28 (s, 3H) 4.76-5.02 (m, 2H) 5.93 (s, 1H) 7.10 (s, 1H) 7.40 (t, J=9.01 Hz, 2H) 7.67 (dd, J=8.82, 5.52 Hz, 2H) 7.79-7.92 (m, 2H) 7.93 (s, 1H) 11.24 (s, 1H), 14.63 (bs, 1H); MS (ESI+) m/z 509.0 (M+H)$^+$. (ESI−) m/z 507.1 (M−H)$^−$.

Example 191

3-[3-(1H-imidazol-2-yl)-2-(4-methoxyphenyl)pyrazolo[1,5-a]pyridin-5-yl]-4-methyl-N-(1-phenylcyclopropyl)benzamide

Example 191A 2-(4-Methoxyphenyl)-5-(4,4,5,5-tetramethyl-1,3,2-dioxaborolan-2-yl)pyrazolo[1,5-a]pyridine In a resealable Schlenk tube, a suspension of Example 19C (2.01 g, 6.63 mmol), bis(pinacolato)diboron (1.85 g, 7.29 mmol) and potassium acetate (1.95 g, 19.9 mmol) in dry dioxane (33 mL) was degassed by nitrogen sparge for 30 minutes. The mixture was treated with 1,1-bis(diphenylphosphine)ferrocene palladium (II) chloride dichloromethane complex (108 mg, 0.13 mmol), followed by degassing for another 5 minutes. The Schlenk tube was sealed and the mixture was warmed at 100° C. for 18 hours. The mixture was cooled and diluted with ethyl acetate. The dark brown solution was extracted with water and saturated sodium chloride solution. The solution was dried ($Na_2SO_4$), filtered, and stirred with 3-mercaptopropyl silica gel for 1 hour. The mixture was then treated with Darco G-60 and filtered through diatomaceous earth. Concentration in vacuo afforded an amber oil, which was concentrated in vacuo with toluene to remove residual pinacol. These procedures afforded an oil, which solidified upon pumping under high vacuum. These procedures afforded the title compound (2.98 g, >90%) as a light brown solid. MS (ESI+) m/z (rel abundance) 350 (26), 351 (100, M+H)$^+$, 352 (18).

Example 191B

Methyl 3-(2-(4-methoxyphenyl)pyrazolo[1,5-a]pyridin-5-yl)-4-methylbenzoate

A suspension of Example 191A (2.32 g, 6.62 mmol), methyl 3-iodo-4-methylbenzoate (1.83 g, 6.62 mmol), cesium fluoride (2.01 g, 13.25 mmol) and [(t-butyl)$_2$PCl]$_2$PdCl$_2$ (PXPd, 108 mg, 0.20 mmol) in N,N-dimethylformamide (33 mL) was warmed at 90° C. for 18 hours. The mixture was cooled and diluted with ethyl acetate and extracted with water (3×) and saturated sodium chloride solution. The solution was dried ($Na_2SO_4$), filtered, and stirred with 3-(mercaptopropyl) silica gel for 1 hour. Concentration in vacuo afforded a brown oil, which was chromatographed over a 220 g silica gel cartridge, eluting with 10-60% ethyl acetate in hexanes. The solid obtained was triturated with ether-hexanes and collected by filtration. After drying in a vacuum oven at 50° C. for 18 hours, these procedures afforded the title compound (1.43 g, 58%) as white solid. MS (ESI+) m/z (rel abundance) 373 (100, M+H)$^+$, 374 (23).

Example 191C

Methyl 3-(3-iodo-2-(4-methoxyphenyl)pyrazolo[1,5-a]pyridin-5-yl)-4-methylbenzoate A solution of Example 191B (1.43 g, 3.84 mmol) in dichloromethane (38 mL) and acetonitrile (5 mL) was treated with N-iodosuccinimide (1.04 g, 4.61 mmol) followed by stirring at room temperature for 2 hours. The mixture was treated with saturated sodium bicarbonate solution to which solid sodium sulfite had been added, immediately discharging the red iodine color. The organic layer was dried ($Na_2SO_4$), filtered and concentrated in vacuo to afford a white solid, which was chromatographed over a 330 g silica gel cartridge, eluting with 0-20% ethyl acetate in dichloromethane. These procedures afforded the title compound (1.84 g, 94%) as a white solid. MS (ESI+) m/z (rel abundance) 499 (100, M+H)$^+$, 500 (23).

Example 191D

Methyl 3-(2-(4-methoxyphenyl)-3-(4,4,5,5-tetramethyl-1,3,2-dioxaborolan-2-yl)pyrazolo[1,5-a]pyridin-5-yl)-4-methylbenzoate In a microwave tube, a solution of Example 191C (624 mg, 1.25 mmol) and 2-dicyclohexylphosphino-2',6'-dimethoxybiphenyl (41 mg, 0.10 mmol) in dioxane (7.0 mL) was degassed by nitrogen sparge for 30 minutes. The mixture was treated with triethylamine (1 mL-excess) followed by degassing for another 5 minutes, and then addition of bis(acetonitrile)palladium (II) chloride (13 mg, 0.050 mmol) and pinacol borane (273 µL, 240 mg, 1.88 mmol). The microwave tube was sealed and the mixture was warmed at 110° C. for 2 hours. The mixture was cooled and diluted with ethyl acetate and extracted with water and saturated sodium chloride solution. The solution was dried ($Na_2SO_4$), filtered, and stirred with 3-(mercaptopropyl) silica gel for 1 hour. Filtration and concentration in vacuo afforded an oil, which was chromatographed over a 120 g silica gel cartridge, eluting with 0-16% ethyl acetate in dichloromethane. These procedures afforded the title compound (644 mg, ca. 90%) as a white solid, containing ca. 3 mol % 2-dicyclohexylphosphino-2',6'-dimethoxybiphenyl. MS (ESI+) m/z (rel abundance) 498 (22), 499 (100, M+H)$^+$, 500 (29).

Example 191E 1-((2-(Trimethylsilyl)ethoxy)methyl)-1H-imidazole

A suspension of sodium hydride (3.08 g of 60% in oil, 1.85 g, 77 mmol) in dry tetrahydrofuran (80 mL) at 0° C. was treated dropwise with a solution of imidazole (5.00 g, 73.4 mmol) in dry tetrahydrofuran (20 mL) over 15 minutes. The mixture was warmed at room temperature for 30 minutes, followed by cooling again to 0° C. and addition of 2-trimethylsilylethyoxymethyl chloride (13.7 mL, 12.86 g, 77 mmol) dropwise. The mixture was allowed to warm to room temperature for 18 hours, and was quenched by addition of saturated ammonium chloride solution. The mixture was diluted with water and concentrated in vacuo to remove tetrahydrofuran. The residue was extracted with ethyl acetate and the organic layer was extracted with saturated sodium chloride solution. Drying ($Na_2SO_4$), filtration, and concentration in vacuo afforded an orange oil, which was distilled (93-94° C./0.2 mm Hg) to afford the title compound (12.97 g, 89%) as a colorless liquid. MS (ESI+) m/z (rel abundance) 199 (100, M+H)$^+$.

Example 191F

2-Iodo-1-((2-(trimethylsilyl)ethoxy)methyl)-1H-imidazole

A solution of Example 191E (1.50 g, 7.56 mmol) in dry tetrahydrofuran (38 mL) at −40° C. was treated dropwise with a solution of n-butyllithium in hexanes (2.5 M, 3.93 mL, 9.83 mmol). After addition of the n-butyllithium, the solution took on a distinct light orange color. The solution was stirred at −40° C. for 45 minutes, followed by dropwise addition of a solution of iodine (2.69 g, 10.59 mmol) in dry tetrahydrofuran (18 mL) followed by warming to room temperature for 20 minutes. The solution was treated with water and with vigorous stirring, solid sodium sulfite was added to discharge the iodine color. The mixture was diluted with ethyl acetate and extracted with water and saturated sodium chloride solution. Drying ($Na_2SO_4$), filtration, and concentration in vacuo afforded an oil, which was chromatographed over a 220 g silica gel cartridge, eluting with 0-20% acetonitrile in chloroform. These procedures afforded the title compound (840 mg, 34%) as a colorless oil that crystallized upon pumping under high vacuum. MS (ESI+) m/z (rel abundance) 325 (100, M+H)$^+$, 326 (12).

Example 191G

Methyl 3-(2-(4-methoxyphenyl)-3-(1-((2-(trimethylsilyl)ethoxy)methyl)-1H-imidazol-2-yl)pyrazolo[1,5-a]pyridin-5-yl)-4-methylbenzoate In a microwave tube, a solution of Example 191D (155 mg, 0.31 mmol), Example 191F (101 mg, 0.31 mmol) and tribasic potassium phosphate (145 mg, 0.68 mmol) in 4:1 tetrahydrofuran-water (2.2 mL) was degassed by nitrogen sparge for 15 minutes. The mixture was then treated with Cytec® PA-Ph (Capretta A, et al. J. Org. Chem. 2004; 69: 5082; Org. Lett. 2003; 5: 953) (18 mg, 0.06 mmol) and tris(dibenzylideneacetone)dipalladium (0) (14 mg, 0.015 mmol) followed by degassing for another 5 minutes. The microwave tube was sealed and the mixture warmed at 90° C. for 18 hours. The mixture was cooled and diluted with ethyl acetate and extracted with water and saturated aqueous sodium chloride solution. The solution was dried ($Na_2SO_4$), filtered and stirred with 3-(mercaptopropyl) silica gel for 1 hour. After filtration and concentration in vacuo, the residue was chromatographed using a 40 g silica gel cartridge, eluting with 0-35% acetonitrile in chloroform. These procedures afforded the title compound (40 mg, 23%) as a light yellow rigid foam. MS (ESI+) m/z (rel abundance) 569 (100, M+H)$^+$, 570 (32).

Example 191H 3-(2-(4-Methoxyphenyl)-3-(1-((2-(trimethylsilyl)ethoxy)methyl)-1H-imidazol-2-yl)pyrazolo[1,5-a]pyridin-5-yl)-4-methylbenzoic acid A solution of Example 191G (86 mg, 0.15 mmol) in 3:1 tetrahydrofuran-water (2.0 mL) was treated with lithium hydroxide hydrate (13 mg, 0.30 mmol) followed by stirring at room temperature for 24 hours. The mixture was concentrated in vacuo to remove tetrahydrofuran. The residue was suspended in water and adjusted to pH 6 by addition of 1 M citric acid solution. The mixture was extracted with ethyl acetate (3×) and the organic layers were washed with saturated sodium chloride solution and dried ($Na_2SO_4$). Filtration and concentration in vacuo afforded a white solid, which was the title compound (98 mg) contaminated with only traces of the ester. This material was used directly in the next step. MS (ELSD+) m/z (rel abundance) 555 (100, M+H)$^+$.

Example 191I 3-(2-(4-Methoxyphenyl)-3-(1-((2-(trimethylsilyl)ethoxy)methyl)-1H-imidazol-2-yl)pyrazolo[1,5-a]pyridin-5-yl)-4-methyl-N-(1-phenylcyclopropyl)benzamide A suspension of Example 191H (84 mg, 0.15 mmol), 1-phenylcyclopropaneamine hydrochloride (51 mg, 0.30 mmol), O-(7-azabenzotriazol-1-yl)-N,N,N',N'-tetramethyluronium hexafluorophosphate (69 mg, 0.18 mmol) in dry N,N-dimethylformamide (1.5 mL) was treated with diisopropylethylamine (132 µL, 98 mg, 0.76 mmol) followed by stirring at room temperature for 18 hours. The mixture was diluted with ethyl acetate and extracted with water (3×) and saturated sodium chloride solution. Drying ($Na_2SO_4$), filtration, and concentration in vacuo afforded a solid, which was chromatographed over a 25 g silica gel cartridge, eluting with 5-70% acetonitrile in chloroform. These procedures afforded the title compound (62 mg, 61%) as a white rigid foam. MS (ESI+) m/z (rel abundance) 670 (100, M+H)$^+$, 671 (44).

Example 191J

3-[3-(1H-imidazol-2-yl)-2-(4-methoxyphenyl)pyrazolo[1,5-a]pyridin-5-yl]-4-methyl-N-(1-phenylcyclopropyl)benzamide Example 191I (58 mg, 0.087 mmol) was dissolved in a solution of hydrogen chloride in dioxane (4.0 N, 6 mL) followed by warming at 50° C. for 18 hours. The mixture was cooled and diluted with ether and the solids were collected by filtration. After drying in a vacuum oven at 50° C. for 3 hours, these procedures afforded the title compound as its hydrochloride (41 mg, 82%) as a white solid. $^1$H NMR (400 MHz, DMSO-$d_6$) δ 9.30 (s, 1H), 8.98 (d, J=7.1 Hz, 1H), 8.04 (s, 1H), 7.90 (m, 1H), 7.82 (d, J=2.9 Hz, 3H), 7.47 (m, 3H), 7.24 (m, 6H), 7.07 (d, J=8.8 Hz, 2H), 3.82 (s, 3H), 2.37 (s, 3H), 1.27 (d, J=14.4 Hz, 4H); MS (ESI+) m/z (rel abundance) 540 (100, M+H)$^+$, 541 (33).

Example 192

N-[5-cyclopropyl-3-(4,5-dimethyl-1H-imidazol-2-yl)-2-(4-fluorophenyl)-1-benzofuran-6-yl]methanesulfonamide $^1$H NMR (trifluoroacetic acid salt) (300 MHz, DMSO-$d_6$) δ ppm 0.66-0.80 (m, 2H) 0.92-1.15 (m, 2H) 2.21-2.41 (m, 1H) 2.30 (s, 6H) 3.09 (s, 3H) 7.23 (s, 1H) 7.40 (t, J=9.01 Hz, 2H) 7.61-7.71 (m, 2H) 7.72 (s, 1H) 9.41 (s, 1H) 14.32 (s, 2H); MS (APCI+) m/z 440 (M+H)$^+$.

All references (patent and non-patent) cited above are incorporated by reference into this patent application. The discussion of those references is intended merely to summarize the assertions made by their authors. No admission is made that any reference (or a portion of any reference) is relevant prior art (or prior art at all). Applicants reserve the right to challenge the accuracy and pertinence of the cited references.

What is claimed is:
1. A compound having formula (I), or a pharmaceutically acceptable salt thereof,

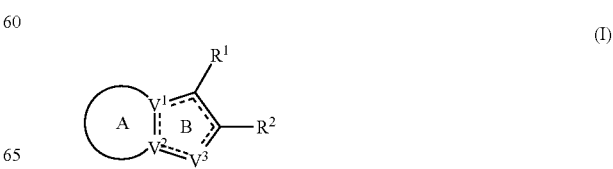

wherein:

$R^1$ is formula (i) or (iii);

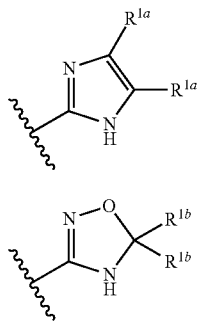

$R^{1a}$, at each occurrence, is each independently hydrogen, halogen, $C_1$-$C_3$alkyl, or $C_1$-$C_3$haloalkyl;

$R^{1b}$, at each occurrence, is each independently hydrogen, halogen, $C_1$-$C_3$alkyl, or $C_1$-$C_3$haloalkyl, wherein, optionally, two geminal $R^{1b}$ taken together are oxo;

$R^2$ is $L^{2A}$-$G^{2a}$;

$L^{2A}$ is a bond, $C_2$alkenylene, or $C_2$alkynylene;

$G^{2a}$ is $C_6$-$C_{10}$aryl or 5- to 10-membered heteroaryl, wherein the aryl or heteroaryl is optionally substituted with 1, 2, or 3 substituents selected from the group consisting of $R^{20}$, $L^{2B}$-$R^{21}$, $G^{2b}$ and $L^{2B}$-$G^{2b}$;

$L^{2B}$ and $L^{2C}$, at each occurrence, are each independently $C_1$-$C_6$alkylene, $C_2$-$C_6$alkenylene, or $C_2$-$C_6$alkynylene;

$R^{20}$ is hydrogen, $C_1$-$C_{10}$alkyl, $C_2$-$C_{10}$alkenyl, $C_2$-$C_{10}$alkynyl, $C_1$-$C_{10}$haloalkyl, $C_2$-$C_{10}$haloalkenyl, $C_2$-$C_{10}$haloalkynyl, halogen, —N($R^{2a}$)C(O)$R^{2b}$, —C(O)N($R^{2a}$)($R^{2b}$), —O—$R^{2b}$, —C(O)$R^{2b}$, —OC(O)$R^{2b}$, —CO$_2$H, —CO$_2$$R^{2b}$, —N($R^{2a}$)C(O)N($R^{2a}$)($R^{2b}$), —S—$R^{2b}$, —S(O)$_2$$R^{2b}$, —S(O)$R^{2b}$, —SO$_2$N($R^{2a}$)($R^{2b}$), —N($R^{2a}$)($R^{2b}$), —N($R^{2a}$)S(O)$_2$$R^{2b}$, N($R^{2a}$)C(O)O($R^{2b}$), or —C(=CH$_2$)$R^{2b}$;

$R^{21}$ is —N($R^{2a}$)C(O)$R^{2b}$, —C(O)N($R^{2a}$)($R^{2b}$), —O—$R^{2b}$, —C(O)$R^{2b}$, —OC(O)$R^{2b}$, —CO$_2$H, —CO$_2$$R^{2b}$, —N($R^{2a}$)C(O)N($R^{2a}$)($R^{2b}$), —S—$R^{2b}$, —S(O)$_2$$R^{2b}$, —S(O)$R^{2b}$, —SO$_2$N($R^{2a}$)($R^{2b}$), —N($R^{2a}$)($R^{2b}$), —N($R^{2a}$)S(O)$_2$$R^{2b}$, N($R^{2a}$)C(O)O($R^{2b}$), or —C(=CH$_2$)$R^{2b}$;

$R^{2a}$, at each occurrence, is each independently hydrogen, $C_1$-$C_6$alkyl, $C_1$-$C_6$haloalkyl, or $C_3$-$C_8$cycloalkyl, wherein the $C_3$-$C_8$cycloalkyl is optionally substituted with 1, 2, 3, or 4 substituents selected from the group consisting of halogen, oxo, $C_1$-$C_3$alkyl, and $C_1$-$C_3$haloalkyl;

$R^{2b}$, at each occurrence, is each independently hydrogen, $C_1$-$C_{10}$alkyl, $C_2$-$C_{10}$alkenyl, $C_2$-$C_{10}$alkynyl, $C_1$-$C_{10}$haloalkyl, $C_2$-$C_{10}$haloalkenyl, $C_2$-$C_{10}$haloalkynyl, -$L^{2C}$-$R^{2c}$, $G^{2b}$ or -$L^{2C}$-$G^{2b}$;

$R^{2c}$ is —N($R^{2d}$)C(O)$R^{2d}$, —C(O)N($R^{2d}$)($R^{2d}$), —O—$R^{2d}$, —C(O)$R^{2d}$, —OC(O)$R^{2d}$, —CO$_2$H, —CO$_2$$R^{2d}$, —N($R^{2d}$)C(O)N($R^{2d}$)($R^{2d}$), —S—$R^{2d}$, —S(O)$_2$$R^{2d}$, —S(O)$R^{2d}$, —SO$_2$N($R^{2d}$)($R^{2d}$), —N($R^{2d}$)($R^{2d}$), —N($R^{2d}$)S(O)$_2$$R^{2d}$, or N($R^{2d}$)C(O)O($R^{2d}$);

$R^{2d}$, at each occurrence, is each independently hydrogen, $C_1$-$C_6$alkyl, $C_1$-$C_6$haloalkyl, $C_1$-$C_6$alkylene-OH, or $C_3$-$C_8$cycloalkyl, wherein the $C_3$-$C_8$cycloalkyl is optionally substituted with 1, 2, 3, or 4 substituents selected from the group consisting of halogen, oxo, $C_1$-$C_3$alkyl, and $C_1$-$C_3$haloalkyl;

$G^{2b}$ is $C_3$-$C_{10}$cycloalkyl, $C_5$-$C_{10}$cycloalkenyl, $C_6$-$C_{10}$aryl, 3- to 10-membered heterocyclyl, or 5- to 10-membered heteroaryl, wherein $G^{2b}$ is optionally substituted with 1, 2, 3, 4, or 5 substituents selected from the group consisting of $C_1$-$C_{10}$alkyl, $C_2$-$C_{10}$alkenyl, $C_2$-$C_{10}$alkynyl, $C_1$-$C_{10}$haloalkyl, $C_2$-$C_{10}$haloalkenyl, $C_2$-$C_{10}$haloalkynyl, halogen, oxo, cyano, hydroxy, —O—$C_1$-$C_6$alkyl, —O—$C_1$-$C_6$haloalkyl, —$C_1$-$C_3$alkylene-O—H, —$C_1$-$C_3$alkylene-O—$C_1$-$C_6$alkyl, C(O)H, —$C_1$-$C_3$alkylene-NH$_2$, —NH$_2$, —NO$_2$, —C(O)$C_1$-$C_6$alkyl, —C(O)O$C_1$-$C_6$alkyl, and $G^{2c}$;

$G^{2c}$ is $C_6$-$C_{10}$aryl or 5- to 10-membered heteroaryl, wherein $G^{2c}$ is optionally substituted with 1, 2, 3, 4, or 5 substituents selected from the group consisting of $C_1$-$C_{10}$alkyl, $C_2$-$C_{10}$alkenyl, $C_2$-$C_{10}$alkynyl, $C_1$-$C_{10}$haloalkyl, $C_2$-$C_{10}$haloalkenyl, $C_2$-$C_{10}$haloalkynyl, halogen, oxo, cyano, hydroxy, —O—$C_1$-$C_6$alkyl, —O—$C_1$-$C_6$haloalkyl, —$C_1$-$C_3$alkylene-O—H, —$C_1$-$C_3$alkylene-O—$C_1$-$C_6$alkyl, C(O)H, —$C_1$-$C_3$alkylene-NH$_2$, —NH$_2$, —NO$_2$, —C(O)$C_1$-$C_6$alkyl, and —C(O)O$C_1$-$C_6$alkyl;

A and B together are a bicyclic heteroaryl, wherein A is formula (vi) or formula (vii):

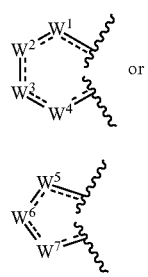

wherein, $V^1$ and $V^2$ are each C, or one of $V^1$ and $V^2$ is N and the other is C, wherein, when $V^3$ is N, O or S or when A is (vii), $V^2$ is C;

when A is (vi), $V^3$ is $CR^7$, $NR^7$, N, O, or S; or, when A is (vii), $V^3$ is N;

$R^7$ is hydrogen, $C_1$-$C_3$alkyl, $C_1$-$C_3$haloalkyl, or $C_3$-$C_6$cycloalkyl;

≈≈≈≈≈ is a single or double bond;

$W^1$ is N or $CR^6$, $W^2$ is N or $CR^5$, $W^3$ is N or $CR^4$, and $W^4$ is N or $CR^3$, wherein none, one or two of $W^1$, $W^2$, $W^3$ and $W^4$ is N;

$W^5$ is N or $CR^6$, and $W^6$ is N or $CR^5$, wherein none or one of $W^5$ and $W^6$ is N;

$W^7$ is N, O, or S;

$R^3$ and $R^6$ are each independently hydrogen, $C_1$-$C_3$alkyl, $C_1$-$C_3$haloalkyl, halogen, —O$C_1$-$C_3$alkyl, or —O$C_1$-$C_3$haloalkyl;

$R^4$ is hydrogen, halogen, $C_1$-$C_6$alkyl, $C_1$-$C_6$haloalkyl, —O—$C_1$-$C_6$alkyl, —O—$C_1$-$C_6$haloalkyl, cyano, —NH$_2$, $L^{4A}$-OH, 5-membered heteroaryl optionally substituted with 1 or 2 alkyl or halogen, 5-membered heterocycle or —N($R^{40}$)(SO$_2$$R^{4a}$);

$R^{40}$ is hydrogen, $C_1$-$C_{10}$alkyl, $C_2$-$C_{10}$alkenyl, $C_2$-$C_{10}$alkynyl, $C_1$-$C_{10}$haloalkyl, $C_2$-$C_{10}$haloalkenyl, $C_2$-$C_{10}$haloalkynyl, $C_3$-$C_8$cycloalkyl, 3- to 8-membered heterocyclyl, -$L^{4A}$-$G^{4a}$, -$L^{4A}$-C(O)-$L^{4B}$-$G^{4a}$, -L$^{4A}$-O-L$^{4B}$-G$^{4a}$, -L$^{4A}$-S(O)$_2$-L$^{4B}$-G$^{4a}$, -L$^{4A}$-N(R$^{4b}$)(L$^{4B}$-G$^{4a}$), -L$^{4A}$-N(R$^{4b}$)C(O)-L$^{4B}$-G$^{4a}$, -L$^{4A}$-N(R$^{4b}$)S(O)$_2$-L$^{4B}$-G$^{4a}$, or -L$^{4A}$-R$^{4c}$, wherein the C$_1$-C$_{10}$alkyl, C$_2$-C$_{10}$alkenyl, and C$_2$-C$_{10}$alkynyl are each optionally substituted with 2, 3, or 4 hydroxy substituents; and wherein the C$_3$-C$_8$cycloalkyl or 3- to 8-membered heterocyclyl is each optionally substituted with L$^{4B}$-G$^{4b}$ and optionally substituted with 1, 2, 3, or 4 substituents selected from the group consisting of halogen, oxo, C$_1$-C$_3$alkyl, C$_1$-C$_3$haloalkyl, —O—C$_1$-C$_3$alkyl, and —O—C$_1$-C$_3$haloalkyl;

L$^{4A}$ is C$_1$-C$_{10}$alkylene, C$_2$-C$_{10}$alkenylene, or C$_2$-C$_{10}$alkynylene, wherein L$^{4A}$ is optionally substituted with 1, 2, 3, 4, or 5 substituents selected from the group consisting of halogen, C$_1$-C$_6$alkyl, and C$_1$-C$_6$haloalkyl;

G$^{4a}$ is C$_3$-C$_{12}$cycloalkyl, C$_6$-C$_{12}$aryl, 3- to 12-membered heterocyclyl, or 5- to 12-membered heteroaryl, wherein G$^{4a}$ is optionally substituted with L$^{4C}$-G$^{4b}$ and optionally substituted with 1, 2, 3, 4, or 5 substituents selected from the group consisting of halogen, oxo, C$_1$-C$_3$haloalkyl, —OH, —O—C$_1$-C$_3$alkyl, —O—C$_1$-C$_3$haloalkyl, thioxo, —NH$_2$, —NH(C$_1$-C$_3$alkyl), and —N(C$_1$-C$_3$alkyl)$_2$;

L$^{4B}$ and L$^{4C}$, at each occurrence, are each independently a bond, C$_1$-C$_6$alkylene, C$_2$-C$_6$alkenylene, or C$_2$-C$_6$alkynylene, wherein L$^{4B}$ and L$^{4C}$ are each optionally substituted with 1, 2, 3, 4, or 5 substituents selected from the group consisting of halogen, C$_1$-C$_6$alkyl, and C$_1$-C$_6$haloalkyl;

G$^{4b}$ is C$_3$-C$_{12}$cycloalkyl, 3- to 12-membered heterocyclyl, C$_6$-C$_{12}$aryl, or 5- to 12-membered heteroaryl, wherein G$^{4b}$ is optionally substituted with 1, 2, 3, 4, or 5 substituents selected from the group consisting of halogen, oxo, C$_1$-C$_6$alkyl, C$_1$-C$_6$haloalkyl, hydroxy, —O—C$_1$-C$_6$alkyl, —O—C$_1$-C$_6$haloalkyl, —S(O)—C$_1$-C$_6$alkyl, —S(O)$_2$—C$_1$-C$_6$alkyl, —C(O)—C$_1$-C$_6$alkyl, C$_1$-C$_3$alkylene-OH, C$_1$-C$_3$alkylene-OH, C$_1$-C$_3$alkylene-O—C$_1$-C$_3$alkyl, C$_1$-C$_3$alkylene-N(C$_1$-C$_3$alkyl)$_2$, and C$_1$-C$_3$alkylene-(N-heterocyclyl);

R$^{4a}$ and R$^{4b}$, at each occurrence, are each independently hydrogen, C$_1$-C$_6$alkyl, C$_1$-C$_6$haloalkyl, or C$_3$-C$_8$cycloalkyl, wherein the C$_3$-C$_8$cycloalkyl is optionally substituted with 1, 2, 3, or 4 substituents selected from the group consisting of halogen, oxo, C$_1$-C$_3$alkyl, and C$_1$-C$_3$haloalkyl;

R$^{4c}$ is —O—R$^{4b}$, —OC(O)R$^{4b}$, —O—Si(C$_1$-C$_6$alkyl)$_3$, —CN, —C(O)R$^{4b}$, —CO$_2$R$^{4b}$, —C(O)N(R$^{4b}$)$_2$, —C(O)N(R$^{4b}$)S(O)$_2$R$^{4b}$, —S—R$^{4b}$, —S(O)$_2$R$^{4b}$, —S(O)R$^{4b}$, —SO$_2$N(R$^{4b}$)$_2$, —N(R$^{4b}$)$_2$, —N(R$^{4b}$)C(O)R$^{4b}$, —N(R$^{4b}$)S(O)$_2$R$^{4b}$, —C(NOH)N(R$^{4b}$)$_2$, —C(O)C(OH)(R$^{4b}$)$_2$, or —P(O)(OR$^{4b}$)$_2$;

R$^5$ is hydrogen, C$_1$-C$_6$alkyl, C$_1$-C$_6$haloalkyl, C$_3$-C$_6$cycloalkyl, —O—C$_1$-C$_6$alkyl, —O—C$_1$-C$_6$haloalkyl, —O—C$_3$-C$_6$cycloalkyl, or G$^{5a}$, wherein the C$_3$-C$_6$cycloalkyl groups are optionally substituted with 1, 2, 3, or 4 substituents selected from the group consisting of halogen, C$_1$-C$_3$alkyl, C$_1$-C$_3$haloalkyl, and oxo;

G$^{5a}$ is phenyl, wherein G$^{5a}$ is substituted with —C(O)N(R$^{5a}$)-L$^{5B}$-G$^{5b}$, —C(O)-G$^{5f}$, or —C(O)N(R$^{5a}$)(R$^{5e}$), and optionally substituted with 1, 2, or 3 substituents selected from the group consisting of C$_1$-C$_{10}$alkyl, C$_2$-C$_{10}$alkenyl, C$_2$-C$_{10}$alkynyl, C$_1$-C$_{10}$haloalkyl, halogen, —O—R$^{5b}$, CN, —N(R$^{5b}$)C(O)R$^{5b}$, —C(O)N(R$^{5a}$)(R$^{5b}$), —C(O)R$^{5b}$, —OC(O)R$^{5b}$, —CO$_2$H, —CO$_2$R$^{5b}$, —N(R$^{5b}$)C(O)N(R$^{5a}$)(R$^{5b}$), —S—R$^{5b}$, —S(O)$_2$R$^{5b}$, —S(O)R$^{5b}$, —SO$_2$N(R$^{5a}$)(R$^{5b}$), —N(R$^{5a}$)(R$^{5b}$), —N(R$^{5b}$)S(O)$_2$R$^{5b}$, N(R$^{5b}$)C(O)O(R$^{5b}$), -L$^{5A}$-O—R$^{5b}$, -L$^{5A}$-CN, -L$^{5A}$-N(R$^{5b}$)C(O)R$^{5b}$, -L$^{5A}$-C(O)N(R$^{5a}$)(R$^{5b}$), -L$^{5A}$-C(O)R$^{5b}$, -L$^{5A}$-OC(O)R$^{5b}$, -L$^{5A}$-CO$_2$H, -L$^{5A}$-CO$_2$R$^{5b}$, -L$^{5A}$-N(R$^{5b}$)C(O)N(R$^{5a}$)(R$^{5b}$), -L$^{5A}$-S—R$^{5b}$, -L$^{5A}$-S(O)$_2$R$^{5b}$, -L$^{5A}$-S(O)R$^{5b}$, -L$^{5A}$-SO$_2$N(R$^{5a}$)(R$^{5b}$), -L$^{5A}$-N(R$^{5a}$)(R$^{5b}$), -L$^{5A}$-N(R$^{5b}$)S(O)$_2$R$^{5b}$, -L$^{5A}$-N(R$^{5b}$)C(O)O(R$^{5b}$), -G$^{5d}$, and -L$^{5A}$-G$^{5d}$;

G$^{5b}$ is C$_3$-C$_{12}$cycloalkyl, C$_6$-C$_{12}$aryl, 3- to 12-membered heterocyclyl, or 5- to 12-membered heteroaryl, wherein each G$^{5b}$ is optionally substituted with 1, 2, 3, 4, or 5 substituents selected from the group consisting of oxo, halogen, C$_1$-C$_6$alkyl, C$_1$-C$_6$haloalkyl, —O—R$^{5d}$, —CN, —N(R$^{5d}$)C(O)R$^{5d}$, —CON(R$^{5a}$)(R$^{5d}$), —C(O)R$^{5d}$, —OC(O)R$^{5d}$, —CO$_2$H, —CO$_2$R$^{5d}$, —N(R$^{5d}$)C(O)N(R$^{5d}$)$_2$, —S—R$^{5d}$, —S(O)$_2$R$^{5d}$, —S(O)R$^{5d}$, —SO$_2$N(R$^{5a}$)(R$^{5d}$), —N(R$^{5a}$)(R$^{5d}$), —N(R$^{5d}$)S(O)$_2$R$^{5d}$, N(R$^{5d}$)C(O)O(R$^{5d}$), -L$^{5C}$-O—R$^{5d}$, -L$^{5C}$-CN, -L$^{5C}$-N(R$^{5d}$)C(O)R$^{5d}$, -L$^{5C}$-CON(R$^{5a}$)(R$^{5d}$), -L$^{5C}$-C(O)R$^{5d}$, -L$^{5C}$-OC(O)R$^{5d}$, -L$^{5C}$-CO$_2$H, -L$^{5C}$-CO$_2$R$^{5d}$, -L$^{5C}$-N(R$^{5d}$)C(O)N(R$^{5d}$)$_2$, -L$^{5C}$-S—R$^{5d}$, -L$^{5C}$-S(O)$_2$R$^{5d}$, -L$^{5C}$-S(O)R$^{5d}$, -L$^{5C}$-SO$_2$N(R$^{5a}$)(R$^{5d}$), -L$^{5C}$-N(R$^{5a}$)(R$^{5d}$), -L$^{5C}$-N(R$^{5d}$)S(O)$_2$R$^{5d}$, -L$^{5C}$-N(R$^{5d}$)C(O)O(R$^{5d}$), G$^{5c}$, and -L$^{5C}$-G$^{5c}$;

G$^{5c}$, at each occurrence, is each independently C$_3$-C$_8$cycloalkyl, C$_6$-C$_{10}$aryl, 4- to 10-membered heterocyclyl, or 5- to 10-membered heteroaryl, wherein G$^{5c}$ is optionally substituted with 1, 2, 3, 4, or 5 substituents selected from the group consisting of halogen, oxo, C$_1$-C$_6$alkyl, C$_1$-C$_6$haloalkyl, —O—C$_1$-C$_6$alkyl, and —O—C$_1$-C$_6$haloalkyl;

G$^{5d}$, is at each occurrence, is each independently C$_3$-C$_8$cycloalkyl, C$_6$-C$_{10}$aryl, 4- to 10-membered heterocyclyl, or 5- to 10-membered heteroaryl, wherein G$^{5d}$ is optionally substituted with 1, 2, 3, 4, or 5 substituents selected from the group consisting of oxo, halogen, C$_1$-C$_6$alkyl, C$_1$-C$_6$haloalkyl, —O—R$^{5d}$, —CN, —N(R$^{5d}$)C(O)R$^{5d}$, —CON(R$^{5a}$)(R$^{5d}$), —C(O)R$^{5d}$, —OC(O)R$^{5d}$, —CO$_2$H, —CO$_2$R$^{5d}$, —N(R$^{5d}$)C(O)N(R$^{5d}$)$_2$, —S—R$^{5d}$, —S(O)$_2$R$^{5d}$, —S(O)R$^{5d}$, —SO$_2$N(R$^{5a}$)(R$^{5d}$), —N(R$^{5a}$)(R$^{5d}$), —N(R$^{5d}$)S(O)$_2$R$^{5d}$, N(R$^{5d}$)C(O)O(R$^{5d}$), -L$^{5C}$-O—R$^{5d}$, -L$^{5C}$-CN, -L$^{5C}$-N(R$^{5d}$)C(O)R$^{5d}$, -L$^{5C}$-CON(R$^{5a}$)(R$^{5d}$), -L$^{5C}$-C(O)R$^{5d}$, -L$^{5C}$-OC(O)R$^{5d}$, -L$^{5C}$-CO$_2$H, -L$^{5C}$-CO$_2$R$^{5d}$, -L$^{5C}$-N(R$^{5d}$)C(O)N(R$^{5d}$)$_2$, -L$^{5C}$-S—R$^{5d}$, -L$^{5C}$-S(O)$_2$R$^{5d}$, -L$^{5C}$-S(O)R$^{5d}$, -L$^{5C}$-SO$_2$N(R$^{5a}$)(R$^{5d}$), -L$^{5C}$-N(R$^{5a}$)(R$^{5d}$), -L$^{5C}$-N(R$^{5d}$)S(O)$_2$R$^{5d}$, -L$^{5C}$-N(R$^{5d}$)C(O)O(R$^{5d}$), G$^{5c}$, and -L$^{5C}$-G$^{5c}$;

R$^{5a}$, at each occurrence, is each independently hydrogen, C$_1$-C$_6$alkyl, C$_1$-C$_6$haloalkyl, or C$_3$-C$_8$cycloalkyl, wherein the C$_3$-C$_8$cycloalkyl is optionally substituted with 1, 2, 3, or 4 substituents selected from the group consisting of halogen, oxo, C$_1$-C$_3$alkyl, and C$_1$-C$_3$haloalkyl;

R$^{5b}$, at each occurrence, is each independently hydrogen, C$_1$-C$_{10}$alkyl, C$_2$-C$_{10}$alkenyl, C$_2$-C$_{10}$alkynyl, C$_1$-C$_{10}$haloalkyl, -L$^{5D}$-G$^{5e}$, or -L$^{5G}$-R$^{5c}$;

R$^{5c}$, at each occurrence, is each independently —CON(R$^{5a}$)(R$^{5g}$), —O—R$^{5g}$, —OC(O)R$^{5g}$, —CN, —C(O)R$^{5g}$, —CO$_2$H, —CO$_2$R$^{5g}$, —N(R$^{5g}$)C(O)N(R$^{5g}$)$_2$, —S—R$^{5g}$, —S(O)$_2$R$^{5g}$, —S(O)R$^{5g}$, —SO$_2$N(R$^{5a}$)(R$^{5g}$), —N(R$^{5a}$)(R$^{5g}$), —N(R$^{5g}$)C(O)R$^{5g}$, or —N(R$^{5g}$)S(O)$_2$R$^{5g}$;

$R^{5d}$, at each occurrence, is each independently hydrogen, $C_1$-$C_6$alkyl, $C_1$-$C_6$haloalkyl, or -$L^{5F}$-$G^{5c}$;

$R^{5e}$, at each occurrence, is each independently hydrogen, $C_1$-$C_{10}$alkyl, $C_2$-$C_{10}$alkenyl, $C_2$-$C_{10}$alkynyl, $C_1$-$C_{10}$haloalkyl, or -$L^{5E}$-$R^{5f}$;

$R^{5f}$ is —CON($R^{5a}$)($R^{5d}$), —O—$R^{5d}$, —OC(O)$R^{5d}$, —CN, —C(O)$R^{5d}$, —$CO_2$H, —$CO_2R^{5d}$, —N($R^{5d}$)C(O)N($R^{5d}$)$_2$, —S—$R^{5d}$, —S(O)$_2R^{5d}$, —S(O)$R^{5d}$, —$SO_2$N($R^{5a}$)($R^{5d}$), —N($R^{5a}$)($R^{5d}$), —N($R^{5d}$)C(O)$R^{5d}$, or —N($R^{5d}$)S(O)$_2R^{5d}$;

$R^{5g}$ is hydrogen, $C_1$-$C_6$alkyl, $C_1$-$C_6$haloalkyl, or -$L^{5H}$-$G^{5e}$;

$G^{5e}$, at each occurrence, is each independently $C_3$-$C_8$cycloalkyl, $C_6$-$C_{10}$aryl, 4- to 10-membered heterocyclyl, or 5- to 10-membered heteroaryl, wherein $G^{5e}$ is optionally substituted with 1, 2, 3, or 4 substituents selected from the group consisting of halogen, oxo, $C_1$-$C_6$alkyl, $C_1$-$C_6$haloalkyl, —OH, —O—$C_1$-$C_6$alkyl, and —O—$C_1$-$C_6$haloalkyl;

$G^{5f}$ is 4- to 10-membered heterocyclyl, wherein $G^{5f}$ is optionally substituted with 1, 2, 3, or 4 substituents selected from the group consisting of halogen, oxo, $C_1$-$C_6$alkyl, $C_1$-$C_6$haloalkyl, —O—$C_1$-$C_6$alkyl, and —O—$C_1$-$C_6$haloalkyl;

$L^{5A}$, at each occurrence, is each independently $C_1$-$C_6$alkylene or $C_3$-$C_8$cycloalkyl, wherein $L^{5A}$ is each optionally substituted with 1, 2, 3, or 4 halogen;

$L^{5B}$ is a bond, $C_1$-$C_6$alkylene, or $C_3$-$C_8$cycloalkyl, wherein $L^{5B}$ is optionally substituted with 1, 2, 3, or 4 halogen and 1 or 2 hydroxy;

$L^{5C}$, at each occurrence, is each independently $C_1$-$C_6$alkylene or $C_3$-$C_8$cycloalkyl, wherein $L^{5C}$ is each optionally substituted with 1, 2, 3, or 4 halogen and 1 or 2 hydroxy;

$L^{5D}$, at each occurrence, is each independently a bond, $C_1$-$C_6$alkylene, or $C_3$-$C_8$cycloalkyl, wherein $L^{5D}$ is each optionally substituted with 1, 2, 3, or 4 halogen and 1 or 2 hydroxy;

$L^{5E}$, at each occurrence, is each independently $C_1$-$C_6$alkylene, wherein $L^{5E}$ is optionally substituted with 1, 2, 3, or 4 halogen and 1 or 2 hydroxy;

$L^{5F}$, at each occurrence, is each independently bond or $C_1$-$C_6$alkylene, wherein $L^{5F}$ is optionally substituted with 1, 2, 3, or 4 halogen and 1 or 2 hydroxy;

$L^{5G}$, at each occurrence, is each independently $C_1$-$C_6$alkylene, wherein $L^{5G}$ is optionally substituted with 1, 2, 3, or 4 halogen and 1 or 2 hydroxy; and $L^{5H}$, at each occurrence, is each independently a bond, $C_1$-$C_6$alkylene, or $C_3$-$C_8$cycloalkyl, wherein $L^{5H}$ is each optionally substituted with 1, 2, 3, or 4 halogen and 1 or 2 hydroxy.

2. The compound or salt of claim 1, wherein:
$L^{2A}$ is a bond;
$W^2$ is $CR^5$;
$W^3$ is $CR^4$;
$R^4$ is hydrogen, —N($R^{40}$)($SO_2R^{4a}$), or a 5-membered heteroaryl optionally substituted with 1 or 2 halogen or alkyl; and
$R^5$ is hydrogen, $C_3$-$C_6$cycloalkyl, —O—$C_1$-$C_6$alkyl, or $G^{5a}$, wherein the $C_3$-$C_6$cycloalkyl is optionally substituted with 1, 2, 3, or 4 substituents selected from the group consisting of halogen, $C_1$-$C_3$alkyl, $C_1$-$C_3$haloalkyl, and oxo.

3. The compound or salt of claim 1, wherein:
$R^1$ is formula (i);

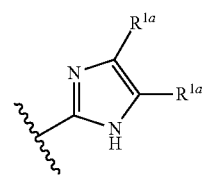

(i)

$L^{2A}$ is a bond;
$R^4$ is hydrogen, —N($R^{40}$)($SO_2R^{4a}$), or a 5-membered heteroaryl optionally substituted with 1 or 2 halogen or alkyl; and
$R^5$ is hydrogen, $C_3$-$C_6$cycloalkyl, —O—$C_1$-$C_6$alkyl, or $G^{5a}$, wherein the $C_3$-$C_6$cycloalkyl is optionally substituted with 1, 2, 3, or 4 substituents selected from the group consisting of halogen, $C_1$-$C_3$alkyl, $C_1$-$C_3$haloalkyl, and oxo.

4. The compound or salt of claim 3, wherein:
$V^1$ and $V^2$ are each C, or one of $V^1$ and $V^2$ is N and the other is C; wherein, when $V^3$ is O or S or when A is formula (vii), $V^2$ is C;
when A is formula (vi), $V^3$ is $CR^7$, $NR^7$, N, O, or S;
when A is formula (vii), $V^3$ is N, O, or S;
$W^1$ is N or $CR^6$, $W^2$ is N or $CR^5$, $W^3$ is N or $CR^4$, $W^4$ is N or $CR^3$, wherein none, one, or two of $W^1$, $W^2$, $W^3$ and $W^4$ is N;
$W^5$ is N or $CR^6$, $W^6$ is N or $CR^5$, wherein none or one of $W^5$ and $W^6$ is N; and
$W^7$ is N, O, or S.

5. The compound or salt of claim 1, wherein:
$R^1$ is formula (iii);

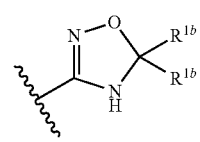

(iii)

$L^{2A}$ is a bond;
$R^4$ is hydrogen, —N($R^{40}$)($SO_2R^{4a}$), or a 5-membered heteroaryl optionally substituted with 1 or 2 halogen or alkyl; and
$R^5$ is hydrogen, $C_3$-$C_6$cycloalkyl, —O—$C_1$-$C_6$alkyl, or $G^{5a}$, wherein the $C_3$-$C_6$cycloalkyl is optionally substituted with 1, 2, 3, or 4 substituents selected from the group consisting of halogen, $C_1$-$C_3$alkyl, $C_1$-$C_3$haloalkyl, and oxo.

6. The compound or salt of claim 5, wherein:
$V^1$ and $V^2$ are each C, or one of $V^1$ and $V^2$ is N and the other is C; wherein, when $V^3$ is O or S or when A is formula (vii), $V^2$ is C;
when A is formula (vi), $V^3$ is $CR^7$, $NR^7$, N, O, or S;
when A is formula (vii), $V^3$ is N, O, or S;
$W^1$ is N or $CR^6$, $W^2$ is N or $CR^5$, $W^3$ is N or $CR^4$, $W^4$ is N or $CR^3$, wherein none, one, or two of $W^1$, $W^2$, $W^3$ and $W^4$ is N;
$W^5$ is N or $CR^6$, $W^6$ is N or $CR^5$, wherein none or one of $W^5$ and $W^6$ is N; and
$W^7$ is N, O, or S.

7. The compound or salt of claim 1, wherein:
$L^{2A}$ is a bond;
$R^4$ is hydrogen, $-N(R^{40})(SO_2R^{4a})$, or a 5-membered heteroaryl optionally substituted with 1 or 2 halogen or alkyl;
$R^5$ is hydrogen, $C_3$-$C_6$cycloalkyl, $-O-C_1$-$C_6$alkyl, or $G^{5a}$, wherein the $C_3$-$C_6$cycloalkyl groups are optionally substituted with 1, 2, 3, or 4 substituents selected from the group consisting of halogen, $C_1$-$C_3$alkyl, $C_1$-$C_3$haloalkyl, and oxo:
$V^1$ and $V^2$ are each C, or one of $V^1$ and $V^2$ is N and the other is C; wherein $V^2$ is C when $V^3$ is O;
$V^3$ is N or O, when A is formula (vi);
$W^1$ is $CR^6$;
$W^2$ is $CR^5$;
$W^3$ is $CR^4$; and
$W^4$ is $CR^3$.

8. The compound or salt of claim 7, wherein:
$R^1$ is formula (i);

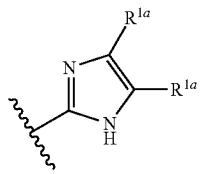
(i)

$L^{2A}$ is a bond;
$G^{2a}$ is phenyl, wherein the phenyl is optionally substituted with 1, 2, or 3 substituents selected from the group consisting of, $R^{20}$, $L^{2B}$, $R^{21}$, $G^{2b}$, and $L^{2B}$-$G^{2b}$;
$R^4$ is $-N(R^{40})(SO_2R^{4a})$;
$V^1$ and $V^2$ are each C;
$V^3$ is O;
$W^1$ is $CR^6$;
$W^2$ is $CR^5$;
$W^3$ is $CR^4$; and
$W^4$ is $CR^3$.

9. The compound or salt of claim 7, wherein:
$R^1$ is formula (iii);

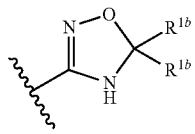
(iii)

$L^{2A}$ is a bond;
$G^{2a}$ is phenyl, wherein the phenyl is optionally substituted with 1, 2, or 3 substituents selected from the group consisting of, $R^{20}$, $L^{2B}$, $R^{21}$, $G^{2b}$, and $L^{2B}$-$G^{2b}$;
$R^4$ is $-N(R^{40})(SO_2R^{4a})$;
$R^5$ is cyclopropyl;
$V^1$ and $V^2$ are each C;
$V^3$ is O;
$W^1$ is $CR^6$;
$W^2$ is $CR^5$;
$W^3$ is $CR^4$; and
$W^4$ is $CR^3$.

10. The compound or salt of claim 7, wherein:
$R^1$ is formula (i);

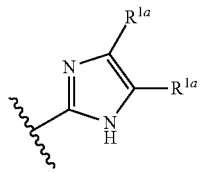
(i)

$L^{2A}$ is a bond;
$G^{2a}$ is phenyl, wherein the phenyl is optionally substituted with 1, 2, or 3 substituents selected from the group consisting of, $R^{20}$, $L^{2B}$-$R^{21}$, $G^{2b}$, and $L^{2B}$-$G^{2b}$;
$R^4$ is 5-membered heteroaryl optionally substituted with 1 or 2 alkyl or halogen;
$R^5$ is hydrogen;
$V^1$ and $V^2$ are each C;
$V^3$ is O;
$W^1$ is $CR^6$;
$W^2$ is $CR^5$;
$W^3$ is $CR^4$; and
$W^4$ is $CR^3$.

11. The compound or salt of claim 7, wherein:
$R^1$ is formula (i);

(i)

$L^{2A}$ is a bond;
$G^{2a}$ is phenyl, wherein the phenyl is optionally substituted with 1, 2, or 3 substituents selected from the group consisting of, $R^{20}$, $L^{2B}$-$R^{21}$, $G^{2b}$, and $L^{2B}$-$G^{2b}$;
$R^4$ is hydrogen;
$R^5$ is $G^{5a}$, wherein $G^{5a}$ is phenyl, wherein said phenyl is substituted with $-C(O)N(R^{5a})$-$L^{5B}$-$G^{5b}$ and optionally with alkyl;
$V^1$ is C;
$V^2$ is N;
$V^3$ is N;
$W^1$ is $CR^6$;
$W^2$ is $CR^5$;
$W^3$ is $CR^4$; and
$W^4$ is $CR^3$.

12. The compound of claim 1, wherein the compound is selected from the group consisting of:
N-[5-cyclopropyl-2-(4-fluorophenyl)-3-(1H-imidazol-2-yl)-1-benzofuran-6-yl]methanesulfonamide;
N-[5-cyclopropyl-2-(4-fluorophenyl)-3-(4-methyl-1H-imidazol-2-yl)-1-benzofuran-6-yl]methanesulfonamide'
N-{[2-(1H-benzimidazol-6-yl)-1,3-thiazol-5-yl]methyl}-N-[3-(1H-imidazol-2-yl)-2-phenyl-1-benzofuran-6-yl]methanesulfonamide;
N-[5-cyclopropyl-2-(4-fluorophenyl)-3-(1H-imidazol-2-yl)-1-benzofuran-6-yl]-N-(3-methylbutyl)methanesulfonamide;
N-[5-cyclopropyl-2-(4-fluorophenyl)-3-(1H-imidazol-2-yl)-1-benzofuran-6-yl]-N-(4-hydroxybutyl)methanesulfonamide;

N-[5-cyclopropyl-2-(4-fluorophenyl)-3-(1H-imidazol-2-yl)-1-benzofuran-6-yl]-N-[4-(methylsulfonyl)butyl]methanesulfonamide;

N-[5-cyclopropyl-2-(4-fluorophenyl)-3-(1H-imidazol-2-yl)-1-benzofuran-6-yl]-N-[3-(3-hydroxy-1,2-oxazol-5-yl)propyl]methanesulfonamide;

N-[5-cyclopropyl-2-(4-fluorophenyl)-3-(5-methyl-4,5-dihydro-1,2,4-oxadiazol-3-yl)-1-benzofuran-6-yl]-N-(4-hydroxybutyl)methanesulfonamide;

N-[5-cyclopropyl-2-(4-fluorophenyl)-3-(5-methyl-4,5-dihydro-1,2,4-oxadiazol-3-yl)-1-benzofuran-6-yl]-N-[2-(methylsulfonyl)ethyl]methanesulfonamide;

N-[5-cyclopropyl-2-(4-fluorophenyl)-3-(5-methyl-4,5-dihydro-1,2,4-oxadiazol-3-yl)-1-benzofuran-6-yl]-N-[2-(methylsulfinyl)ethyl]methanesulfonamide;

N-[5-cyclopropyl-2-(4-fluorophenyl)-3-(5-methyl-4,5-dihydro-1,2,4-oxadiazol-3-yl)-1-benzofuran-6-yl]-N-(3-methylbutyl)methanesulfonamide;

3-{[5-cyclopropyl-3-(4,5-dihydro-1,2,4-oxadiazol-3-yl)-2-(4-fluorophenyl)-1-benzofuran-6-yl](methylsulfonyl)amino}propane-1-sulfonamide;

N-[5-cyclopropyl-3-(4,5-dihydro-1,2,4-oxadiazol-3-yl)-2-(4-fluorophenyl)-1-benzofuran-6-yl]-N-(4-hydroxybutyl)methanesulfonamide;

N-[5-cyclopropyl-2-(4-fluorophenyl)-3-(1H-imidazol-2-yl)pyrazolo[1,5-a]pyridin-6-yl]-N-(3-methylbutyl)methanesulfonamide;

N-[2-(4-anilinophenyl)-5-cyclopropyl-3-(1H-imidazol-2-yl)-1-benzofuran-6-yl]-N-(3-methylbutyl)methanesulfonamide;

N-[3-(1H-imidazol-2-yl)-2-phenyl-1-benzofuran-6-yl]-N-(1-phenylethyl)methanesulfonamide;

N-benzyl-N-[3-(1H-imidazol-2-yl)-2-phenyl-1-benzofuran-6-yl]methanesulfonamide;

N-{[2-bromo-4-(trifluoromethyl)-1,3-thiazol-5-yl]methyl}-N-[3-(1H-imidazol-2-yl)-2-phenyl-1-benzofuran-6-yl]methanesulfonamide;

N-[3-(1H-imidazol-2-yl)-2-phenyl-1-benzofuran-6-yl]-N-{[2-(1H-indol-5-yl)-1,3-thiazol-5-yl]methyl}methanesulfonamide;

N-[3-(1H-imidazol-2-yl)-2-phenyl-1-benzofuran-6-yl]-N-({2-[4-(methylsulfinyl)phenyl]-1,3-thiazol-5-yl}methyl)methanesulfonamide;

N-[3-(1H-imidazol-2-yl)-2-phenyl-1-benzofuran-6-yl]-N-{[2-(1-methyl-1H-indol-5-yl)-1,3-thiazol-5-yl]methyl}methanesulfonamide;

N-[3-(1H-imidazol-2-yl)-2-phenyl-1-benzofuran-6-yl]-N-{[2-(1-methyl-1H-pyrazol-4-yl)-1,3-thiazol-5-yl]methyl}methanesulfonamide;

N-{[2-(2,4-di-tert-butoxypyrimidin-5-yl)-1,3-thiazol-5-yl]methyl}-N-[3-(1H-imidazol-2-yl)-2-phenyl-1-benzofuran-6-yl]methanesulfonamide;

N-({2-[3-(hydroxymethyl)phenyl]-1,3-thiazol-5-yl}methyl)-N-[3-(1H-imidazol-2-yl)-2-phenyl-1-benzofuran-6-yl]methanesulfonamide;

N-{[2-(2,4-dioxo-1,2,3,4-tetrahydropyrimidin-5-yl)-1,3-thiazol-5-yl]methyl}-N-[3-(1H-imidazol-2-yl)-2-phenyl-1-benzofuran-6-yl]methanesulfonamide;

N-[3-(1H-imidazol-2-yl)-2-phenyl-1-benzofuran-6-yl]-N-{[2-(1-methyl-1H-benzimidazol-6-yl)-1,3-thiazol-5-yl]methyl}methanesulfonamide;

N-[5-cyclopropyl-2-(4-fluorophenyl)-3-(1H-imidazol-2-yl)-1-benzofuran-6-yl]-N-{[2-(1H-indol-5-yl)-1,3-thiazol-5-yl]methyl}methanesulfonamide;

N-[3-(1H-imidazol-2-yl)-2-phenyl-1-benzofuran-6-yl]-N-[3-(trifluoromethyl)benzyl]methanesulfonamide;

ethyl N-[5-cyclopropyl-2-(4-fluorophenyl)-3-(1H-imidazol-2-yl)-1-benzofuran-6-yl]-Nethylsulfonyl)glycinate;

N-(cyclopentylmethyl)-N-[5-cyclopropyl-2-(4-fluorophenyl)-3-(1H-imidazol-2-yl)-1-benzofuran-6-yl]methanesulfonamide;

N-[5-cyclopropyl-2-(4-fluorophenyl)-3-(1H-imidazol-2-yl)-1-benzofuran-6-yl]-N-(2-phenylethyl)methanesulfonamide;

$N^2$-[5-cyclopropyl-2-(4-fluorophenyl)-3-(1H-imidazol-2-yl)-1-benzofuran-6-yl]-$N^2$-(methylsulfonyl)glycinamide;

N-[5-cyclopropyl-2-(4-fluorophenyl)-3-(1H-imidazol-2-yl)-1-benzofuran-6-yl]-N-(3-phenoxypropyl)methanesulfonamide;

N-[5-cyclopropyl-2-(4-fluorophenyl)-3-(1H-imidazol-2-yl)-1-benzofuran-6-yl]-Netrahydro-2H-pyran-4-ylmethyl)methanesulfonamide;

N-butyl-N-[5-cyclopropyl-2-(4-fluorophenyl)-3-(1H-imidazol-2-yl)-1-benzofuran-6-yl]methanesulfonamide;

N-[5-cyclopropyl-2-(4-fluorophenyl)-3-(1H-imidazol-2-yl)-1-benzofuran-6-yl]-N-(4-methylpentyl)methanesulfonamide;

N-[5-cyclopropyl-2-(4-fluorophenyl)-3-(1H-imidazol-2-yl)-1-benzofuran-6-yl]-N-(3-phenylpropyl)methanesulfonamide;

N-(4-{[tert-butyl(dimethyl)silyl]oxy}butyl)-N-[5-cyclopropyl-2-(4-fluorophenyl)-3-(1H-imidazol-2-yl)-1-benzofuran-6-yl]methanesulfonamide;

N-[5-cyclopropyl-2-(4-fluorophenyl)-3-(1H-imidazol-2-yl)-1-benzofuran-6-yl]-N-(2-phenoxyethyl)methanesulfonamide;

N-[5-cyclopropyl-2-(4-fluorophenyl)-3-(1H-imidazol-2-yl)-1-benzofuran-6-yl]-N-(4,4,4-trifluorobutyl)methanesulfonamide;

N-(cyclohexylmethyl)-N-[5-cyclopropyl-2-(4-fluorophenyl)-3-(1H-imidazol-2-yl)-1-benzofuran-6-yl]methanesulfonamide;

5-{[5-cyclopropyl-2-(4-fluorophenyl)-3-(1H-imidazol-2-yl)-1-benzofuran-6-yl](methylsulfonyl)amino}pentyl acetate;

N-[5-cyclopropyl-2-(4-fluorophenyl)-3-(1H-imidazol-2-yl)-1-benzofuran-6-yl]-N-(2-methoxyethyl)methanesulfonamide;

N-[5-cyclopropyl-2-(4-fluorophenyl)-3-(1H-imidazol-2-yl)-1-benzofuran-6-yl]-N-[2-(tetrahydro-2H-pyran-4-yl)ethyl]methanesulfonamide;

N-(3-cyanopropyl)-N-[5-cyclopropyl-2-(4-fluorophenyl)-3-(1H-imidazol-2-yl)-1-benzofuran-6-yl]methanesulfonamide;

ethyl 5-{[5-cyclopropyl-2-(4-fluorophenyl)-3-(1H-imidazol-2-yl)-1-benzofuran-6-yl](methylsulfonyl)amino}pentanoate;

N-[5-cyclopropyl-2-(4-fluorophenyl)-3-(1H-imidazol-2-yl)-1-benzofuran-6-yl]-Nyrrolidin-3-ylmethyl)methanesulfonamide;

N-[5-cyclopropyl-2-(4-fluorophenyl)-3-(1H-imidazol-2-yl)-1-benzofuran-6-yl]-N-isopropylmethanesulfonamide;

N-[5-cyclopropyl-2-(4-fluorophenyl)-3-(1H-imidazol-2-yl)-1-benzofuran-6-yl]-Nyclopropylmethyl)methanesulfonamide;

N-[5-cyclopropyl-2-(4-fluorophenyl)-3-(1H-imidazol-2-yl)-1-benzofuran-6-yl]-N-(3-methylbut-2-en-1-yl)methanesulfonamide;

N-[5-cyclopropyl-2-(4-fluorophenyl)-3-(1H-imidazol-2-yl)-1-benzofuran-6-yl]-N-[(2,2-difluorocyclopropyl)methyl]methanesulfonamide;
N-[5-cyclopropyl-2-(4-fluorophenyl)-3-(1H-imidazol-2-yl)-1-benzofuran-6-yl]-N-ethylmethanesulfonamide;
N-allyl-N-[5-cyclopropyl-2-(4-fluorophenyl)-3-(1H-imidazol-2-yl)-1-benzofuran-6-yl]methanesulfonamide;
N-[5-cyclopropyl-2-(4-fluorophenyl)-3-(1H-imidazol-2-yl)-1-benzofuran-6-yl]-N-[2-(morpholin-4-yl)ethyl]methanesulfonamide;
N-[5-cyclopropyl-2-(4-fluorophenyl)-3-(1H-imidazol-2-yl)-1-benzofuran-6-yl]-N-[3-(dimethylamino)propyl]methanesulfonamide;
N-[5-cyclopropyl-2-(4-fluorophenyl)-3-(1H-imidazol-2-yl)-1-benzofuran-6-yl]-N-[3-(morpholin-4-yl)propyl]methanesulfonamide;
N-[5-cyclopropyl-2-(4-fluorophenyl)-3-(1H-imidazol-2-yl)-1-benzofuran-6-yl]-N-[2-(1,1-dioxidotetrahydrothiophen-3-yl)ethyl]methanesulfonamide;
N-[5-cyclopropyl-2-(4-fluorophenyl)-3-(1H-imidazol-2-yl)-1-benzofuran-6-yl]-N-{3-[2-(2,5-dimethyl-1H-pyrrol-1-yl)-1,3-thiazol-4-yl]propyl}methanesulfonamide;
N-(cyanomethyl)-N-[5-cyclopropyl-2-(4-fluorophenyl)-3-(1H-imidazol-2-yl)-1-benzofuran-6-yl]methanesulfonamide;
N-[5-cyclopropyl-2-(4-fluorophenyl)-3-(1H-imidazol-2-yl)-1-benzofuran-6-yl]-N-propylmethanesulfonamide;
N-[5-cyclopropyl-2-(4-fluorophenyl)-3-(1H-imidazol-2-yl)-1-benzofuran-6-yl]-N-(3-hydroxypropyl)methanesulfonamide;
N-[5-cyclopropyl-2-(4-fluorophenyl)-3-(1H-imidazol-2-yl)-1-benzofuran-6-yl]-N-isobutylmethanesulfonamide;
N-[(2-bromo-1,3-thiazol-5-yl)methyl]-N-[5-cyclopropyl-2-(4-fluorophenyl)-3-(1H-imidazol-2-yl)-1-benzofuran-6-yl]methanesulfonamide;
methyl 4-{[5-cyclopropyl-2-(4-fluorophenyl)-3-(1H-imidazol-2-yl)-1-benzofuran-6-yl](methylsulfonyl)amino}butanoate;
N-[5-cyclopropyl-2-(4-fluorophenyl)-3-(1H-imidazol-2-yl)-1-benzofuran-6-yl]-N-(3-methoxypropyl)methanesulfonamide;
N-[5-cyclopropyl-2-(4-fluorophenyl)-3-(1H-imidazol-2-yl)-1-benzofuran-6-yl]-N-pentylmethanesulfonamide;
N-[5-cyclopropyl-2-(4-fluorophenyl)-3-(1H-imidazol-2-yl)-1-benzofuran-6-yl]-N-hexylmethanesulfonamide;
N-(2-cyclohexylethyl)-N-[5-cyclopropyl-2-(4-fluorophenyl)-3-(1H-imidazol-2-yl)-1-benzofuran-6-yl]methanesulfonamide;
N-[5-cyclopropyl-2-(4-fluorophenyl)-3-(1H-imidazol-2-yl)-1-benzofuran-6-yl]-N-(4-oxopentyl)methanesulfonamide;
N-[5-cyclopropyl-2-(4-fluorophenyl)-3-(1H-imidazol-2-yl)-1-benzofuran-6-yl]-N-[2-(methylthio)ethyl]methanesulfonamide;
N-[5-cyclopropyl-2-(4-fluorophenyl)-3-(1H-imidazol-2-yl)-1-benzofuran-6-yl]-Netrahydrofuran-2-ylmethyl)methanesulfonamide;
N-[5-cyclopropyl-2-(4-fluorophenyl)-3-(1H-imidazol-2-yl)-1-benzofuran-6-yl]-N-(4-methylpent-3-en-1-yl)methanesulfonamide;
N-[5-cyclopropyl-2-(4-fluorophenyl)-3-(1H-imidazol-2-yl)-1-benzofuran-6-yl]-N-(5-oxohexyl)methanesulfonamide;
N-[5-cyclopropyl-2-(4-fluorophenyl)-3-(1H-imidazol-2-yl)-1-benzofuran-6-yl]-N-[2-(4-methyl-1,3-thiazol-5-yl)ethyl]methanesulfonamide;
N-[5-cyclopropyl-2-(4-fluorophenyl)-3-(1H-imidazol-2-yl)-1-benzofuran-6-yl]-N-[3-(morpholin-4-ylsulfonyl)propyl]methanesulfonamide;
3-{[5-cyclopropyl-2-(4-fluorophenyl)-3-(1H-imidazol-2-yl)-1-benzofuran-6-yl](methylsulfonyl)amino}propane-1-sulfonamide;
N-[5-cyclopropyl-2-(4-fluorophenyl)-3-(1H-imidazol-2-yl)-1-benzofuran-6-yl]-N-[2-(pyrrolidin-1-yl)ethyl]methanesulfonamide;
N-[5-cyclopropyl-2-(4-fluorophenyl)-3-(1H-imidazol-2-yl)-1-benzofuran-6-yl]-N-[(1,3-dioxo-1,3-dihydro-2H-isoindol-2-yl)methyl]methanesulfonamide;
N-[5-cyclopropyl-2-(4-fluorophenyl)-3-(1H-imidazol-2-yl)-1-benzofuran-6-yl]-N-(4-fluorobutyl)methanesulfonamide;
N-[5-cyclopropyl-2-(4-fluorophenyl)-3-(1H-imidazol-2-yl)-1-benzofuran-6-yl]-N-(3,4-dihydroxy-4-methylpentyl)methanesulfonamide;
N-[5-cyclopropyl-2-(4-fluorophenyl)-3-(1H-imidazol-2-yl)-1-benzofuran-6-yl]-N-(3-fluoropropyl)methanesulfonamide;
3-{[5-cyclopropyl-2-(4-fluorophenyl)-3-(1H-imidazol-2-yl)-1-benzofuran-6-yl](methylsulfonyl)amino}-N-methylpropane-1-sulfonamide;
N-[5-cyclopropyl-2-(4-fluorophenyl)-3-(1H-imidazol-2-yl)-1-benzofuran-6-yl]-N-[2-(methylsulfonyl)ethyl]methanesulfonamide;
N-[5-cyclopropyl-2-(4-fluorophenyl)-3-(1H-imidazol-2-yl)-1-benzofuran-6-yl]-N-(5-hydroxypentyl)methanesulfonamide;
4-{[5-cyclopropyl-2-(4-fluorophenyl)-3-(1H-imidazol-2-yl)-1-benzofuran-6-yl](methylsulfonyl)amino}butanoic acid;
N-[5-cyclopropyl-2-(4-fluorophenyl)-3-(1H-imidazol-2-yl)-1-benzofuran-6-yl]-N-[3-(phenylsulfonyl)propyl]methanesulfonamide;
5-{[5-cyclopropyl-2-(4-fluorophenyl)-3-(1H-imidazol-2-yl)-1-benzofuran-6-yl](methylsulfonyl)amino}pentanamide;
5-{[5-cyclopropyl-2-(4-fluorophenyl)-3-(1H-imidazol-2-yl)-1-benzofuran-6-yl](methylsulfonyl)amino}pentanoic acid;
N-[5-cyclopropyl-2-(4-fluorophenyl)-3-(1H-imidazol-2-yl)-1-benzofuran-6-yl]-N-(2,3-dihydroxypropyl)methanesulfonamide;
N-[5-cyclopropyl-2-(4-fluorophenyl)-3-(1H-imidazol-2-yl)-1-benzofuran-6-yl]-N-(2,3-dihydroxy-3-methylbutyl)methanesulfonamide;
N-[5-cyclopropyl-2-(4-fluorophenyl)-3-(1H-imidazol-2-yl)-1-benzofuran-6-yl]-N-{3-[(methylsulfonyl)amino]propyl}methanesulfonamide;
N-[5-cyclopropyl-2-(4-fluorophenyl)-3-(1H-imidazol-2-yl)-1-benzofuran-6-yl]-N-[2-(ethylsulfonyl)ethyl]methane sulfonamide;
N-[2-(2-amino-1,3-thiazol-4-yl)ethyl]-N-[5-cyclopropyl-2-(4-fluorophenyl)-3-(1H-imidazol-2-yl)-1-benzofuran-6-yl]methanesulfonamide;
N-[5-cyclopropyl-2-(4-fluorophenyl)-3-(1H-imidazol-2-yl)-1-benzofuran-6-yl]-N-(2-hydroxypropyl)methanesulfonamide;
N-[5-cyclopropyl-2-(4-fluorophenyl)-3-(1H-imidazol-2-yl)-1-benzofuran-6-yl]-N-(4-hydroxy-4-methylpentyl)methanesulfonamide;
N-[5-cyclopropyl-2-(4-fluorophenyl)-3-(1H-imidazol-2-yl)-1-benzofuran-6-yl]-N-(4-hydroxypentyl)methanesulfonamide;

N-[5-cyclopropyl-2-(4-fluorophenyl)-3-(1H-imidazol-2-yl)-1-benzofuran-6-yl]-N-[3-(methylsulfonyl)propyl]methanesulfonamide;

4-{[5-cyclopropyl-2-(4-fluorophenyl)-3-(1H-imidazol-2-yl)-1-benzofuran-6-yl](methylsulfonyl)amino}-N,N-dimethylbutanamide;

N-[5-cyclopropyl-2-(4-fluorophenyl)-3-(1H-imidazol-2-yl)-1-benzofuran-6-yl]-N-[4-(morpholin-4-yl)-4-oxobutyl]methanesulfonamide;

N-[5-cyclopropyl-2-(4-fluorophenyl)-3-(1H-imidazol-2-yl)-1-benzofuran-6-yl]-N-[4-oxo-4-(piperidin-1-yl)butyl]methanesulfonamide;

4-{[5-cyclopropyl-2-(4-fluorophenyl)-3-(1H-imidazol-2-yl)-1-benzofuran-6-yl](methylsulfonyl)amino}-N-(methylsulfonyl)butanamide;

N-[5-cyclopropyl-2-(4-fluorophenyl)-3-(1H-imidazol-2-yl)-1-benzofuran-6-yl]-N-(4-hydroxy-4-methyl-3-oxopentyl)methanesulfonamide;

4-{[5-cyclopropyl-2-(4-fluorophenyl)-3-(1H-imidazol-2-yl)-1-benzofuran-6-yl](methylsulfonyl)amino}-N-methylbutanamide;

4-{[5-cyclopropyl-2-(4-fluorophenyl)-3-(1H-imidazol-2-yl)-1-benzofuran-6-yl](methylsulfonyl)amino}butanamide;

N-[5-cyclopropyl-2-(4-fluorophenyl)-3-(1H-imidazol-2-yl)-1-benzofuran-6-yl]-N-(2-hydroxyethyl)methanesulfonamide;

N-[5-cyclopropyl-2-(4-fluorophenyl)-3-(1H-imidazol-2-yl)-1-benzofuran-6-yl]-N-(3,4-dihydroxybutyl)methanesulfonamide;

N-(2-aminoethyl)-N-[5-cyclopropyl-2-(4-fluorophenyl)-3-(1H-imidazol-2-yl)-1-benzofuran-6-yl]methanesulfonamide;

N-(3-aminopropyl)-N-[5-cyclopropyl-2-(4-fluorophenyl)-3-(1H-imidazol-2-yl)-1-benzofuran-6-yl]methanesulfonamide;

N-[5-cyclopropyl-2-(4-fluorophenyl)-3-(1H-imidazol-2-yl)-1-benzofuran-6-yl]-N-[(1,1-$^2$H$_2$)hexyl]methanesulfonamide;

N-[5-cyclopropyl-3-(4,5-dihydro-1,2,4-oxadiazol-3-yl)-2-(4-fluorophenyl)-1-benzofuran-6-yl]-N-(4-methoxybenzyl)methane sulfonamide;

N-[5-cyclopropyl-3-(4,5-dihydro-1,2,4-oxadiazol-3-yl)-2-(4-fluorophenyl)-1-benzofuran-6-yl]-N-(3,4-dihydroxy-4-methylpentyl)methanesulfonamide;

N-[5-cyclopropyl-3-(4,5-dihydro-1,2,4-oxadiazol-3-yl)-2-(4-fluorophenyl)-1-benzofuran-6-yl]-N-(5-hydroxypentyl)methanesulfonamide;

N-[5-cyclopropyl-3-(4,5-dihydro-1,2,4-oxadiazol-3-yl)-2-(4-fluorophenyl)-1-benzofuran-6-yl]-N-[4-(methylsulfonyl)butyl]methanesulfonamide;

N-[5-cyclopropyl-3-(4,5-dihydro-1,2,4-oxadiazol-3-yl)-2-(4-fluorophenyl)-1-benzofuran-6-yl]-N-[2-(1,1-dioxidotetrahydrothiophen-3-yl)ethyl]methanesulfonamide;

N-{5-cyclopropyl-3-[(5,5-$^2$H$_2$)-4,5-dihydro-1,2,4-oxadiazol-3-yl]-2-(4-fluorophenyl)-1-benzofuran-6-yl}-N-[4-(methylsulfonyl)butyl]methanesulfonamide;

N-[5-cyclopropyl-2-(4-fluorophenyl)-3-(5-methyl-4,5-dihydro-1,2,4-oxadiazol-3-yl)-1-benzofuran-6-yl]-N-(4-methoxybenzyl)methanesulfonamide;

N-[5-cyclopropyl-3-(5,5-dimethyl-4,5-dihydro-1,2,4-oxadiazol-3-yl)-2-(4-fluorophenyl)-1-benzofuran-6-yl]-N-(3-methylbutyl)methanesulfonamide;

N-[5-cyclopropyl-2-(4-fluorophenyl)-3-(5-propyl-1,2,4-oxadiazol-3-yl)-1-benzofuran-6-yl]-N-(3-methylbutyl)methanesulfonamide;

N-[5-cyclopropyl-2-(4-fluorophenyl)-3-(5-propyl-4,5-dihydro-1,2,4-oxadiazol-3-yl)-1-benzofuran-6-yl]-N-(3-methylbutyl)methanesulfonamide;

N-[5-cyclopropyl-3-(5-ethyl-4,5-dihydro-1,2,4-oxadiazol-3-yl)-2-(4-fluorophenyl)-1-benzofuran-6-yl]-N-(3-methylbutyl)methanesulfonamide;

N-[5-cyclopropyl-3-(4,5-dihydro-1,2,4-oxadiazol-3-yl)-2-(4-fluorophenyl)-1-benzofuran-6-yl]-N-(3-methylbutyl)methanesulfonamide;

4-{[5-cyclopropyl-3-(4,5-dihydro-1,2,4-oxadiazol-3-yl)-2-(4-fluorophenyl)-1-benzofuran-6-yl](methylsulfonyl)amino}butanoic acid;

N-[5-cyclopropyl-2-(4-fluorophenyl)-3-(5-methyl-4,5-dihydro-1,2,4-oxadiazol-3-yl)-1-benzofuran-6-yl]-N-(2-hydroxyethyl)methanesulfonamide;

N-[3-(4-chloro-1H-imidazol-2-yl)-5-cyclopropyl-2-(4-fluorophenyl)-1-benzofuran-6-yl]-N-(4-methoxybenzyl)methanesulfonamide;

N-[5-cyclopropyl-3-(4,5-dichloro-1H-imidazol-2-yl)-2-(4-fluorophenyl)-1-benzofuran-6-yl]methanesulfonamide;

N-[3-(4-chloro-1H-imidazol-2-yl)-5-cyclopropyl-2-(4-fluorophenyl)-1-benzofuran-6-yl]methanesulfonamide;

N-[5-cyclopropyl-3-(4,5-dibromo-1H-imidazol-2-yl)-2-(4-fluorophenyl)-1-benzofuran-6-yl]methanesulfonamide;

2-[6-(2,5-dimethyl-1H-pyrrol-1-yl)-2-phenyl-1-benzofuran-3-yl]-1H-imidazole;

N-{5-cyclopropyl-3-(1H-imidazol-2-yl)-2-[4-(1-phenylvinyl)phenyl]-1-benzofuran-6-yl}-N-(3-methylbutyl)methanesulfonamide;

N-[5-cyclopropyl-2-{4-[(1E)-hex-1-en-1-yl]phenyl}-3-(1H-imidazol-2-yl)-1-benzofuran-6-yl]-N-[4-(methylsulfonyl)butyl]methanesulfonamide;

N-[2-(4-anilinophenyl)-5-cyclopropyl-3-(1H-imidazol-2-yl)-1-benzofuran-6-yl]-N-[4-(methylsulfonyl)butyl]methanesulfonamide;

N-[2-(4-fluorophenyl)-3-(1H-imidazol-2-yl)-5-isopropoxy-1-benzofuran-6-yl]-N-(4-methoxybenzyl)methanesulfonamide;

N-{5-cyclopropyl-2-(4-fluorophenyl)-3-[4-(trifluoromethyl)-1H-imidazol-2-yl]-1-benzofuran-6-yl}-N-(3-methylbutyl)methanesulfonamide;

N-[5-cyclopropyl-2-(4-fluorophenyl)-3-(5-methyl-1H-imidazol-2-yl)-1-benzofuran-6-yl]-N-(3-methylbutyl)methanesulfonamide;

N-[5-cyclopropyl-3-(4,5-dihydro-1,2,4-oxadiazol-3-yl)-2-(4-fluorophenyl)-1-benzofuran-6-yl]methanesulfonamide;

N-[5-cyclopropyl-2-(4-fluorophenyl)-3-(1H-imidazol-2-yl)-1-benzofuran-6-yl]-N-[3-(1H-tetrazol-5-yl)propyl]methanesulfonamide;

N-[5-cyclopropyl-2-(4-fluorophenyl)-3-(1H-imidazol-2-yl)-1-benzofuran-6-yl]-N-[3-(5-oxo-4,5-dihydro-1,2,4-oxadiazol-3-yl)propyl]methanesulfonamide;

(1Z)-4-{[5-cyclopropyl-2-(4-fluorophenyl)-3-(1H-imidazol-2-yl)-1-benzofuran-6-yl](methylsulfonyl)amino}-N-hydroxybutanimidamide;

N-[5-cyclopropyl-2-(4-fluorophenyl)-3-(1H-imidazol-2-yl)-1-benzofuran-6-yl]-N-[3-(5-thioxo-4,5-dihydro-1,2,4-oxadiazol-3-yl)propyl]methanesulfonamide;

N-[5-cyclopropyl-2-(4-fluorophenyl)-3-(1H-imidazol-2-yl)-1-benzofuran-6-yl]-N-[3-(5-oxo-4,5-dihydro-1,2,4-thiadiazol-3-yl)propyl]methanesulfonamide;

N-[5-cyclopropyl-2-(4-fluorophenyl)-3-(1H-imidazol-2-yl)-1-benzofuran-6-yl]-N-[3-(5-oxo-4,5-dihydro-1,3,4-oxadiazol-2-yl)propyl]methanesulfonamide;

N-[5-cyclopropyl-2-(4-fluorophenyl)-3-(5-oxo-4,5-dihydro-1,2,4-oxadiazol-3-yl)-1-benzofuran-6-yl]-N-(4-hydroxybutyl)methanesulfonamide;

N-[5-cyclopropyl-3-(4,5-dimethyl-1H-imidazol-2-yl)-2-(4-fluorophenyl)-1-benzofuran-6-yl]-N-(4-methoxybenzyl)methanesulfonamide;

N-[5-cyclopropyl-2-(4-fluorophenyl)-3-(4-methyl-1H-imidazol-2-yl)-1-benzofuran-6-yl]-N-(4-hydroxybutyl)methanesulfonamide;

N-[5-cyclopropyl-2-(4-fluorophenyl)-3-(5-methyl-1H-imidazol-2-yl)-1-benzofuran-6-yl]-N-(4-methoxybenzyl)methanesulfonamide;

N-[5-cyclopropyl-2-(4-fluorophenyl)-3-(4-methyl-1H-imidazol-2-yl)-1-benzofuran-6-yl]-N-(2-hydroxyethyl)methanesulfonamide;

N-[5-cyclopropyl-2-(4-fluorophenyl)-3-(1H-imidazol-2-yl)-1-benzofuran-6-yl]-N-[(3-hydroxy-1,2-oxazol-5-yl)methyl]methanesulfonamide;

3-[3-(1H-imidazol-2-yl)-2-(4-methoxyphenyl)pyrazolo[1,5-a]pyridin-5-yl]-4-methyl-N-(1-phenylcyclopropyl)benzamide; and N-[5-cyclopropyl-3-(4,5-dimethyl-1H-imidazol-2-yl)-2-(4-fluorophenyl)-1-benzofuran-6-yl]methanesulfonamide.

13. A pharmaceutical composition comprising one or more compounds of claim 1 or pharmaceutically acceptable salts thereof; one or more excipients; and optionally one or more additional therapeutic agents.

14. A method of treating HCV infection, comprising administering a therapeutically effective amount of a compound having formula (I), or a pharmaceutically acceptable salt thereof,

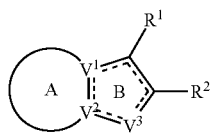

(I)

wherein:
$R^1$ is formula (i) or (iii);

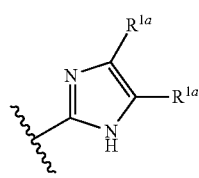

(i)

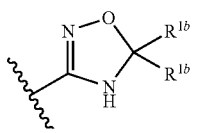

(iii)

$R^{1a}$, at each occurrence, is each independently hydrogen, halogen, $C_1$-$C_3$alkyl, or $C_1$-$C_3$haloalkyl;

$R^{1b}$, at each occurrence, is each independently hydrogen, halogen, $C_1$-$C_3$alkyl, or $C_1$-$C_3$haloalkyl, wherein, optionally, two geminal $R^{1b}$ taken together are oxo;

$R^2$ is $C_1$-$C_{10}$alkyl, $C_2$-$C_{10}$alkenyl, $C_2$-$C_{10}$alkynyl, $C_1$-$C_{10}$haloalkyl, $C_2$-$C_{10}$haloalkenyl, $C_2$-$C_{10}$haloalkynyl, or $L^{2A}$-$G^{2a}$;

$L^{2A}$ is a bond, $C_2$alkenylene, or $C_2$alkynylene;

$G^{2a}$ is $C_6$-$C_{10}$aryl or 5- to 10-membered heteroaryl, wherein the aryl or heteroaryl is optionally substituted with 1, 2, or 3 substituents selected from the group consisting of $R^{20}$, $L^{2B}$-$R^{21}$, $G^{2b}$ and $L^{2B}$-$G^{2b}$;

$L^{2B}$ and $L^{2C}$, at each occurrence, are each independently $C_1$-$C_6$alkylene, $C_2$-$C_6$alkenylene, or $C_2$-$C_6$alkynylene;

$R^{20}$ is hydrogen, $C_1$-$C_{10}$alkyl, $C_2$-$C_{10}$alkenyl, $C_2$-$C_{10}$alkynyl, $C_1$-$C_{10}$haloalkyl, $C_2$-$C_{10}$haloalkenyl, $C_2$-$C_{10}$haloalkynyl, halogen, —N($R^{2a}$)C(O)$R^{2b}$, —C(O)N($R^{2a}$)($R^{2b}$), —O—$R^{2b}$, —C(O)$R^{2b}$, —OC(O)$R^{2b}$, —CO$_2$H, —CO$_2R^{2b}$, —N($R^{2a}$)C(O)N($R^{2a}$)($R^{2b}$), —S—$R^{2b}$, —S(O)$_2R^{2b}$, —S(O)$R^{2b}$, —SO$_2$N($R^{2a}$)($R^{2b}$), —N($R^{2a}$)($R^{2b}$), —N($R^{2a}$)S(O)$_2R^{2b}$, N($R^{2a}$)C(O)O($R^{2b}$), or —C(=CH$_2$)$R^{2b}$;

$R^{21}$ is —N($R^{2a}$)C(O)$R^{2b}$, —C(O)N($R^{2a}$)($R^{2b}$), —O—$R^{2b}$, —C(O)$R^{2b}$, —OC(O)$R^{2b}$, —CO$_2$H, —CO$_2R^{2b}$, —N($R^{2a}$)C(O)N($R^{2a}$)($R^{2b}$), —S—$R^{2b}$, —S(O)$_2R^{2b}$, —S(O)$R^{2b}$, —SO$_2$N($R^{2a}$)($R^{2b}$), —N($R^{2a}$)($R^{2b}$), —N($R^{2a}$)S(O)$_2R^{2b}$, N($R^{2a}$)C(O)O($R^{2b}$), or —C(=CH$_2$)$R^{2b}$;

$R^{2a}$, at each occurrence, is each independently hydrogen, $C_1$-$C_6$alkyl, $C_1$-$C_6$haloalkyl, or $C_3$-$C_8$cycloalkyl, wherein the $C_3$-$C_8$cycloalkyl is optionally substituted with 1, 2, 3, or 4 substituents selected from the group consisting of halogen, oxo, $C_1$-$C_3$alkyl, and $C_1$-$C_3$haloalkyl;

$R^{2b}$, at each occurrence, is each independently hydrogen, $C_1$-$C_{10}$alkyl, $C_2$-$C_{10}$alkenyl, $C_2$-$C_{10}$alkynyl, $C_1$-$C_{10}$haloalkyl, $C_2$-$C_{10}$haloalkenyl, $C_2$-$C_{10}$haloalkynyl, -$L^{2C}$-$R^{2c}$, $G^{2b}$ or -$L^{2C}$-$G^{2b}$;

$R^{2c}$ is —N($R^{2d}$)C(O)$R^{2d}$, —C(O)N($R^{2d}$)($R^{2d}$), —O—$R^{2d}$, —C(O)$R^{2d}$, —OC(O)$R^{2d}$, —CO$_2$H, —CO$_2R^{2d}$, —N($R^{2d}$)C(O)N($R^{2d}$)($R^{2d}$), —S—$R^{2d}$, —S(O)$_2R^{2d}$, —S(O)$R^{2d}$, —SO$_2$N($R^{2d}$)($R^{2d}$), —N($R^{2d}$)($R^{2d}$), —N($R^{2d}$)S(O)$_2R^{2d}$, or N($R^{2d}$)C(O)O($R^{2d}$);

$R^{2d}$, at each occurrence, is each independently hydrogen, $C_1$-$C_6$alkyl, $C_1$-$C_6$haloalkyl, $C_1$-$C_6$alkylene-OH, or $C_3$-$C_8$cycloalkyl, wherein the $C_3$-$C_8$cycloalkyl is optionally substituted with 1, 2, 3, or 4 substituents selected from the group consisting of halogen, oxo, $C_1$-$C_3$alkyl, and $C_1$-$C_3$haloalkyl;

$G^{2b}$ is $C_3$-$C_{10}$cycloalkyl, $C_5$-$C_{10}$cycloalkenyl, $C_6$-$C_{10}$aryl, 3- to 10-membered heterocyclyl, or 5- to 10-membered heteroaryl, wherein $G^{2b}$ is optionally substituted with 1, 2, 3, 4, or 5 substituents selected from the group consisting of $C_1$-$C_{10}$alkyl, $C_2$-$C_{10}$alkenyl, $C_2$-$C_{10}$alkynyl, $C_1$-$C_{10}$haloalkyl, $C_2$-$C_{10}$haloalkenyl, $C_2$-$C_{10}$haloalkynyl, halogen, oxo, cyano, hydroxy, —O—$C_1$-$C_6$alkyl, —O—$C_1$-$C_6$haloalkyl, —$C_1$-$C_3$alkylene-O—H, —$C_1$-$C_3$alkylene-O—$C_1$-$C_6$alkyl, C(O)H, —$C_1$-$C_3$alkylene-NH$_2$, —NH$_2$, —NO$_2$, —C(O)$C_1$-$C_6$alkyl, —C(O)O$C_1$-$C_6$alkyl, and $G^{2c}$;

$G^{2c}$ is $C_6$-$C_{10}$aryl or 5- to 10-membered heteroaryl, wherein $G^{2c}$ is optionally substituted with 1, 2, 3, 4, or 5 substituents selected from the group consisting of $C_1$-$C_{10}$alkyl, $C_2$-$C_{10}$alkenyl, $C_2$-$C_{10}$alkynyl, $C_1$-$C_{10}$haloalkyl, $C_2$-$C_{10}$haloalkenyl, $C_2$-$C_{10}$haloalkynyl, halogen, oxo, cyano, hydroxy, —O—$C_1$-$C_6$alkyl, —O—$C_1$-$C_6$haloalkyl, —$C_1$-$C_3$alkylene-O—H, —$C_1$-$C_3$alkylene-O—$C_1$-

$C_6$alkyl, $C(O)H$, —$C_1$-$C_3$alkylene-$NH_2$, —$NH_2$, —$NO_2$, —$C(O)C_1$-$C_6$alkyl, and —$C(O)OC_1$-$C_6$alkyl;

A and B together are a bicyclic heteroaryl, wherein A is formula (vi) or formula (vii):

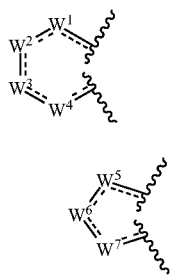

wherein, $V^1$ and $V^2$ are each C, or one of $V^1$ and $V^2$ is N and the other is C, wherein, when $V^3$ is N, O or S or when A is (vii), $V^2$ is C;

when A is (vi), $V^3$ is $CR^7$, $NR^7$, N, O, or S; or, when A is (vii), $V^3$ is N;

$R^7$ is hydrogen, $C_1$-$C_3$alkyl, $C_1$-$C_3$haloalkyl, or $C_3$-$C_6$cycloalkyl;

----- is a single or double bond;

$W^1$ is N or $CR^6$, $W^2$ is N or $CR^5$, $W^3$ is N or $CR^4$, and $W^4$ is N or $CR^3$, wherein none, one or two of $W^1$, $W^2$, $W^3$ and $W^4$ is N;

$W^5$ is N or $CR^6$, and $W^6$ is N or $CR^5$, wherein none or one of $W^5$ and $W^6$ is N;

$W^7$ is N, O, or S;

$R^3$ and $R^6$ are each independently hydrogen, $C_1$-$C_3$alkyl, $C_1$-$C_3$haloalkyl, halogen, —$OC_1$-$C_3$alkyl, or —$OC_1$-$C_3$haloalkyl;

$R^4$ is hydrogen, halogen, $C_1$-$C_6$alkyl, $C_1$-$C_6$haloalkyl, —O—$C_1$-$C_6$haloalkyl, cyano, —$NH_2$, $L^{4A}$-OH, 5-membered heteroaryl optionally substituted with 1 or 2 alkyl or halogen, 5-membered heterocycle or —$N(R^{40})(SO_2R^{4a})$;

$R^{40}$ is hydrogen, $C_1$-$C_{10}$alkyl, $C_2$-$C_{10}$alkenyl, $C_2$-$C_{10}$alkynyl, $C_1$-$C_{10}$haloalkyl, $C_2$-$C_{10}$haloalkenyl, $C_2$-$C_{10}$haloalkynyl, $C_3$-$C_8$cycloalkyl, 3- to 8-membered heterocyclyl, -$L^{4A}$-$G^{4a}$, -$L^{4A}$-$C(O)$-$L^{4B}$-$G^{4a}$, -$L^{4A}$-O-$L^{4B}$-$G^{4a}$, -$L^{4A}$-$S(O)_2$-$L^{4B}$-$G^{4a}$, -$L^{4A}$-$N(R^{4b})(L^{4B}$-$G^{4a})$, -$L^{4A}$-$N(R^{4b})C(O)$-$L^{4B}$-$G^{4a}$, -$L^{4A}$-$N(R^{4b})S(O)_2$-$L^{4B}$-$G^{4a}$, or -$L^{4A}$-$R^{4c}$, wherein the $C_1$-$C_{10}$alkyl, $C_2$-$C_{10}$alkenyl, and $C_2$-$C_{10}$alkynyl are each optionally substituted with 2, 3, or 4 hydroxy substituents; and wherein the $C_3$-$C_8$cycloalkyl or 3- to 8-membered heterocyclyl is each optionally substituted with $L^{4B}$-$G^{4b}$ and optionally substituted with 1, 2, 3, or 4 substituents selected from the group consisting of halogen, oxo, $C_1$-$C_3$alkyl, $C_1$-$C_3$haloalkyl, —O—$C_1$-$C_3$alkyl, and —O—$C_1$-$C_3$haloalkyl;

$L^{4A}$ is $C_1$-$C_{10}$alkylene, $C_2$-$C_{10}$alkenylene, or $C_2$-$C_{10}$alkynylene, wherein $L^{4A}$ is optionally substituted with 1, 2, 3, 4, or 5 substituents selected from the group consisting of halogen, $C_1$-$C_6$alkyl, and $C_1$-$C_6$haloalkyl;

$G^{4a}$ is $C_3$-$C_{12}$cycloalkyl, $C_6$-$C_{12}$aryl, 3- to 12-membered heterocyclyl, or 5- to 12-membered heteroaryl, wherein $G^{4a}$ is optionally substituted with $L^{4C}$-$G^{4b}$ and optionally substituted with 1, 2, 3, 4, or 5 substituents selected from the group consisting of halogen, oxo, $C_1$-$C_3$alkyl, $C_1$-$C_3$haloalkyl, —OH, —O—$C_1$-$C_3$alkyl, —O—$C_1$-$C_3$haloalkyl, thioxo, —$NH_2$, —$NH(C_1$-$C_3$alkyl), and —$N(C_1$-$C_3$alkyl)$_2$;

$L^{4B}$ and $L^{4C}$, at each occurrence, are each independently a bond, $C_1$-$C_6$alkylene, $C_2$-$C_6$alkenylene, or $C_2$-$C_6$alkynylene, wherein $L^{4B}$ and $L^{4C}$ are each optionally substituted with 1, 2, 3, 4, or 5 substituents selected from the group consisting of halogen, $C_1$-$C_6$alkyl, and $C_1$-$C_6$haloalkyl;

$G^{4b}$ is $C_3$-$C_{12}$cycloalkyl, 3- to 12-membered heterocyclyl, $C_6$-$C_{12}$aryl, or 5- to 12-membered heteroaryl, wherein $G^{4b}$ is optionally substituted with 1, 2, 3, 4, or 5 substituents selected from the group consisting of halogen, oxo, $C_1$-$C_6$alkyl, $C_1$-$C_6$haloalkyl, hydroxy, —O—$C_1$-$C_6$alkyl, —O—$C_1$-$C_6$haloalkyl, —S(O)—$C_1$-$C_6$alkyl, —$S(O)_2$—$C_1$-$C_6$alkyl, —$C(O)$—$C_1$-$C_6$alkyl, $C_1$-$C_3$alkylene-OH, $C_1$-$C_3$alkylene-O—$C_1$-$C_3$alkyl, $C_1$-$C_3$alkylene-$N(C_1$-$C_3$alkyl)$_2$, and $C_1$-$C_3$alkylene-(N-heterocyclyl);

$R^{4a}$ and $R^{4b}$, at each occurrence, are each independently hydrogen, $C_1$-$C_6$alkyl, $C_1$-$C_6$haloalkyl, or $C_3$-$C_8$cycloalkyl, wherein the $C_3$-$C_8$cycloalkyl is optionally substituted with 1, 2, 3, or 4 substituents selected from the group consisting of halogen, oxo, $C_1$-$C_3$alkyl, and $C_1$-$C_3$haloalkyl;

$R^{4c}$ is —O—$R^{4b}$, —$OC(O)R^{4b}$, —O—$Si(C_1$-$C_6$alkyl)$_3$, —CN, —$C(O)R^{4b}$, —$CO_2R^{4b}$, —$C(O)N(R^{4b})_2$, —$C(O)N(R^{4b})S(O)_2R^{4b}$, —S—$R^{4b}$, —$S(O)_2R^{4b}$, —$S(O)R^{4b}$, —$SO_2N(R^{4b})_2$, —$N(R^{4b})_2$, —$N(R^{4b})C(O)R^{4b}$, —$N(R^{4b})S(O)_2R^{4b}$, —$C(NOH)N(R^{4b})_2$, —$C(O)C(OH)(R^{4b})_2$, or —$P(O)(OR^{4b})_2$;

$R^5$ is hydrogen, $C_1$-$C_6$alkyl, $C_1$-$C_6$haloalkyl, $C_3$-$C_6$cycloalkyl, —O—$C_1$-$C_6$alkyl, —O—$C_1$-$C_6$haloalkyl, —O—$C_3$-$C_6$cycloalkyl, or $G^{5a}$, wherein the $C_3$-$C_6$cycloalkyl groups are optionally substituted with 1, 2, 3, or 4 substituents selected from the group consisting of halogen, $C_1$-$C_3$alkyl, $C_1$-$C_3$haloalkyl, and oxo;

$G^{5a}$ is phenyl, wherein $G^{5a}$ is substituted with —$C(O)N(R^{5a})$-$L^{5B}$-$G^{5b}$, —$C(O)$-$G^{5f}$, or —$C(O)N(R^{5a})(R^{5e})$, and optionally substituted with 1, 2, or 3 substituents selected from the group consisting of $C_1$-$C_{10}$alkyl, $C_2$-$C_{10}$alkenyl, $C_2$-$C_{10}$alkynyl, $C_1$-$C_{10}$haloalkyl, halogen, —O—$R^{5b}$, CN, —$N(R^{5b})C(O)R^{5b}$, —$C(O)N(R^{5a})(R^{5b})$, —$C(O)R^{5b}$, —$OC(O)R^{5b}$, —$CO_2H$, —$CO_2R^{5b}$, —$N(R^{5b})C(O)N(R^{5a})(R^{5b})$, —S—$R^{5b}$, —$S(O)_2R^{5b}$, —$S(O)R^{5b}$, —$SO_2N(R^{5a})(R^{5b})$, —$N(R^{5a})(R^{5b})$, —$N(R^{5b})S(O)_2R^{5b}$, $N(R^{5b})C(O)O(R^{5b})$, -$L^{5A}$-O—$R^{5b}$, -$L^{5A}$-CN, -$L^{5A}$-$N(R^{5b})C(O)R^{5b}$, -$L^{5A}$-$C(O)N(R^{5a})(R^{5b})$, -$L^{5A}$-$C(O)R^{5b}$, -$L^{5A}$-$OC(O)R^{5b}$, -$L^{5A}$-$CO_2H$, -$L^{5A}$-$CO_2R^{5b}$, -$L^{5A}$-$N(R^{5b})C(O)N(R^{5a})(R^{5b})$, -$L^{5A}$-S—$R^{5b}$, -$L^{5A}$-$S(O)_2R^{5b}$, -$L^{5A}$-$S(O)R^{5b}$, -$L^{5A}$-$SO_2N(R^{5a})(R^{5b})$, -$L^{5A}$-$N(R^{5a})(R^{5b})$, -$L^{5A}$-$N(R^{5b})S(O)_2R^{5b}$, -$L^{5A}$-$N(R^{5b})C(O)O(R^{5b})$, -$G^{5d}$, and -$L^{5A}$-$G^{5d}$;

$G^{5b}$ is $C_3$-$C_{12}$cycloalkyl, $C_6$-$C_{12}$aryl, 3- to 12-membered heterocyclyl, or 5- to 12-membered heteroaryl, wherein each $G^{5b}$ is optionally substituted with 1, 2, 3, 4, or 5 substituents selected from the group consisting of oxo, halogen, $C_1$-$C_6$alkyl, $C_1$-$C_6$haloalkyl, —O—$R^{5d}$, —CN, —$N(R^{5d})C(O)R^{5d}$, —$CON(R^{5a})(R^{5d})$, —$C(O)R^{5d}$, —$OC(O)R^{5d}$, —$CO_2H$, —$CO_2R^{5d}$, —$N(R^{5d})C(O)N(R^{5d})_2$, —S—$R^{5d}$, —$S(O)_2R^{5d}$, —$S(O)R^{5d}$, —$SO_2N(R^{5a})(R^{5d})$, —$N(R^{5a})(R^{5d})$, —$N(R^{5d})S(O)_2R^{5d}$, $N(R^{5d})C(O)O(R^{5d})$, -$L^{5C}$-O—$R^{5d}$, -$L^{5C}$-CN, -$L^{5C}$-$N(R^{5d})C(O)R^{5d}$, -L$^{5C}$-CON(R$^{5a}$)(R$^{5d}$), -L$^{5C}$-C(O)R$^{5d}$, -L$^{5C}$-OC(O)R$^{5d}$, -L$^{5C}$-CO$_2$H, -L$^{5C}$-CO$_2$R$^{5d}$, -L$^{5C}$-N(R$^{5d}$)C(O)N(R$^{5d}$)$_2$, -L$^{5C}$-S-R$^{5d}$, -L$^{5C}$-S(O)$_2$R$^{5d}$, -L$^{5C}$-S(O)R$^{5d}$, -L$^{5C}$-SO$_2$N(R$^{5a}$)(R$^{5d}$), -L$^{5C}$-N(R$^{5a}$)(R$^{5d}$), -L$^{5C}$-N(R$^{5d}$)S(O)$_2$R$^{5d}$, -L$^{5C}$-N(R$^{5d}$)C(O)O(R$^{5d}$), G$^{5c}$, and -L$^{5C}$-G$^{5c}$;

G$^{5c}$, at each occurrence, is each independently C$_3$-C$_8$cycloalkyl, C$_6$-C$_{10}$aryl, 4- to 10-membered heterocyclyl, or 5- to 10-membered heteroaryl, wherein G$^{5c}$ is optionally substituted with 1, 2, 3, 4, or 5 substituents selected from the group consisting of halogen, oxo, C$_1$-C$_6$alkyl, C$_1$-C$_6$haloalkyl, —O—C$_1$-C$_6$alkyl, and —O—C$_1$-C$_6$haloalkyl;

G$^{5d}$, is at each occurrence, is each independently C$_3$-C$_8$cycloalkyl, C$_6$-C$_{10}$aryl, 4- to 10-membered heterocyclyl, or 5- to 10-membered heteroaryl, wherein G$^{5d}$ is optionally substituted with 1, 2, 3, 4, or 5 substituents selected from the group consisting of oxo, halogen, C$_1$-C$_6$alkyl, C$_1$-C$_6$haloalkyl, —O—R$^{5d}$, —CN, —N(R$^{5d}$)C(O)R$^{5d}$, —CON(R$^{5a}$)(R$^{5d}$), —C(O)R$^{5d}$, —OC(O)R$^{5d}$, —CO$_2$H, —CO$_2$R$^{5d}$, —N(R$^{5d}$)C(O)N(R$^{5d}$)$_2$, —S—R$^{5d}$, —S(O)$_2$R$^{5d}$, —S(O)R$^{5d}$, —SO$_2$N(R$^{5a}$)(R$^{5d}$), —N(R$^{5a}$)(R$^{5d}$), —N(R$^{5d}$)S(O)$_2$R$^{5d}$, N(R$^{5d}$)C(O)O(R$^{5d}$), -L$^{5C}$-O—R$^{5d}$, -L$^{5C}$-CN, -L$^{5C}$-N(R$^{5d}$)C(O)R$^{5d}$, -L$^{5C}$-CON(R$^{5a}$)(R$^{5d}$), -L$^{5C}$-C(O)R$^{5d}$, -L$^{5C}$-OC(O)R$^{5d}$, -L$^{5C}$-CO$_2$H, -L$^{5C}$-CO$_2$R$^{5d}$, -L$^{5C}$-N(R$^{5d}$)C(O)N(R$^{5d}$)$_2$, -L$^{5C}$-S-R$^{5d}$, -L$^{5C}$-S(O)$_2$R$^{5d}$, -L$^{5C}$-S(O)R$^{5d}$, -L$^{5C}$-SO$_2$N(R$^{5a}$)(R$^{5d}$), -L$^{5C}$-N(R$^{5a}$)(R$^{5d}$), -L$^{5C}$-N(R$^{5d}$)S(O)$_2$R$^{5d}$, -L$^{5C}$-N(R$^{5d}$)C(O)O(R$^{5d}$), G$^{5c}$, and -L$^{5C}$-G$^{5c}$;

R$^{5a}$, at each occurrence, is each independently hydrogen, C$_1$-C$_6$alkyl, C$_1$-C$_6$haloalkyl, or C$_3$-C$_8$cycloalkyl, wherein the C$_3$-C$_8$cycloalkyl is optionally substituted with 1, 2, 3, or 4 substituents selected from the group consisting of halogen, oxo, C$_1$-C$_3$alkyl, and C$_1$-C$_3$haloalkyl;

R$^{5b}$, at each occurrence, is each independently hydrogen, C$_1$-C$_{10}$alkyl, C$_2$-C$_{10}$alkenyl, C$_2$-C$_{10}$alkynyl, C$_1$-C$_{10}$haloalkyl, -L$^{5D}$-G$^{5e}$, or -L$^{5G}$-R$^{5c}$;

R$^{5c}$, at each occurrence, is each independently —CON(R$^{5a}$)(R$^{5g}$), —O—R$^{5g}$, —OC(O)R$^{5g}$, —CN, —C(O)R$^{5g}$, —CO$_2$H, —CO$_2$R$^{5g}$, —N(R$^{5g}$)C(O)N(R$^{5g}$)$_2$, —S—R$^{5g}$, —S(O)$_2$R$^{5g}$, —S(O)R$^{5g}$, —SO$_2$N(R$^{5a}$)(R$^{5g}$), —N(R$^{5a}$)(R$^{5g}$), —N(R$^{5g}$)C(O)R$^{5g}$, or —N(R$^{5g}$)S(O)$_2$R$^{5g}$;

R$^{5d}$, at each occurrence, is each independently hydrogen, C$_1$-C$_6$alkyl, C$_1$-C$_6$haloalkyl, or -L$^{5F}$-G$^{5c}$;

R$^{5e}$, at each occurrence, is each independently hydrogen, C$_1$-C$_{10}$alkyl, C$_2$-C$_{10}$alkenyl, C$_2$-C$_{10}$alkynyl, C$_1$-C$_{10}$haloalkyl, or -L$^{5E}$-R$^{5f}$;

R$^{5f}$ is —CON(R$^{5a}$)(R$^{5d}$), —O—R$^{5d}$, —OC(O)R$^{5d}$, —CN, —C(O)R$^{5d}$, —CO$_2$H, —CO$_2$R$^{5d}$, —N(R$^{5d}$)C(O)N(R$^{5d}$)$_2$, —S—R$^{5d}$, —S(O)$_2$R$^{5d}$, —S(O)R$^{5d}$, —SO$_2$N(R$^{5a}$)(R$^{5d}$), —N(R$^{5a}$)(R$^{5d}$), —N(R$^{5d}$)C(O)R$^{5d}$, or —N(R$^{5d}$)S(O)$_2$R$^{5d}$;

R$^{5g}$ is hydrogen, C$_1$-C$_6$alkyl, C$_1$-C$_6$haloalkyl, or -L$^{5H}$-G$^{5e}$;

G$^{5e}$, at each occurrence, is each independently C$_3$-C$_8$cycloalkyl, C$_6$-C$_{10}$aryl, 4- to 10-membered heterocyclyl, or 5- to 10-membered heteroaryl, wherein G$^{5e}$ is optionally substituted with 1, 2, 3, or 4 substituents selected from the group consisting of halogen, oxo, C$_1$-C$_6$alkyl, C$_1$-C$_6$haloalkyl, —OH, —O—C$_1$-C$_6$alkyl, and —O—C$_1$-C$_6$haloalkyl;

G$^{5f}$ is 4- to 10-membered heterocyclyl, wherein G$^{5f}$ is optionally substituted with 1, 2, 3, or 4 substituents selected from the group consisting of halogen, oxo, C$_1$-C$_6$alkyl, C$_1$-C$_6$haloalkyl, —O—C$_1$-C$_6$alkyl, and —O—C$_1$-C$_6$haloalkyl;

L$^{5A}$, at each occurrence, is each independently C$_1$-C$_6$alkylene or C$_3$-C$_8$cycloalkyl, wherein L$^{5A}$ is each optionally substituted with 1, 2, 3, or 4 halogen;

L$^{5B}$ is a bond, C$_1$-C$_6$alkylene, or C$_3$-C$_8$cycloalkyl, wherein L$^{5B}$ is optionally substituted with 1, 2, 3, or 4 halogen and 1 or 2 hydroxy;

L$^{5C}$, at each occurrence, is each independently C$_1$-C$_6$alkylene or C$_3$-C$_8$cycloalkyl, wherein L$^{5C}$ is each optionally substituted with 1, 2, 3, or 4 halogen and 1 or 2 hydroxy;

L$^{5D}$, at each occurrence, is each independently a bond, C$_1$-C$_6$alkylene, or C$_3$-C$_8$cycloalkyl, wherein L$^{5D}$ is each optionally substituted with 1, 2, 3, or 4 halogen and 1 or 2 hydroxy;

L$^{5E}$, at each occurrence, is each independently C$_1$-C$_6$alkylene, wherein L$^{5E}$ is optionally substituted with 1, 2, 3, or 4 halogen and 1 or 2 hydroxy;

L$^{5F}$, at each occurrence, is each independently bond or C$_1$-C$_6$alkylene, wherein L$^{5F}$ is optionally substituted with 1, 2, 3, or 4 halogen and 1 or 2 hydroxy;

L$^{5G}$, at each occurrence, is each independently C$_1$-C$_6$alkylene, wherein L$^{5G}$ is optionally substituted with 1, 2, 3, or 4 halogen and 1 or 2 hydroxy; and L$^{5H}$, at each occurrence, is each independently a bond, C$_1$-C$_6$alkylene, or C$_3$-C$_8$cycloalkyl, wherein L$^{5H}$ is each optionally substituted with 1, 2, 3, or 4 halogen and 1 or 2 hydroxy, optionally in combination with one or more additional therapeutic agents.

15. A method for inhibiting replication of an HCV virus, comprising exposing the virus to one or more compounds of claim 1 or pharmaceutically acceptable salts thereof, optionally in combination with one or more additional therapeutic agents.

16. The method of claim 14, wherein the HCV infection is from an HCV virus of genotype 1a, 1b, 2a, 3a or 4a.

17. The method of claim 16, wherein the HCV infection is from a mutant of an HCV virus.

18. A method for preparing compounds of formula (3), comprising treating a compound of formula (2) with iodobenzene diacetate and excess potassium carbonate in DMSO at ambient temperature for 24-48 hours

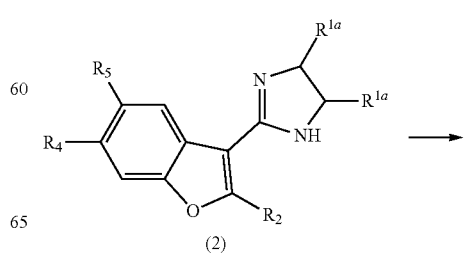

(2)

-continued
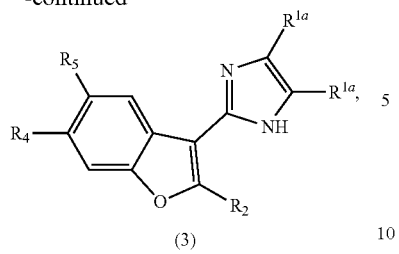
wherein $R^{1a}$, $R^2$, $R^4$ and $R^5$ are as described in claim 1.
* * * * *

UNITED STATES PATENT AND TRADEMARK OFFICE
CERTIFICATE OF CORRECTION

PATENT NO. : 9,173,887 B2  
APPLICATION NO. : 13/995701  
DATED : November 3, 2015  
INVENTOR(S) : Maring et al.

Page 1 of 1

It is certified that error appears in the above-identified patent and that said Letters Patent is hereby corrected as shown below:

On the title page

Item 75, inventor name: "Adreas Witte" to read as --Andreas Witte--

In the claims

Column 205, line 22, claim 1: "oxo, $C_1$-$C_3$haloalkyl," to read as --oxo, $C_1$-$C_3$alkyl, $C_1$-$C_3$haloalkyl,--

Column 209, line 35, claim 8: "$L_{2B}$, $R_{21}$," to read as --$L_{2B}$-$R_{21}$,--

Column 210, line 16, claim 10: "$G^{2b}$;" to read as --$G^{2b}$,--

Column 210, line 59, claim 12: "methanesulfonamide'" to read as --methanesulfonamide;--

Column 212, line 4, claim 12: "Nethylsulfonyl)" to read as --N-(methylsulfonyl)--

Column 212, line 19, claim 12: "Netrahydro" to read as --N-(tetrahydro--

Column 212, line 59, claim 12: "Nyrrolidin" to read as --N-(pyrrolidin--

Column 212, line 63, claim 12: "Nyclopropylmethyl)" to read as --N-(cyclopropylmethyl)--

Column 212, line 57, claim 12: "Netrahydrofuran" to read as --N-(tetrahydrofuran--

Column 216, line 58, claim 12: "N-hydroxybutanimidamide;" to read as --N'-hydroxybutanimidamide;--

Column 219, line 40, claim 14: "-O-$C_1$-$C_6$haloalkyl," to read as -- -O-$C_1$-$C_6$alkyl, -O-$C_1$-$C_6$haloalkyl,--

Signed and Sealed this  
Ninth Day of August, 2016

Michelle K. Lee  
*Director of the United States Patent and Trademark Office*